United States Patent
Xu et al.

(10) Patent No.: US 12,084,432 B2
(45) Date of Patent: Sep. 10, 2024

(54) NITROGEN-CONTAINING COMPOUND, AND ORGANIC ELECTROLUMINESCENT DEVICE AND ELECTRONIC APPARATUS THEREOF

(71) Applicant: Shaanxi Lighte Optoelectronics Material Co., Ltd., Xi'an (CN)

(72) Inventors: Xianbin Xu, Xi'an (CN); Lei Yang, Xi'an (CN)

(73) Assignee: Shaanxi Lighte Optoelectronics Material Co., Ltd., Xi'an (CN)

( * ) Notice: Subject to any disclaimer, the term of this patent is extended or adjusted under 35 U.S.C. 154(b) by 0 days.

(21) Appl. No.: 18/288,600

(22) PCT Filed: Sep. 28, 2022

(86) PCT No.: PCT/CN2022/122326
§ 371 (c)(1),
(2) Date: Oct. 27, 2023

(87) PCT Pub. No.: WO2023/134228
PCT Pub. Date: Jul. 20, 2023

(65) Prior Publication Data
US 2024/0246938 A1    Jul. 25, 2024

(30) Foreign Application Priority Data

Jan. 12, 2022  (CN) .......... 202210032719.8
Aug. 30, 2022  (CN) .......... 202211051681.5

(51) Int. Cl.
*C07D 403/10*    (2006.01)
*C07D 403/14*    (2006.01)
(Continued)

(52) U.S. Cl.
CPC ......... *C07D 403/10* (2013.01); *C07D 403/14* (2013.01); *C07D 405/14* (2013.01);
(Continued)

(58) Field of Classification Search
CPC .. C07D 403/10; C07D 403/12; C07D 403/14; C07D 413/10; C07D 413/12;
(Continued)

(56) References Cited

U.S. PATENT DOCUMENTS

2020/0140440 A1    5/2020   Jatsch

FOREIGN PATENT DOCUMENTS

CN    102186819 A    9/2011
CN    113773290 A    12/2021
(Continued)

OTHER PUBLICATIONS

International Search Report from corresponding International Application No. PCT/CN2022/122326, mailed on Dec. 12, 2022, 4 pages with translation.

*Primary Examiner* — Vu A Nguyen
(74) *Attorney, Agent, or Firm* — Tucker Ellis LLP

(57) ABSTRACT

The present disclosure relates to a nitrogen-containing compound, and an organic electroluminescent device and an electronic apparatus including the same. The nitrogen-containing compound of the present disclosure includes a tetramethylcyclohexanocarbazole group and a nitrogen-containing heteroaryl group, and when the nitrogen-containing compound is used as a host material of an organic electroluminescent device, the luminous efficiency of the device can be significantly improved.

9 Claims, 1 Drawing Sheet

(51) Int. Cl.
  *C07D 405/14* (2006.01)
  *C07D 409/14* (2006.01)
  *C07D 495/04* (2006.01)
  *H10K 50/11* (2023.01)
  *H10K 85/60* (2023.01)

(52) U.S. Cl.
  CPC ......... *C07D 409/14* (2013.01); *C07D 495/04* (2013.01); *H10K 50/11* (2023.02); *H10K 85/6572* (2023.02)

(58) Field of Classification Search
  CPC .. C07D 413/14; C07D 417/10; C07D 417/12; C07D 417/14; H10K 85/6572; H10K 85/6574; H10K 85/6576
  See application file for complete search history.

(56) References Cited

FOREIGN PATENT DOCUMENTS

| | | | | | |
|---|---|---|---|---|---|
| CN | 114805179 | A | * | 7/2022 | ........... C07D 209/80 |
| CN | 114805179 | A | | 7/2022 | |
| KR | 20140004005 | A | * | 1/2014 | ........... C07D 401/14 |
| KR | 20140004005 | A | | 1/2014 | |
| KR | 20140105634 | A | | 9/2014 | |
| KR | 20160060572 | A | | 5/2016 | |

* cited by examiner

NITROGEN-CONTAINING COMPOUND, AND ORGANIC ELECTROLUMINESCENT DEVICE AND ELECTRONIC APPARATUS THEREOF

CROSS REFERENCE TO RELATED APPLICATIONS

The present application claims the priority of Chinese patent application No. CN202210032719.8, filed on Jan. 12, 2022, and Chinese patent application No. CN202211051681.5, filed on Aug. 30, 2022, the contents of which are incorporated herein by reference in their entirety as part of the present application.

FIELD

The present disclosure relates to the technical field of organic electroluminescent materials, in particular to a nitrogen-containing compound, and an organic electroluminescent device and an electronic apparatus thereof.

BACKGROUND

With the development of electronic technology and the progress of material science, the application range of electronic components for realizing electroluminescence or photoelectric conversion is wider and wider. An organic electroluminescent device (OLED) typically includes a cathode and an anode which are disposed oppositely, and a functional layer disposed between the cathode and the anode. The functional layer is composed of a plurality of organic or inorganic film layers, and generally includes an organic electroluminescent layer, a hole transport layer, an electron transport layer, and the like. When voltage is applied to the cathode and the anode, an electric field is generated between the cathode and the anode, electrons on a cathode side move towards an electroluminescent layer and holes on an anode side also move towards the electroluminescent layer under the action of the electric field, the electrons and the holes are combined in the electroluminescent layer to form excitons, the excitons are in an excited state and release energy outwards, and then the electroluminescent layer emits light outwards.

In the existing organic electroluminescent device, the most major problems are service life and efficiency, as an area of a display becomes larger, the driving voltage also increases, and the luminous efficiency and the current efficiency also need to be improved, and thus, it is necessary to continue to develop new materials to further improve the performance of the organic electroluminescent device.

SUMMARY

In view of the above problems existing in the prior art, an object of the present disclosure is to provide a nitrogen-containing compound, and an organic electroluminescent device and an electronic apparatus thereof. When the nitrogen-containing compound is used in an organic electroluminescent device, the performance of the device can be improved.

According to a first aspect of the present disclosure, provided is a nitrogen-containing compound, having a structure represented by a formula 1:

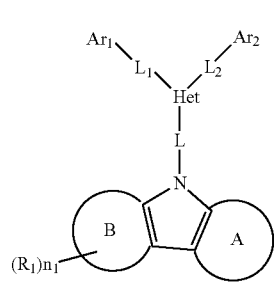

Formula 1 where a ring A has a structure shown in a formula A-1 or a structure shown in a formula A-2

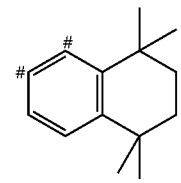

A-1

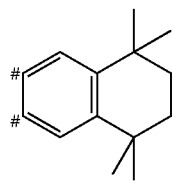

A-2 and a # position represents a site that is fused with a # position of

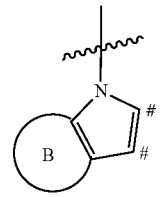

in the formula 1;
a ring B is an aromatic ring with 6 to 14 carbon atoms;
Het is 6- to 18-membered nitrogen-containing heteroarylene, and the Het includes at least 2 nitrogen atoms;
each $R_1$ is independently selected from deuterium, a halogen group, cyano, alkyl with 1 to 10 carbon atoms, cycloalkyl with 1 to 10 carbon atoms, haloalkyl with 1 to 10 carbon atoms, deuteroalkyl with 1 to 10 carbon atoms, aryl with 6 to 20 carbon atoms, and heteroaryl with 3 to 20 carbon atoms;
$n_1$ is selected from 0, 1, 2, 3, 4, 5 or 6;
L is selected from substituted or unsubstituted arylene with 6 to 30 carbon atoms, and substituted or unsubstituted heteroarylene with 3 to 30 carbon atoms;
$L_1$ and $L_2$ are the same or different, and are each independently selected from a single bond, substituted or unsubstituted arylene with 6 to 30 carbon atoms, and substituted or unsubstituted heteroarylene with 3 to 30 carbon atoms;

Ar₁ is selected from substituted or unsubstituted aryl with 6 to 30 carbon atoms, and substituted or unsubstituted heteroaryl with 3 to 30 carbon atoms;

Ar₂ is selected from hydrogen, substituted or unsubstituted aryl with 6 to 30 carbon atoms, and substituted or unsubstituted heteroaryl with 3 to 30 carbon atoms; and substituents in L₁, L₂, L, Ar₁ and Ar₂ are the same or different, and are each independently selected from deuterium, cyano, a halogen group, alkyl with 1 to 10 carbon atoms, haloalkyl with 1 to 10 carbon atoms, deuteroalkyl with 1 to 10 carbon atoms, trialkylsilyl with 3 to 12 carbon atoms, triphenylsilyl, aryl with 6 to 20 carbon atoms, heteroaryl with 3 to 20 carbon atoms, and cycloalkyl with 3 to 10 carbon atoms; and optionally, any two adjacent substituents form a saturated or unsaturated 3- to 15-membered ring.

According to a second aspect of the present disclosure, provided is an organic electroluminescent device, including an anode and a cathode which are oppositely disposed, and a functional layer disposed between the anode and the cathode; where the functional layer includes the nitrogen-containing compound described above.

According to a third aspect of the present disclosure, provided is an electronic apparatus, including the organic electroluminescent device in the second aspect.

A structure of the nitrogen-containing compound of the present disclosure includes tetramethylcyclohexanocarbazole and nitrogen-containing heteroarylene, where the nitrogen-containing heteroarylene is connected to a nitrogen atom of a carbazole group through an aromatic group, and this special connection mode enables a target molecule to make full use of a larger conjugation plane of a carbazole molecule, improving the charge mobility of the target molecule. At the same time, the structure of tetramethylcyclohexane can further enhance the charge transport ability of the carbazole group through a hyperconjugation effect. In addition, four methyl are located outside the conjugation plane of the carbazole group in steric configuration, forming a certain steric hindrance, and intermolecular stacking of the compound is finely regulated, so that the compound may form an amorphous thin film with better stability in a functional layer of a device. Thus, when the nitrogen-containing compound of the present disclosure is used as a host material, the carrier balance in a electroluminescent layer can be improved, a carrier recombination region can be broadened, the exciton generation and utilization efficiency can be increased, and the luminous efficiency of the device can be improved; and at the same time, the compound of the present disclosure can form a better amorphous film when used as the host material, improving the service life of the device.

DESCRIPTION OF REFERENCE SIGNS

Figure 1:
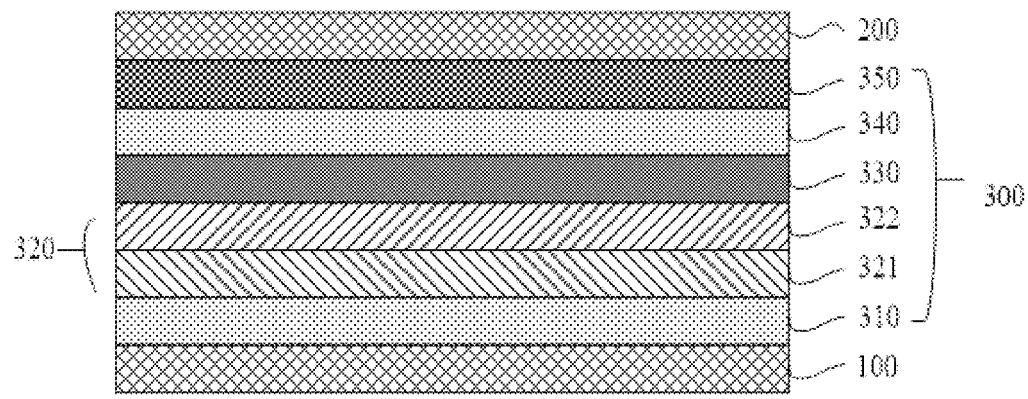
FIG. 1 is a structural schematic diagram of an organic electroluminescent device according to an embodiment of the present disclosure.

100, anode; 200, cathode; 300, functional layer; 310, hole injection layer; 320, hole transport layer; 321, first hole transport layer; 322, second hole transport layer; 330, organic luminescent layer; 340, electron transport layer; 350, electron injection layer; and 400, electronic apparatus.

DETAILED DESCRIPTION

Embodiments will now be described more fully with reference to the accompanying drawings. However, the embodiments can be implemented in a variety of forms, and should not be understood as a limitation to the instances set forth here; and on the contrary, these embodiments are provided such that the present disclosure will be more comprehensive and complete, and the concepts of the examples are comprehensively conveyed to those skilled in the art. The described features, structures, or characteristics may be incorporated in one or more embodiments in any suitable manner. In the following description, many specific details are provided to give a sufficient understanding of the examples of the present disclosure.

In a first aspect, the present disclosure provides a nitrogen-containing compound, having a structure represented by a formula 1:

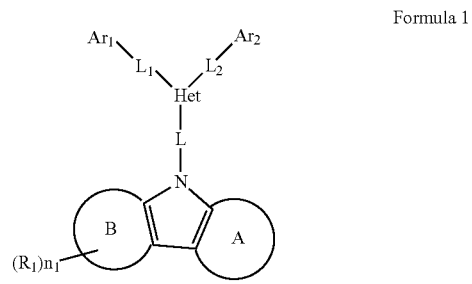

Formula 1 where a ring A has a structure shown in a formula A-1 or a structure shown in a formula A-2:

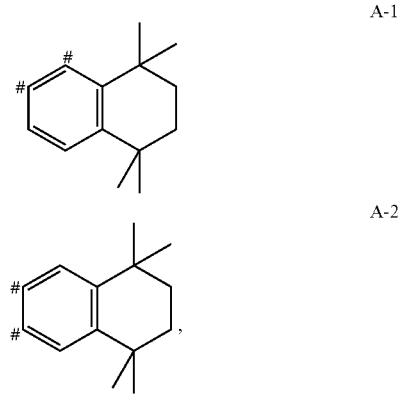

A-1

A-2 and a # position represents a site that is fused with a # position of

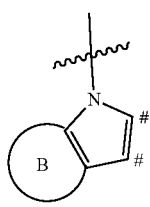

in the formula 1;
a ring B is an aromatic ring with 6 to 14 carbon atoms;
Het is 6- to 18-membered nitrogen-containing heteroarylene, and includes at least 2 nitrogen atoms;
each $R_1$ is independently selected from deuterium, a halogen group, cyano, alkyl with 1 to 10 carbon atoms, cycloalkyl with 1 to 10 carbon atoms, haloalkyl with 1 to 10 carbon atoms, deuteroalkyl with 1 to 10 carbon atoms, aryl with 6 to 20 carbon atoms, and heteroaryl with 3 to 20 carbon atoms;
$n_1$ is selected from 0, 1, 2, 3, 4, 5 or 6;
L is selected from substituted or unsubstituted arylene with 6 to 30 carbon atoms, and substituted or unsubstituted heteroarylene with 3 to 30 carbon atoms;
$L_1$ and $L_2$ are the same or different, and are each independently selected from a single bond, substituted or unsubstituted arylene with 6 to 30 carbon atoms, and substituted or unsubstituted heteroarylene with 3 to 30 carbon atoms;
$Ar_1$ is selected from substituted or unsubstituted aryl with 6 to 30 carbon atoms, and substituted or unsubstituted heteroaryl with 3 to 30 carbon atoms;
$Ar_2$ is selected from hydrogen, substituted or unsubstituted aryl with 6 to 30 carbon atoms, and substituted or unsubstituted heteroaryl with 3 to 30 carbon atoms; and
substituents in $L_1$, $L_2$, L, $Ar_1$ and $Ar_2$ are the same or different, and are each independently selected from deuterium, cyano, a halogen group, alkyl with 1 to 10 carbon atoms, haloalkyl with 1 to 10 carbon atoms, deuteroalkyl with 1 to 10 carbon atoms, trialkylsilyl with 3 to 12 carbon atoms, triphenylsilyl, aryl with 6 to 20 carbon atoms, heteroaryl with 3 to 20 carbon atoms, and cycloalkyl with 3 to 10 carbon atoms; and optionally, any two adjacent substituents form a saturated or unsaturated 3- to 15-membered ring.

In the present disclosure, the terms "optional" and "optionally" mean that the subsequently described event or circumstance may or may not occur. For example, "optionally, any two adjacent substituents form a ring", which means that the two substituents may or may not form a ring, i.e., includes a scenario where two adjacent substituents form a ring and a scenario where two adjacent substituents do not form a ring. For another example, "optionally, any two adjacent substituents in $Ar_1$ form a ring", which means that any two adjacent substituents in $Ar_1$ may be connected to each other to form a ring, or any two adjacent substituents in $Ar_1$ may also be present independently of each other. "Any two adjacent" may include the condition that a same atom has two substituents, and may also include the condition that two adjacent atoms each have one substituent; when the same atom has two substituents, the two substituents may form a saturated or unsaturated spiro ring with the atom to which they are connected; and when two adjacent atoms each have one substituent, the two substituents may be fused to form a ring.

In the present disclosure, the adopted description modes "each . . . is (are) independently", " . . . is(are) respectively and independently" and " . . . is each independently" can be interchanged, and should be understood in a broad sense, which means that in different groups, specific options expressed between the same symbols do not influence each other, or in a same group, specific options expressed between the same symbols do not influence each other. For example, the meaning of

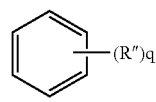

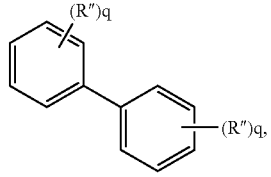

where each q is independently 0, 1, 2 or 3, and each R"is independently selected from hydrogen, deuterium, fluorine and chlorine" is as follows: a formula Q-1 represents that q substituents R" exist on a benzene ring, each R" can be the same or different, and options of each R" do not influence each other; and a formula Q-2 represents that each benzene ring of biphenyl has q substituents R", the number q of the substituents R" on the two benzene rings can be the same or different, each R" can be the same or different, and options of each R" do not influence each other.

In the present disclosure, the term such as "substituted or unsubstituted" means that a functional group described behind the term may have or do not have a substituent (in the following, the substituent is collectively referred to as Rc in order to facilitate description). For example, the "substituted or unsubstituted aryl" refers to aryl having the substituent Rc or unsubstituted aryl. The above substituent, i.e., Rc, may be, for example, deuterium, a halogen group, cyano, heteroaryl, aryl, trialkylsilyl, alkyl, haloalkyl, cycloalkyl, and the like. The number of the substituents may be one or more.

In the present disclosure, "a plurality of" refers to two or more, e.g., two, three, four, five, six, etc.

In the present disclosure, the number of carbon atoms in a substituted or unsubstituted functional group refers to the number of all carbon atoms. For example, if $L_1$ is substituted arylene with 12 carbon atoms, the number of all carbon atoms of the arylene and substituents on the arylene is 12.

In the present disclosure, aryl refers to an optional functional group or substituent derived from an aromatic carbocyclic ring. The aryl may be monocyclic aryl (e.g., phenyl) or polycyclic aryl, in other words, the aryl can be monocyclic aryl, fused aryl, two or more monocyclic aryl conjugatedly connected through carbon-carbon bonds, monocyclic aryl and fused aryl which are conjugatedly connected through a carbon-carbon bond, or two or more fused aryl conjugatedly connected through carbon-carbon bonds. That is, unless otherwise noted, two or more aromatic groups conjugatedly connected through carbon-carbon bonds can also be regarded as the aryl of the present disclosure. The fused aryl may include, for example, bicyclic fused aryl (e.g., naphthyl), tricyclic fused aryl (e.g., phenanthryl, fluorenyl, and anthryl), and the like. The aryl does not contain heteroatoms such as B, N, O, S, P, Se and Si. Examples of the aryl may include, but are not limited to, phenyl, naphthyl, fluorenyl, anthryl, phenanthryl, biphenyl, terphenyl, triphenylene, perylenyl, benzo[9,10]phenanthryl, pyrenyl, benzofluoranthenyl, chrysenyl, and the like. In the present disclosure, the arylene involved refers to a divalent group formed by further loss of one hydrogen atom from aryl.

In the present disclosure, terphenyl includes

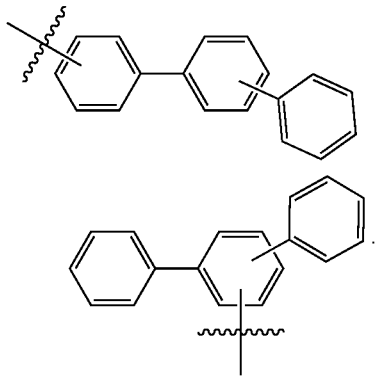

and

In the present disclosure, the number of carbon atoms of the substituted aryl refers to the total number of carbon atoms of the aryl and substituents on the aryl, for example, substituted aryl with 18 carbon atoms means that the total number of carbon atoms of the aryl and substituents is 18.

In the present disclosure, the number of carbon atoms of the substituted or unsubstituted aryl may be 6, 10, 12, 13, 14, 15, 16, 17, 18, 20, 25 or 30. In some embodiments, the substituted or unsubstituted aryl is substituted or unsubstituted aryl with 6 to 30 carbon atoms; in other embodiments, the substituted or unsubstituted aryl is substituted or unsubstituted aryl with 6 to 25 carbon atoms; in other embodiments, the substituted or unsubstituted aryl is substituted or unsubstituted aryl with 6 to 18 carbon atoms; and in other embodiments, the substituted or unsubstituted aryl is substituted or unsubstituted aryl with 6 to 15 carbon atoms.

In the present disclosure, fluorenyl may be substituted by one or more substituents, where any two adjacent substituents may be bonded to each other to form a substituted or unsubstituted spirocyclic structure. In the case where the above fluorenyl is substituted, the substituted fluorenyl may be

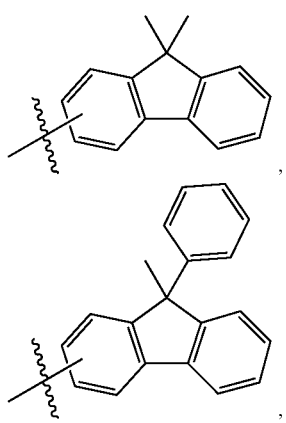

-continued

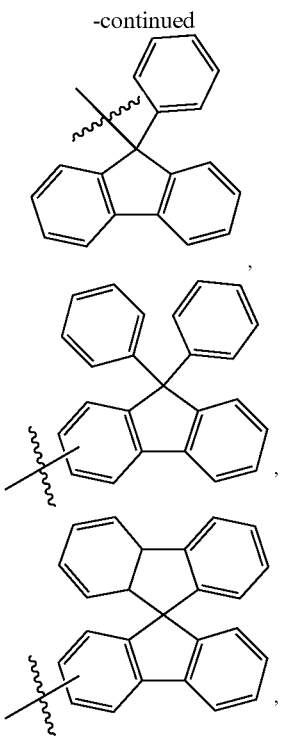

and the like, but is not limited to this.

In the present disclosure, aryl as a substituent of $L_1$, $L_2$, L, $Ar_1$ and $Ar_2$ is, for example, but is not limited to, phenyl, naphthyl, phenanthryl, biphenyl, fluorenyl, dimethylfluorenyl and the like.

In the present disclosure, heteroaryl refers to a monovalent aromatic ring containing 1, 2, 3, 4, 5 or 6 heteroatoms in the ring or its derivative, and the heteroatom may be one or more of B, O, N, P, Si, Se and S. The heteroaryl may be monocyclic heteroaryl or polycyclic heteroaryl, in other words, the heteroaryl may be a single aromatic ring system or a plurality of aromatic ring systems conjugatedly connected through carbon-carbon bonds, and any aromatic ring system is one aromatic monocyclic ring or one aromatic fused ring. For example, the heteroaryl may include thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolyl, quinazolinyl, quinoxalinyl, phenoxazinyl, phthalazinyl, pyridopyrimidinyl, pyridopyrazinyl, pyrazinopyrazinyl, isoquinolyl, indolyl, carbazolyl, benzoxazolyl, benzimidazolyl, benzothiazolyl, benzocarbazolyl, benzothienyl, dibenzothienyl, thienothienyl, benzofuranyl, phenanthrolinyl, isoxazolyl, thiadiazolyl, phenothiazinyl, silafluorenyl, dibenzofuranyl, as well as N-phenylcarbazolyl, N-pyridylcarbazolyl, N-methylcarbazolyl and the like, but is not limited to this.

In the present disclosure, the number of carbon atoms of the substituted or unsubstituted heteroaryl may be selected from 3, 4, 5, 6, 7, 8, 9, 10, 11, 12, 13, 14, 15, 16, 17, 18, 20, 21, 22, 23, 24, 25, 26, 27, 28, 29 or 30. In some embodiments, the substituted or unsubstituted heteroaryl is substituted or unsubstituted heteroaryl having a total of 3 to 30 carbon atoms; in other embodiments, the substituted or unsubstituted heteroaryl is substituted or unsubstituted heteroaryl having a total of 12 to 18 carbon atoms; and in other embodiments, the substituted or unsubstituted heteroaryl is substituted or unsubstituted heteroaryl having a total of 5 to 12 carbon atoms.

In the present disclosure, heteroaryl as a substituent of $L_1$, $L_2$, L, $Ar_1$ and $Ar_2$ is, for example, but is not limited to, pyridyl, carbazolyl, dibenzothienyl or dibenzofuranyl.

In the present disclosure, the substituted heteroaryl may be that one or two or more hydrogen atoms in the heteroaryl are substituted by groups such as a deuterium atom, a halogen group, cyano, aryl, heteroaryl, trialkylsilyl, alkyl, cycloalkyl, haloalkyl, and the like. It should be understood that the number of carbon atoms of the substituted heteroaryl refers to the total number of carbon atoms of heteroaryl and substituents on the heteroaryl.

In the present disclosure, the alkyl with 1 to 10 carbon atoms may include linear alkyl with 1 to 10 carbon atoms and branched alkyl with 3 to 10 carbon atoms. The number of carbon atoms of the alkyl may be, for example, 1, 2, 3, 4, 5, 6, 7, 8, 9, or 10, and specific examples of the alkyl include, but are not limited to, methyl, ethyl, n-propyl, isopropyl, n-butyl, isobutyl, tert-butyl, n-pentyl, isopentyl, neopentyl, n-hexyl, and the like.

In the present disclosure, the halogen group may be, for example, fluorine, chlorine, bromine or iodine.

In the present disclosure, specific examples of trialkylsilyl include, but are not limited to, trimethylsilyl, triethylsilyl, and the like.

In the present disclosure, specific examples of haloalkyl include, but are not limited to, trifluoromethyl.

In the present disclosure, the number of carbon atoms of cycloalkyl with 3 to 10 carbon atoms may be, for example, 3, 4, 5, 6, 7, 8, or 10. Specific examples of cycloalkyl include, but are not limited to, cyclopentyl, cyclohexyl, and adamantyl.

In the present disclosure, a ring system formed by n atoms is an n-membered ring. For example, phenyl is 6-membered aryl. 6- to 18-membered nitrogen-containing heteroarylene refers to heteroarylene with 6 to 18 ring atoms including nitrogen atoms.

In the disclosure, "$-\xi-$", "$*-\xi-$", "$\underline{\quad}*$", "$-\xi-*$" and "$\underline{\quad}*$" all refer to chemical bonds connected to other groups.

In the present disclosure, an unpositioned connecting bond refers to a single bond "$-\xi-$" extending from a ring system, which means that one end of the connecting bond can be connected with any position in the ring system through which the bond penetrates, and the other end of the connecting bond is connected with the remaining part of a compound molecule. For example, as shown in the following formula (f), naphthyl represented by the formula (f) is connected to other positions of a molecule through two unpositioned connecting bonds penetrating a dicyclic ring, and its meaning includes any one possible connecting mode represented by formulae (f-1) to (f-10):

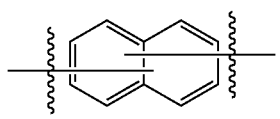

(f)

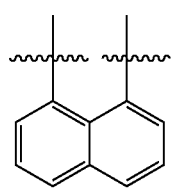

(f-1)

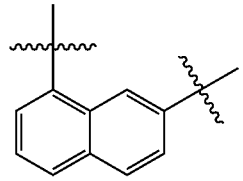

(f-2)

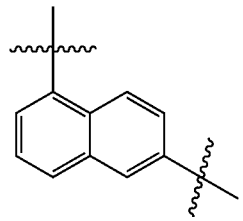

(f-3)

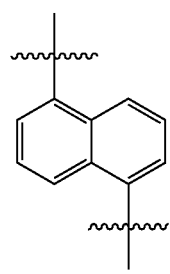

(f-4)

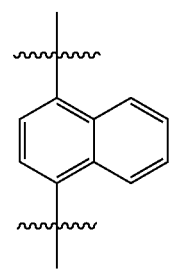

(f-5)

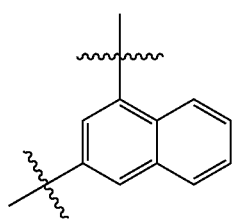

(f-6)

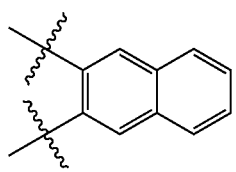

(f-7)

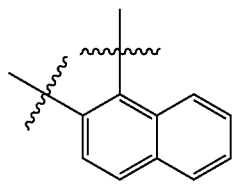

(f-8)

-continued

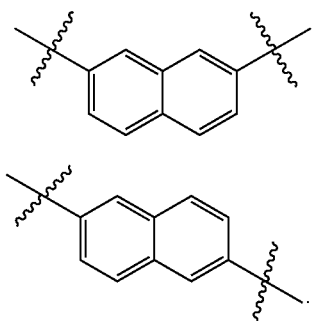

(f-9)

(f-10)

For another example, as shown in the following formula (X'), dibenzofuranyl represented by the formula (X') is connected with other positions of a molecule through one unpositioned connecting bond extending from the middle of a benzene ring on one side, and its meaning includes any one possible connecting mode represented by formulae (X'-1) to (X'-4):

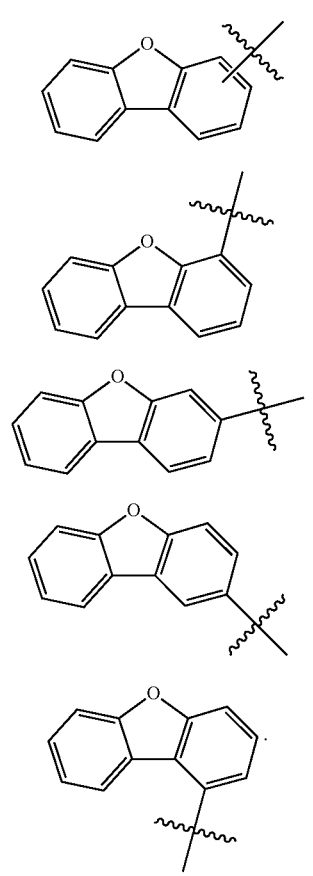

(X')

(X'-1)

(X'-2)

(X'-3)

(X'-4)

In some embodiments, the ring B in the formula 1 is a naphthalene ring or a phenanthrene ring. When an aromatic ring continues to be fused to a carbazolotetramethylcyclohexane core structure, the stability of the core structure is further improved, and the molecular thermal stability is improved, and when applied in a luminescent layer of a device, the service life of the device can be improved.

In some embodiments, in the formula 1, the ring B is selected from the following structures:

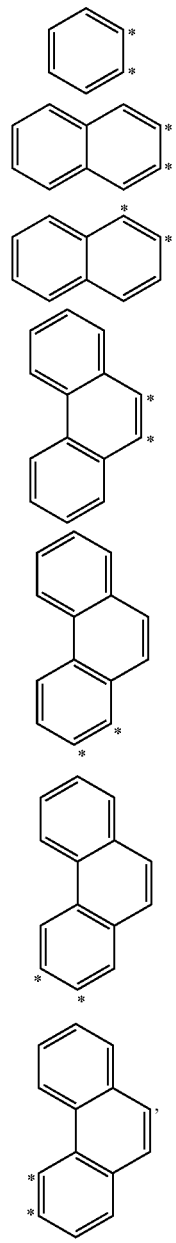

and a position represents a site that is fused with a * position of

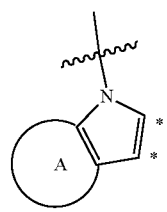

in the formula 1.

In some embodiments,
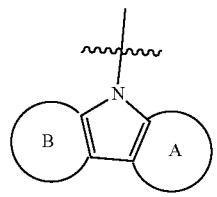
in the formula 1 is selected from the following structures:
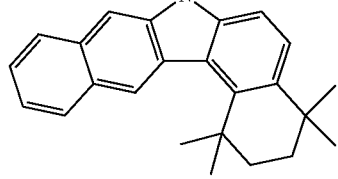
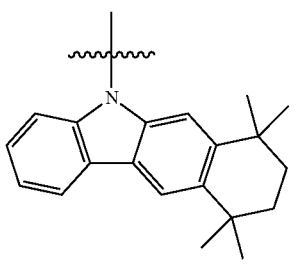
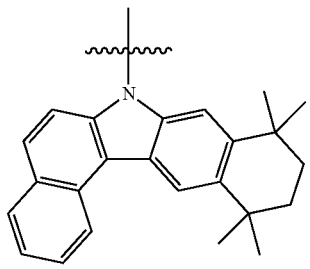
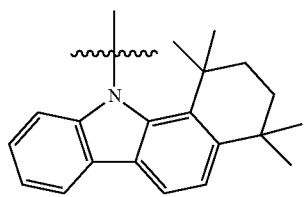
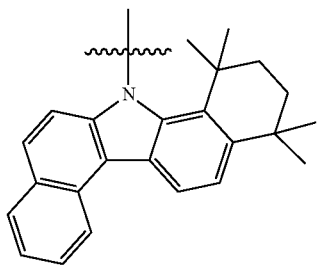
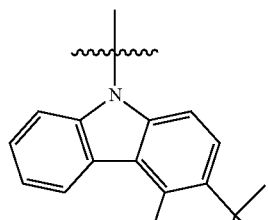
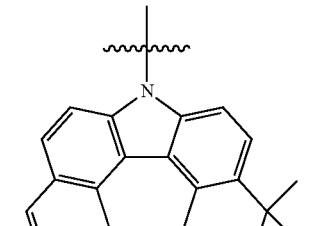
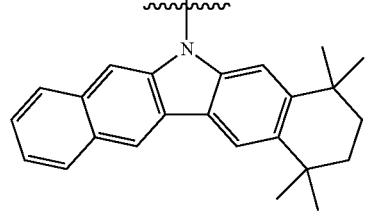
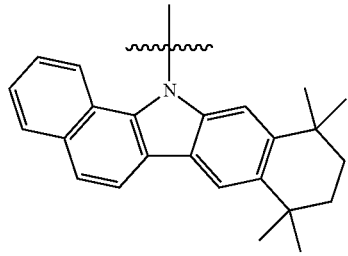
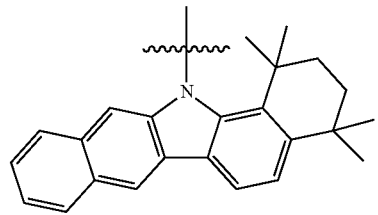
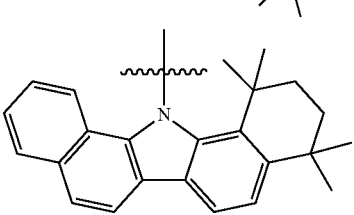

-continued

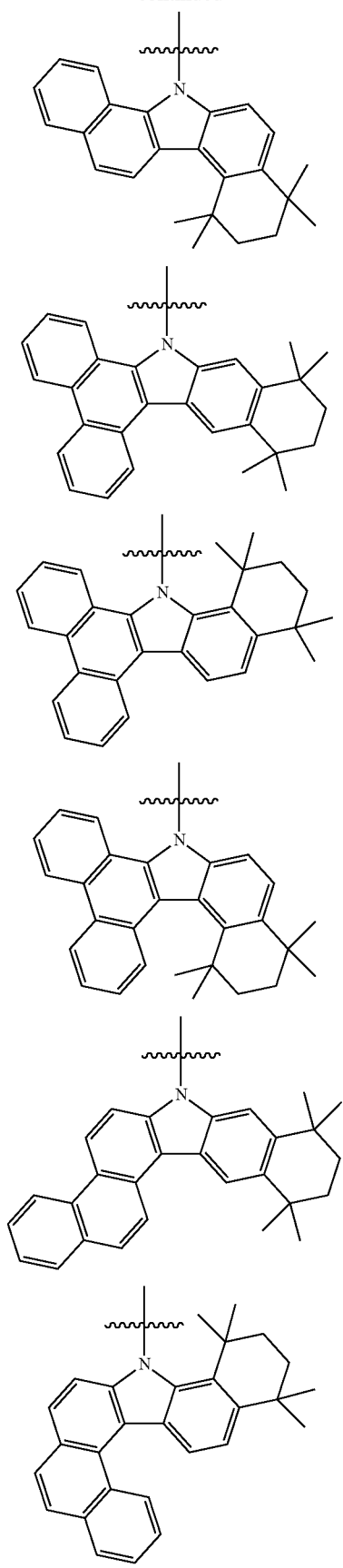

-continued

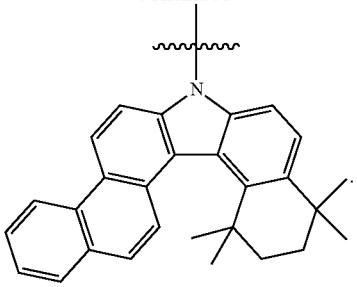

In some embodiments, Het is 6- to 16-membered nitrogen-containing heteroarylene, and at least two nitrogen atoms are included in the Het group, for example, 2, 3 or 4 nitrogen atoms are included in the Het group. In other embodiments of the present disclosure, Het is 6-membered nitrogen-containing heteroarylene, 10-membered nitrogen-containing heteroarylene, or 13-membered nitrogen-containing heteroarylene, and at least two nitrogen atoms are included in the Het group.

In some embodiments, Het is 6- to 18-membered electron-deficient nitrogen-containing heteroaryl (also referred to as electron-deficient heteroaryl), and at least two nitrogen atoms are included in the Het group. An $sp^2$ hybridized nitrogen atom on the Het can reduce the electron cloud density of a conjugated system of the heteroaryl as a whole, instead of increasing the electron cloud density of the conjugated system of the heteroaryl, lone pair electrons on a heteroatom does not participate in the conjugated system, and the heteroatom decreases the electron cloud density of the conjugated system due to the stronger electronegativity. For example, electron-deficient nitrogen-containing heteroaryl may include, but is not limited to, triazinyl, pyrimidinyl, quinolyl, quinoxalinyl, quinazolinyl, isoquinolyl, benzimidazolyl, benzothiazolyl, benzoxazolyl, phenanthrolinyl, benzoquinazolinyl, phenanthroimidazolyl, benzofuropyrimidinyl, benzothienopyrimidinyl, and the like. The Het group may form an electron transport core group of the compound, so that the compound can effectively achieve electron transport and then can effectively balance the mobility of electrons and holes in an organic luminescent layer. Thus, the compound can not only be used as a bipolar host material for the organic luminescent layer to simultaneously transport electrons and holes, and can also be used as an electron-type host material for the organic luminescent layer to cooperate with a hole-type host material for the organic luminescent layer.

In some embodiments, Het is selected from the group consisting of:

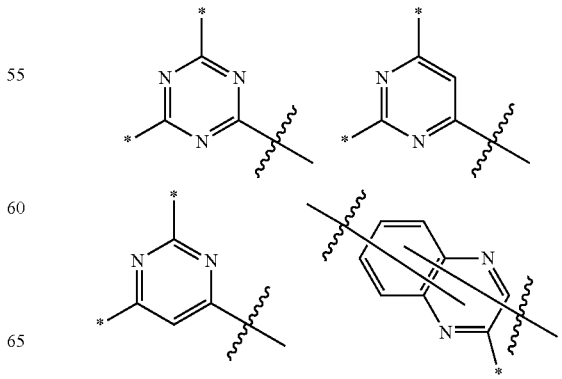

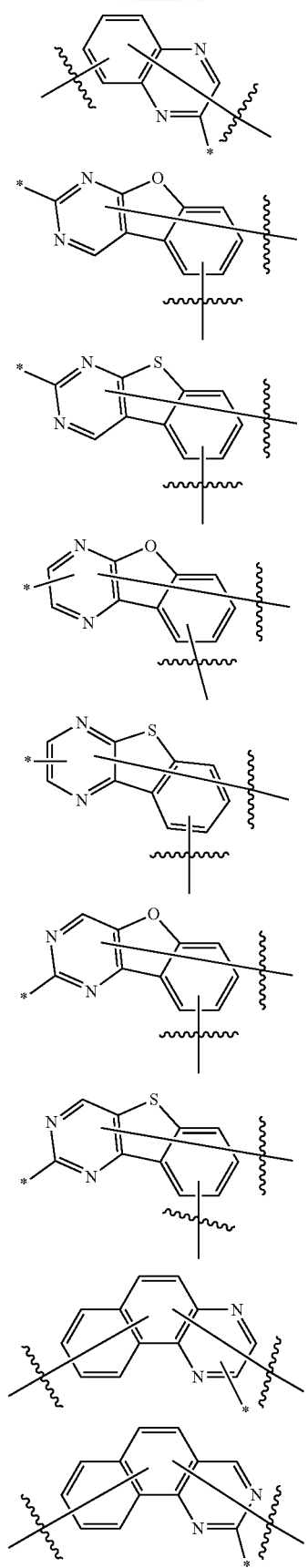
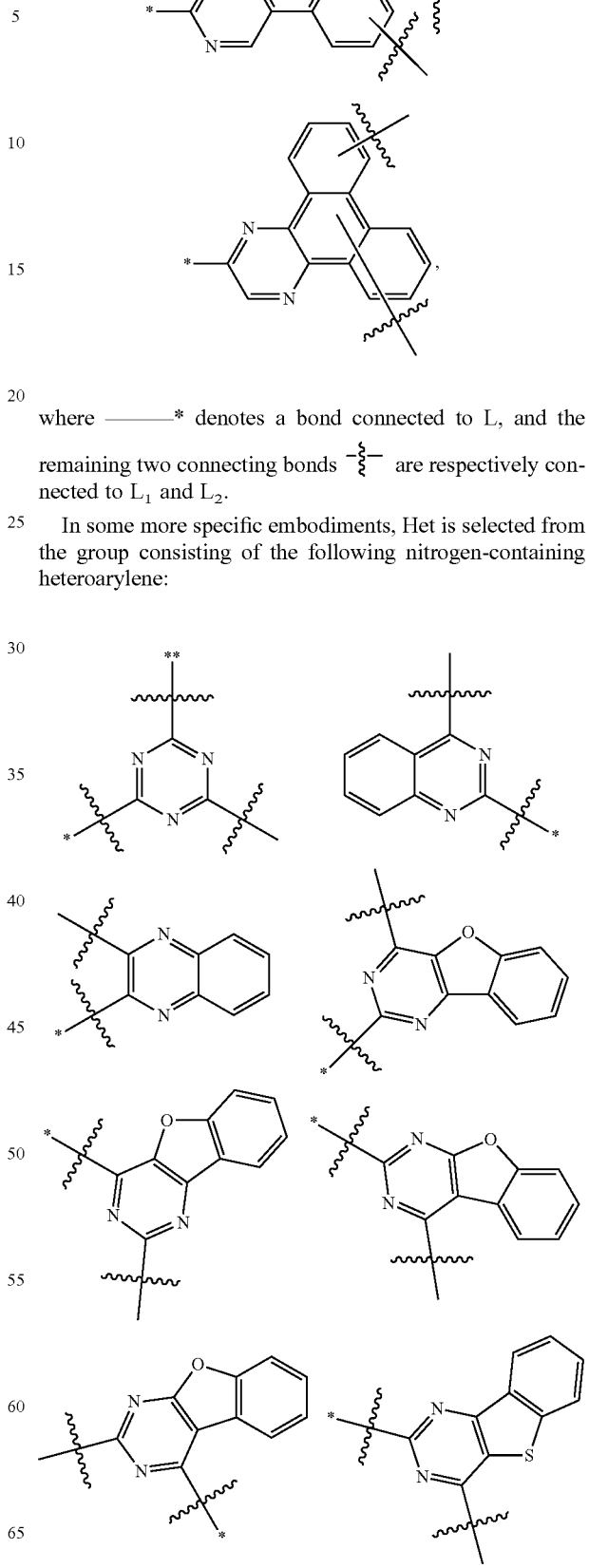
where ——* denotes a bond connected to L, and the remaining two connecting bonds -ξ- are respectively connected to $L_1$ and $L_2$.
In some more specific embodiments, Het is selected from the group consisting of the following nitrogen-containing heteroarylene:

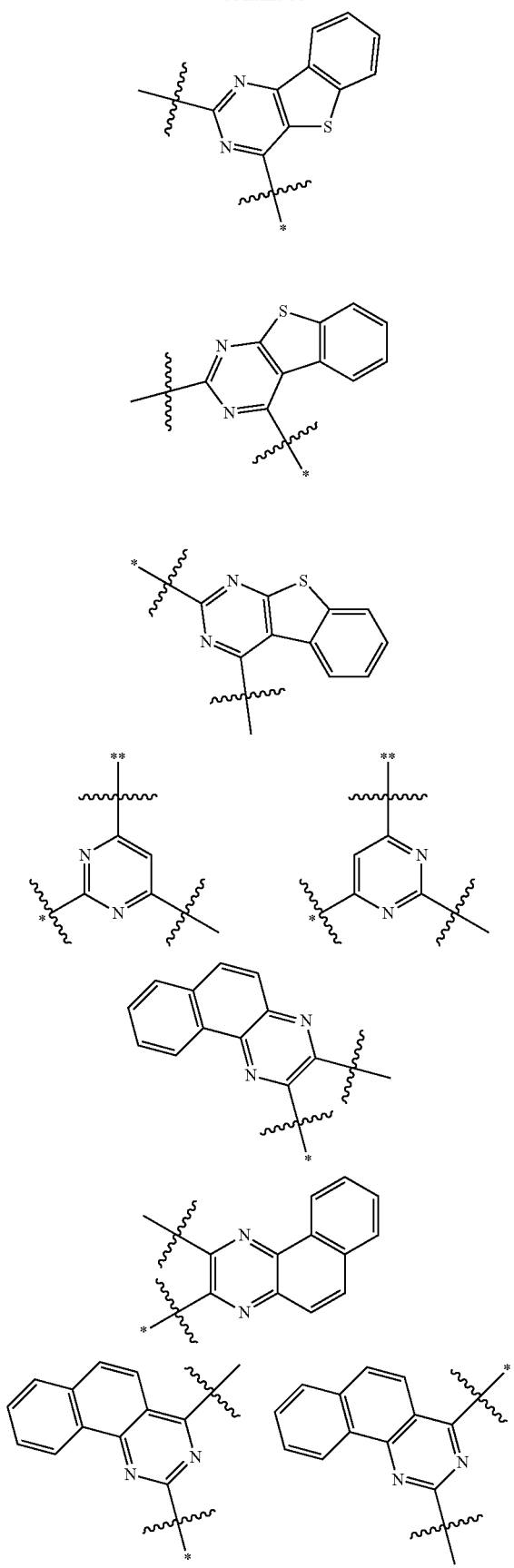
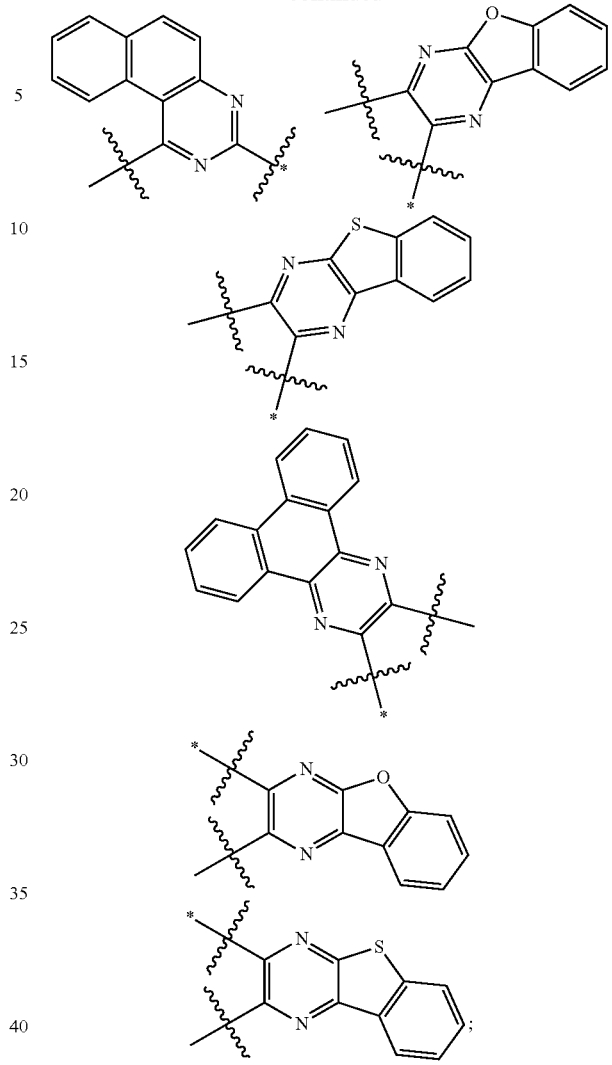

where **⁻§⁻ denotes a position where Het is connected to L, ⁻§⁻ denotes a position where Het is connected to L₁, *⁻§⁻ denotes a position that is connected to L₂, and where *⁻§⁻ is absent in the formula means that L₂ is a single bond and Ar₂ is hydrogen in

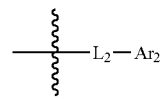

connected at this position.

In some embodiments, each $R_1$ is the same or different from each other, and is independently selected from deuterium, fluorine, cyano, trimethylsilyl, trideuteromethyl, trifluoromethyl, cyclopentyl, cyclohexyl, methyl, ethyl, isopropyl, tert-butyl, or phenyl; and $n_1$ represents the number of $R_1$, and $n_1$ is selected from 0, 1, 2, 3 or 4.

In some embodiments, $Ar_1$ is selected from substituted or unsubstituted aryl with 6 to 25 carbon atoms, and substituted or unsubstituted heteroaryl with 12 to 18 carbon atoms; and Ar$_2$ is selected from hydrogen, substituted or unsubstituted aryl with 6 to 25 carbon atoms, and substituted or unsubstituted heteroaryl with 12 to 18 carbon atoms.

In some embodiments, substituents in Ar$_1$ and Ar$_2$ are the same or different, and are each independently selected from deuterium, halogen, cyano, haloalkyl with 1 to 4 carbon atoms, deuteroalkyl with 1 to 4 carbon atoms, alkyl with 1 to 4 carbon atoms, cycloalkyl with 5 to 10 carbon atoms, aryl with 6 to 12 carbon atoms, heteroaryl with 5 to 12 carbon atoms, and trialkylsilyl with 3 to 8 carbon atoms, and optionally, any two adjacent substituents form a fluorene ring.

In some embodiments, Ar$_1$ is selected from substituted or unsubstituted aryl with 6, 7, 8, 9, 10, 11, 12, 13, 14, 15, 16, 17, 18, 19, 20, 21, 22, 23, 24 or 25 carbon atoms, and substituted or unsubstituted heteroaryl with 12, 13, 14, 15, 16, 17, or 18 carbon atoms.

In some embodiments, Ar$_2$ is selected from hydrogen, substituted or unsubstituted aryl with 6, 7, 8, 9, 10, 11, 12, 13, 14, 15, 16, 17, 18, 19, 20, 21, 22, 23, 24 or 25 carbon atoms, and substituted or unsubstituted heteroaryl with 12, 13, 14, 15, 16, 17, or 18 carbon atoms.

In some embodiments, Ar$_1$ is selected from a substituted or unsubstituted group W, and Ar$_2$ is selected from hydrogen, and a substituted or unsubstituted group W, where the unsubstituted group W is selected from the group consisting of:

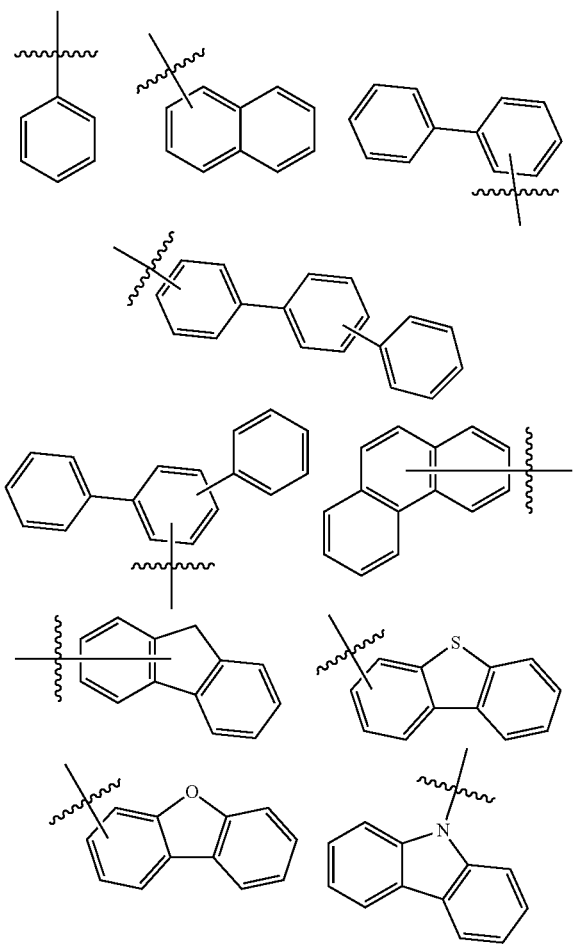

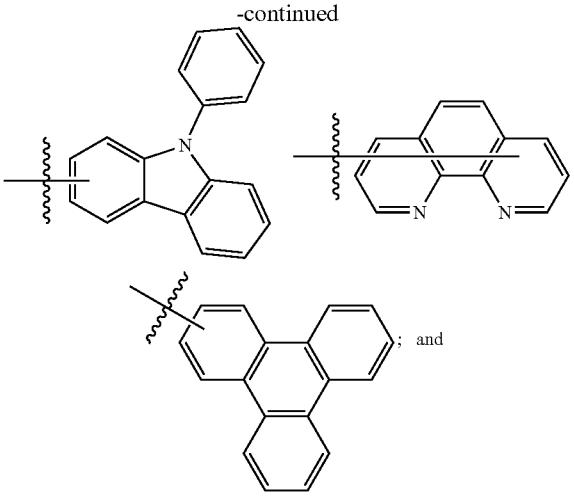

the substituted group W has one or two or more substituents, the substituents in the substituted group W are each independently selected from deuterium, fluorine, cyano, trideuteromethyl, trimethylsilyl, trifluoromethyl, cyclopentyl, cyclohexyl, adamantyl, methyl, ethyl, isopropyl, tert-butyl, phenyl, naphthyl, pyridyl, dibenzofuranyl, dibenzothienyl or carbazolyl, and when the number of the substituents on the group W is greater than 1, the substituents are the same or different. It should be noted that when Ar$_1$ and Ar$_2$ are both selected from the substituted or unsubstituted group W, Ar$_1$ and Ar$_2$ may be the same or different, i.e., Ar$_1$ and Ar$_2$ are each independently selected from the substituted or unsubstituted group W without affecting each other.

In some embodiments, Ar$_1$ is selected from substituted or unsubstituted phenyl, substituted or unsubstituted naphthyl, substituted or unsubstituted biphenyl, substituted or unsubstituted terphenyl, substituted or unsubstituted fluorenyl, substituted or unsubstituted phenanthryl, substituted or unsubstituted dibenzofuranyl, substituted or unsubstituted dibenzothienyl, substituted or unsubstituted carbazolyl, substituted or unsubstituted spirobifluorenyl, substituted or unsubstituted triphenylene, and substituted or unsubstituted phenanthrolinyl.

In some embodiments, Ar$_2$ is selected from hydrogen, substituted or unsubstituted phenyl, substituted or unsubstituted naphthyl, substituted or unsubstituted biphenyl, substituted or unsubstituted terphenyl, substituted or unsubstituted fluorenyl, substituted or unsubstituted phenanthryl, substituted or unsubstituted dibenzofuranyl, substituted or unsubstituted dibenzothienyl, substituted or unsubstituted carbazolyl, substituted or unsubstituted spirobifluorenyl, substituted or unsubstituted triphenylene, and substituted or unsubstituted phenanthrolinyl.

Optionally, substituents in Ar$_1$ and Ar$_2$ are the same or different, and are each independently selected from deuterium, fluorine, cyano, trimethylsilyl, triphenylsilyl, trideuteromethyl, trifluoromethyl, cyclopentyl, cyclohexyl, methyl, ethyl, isopropyl, tert-butyl, phenyl, naphthyl, biphenyl, pyridyl, dibenzofuranyl, dibenzothienyl or carbazolyl.

In some embodiments, Ar$_1$ is selected from the group consisting of the following groups, and Ar$_2$ is selected from hydrogen or the group consisting of the following groups:

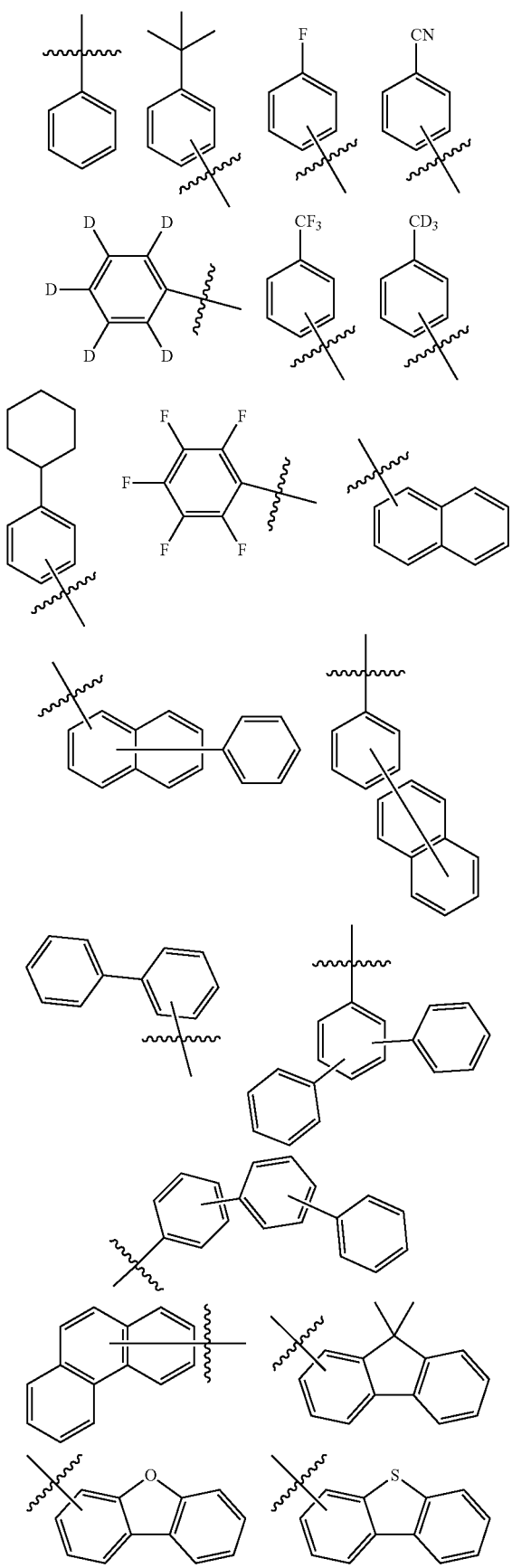
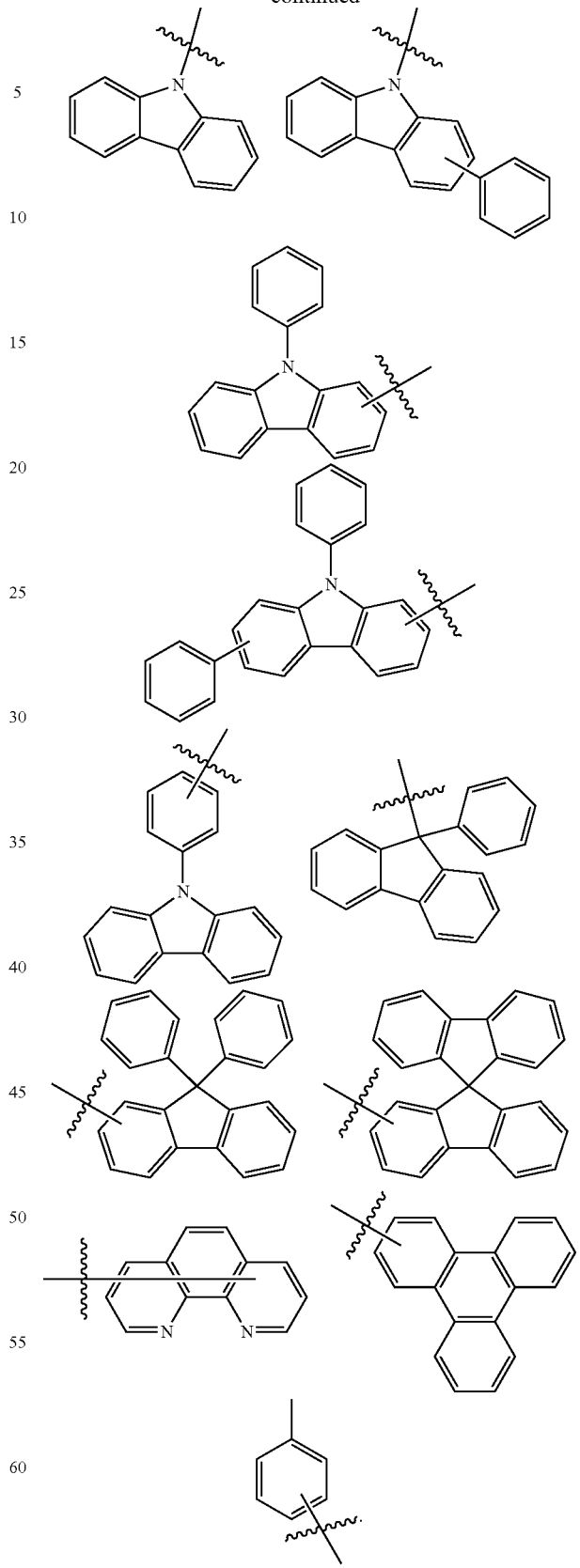
In some more specific embodiments, Ani is selected from the group consisting of,

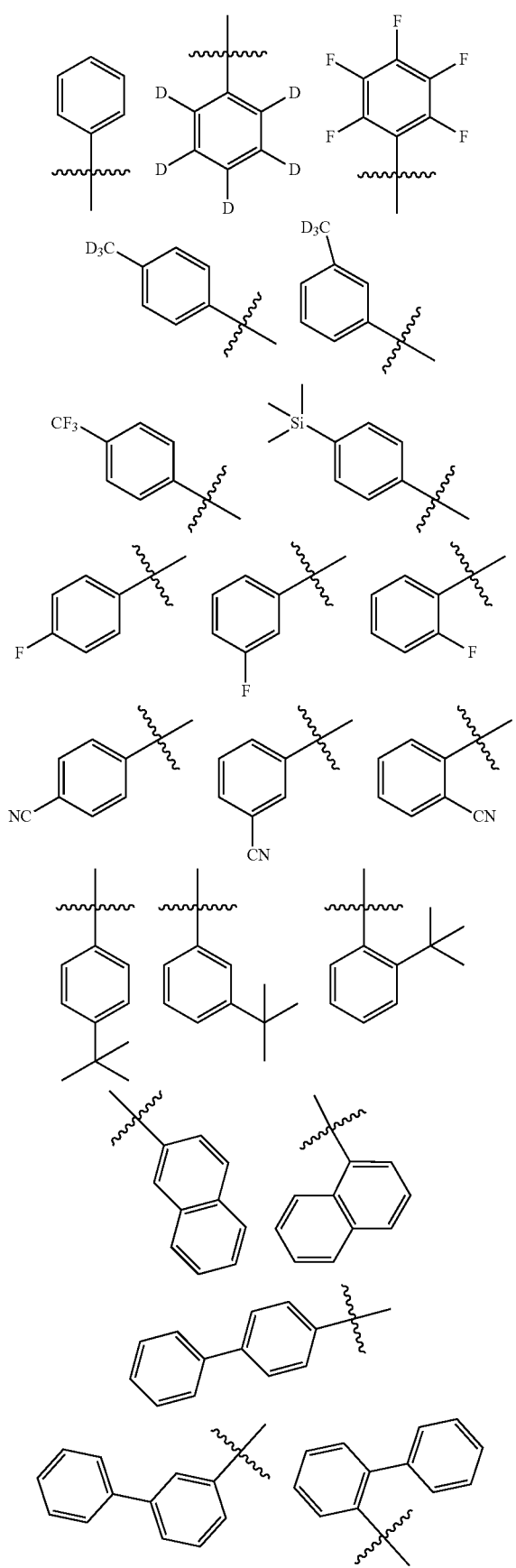
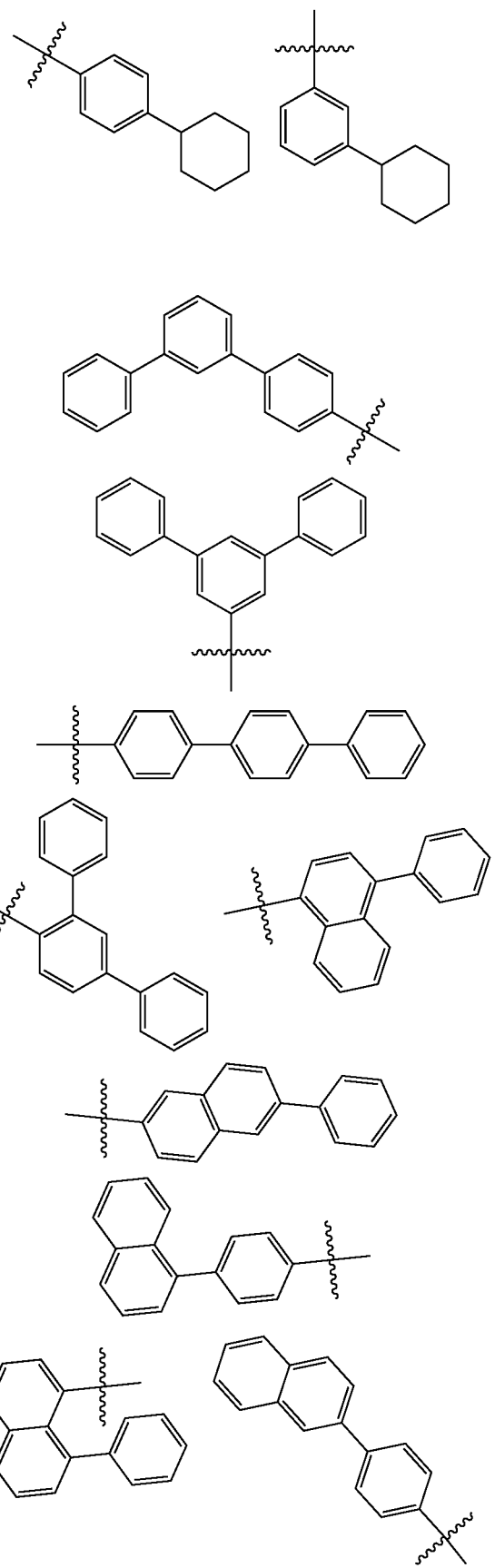

27
-continued
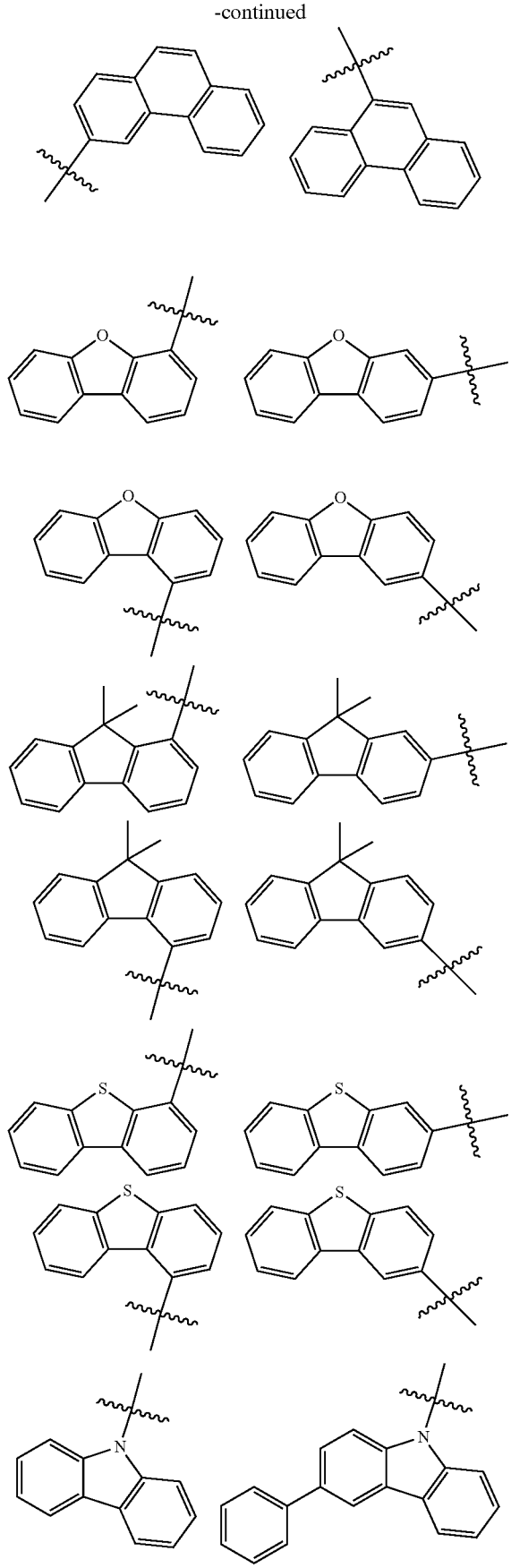
28
-continued
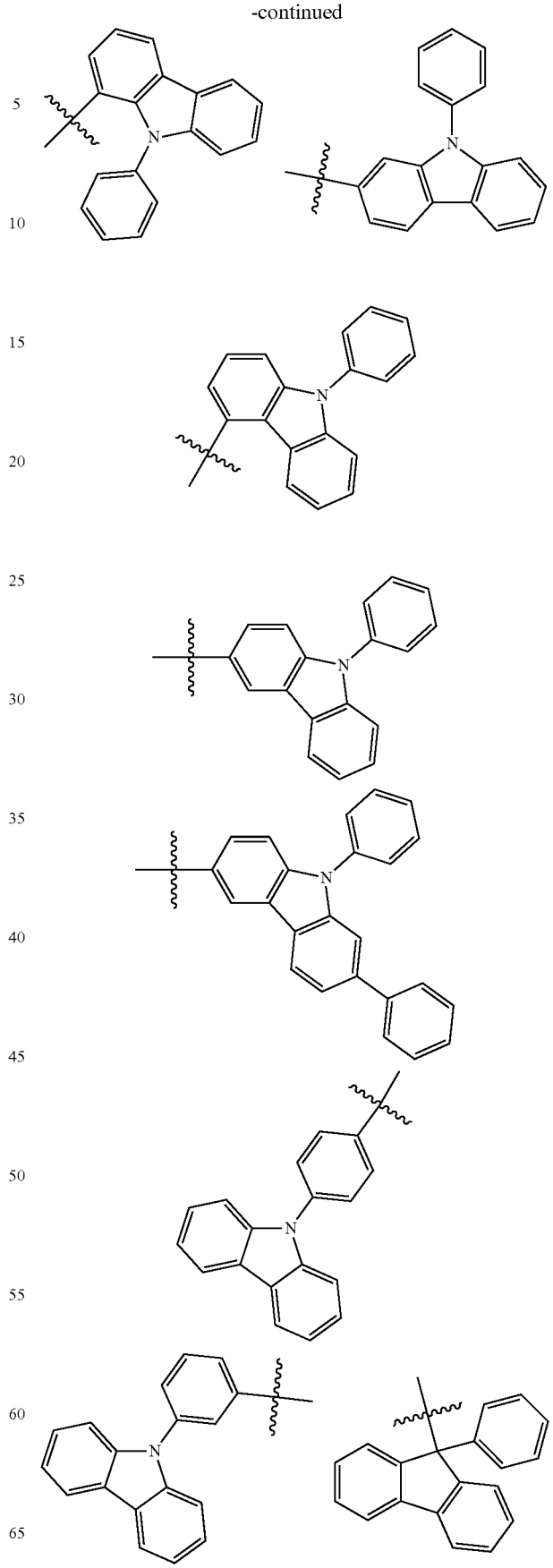

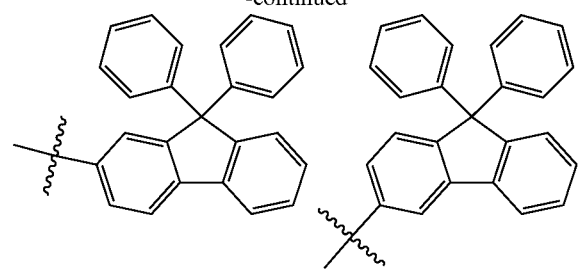
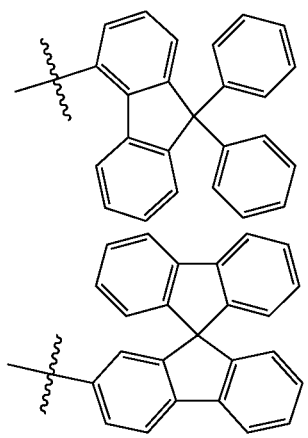
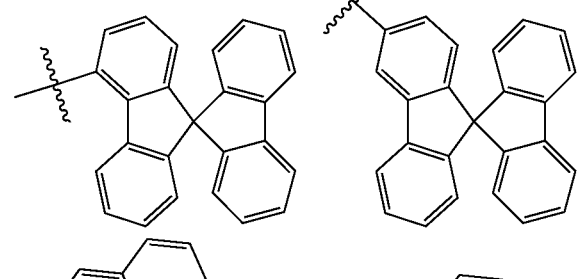
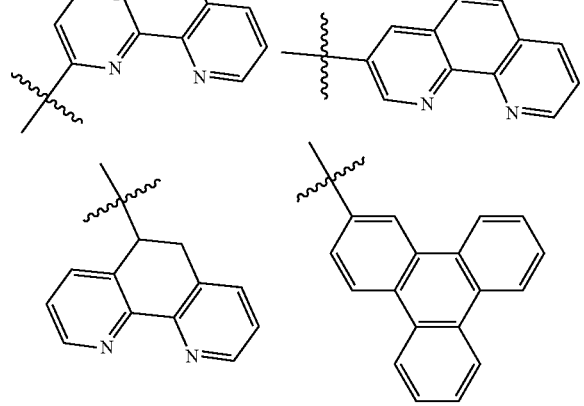
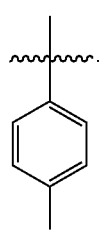
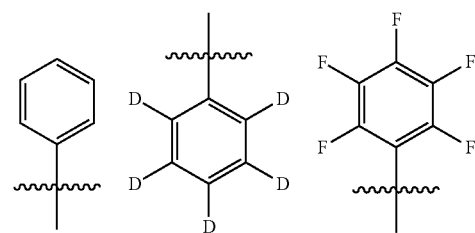
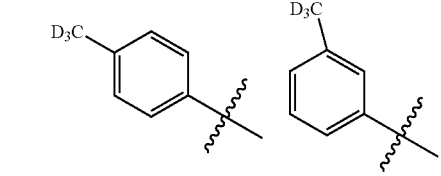
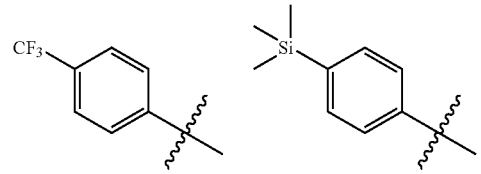
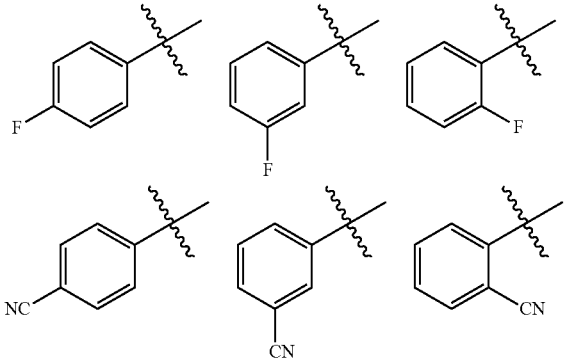
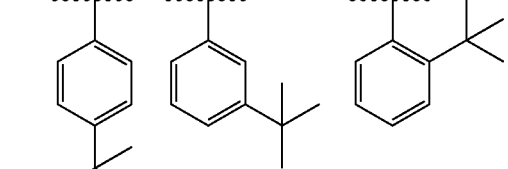
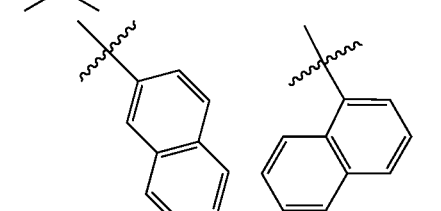
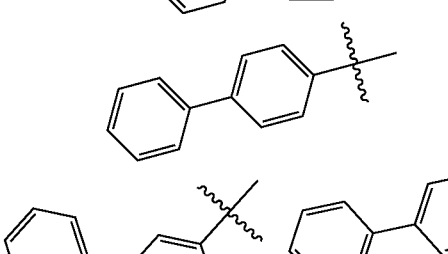
In some more specific embodiments, Ara is selected from hydrogen or the group consisting of:

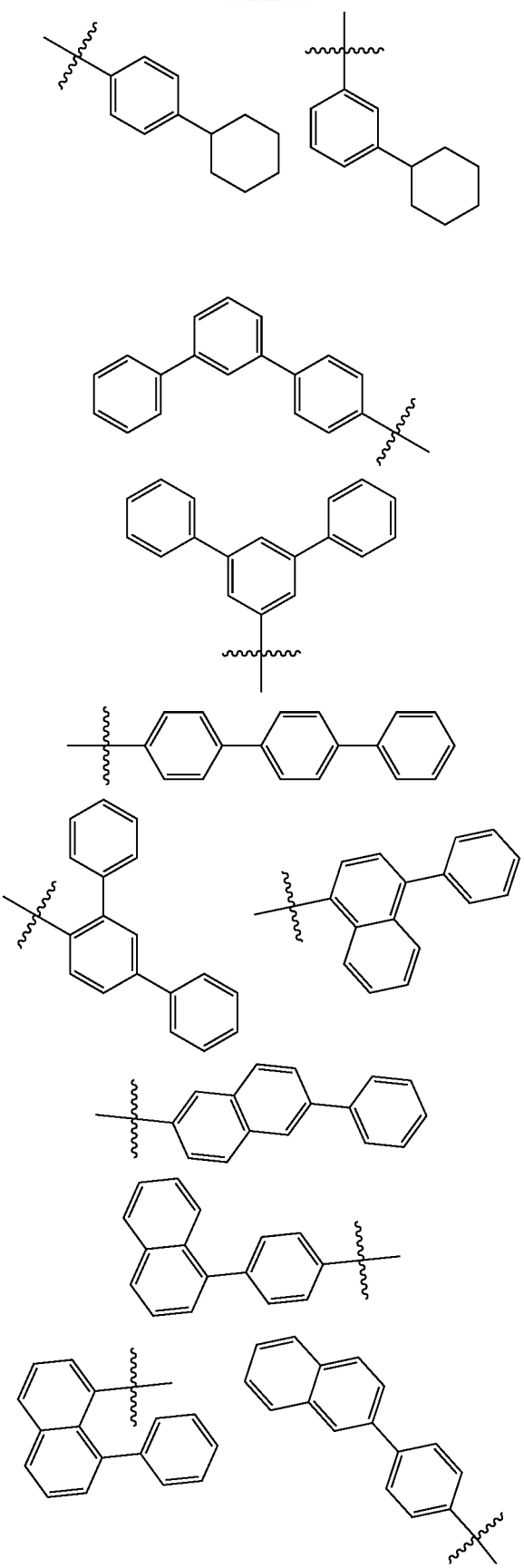
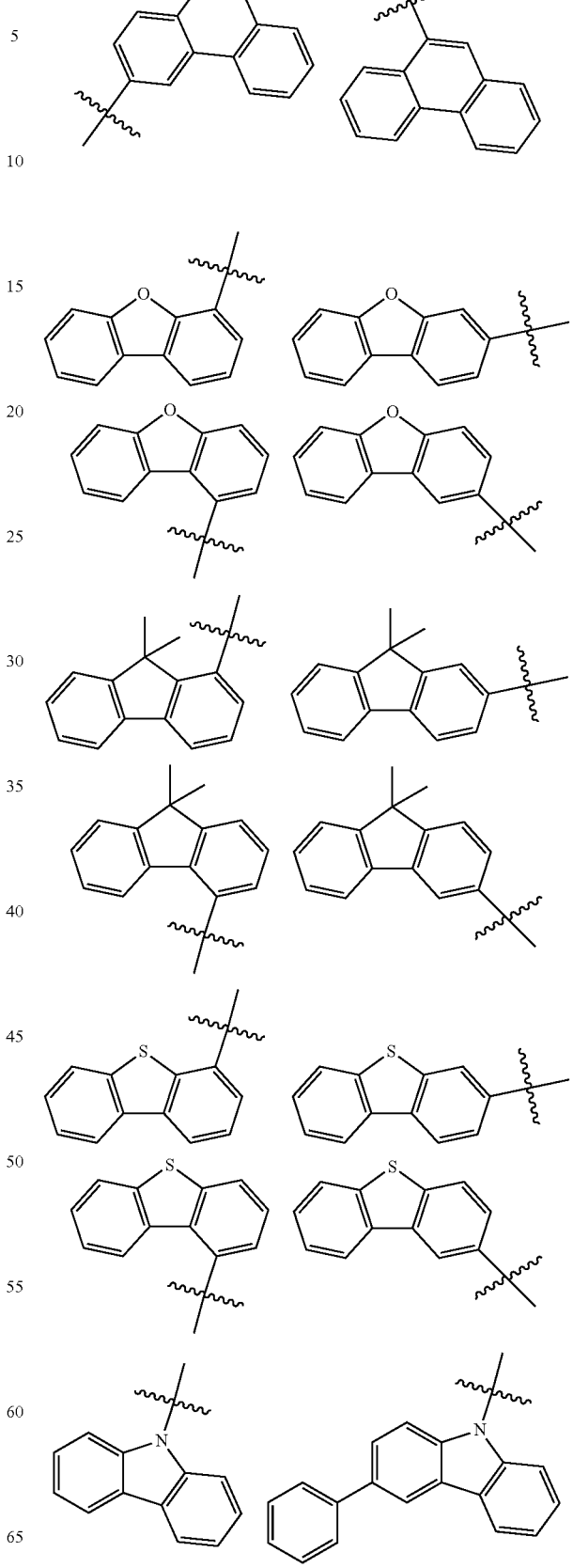

-continued
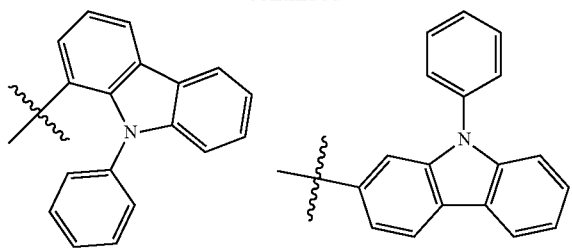
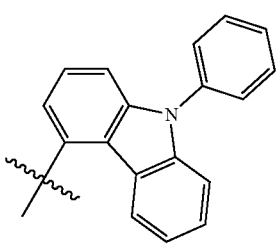
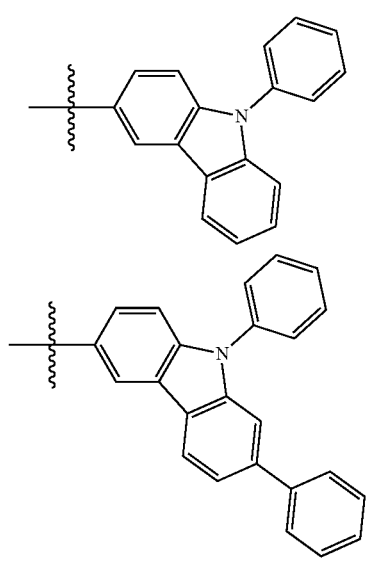
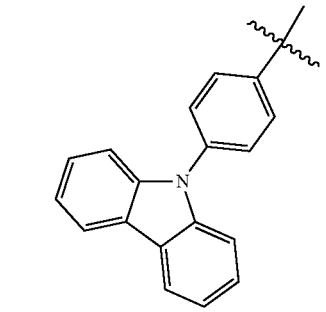
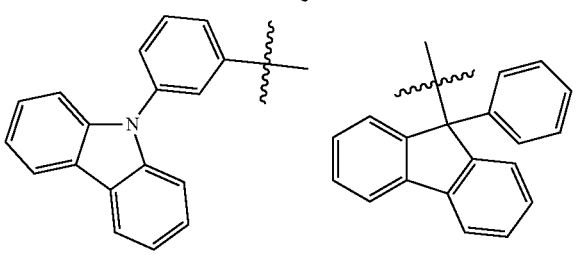
-continued
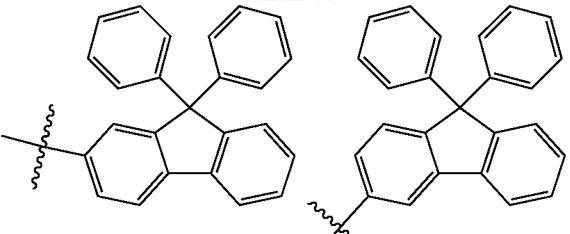
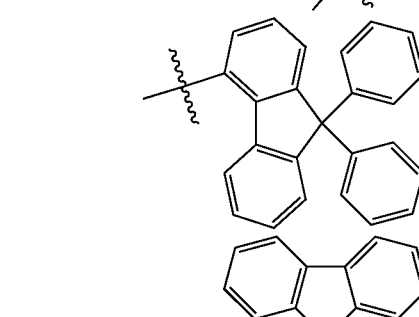
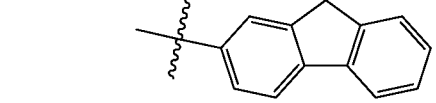
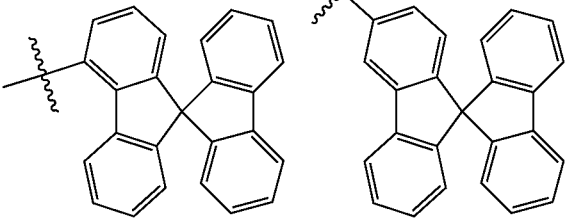
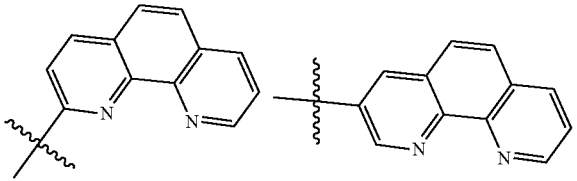
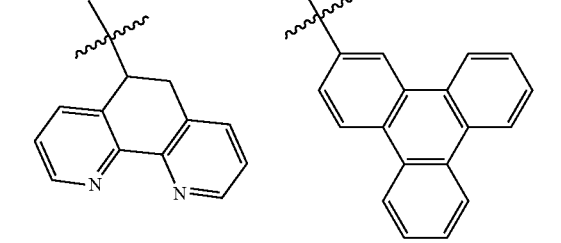
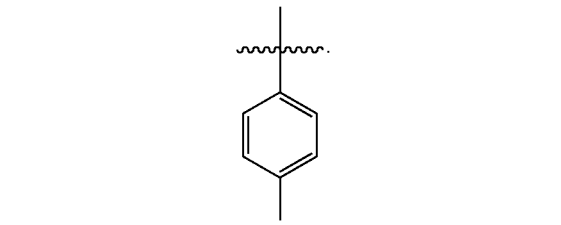 [SMILES: *c1ccc(C)cc1]
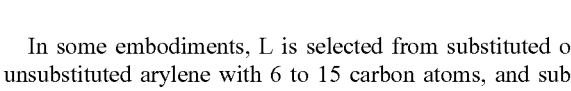
In some embodiments, L is selected from substituted or unsubstituted arylene with 6 to 15 carbon atoms, and substituted or unsubstituted heteroarylene with 5 to 12 carbon atoms; and $L_1$ and $L_2$ are each independently selected from a single bond, substituted or unsubstituted arylene with 6 to 15 carbon atoms, and substituted or unsubstituted heteroarylene with 12 to 18 carbon atoms.

In some embodiments, L is selected from substituted or unsubstituted arylene with 6, 10, or 12 carbon atoms, and substituted or unsubstituted heteroarylene with 12 carbon atoms.

In some embodiments, $L_1$ and $L_2$ are each independently selected from a single bond, substituted or unsubstituted arylene with 6, 10, 12, 14, 15, or 18 carbon atoms, and substituted or unsubstituted heteroarylene with 12 or 18 carbon atoms.

Optionally, substituents in $L_1$, $L_2$ and L are each independently selected from deuterium, fluorine, cyano, alkyl with 1 to 5 carbon atoms, trialkylsilyl with 3 to 8 carbon atoms, fluoroalkyl with 1 to 4 carbon atoms, deuteroalkyl with 1 to 4 carbon atoms, phenyl or naphthyl.

In some specific embodiments, L is selected from substituted or unsubstituted phenylene, substituted or unsubstituted naphthylene, substituted or unsubstituted biphenylene, substituted or unsubstituted dibenzothienylene, substituted or unsubstituted dibenzofurylene, and substituted or unsubstituted fluorenylene; and $L_1$ and $L_2$ are each independently selected from a single bond, substituted or unsubstituted phenylene, substituted or unsubstituted naphthylene, substituted or unsubstituted biphenylene, substituted or unsubstituted dibenzothienylene, substituted or unsubstituted dibenzofurylene, substituted or unsubstituted carbazolylene, and substituted or unsubstituted fluorenylene.

Optionally, substituents in $L_1$, $L_2$ and L are the same or different, and are each independently selected from deuterium, fluorine, cyano, methyl, ethyl, isopropyl, tert-butyl, trifluoromethyl, trideuteromethyl, trimethylsilyl or phenyl.

In some embodiments, L is selected from the following groups:

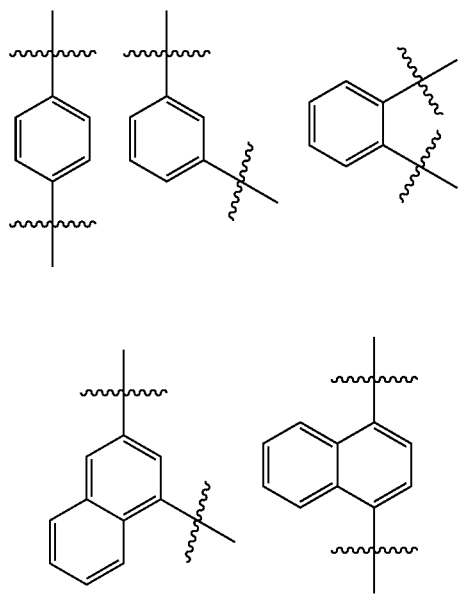

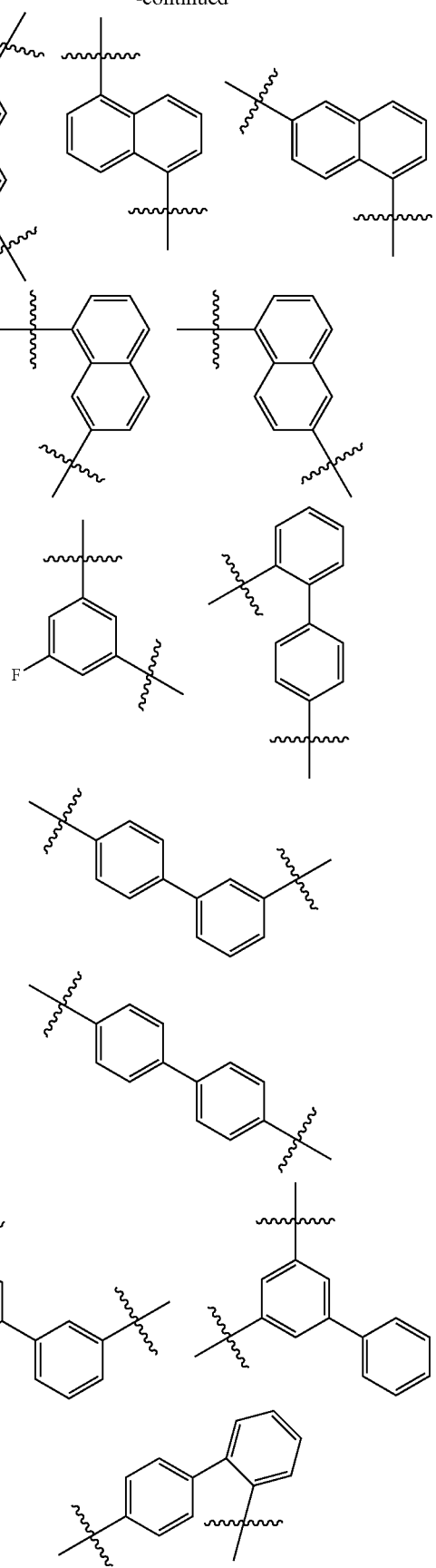

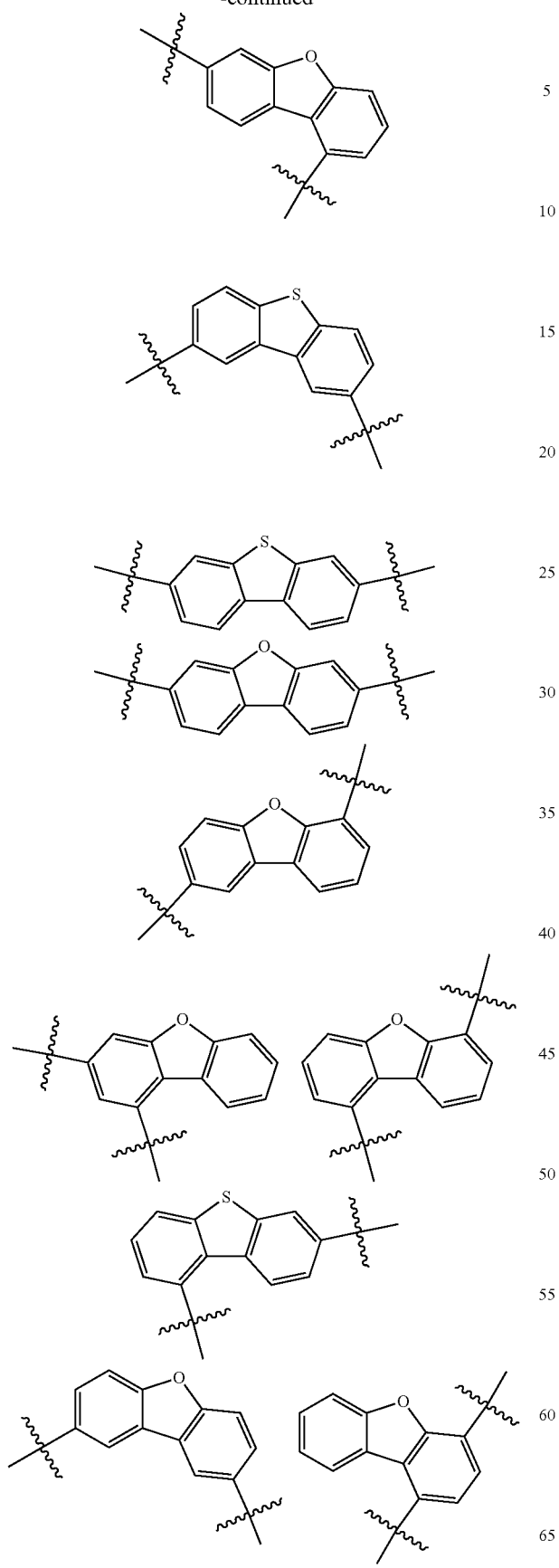
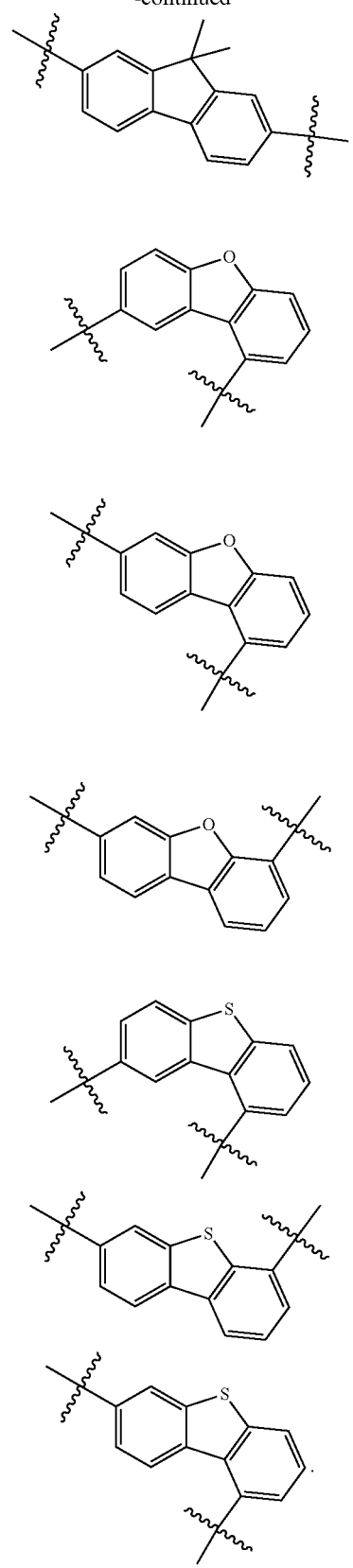
In some embodiments, $L_1$ and $L_2$ are each independently selected from a single bond or the group consisting of:

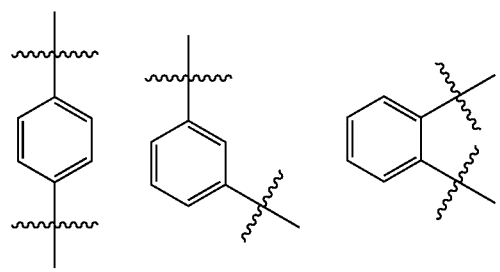
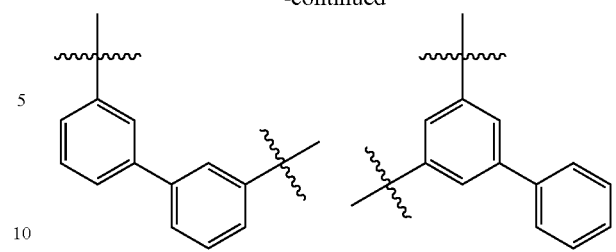
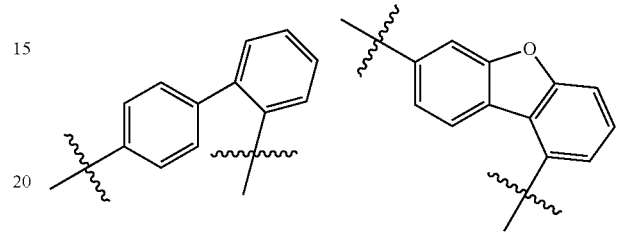
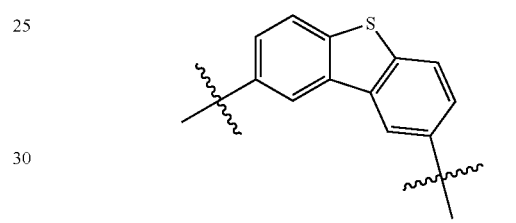
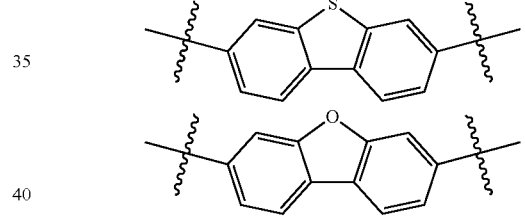
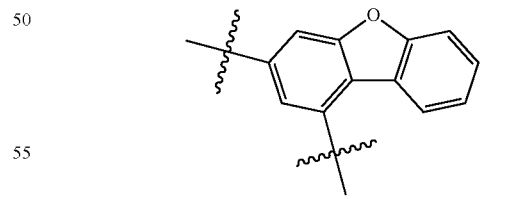
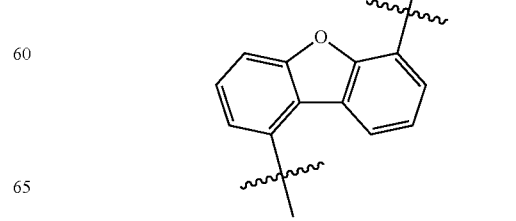

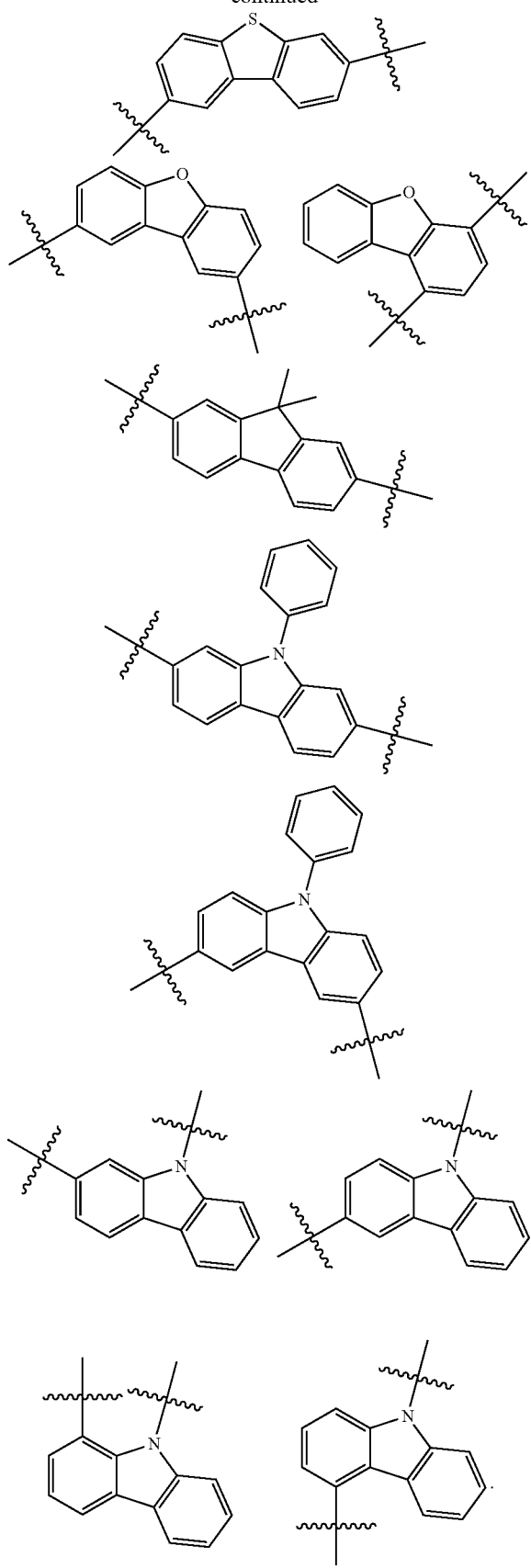
In some embodiments,
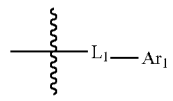
is selected from the group consisting of the following groups, and
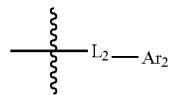
is selected from hydrogen or the group consisting of the following groups:
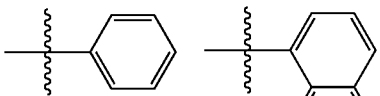
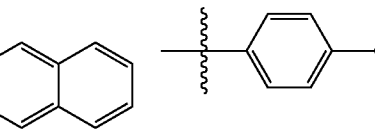
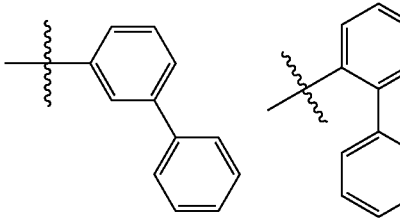
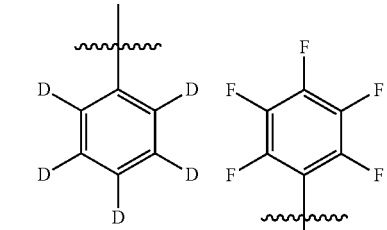
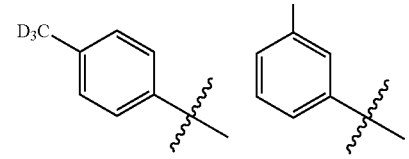
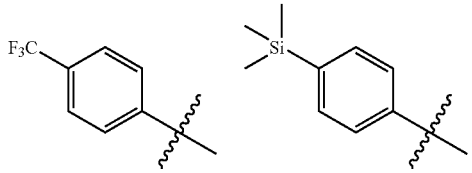

-continued
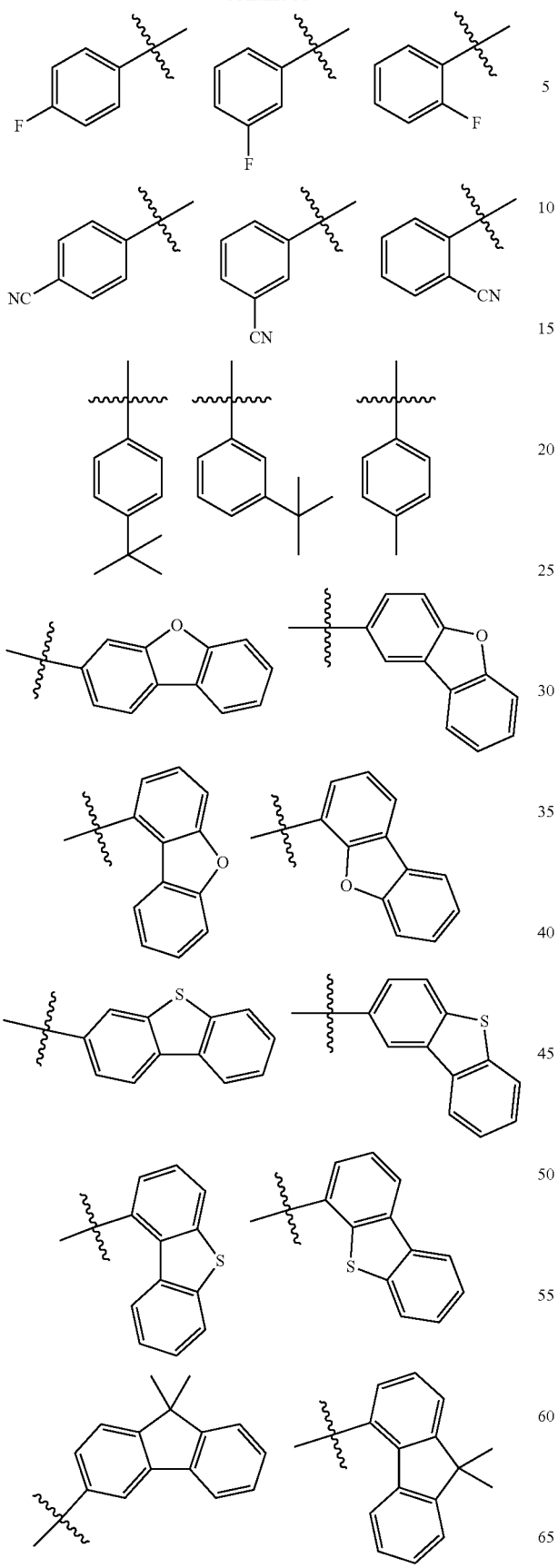
-continued
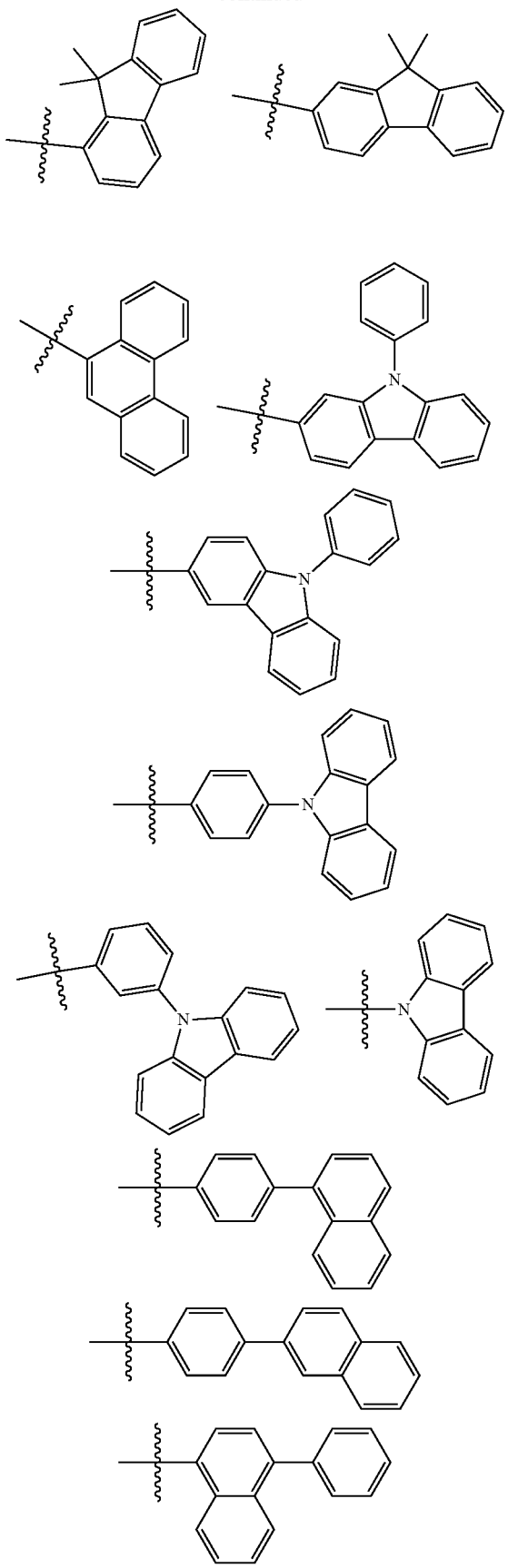

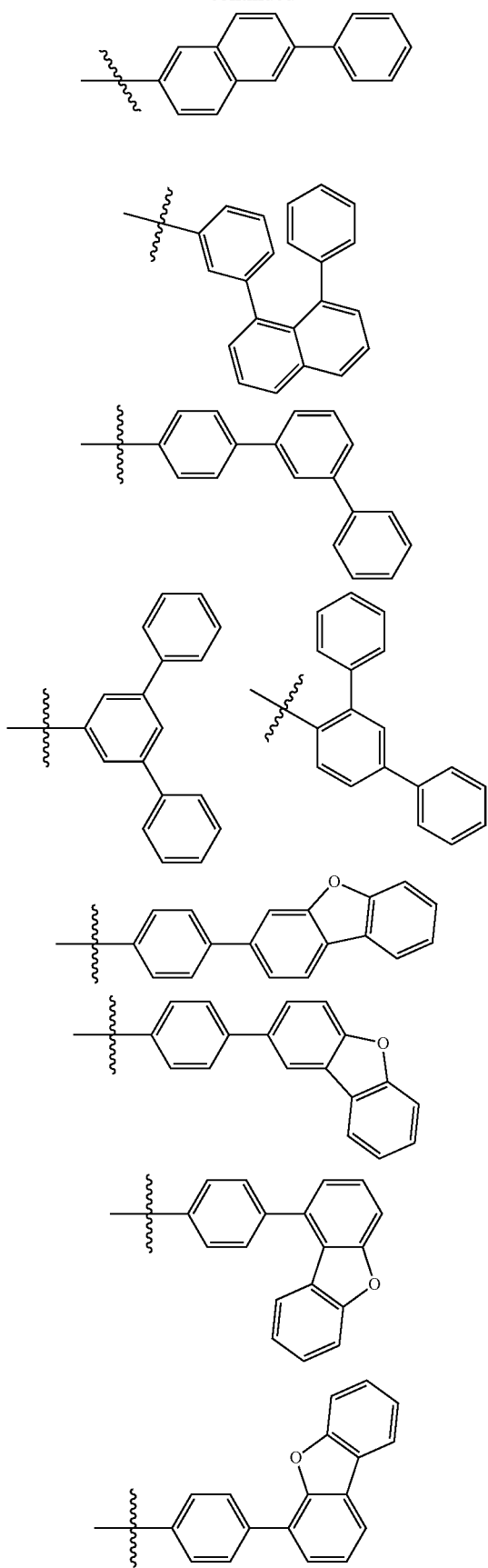

-continued
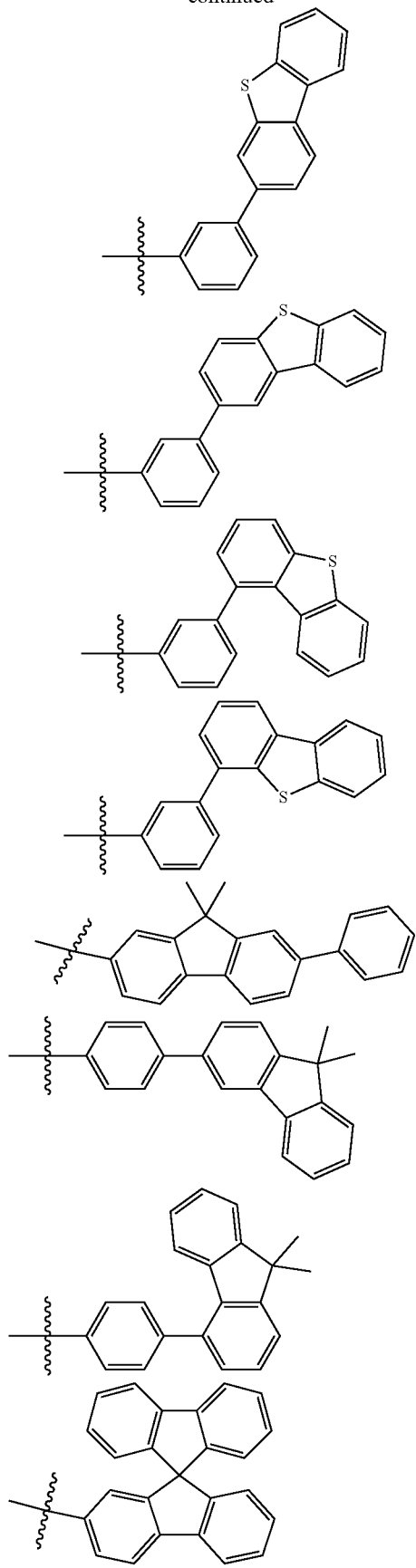
-continued
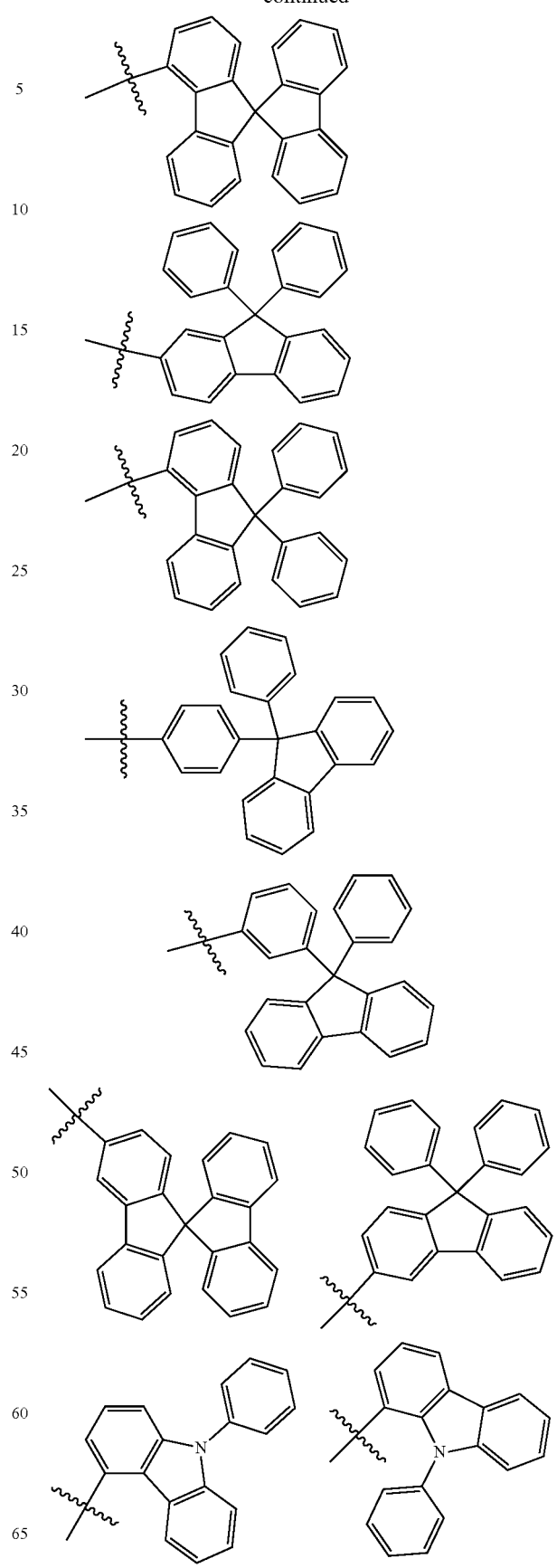

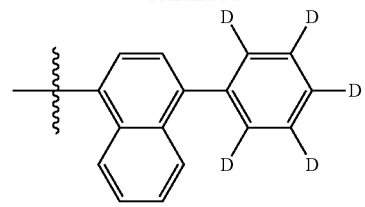
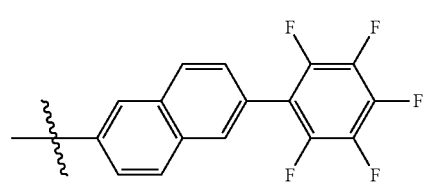
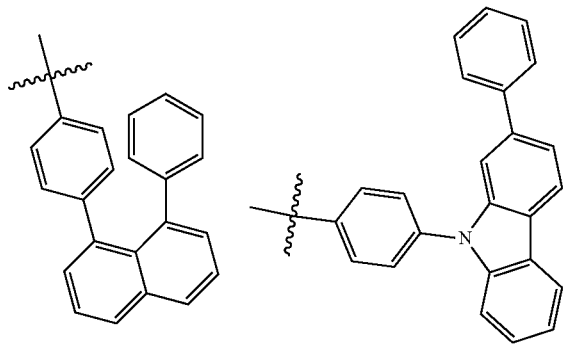
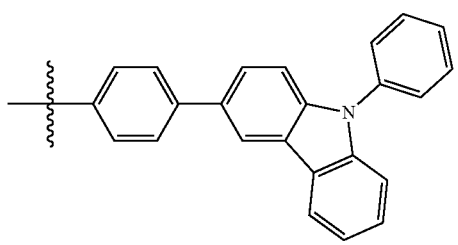
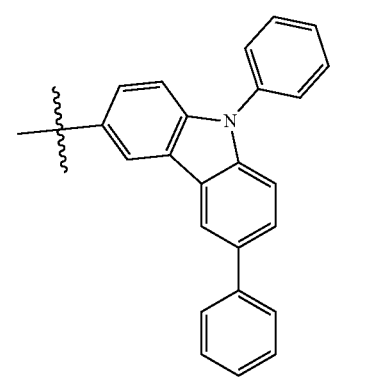
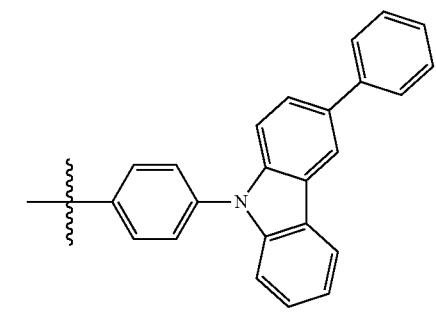
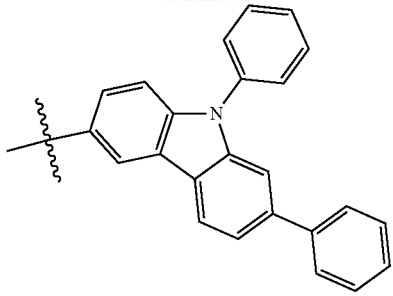
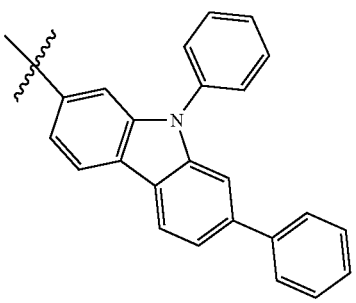
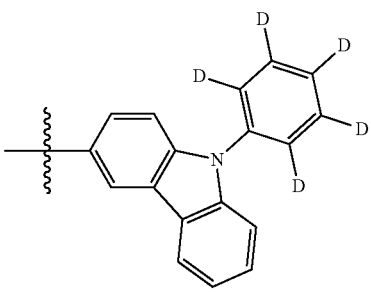
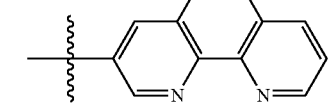
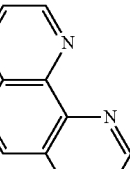
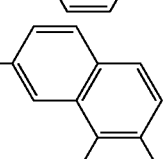
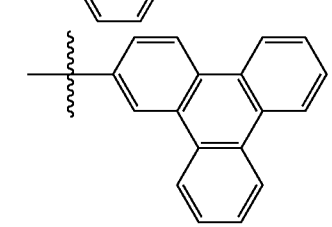

-continued
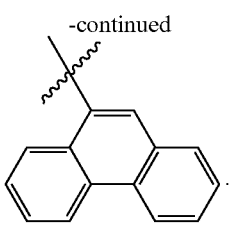
In some embodiments,
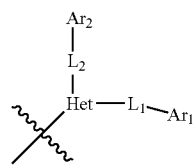
in the nitrogen-containing compound is selected from the group consisting of:
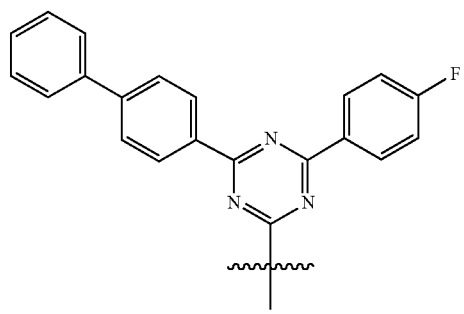
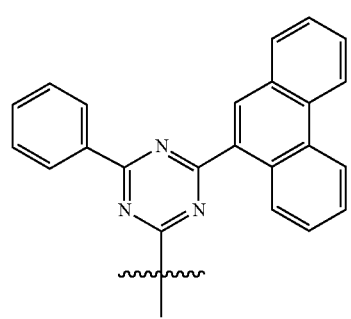
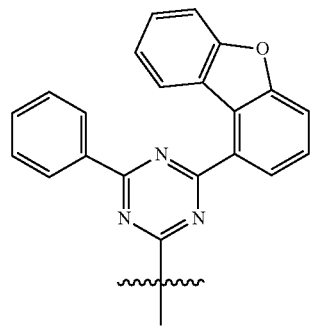
-continued
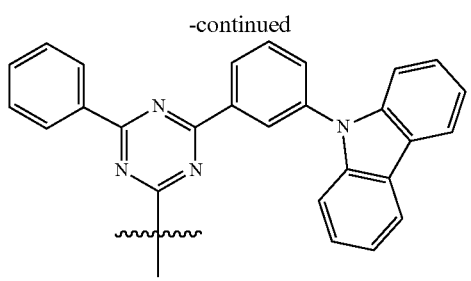
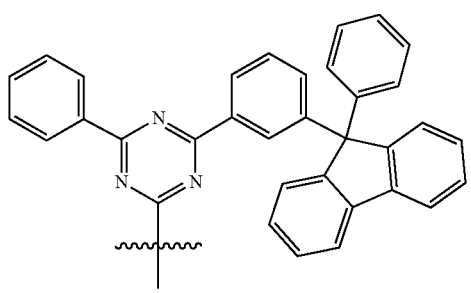
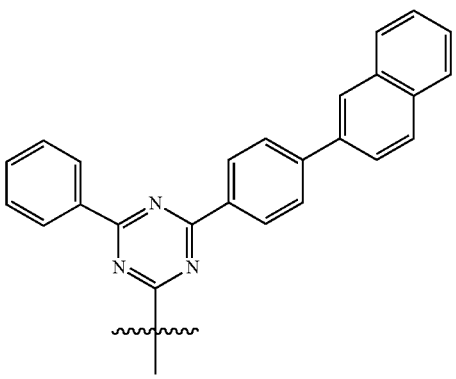
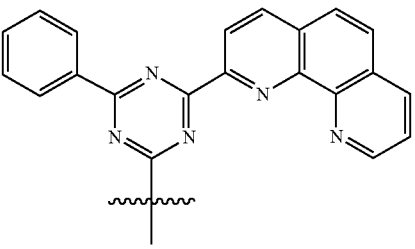
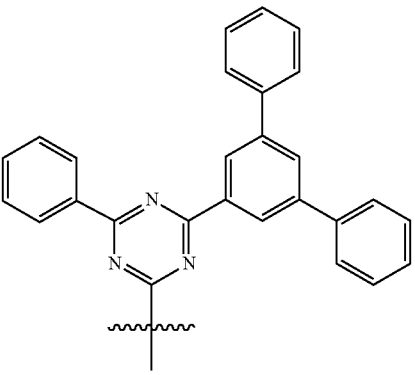

53
-continued
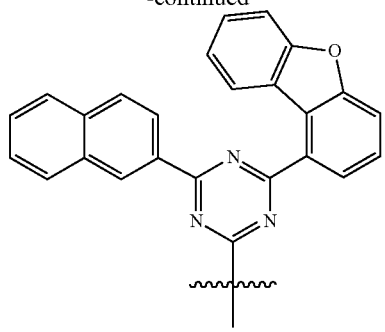
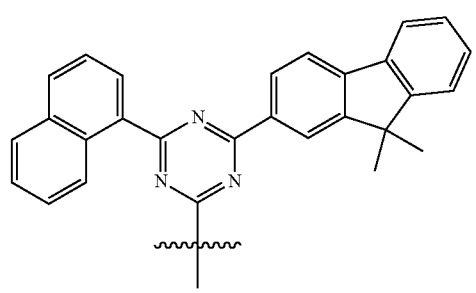
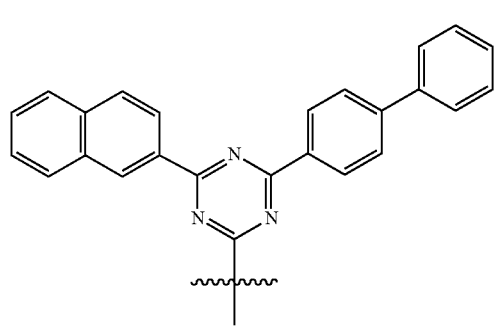
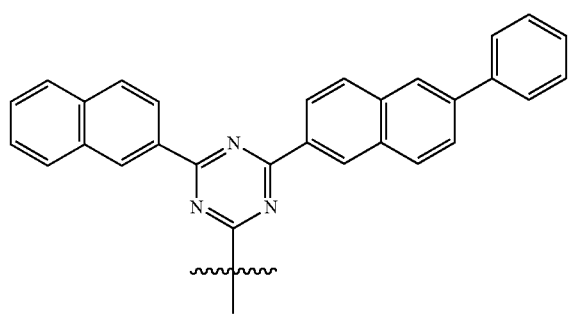
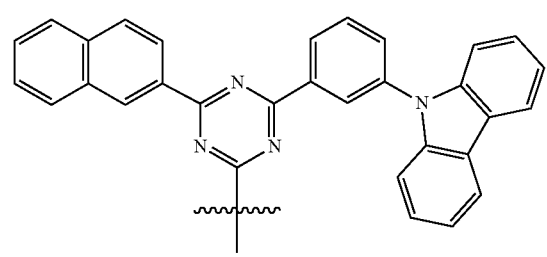
54
-continued
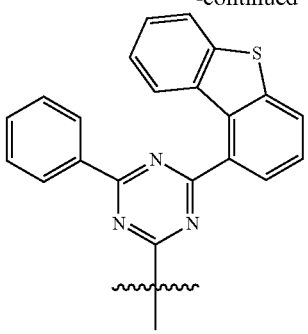
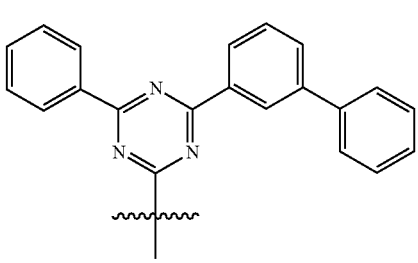
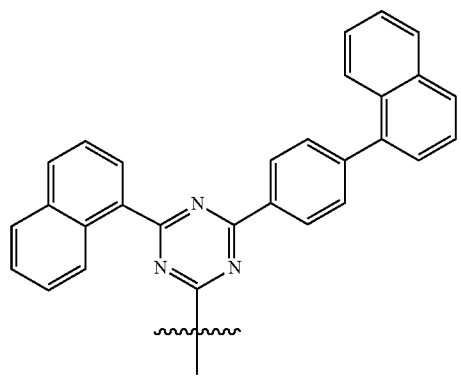
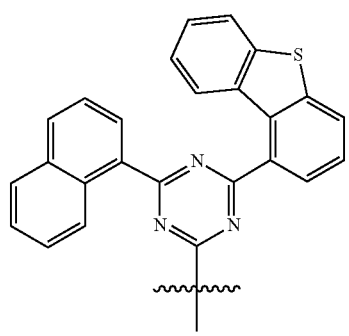
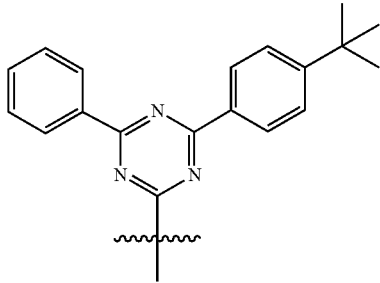

-continued
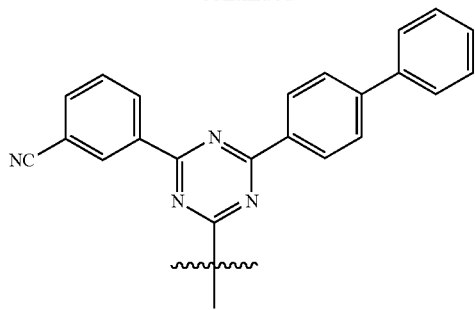
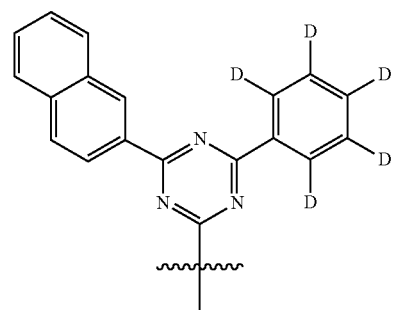
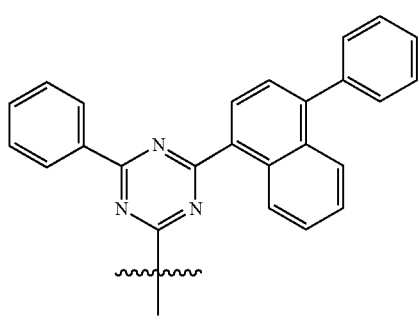
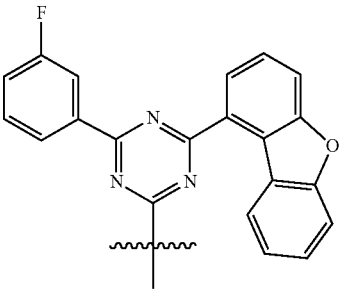
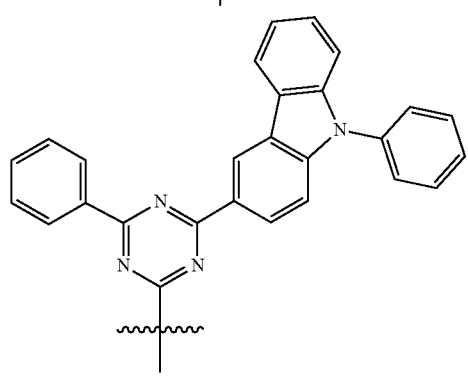
-continued
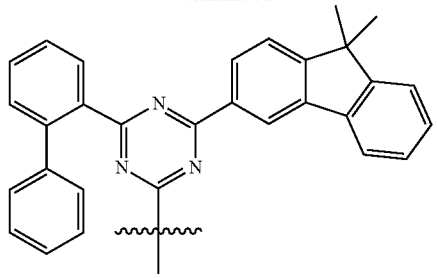
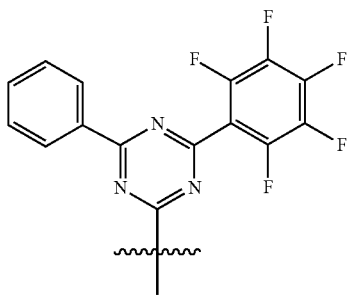
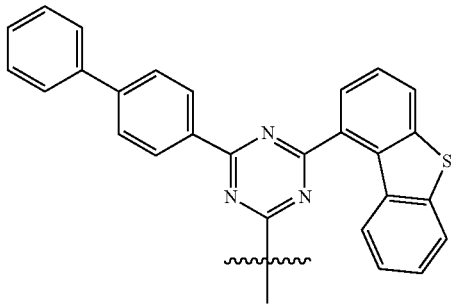
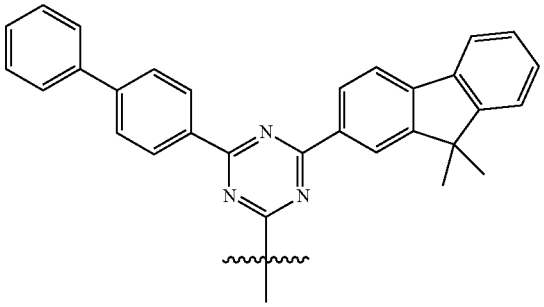
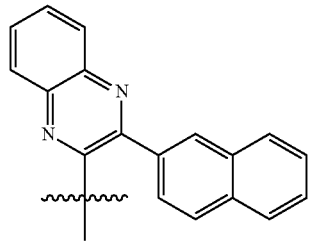
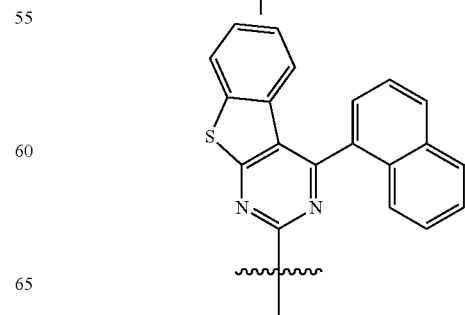

-continued
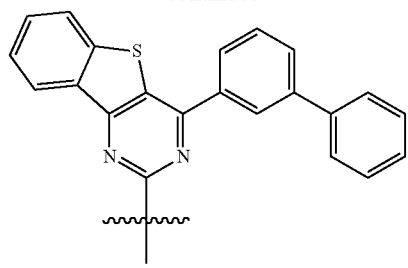
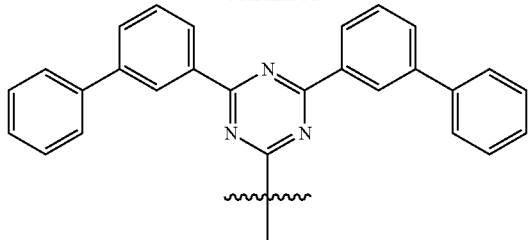
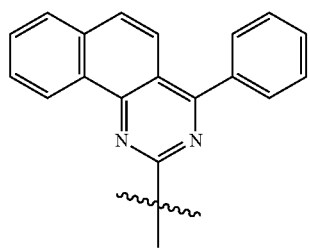
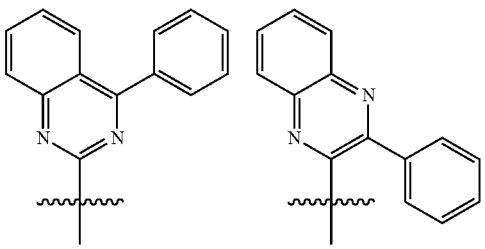
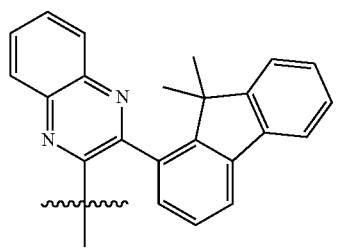
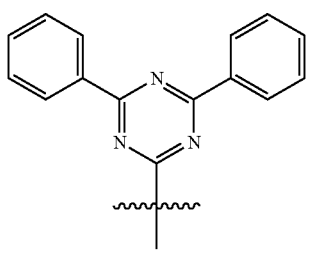
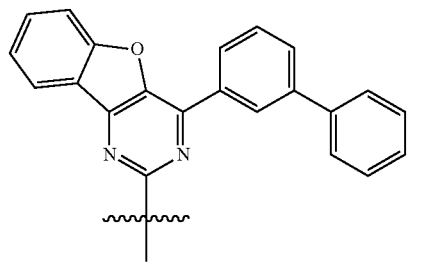
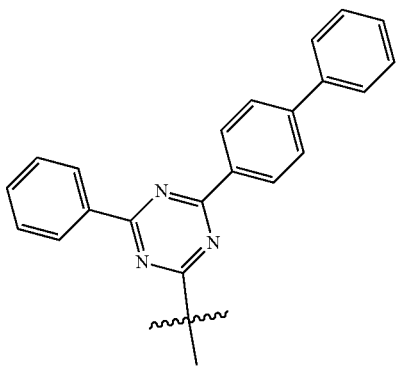
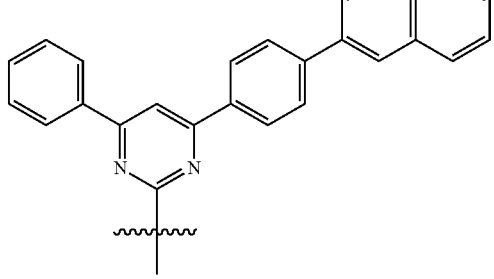
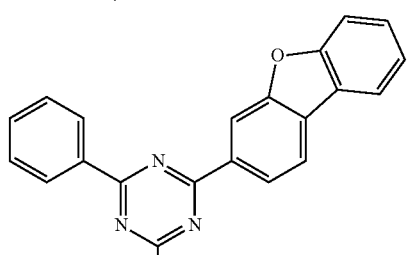
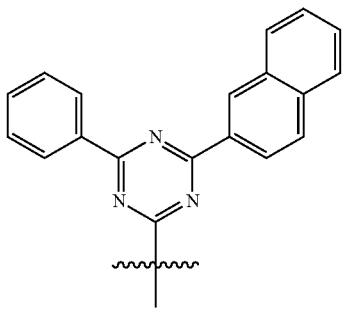
Optionally, the nitrogen-containing compound is selected from the group consisting of the following compounds:

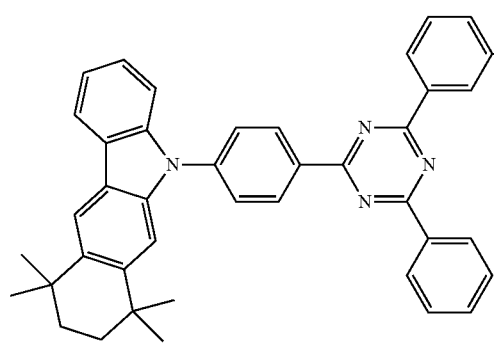
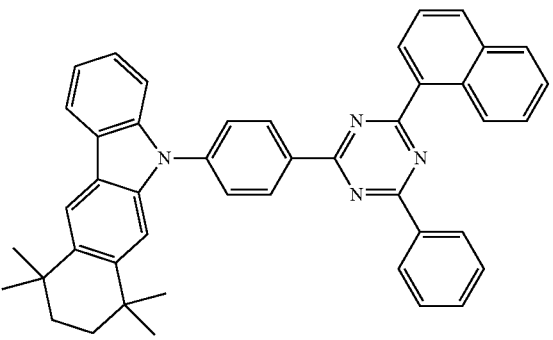
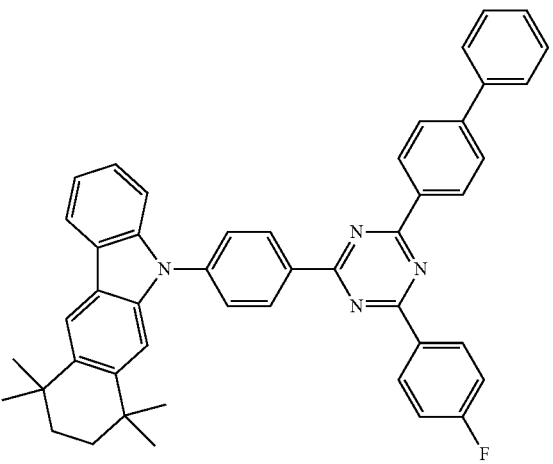
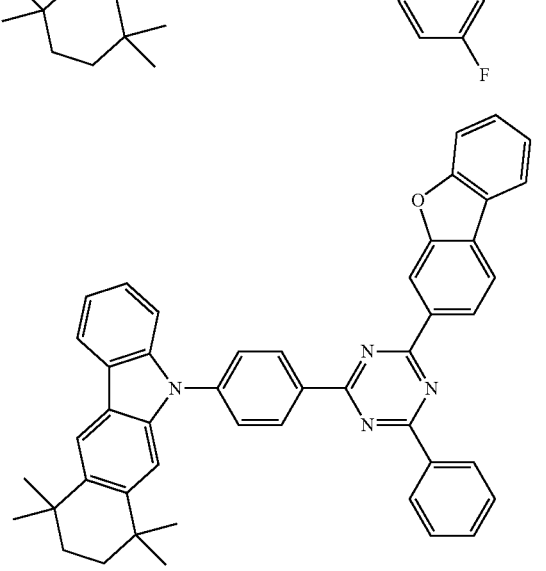
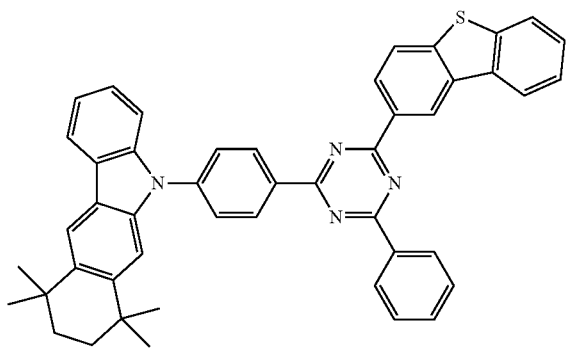

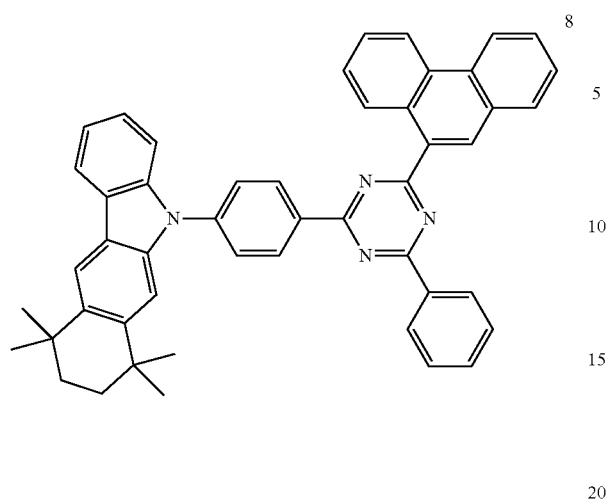
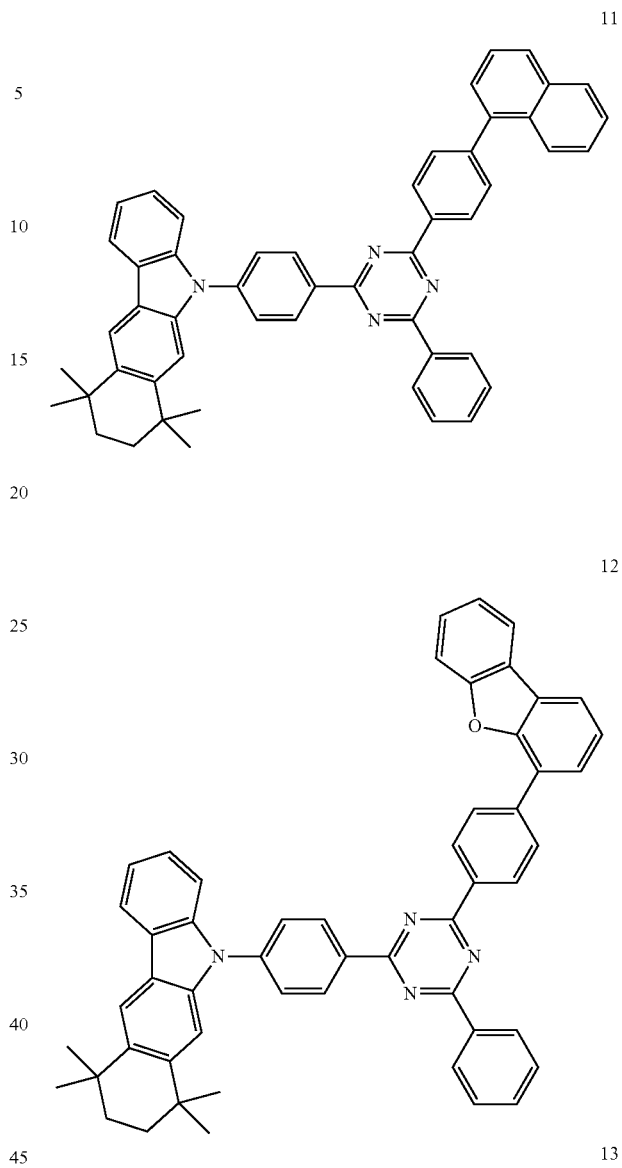
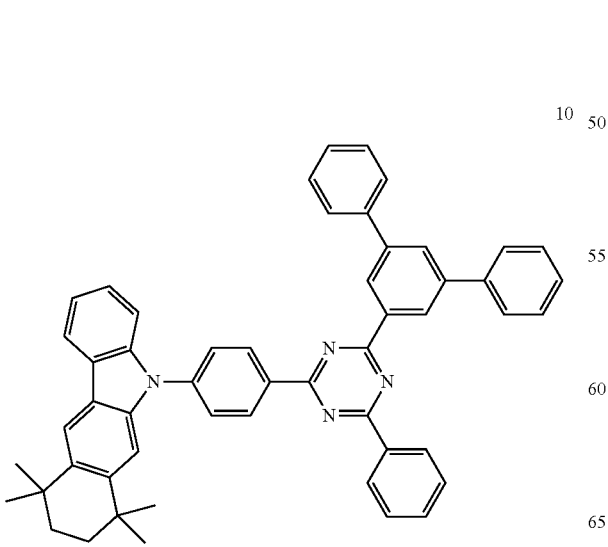

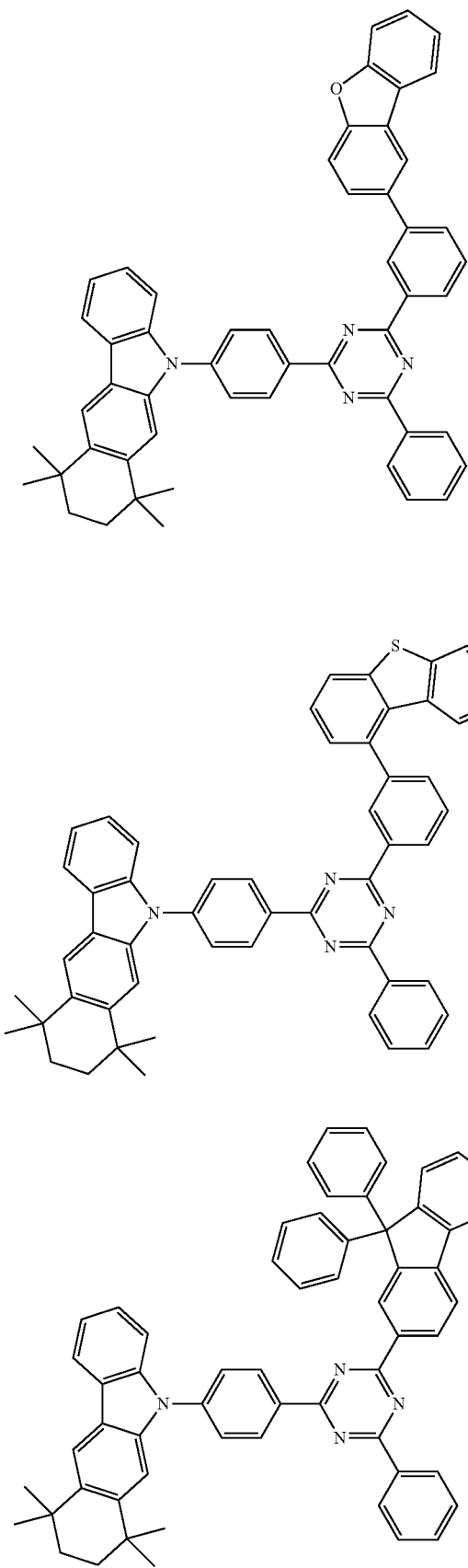
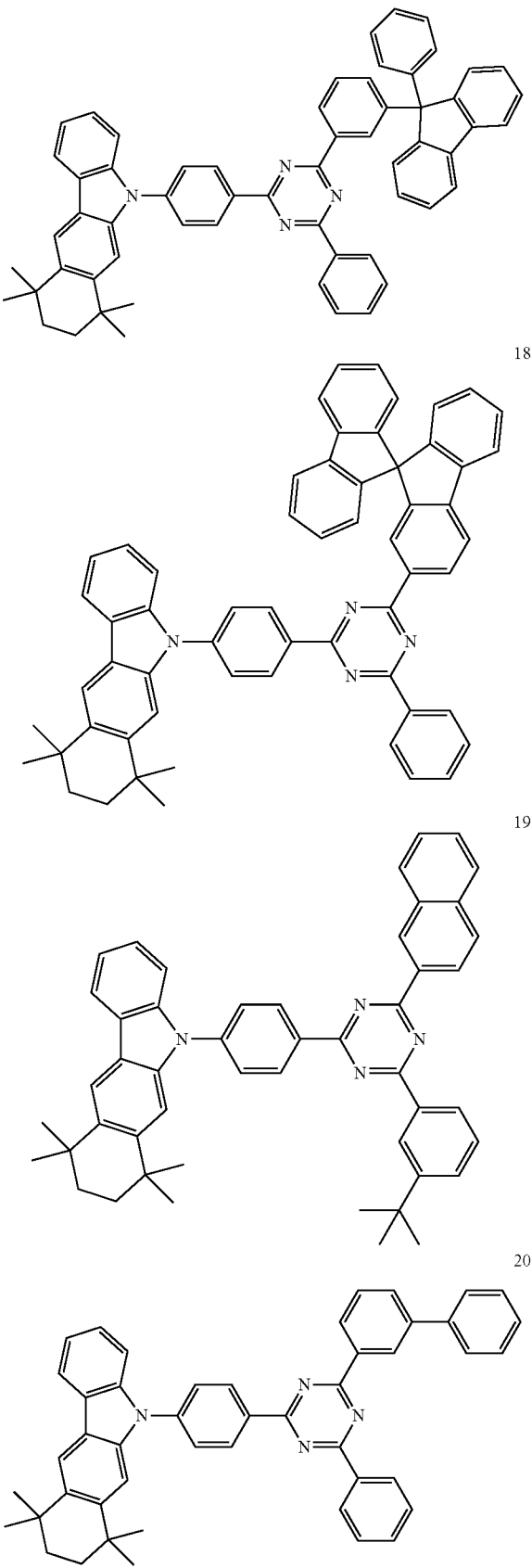

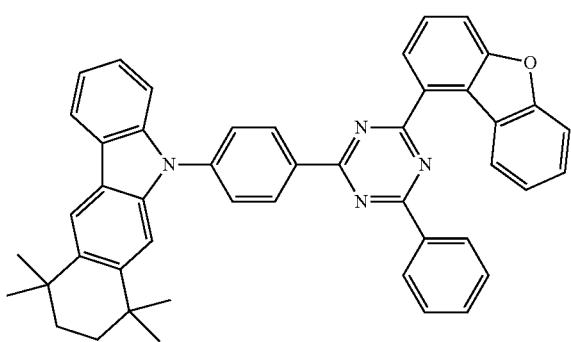
21
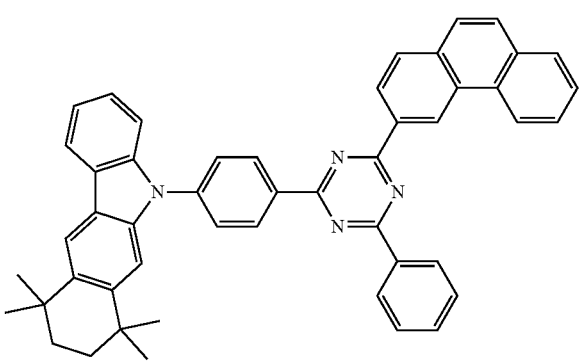
25
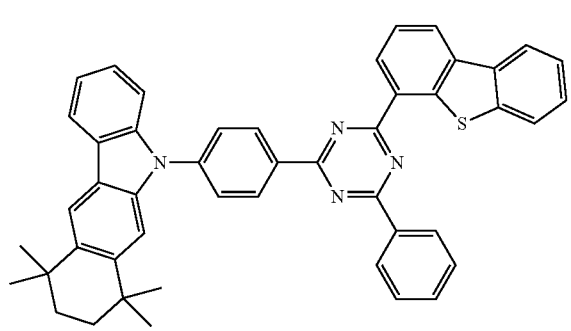
22
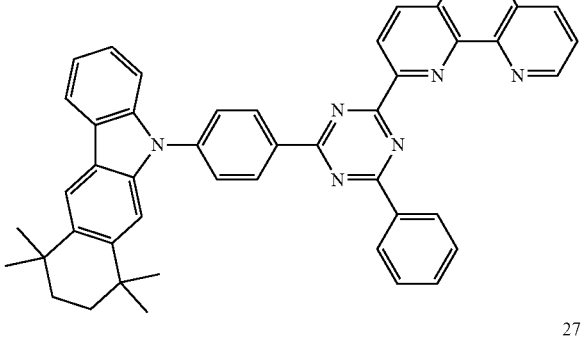
26
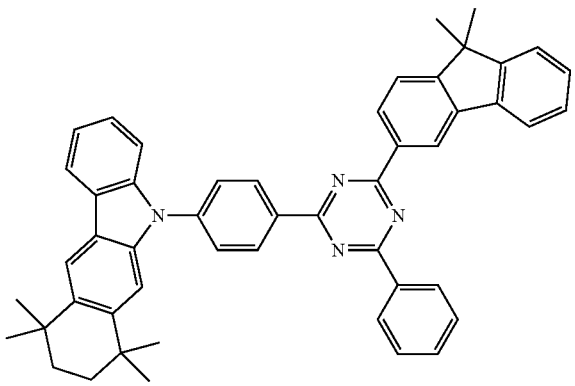
23
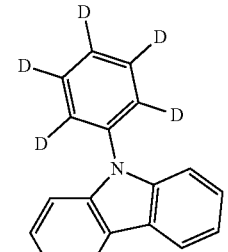
27
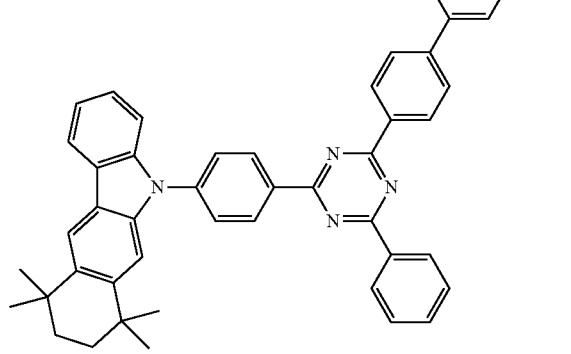
24
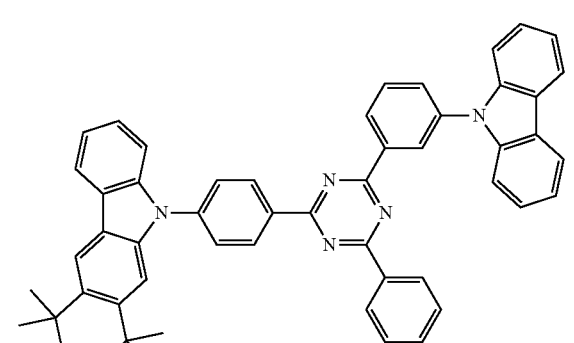
28

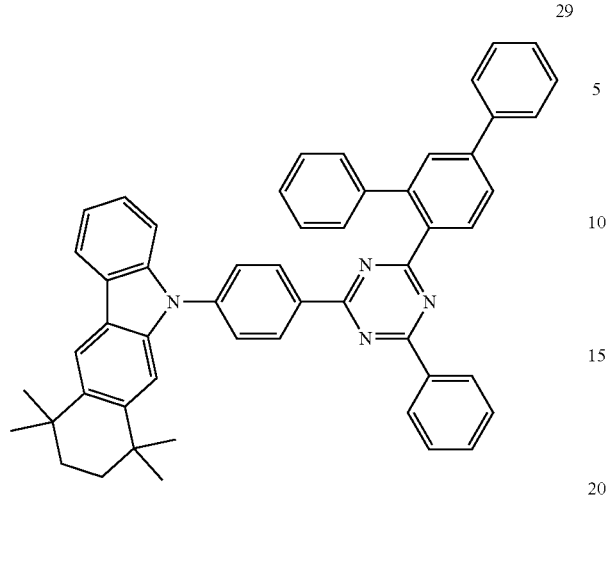
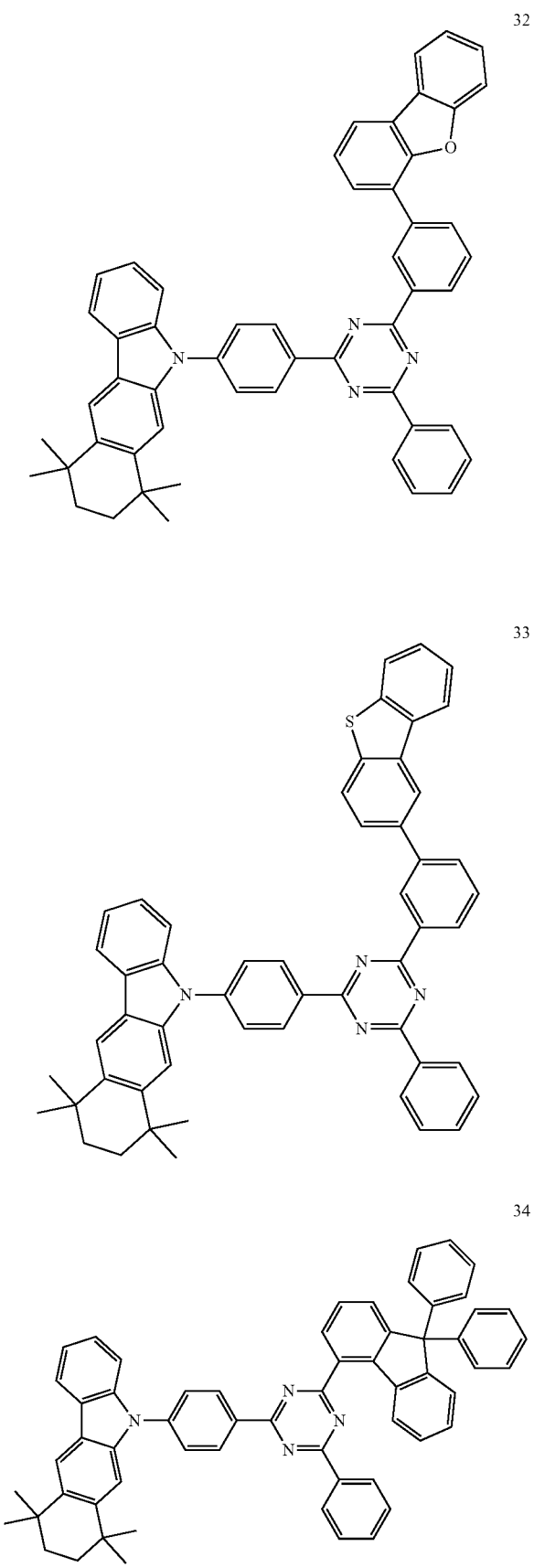

35
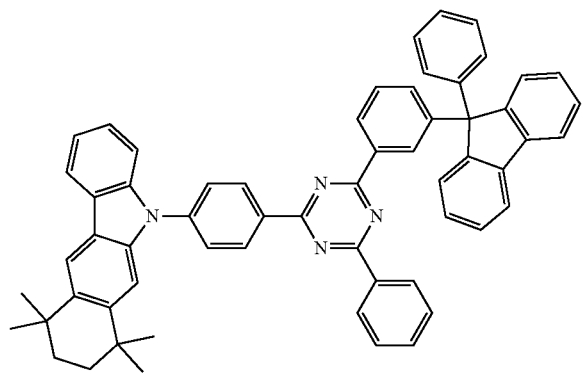
36
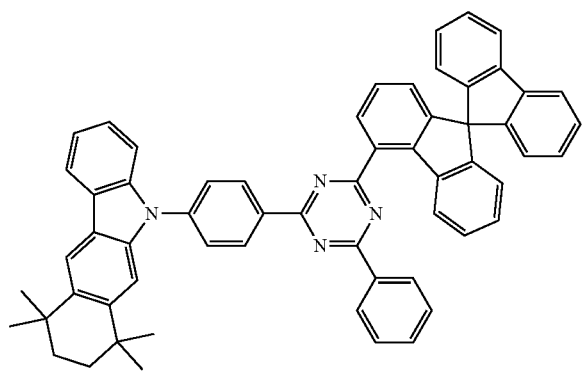
37
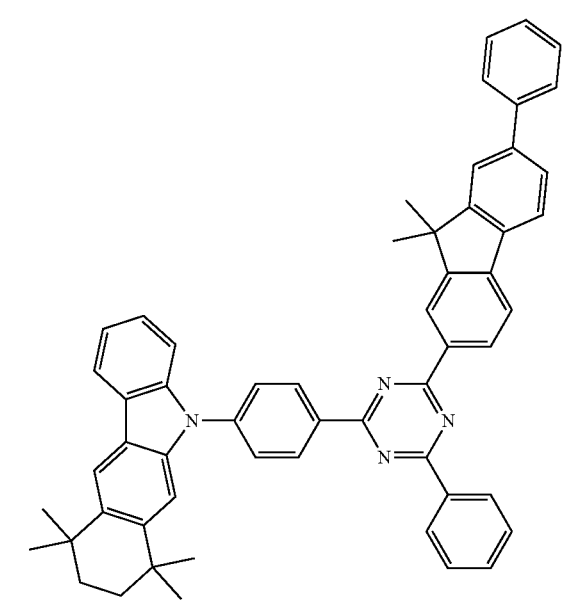
38
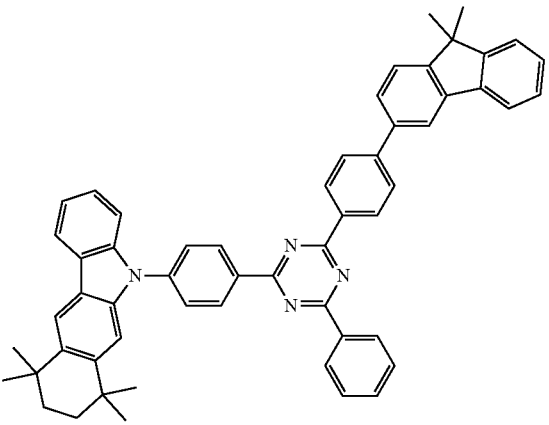
39
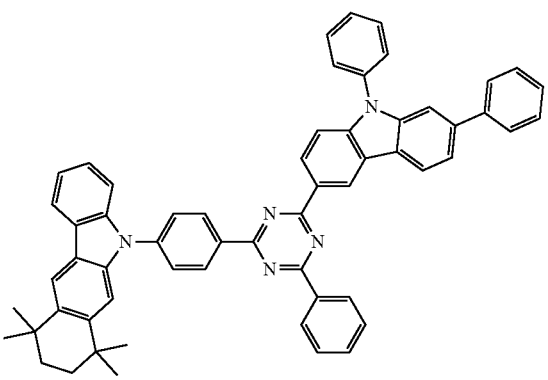
40
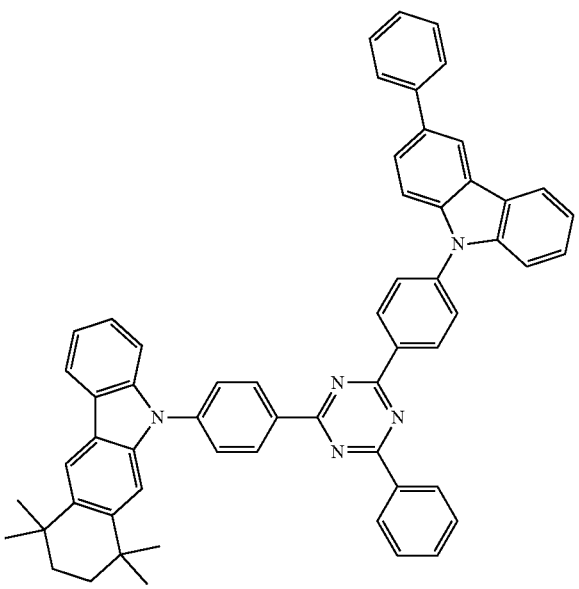

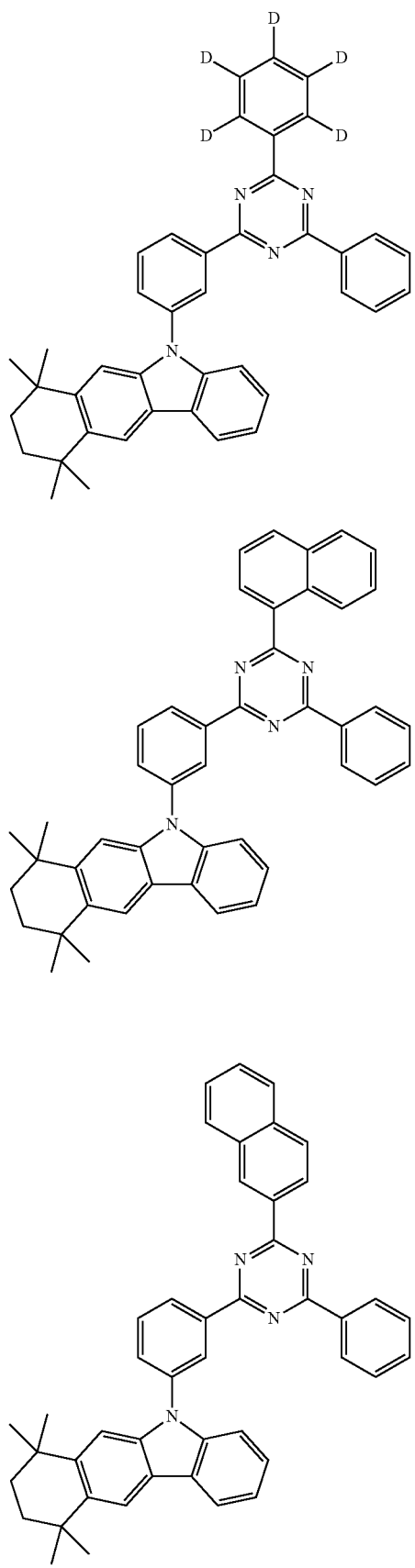
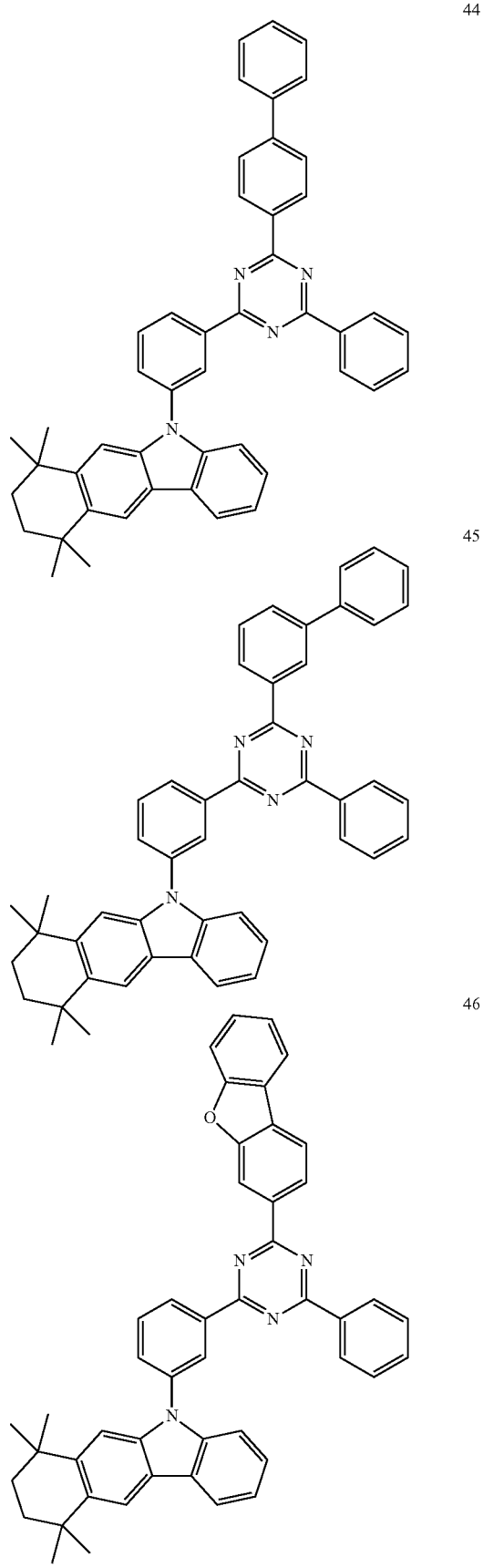

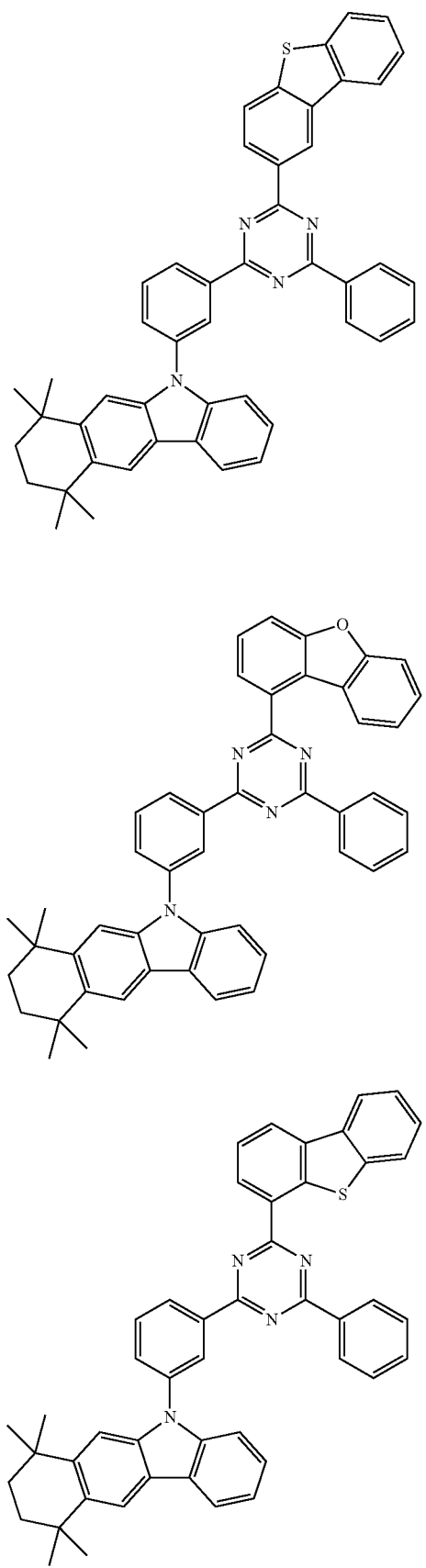
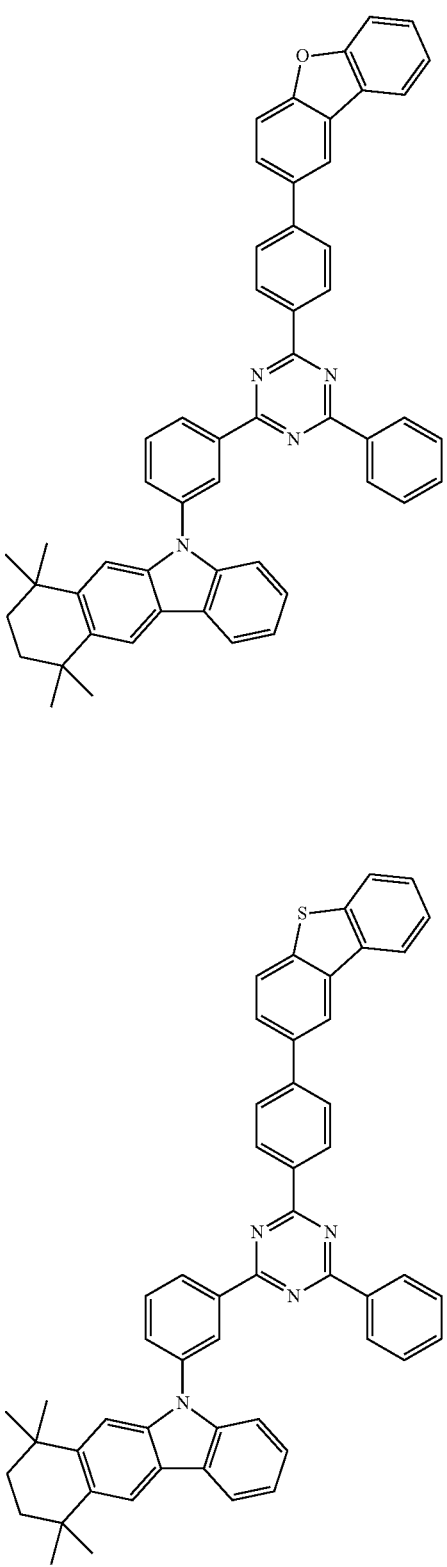

52
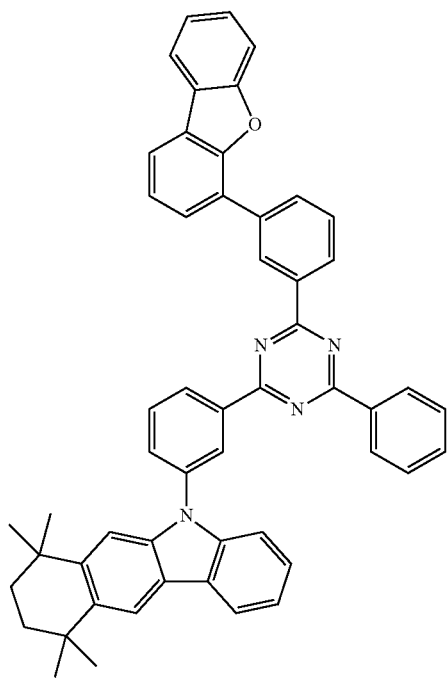
53
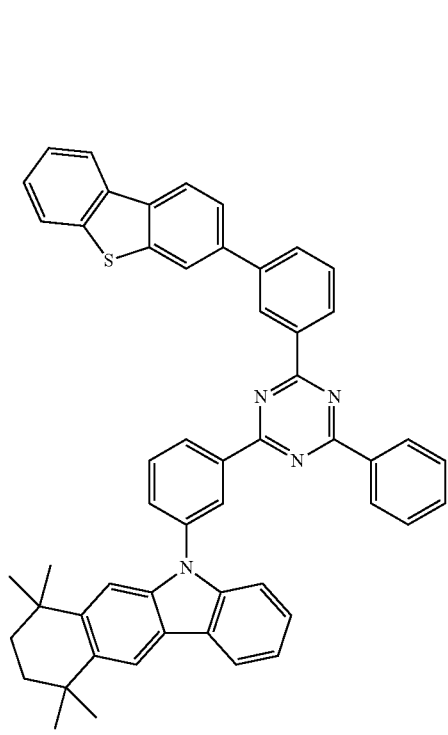
54
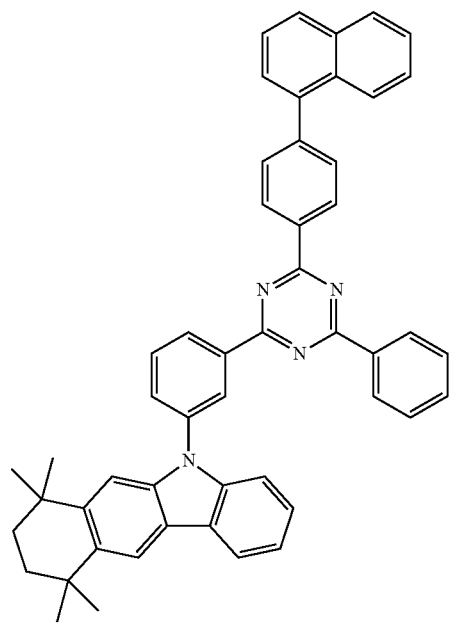
55
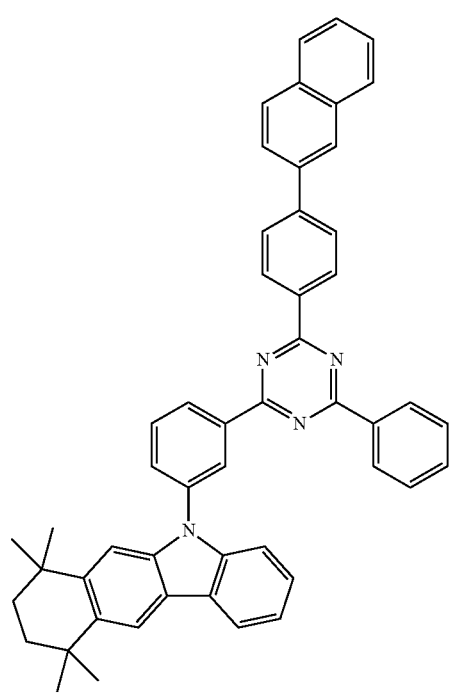

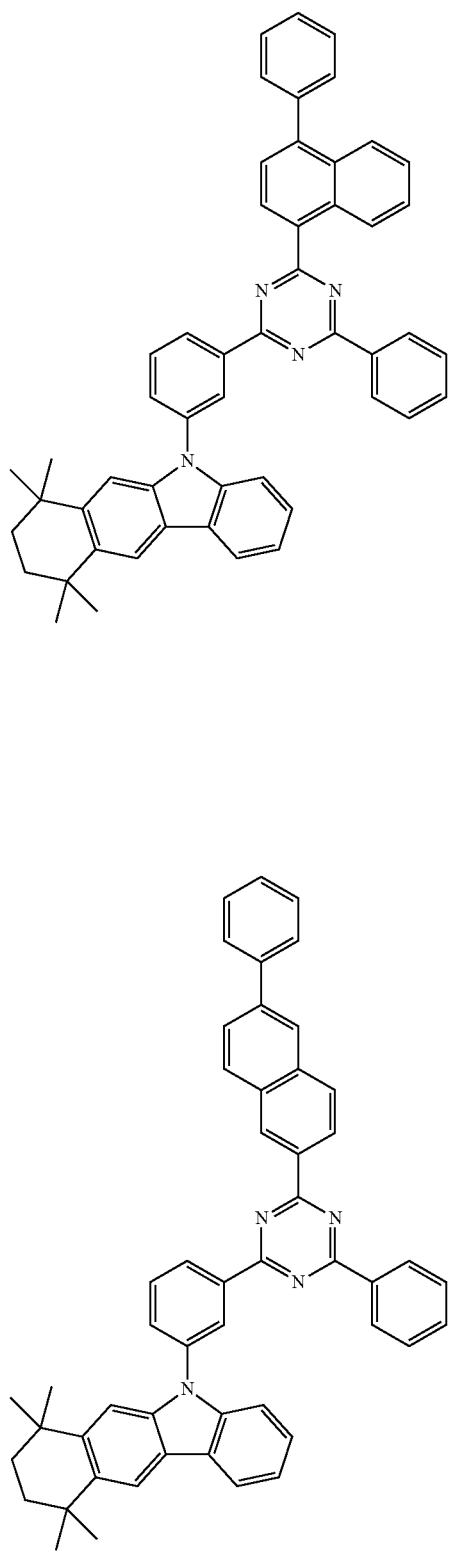
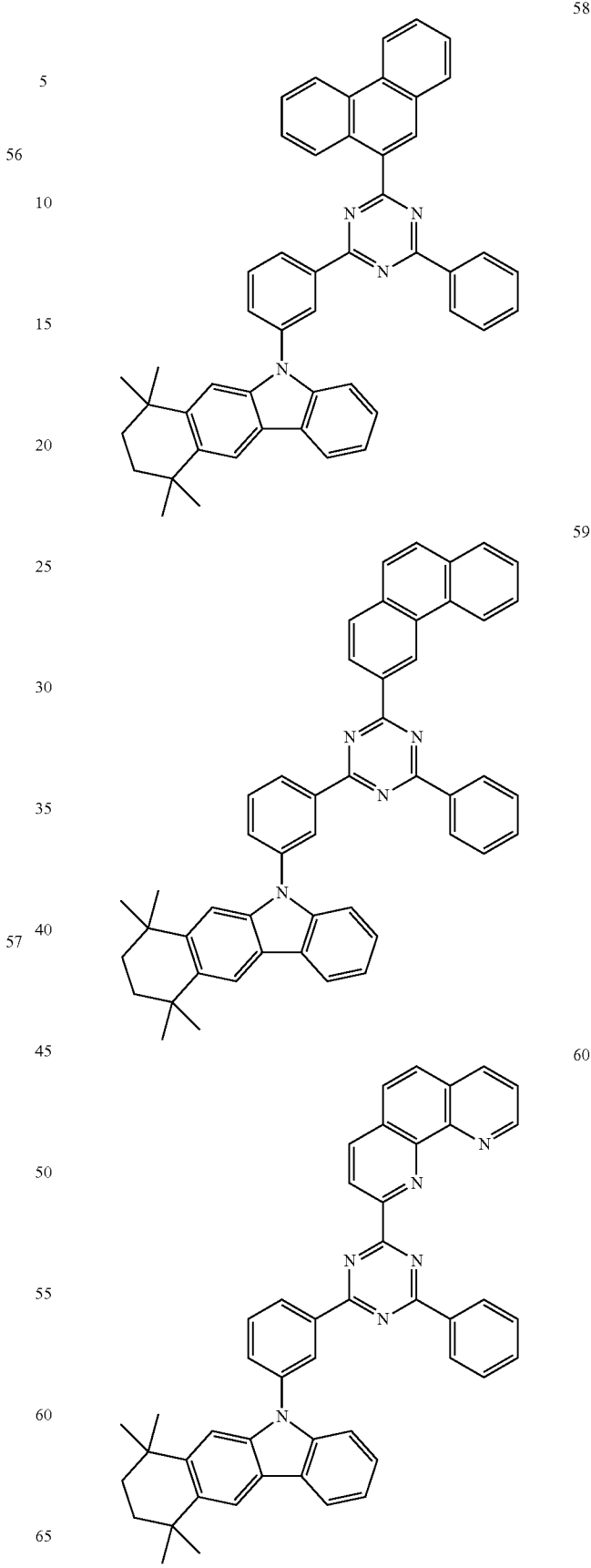

61
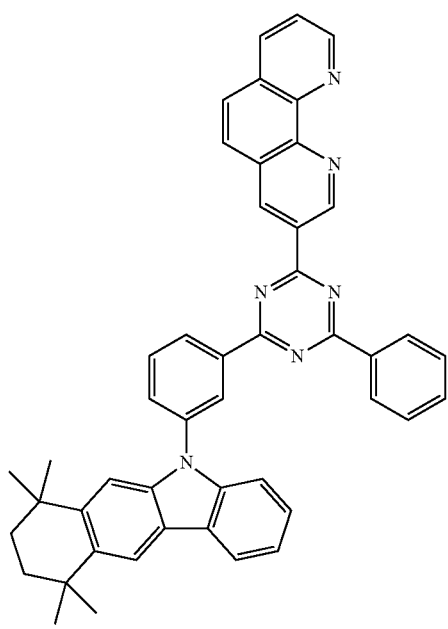
62
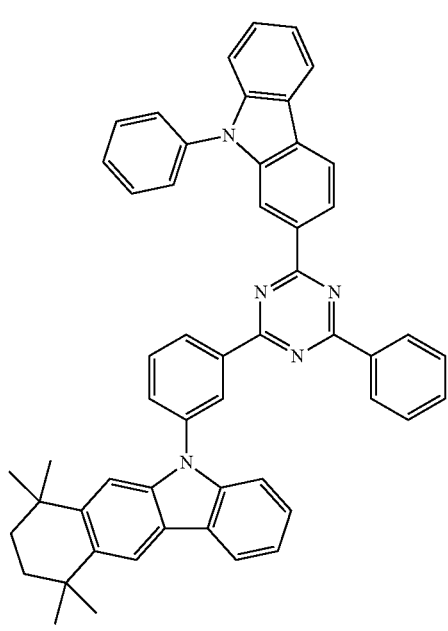
63
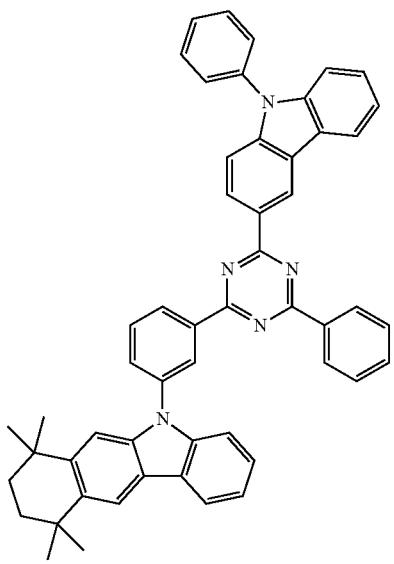
64

81
-continued
65
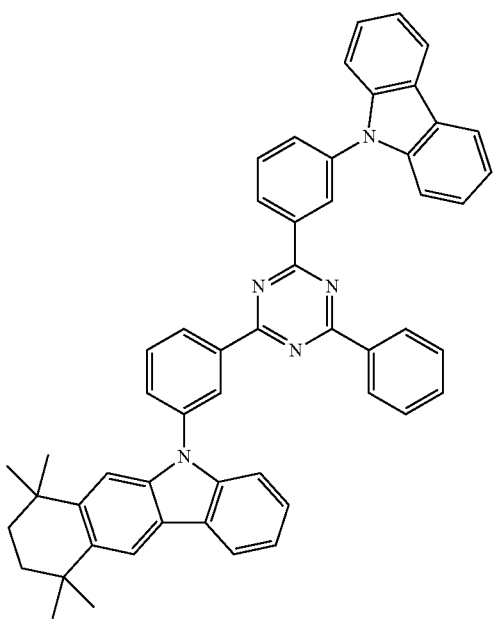
66
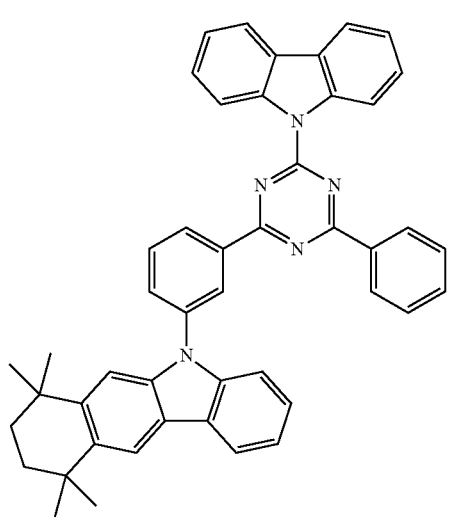
82
-continued
67
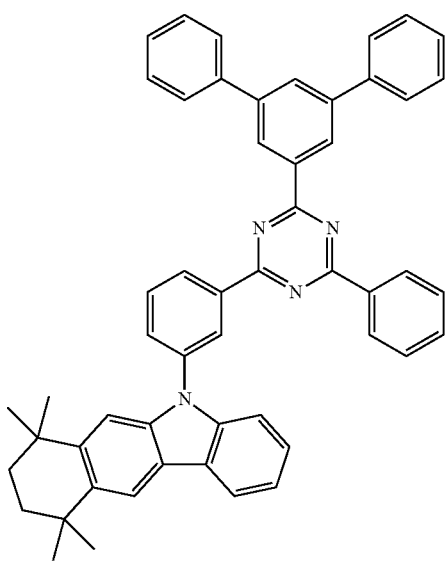
68
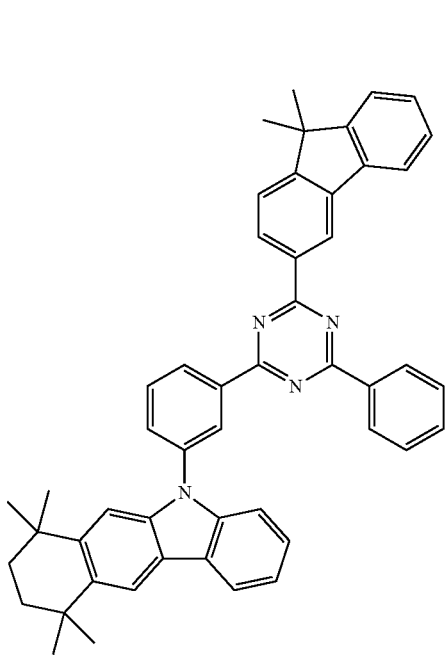

69
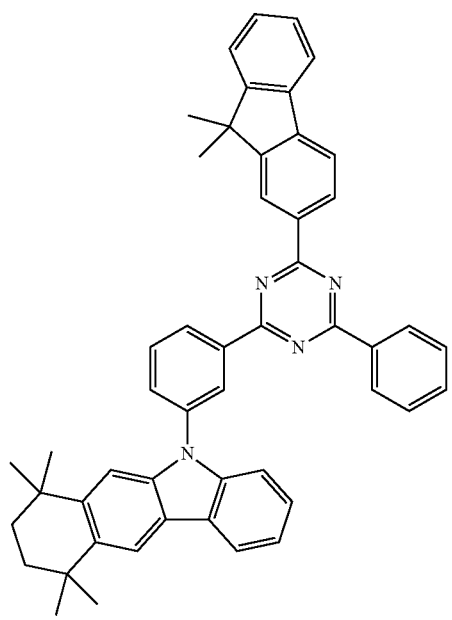
70
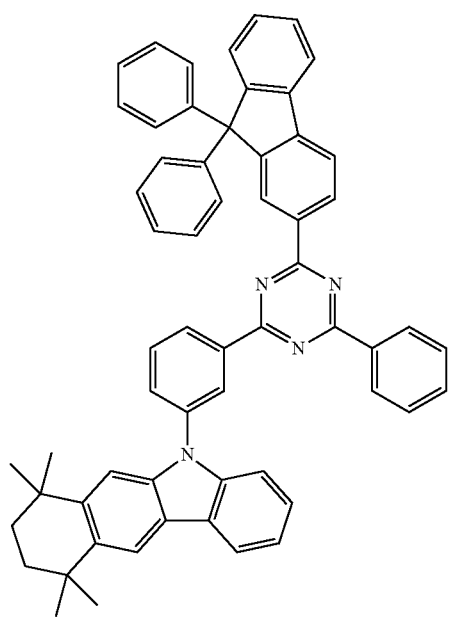
71
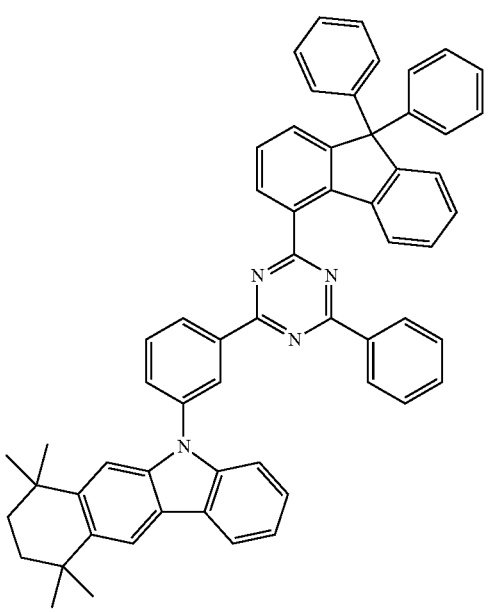
72
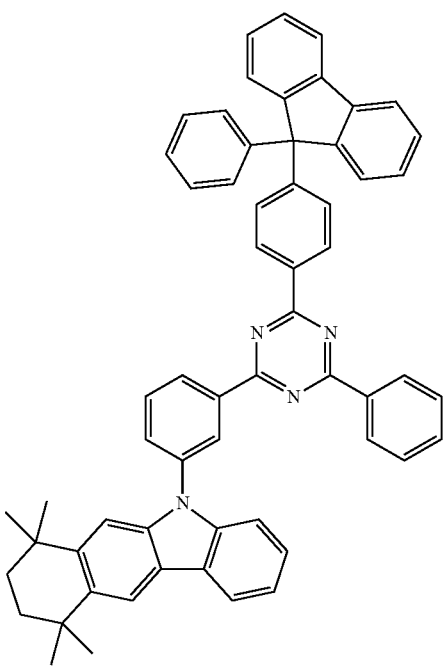

73
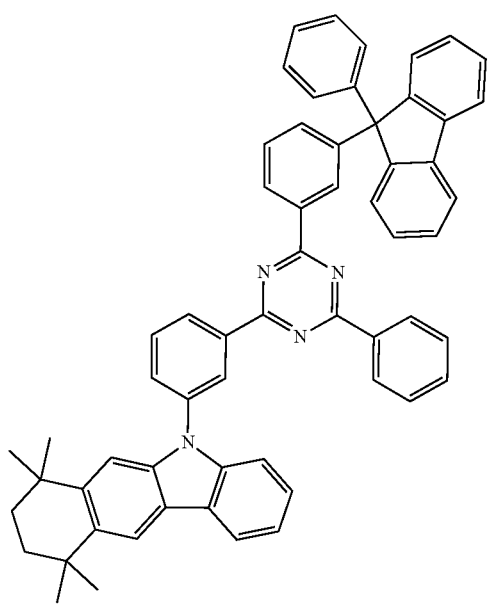
74
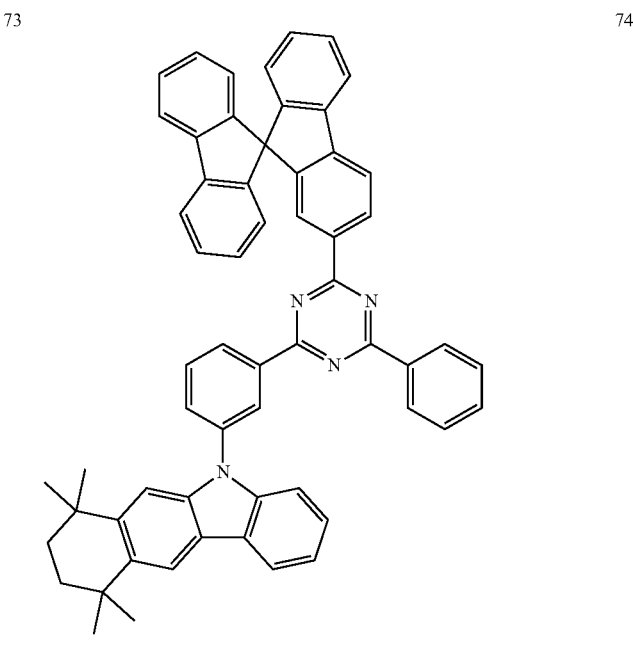
75
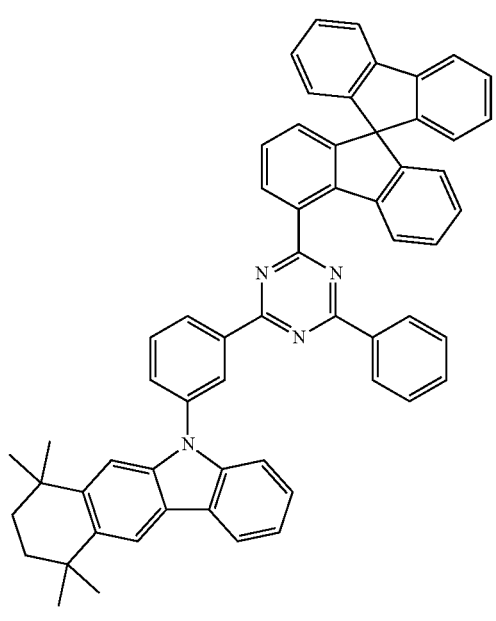
76
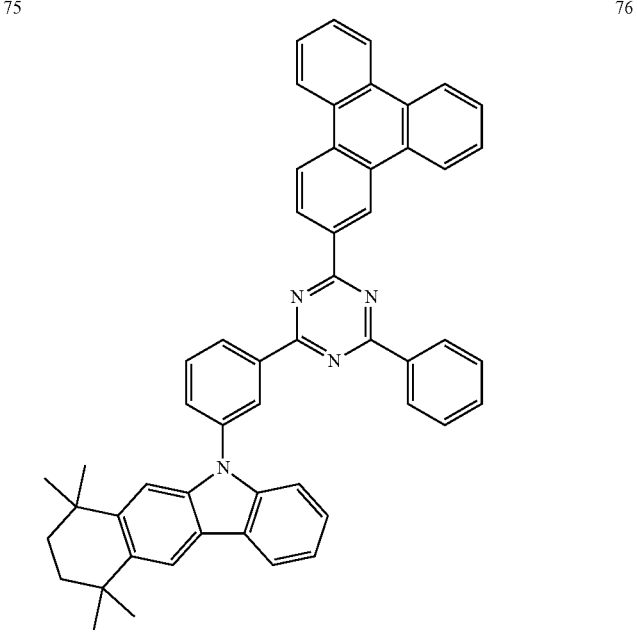
77
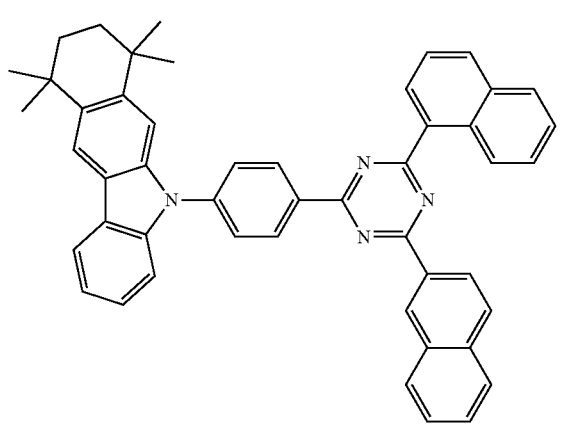
78
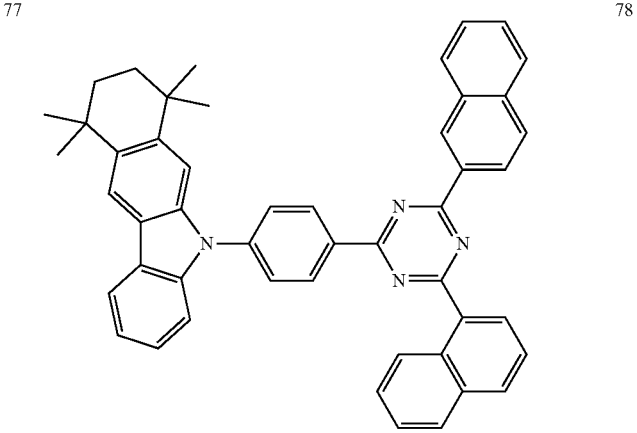

-continued
79
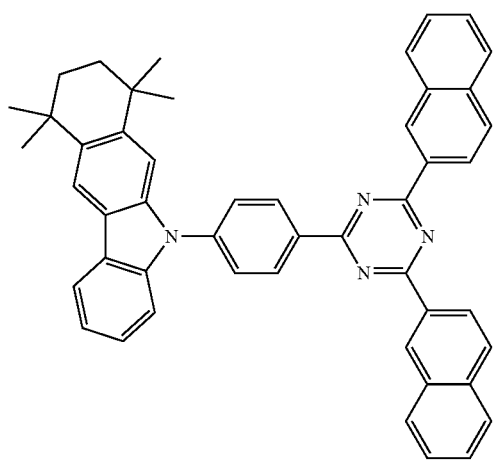
80
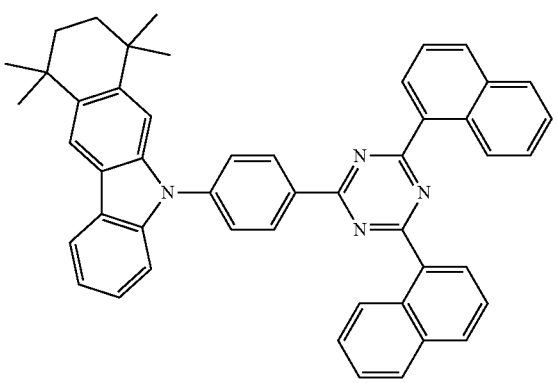
81
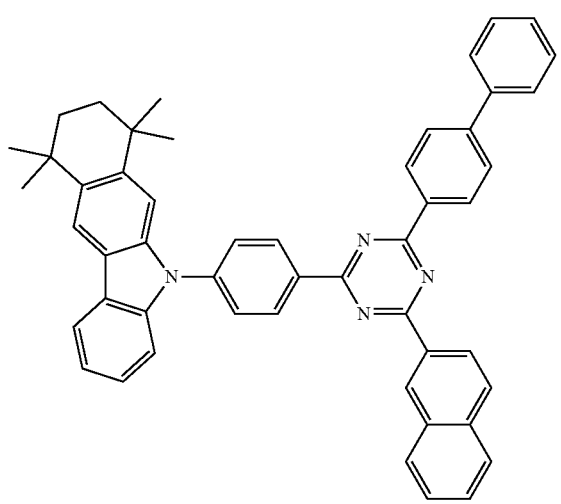
82
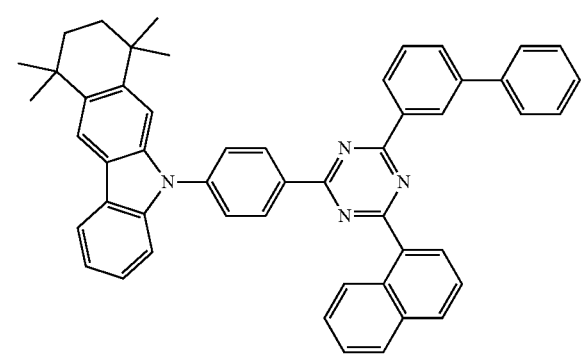
83
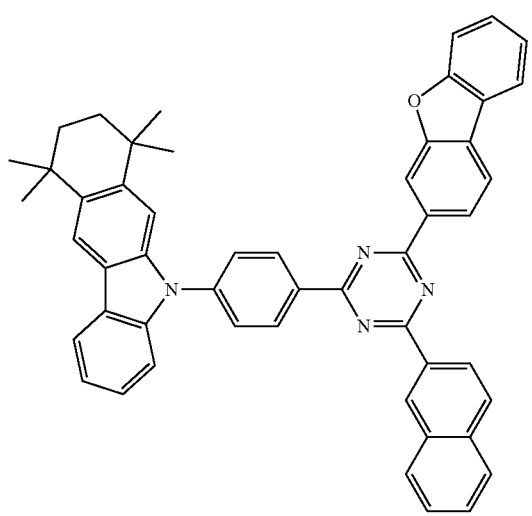
84
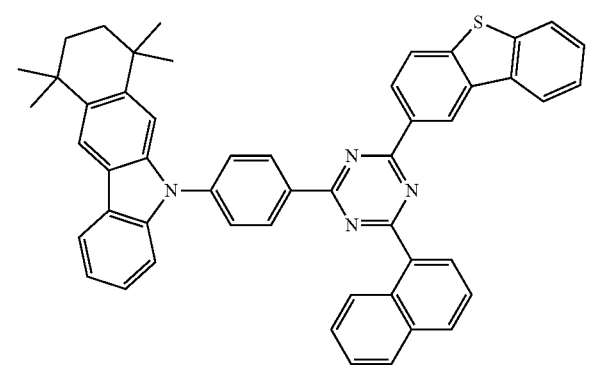

-continued
85
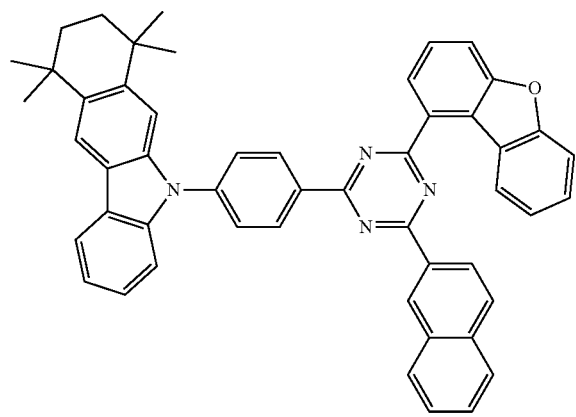
86
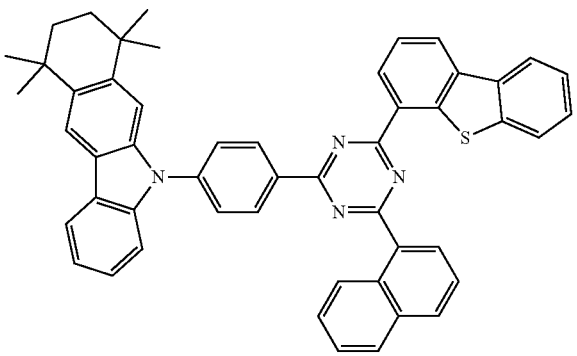
87
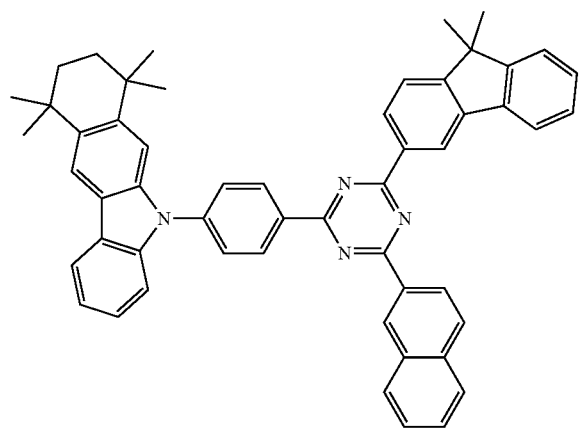
88
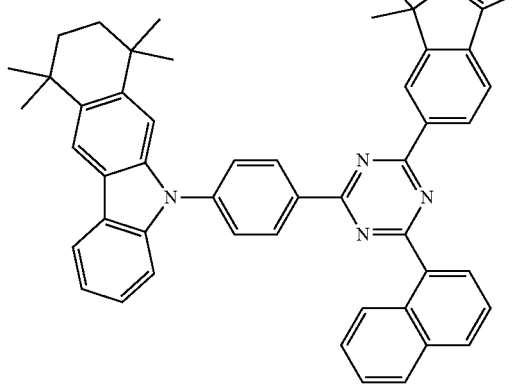
89
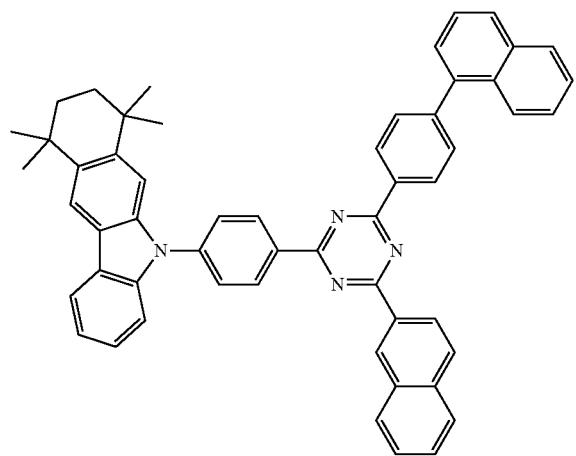
90
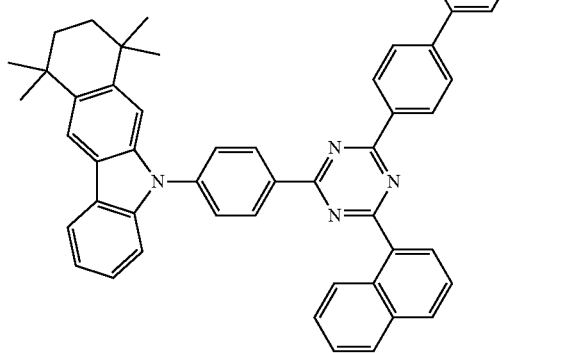

-continued
91
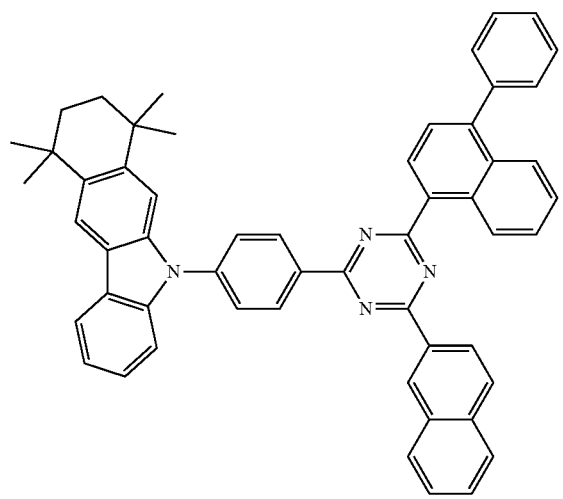
92
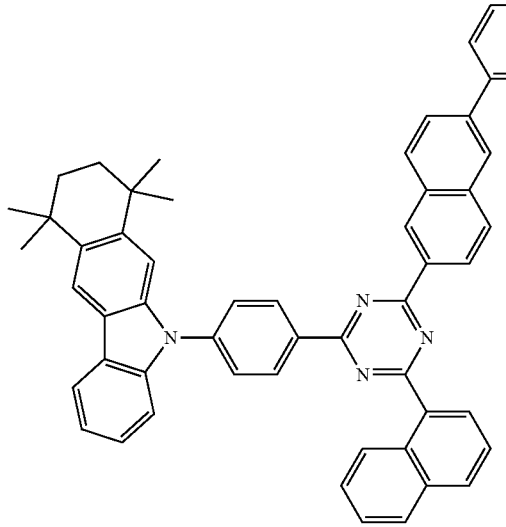
93
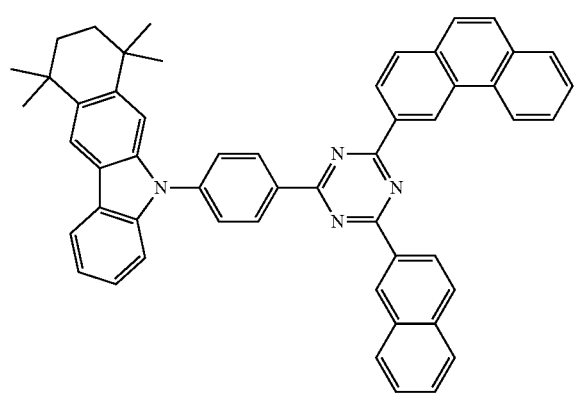
94
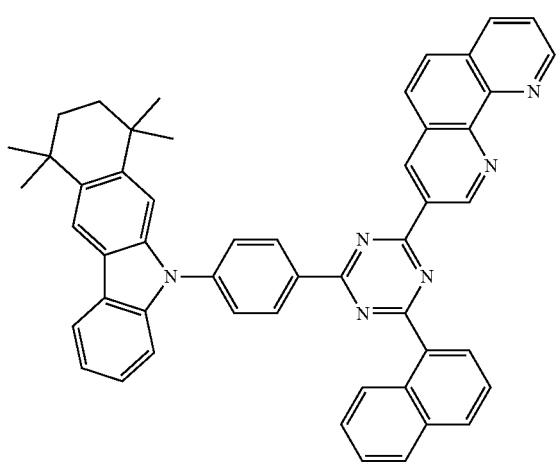
95
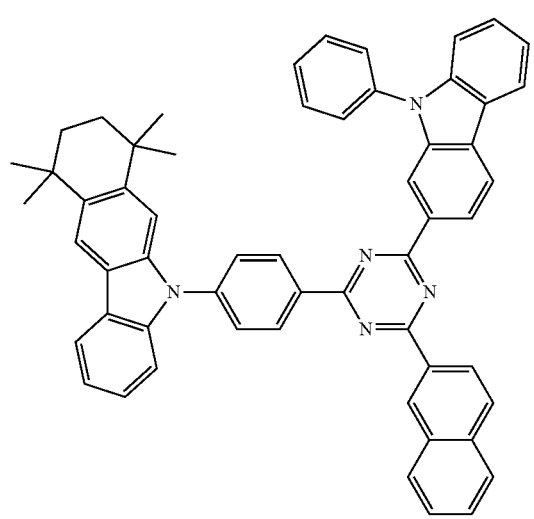
96
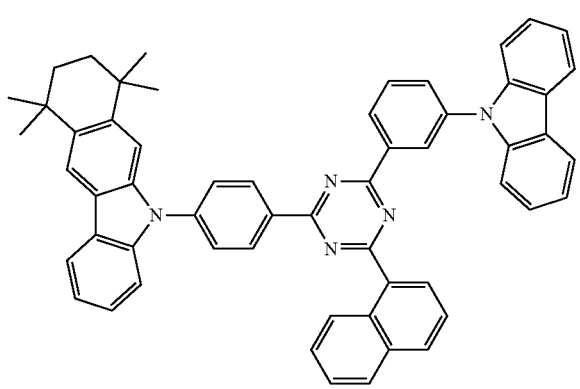

97
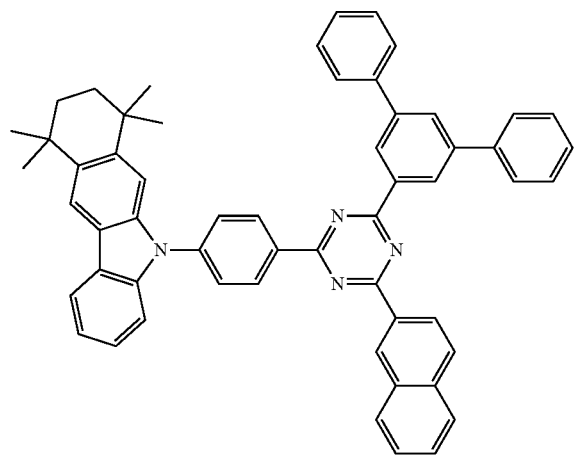
98
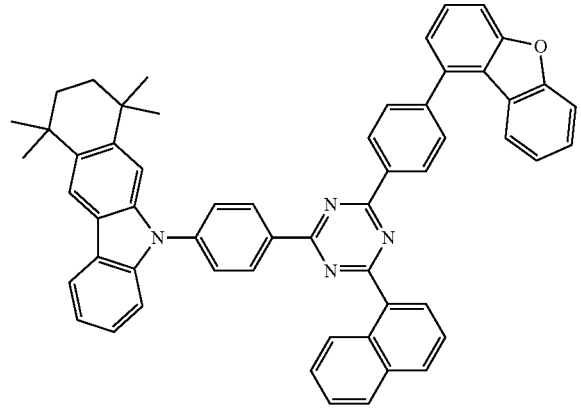
99
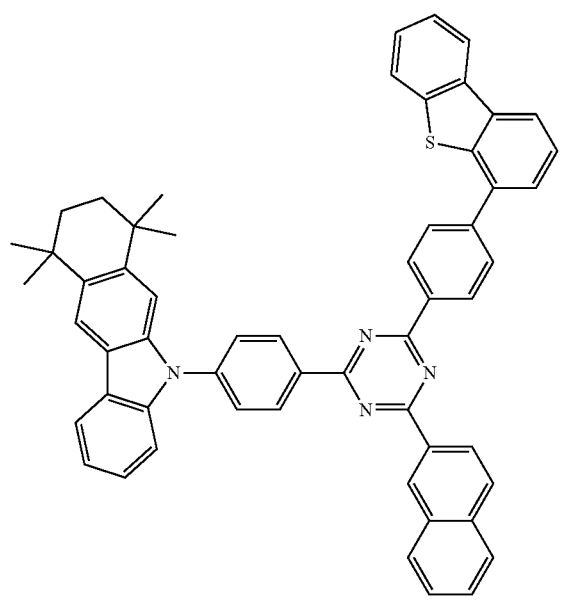
100
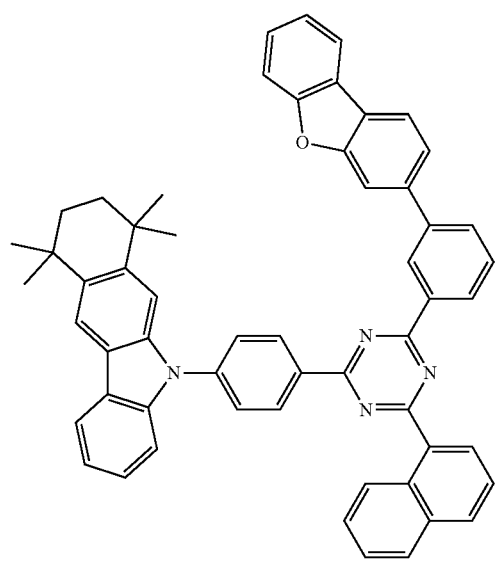

-continued
101
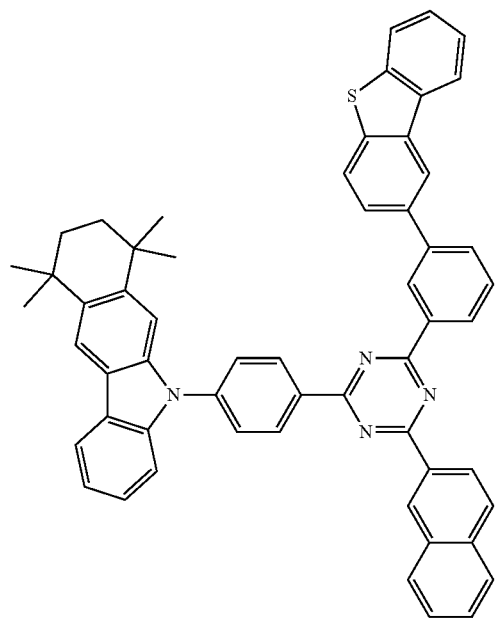
102
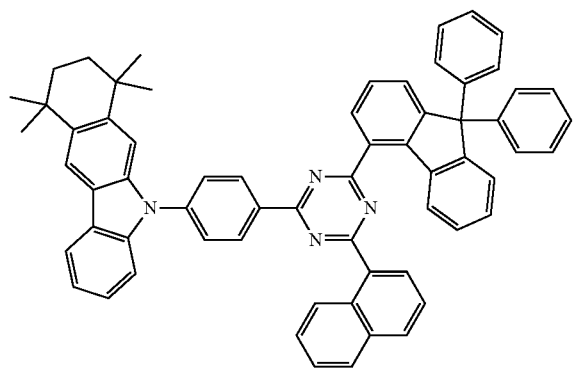
103
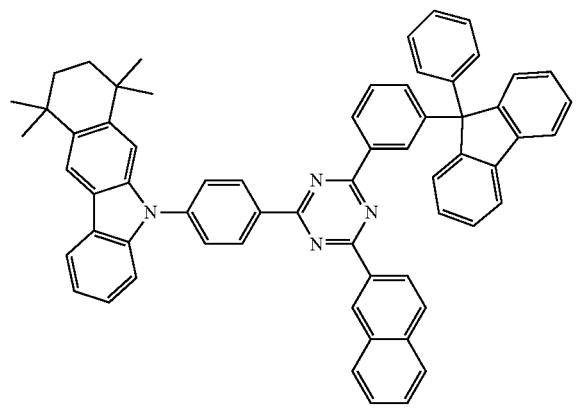
104
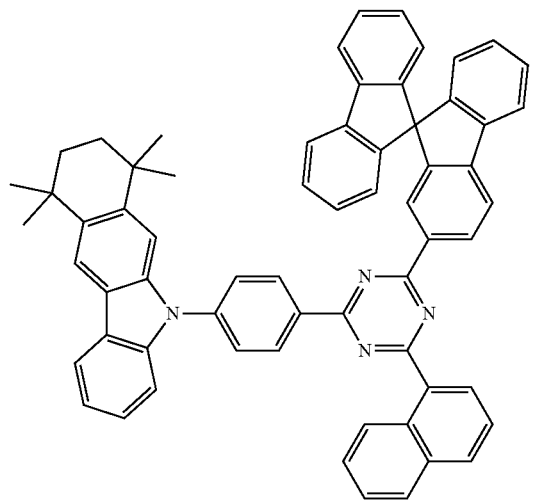
105
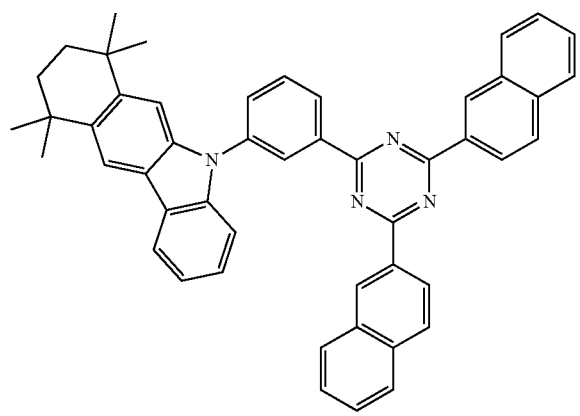
106
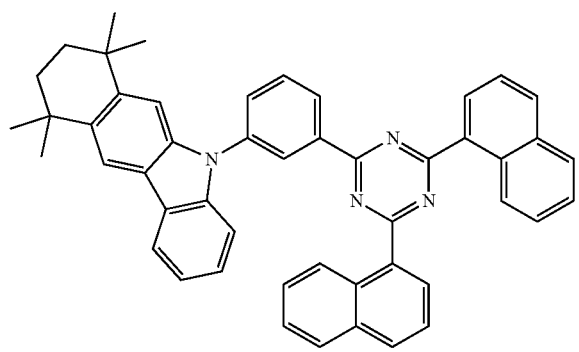

107
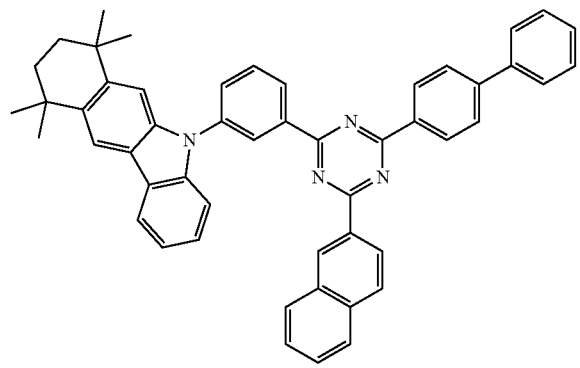
108
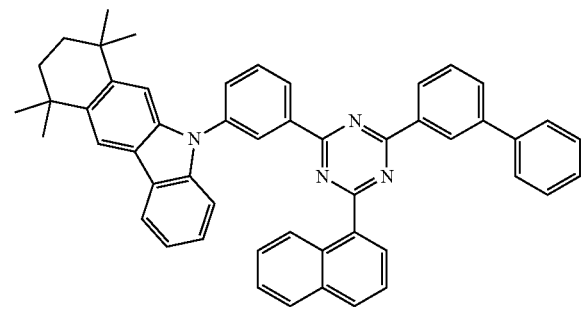
109
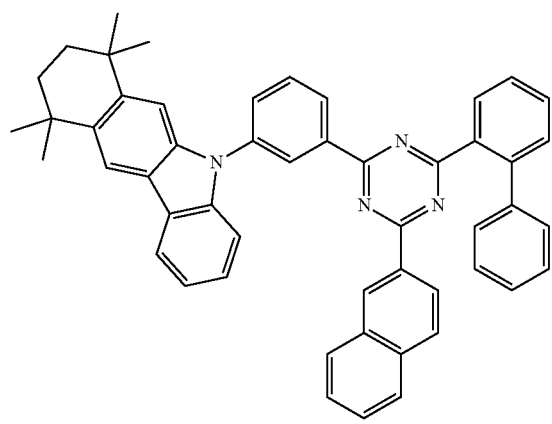
110
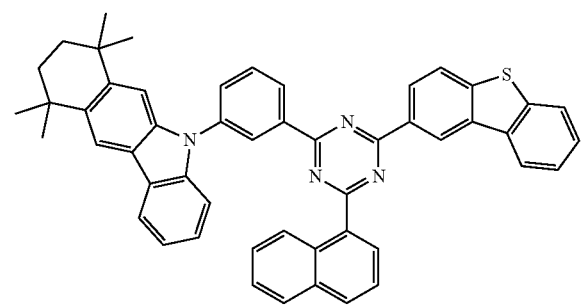
111
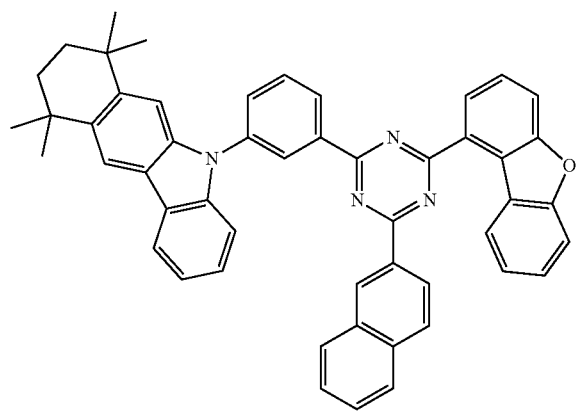
112
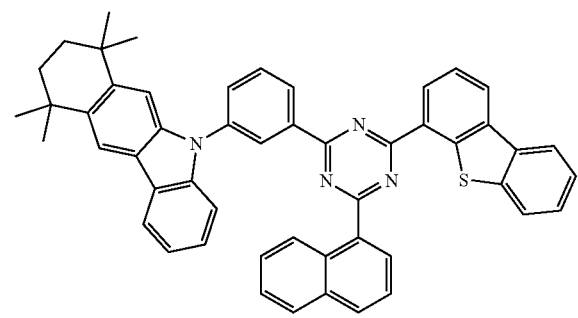

113 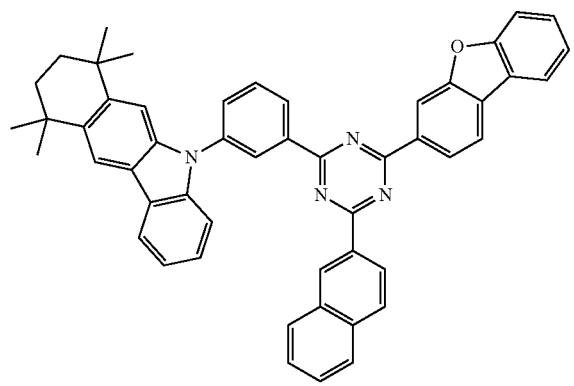
114 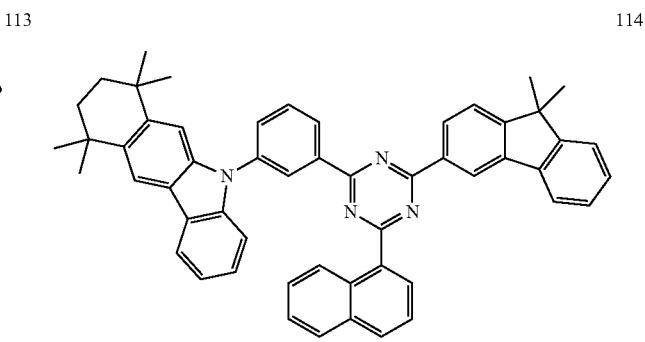
115 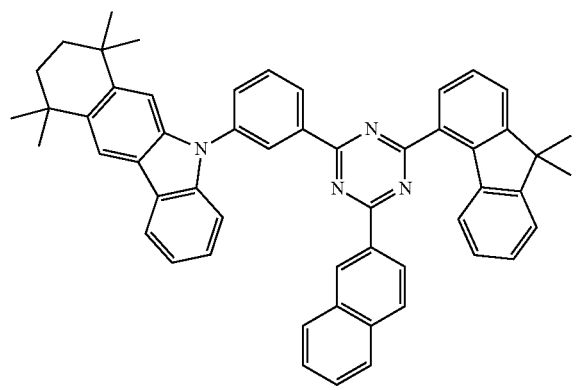
116 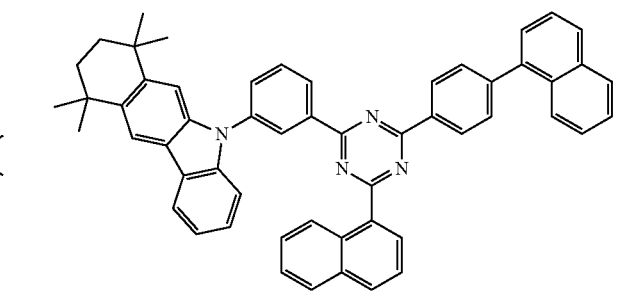
117 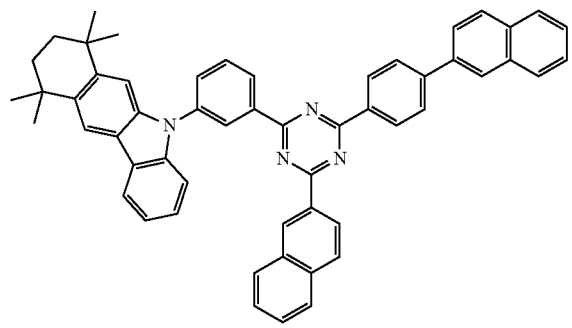
118 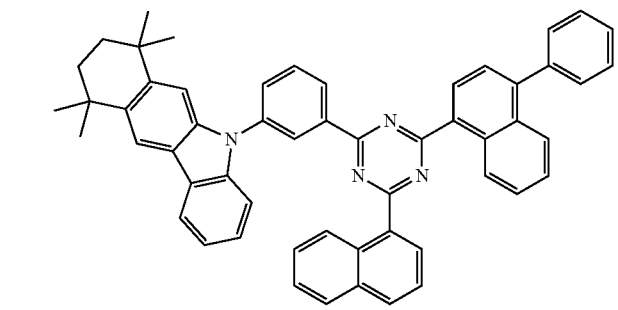
119 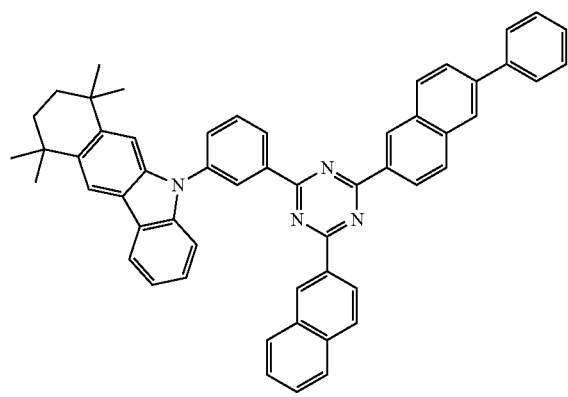
120 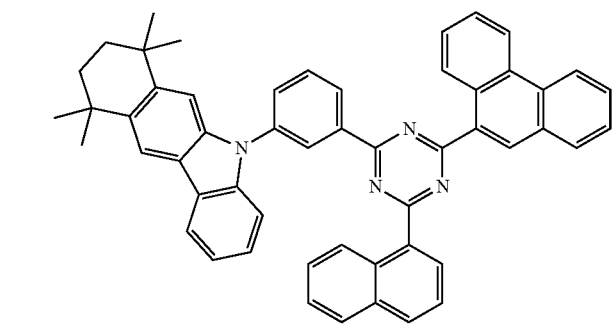

-continued
| 121 | 122 |
|---|---|
| 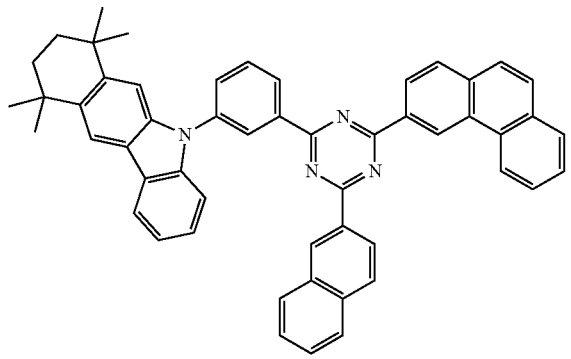 | 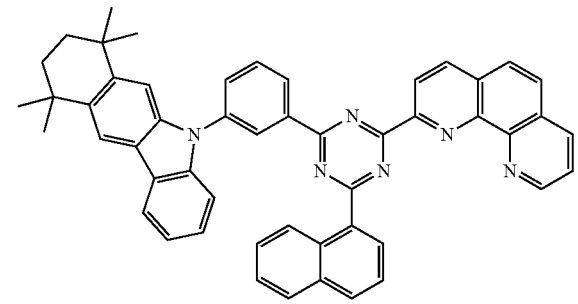 |
| 123 | 124 |
| 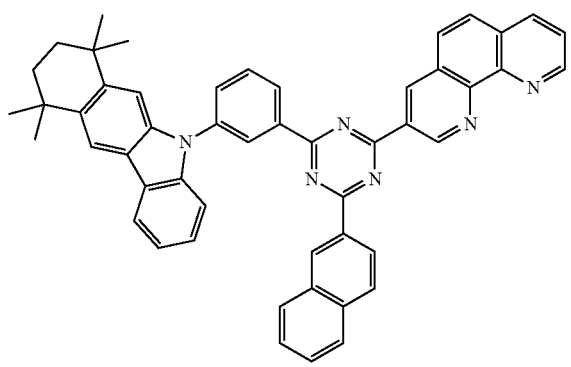 | 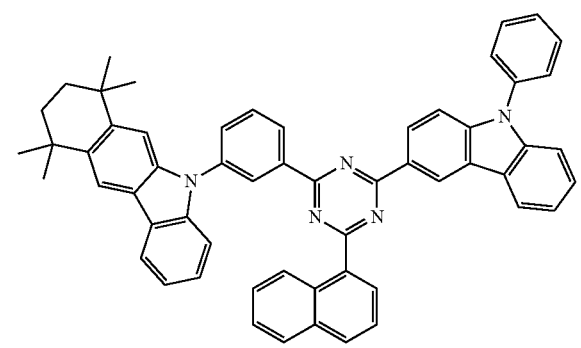 |
| 125 | 126 |
| 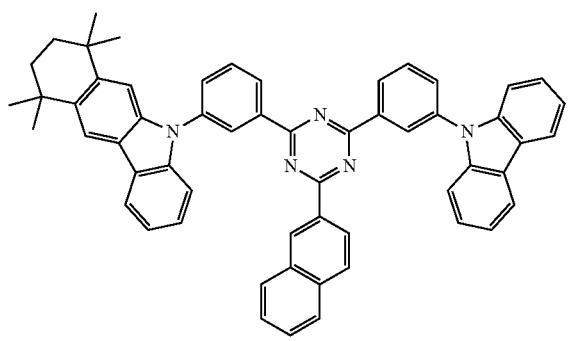 | 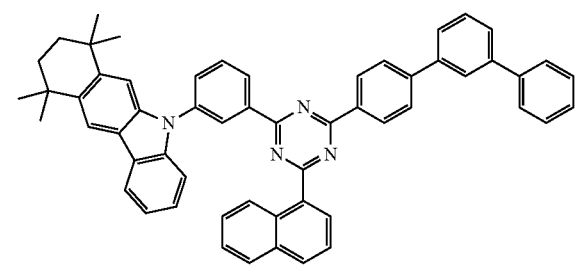 |
| 127 | 128 |
| 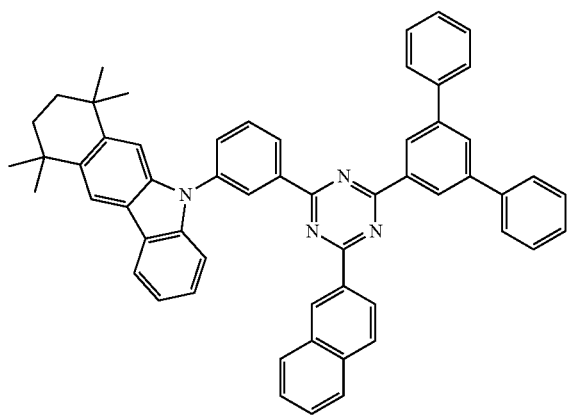 | 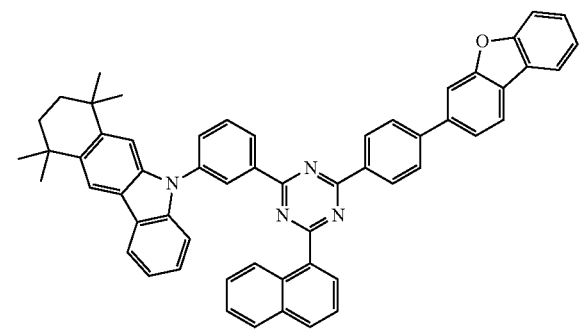 |

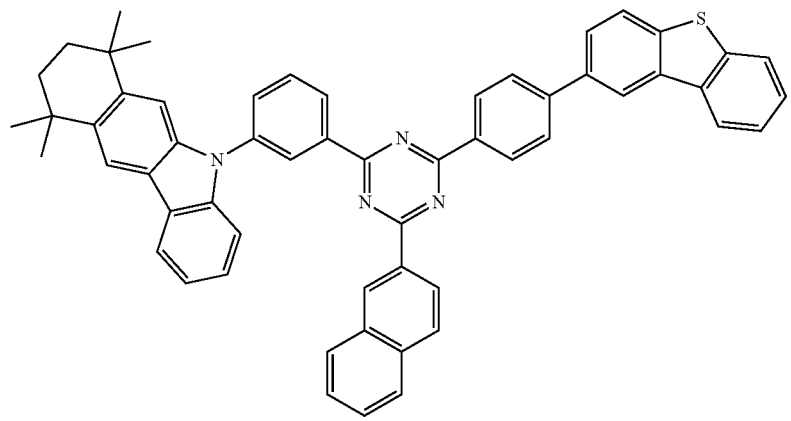
129
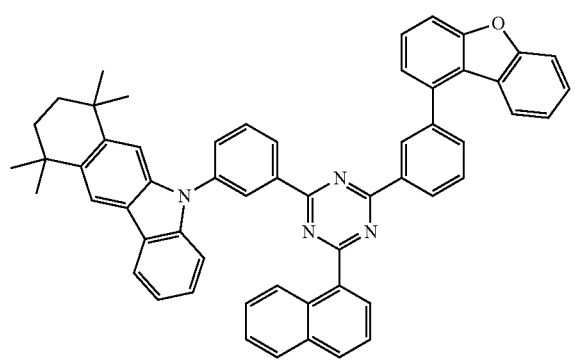
130
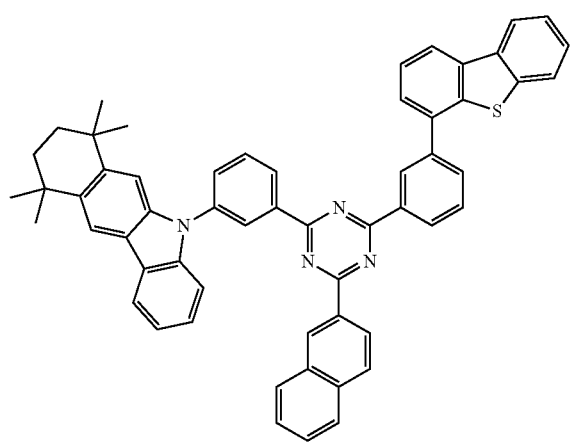
131
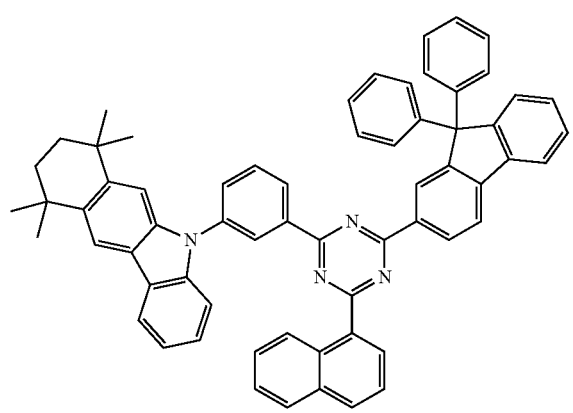
132
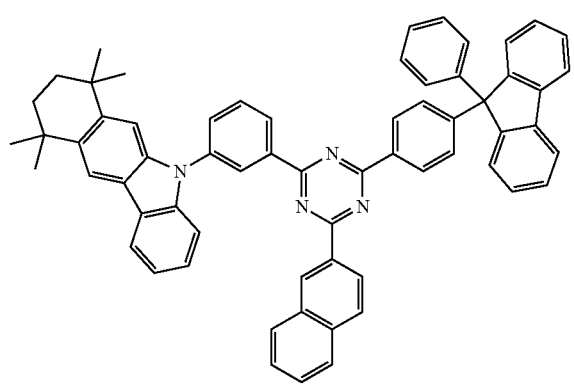
133

-continued
| 134 | 135 |
|---|---|
| 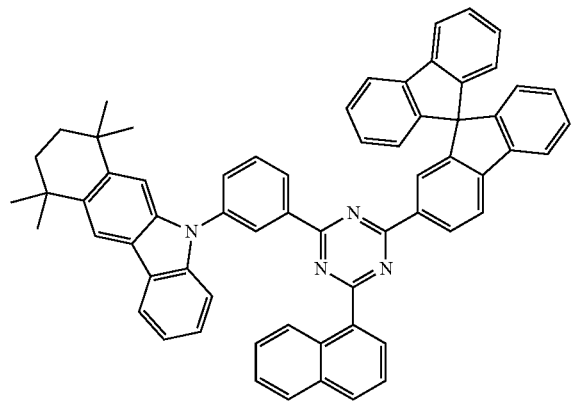 | 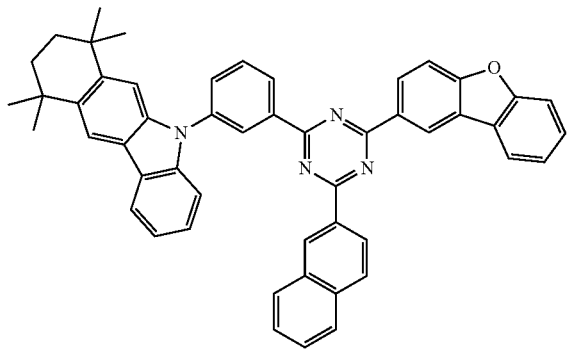 |
| 136 | 137 |
| 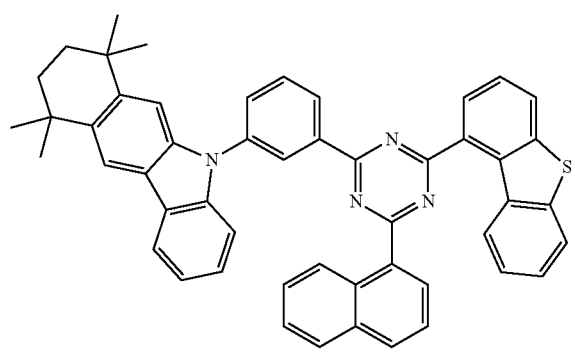 | 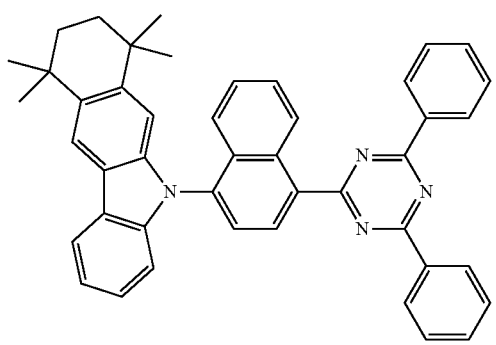 |
| 138 | 139 |
| 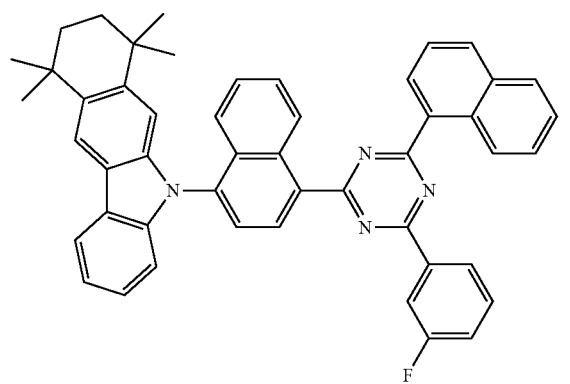 | 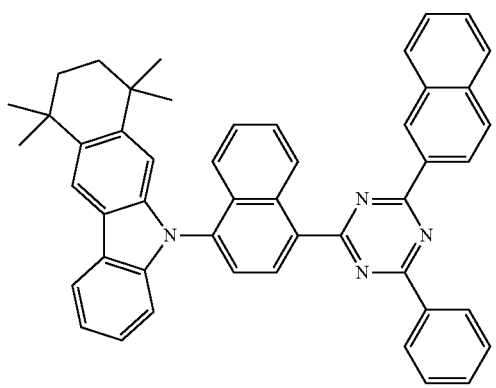 |
| 140 | 141 |
| 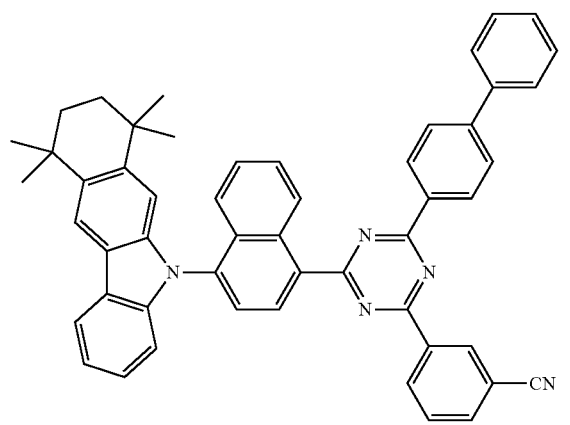 | 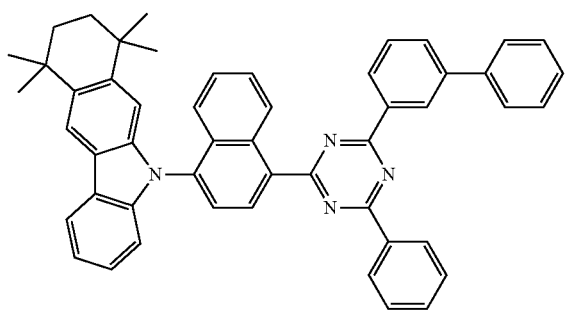 |

-continued
142
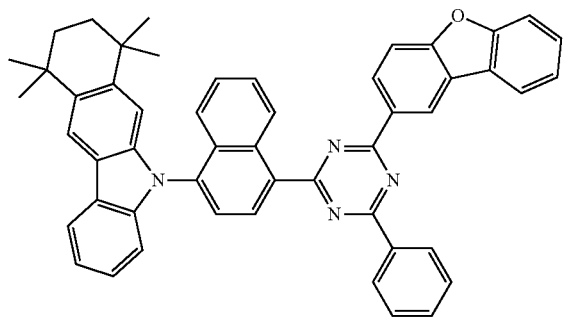
143
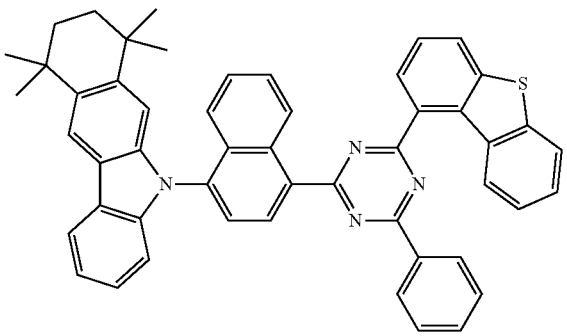
144
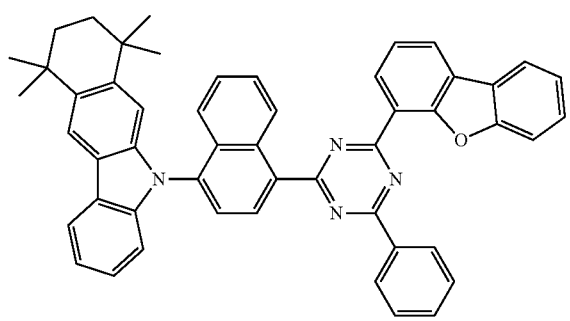
145
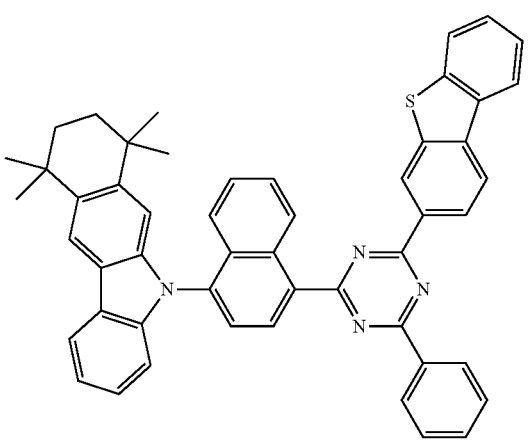
146
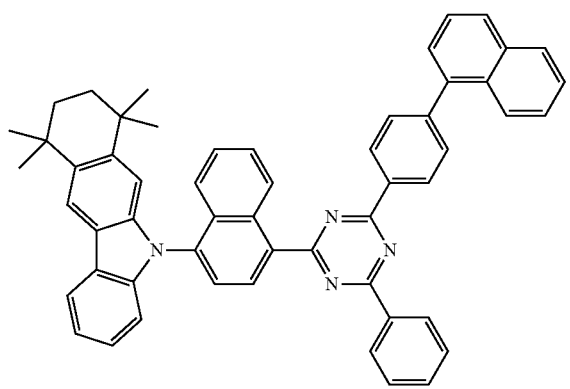
147
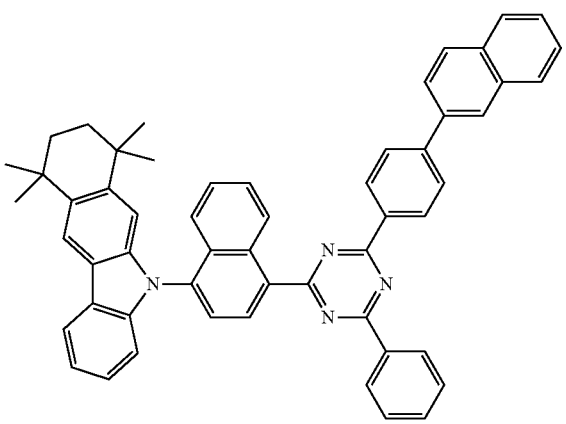

-continued
148
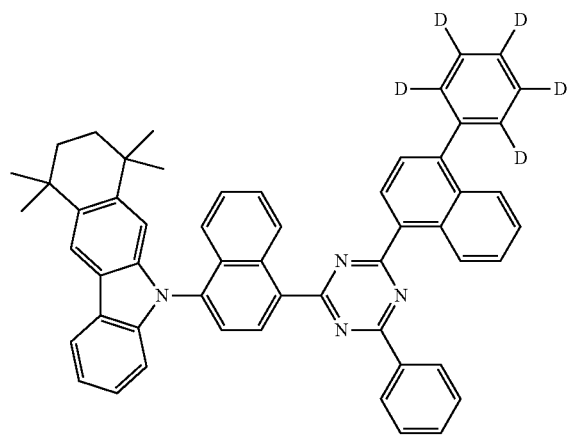
149
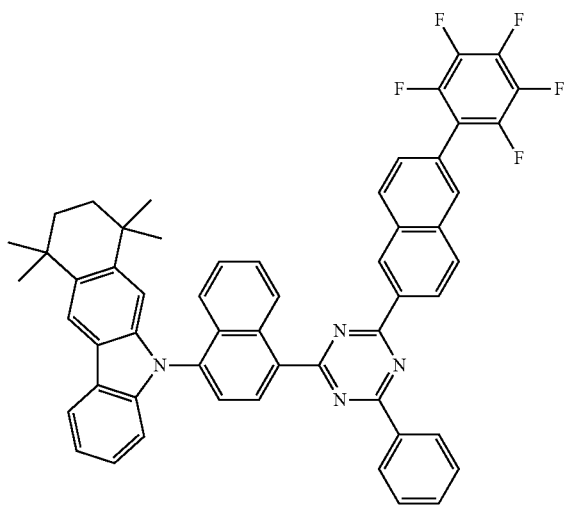
150
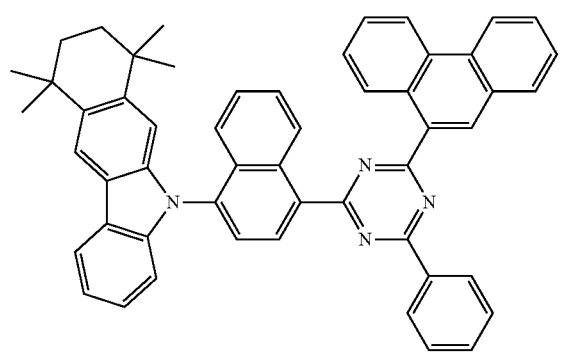
151
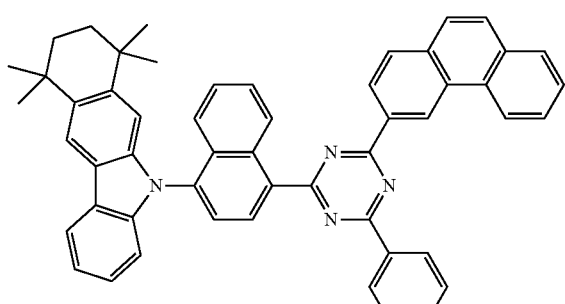
152
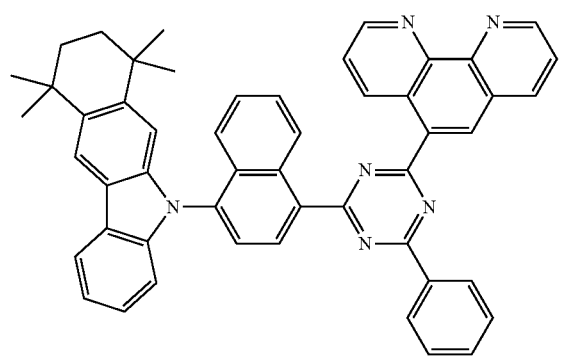

153
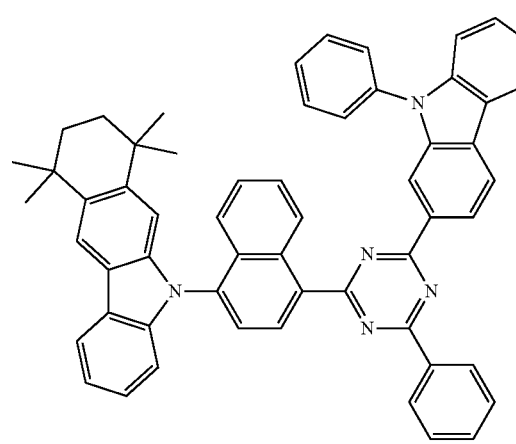
154
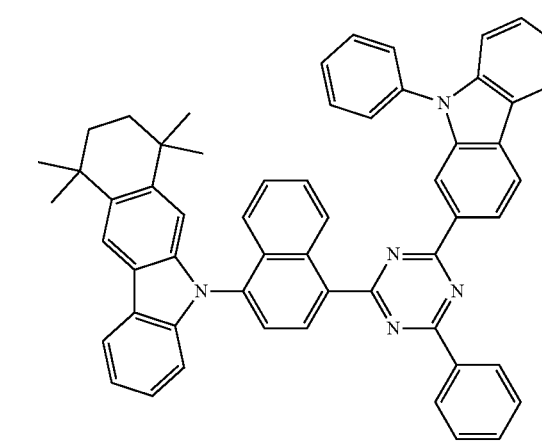
155
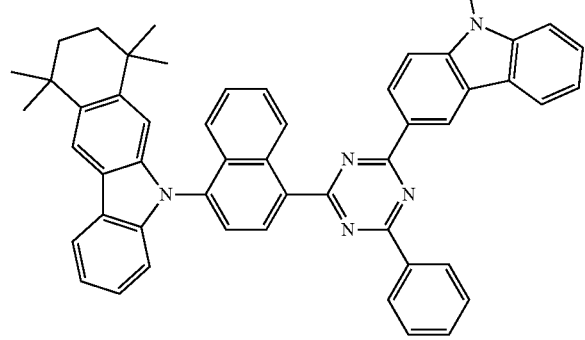
156
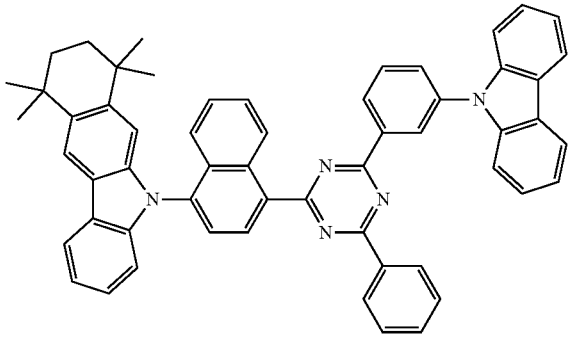
157
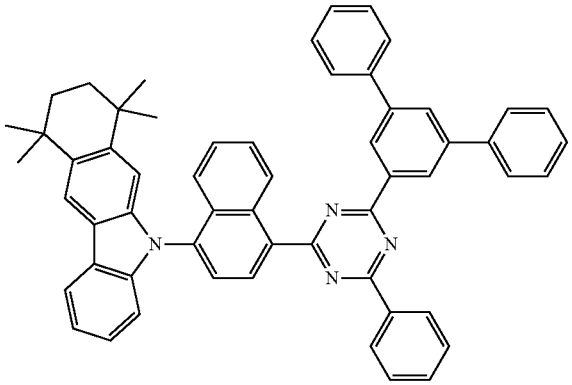
158
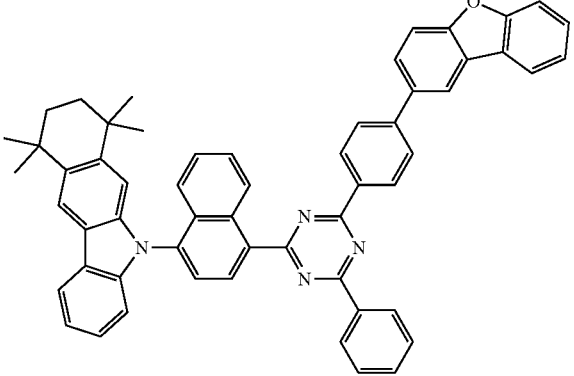
159
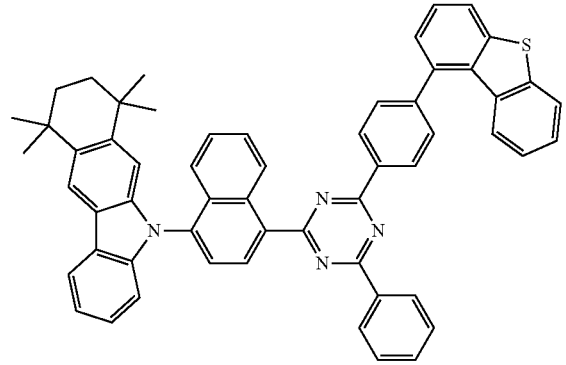

160
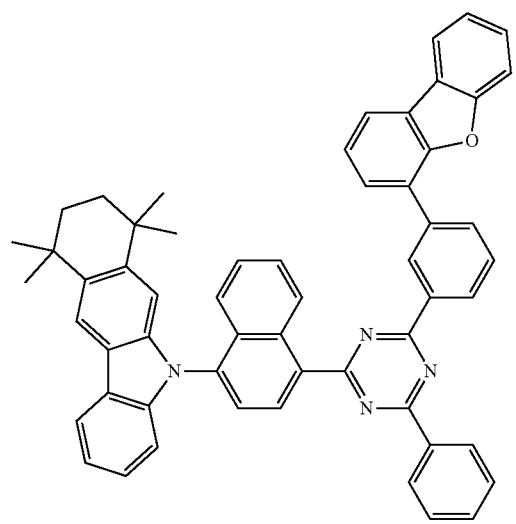
161
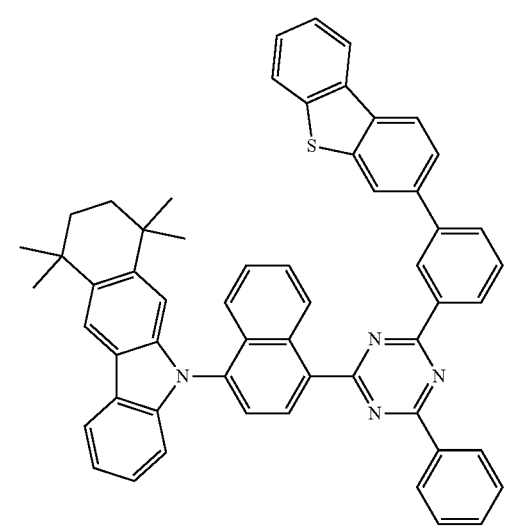
162
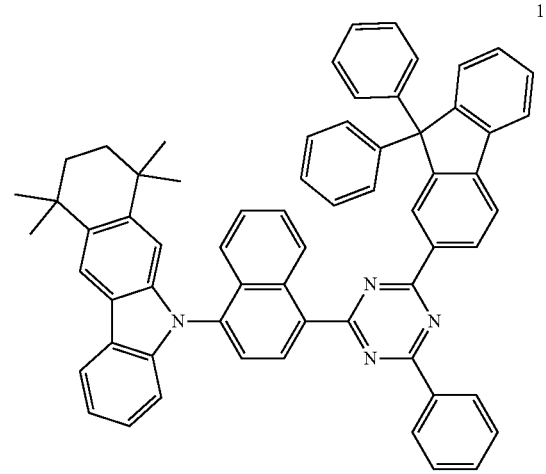
163
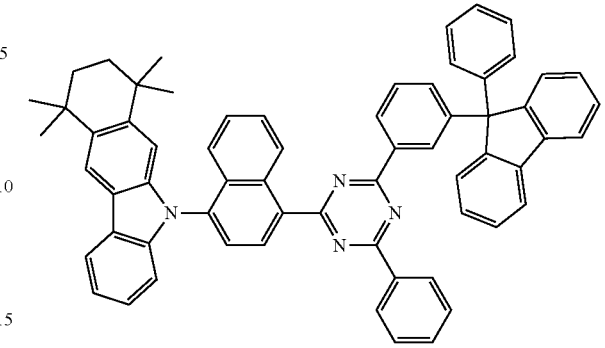
164
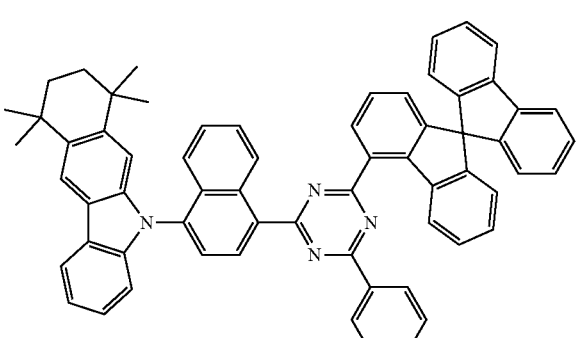
165
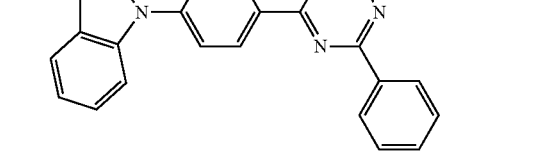
166
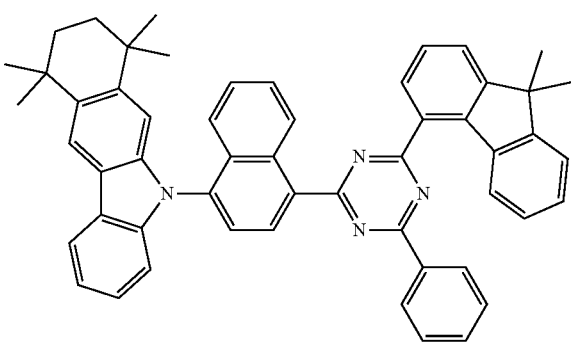

167
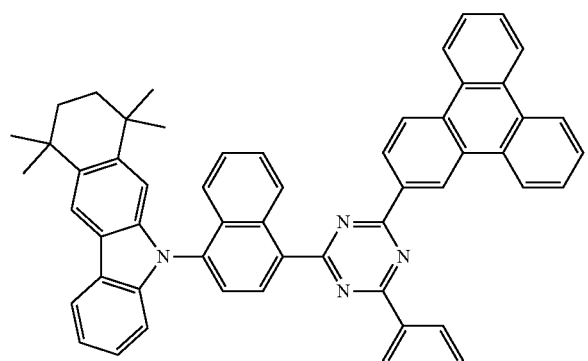
171
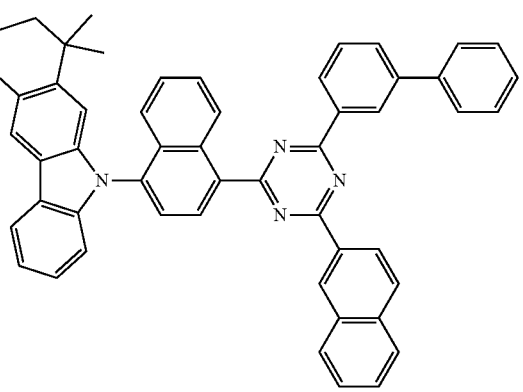
168
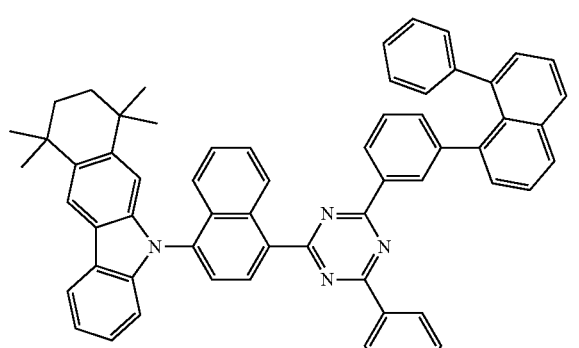
169
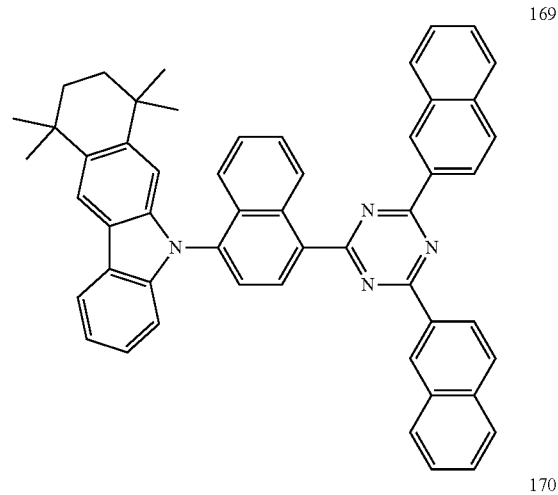
172
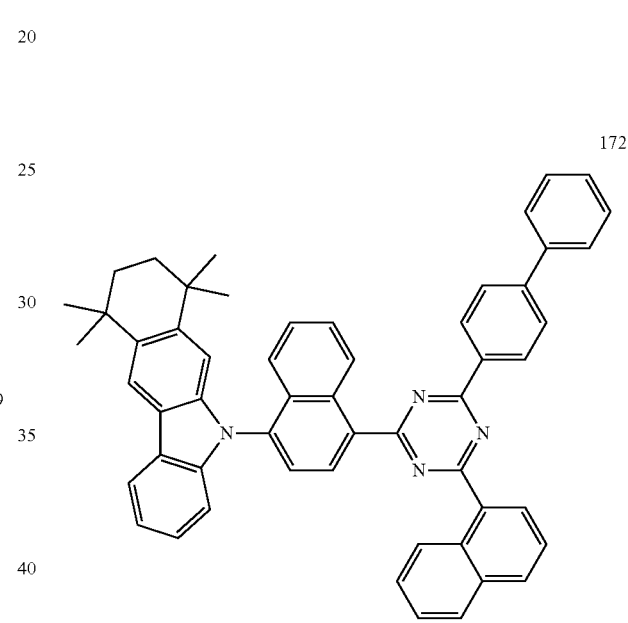
170
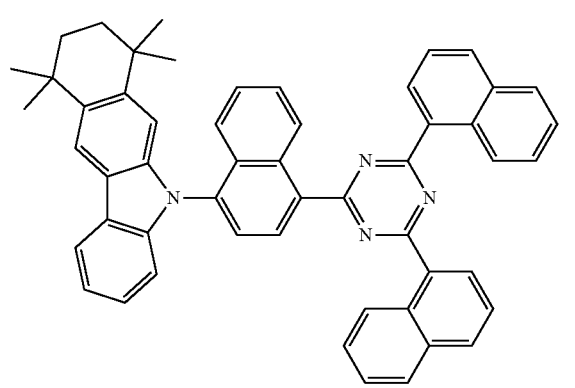
173
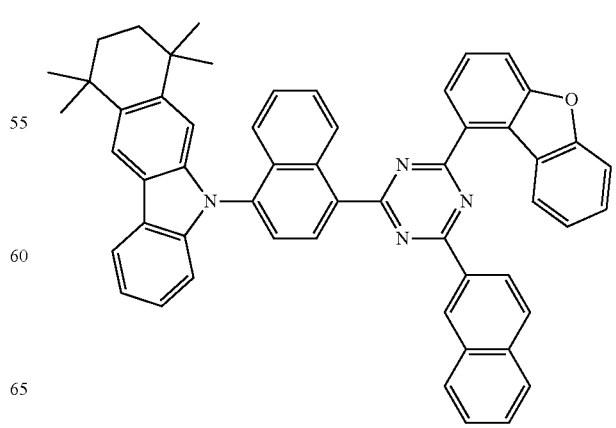

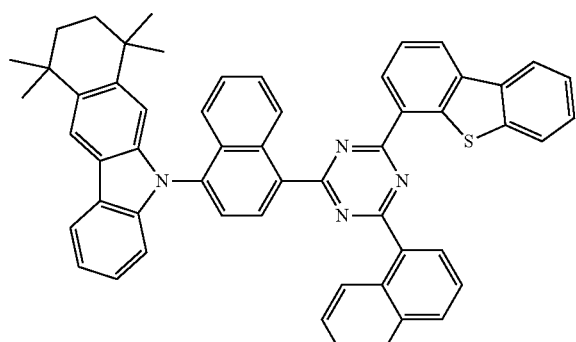
174
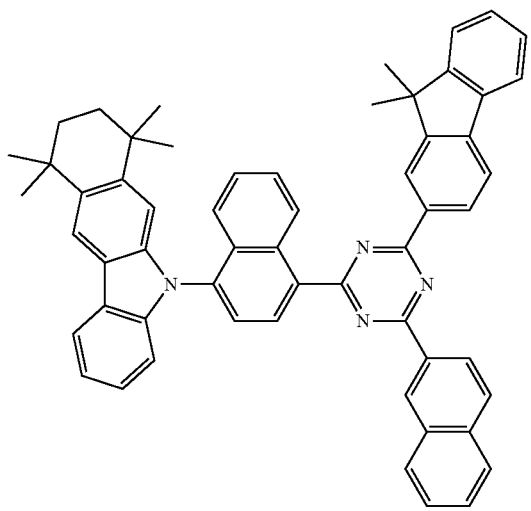
177
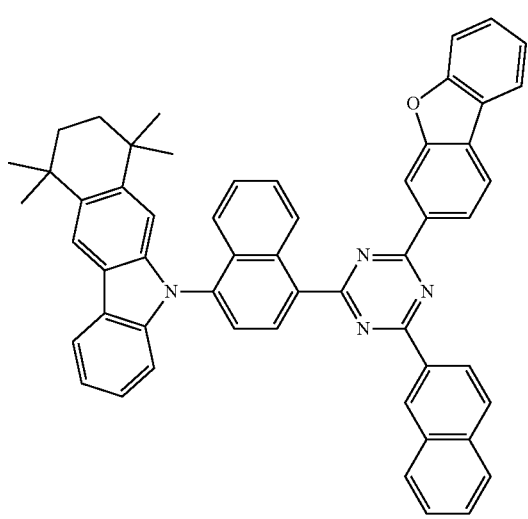
175
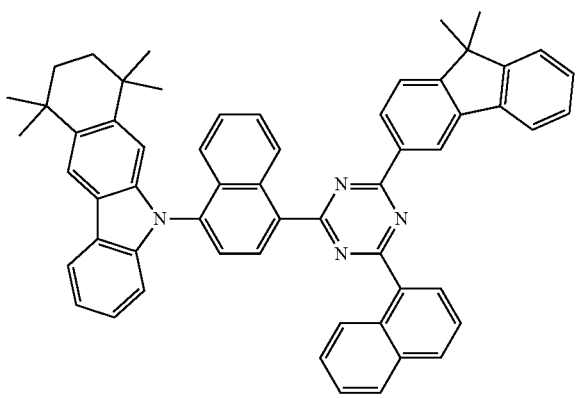
178
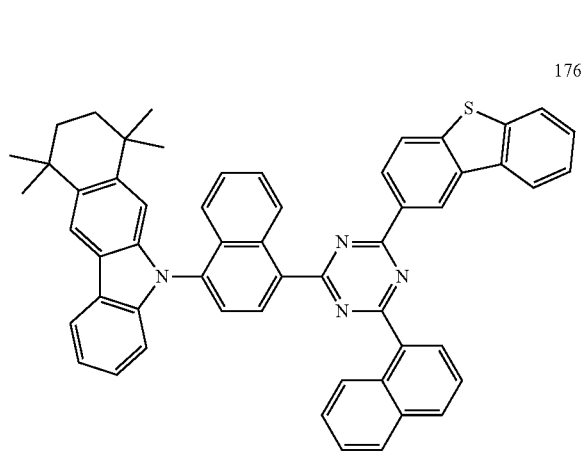
176
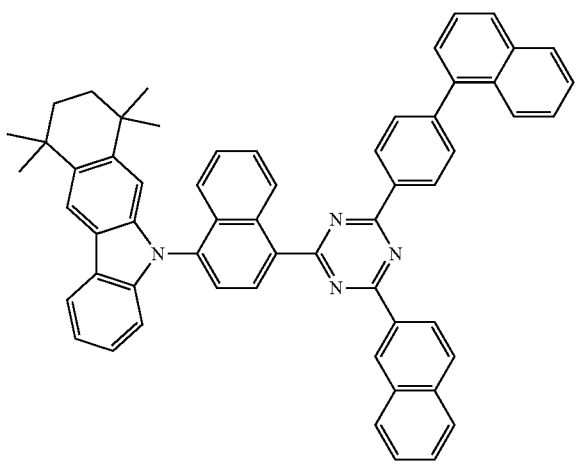
179

-continued
180
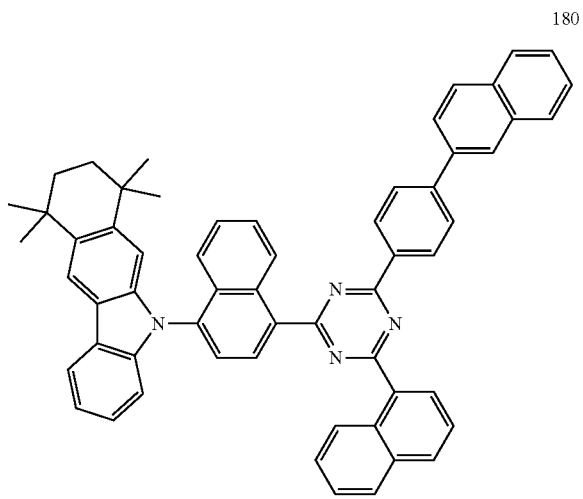
181
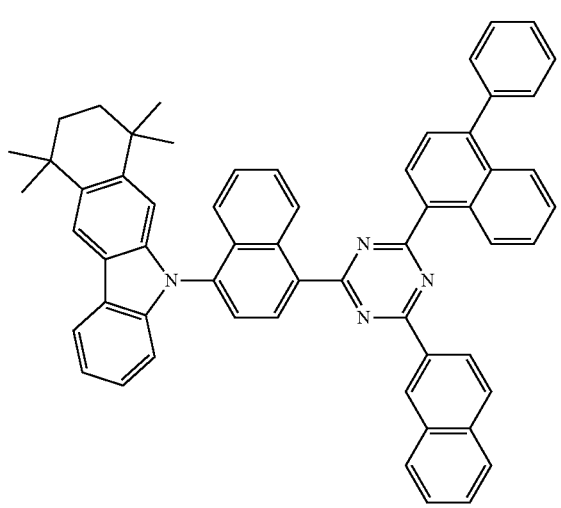
182
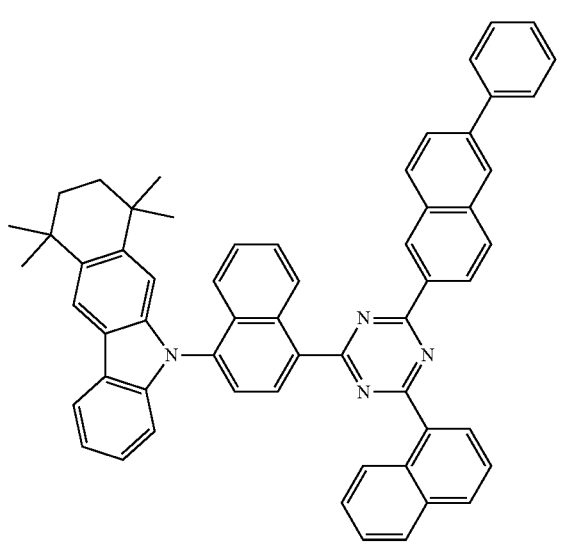
-continued
183
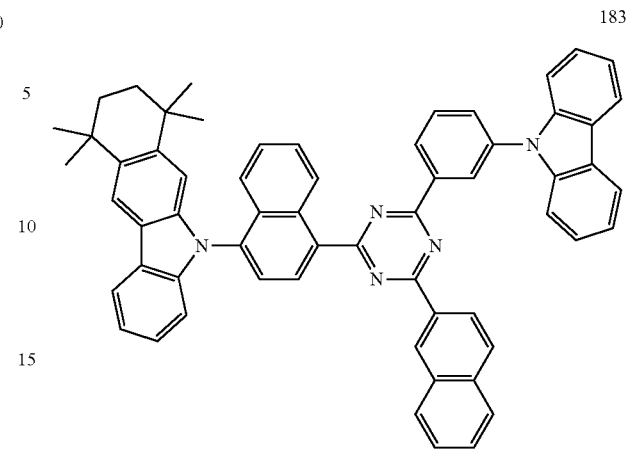
184
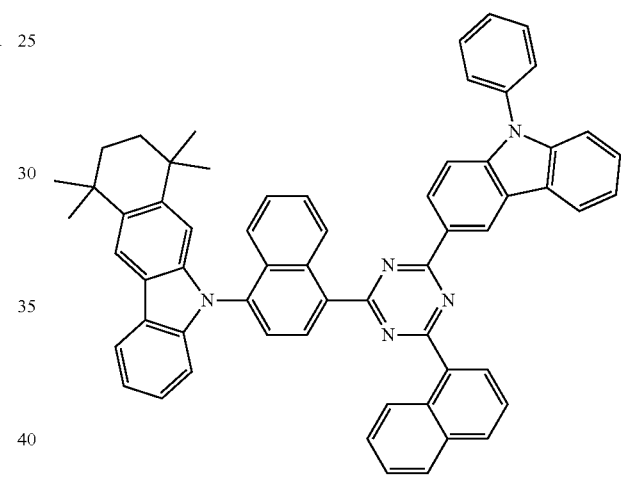
185
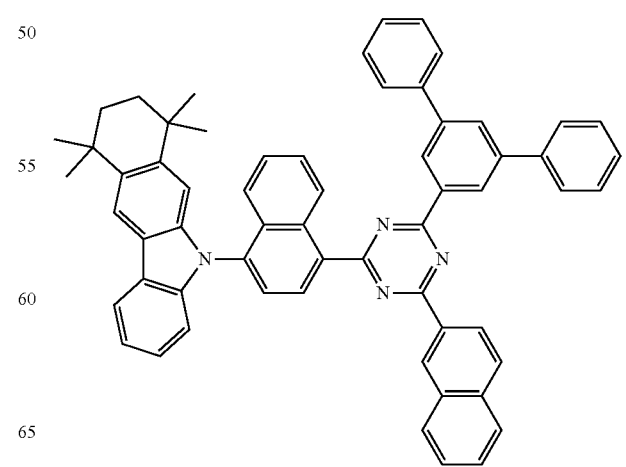

-continued
186
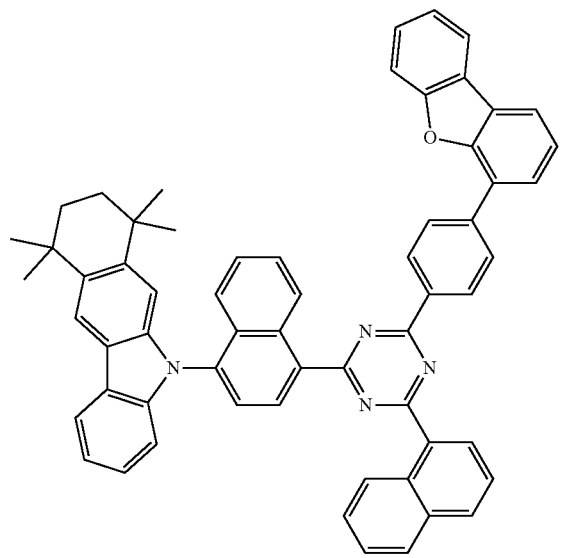
187
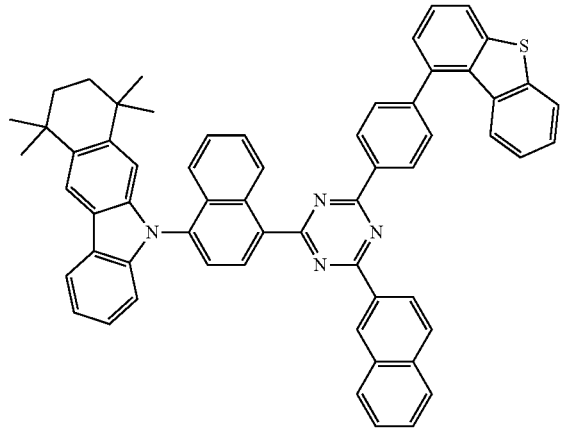
188
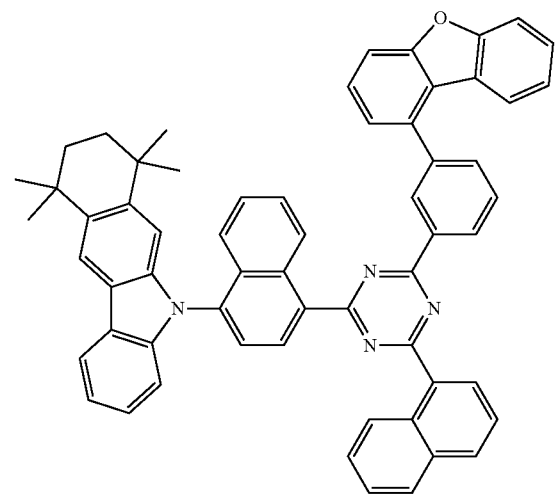
189
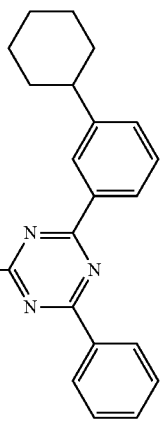
190
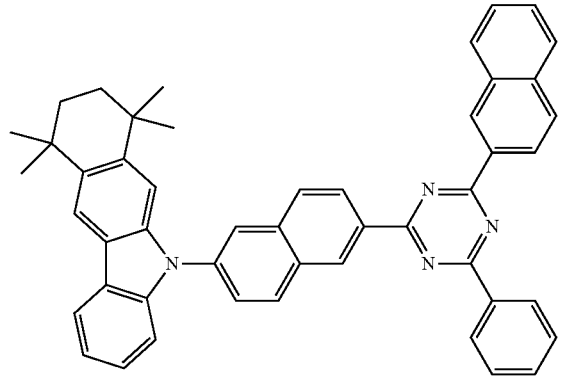
191
192
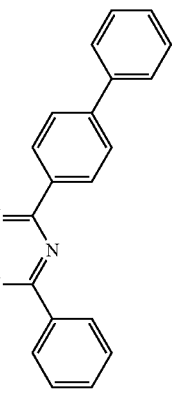

193
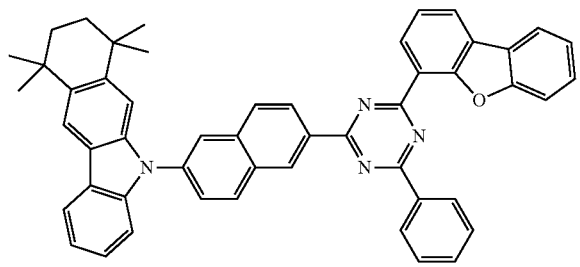
194
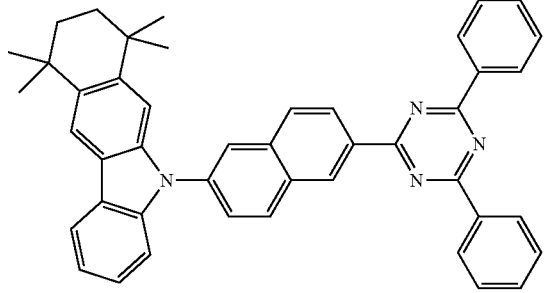
195
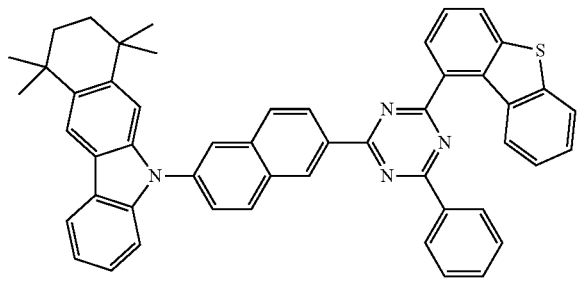
196
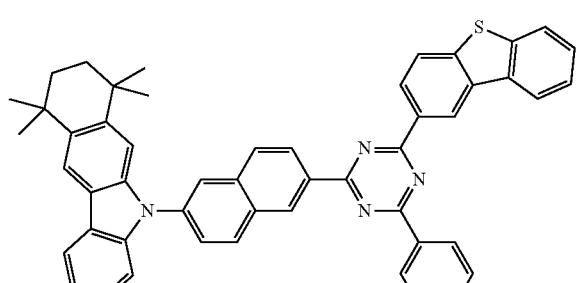
197
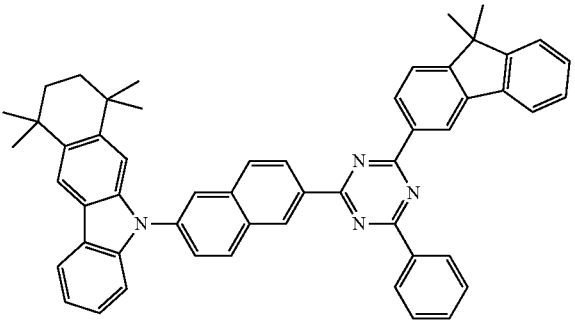
198
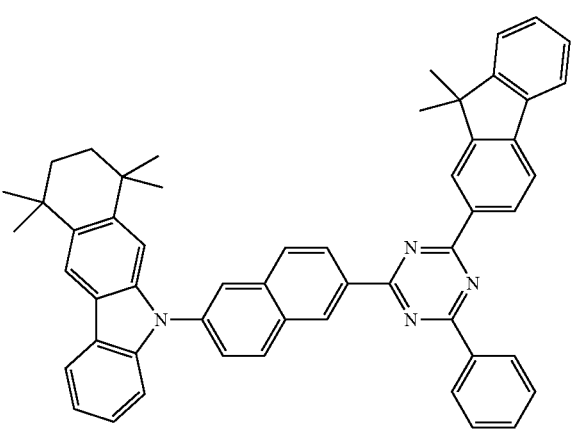
199
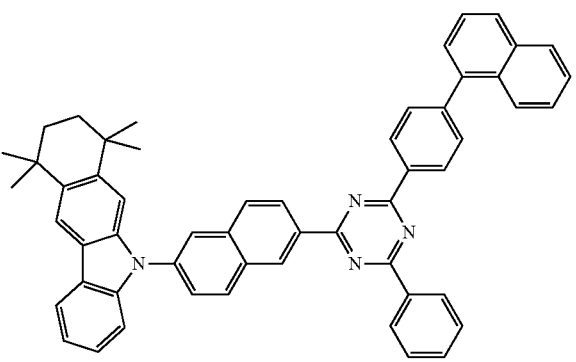
200
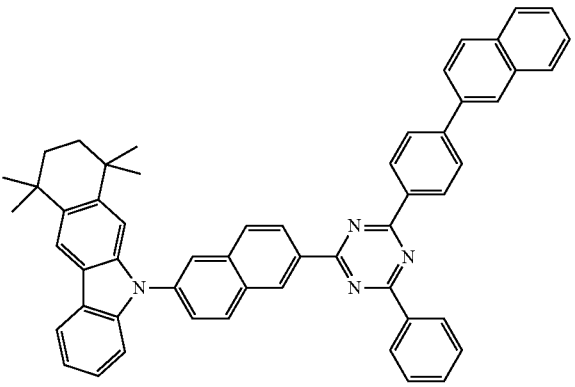

201
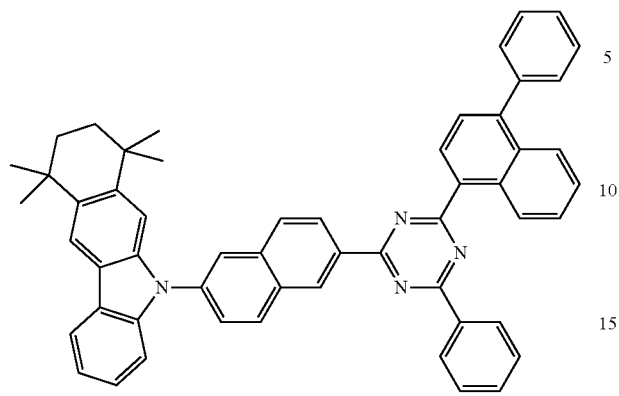
202
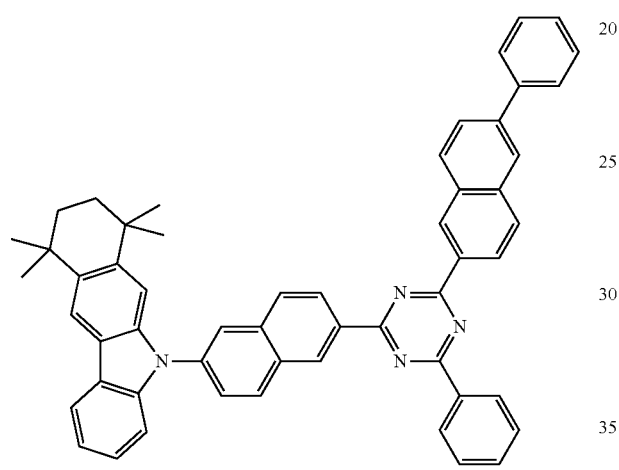
203
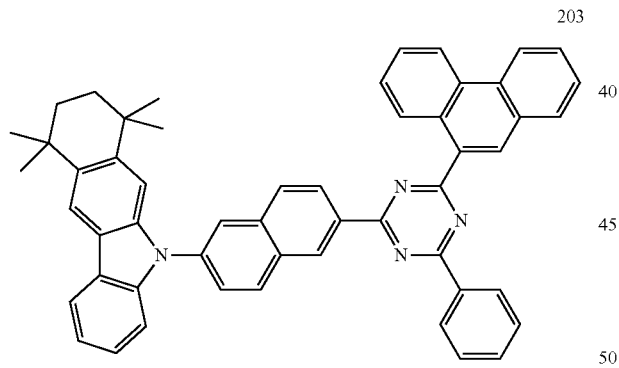
204
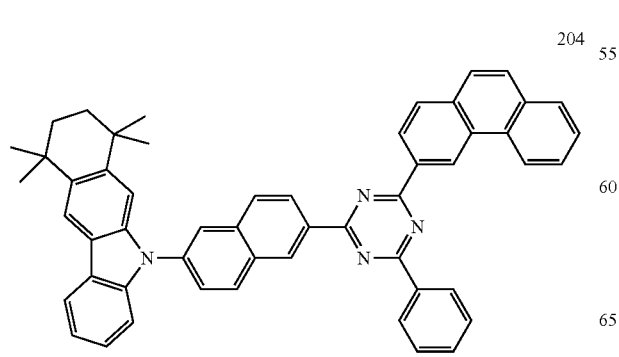
205
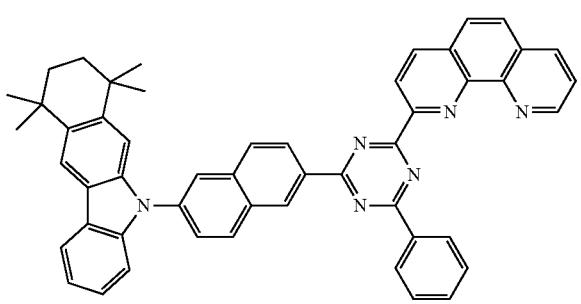
206
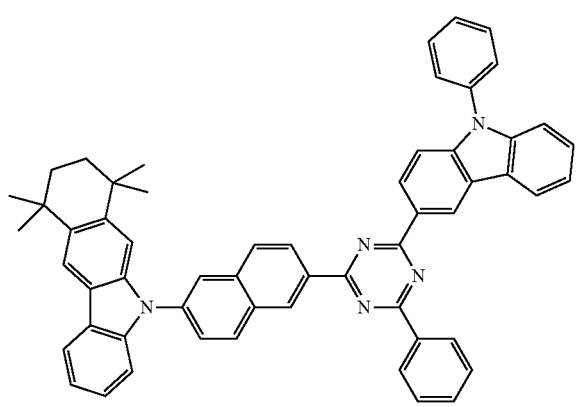
207
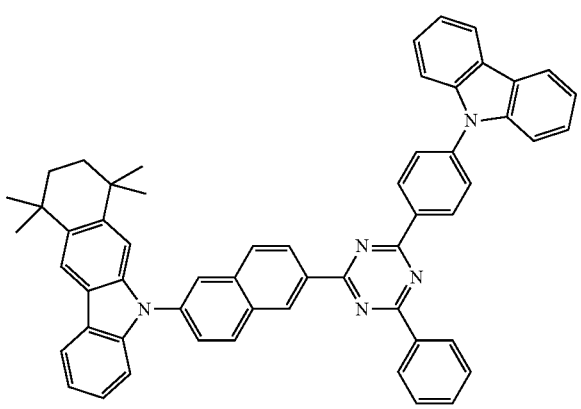
208
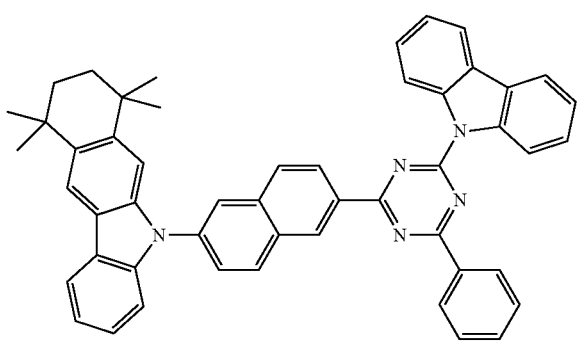

209
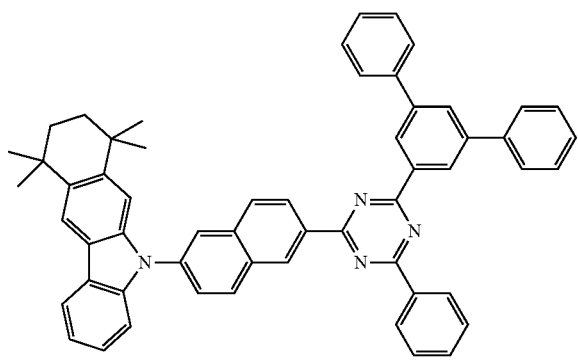
210
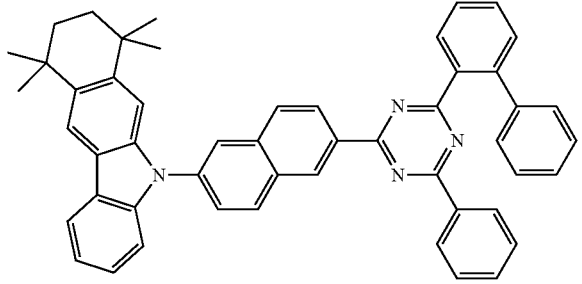
211
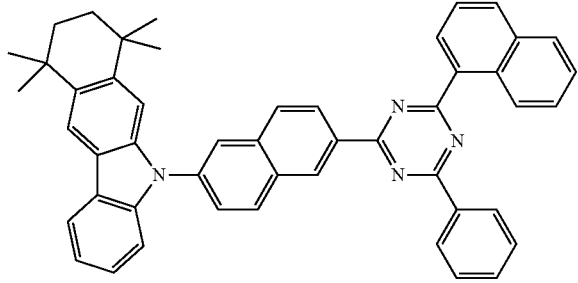
212
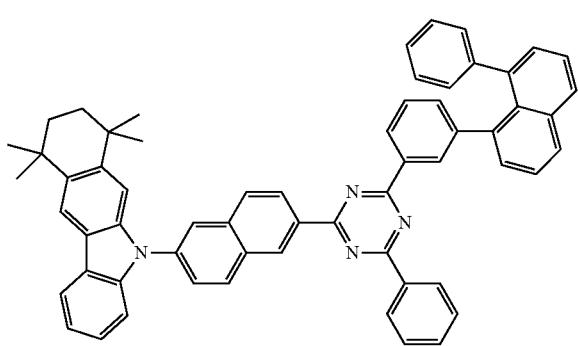
213
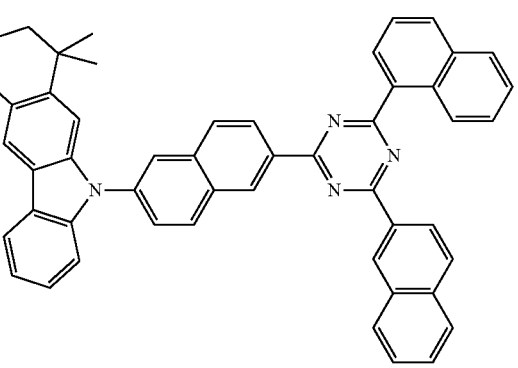
214
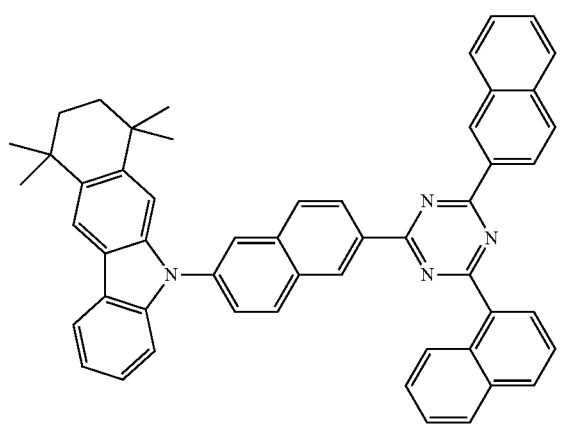
215
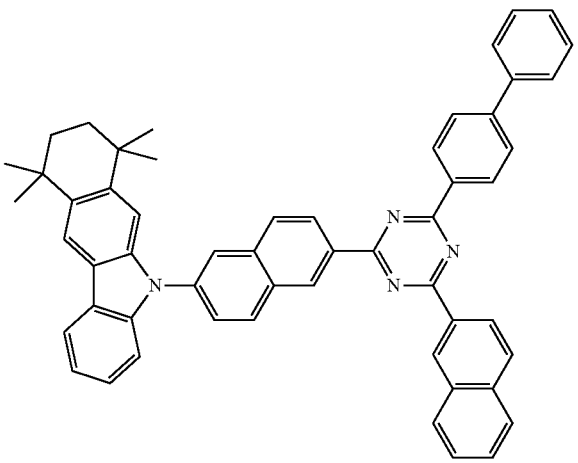
216
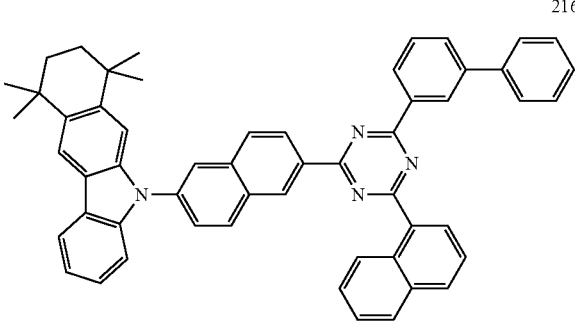

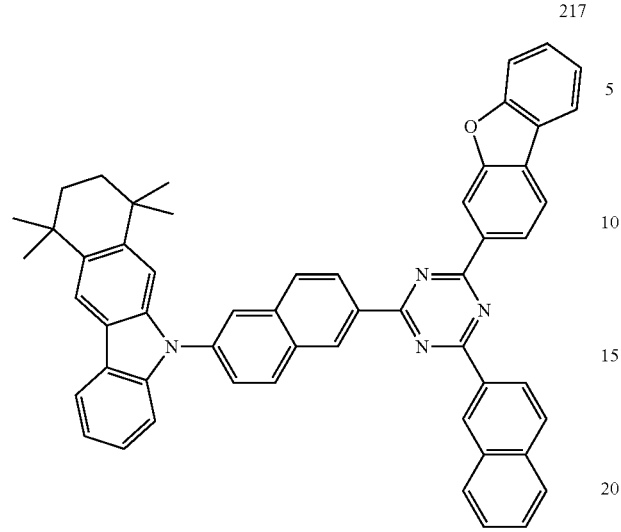
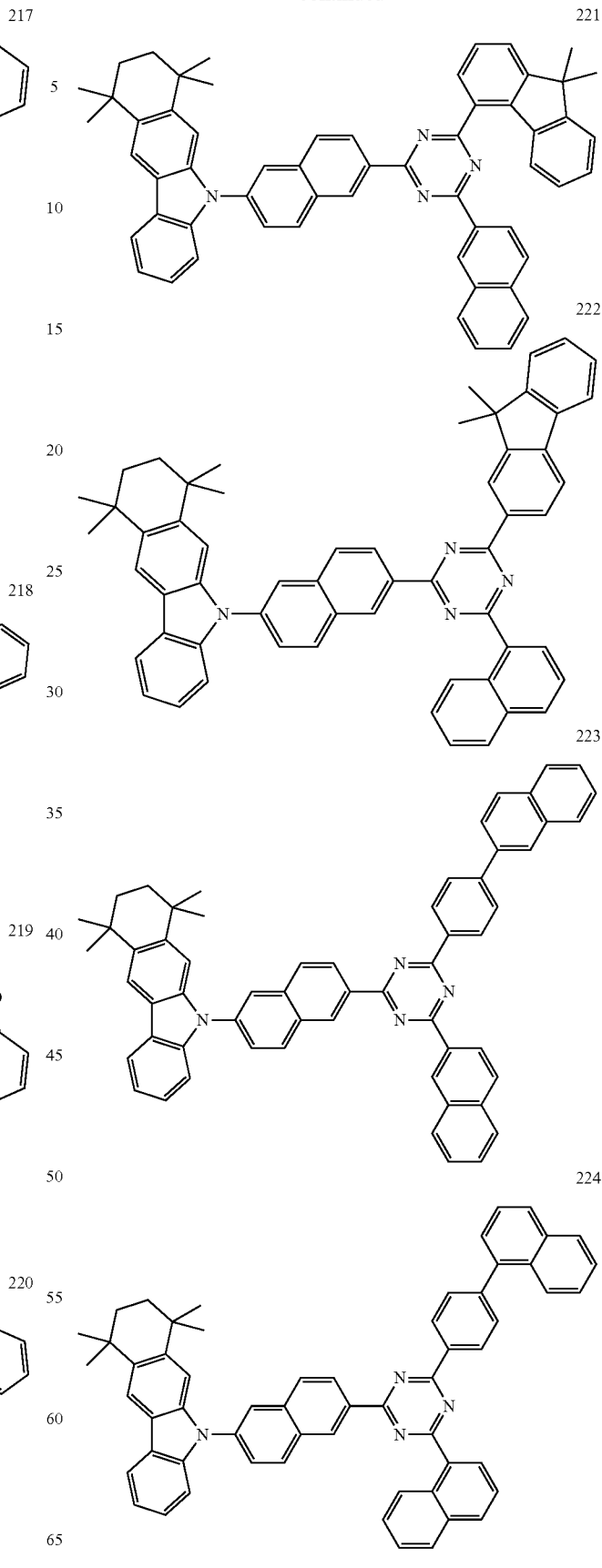

131 132
225 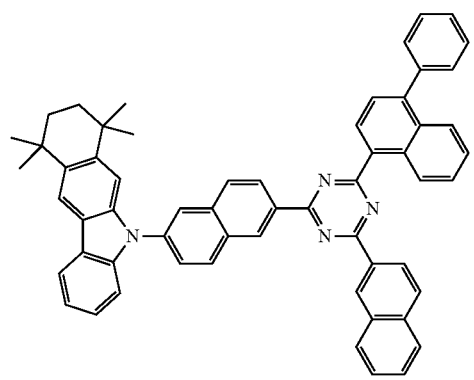
226 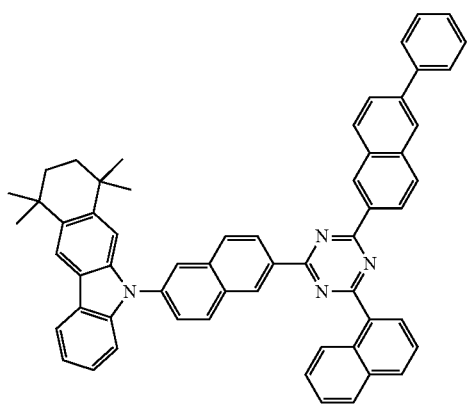
227 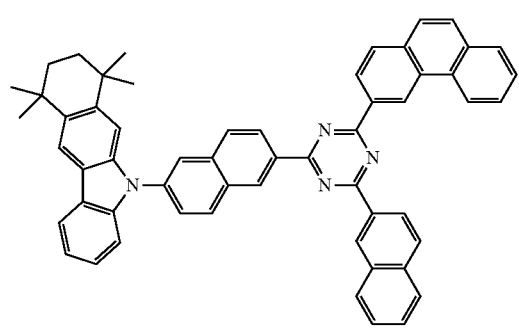
228 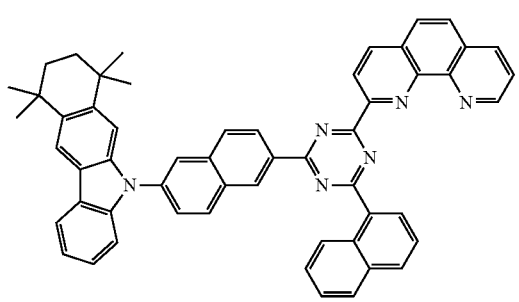
229 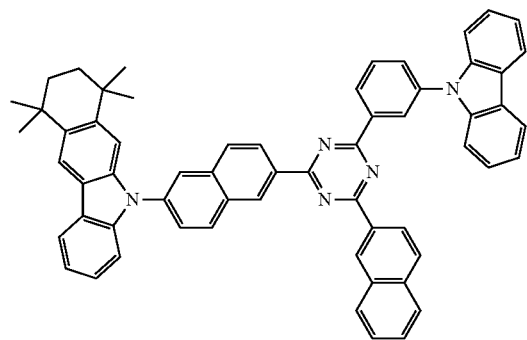
230 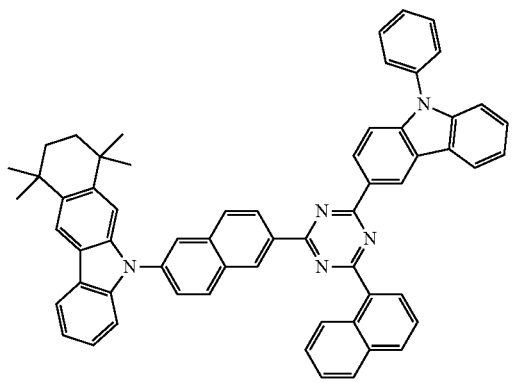
231 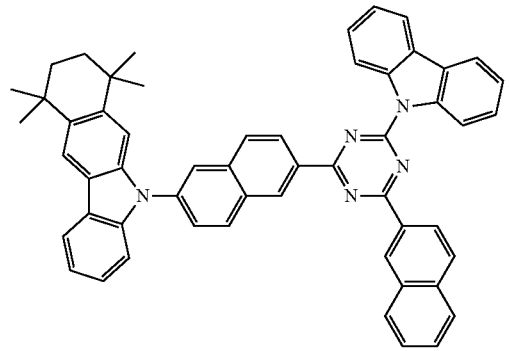
232 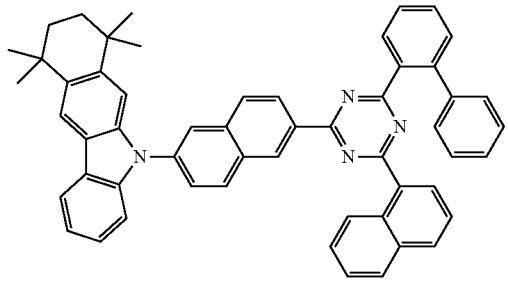

-continued
| 233 | 234 |
|---|---|
| 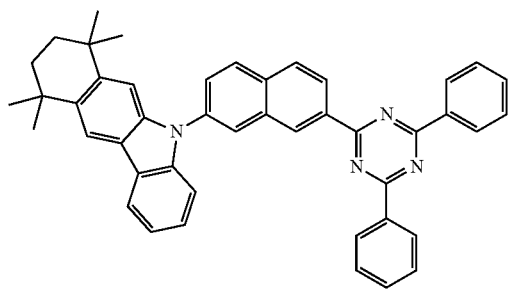 | 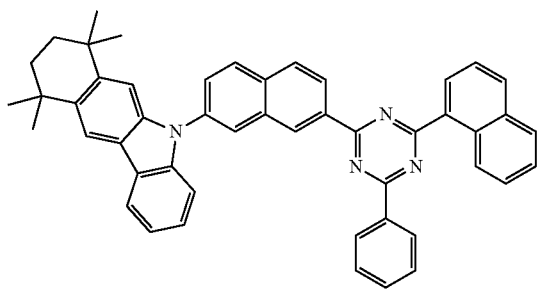 |
| 235 | 236 |
| 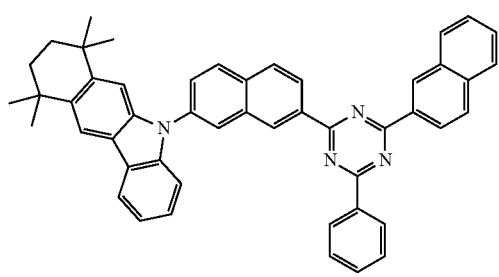 | 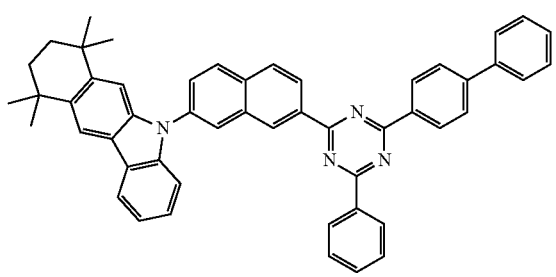 |
| 237 | 238 |
| 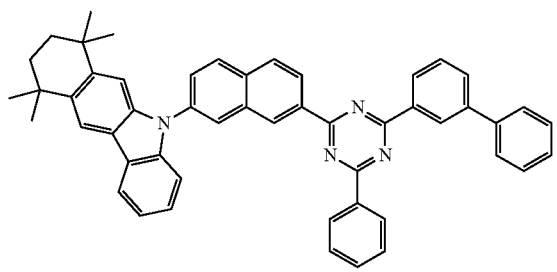 | 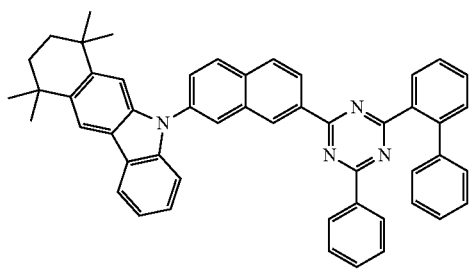 |
| 239 | 240 |
| 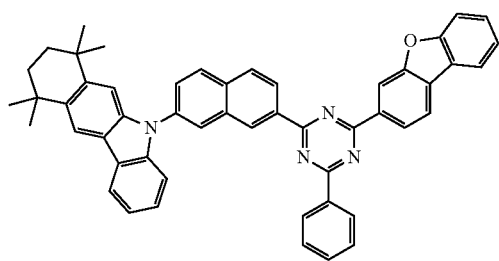 | 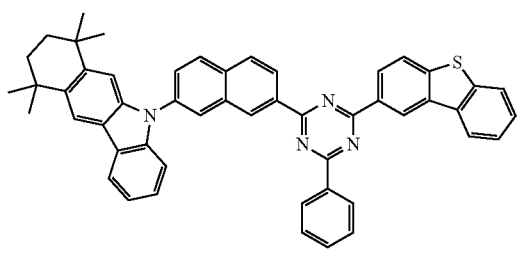 |
| 241 | 242 |
| 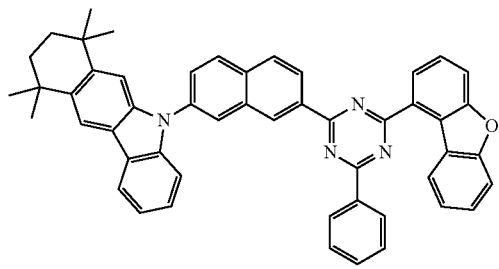 | 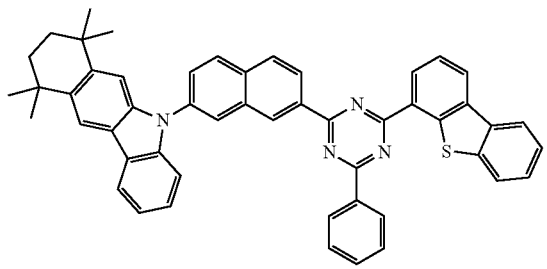 |

243
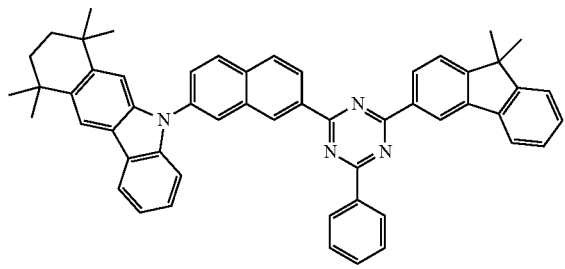
244
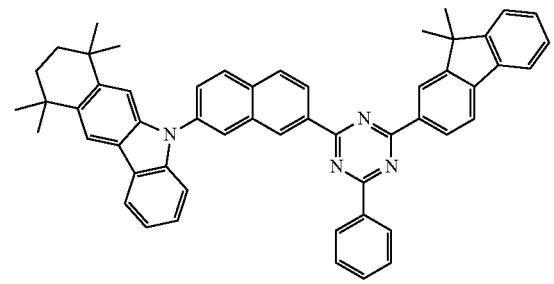
245
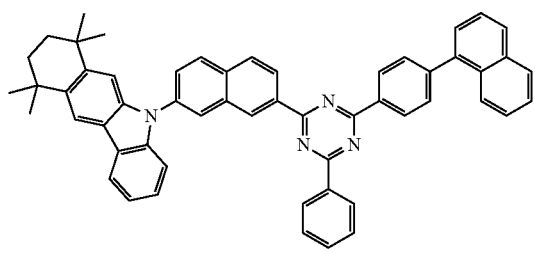
246
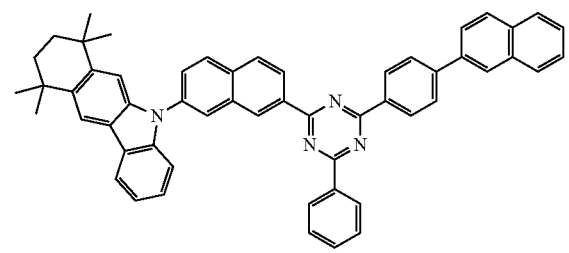
247
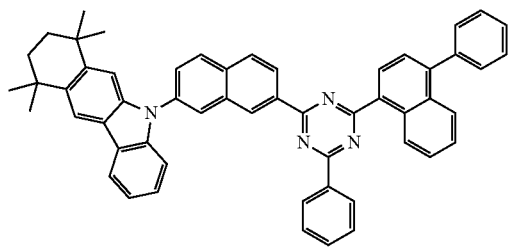
248
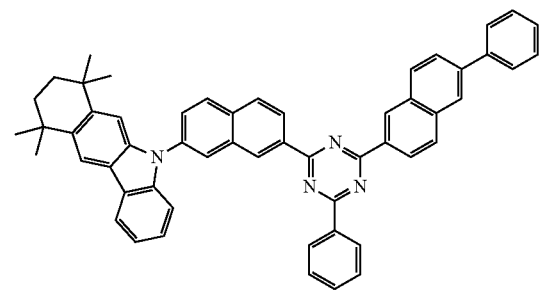
249
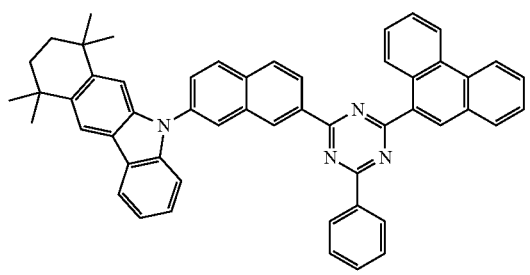
250
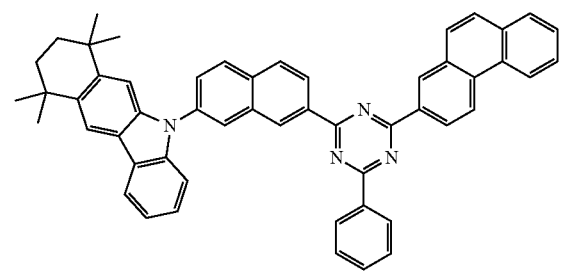
251
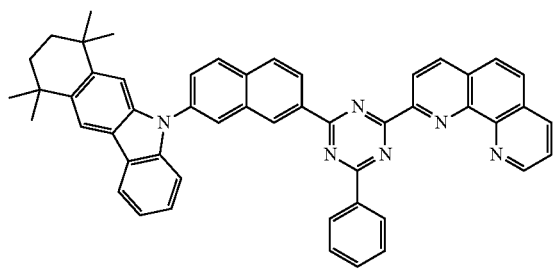
252
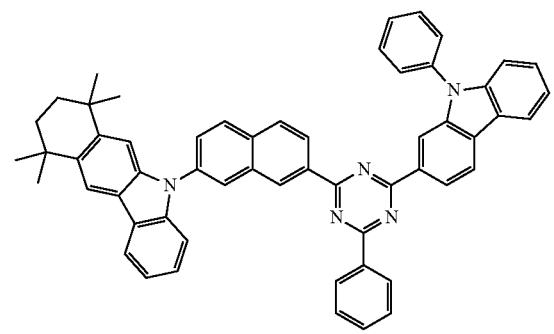

-continued
253
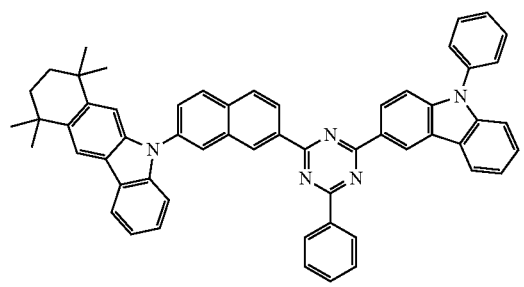
254
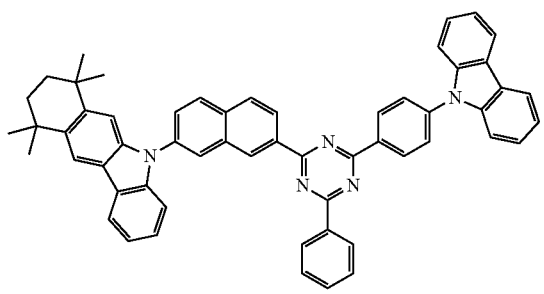
255
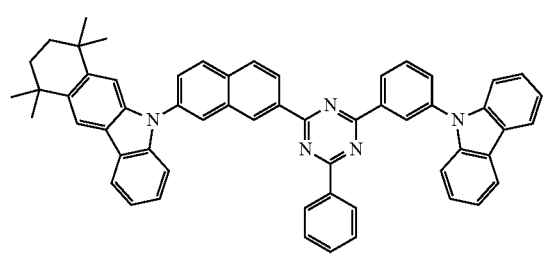
256
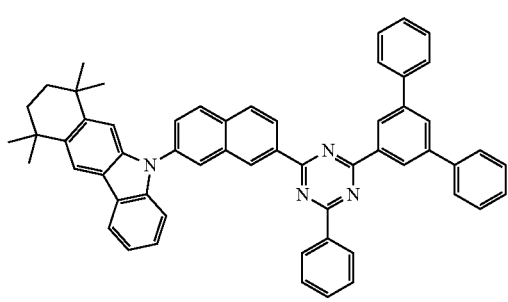
257
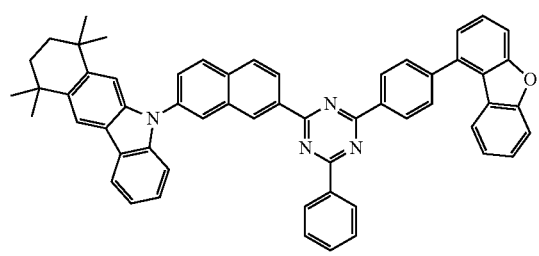
258
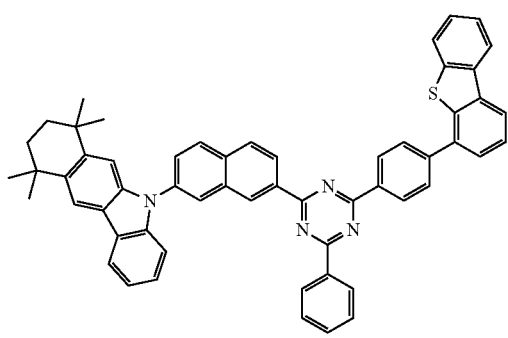
259
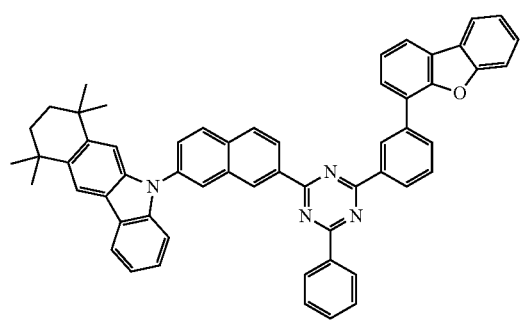
260
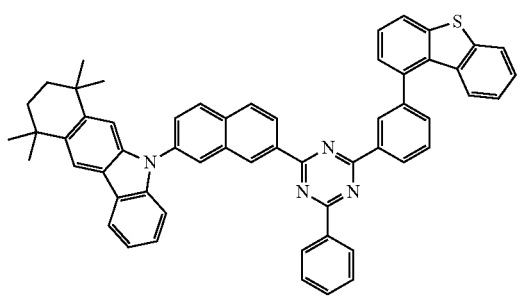

261 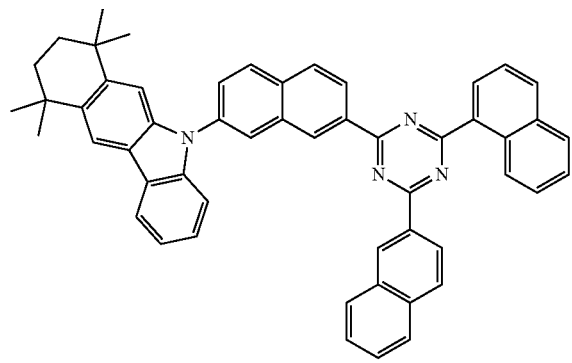
262 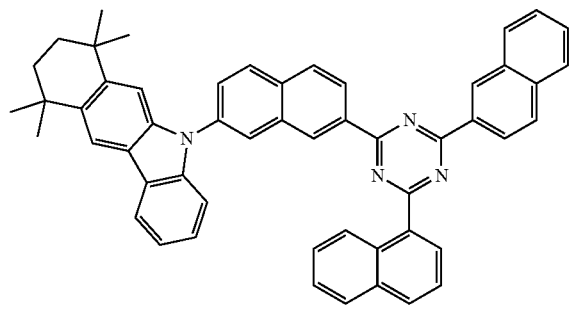
263 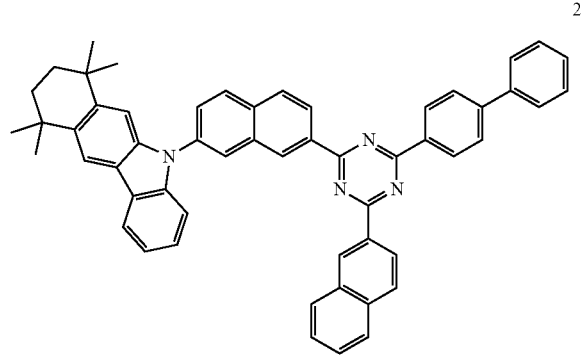
264 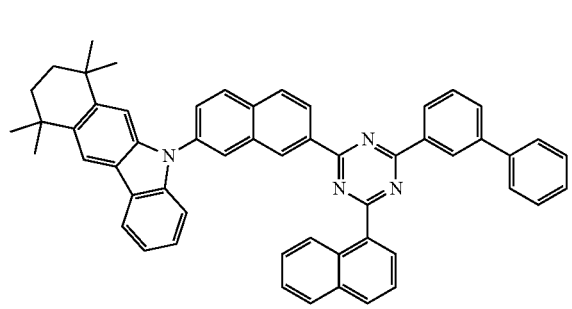
265 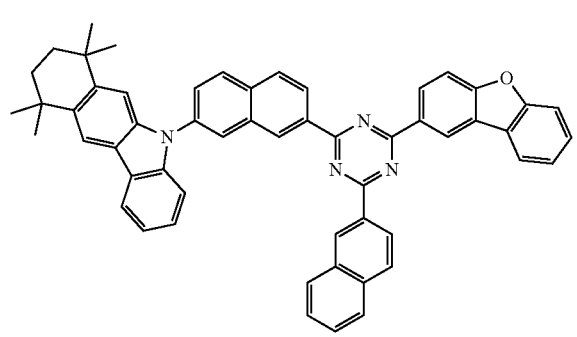
266 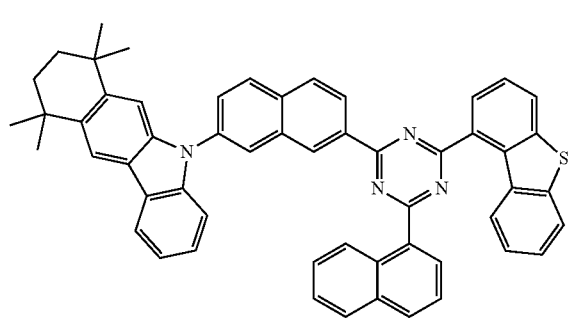
267 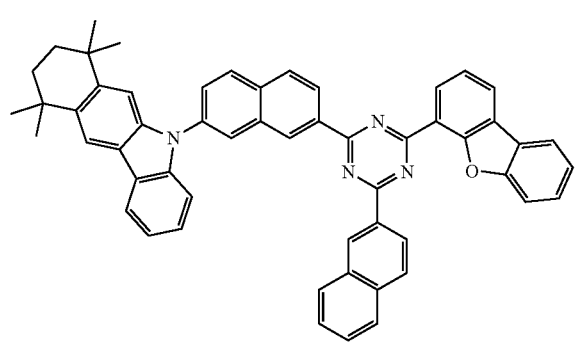
268 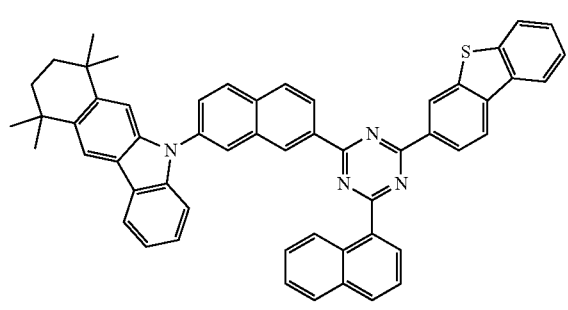

-continued
269
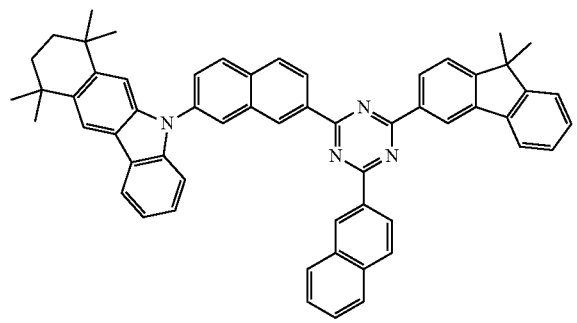
270
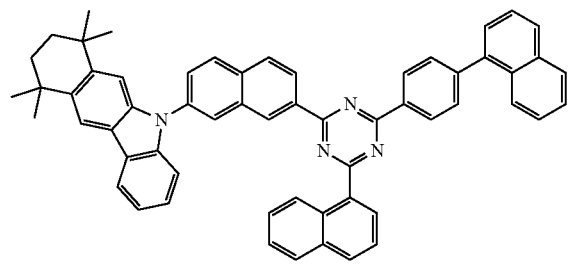
271
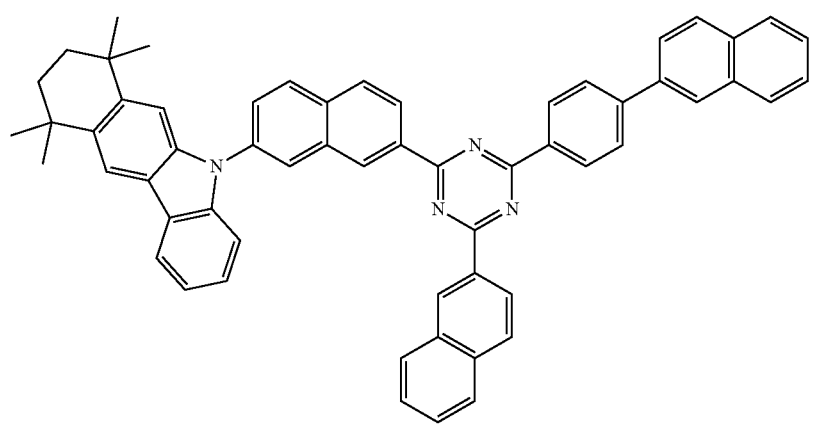
272
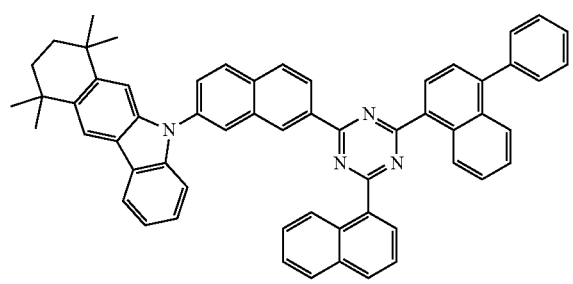
273
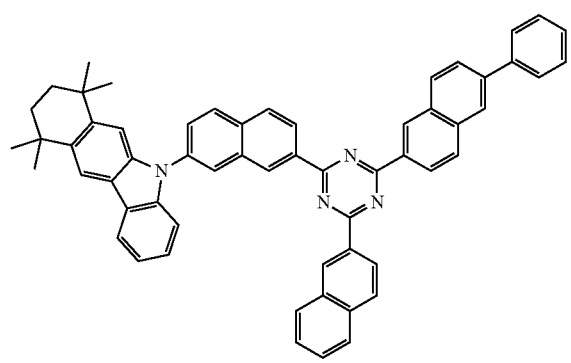
274
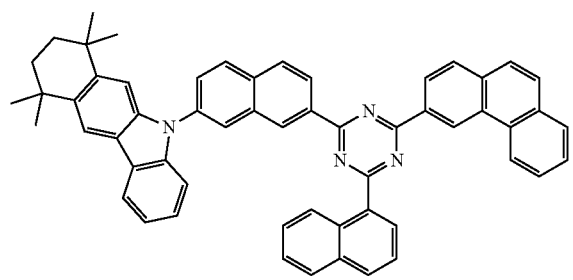
275
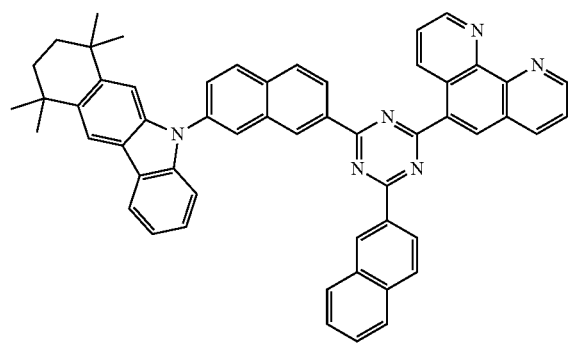

276
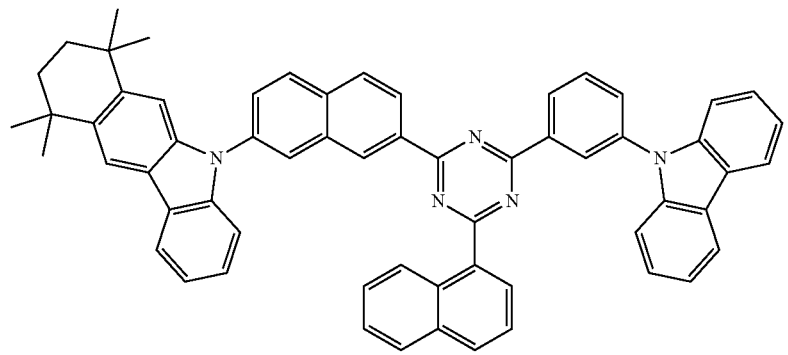
277 278
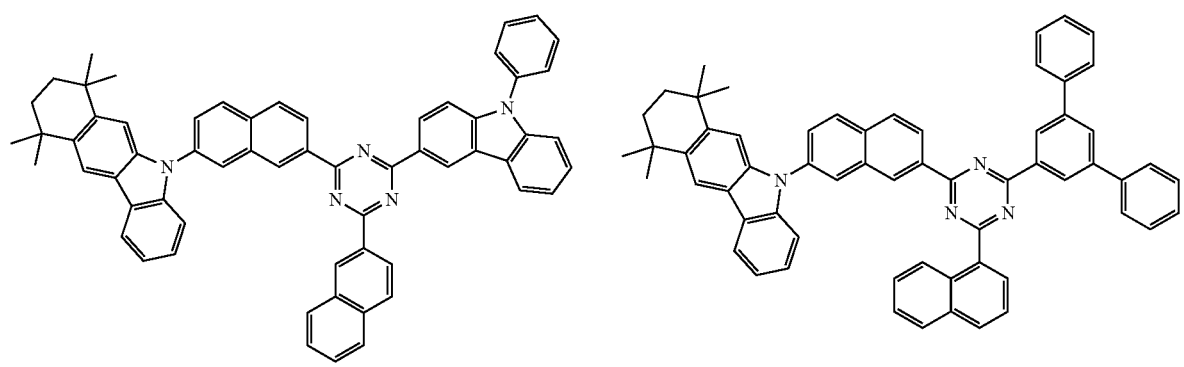
279 280
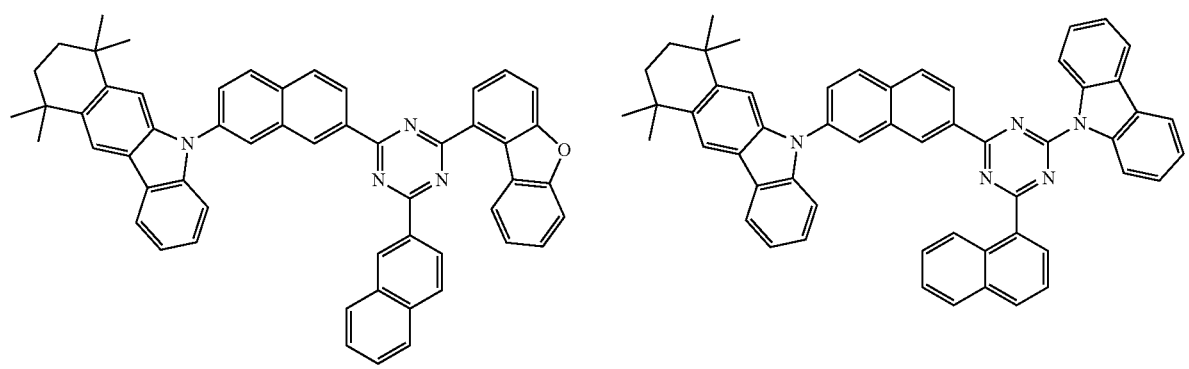

281
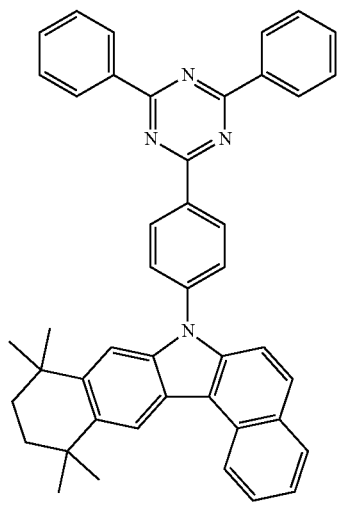
282
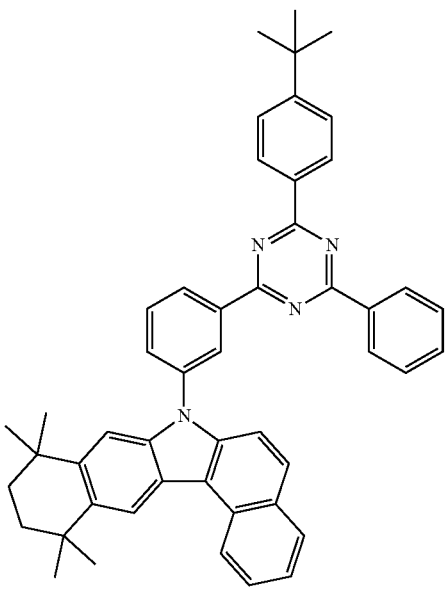
283
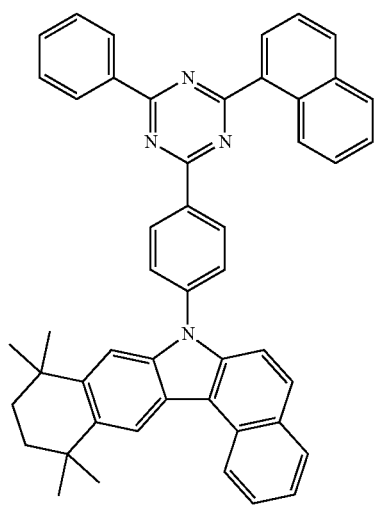
284
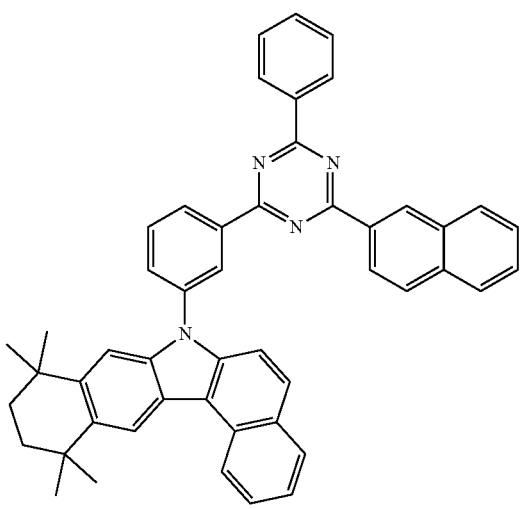
285
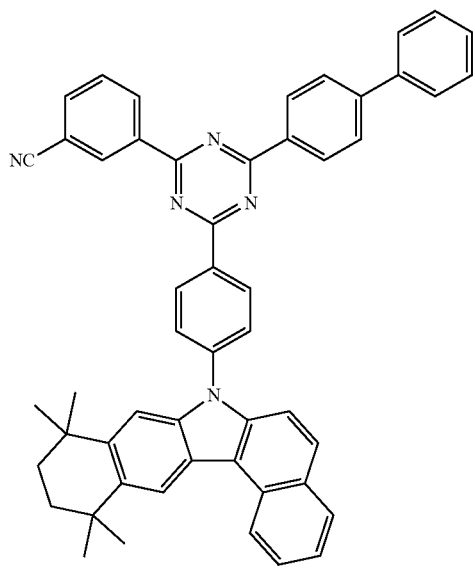
286
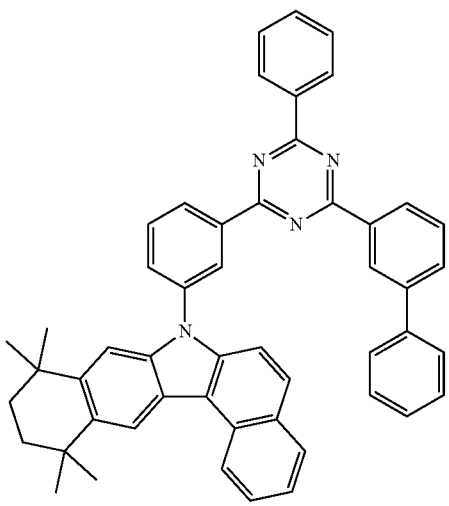

-continued
287
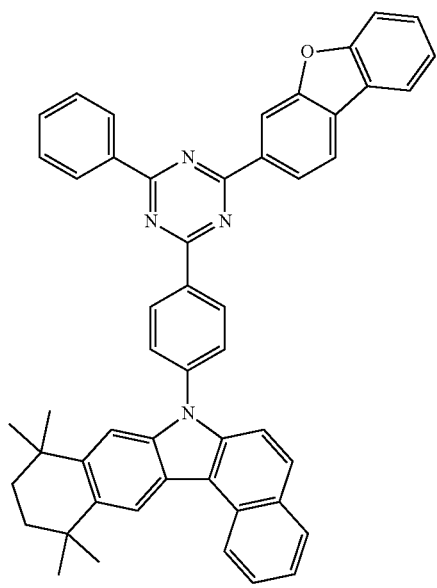
288
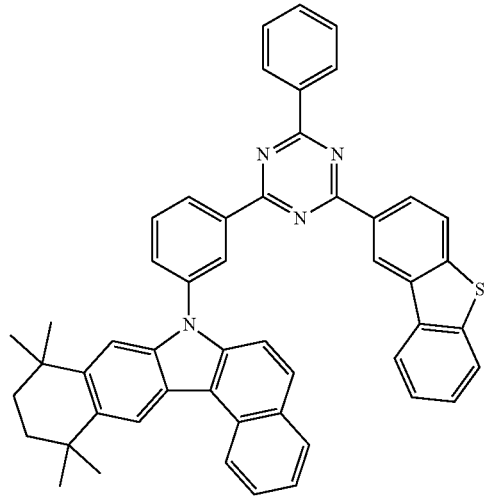
289
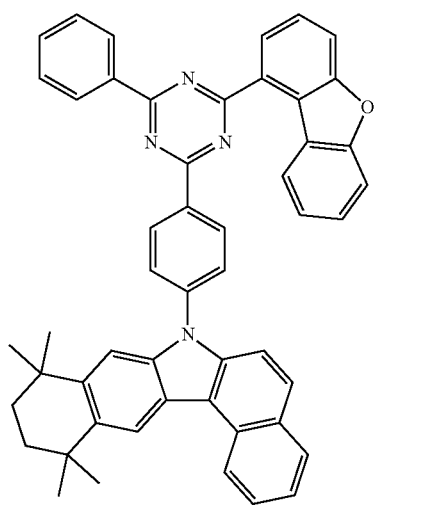
290
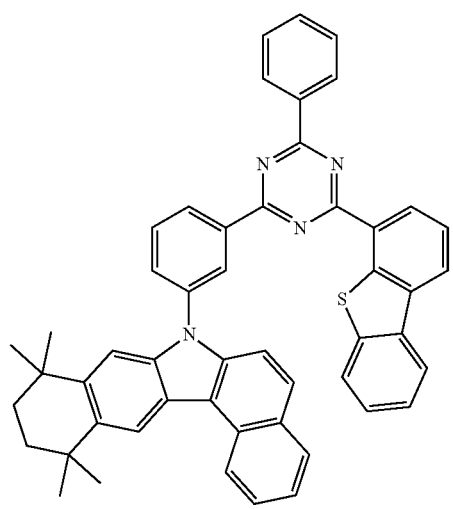
291
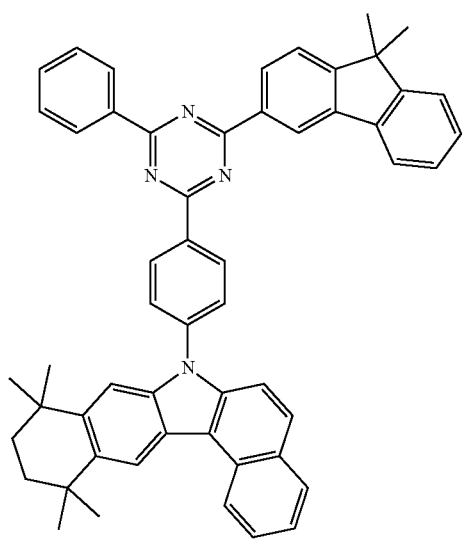
292
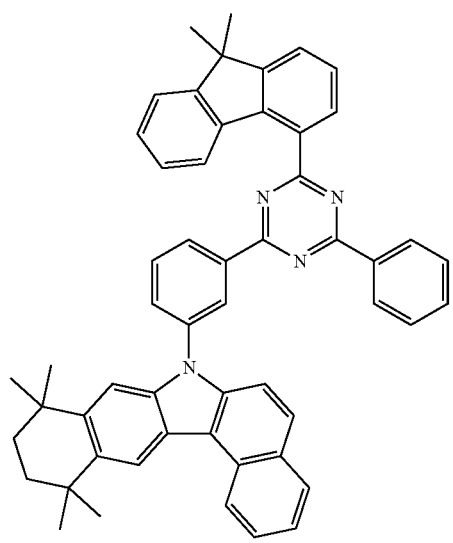

-continued
293
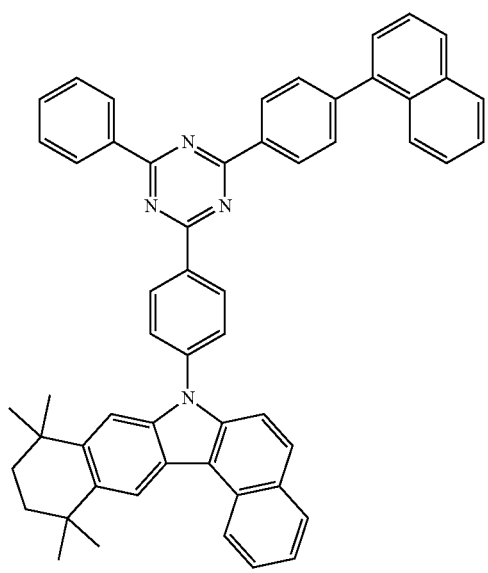
294
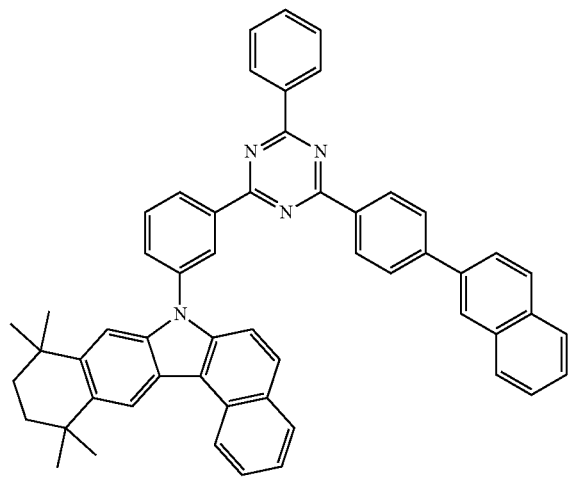
295
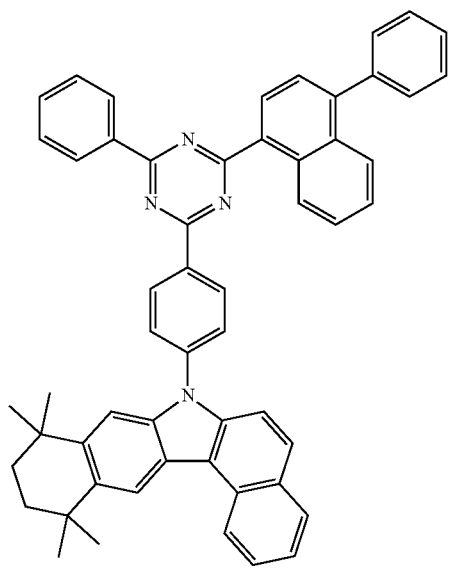
296
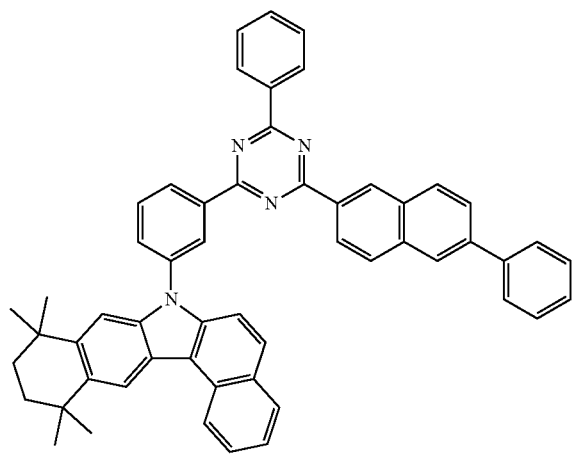

151  152
-continued
297
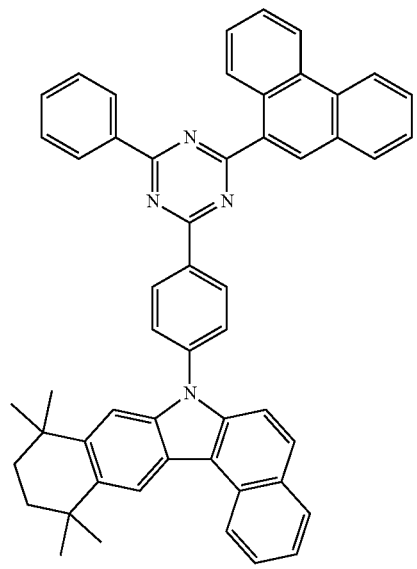
298
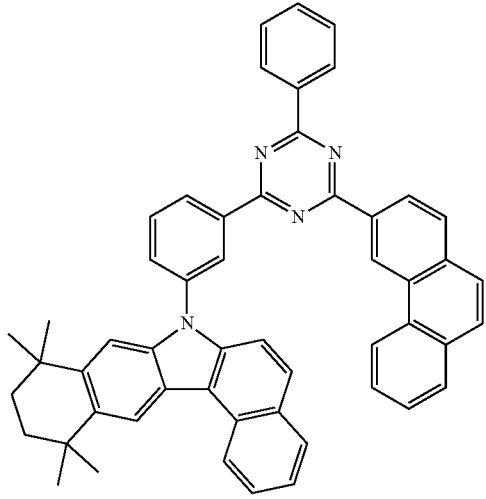
299
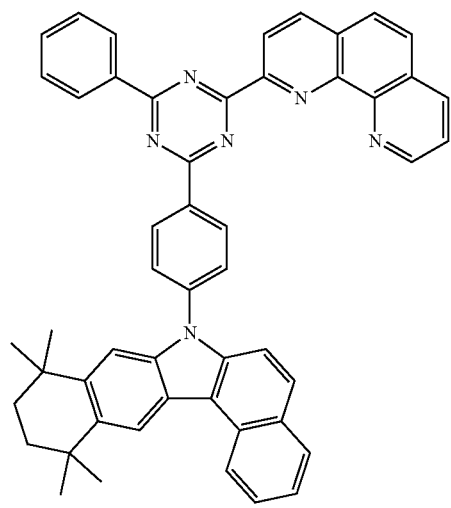
300
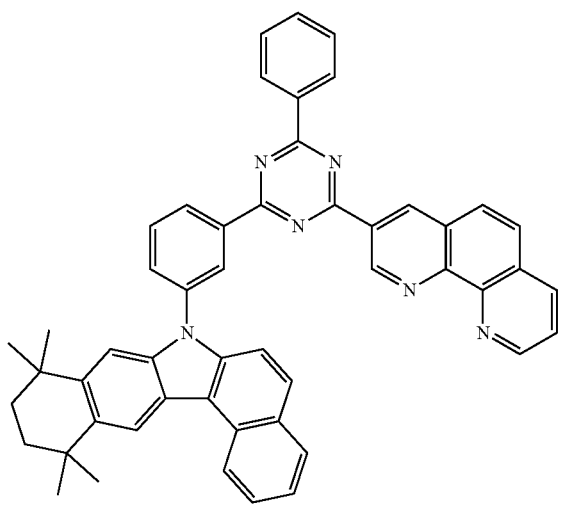

-continued
153     301
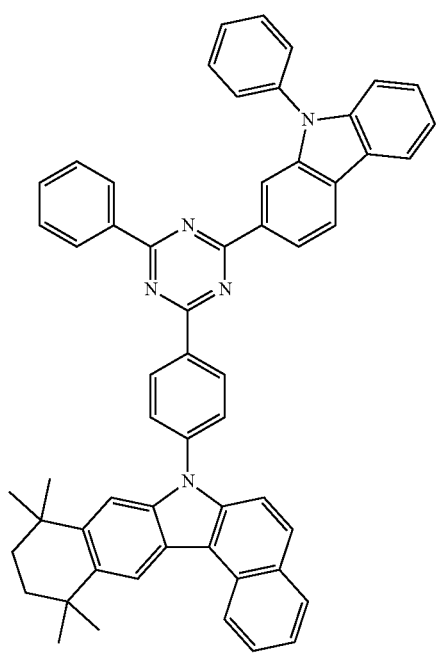
154     302
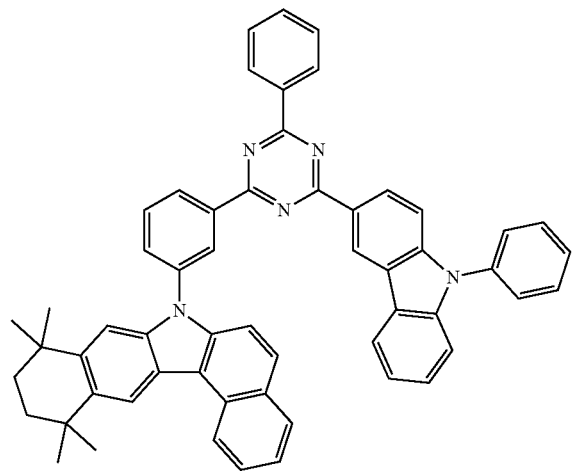
303
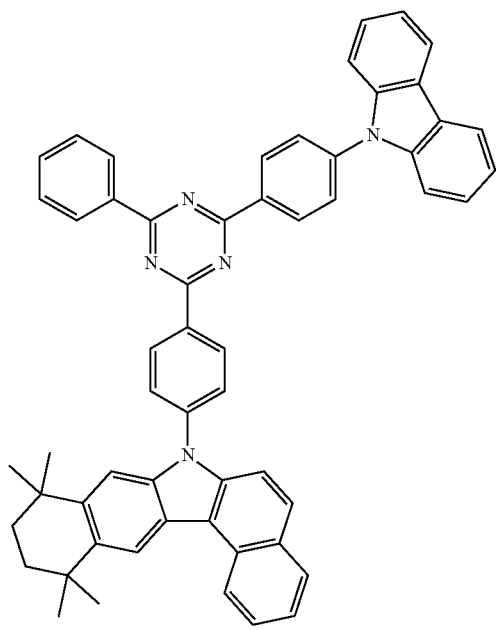
304
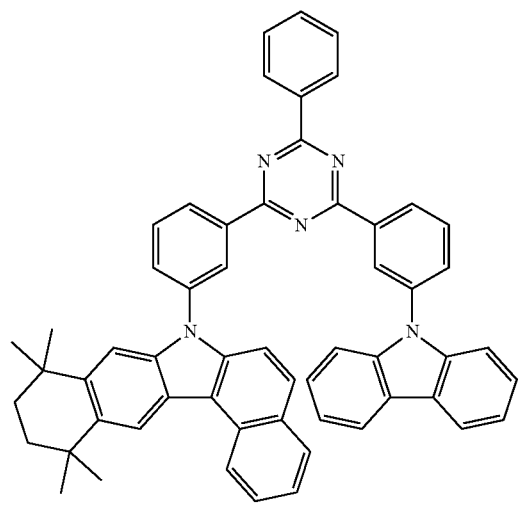

-continued
305
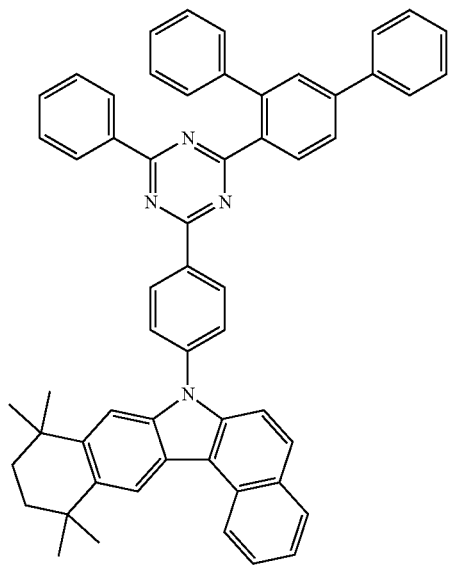
306
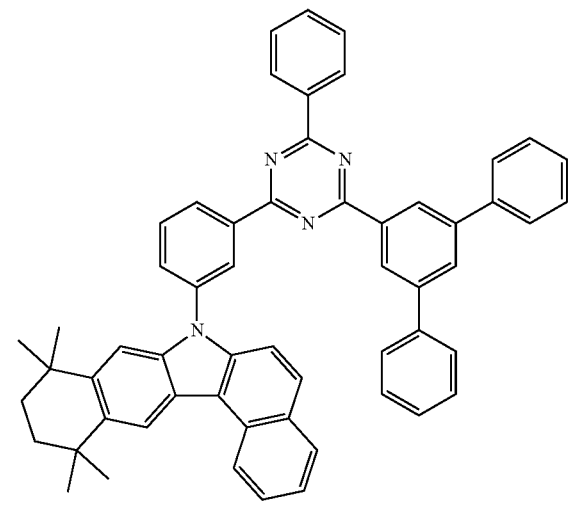
307
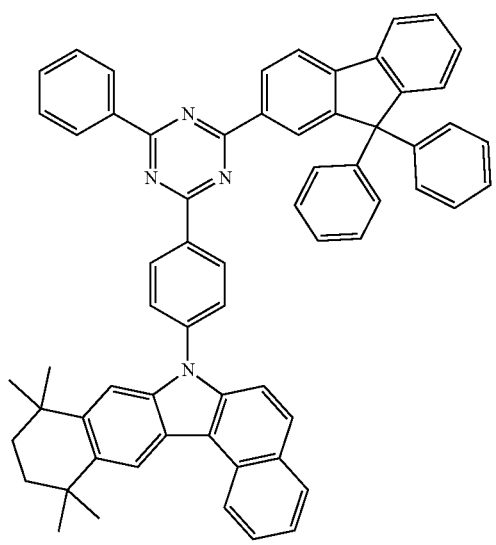
308
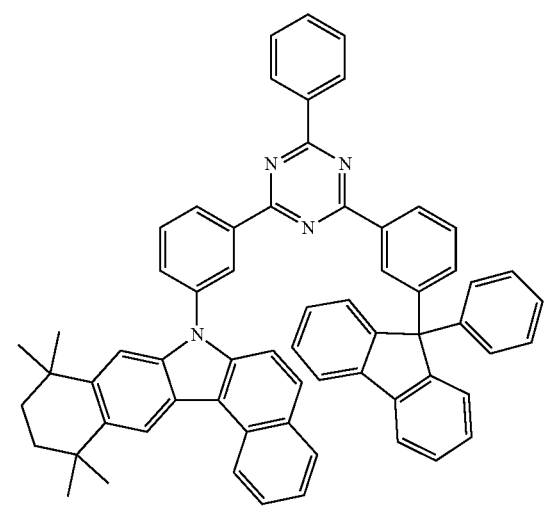
309
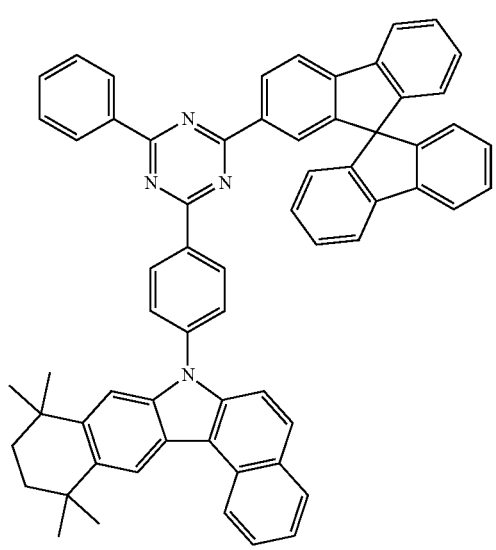
310
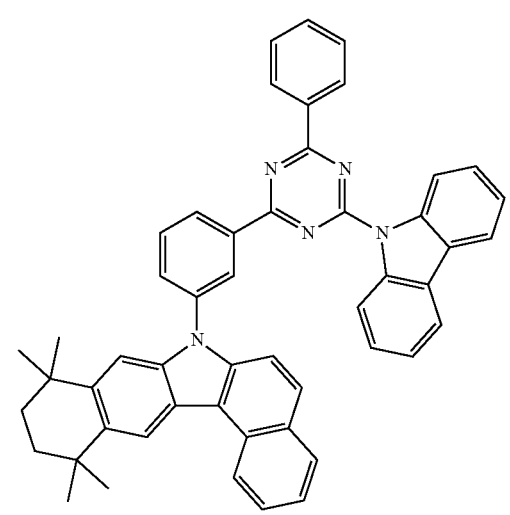

-continued
311
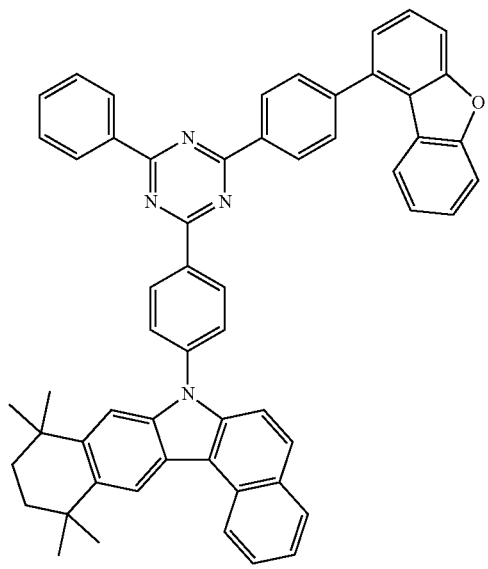
312
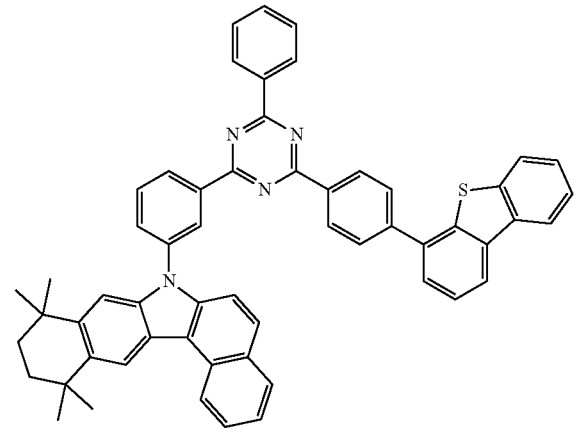
313
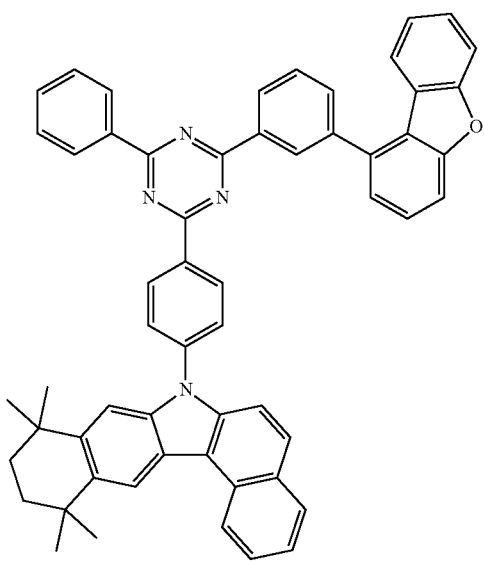
-continued
315
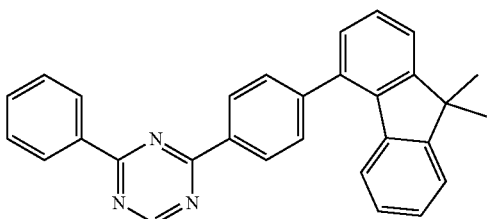
314
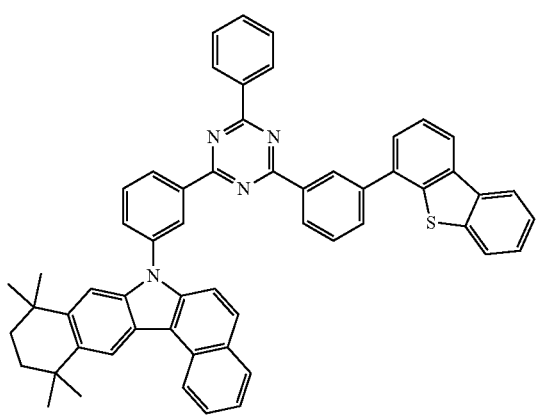
316
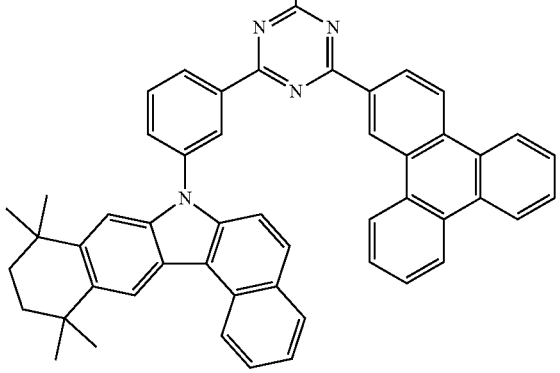

317 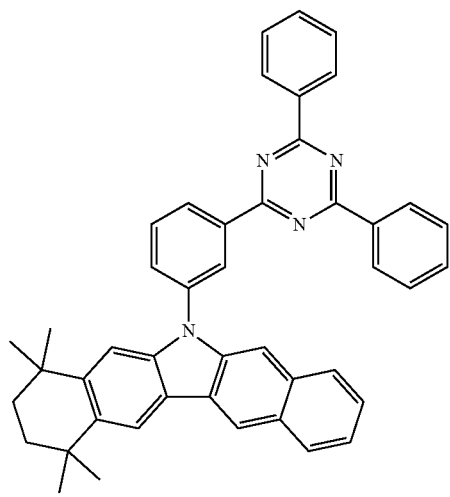
318 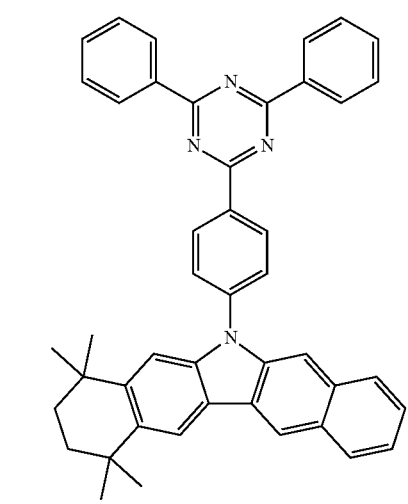
319 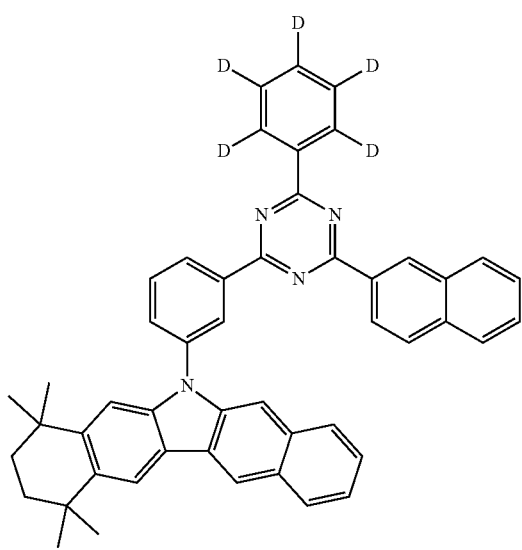
320 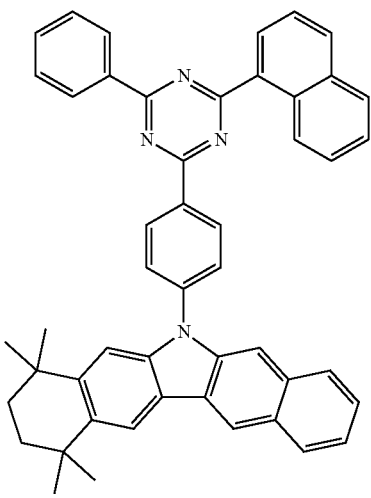
321 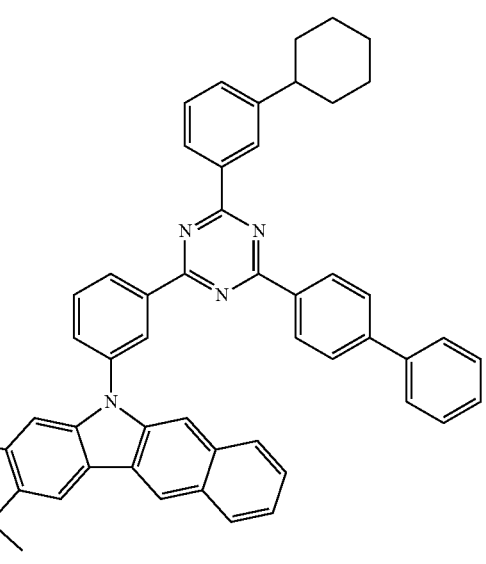
322 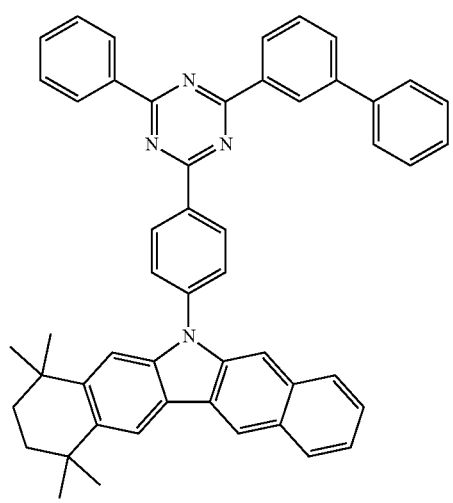

323
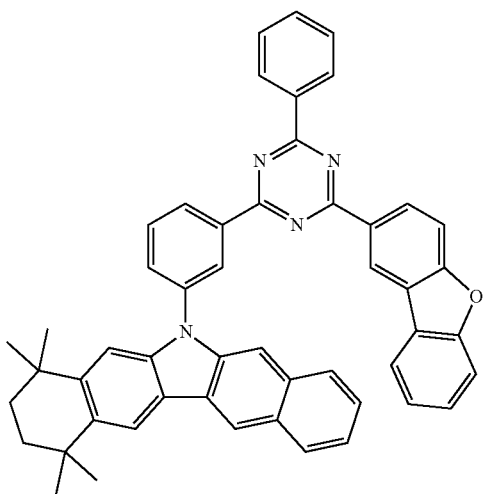
324
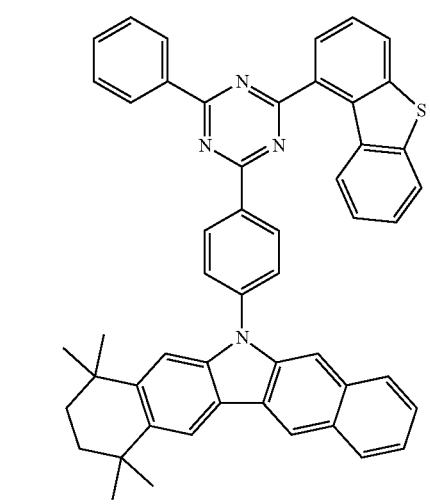
325
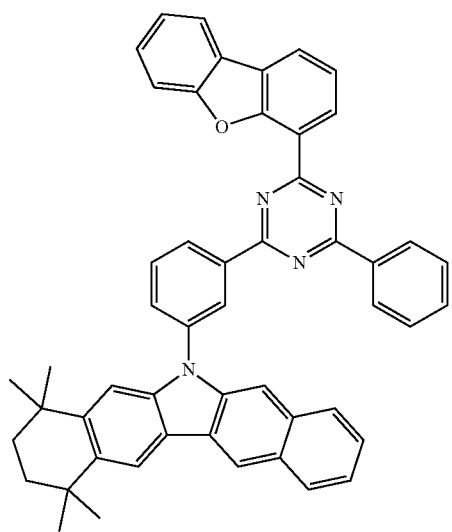
326
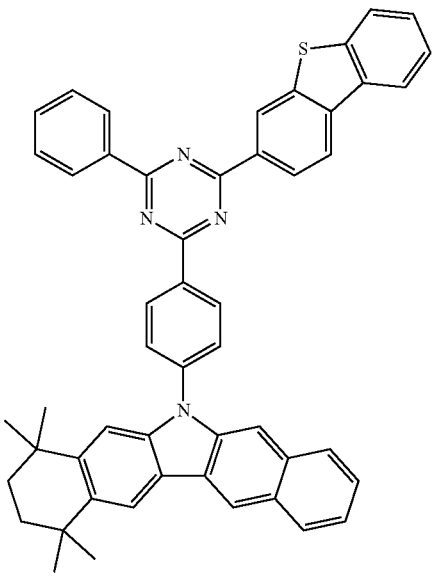
327
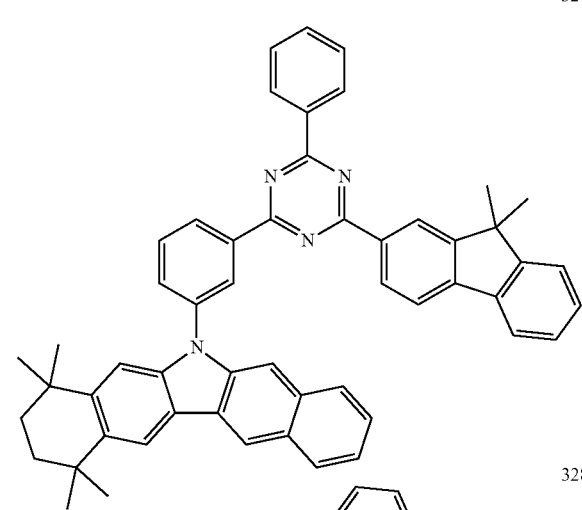
328
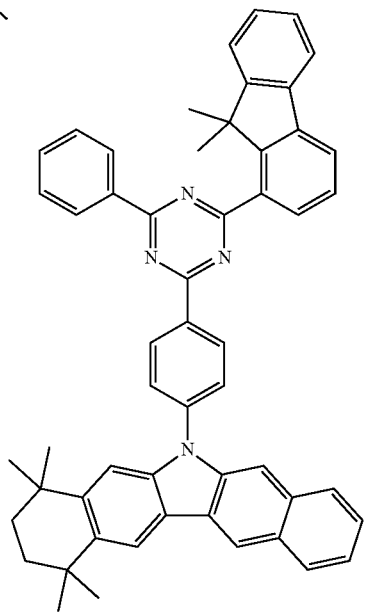

329
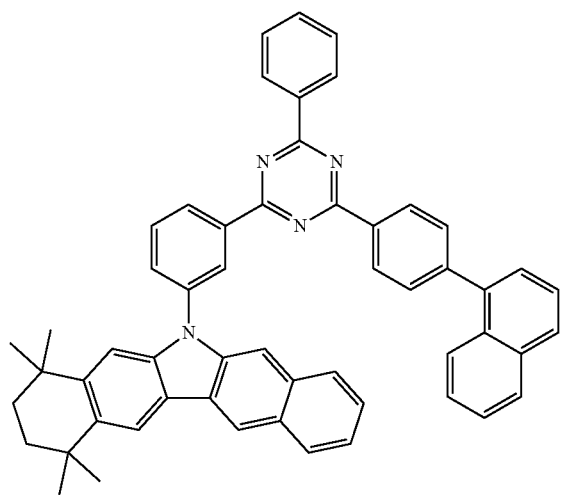
330
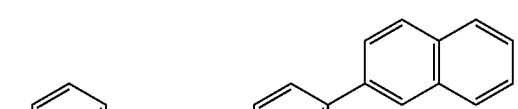
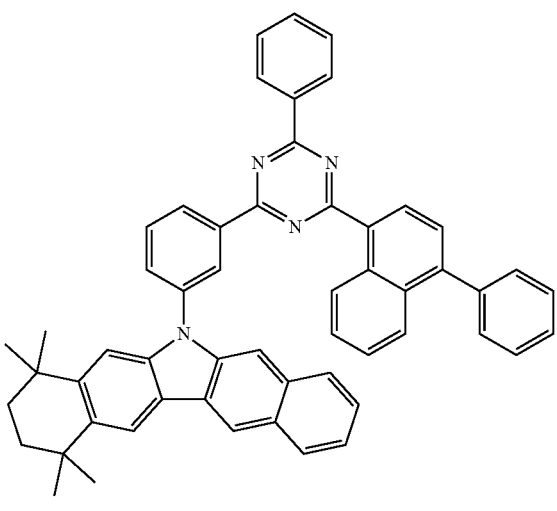
331
332
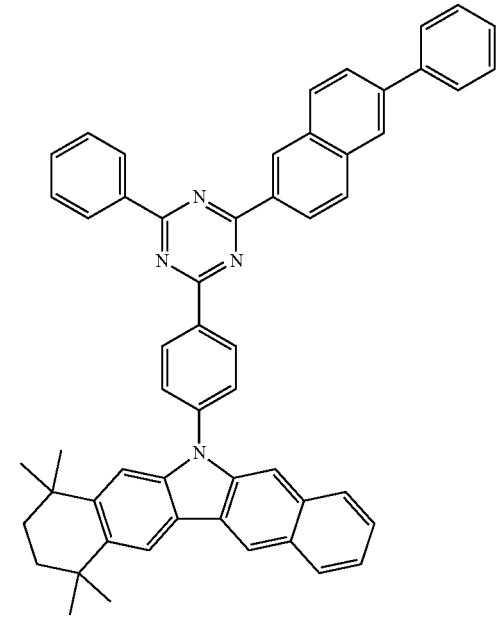
333
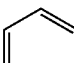
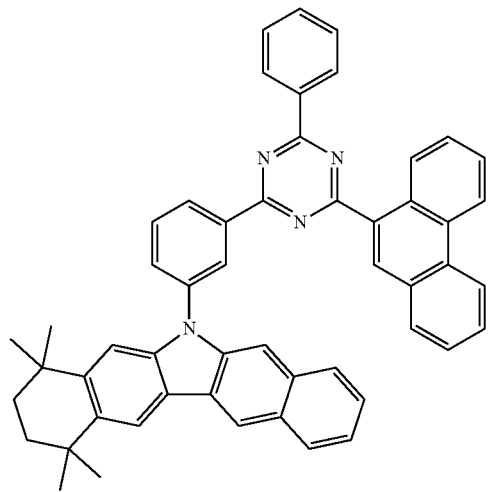
334
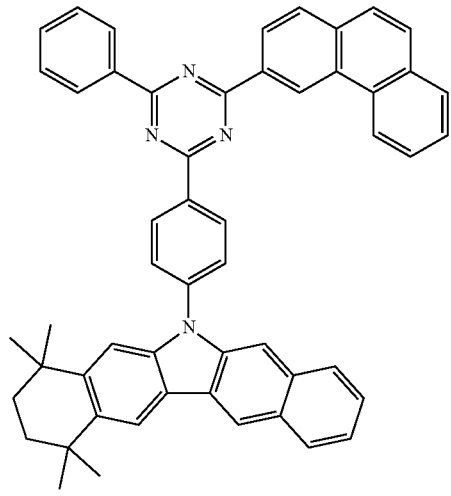

335
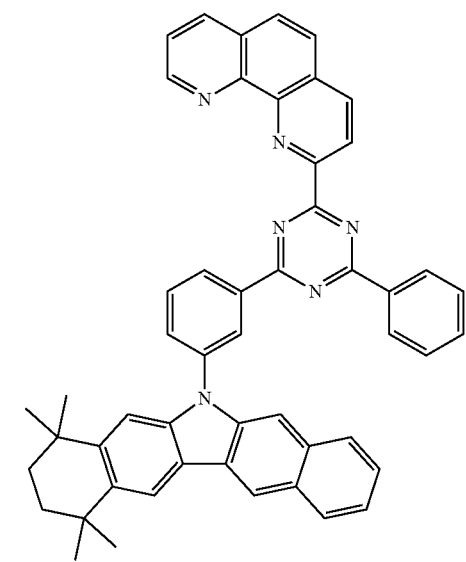
336
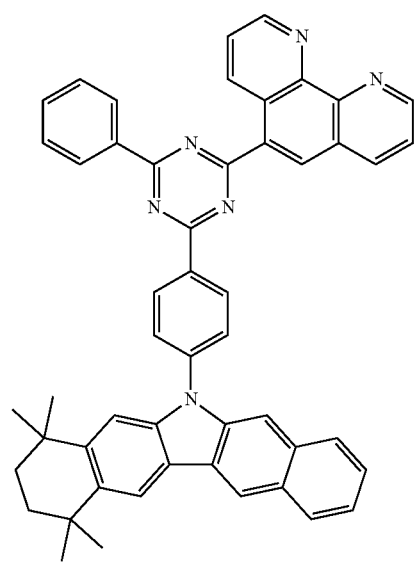
337
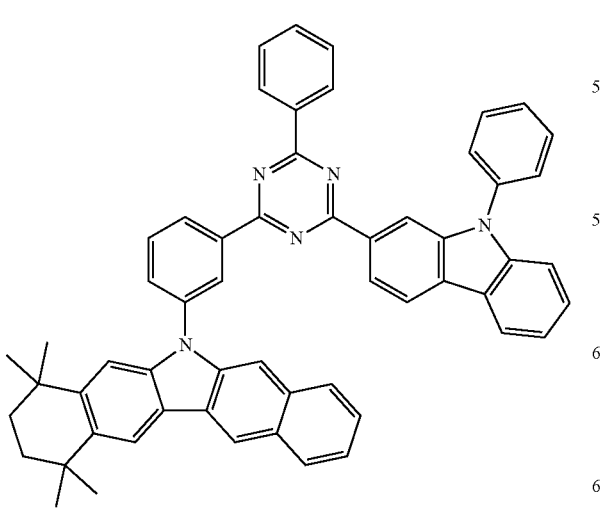
338
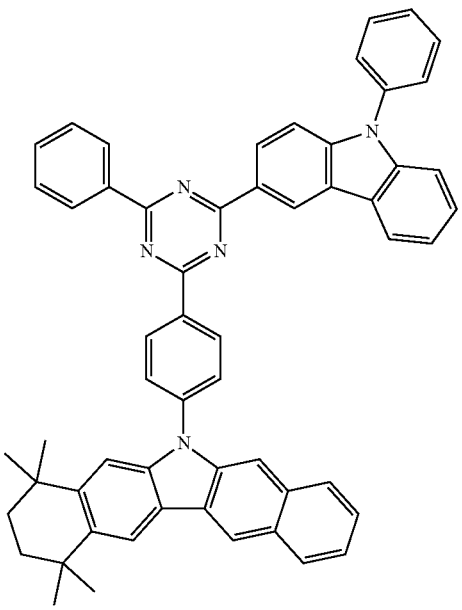
339
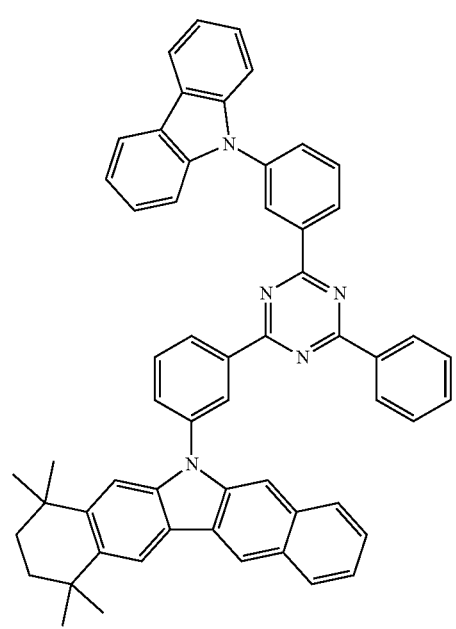

340
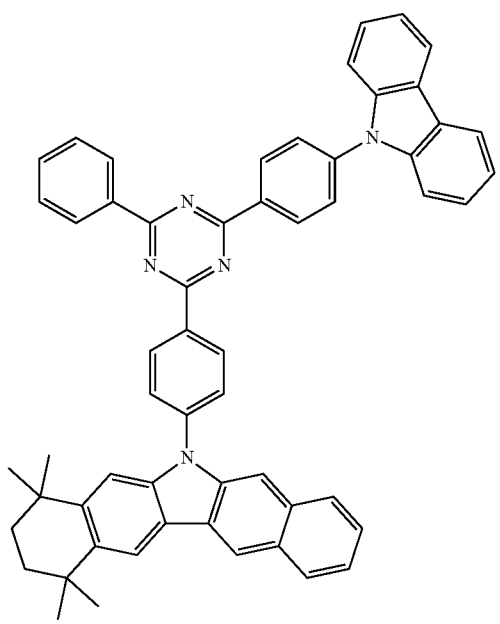
342
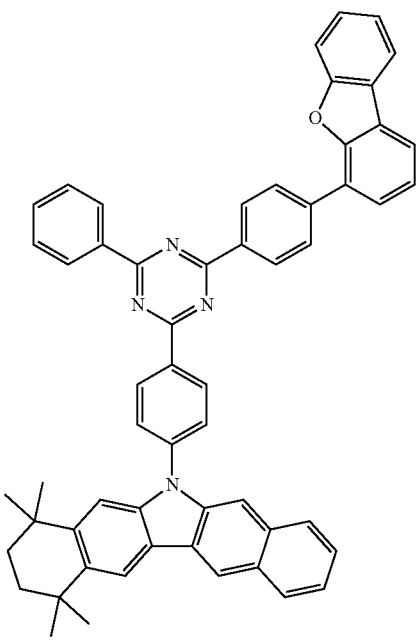
341
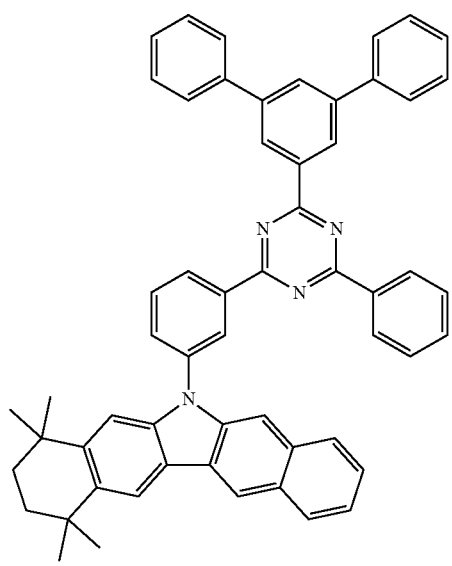
342
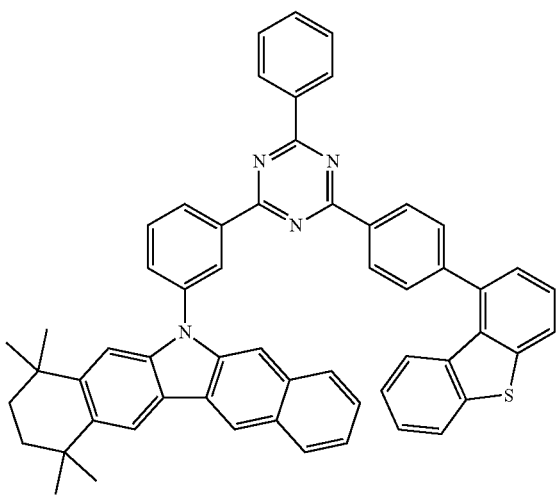

-continued
344
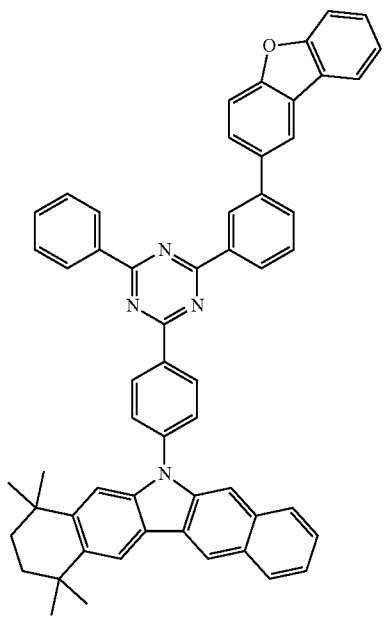
345
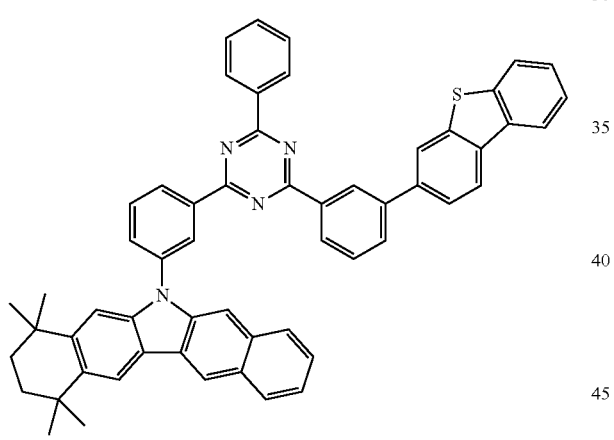
346
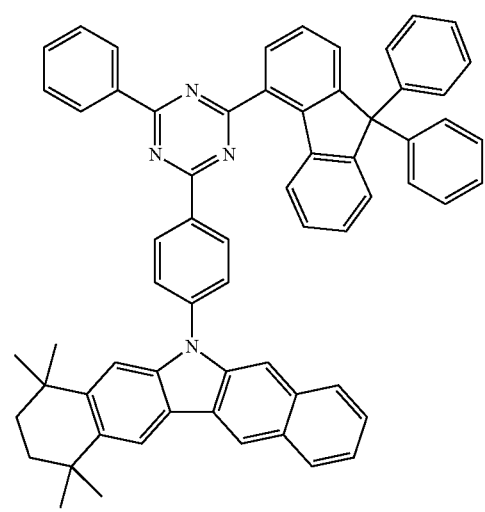
-continued
347
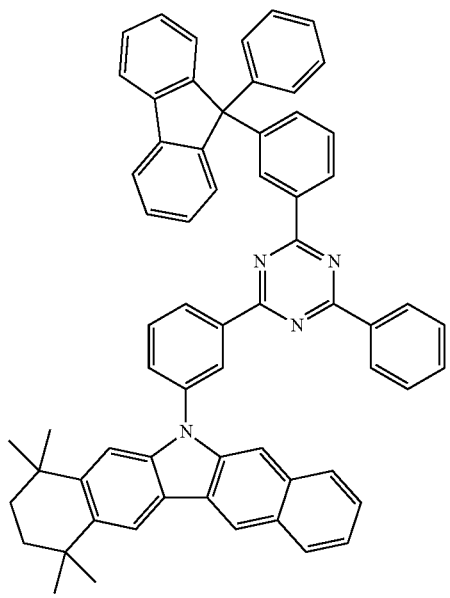
348
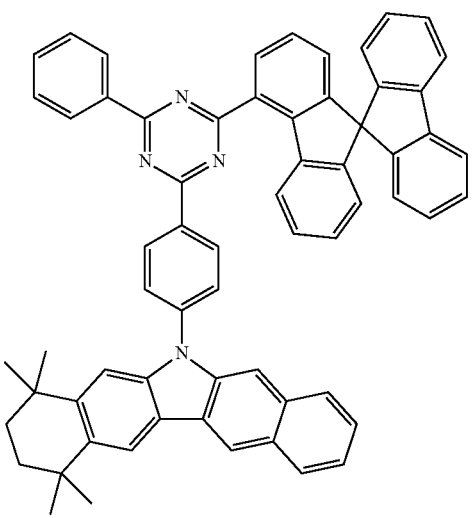
349
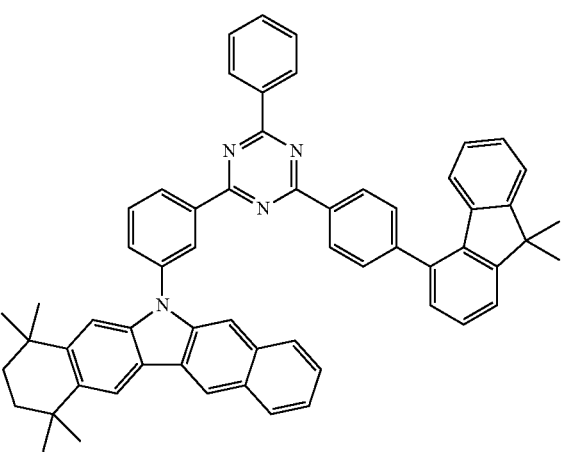

171
-continued
350
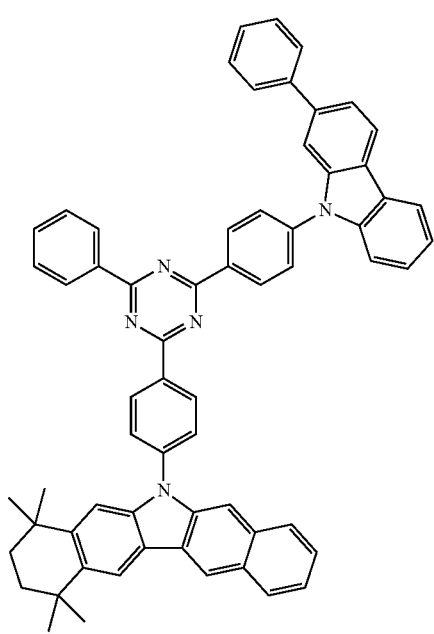
351
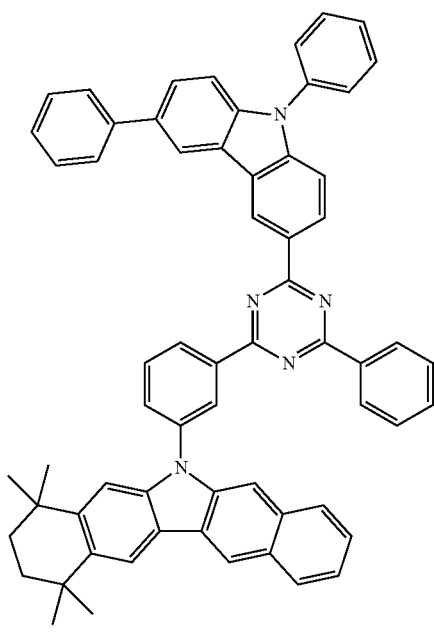
172
-continued
352
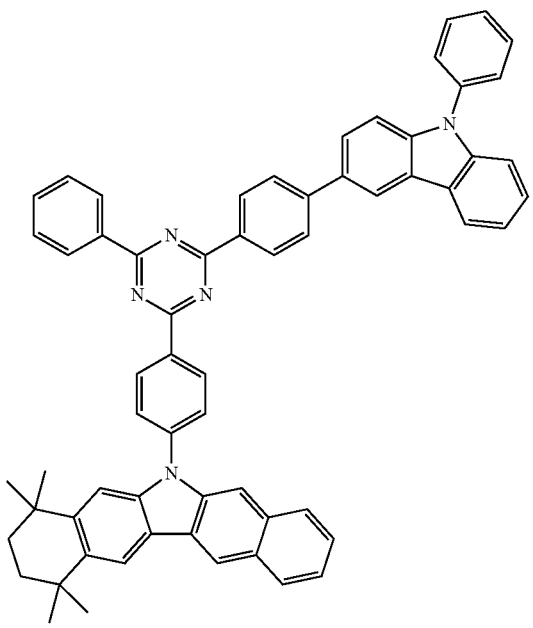
353
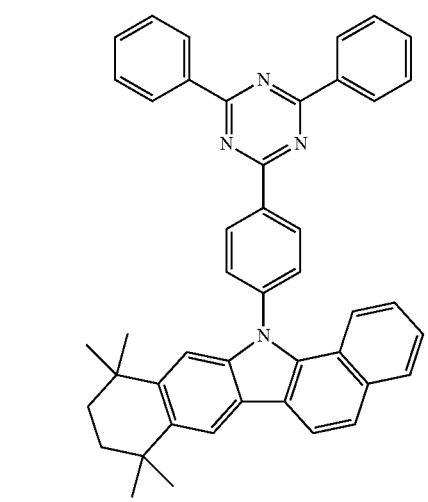
354
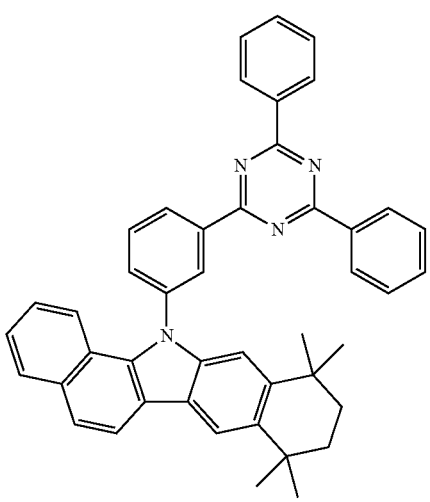

-continued
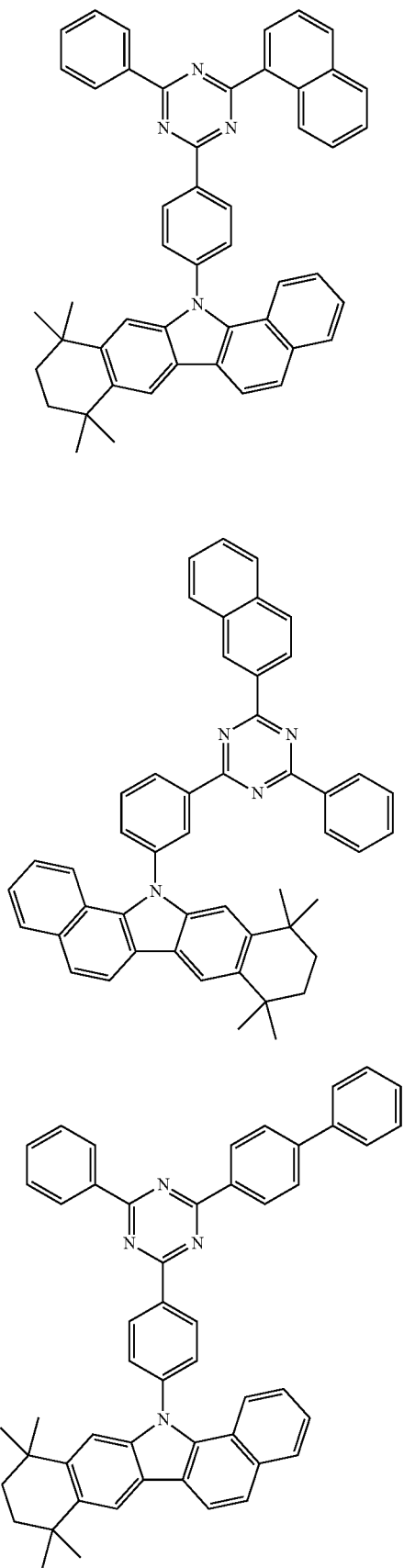
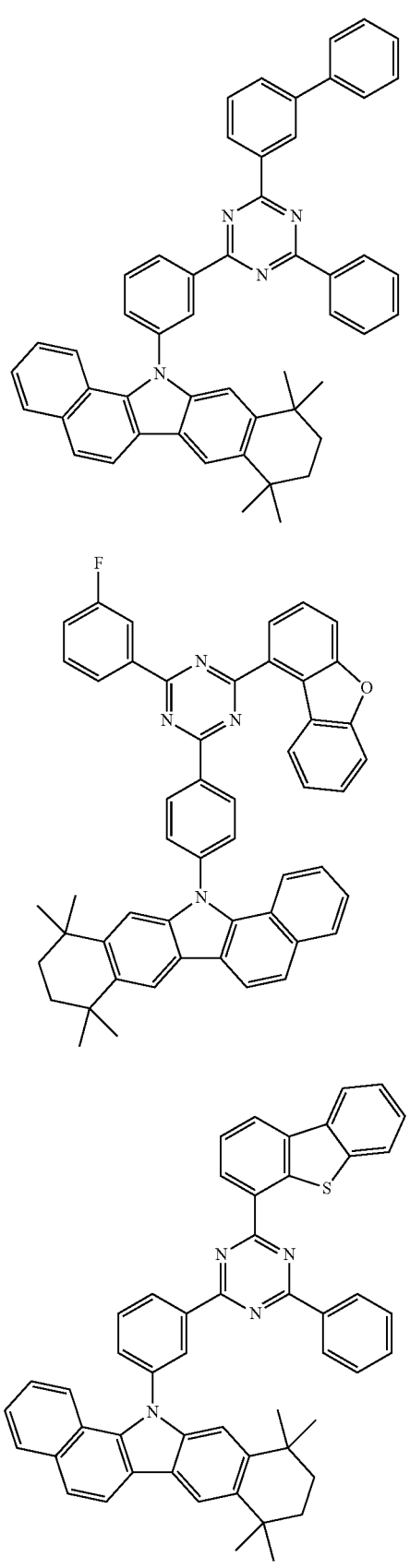

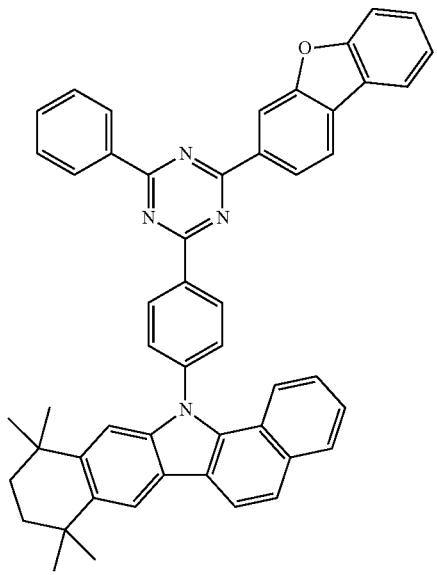
361
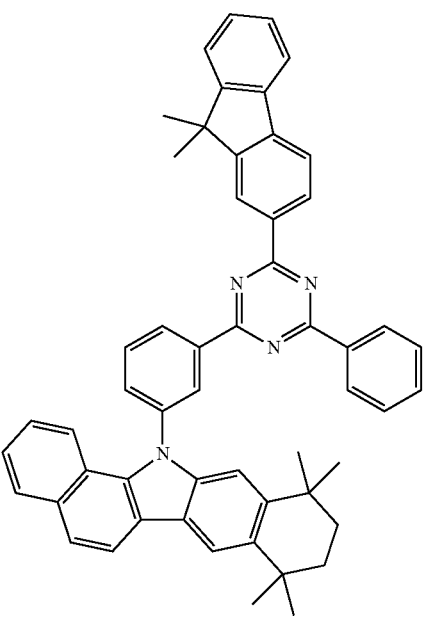
364
362
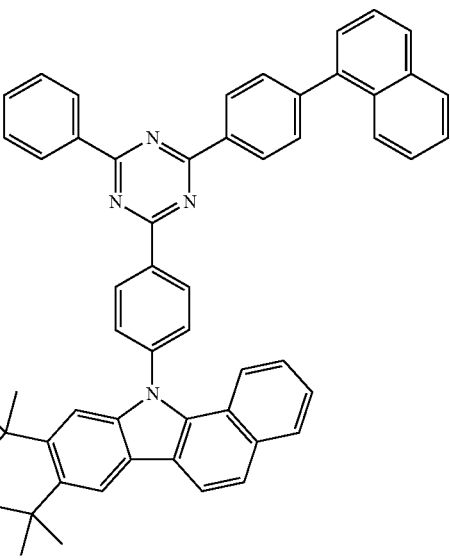
365

366
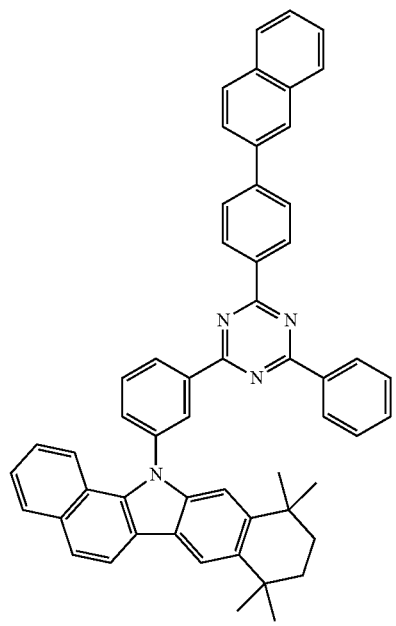
367
368
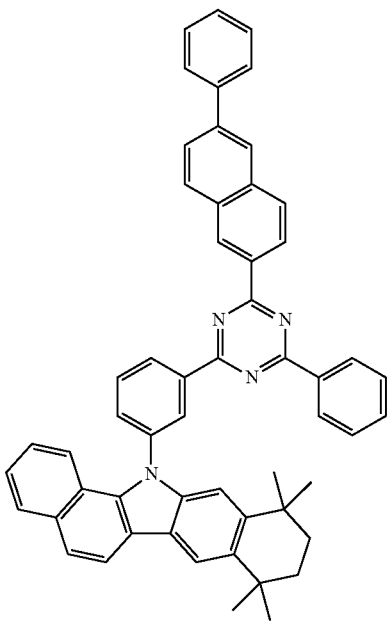
369
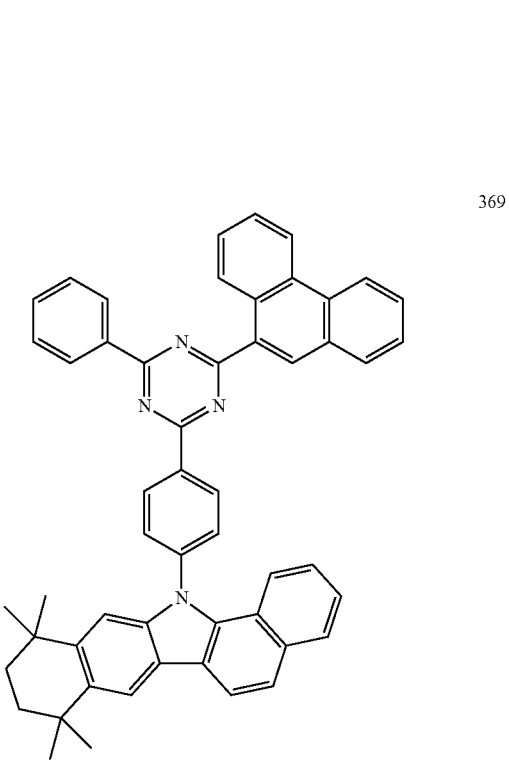

179
-continued
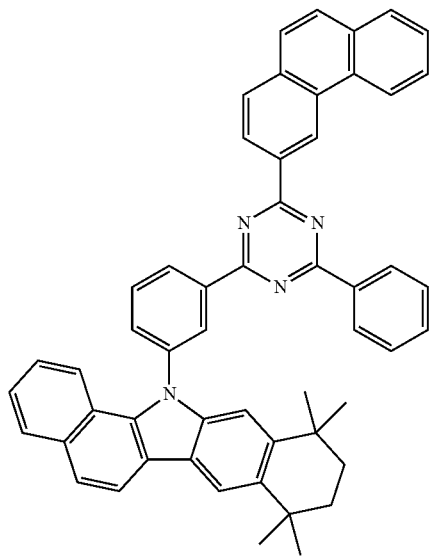
370
180
-continued
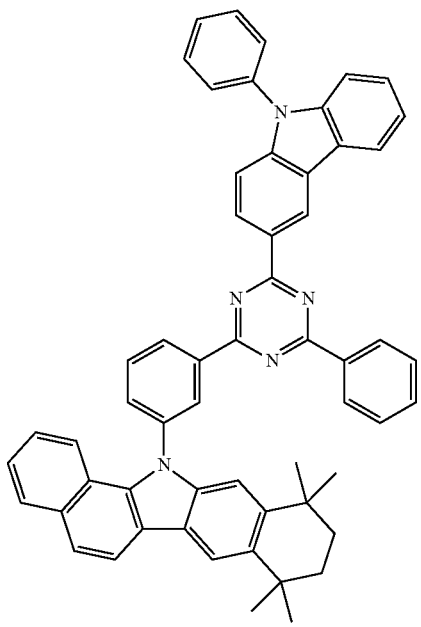
372
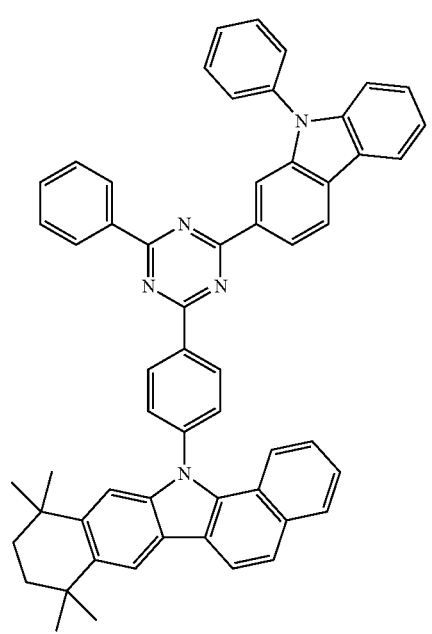
371
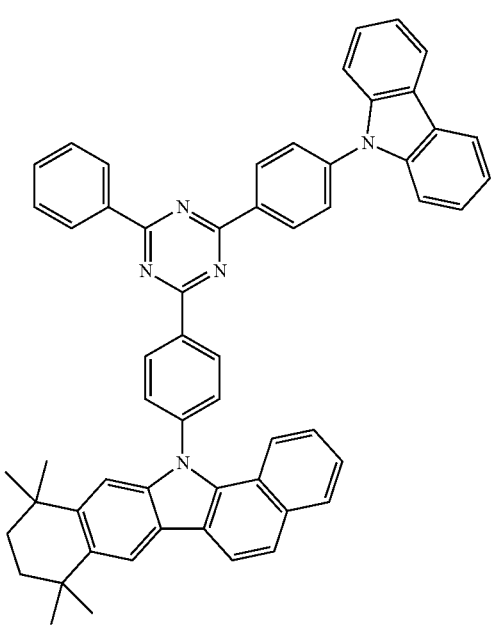
373

374
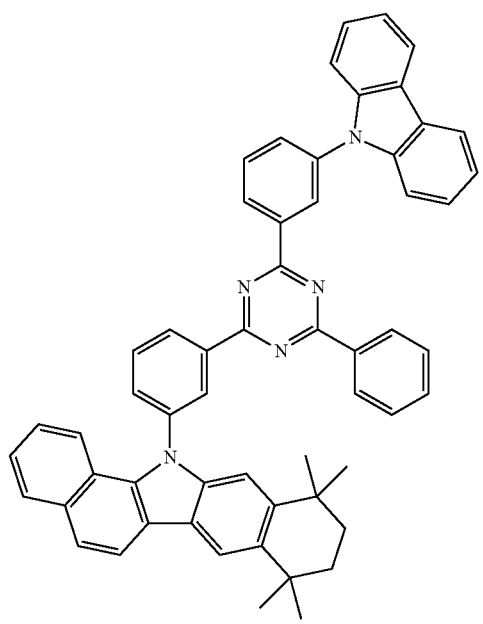
375
376
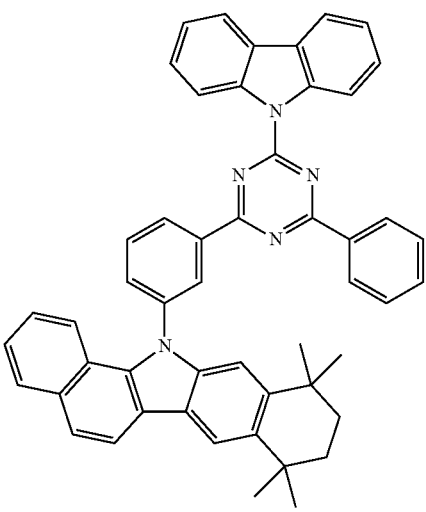
377

378
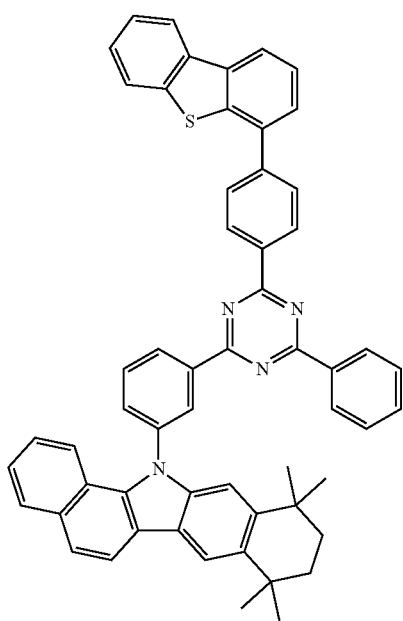
380
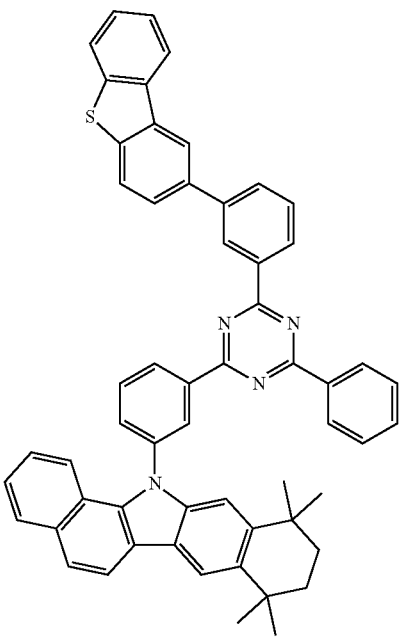
379
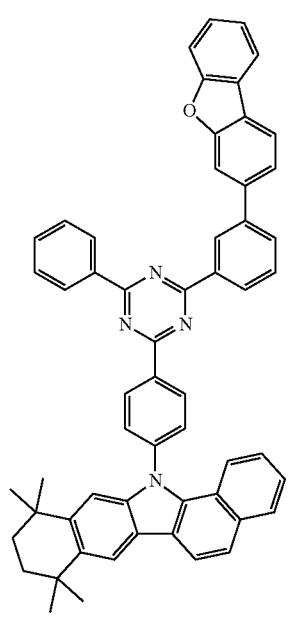
381
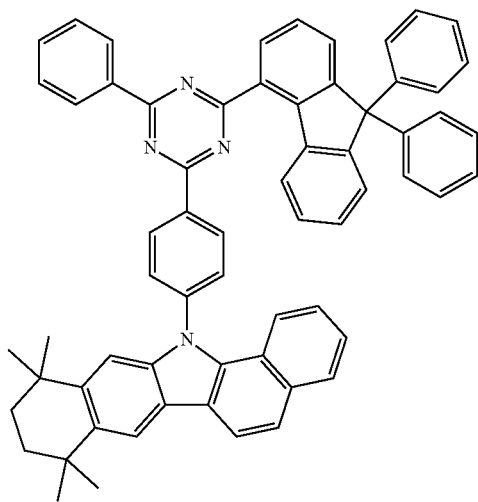

382
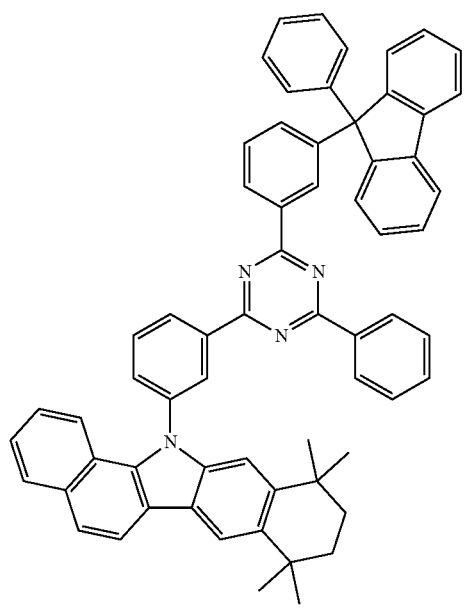
383
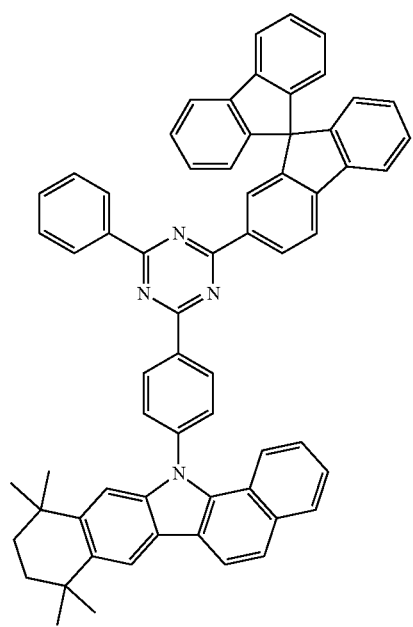
384
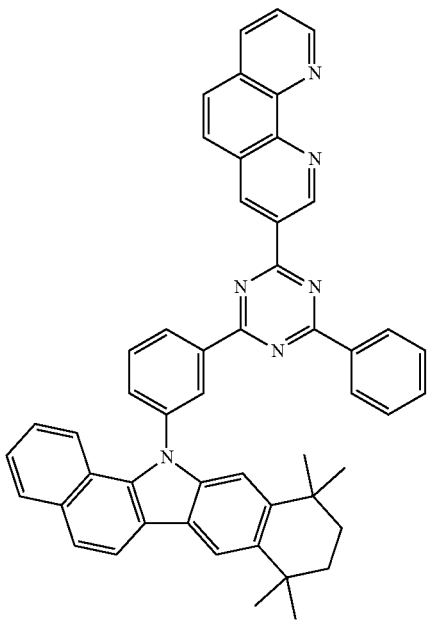
385
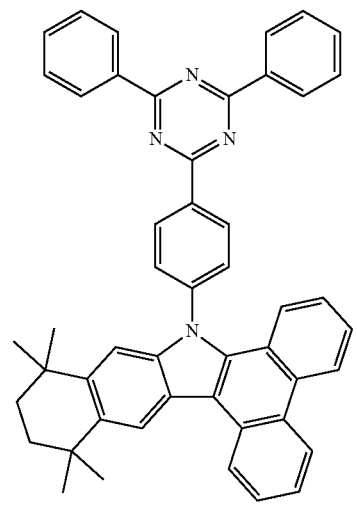
386
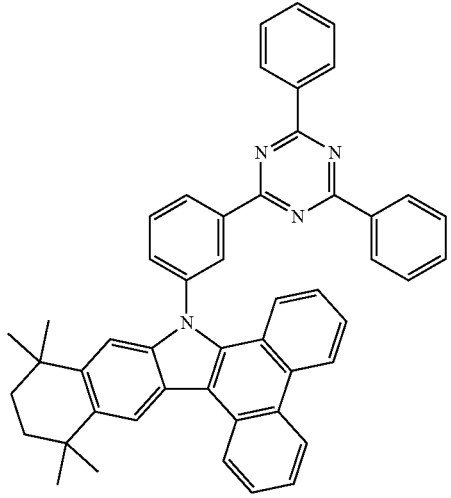

387
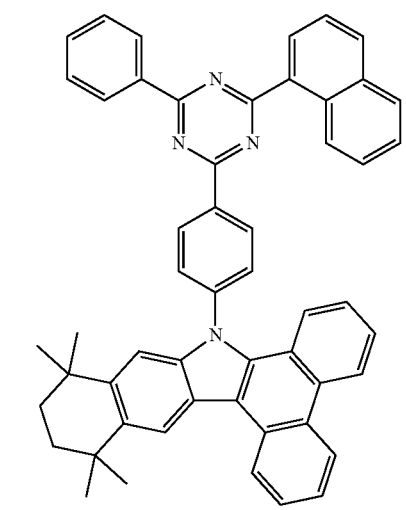
388
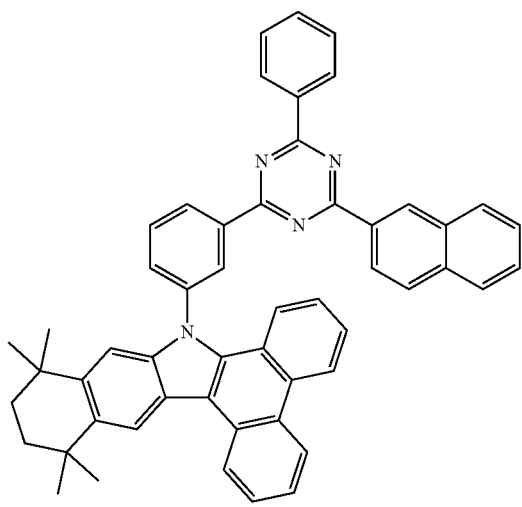
389
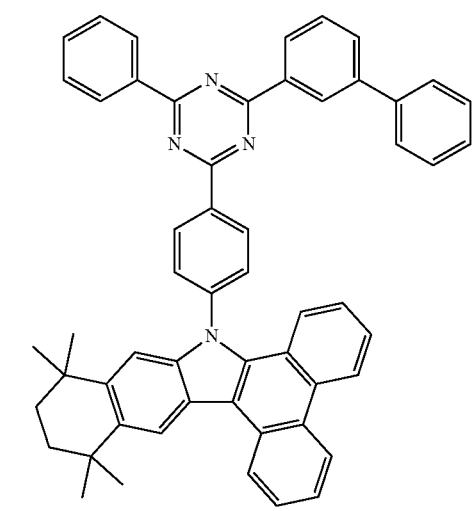
390
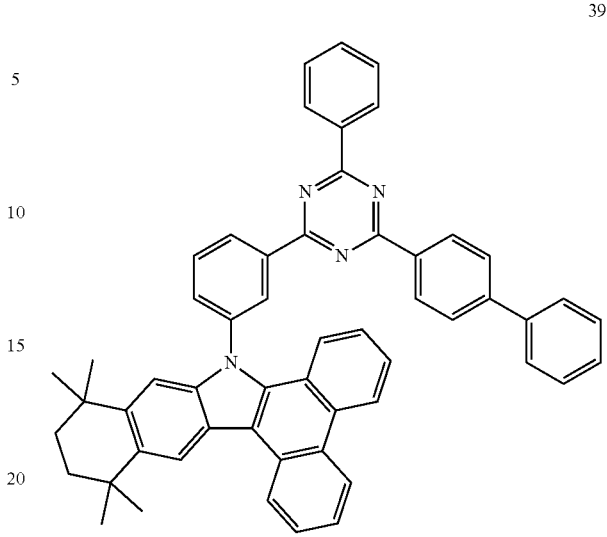
391
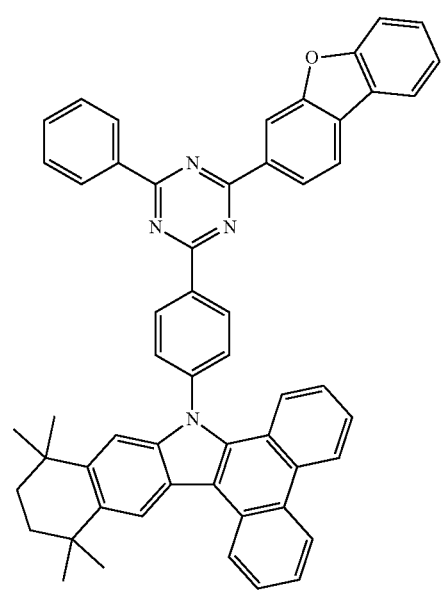
392
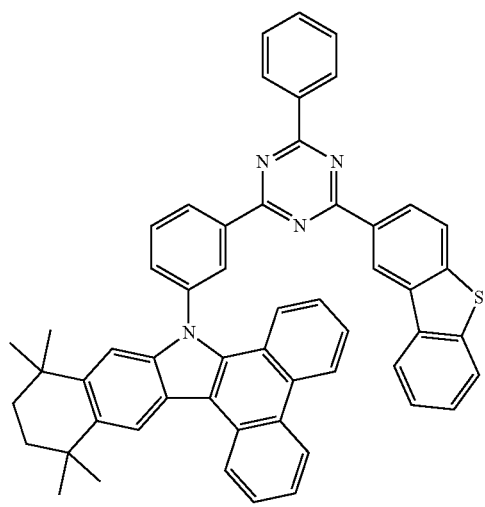

-continued
393
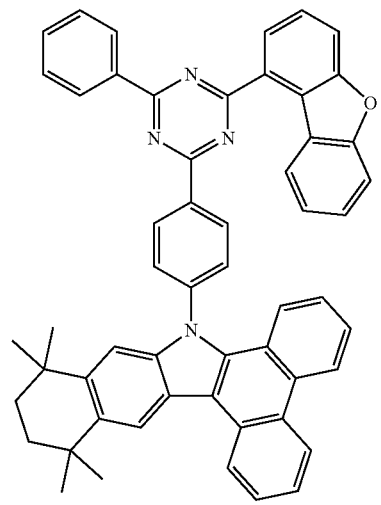
394
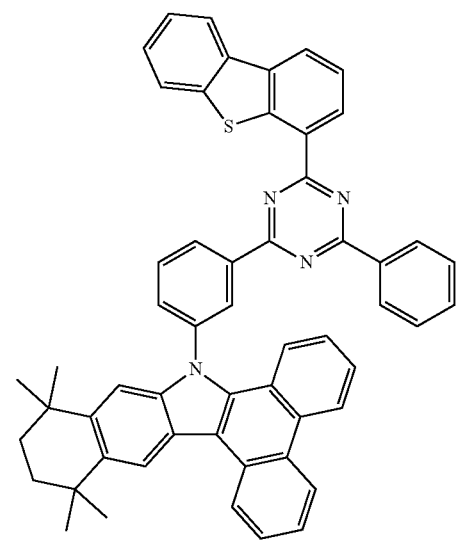
395
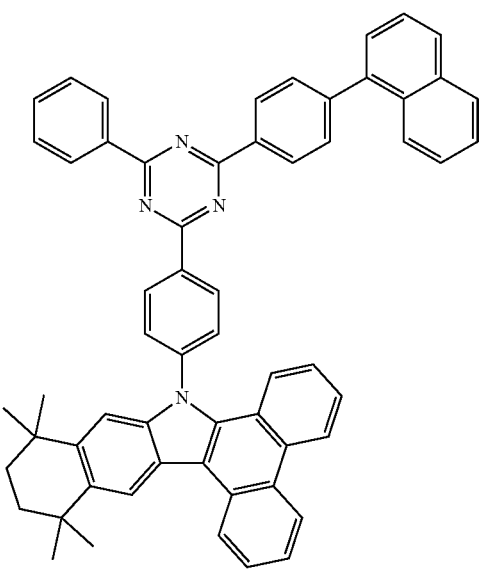
-continued
396
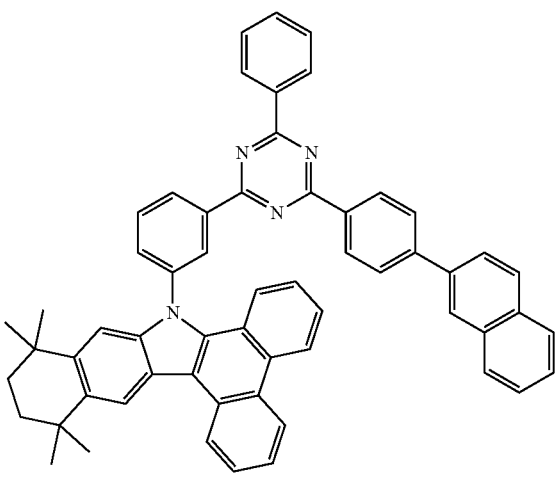
397
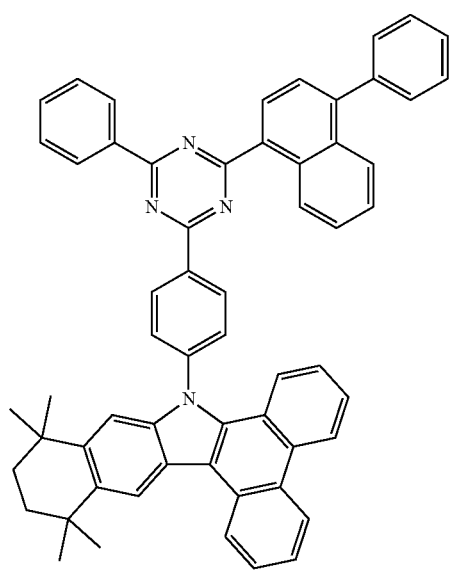
398
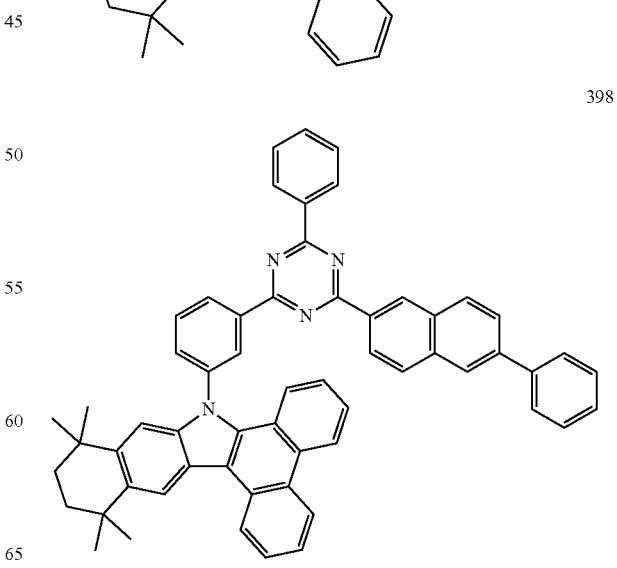

-continued
399
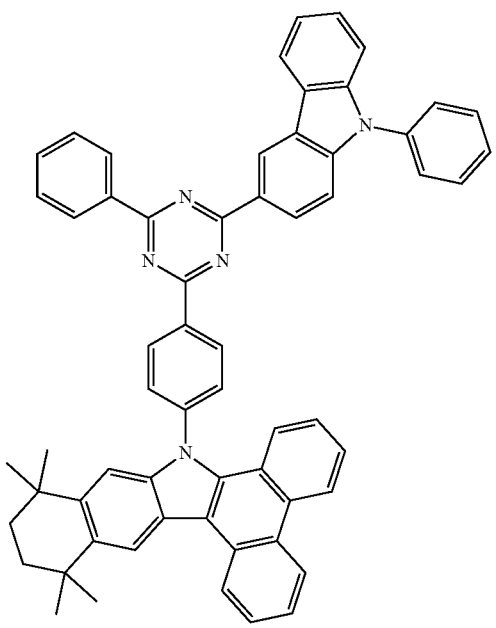
401
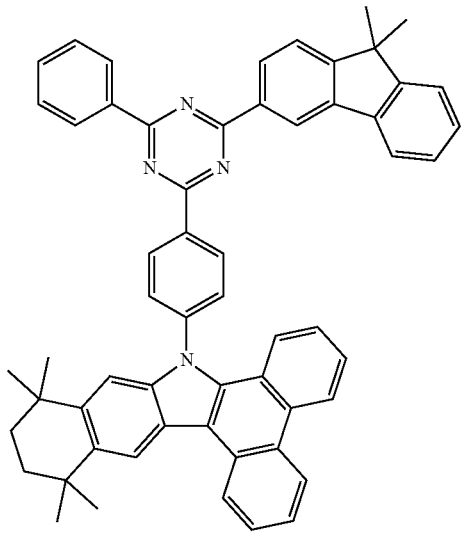
402
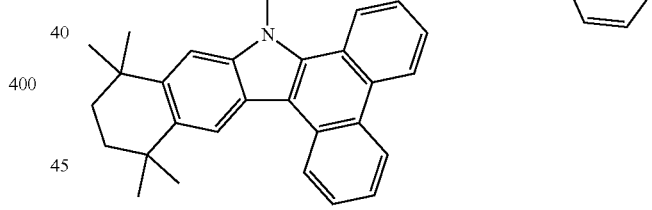
403
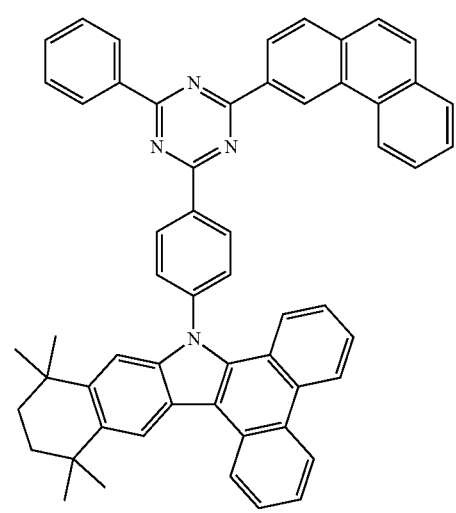
400
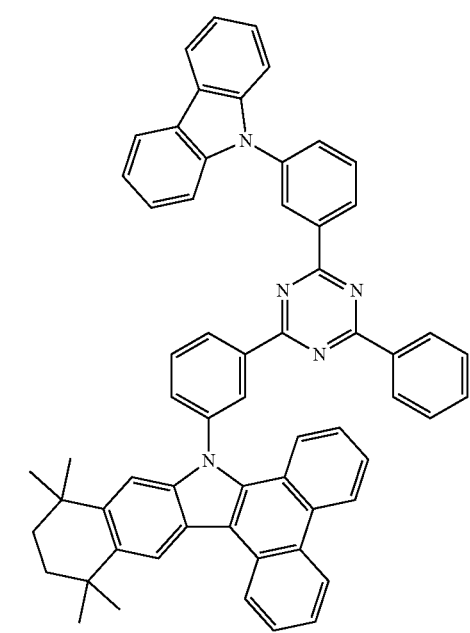

404
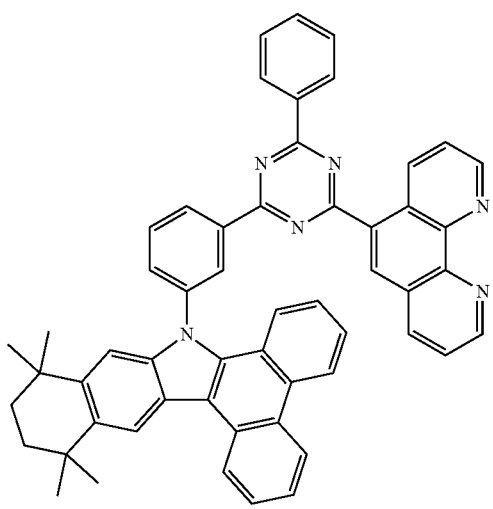
405
407
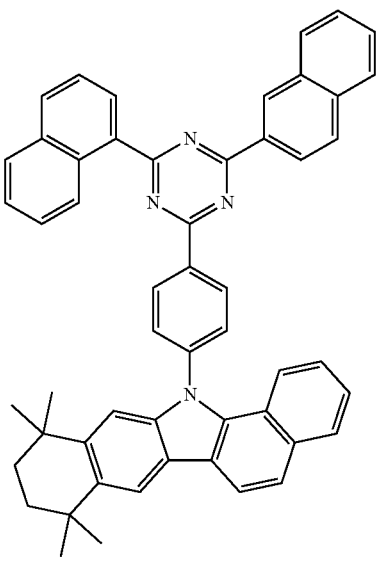
408
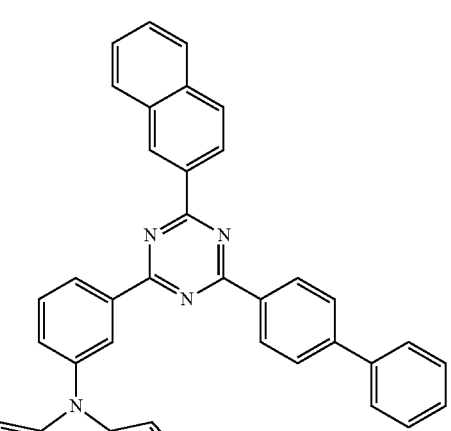
406
409
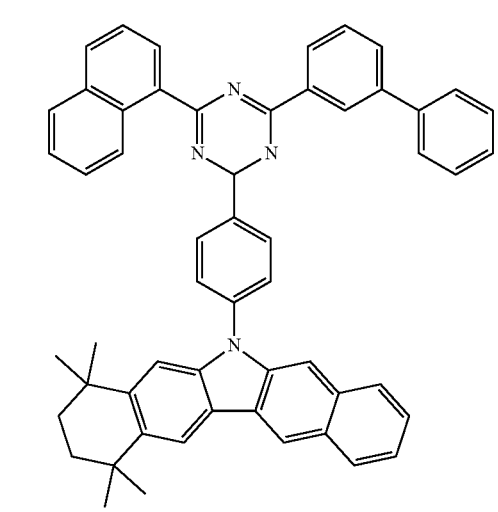

410
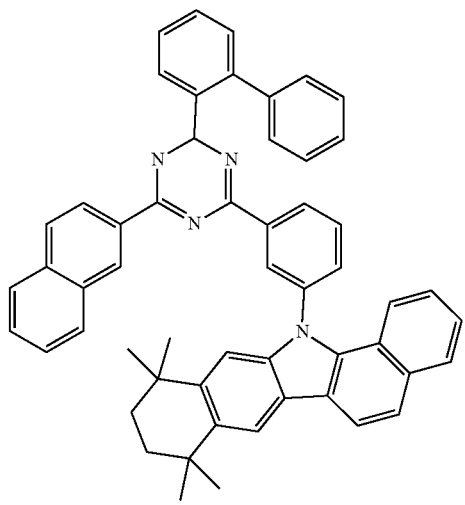
411
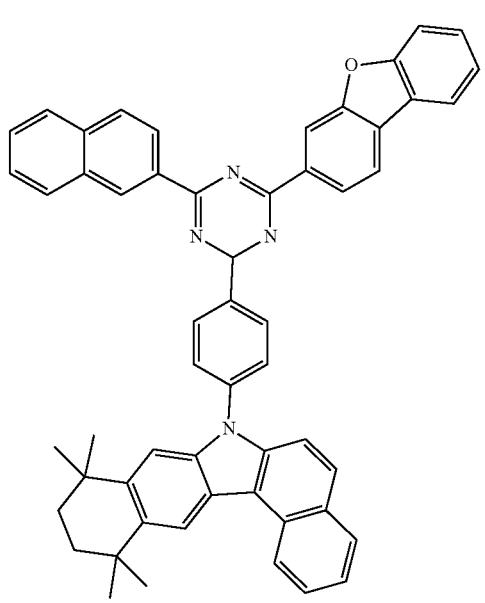
412
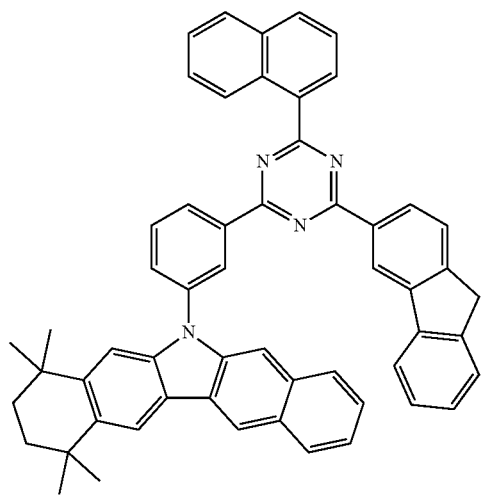
413
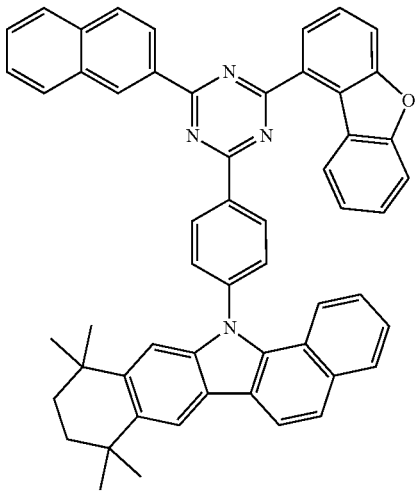
414
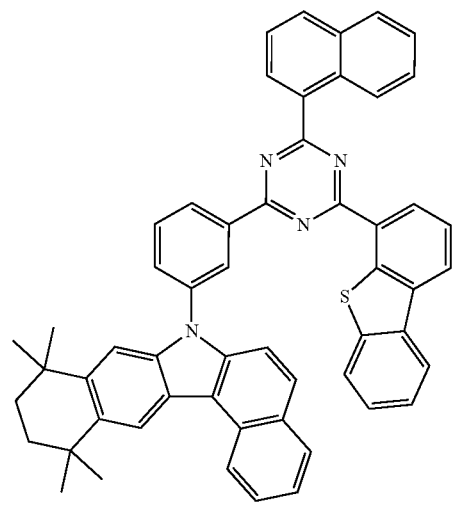
415
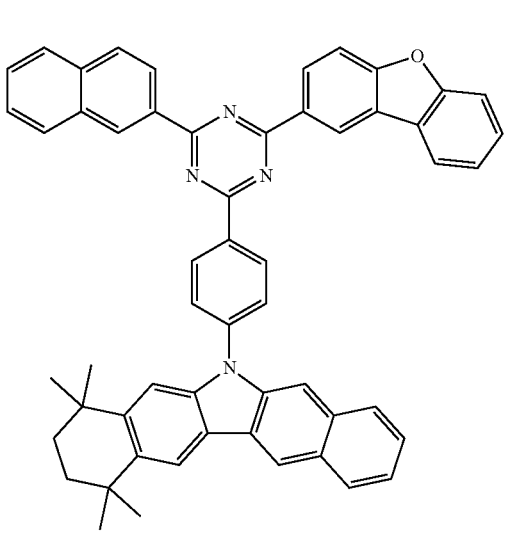

416
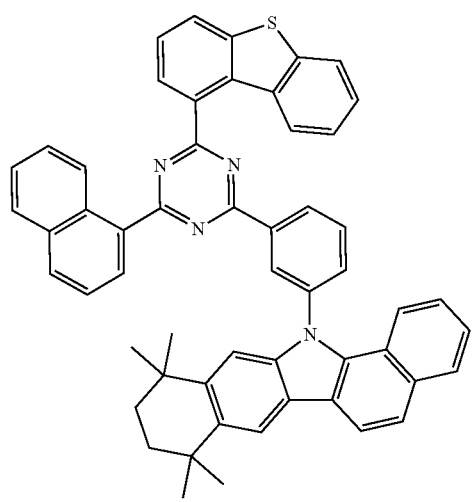
417
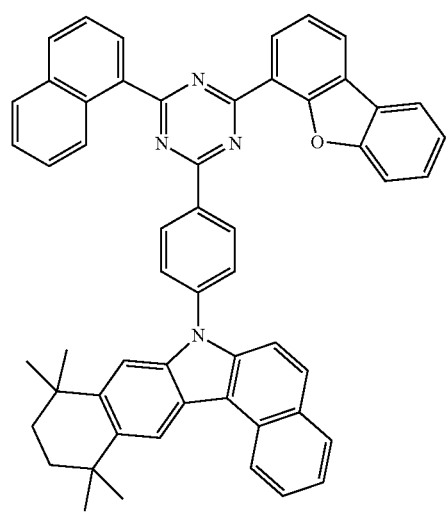
418
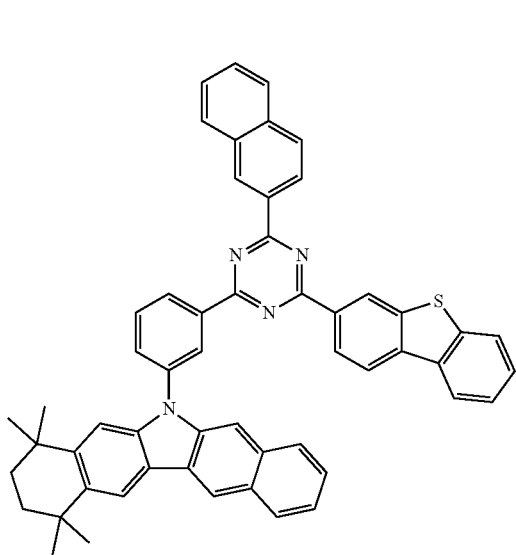
419
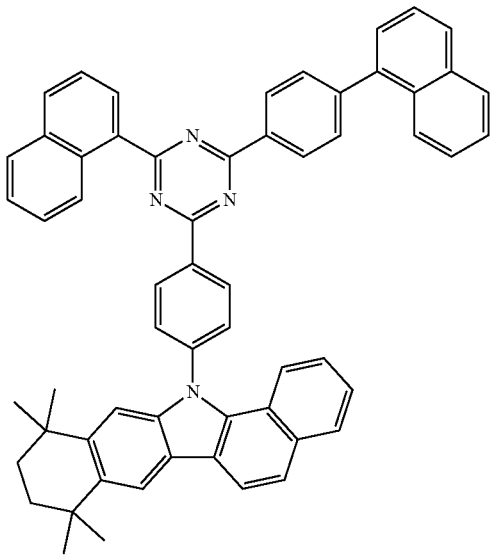
420
421
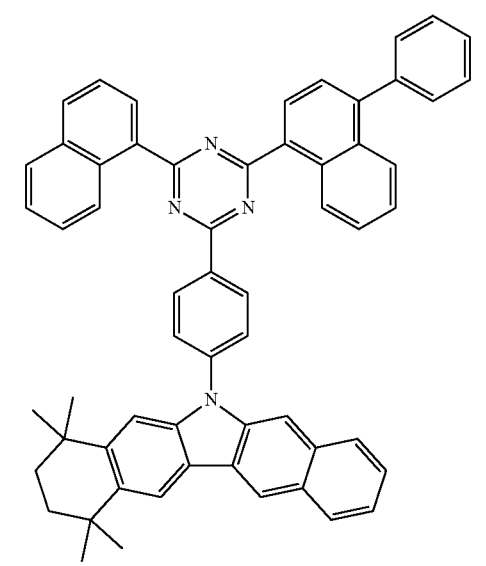

199 -continued
422
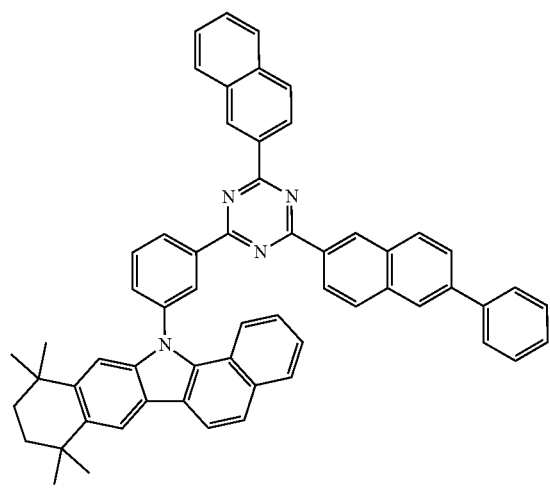
423
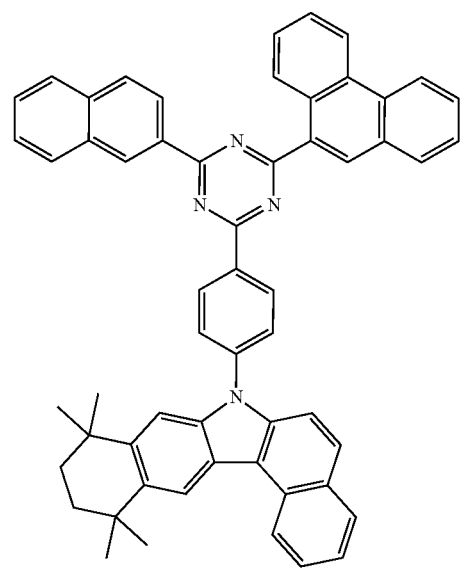
424
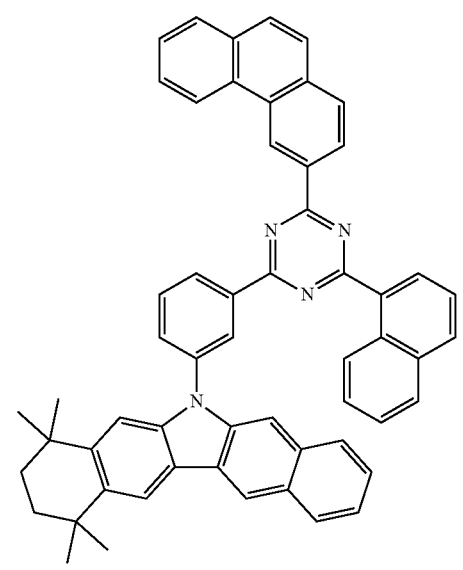
200 -continued
425
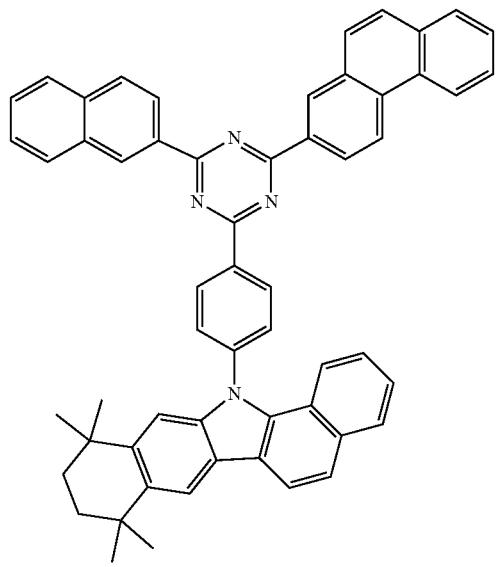
426
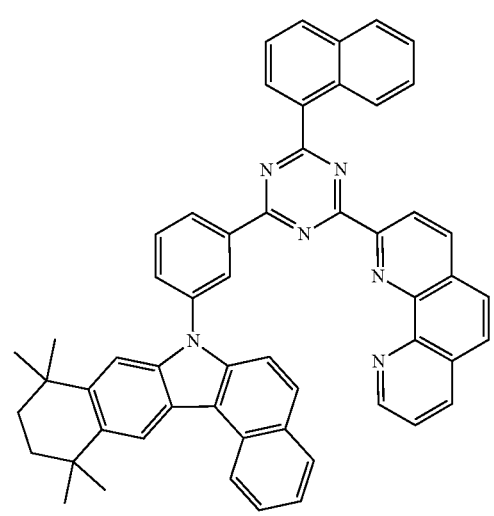
427
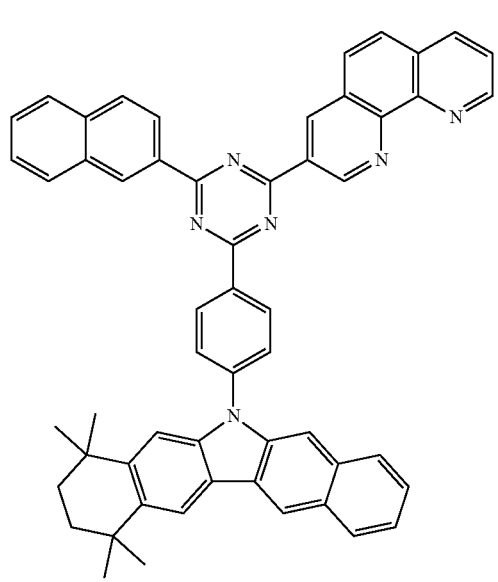

-continued
428
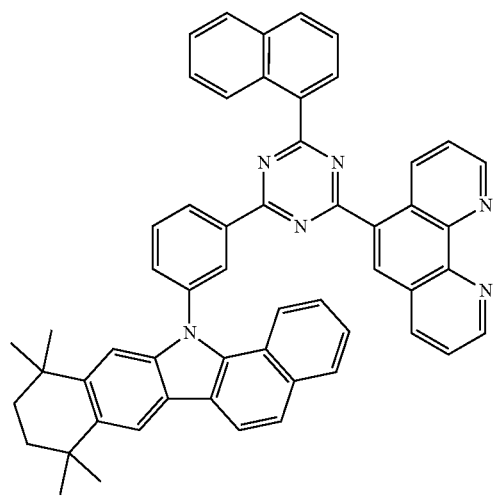
429
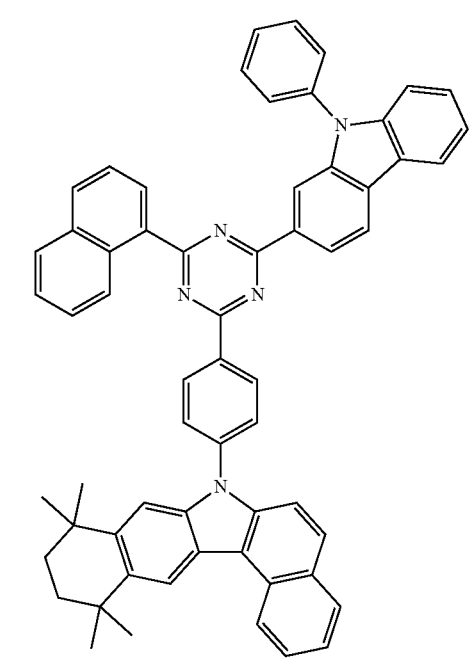
430
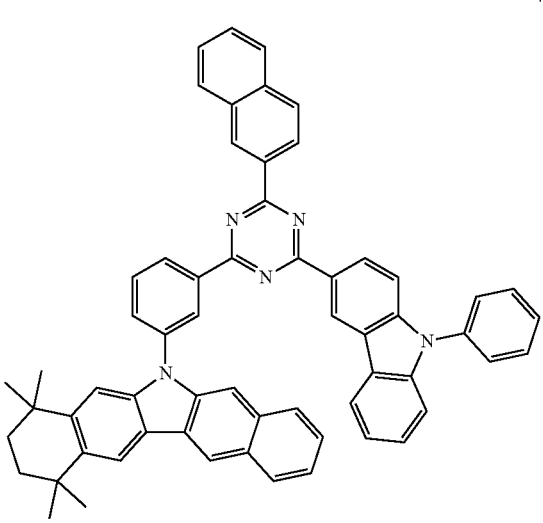
-continued
431
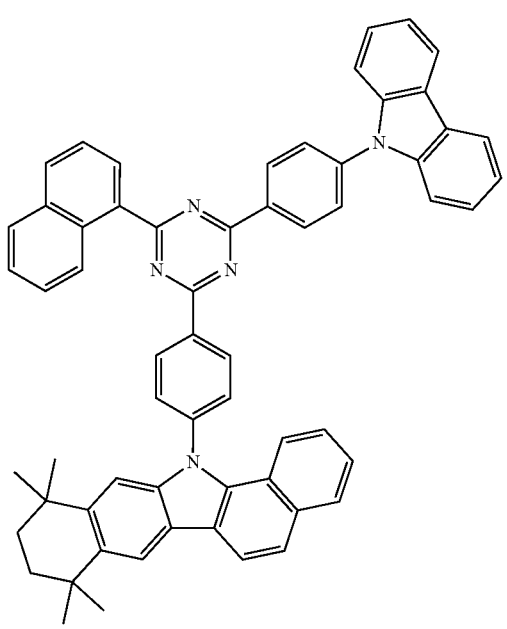
432
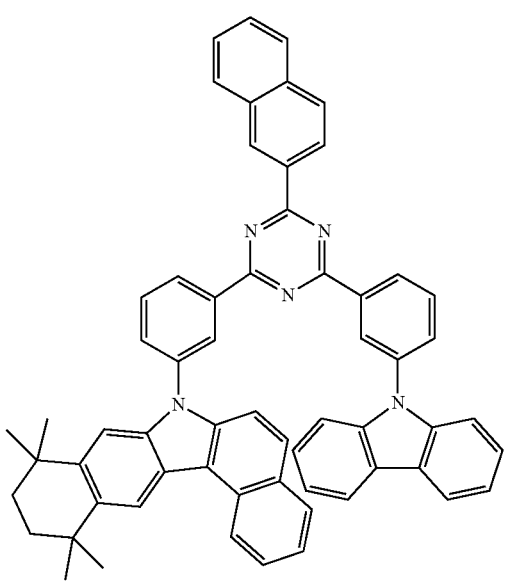

433
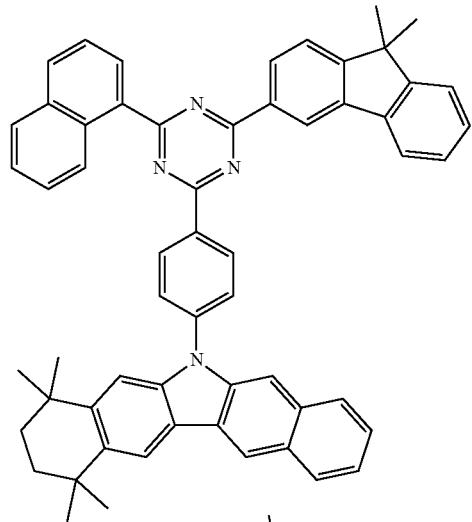
434
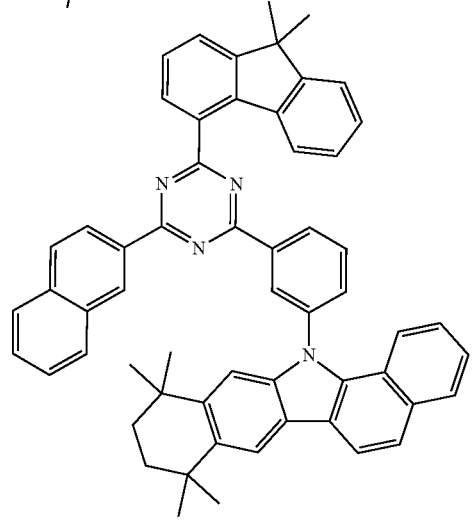
435
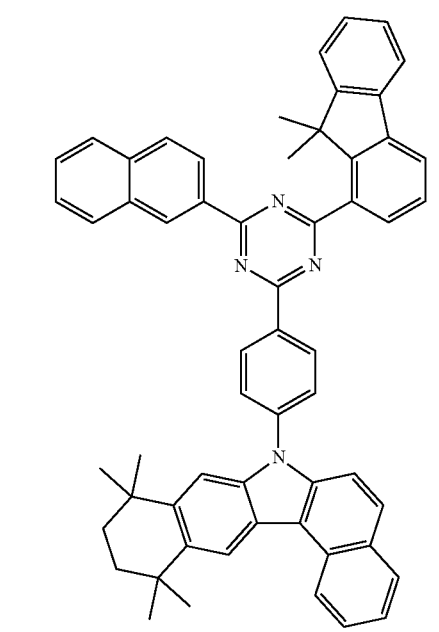
436
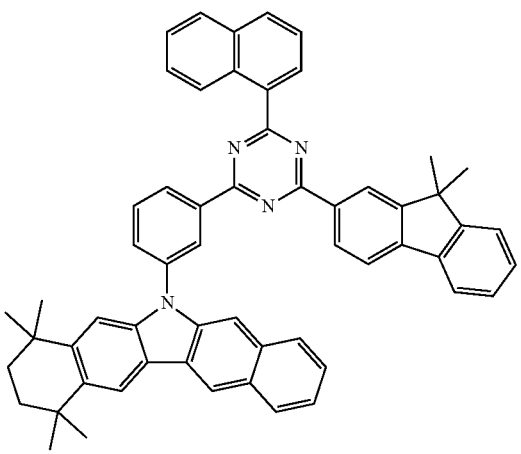
437
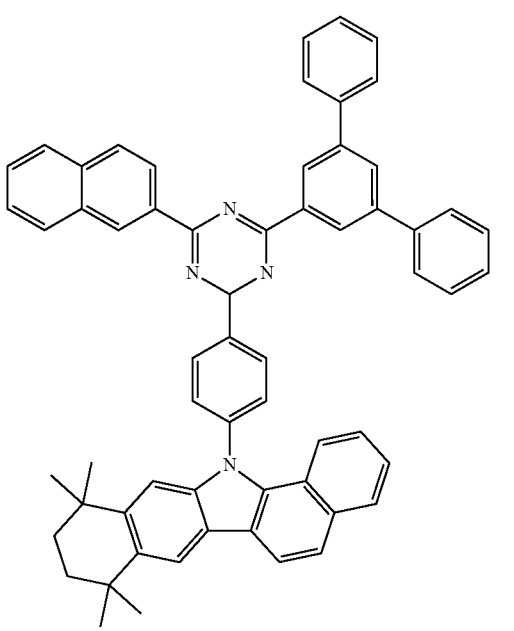
438
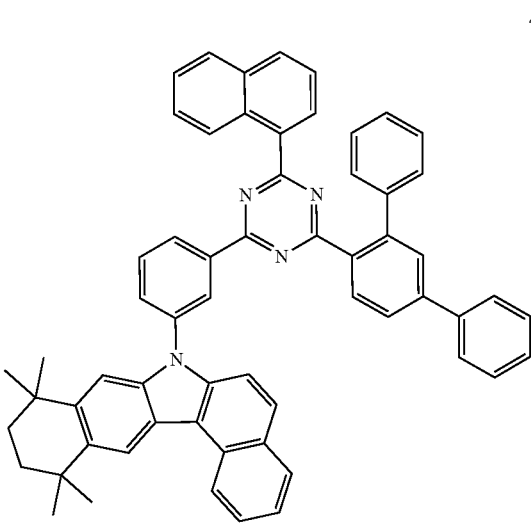

439
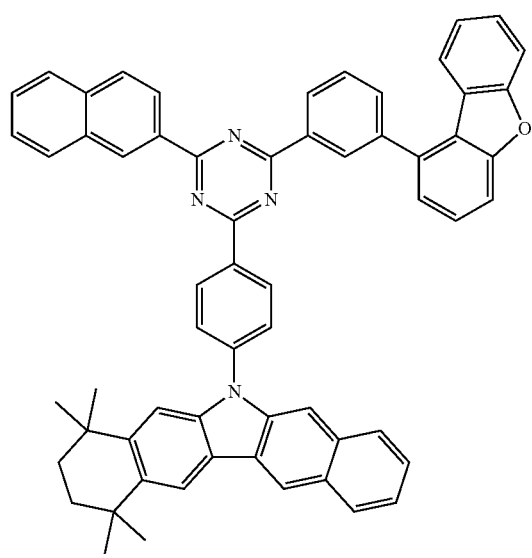
440
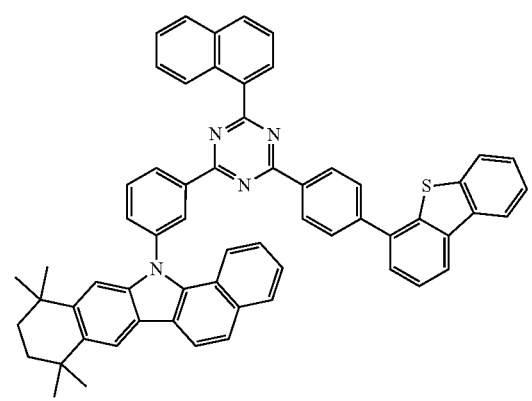
441
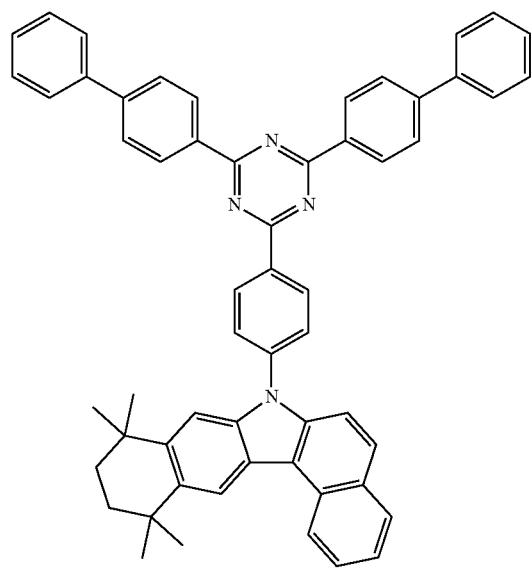
442
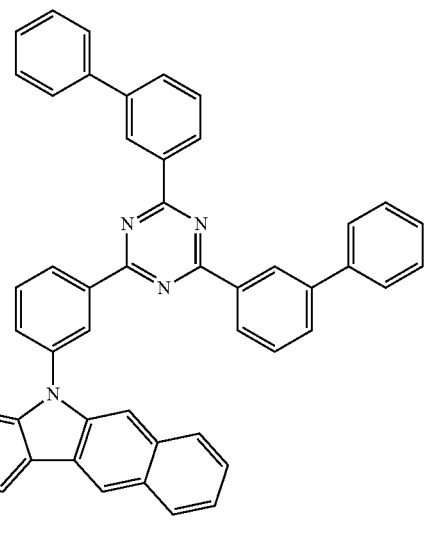
443
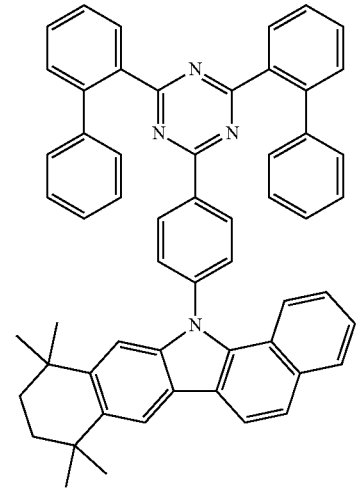
444
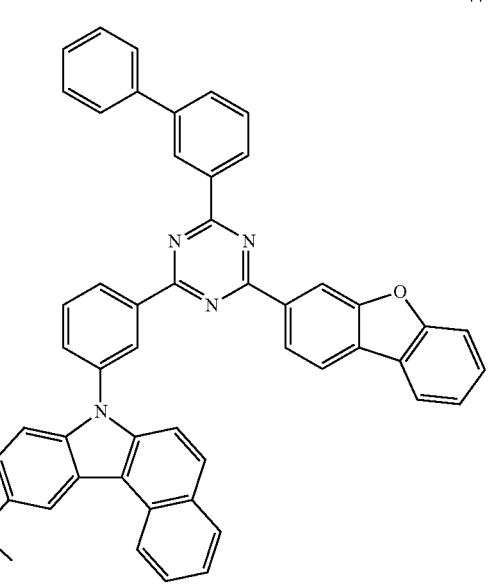

207
-continued
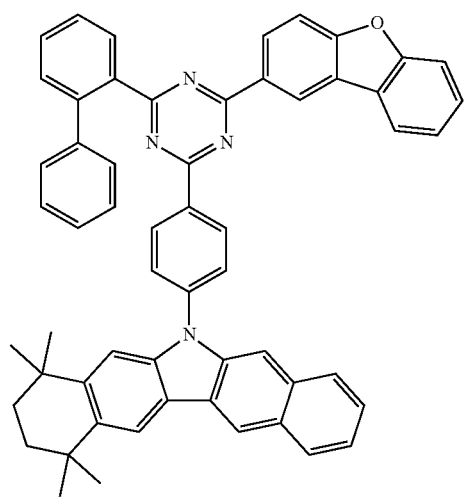
445
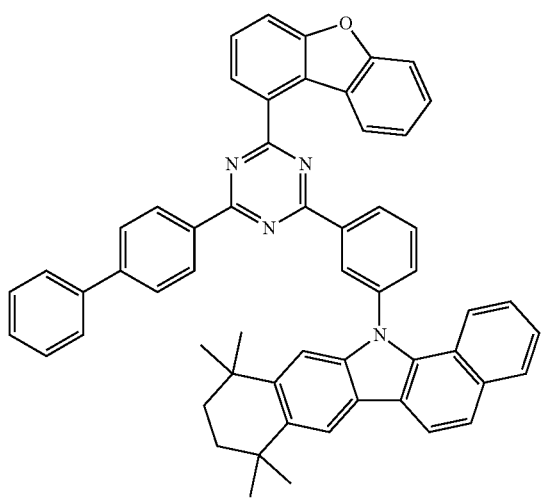
446
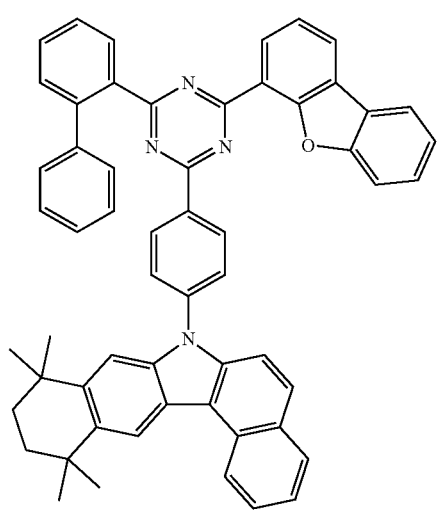
447
208
-continued
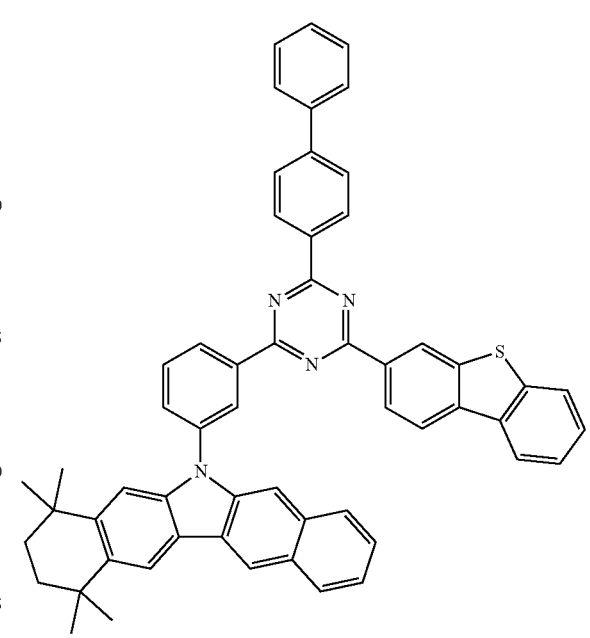
448
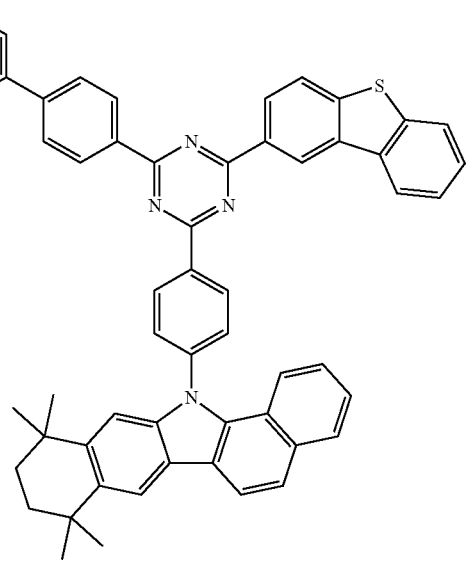
449

209
-continued
450
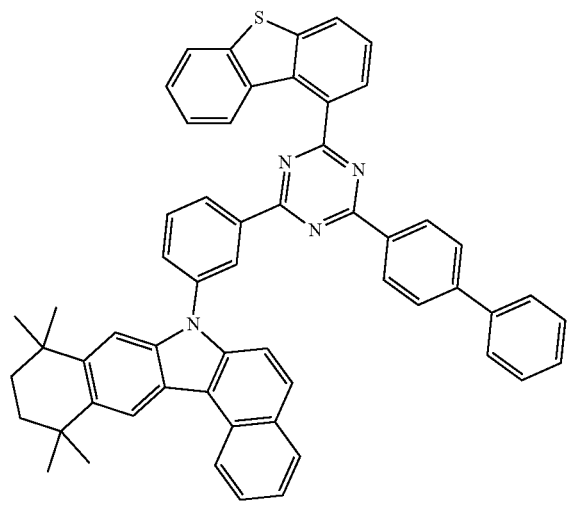
451
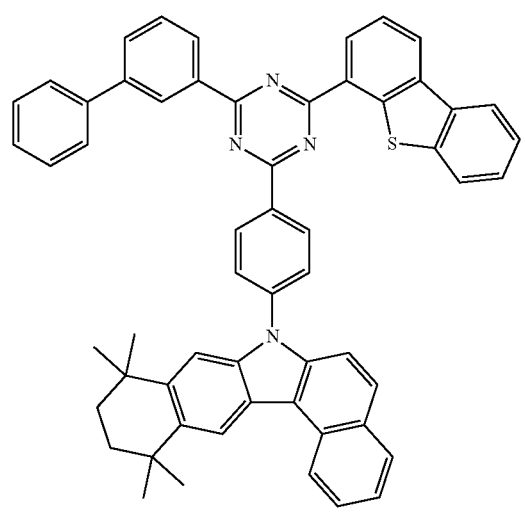
452
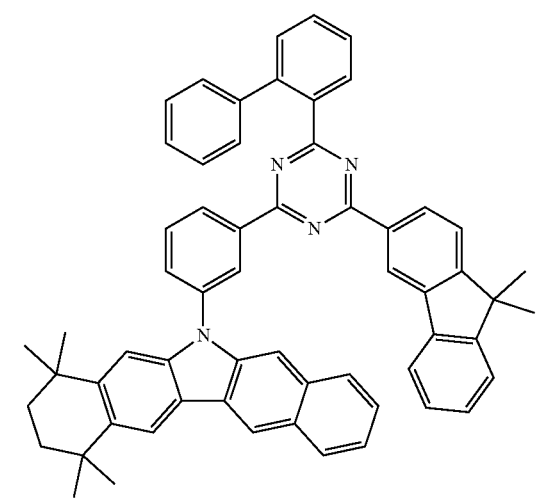
210
-continued
453
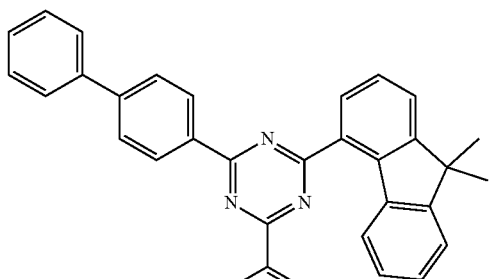
454
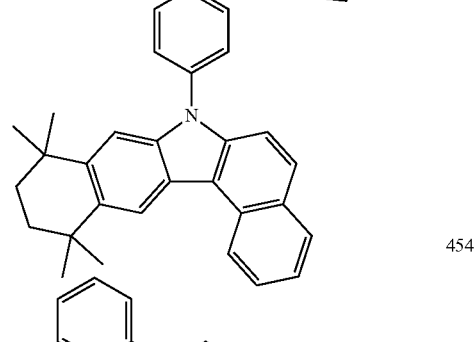
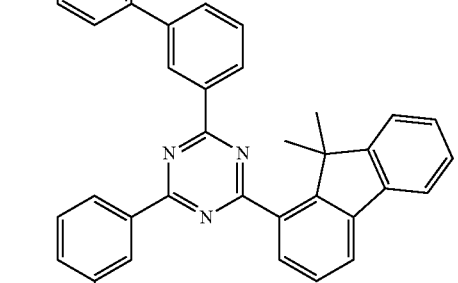
455
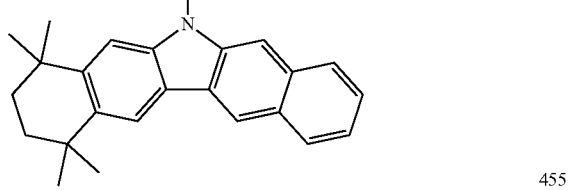
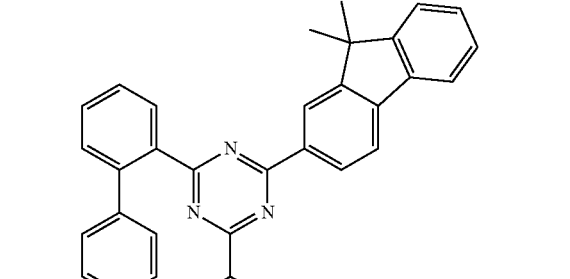
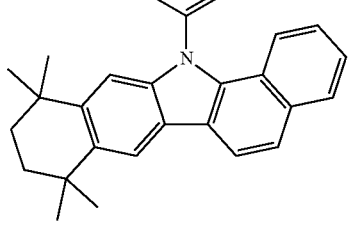

211
-continued
456
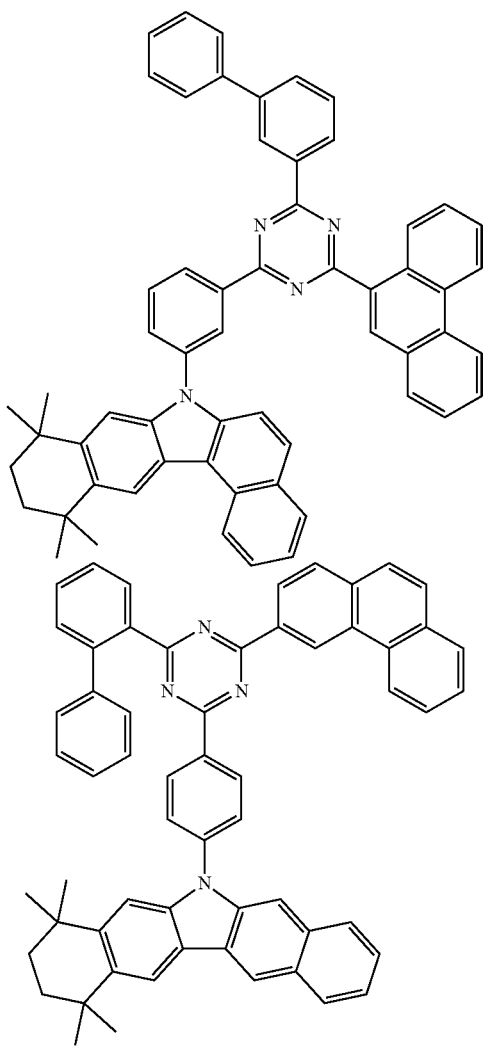
457
458
212
-continued
459
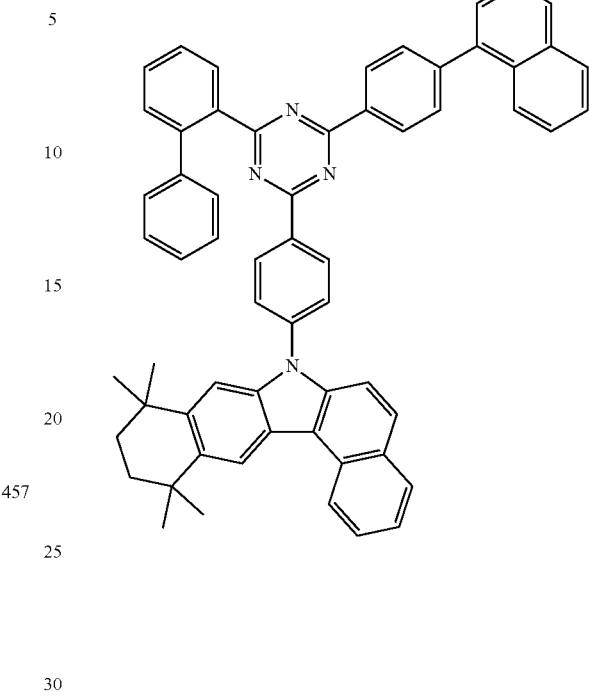
460
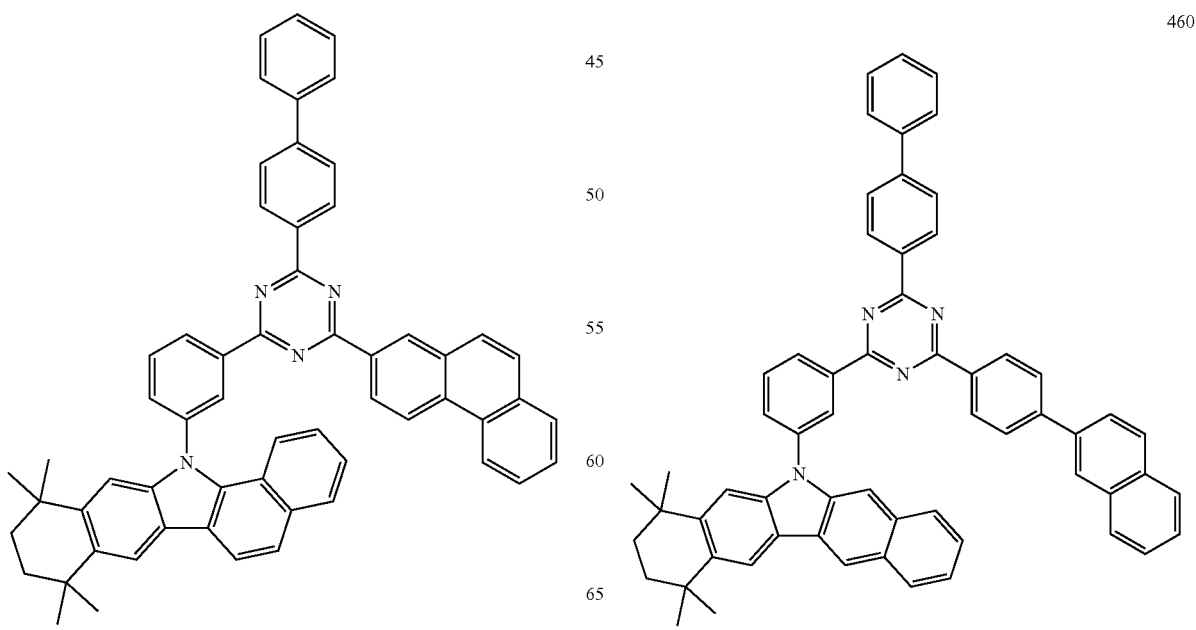

213
-continued
461
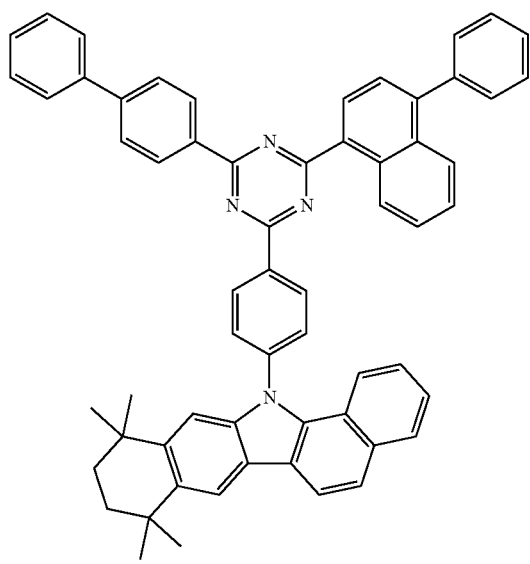
462
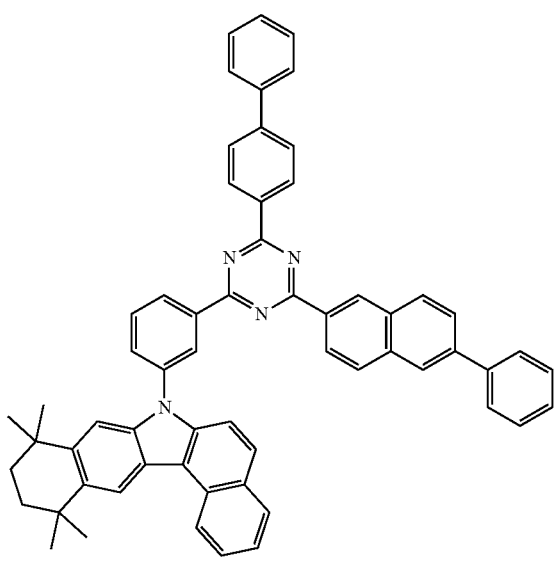
214
-continued
464
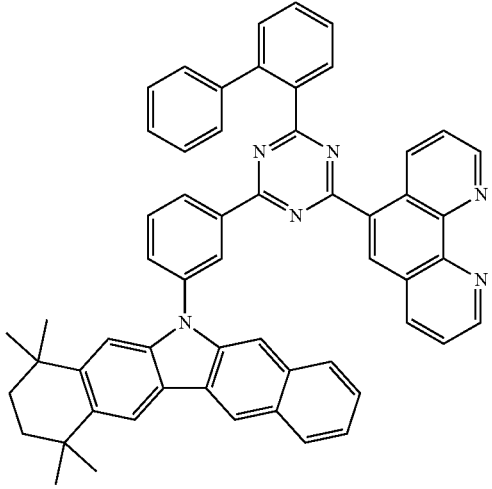
465
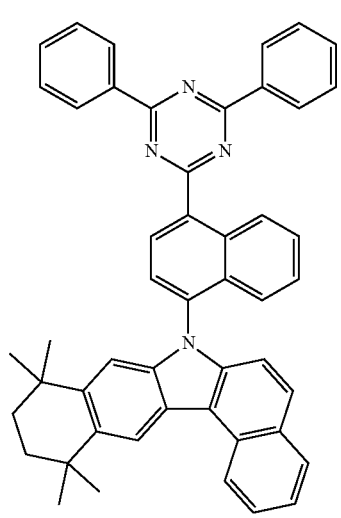
463
466
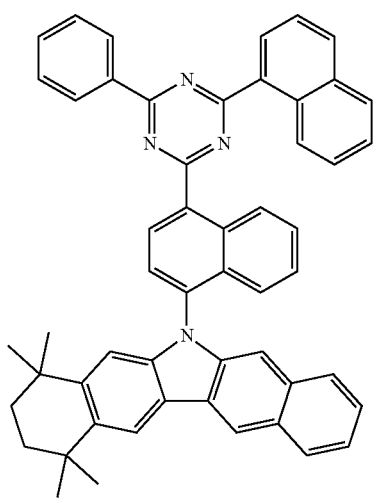

215
-continued
467
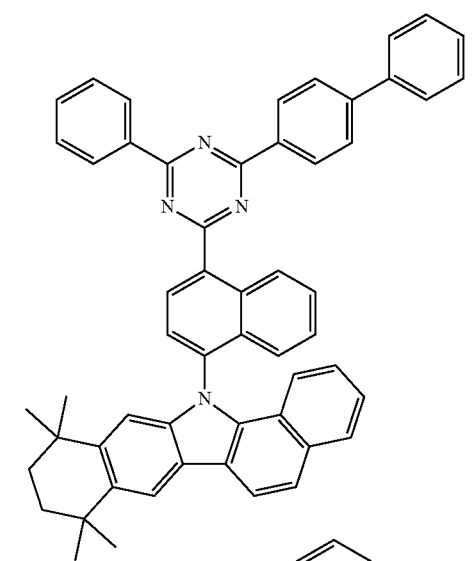
468
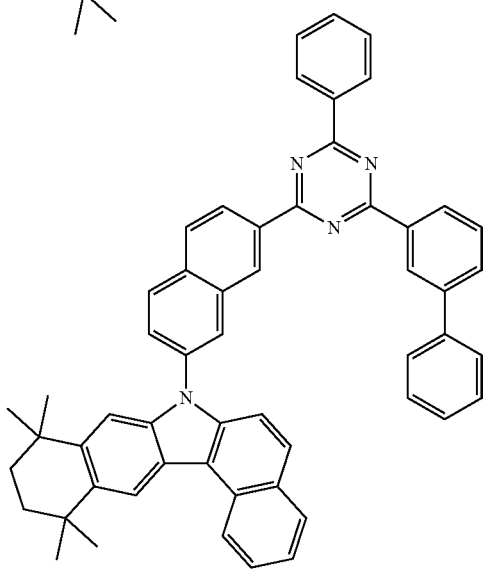
469
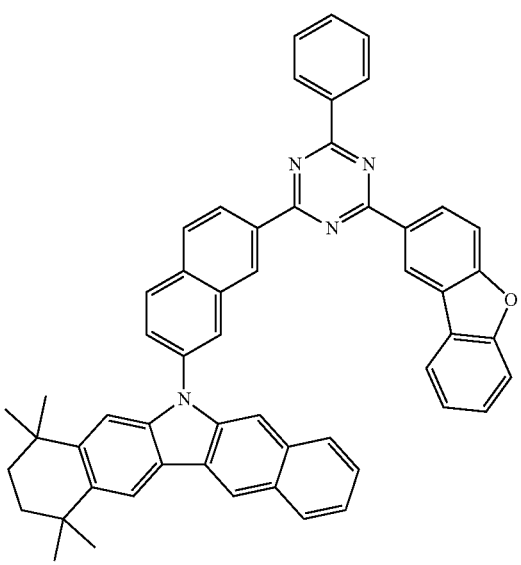
216
-continued
470
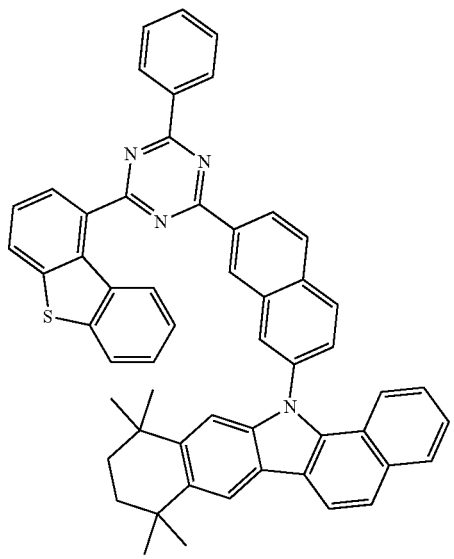
471
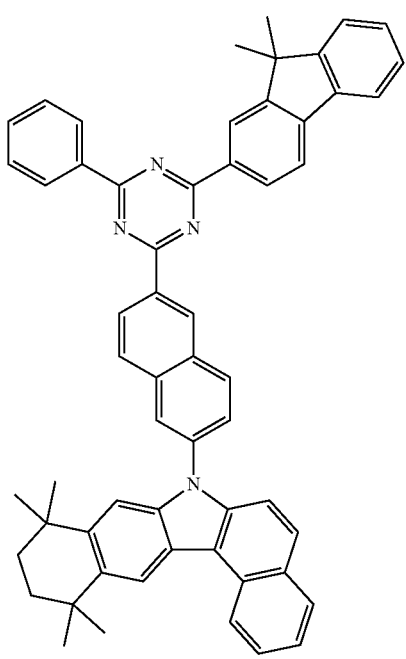

472
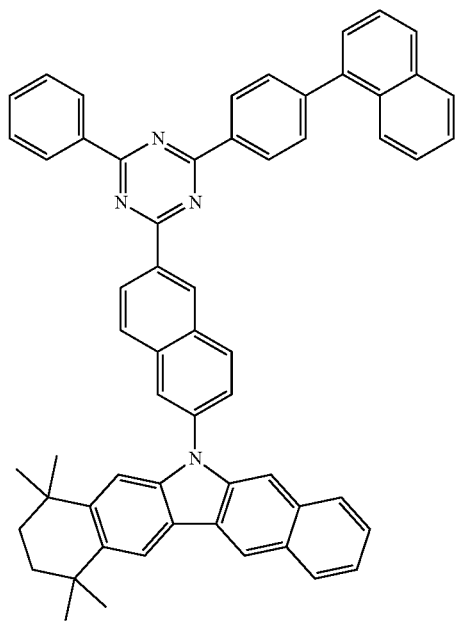
473
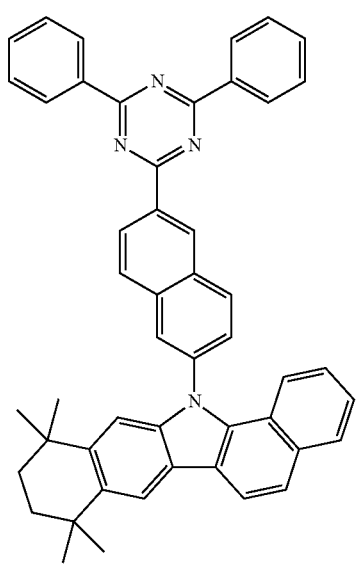
474
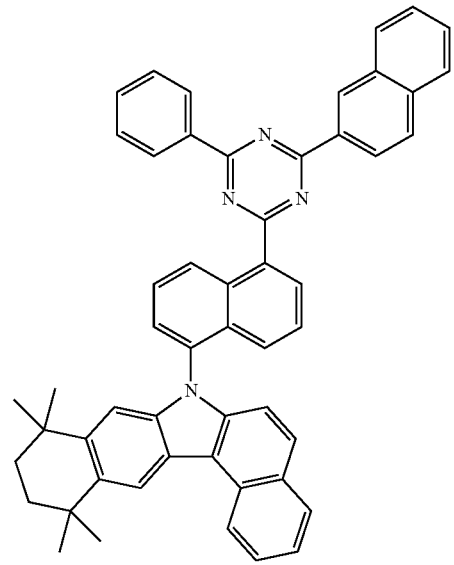
475
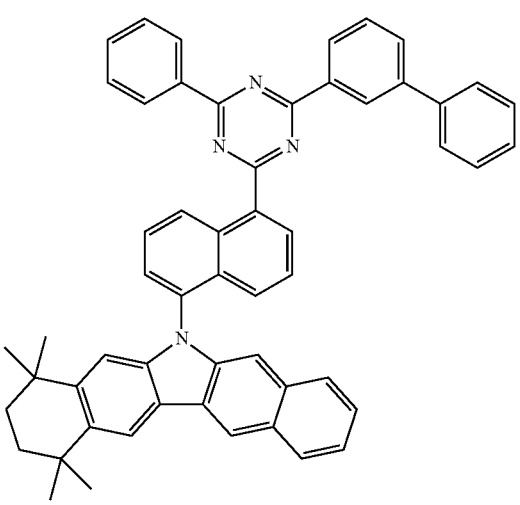
476
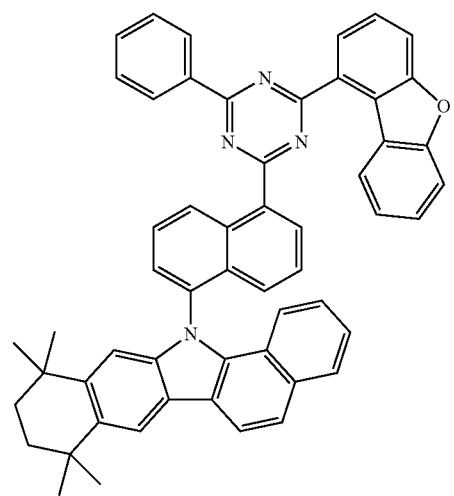

219
-continued
477
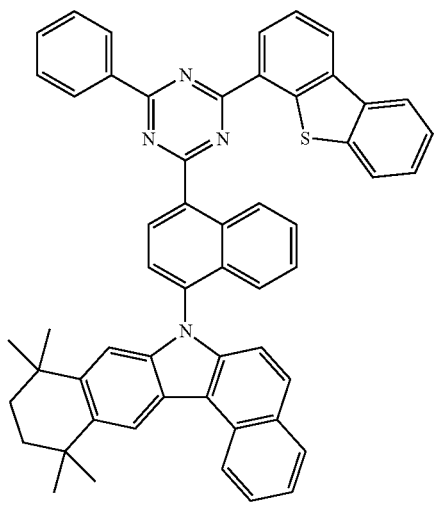
478
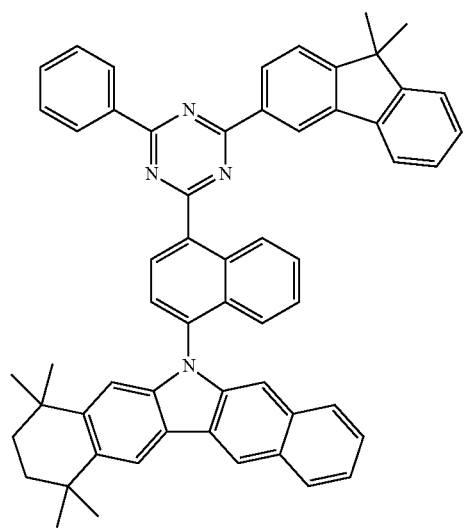
479
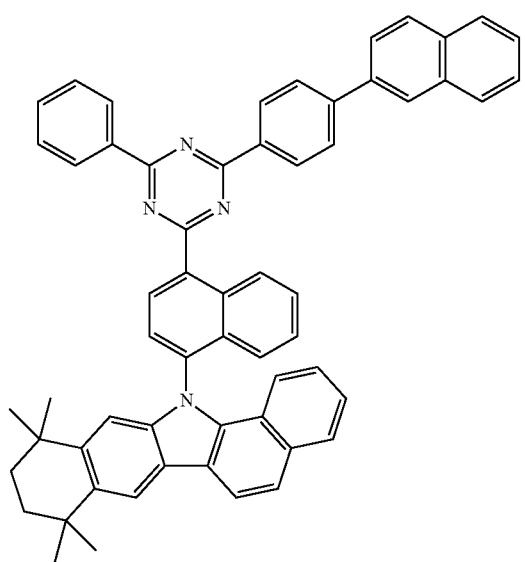
220
-continued
480
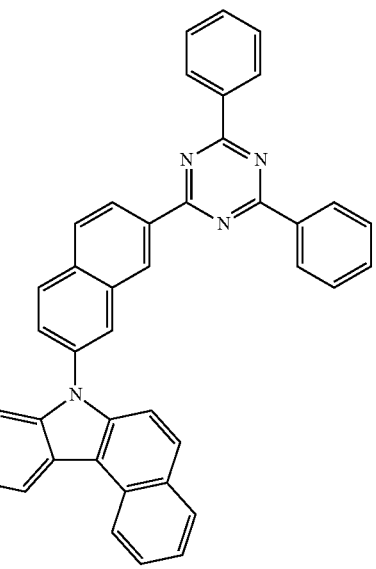
481
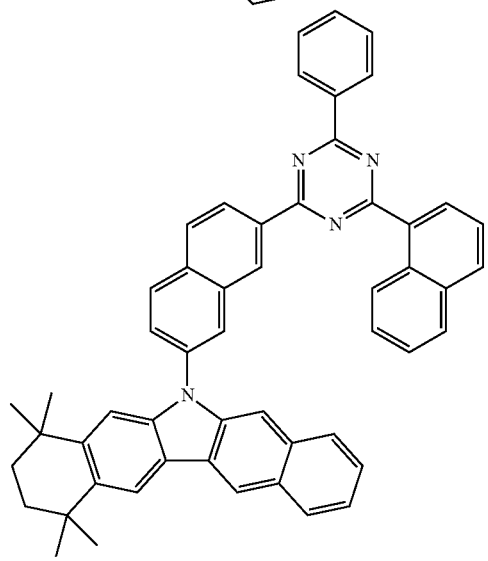
482
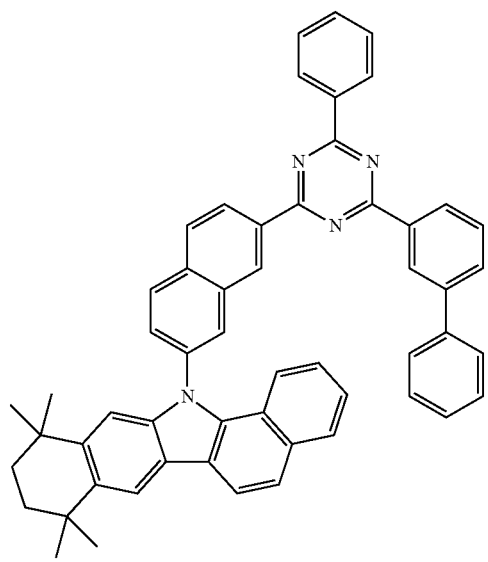

221
-continued
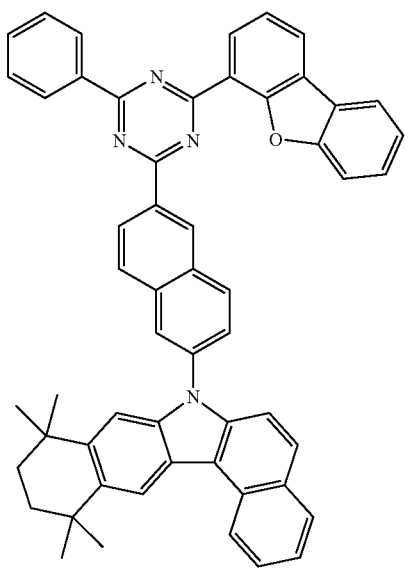
483
222
-continued
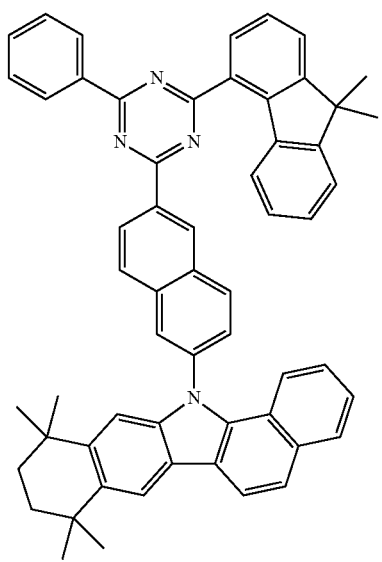
485
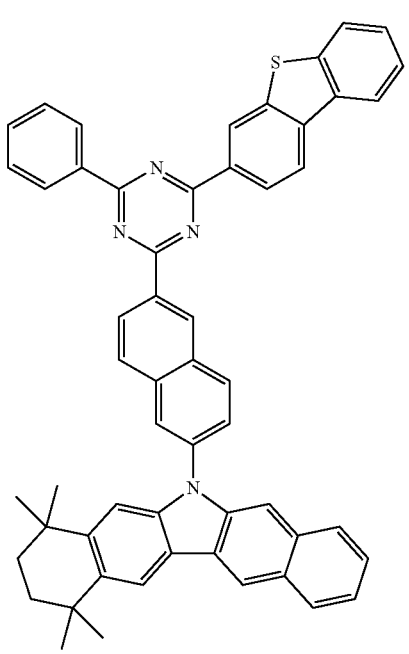
484
486

223
-continued
487
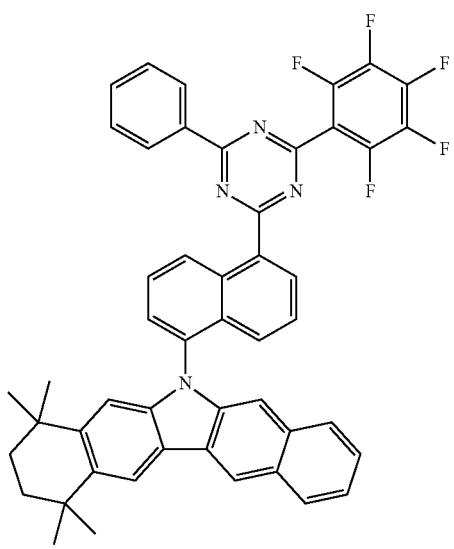
488
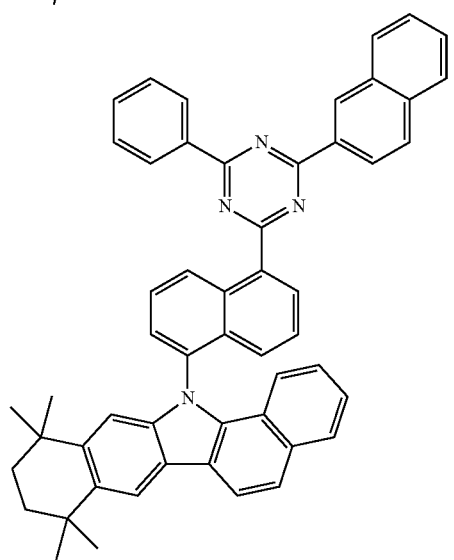
489
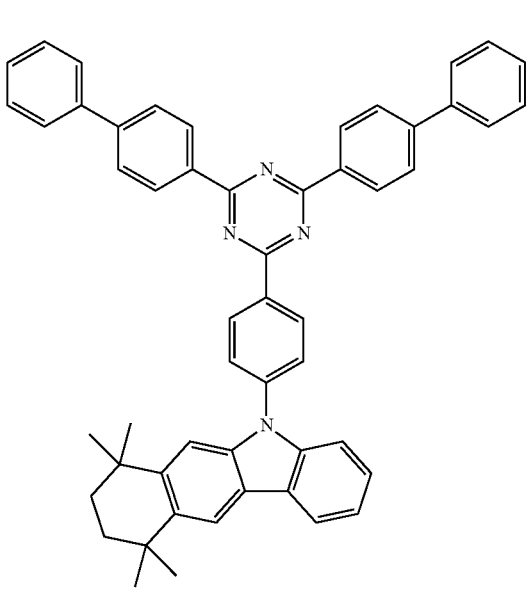
224
-continued
490
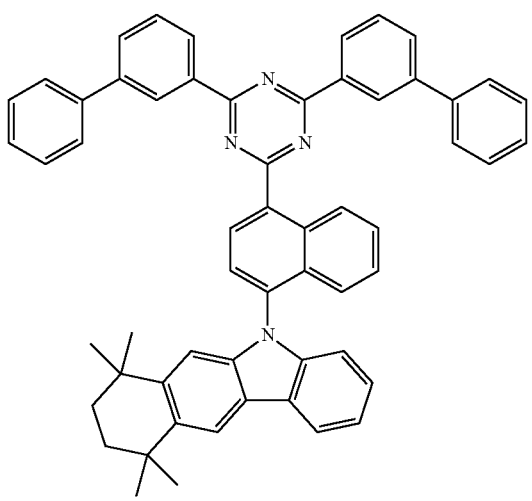
491
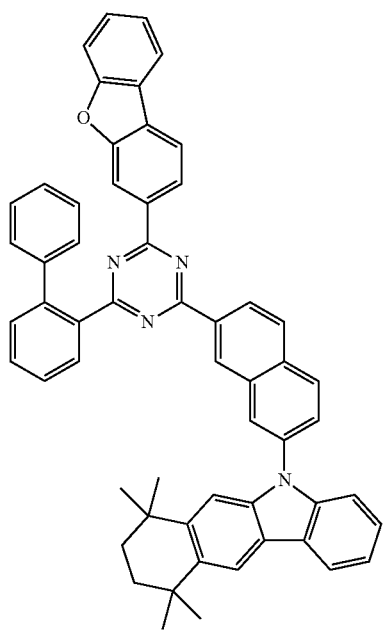

492
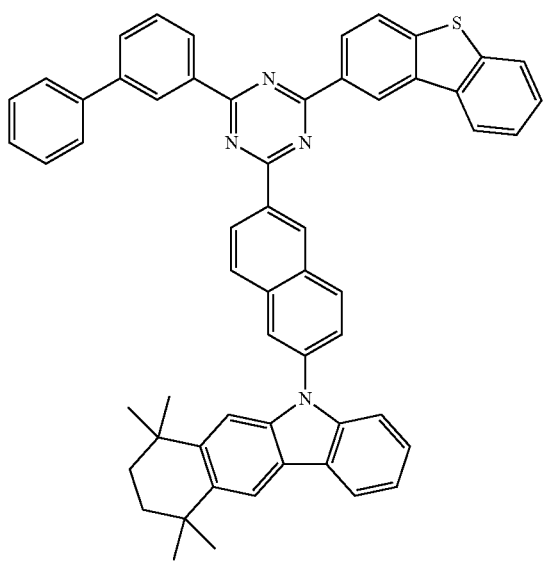
493
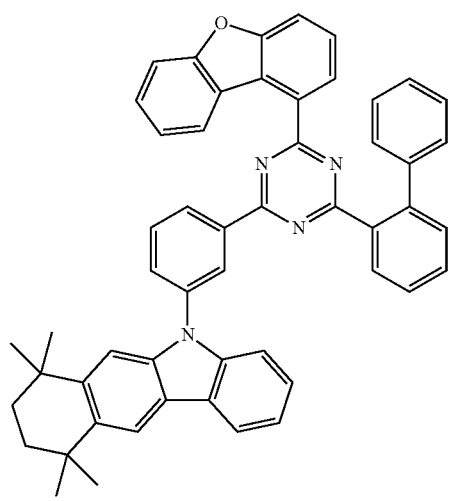
494
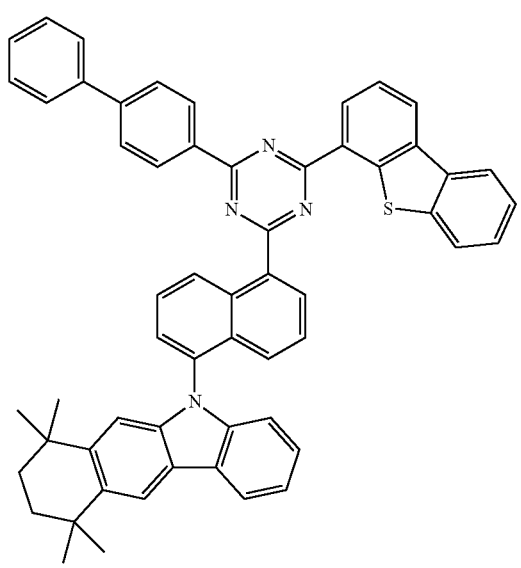
495
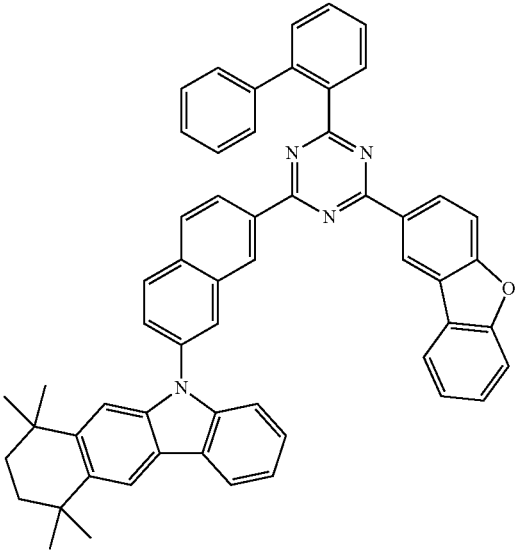
496
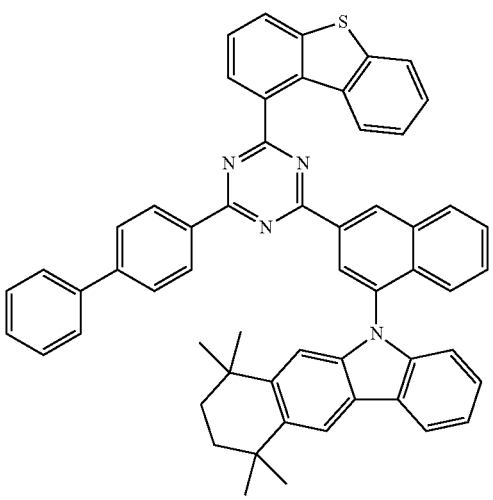
497
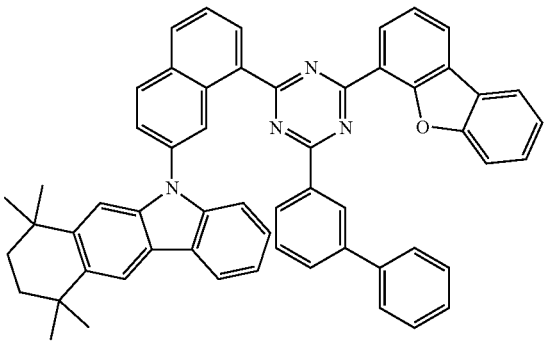

227
-continued
498
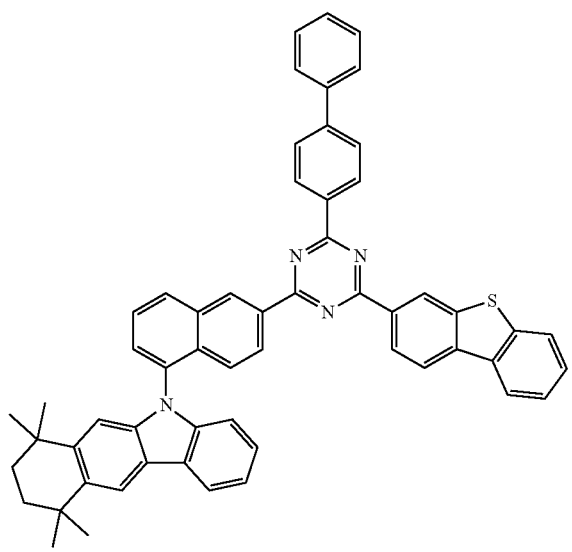
499
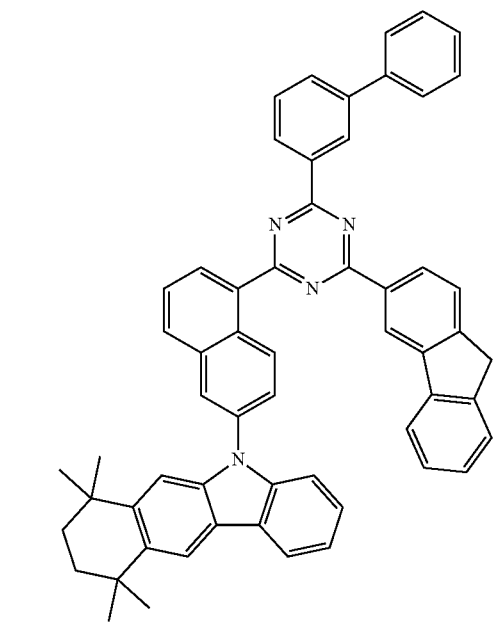
500
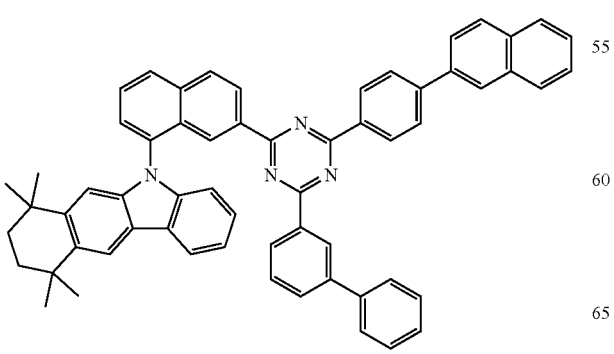
228
-continued
501
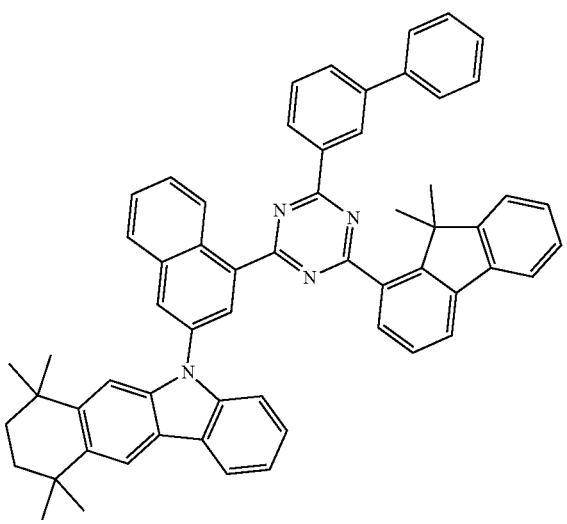
502
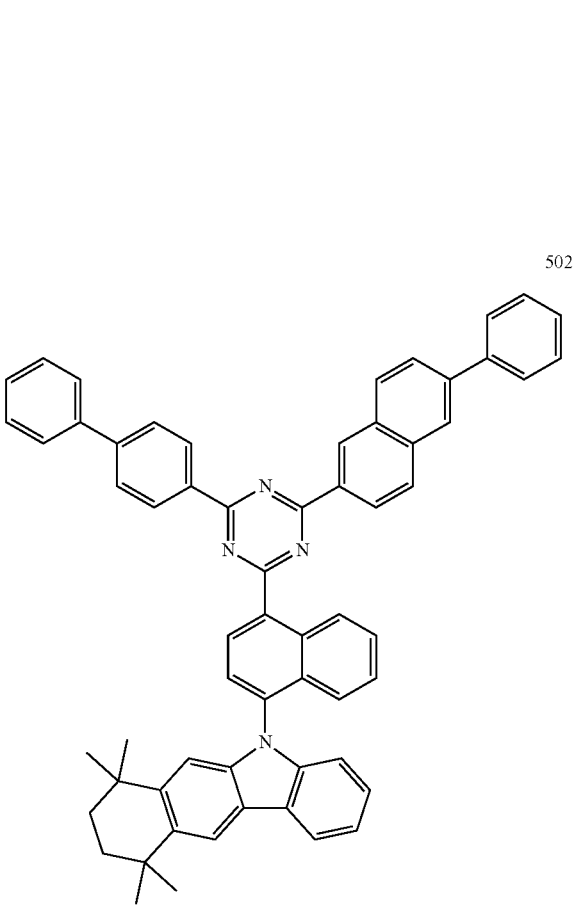

229
-continued
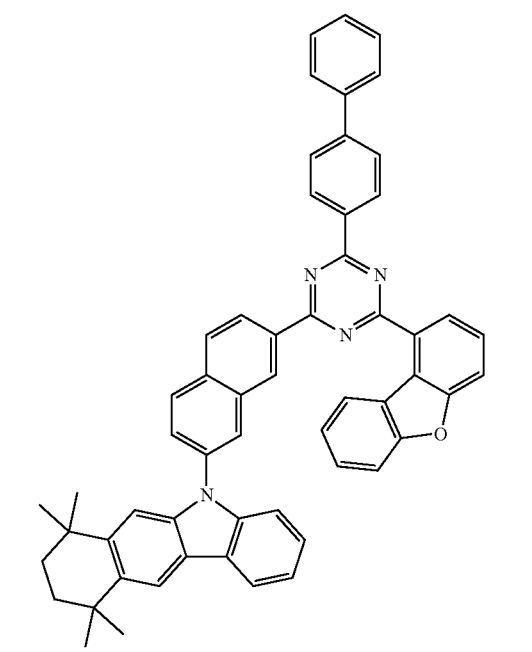
503
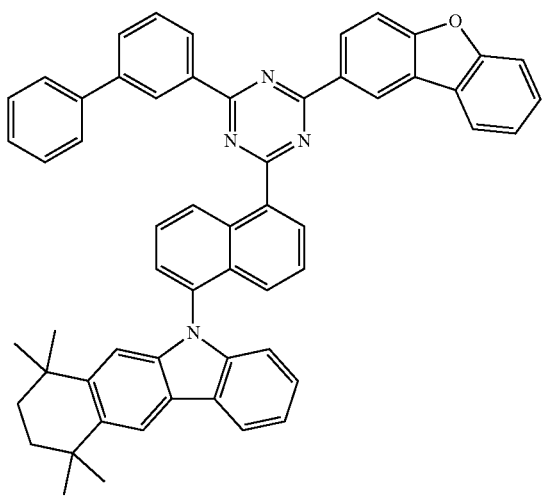
504
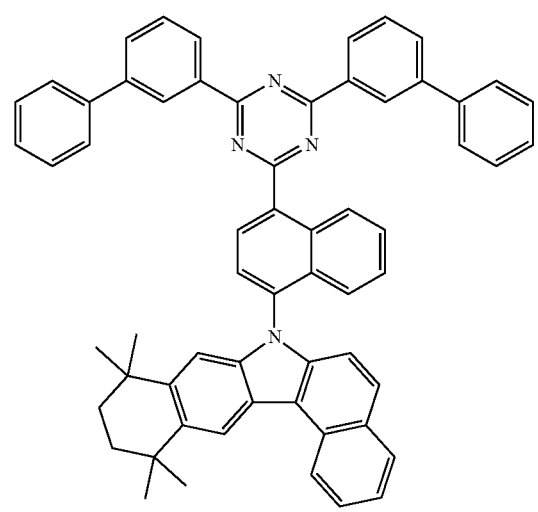
505
230
-continued
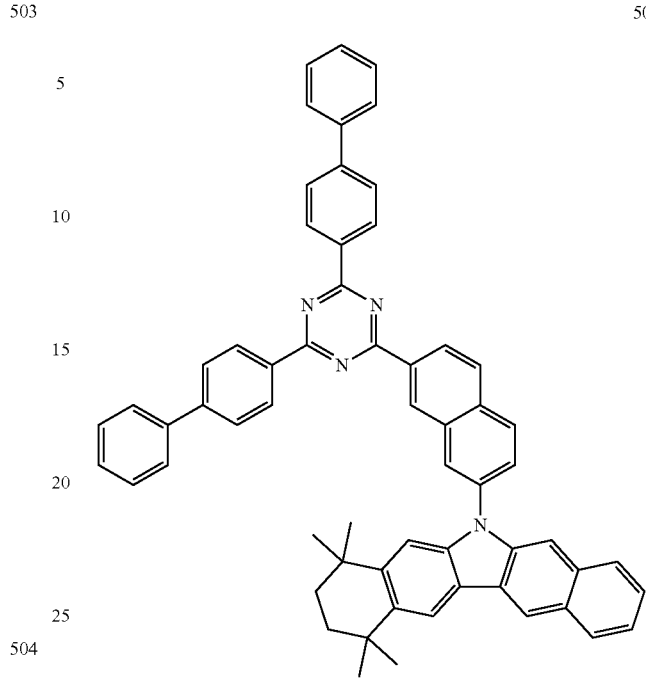
506
507

231
-continued
232
-continued
508
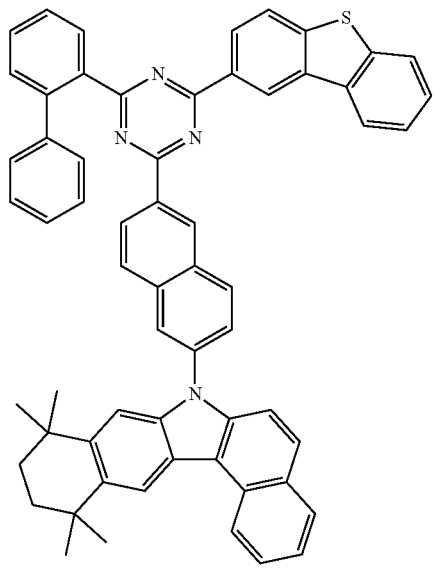
509
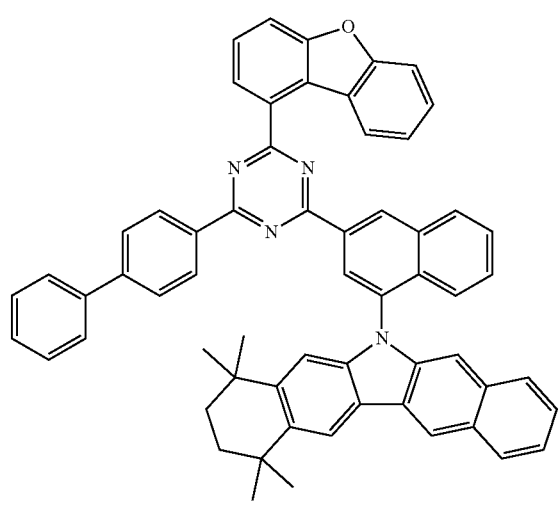
510
511
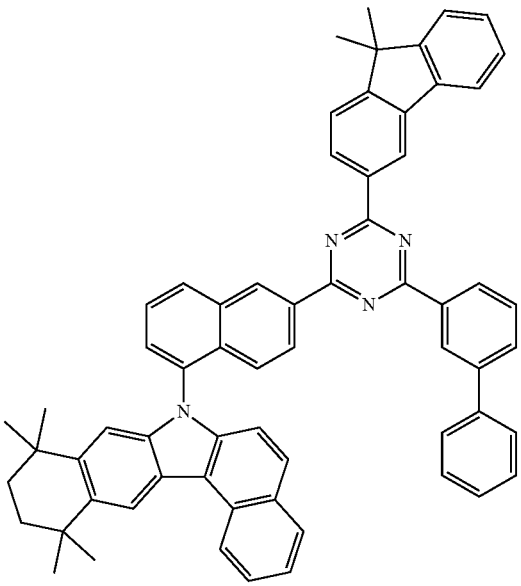
512
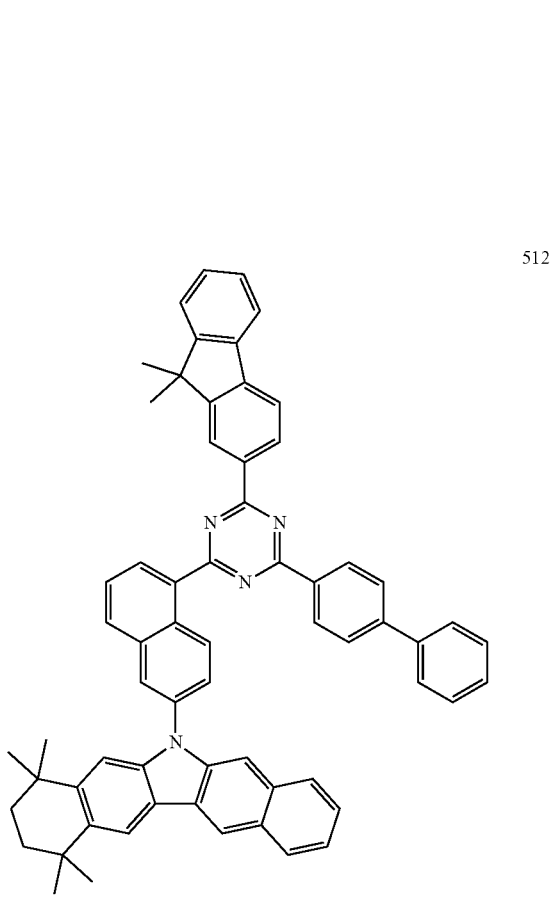

513
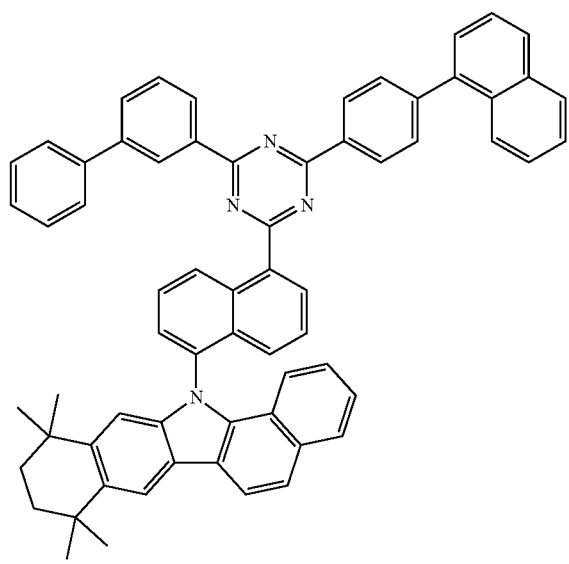
514
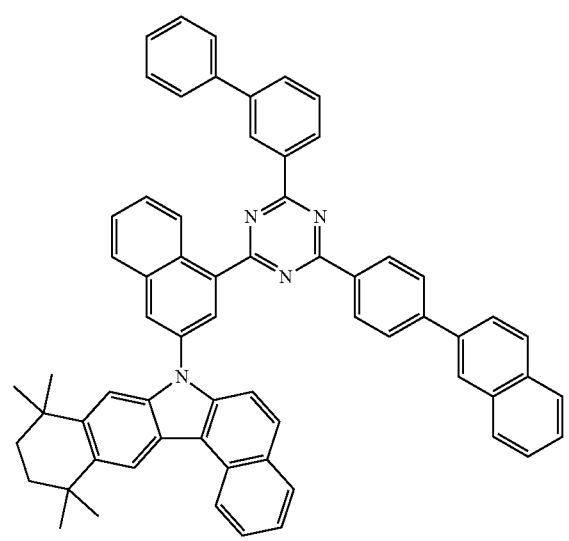
515
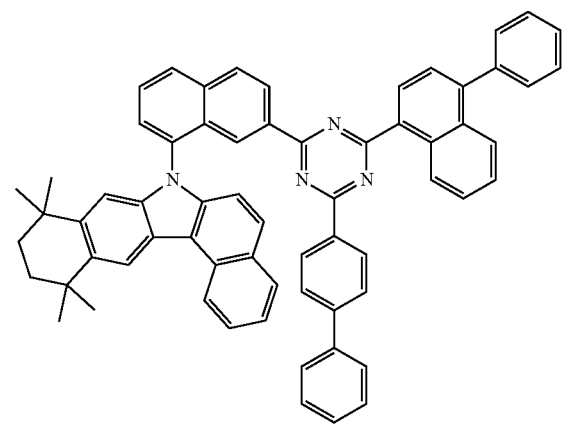
516
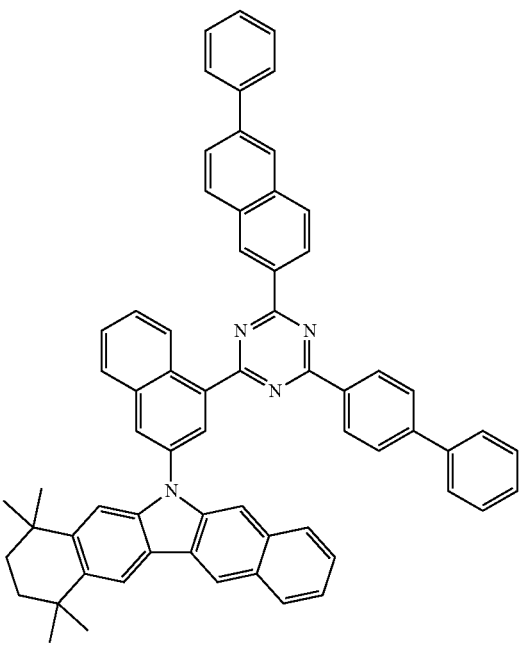
517
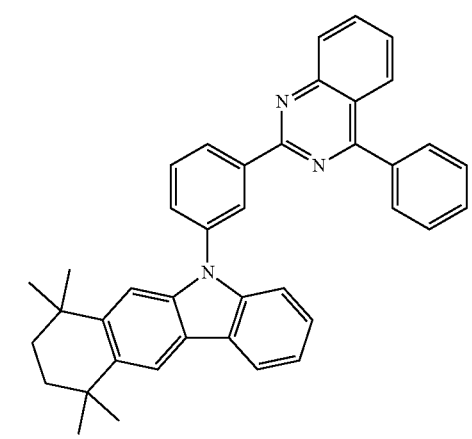
518
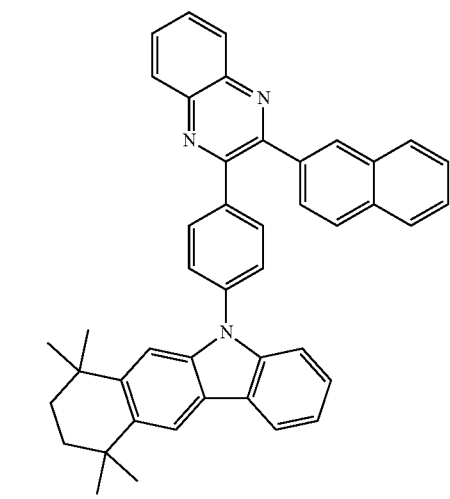

519
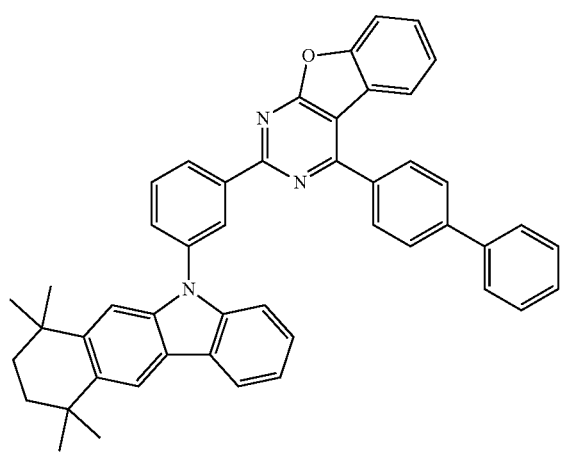
520
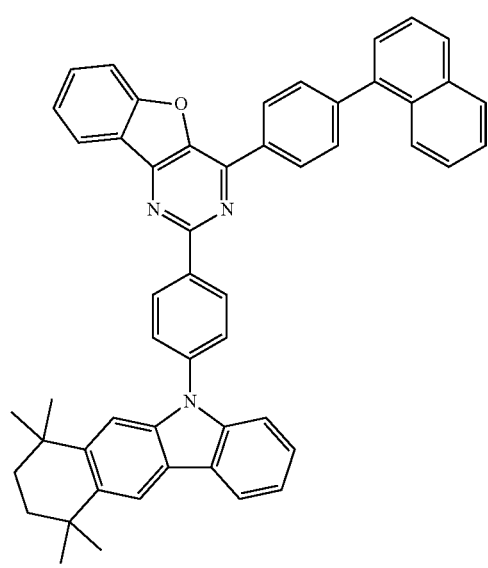
521
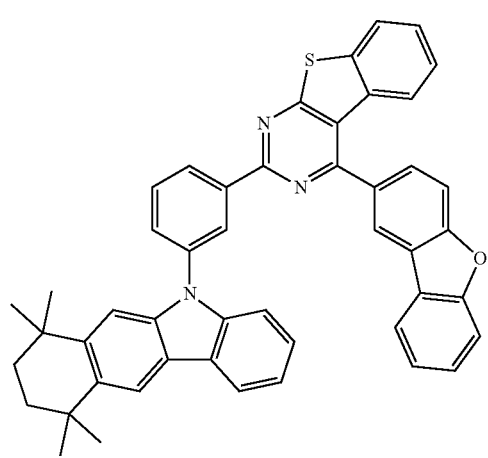
522
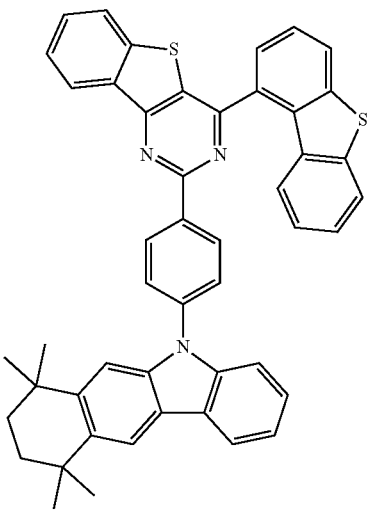
523
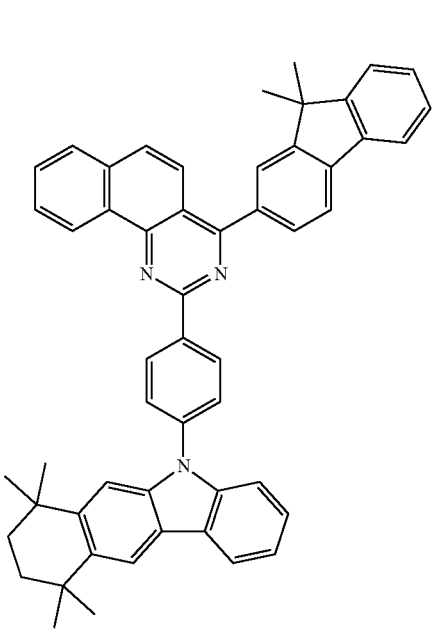
524
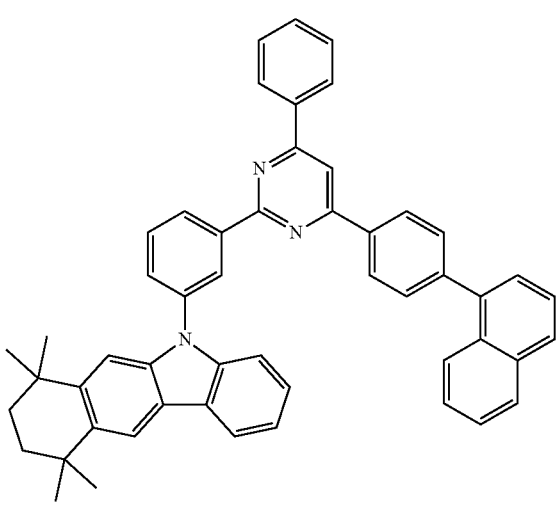

525
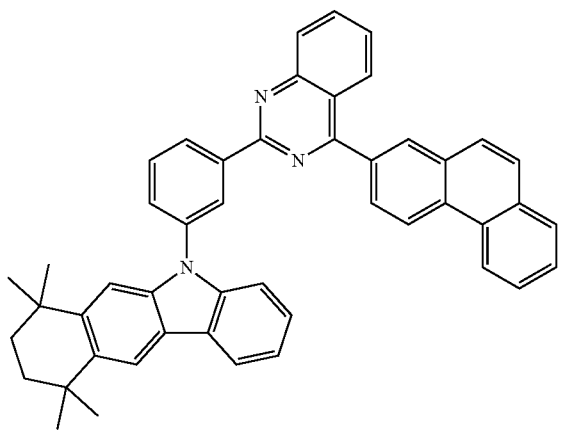
526
528
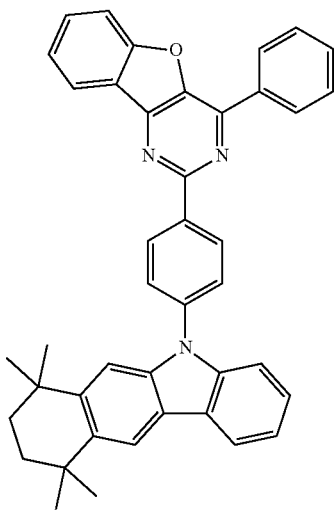
529
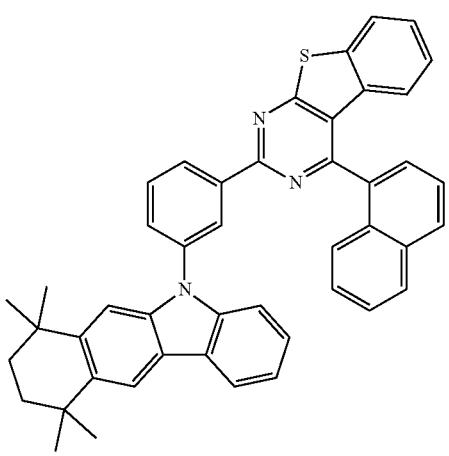
527
530
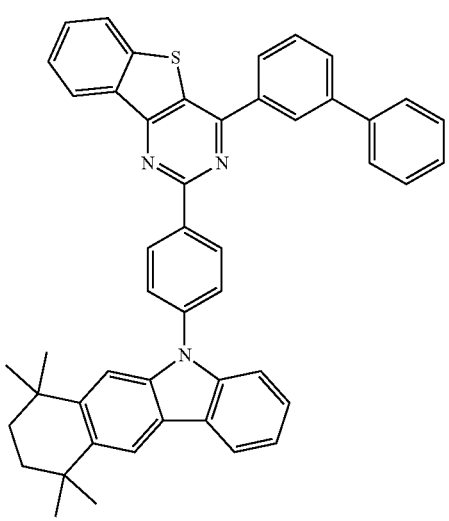

531
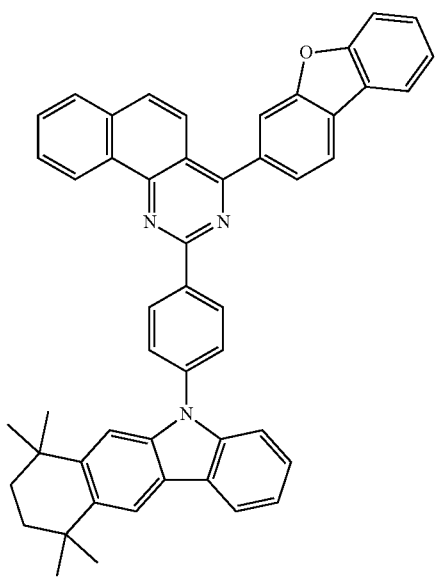
532
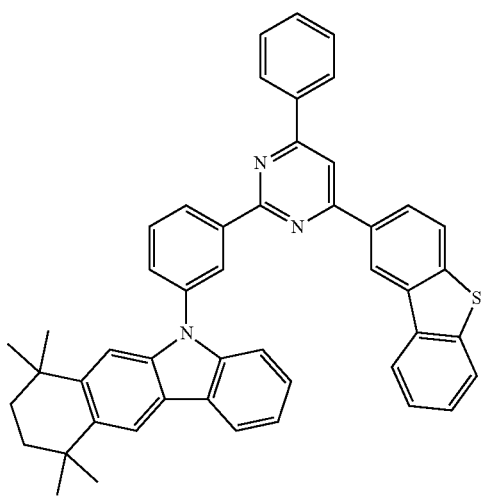
533
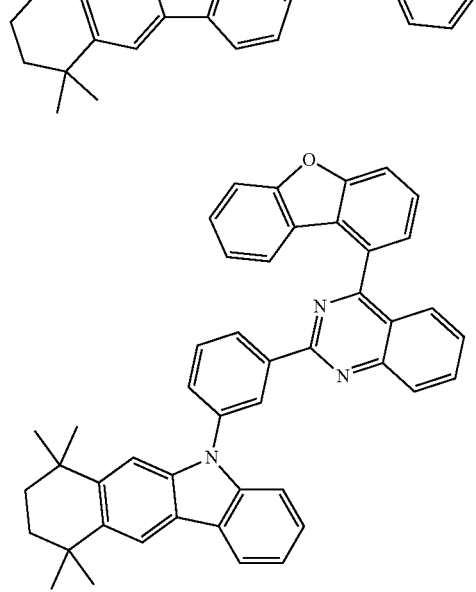
534
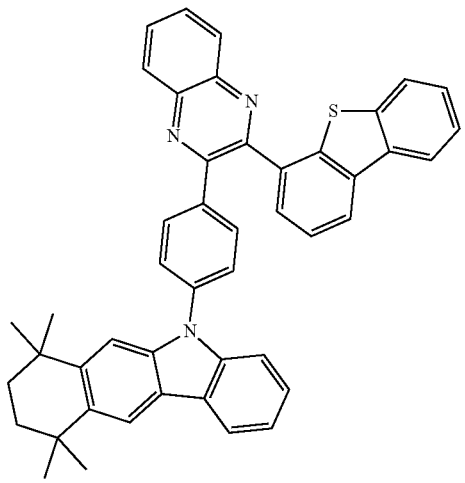
535
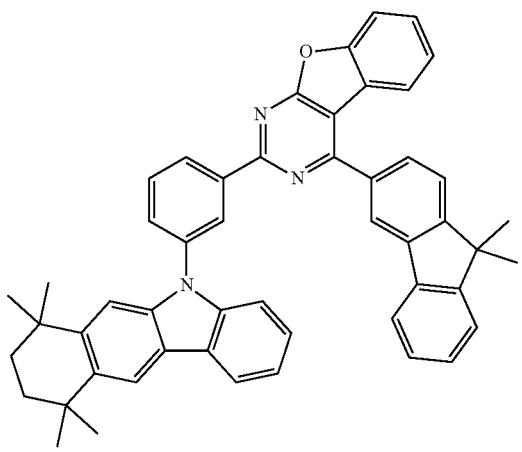
536
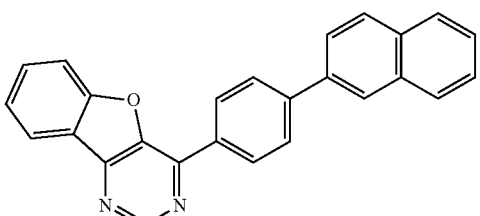
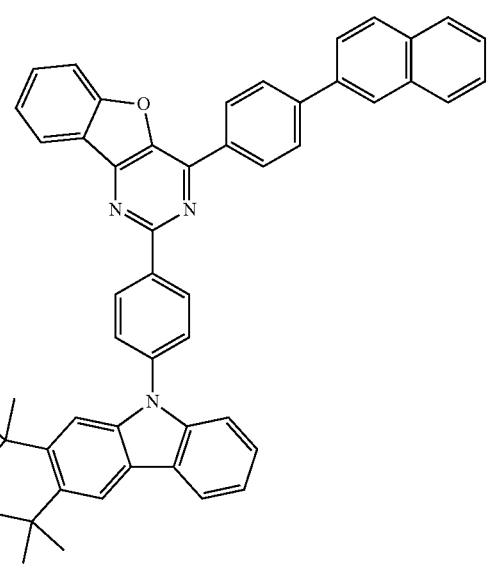

537
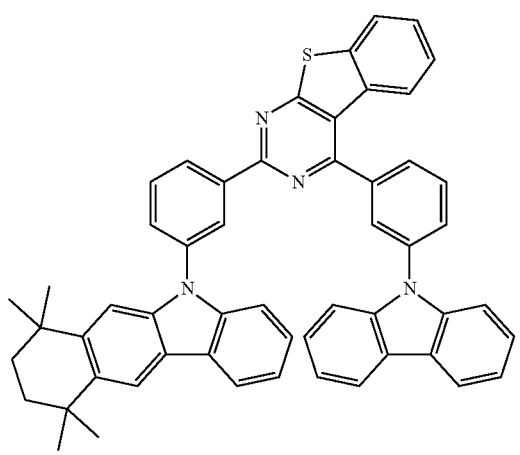
538
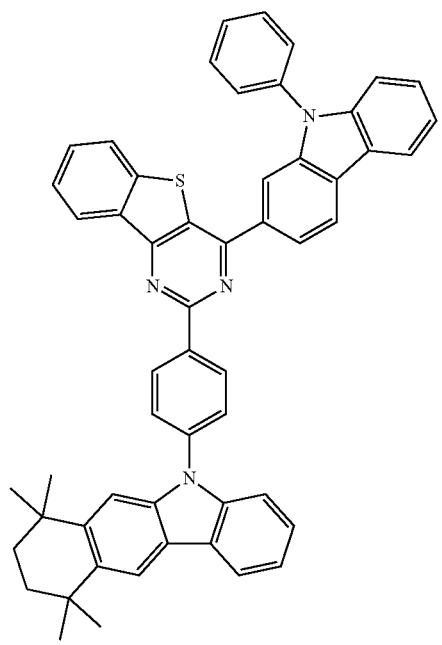
539
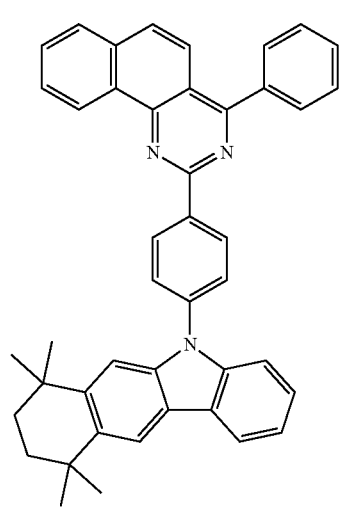
540
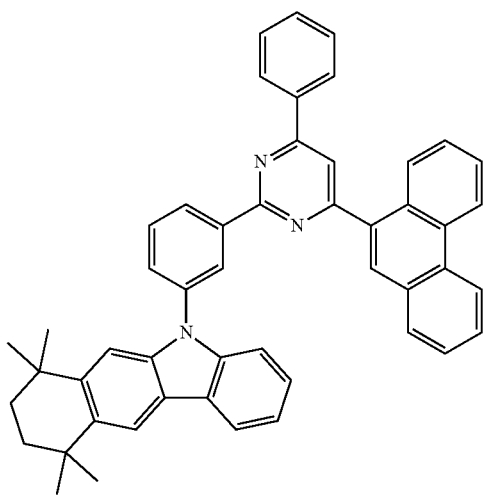
541
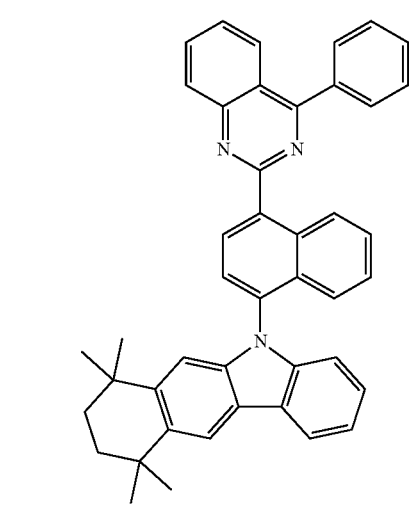
542
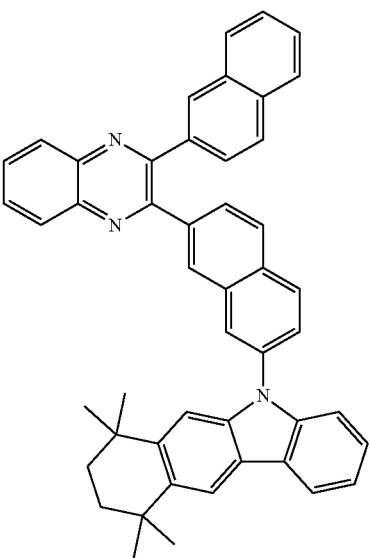

243
-continued
244
-continued
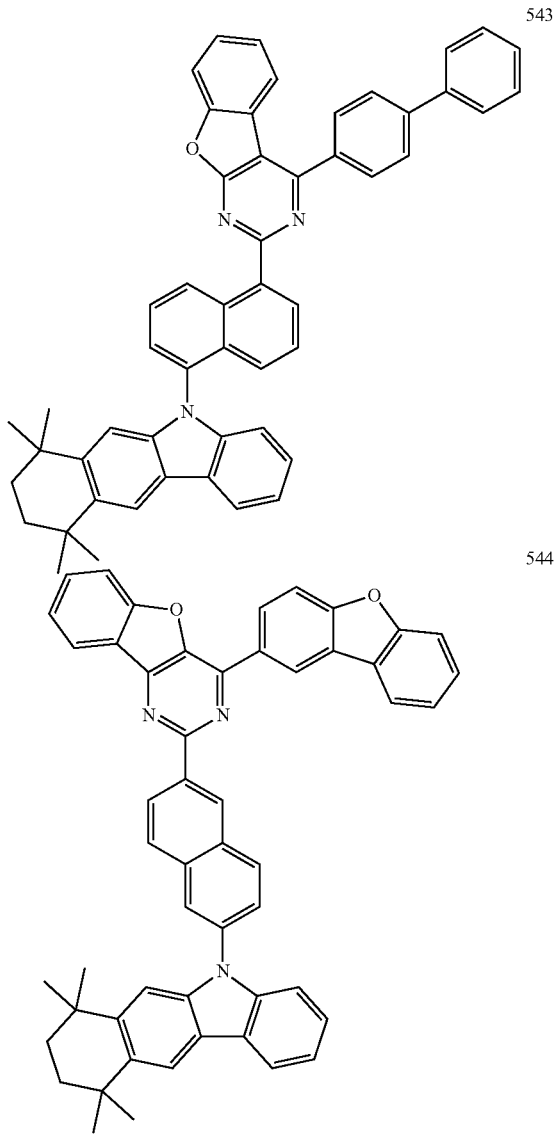
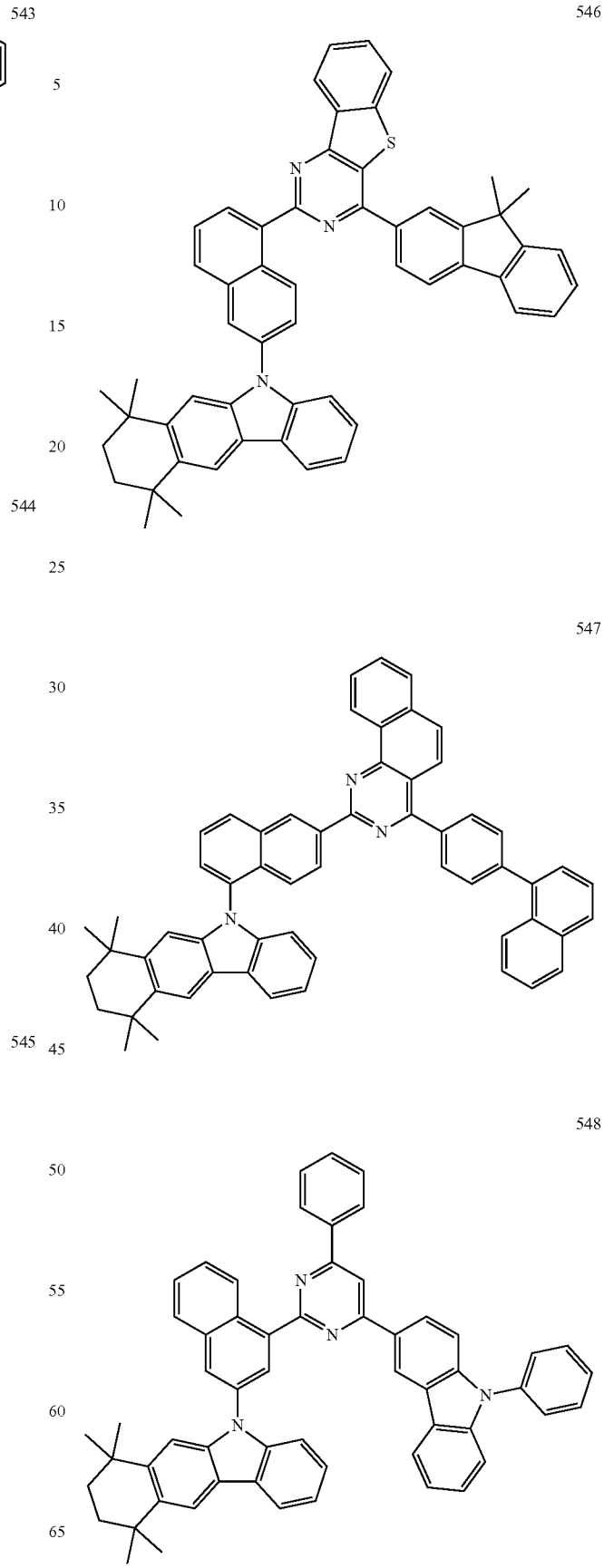

-continued
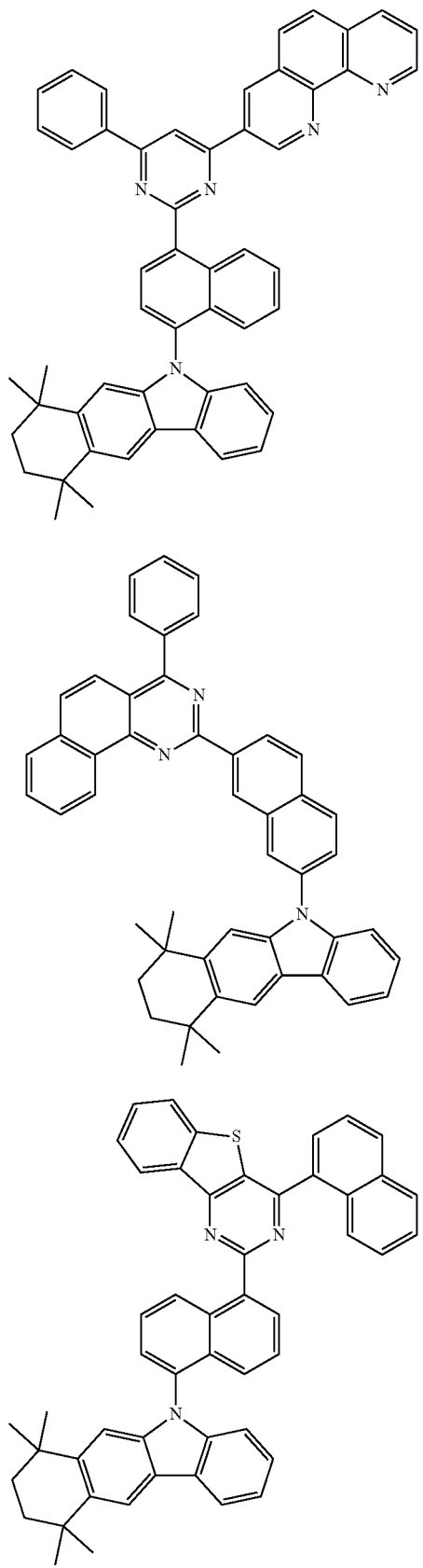

-continued
554
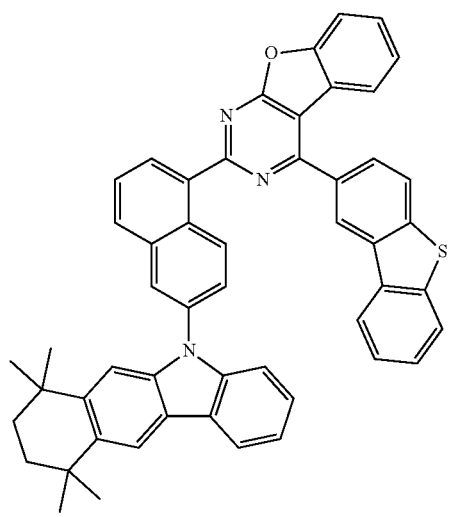
555
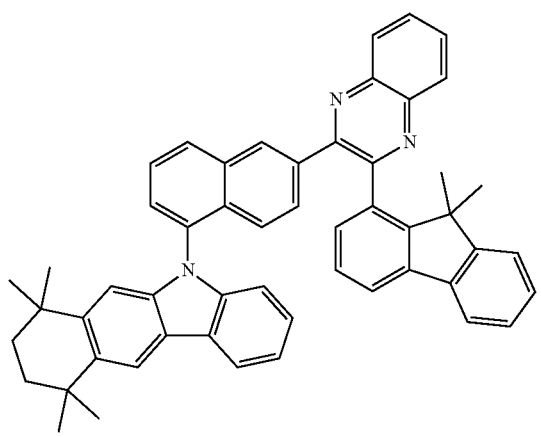
556
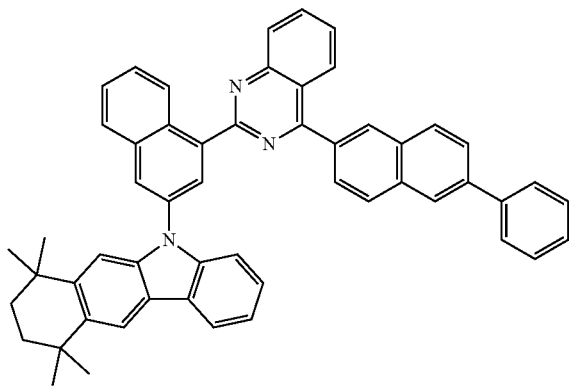
-continued
557
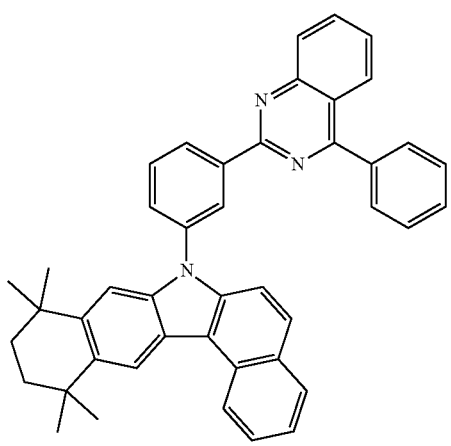
558
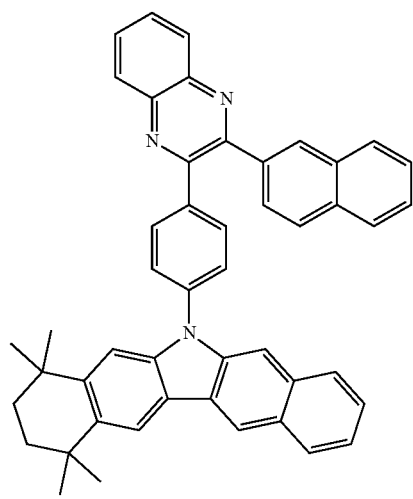
559
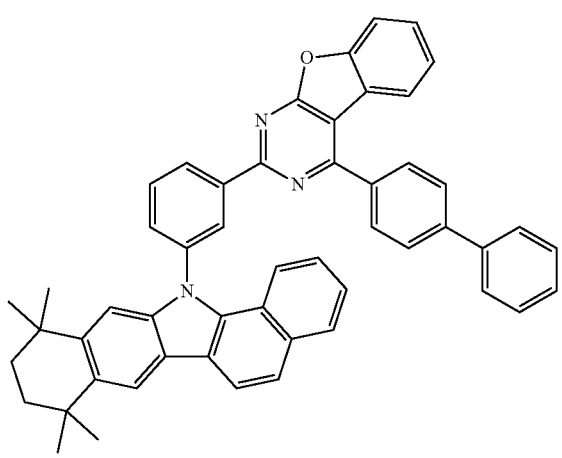

249
-continued
250
-continued
560
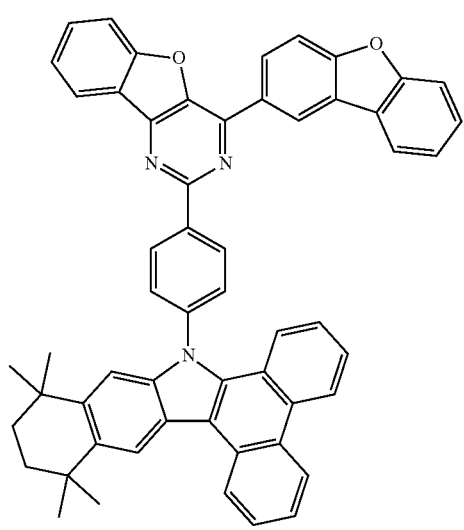
563
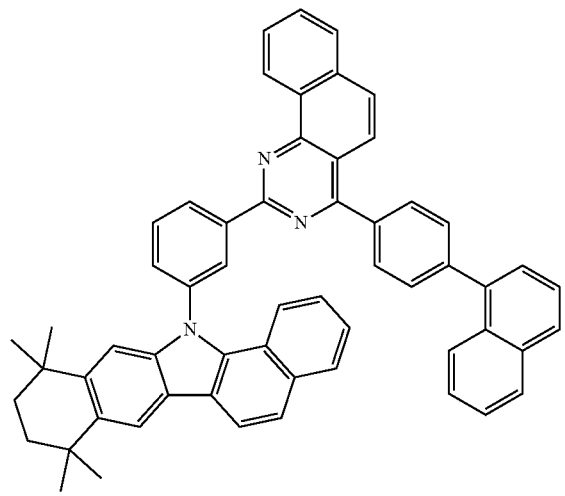
561
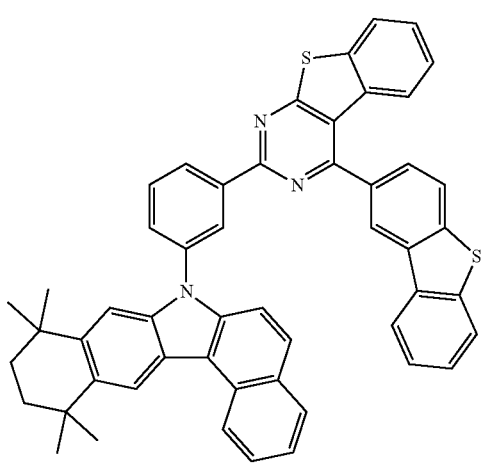
564
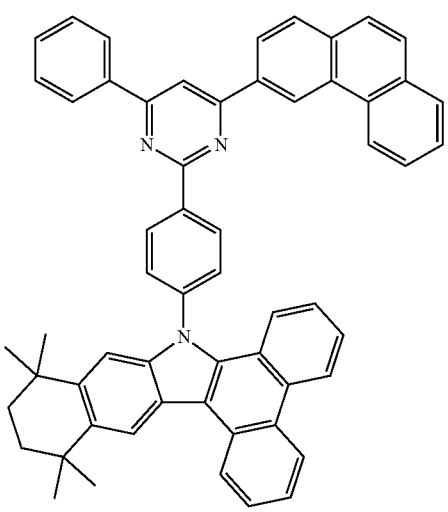
562
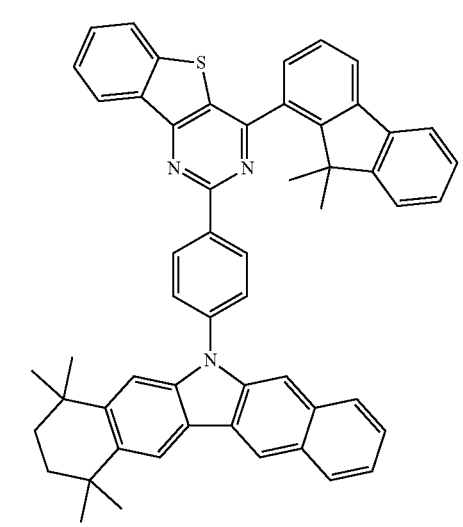
565
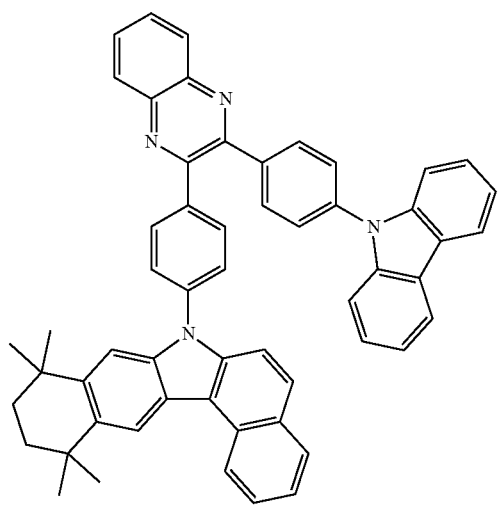

-continued
566
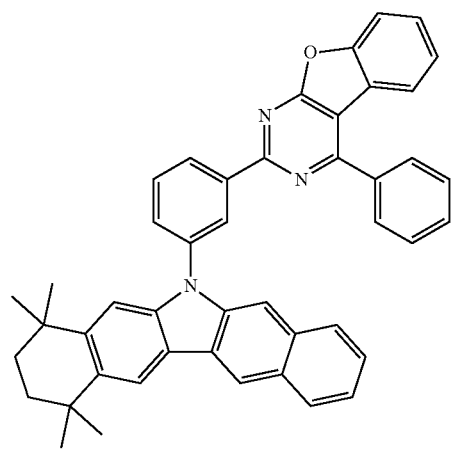
567
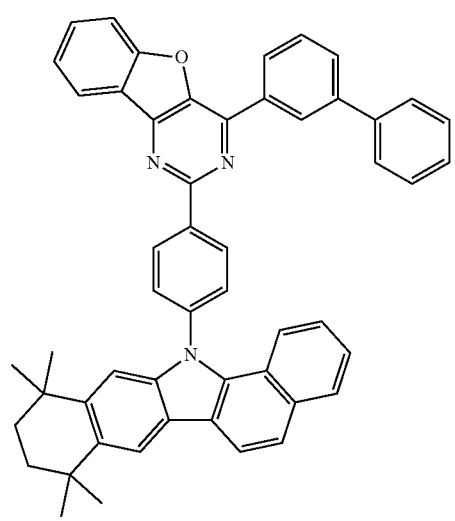
568
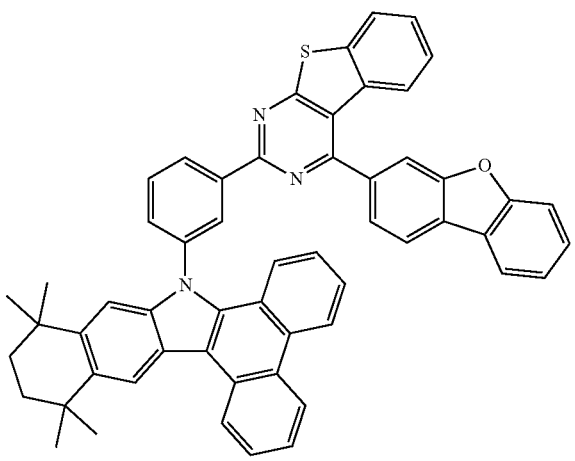
569
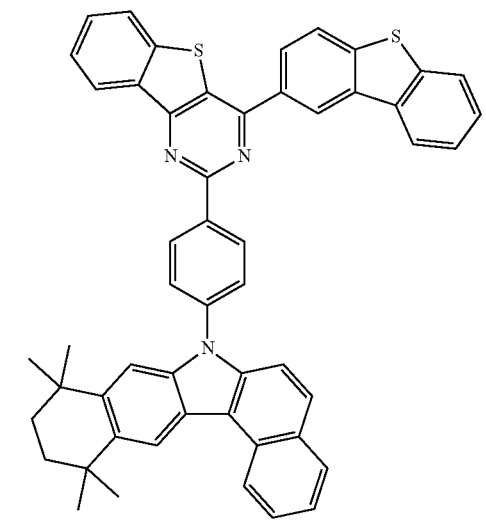
570
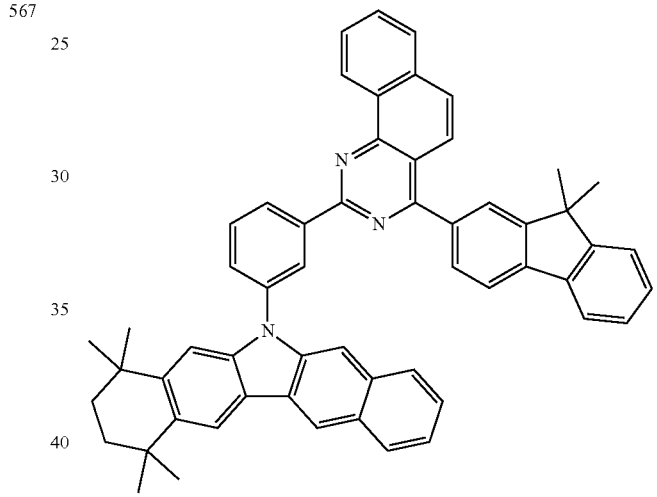
571
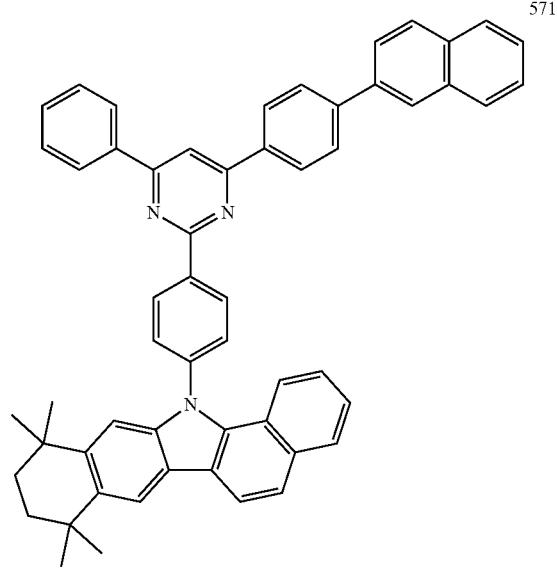

253
-continued
572
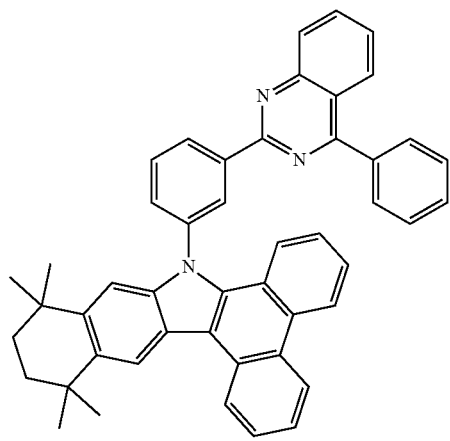
573
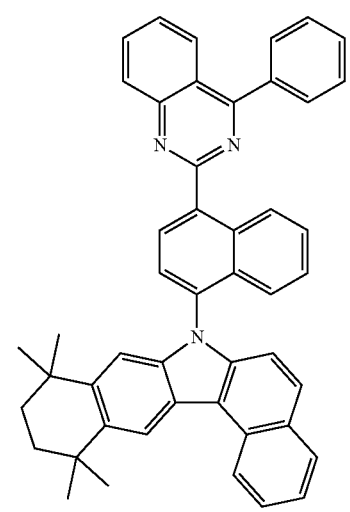
574
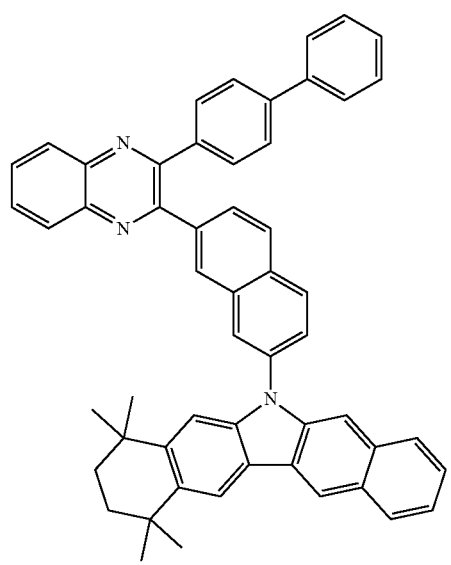
254
-continued
575
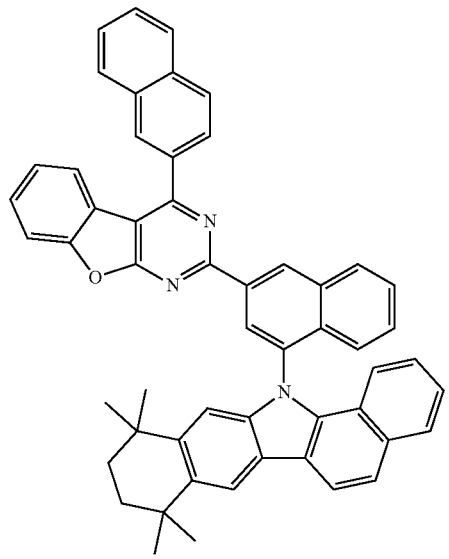
576
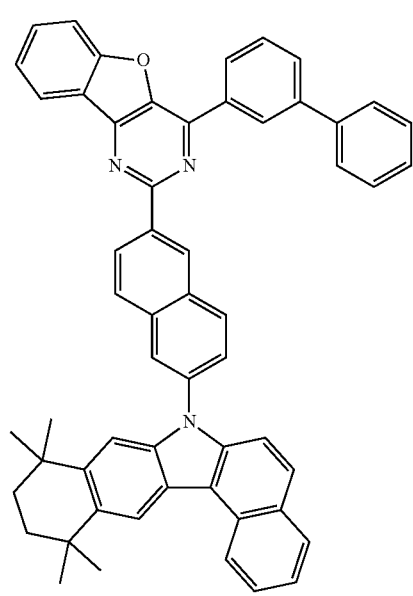

255
-continued
577
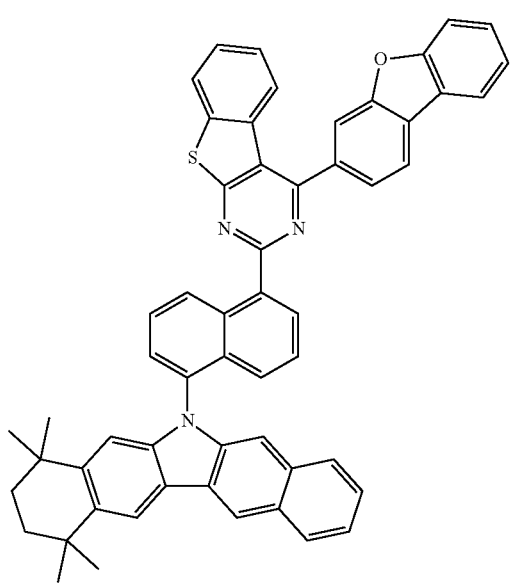
578
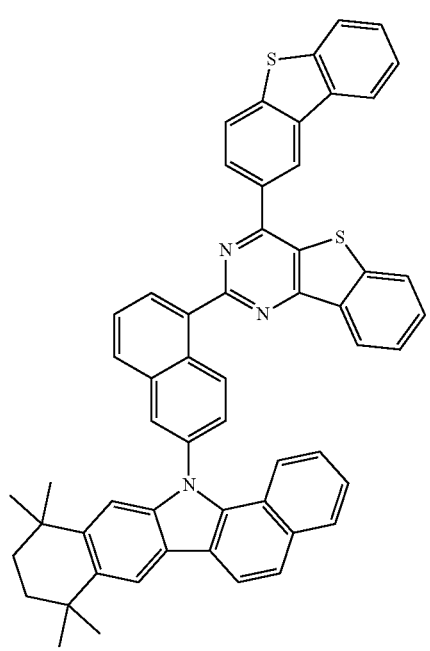
256
-continued
579
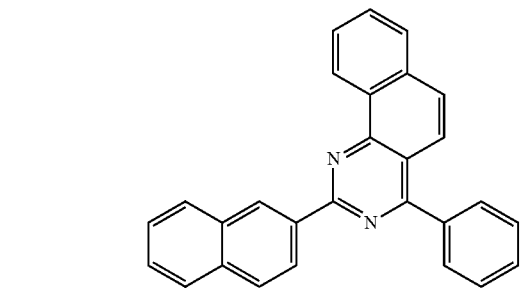
580
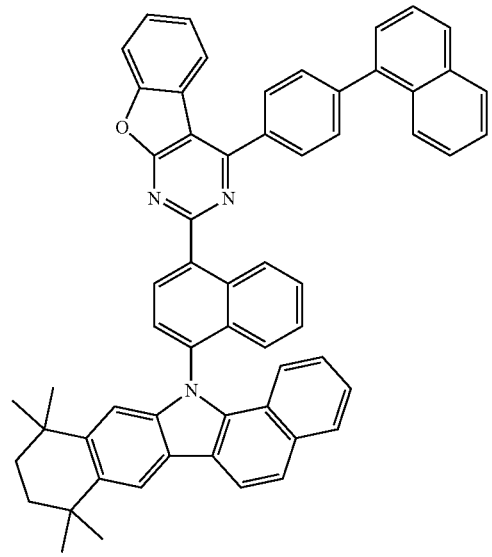
581

-continued
582
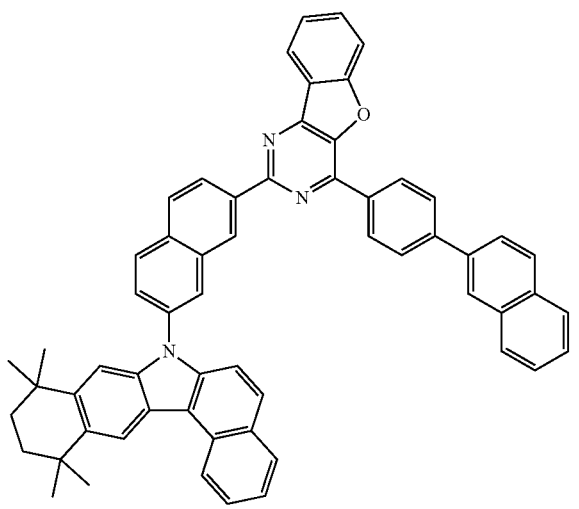
583
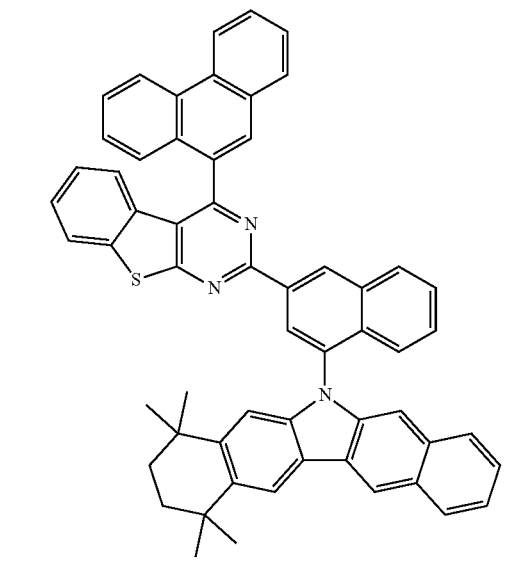
584
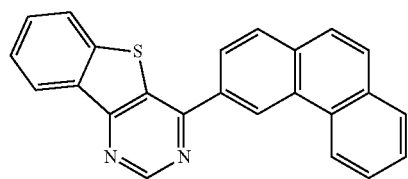
-continued
585
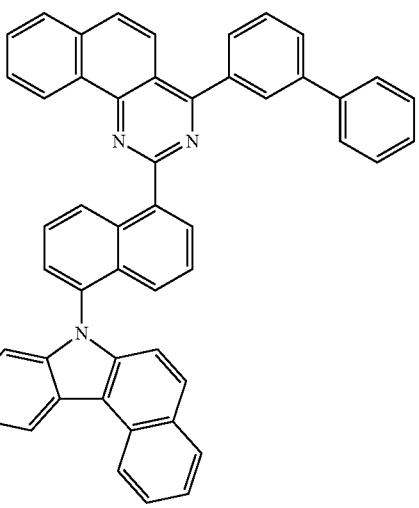
586
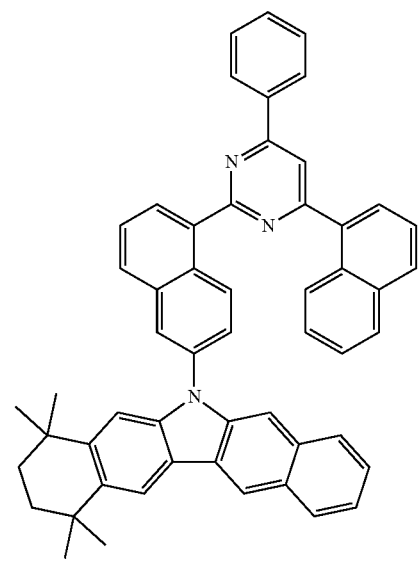
587
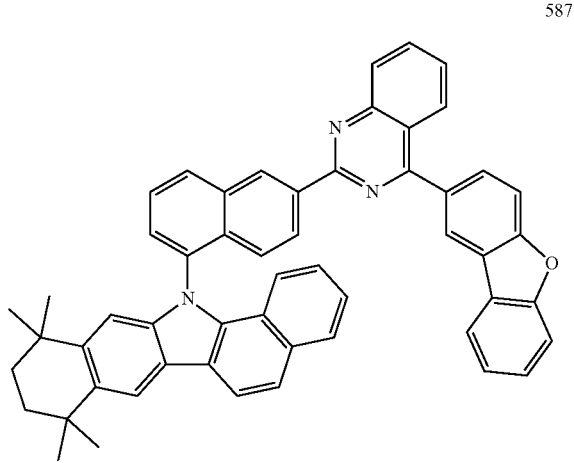

588
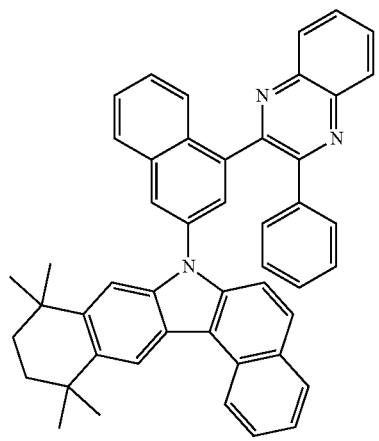
589
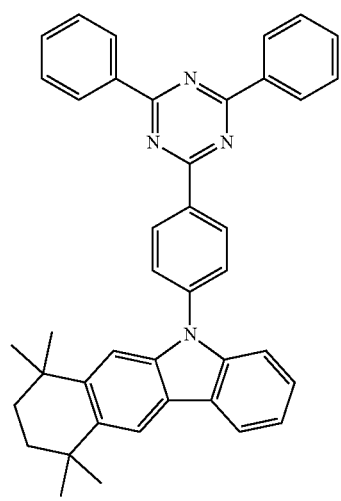
590
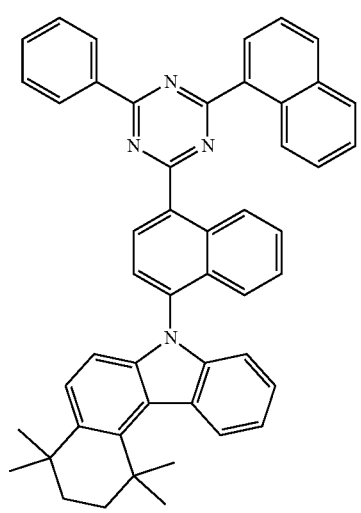
591
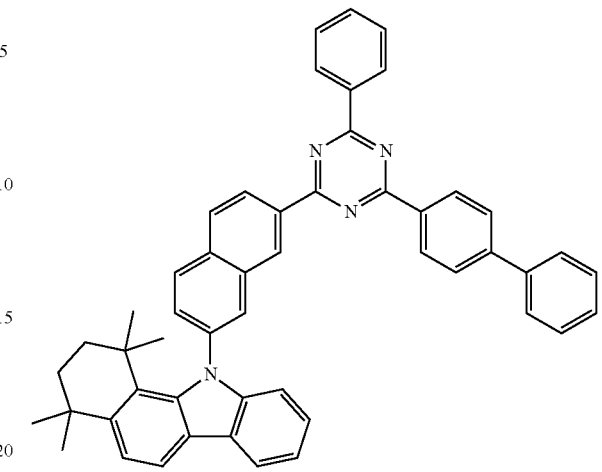
592
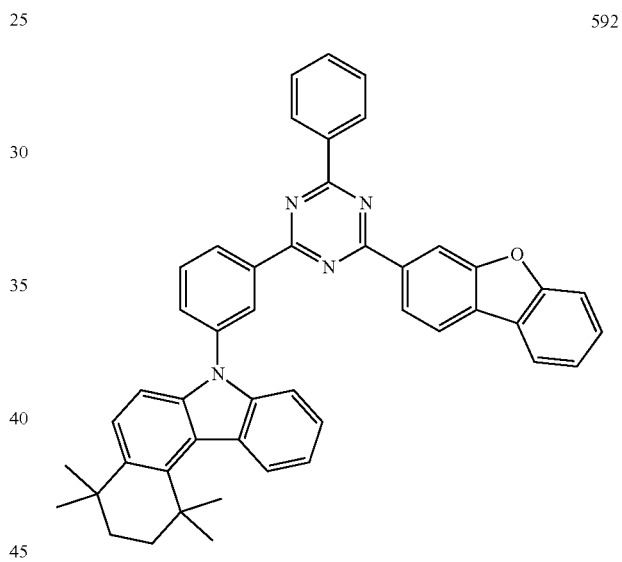
593
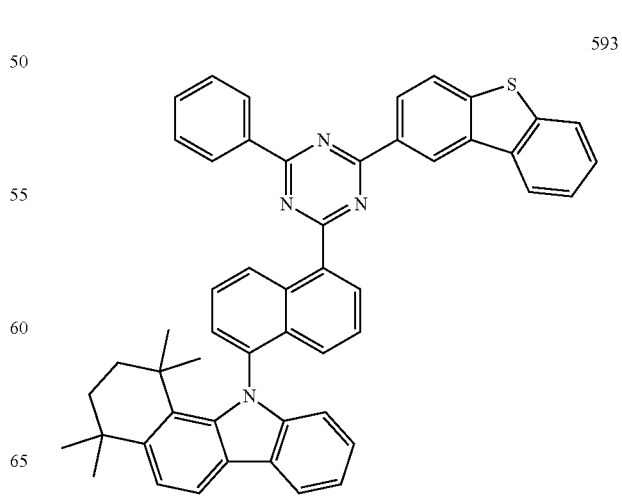

261
-continued
594
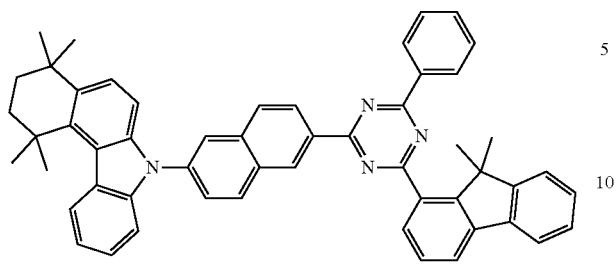
595
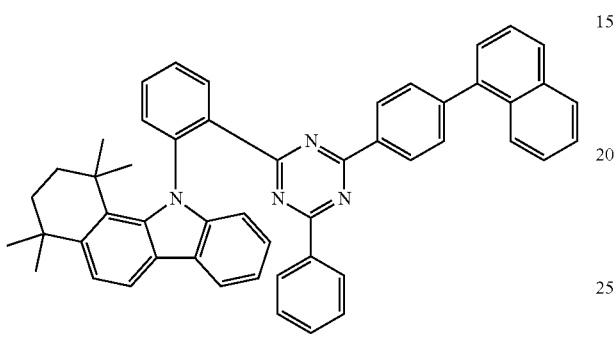
596
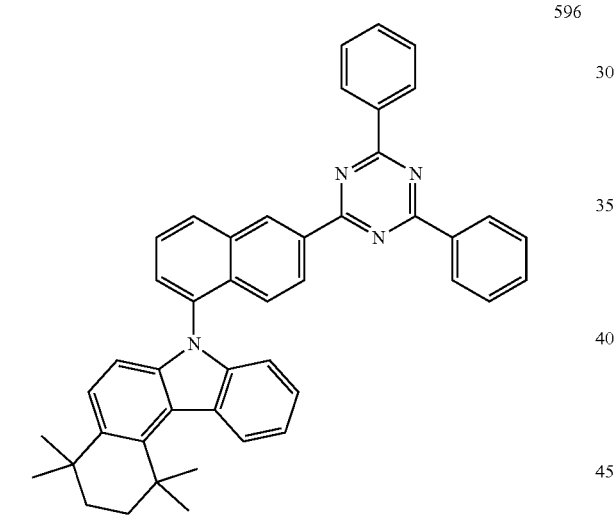
597

262
-continued
598
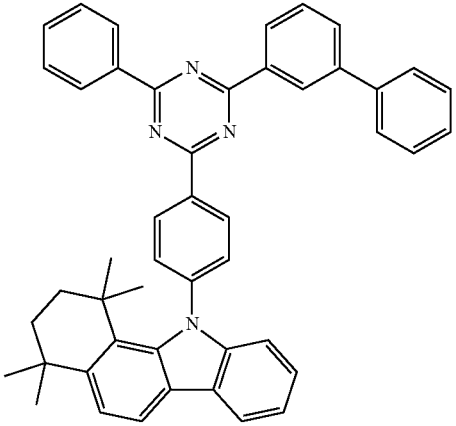
599
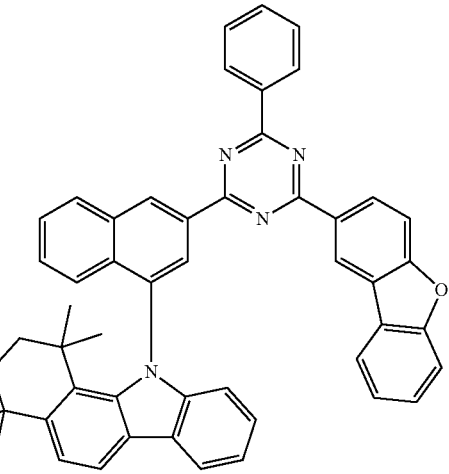
600
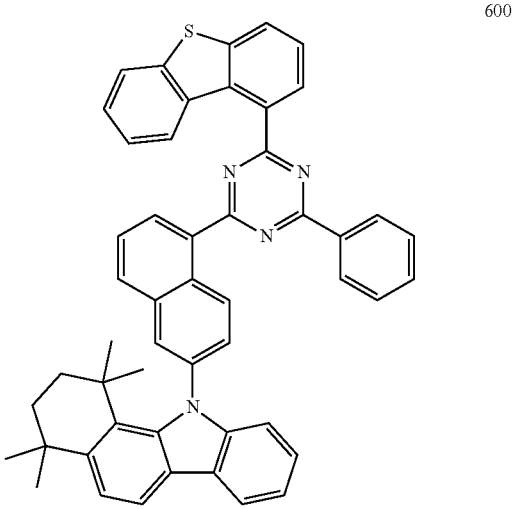

601
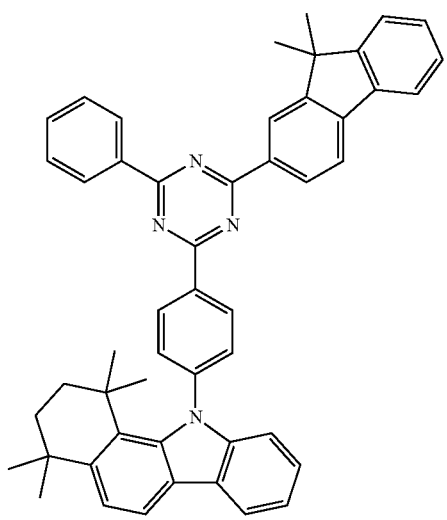
602
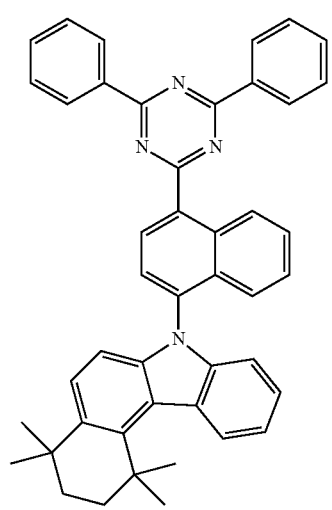
604
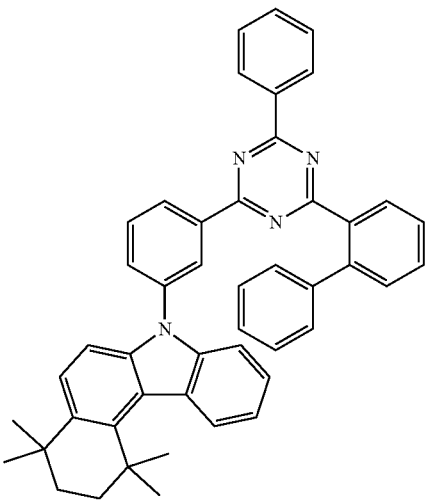
605
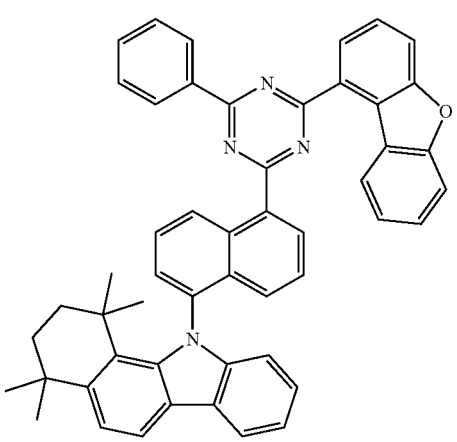
606
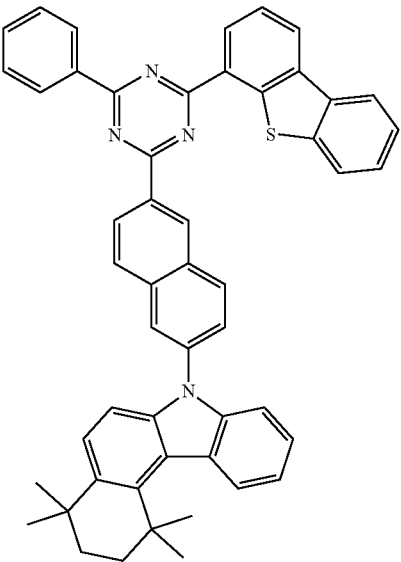

607
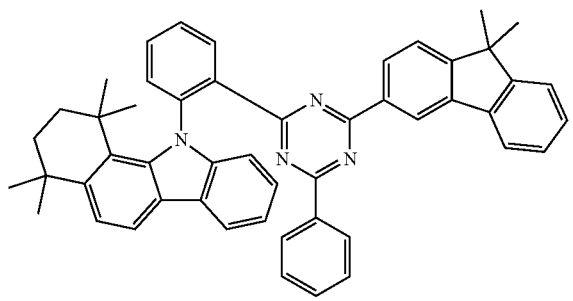
608
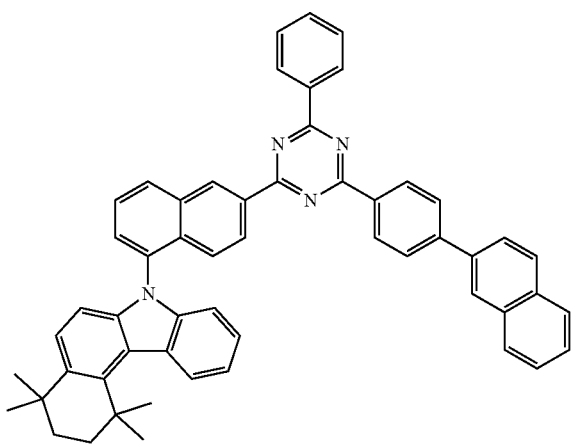
609
610
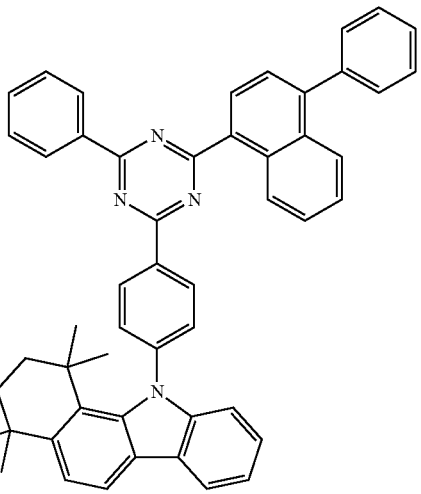
611
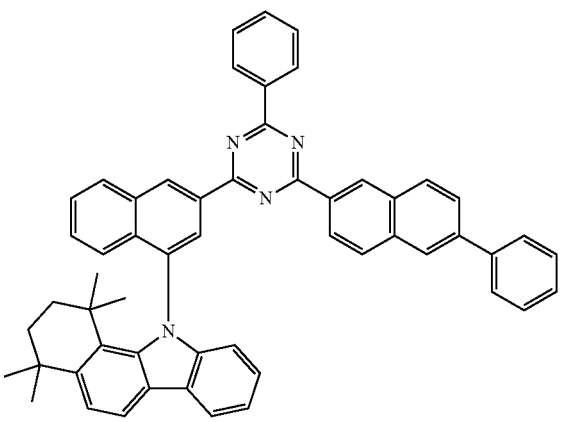
612
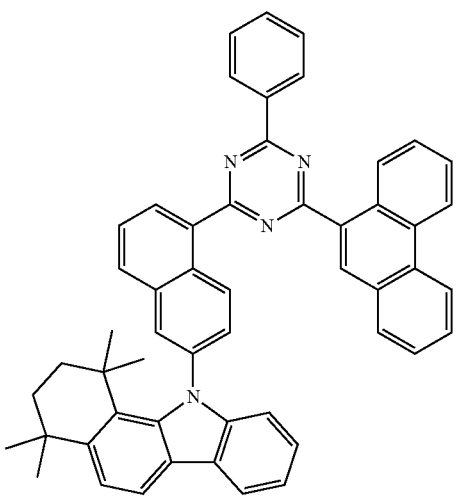

267
-continued
613
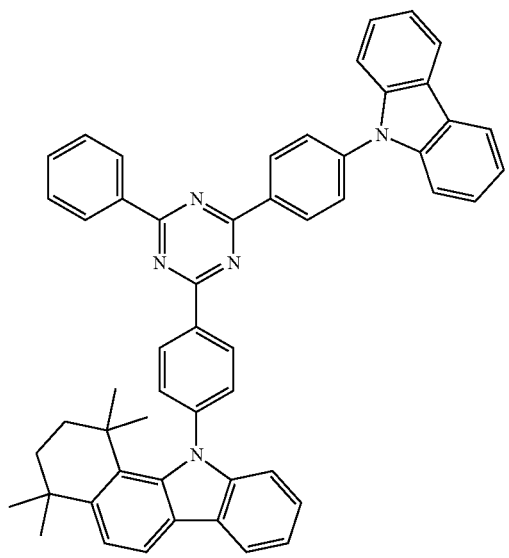
614
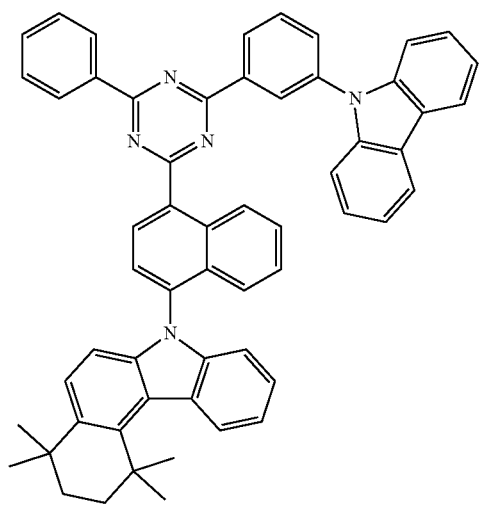
615
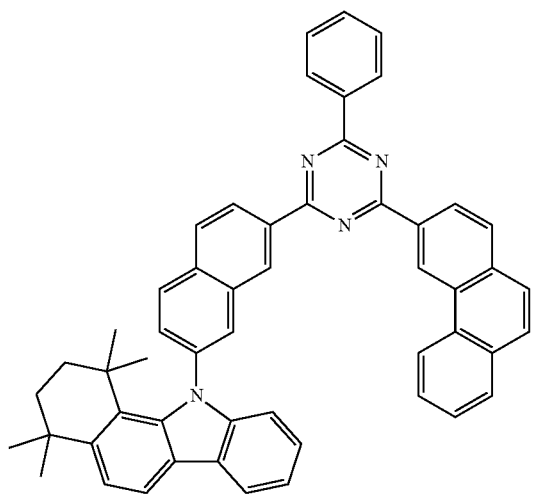
268
-continued
616
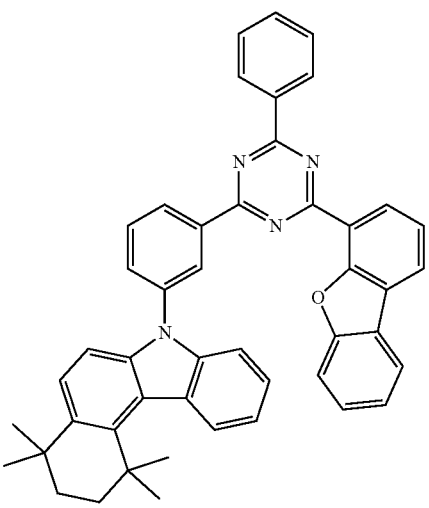
617
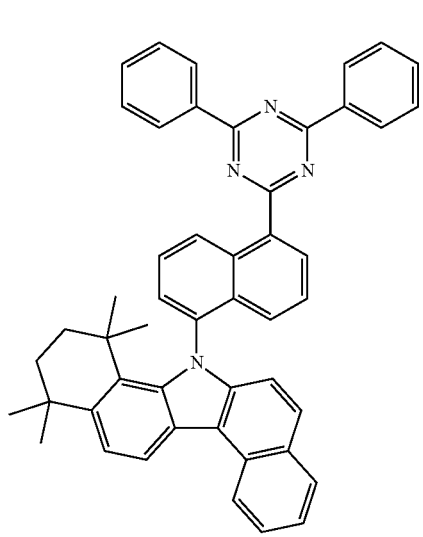
618
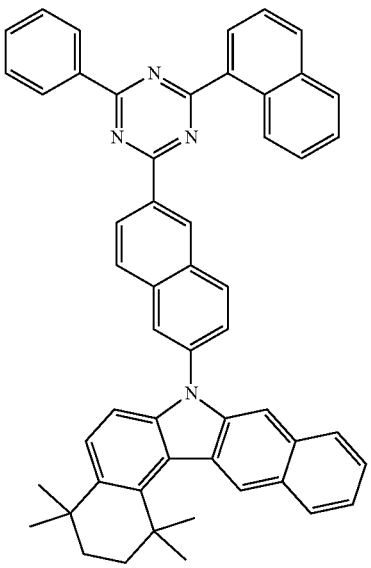

619
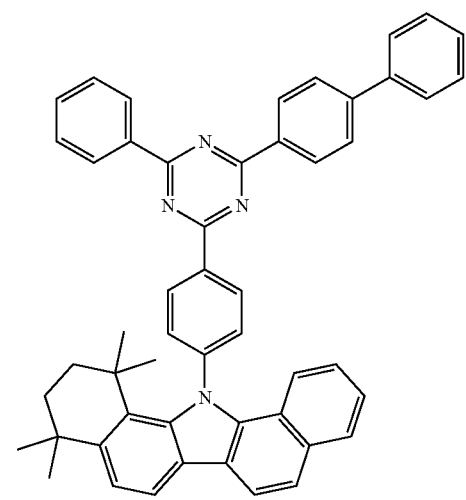
620
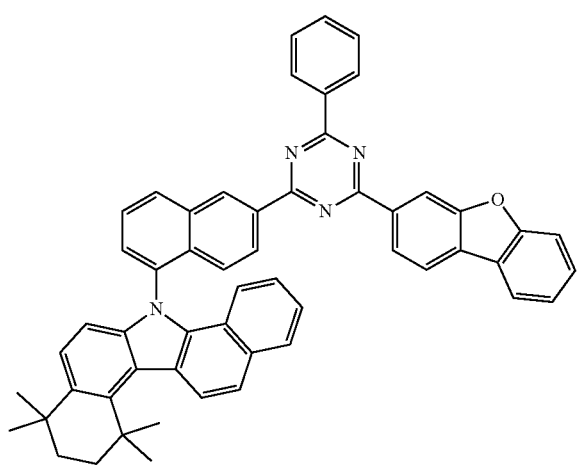
621
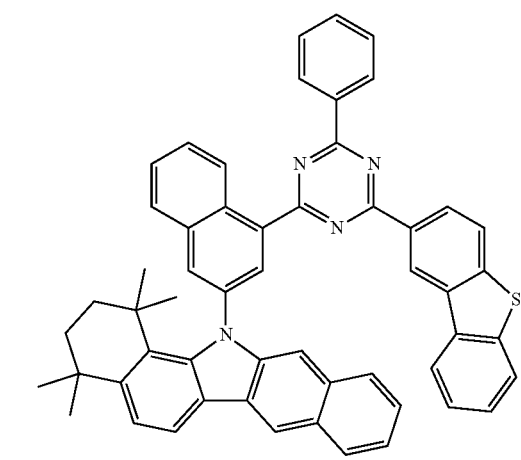
622
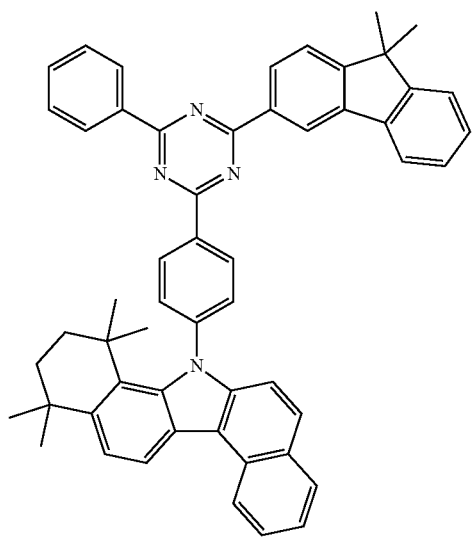
623
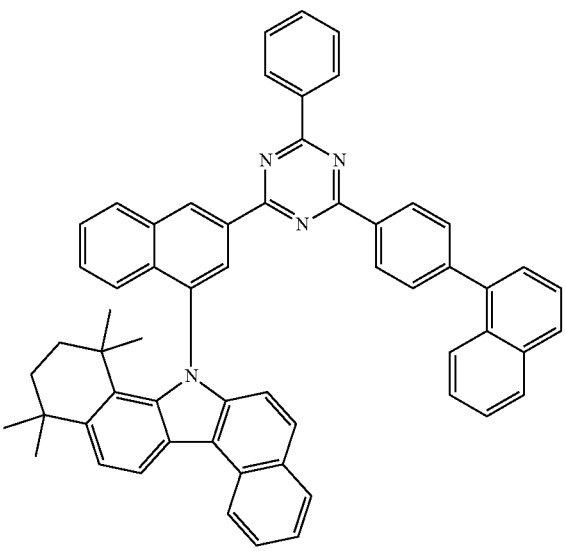
624
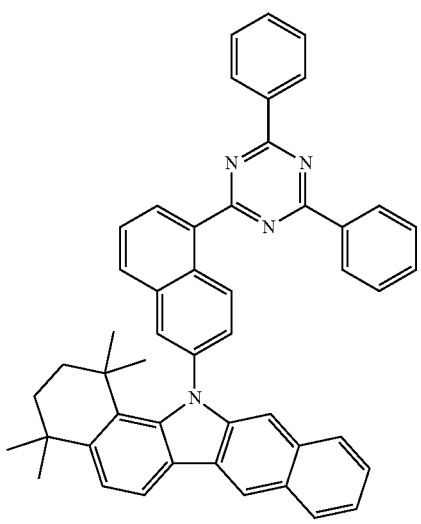

271
-continued
625
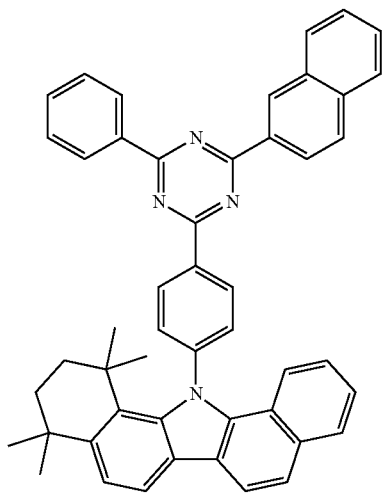
626
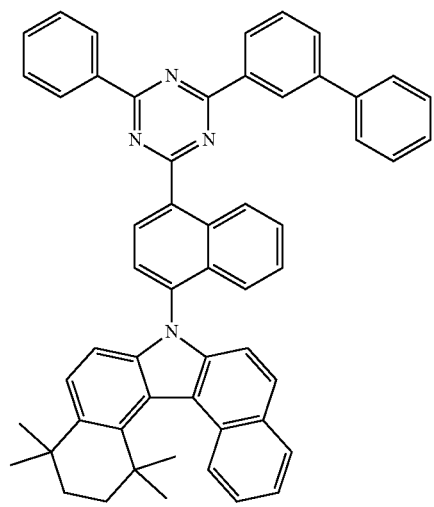
627
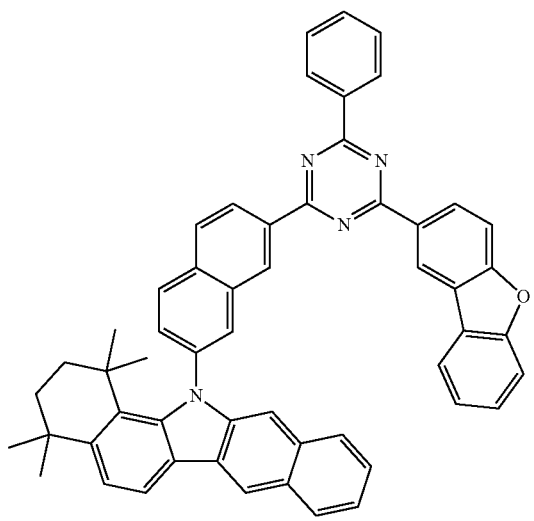
272
-continued
628
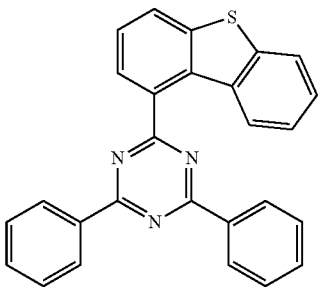
629
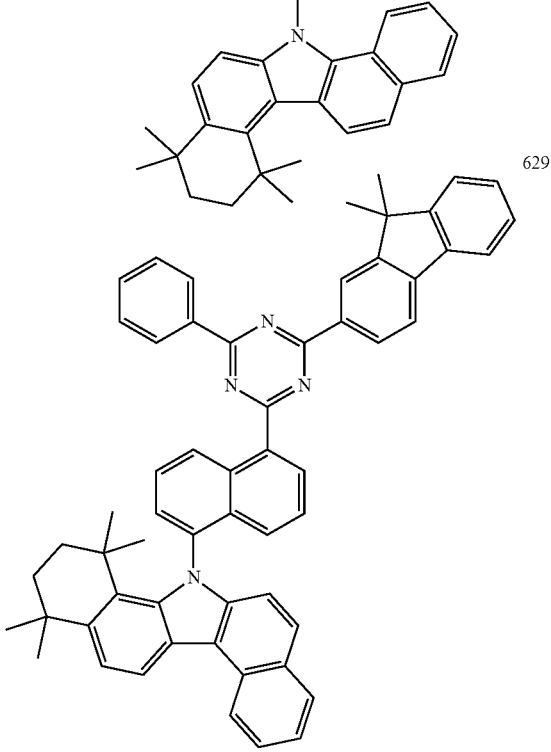
630
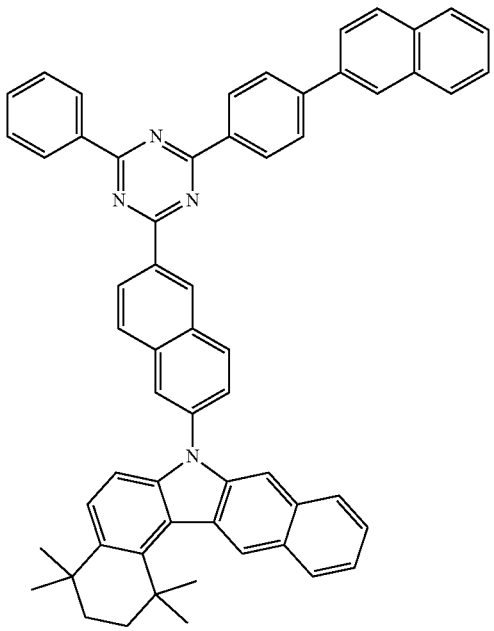

273
-continued
631
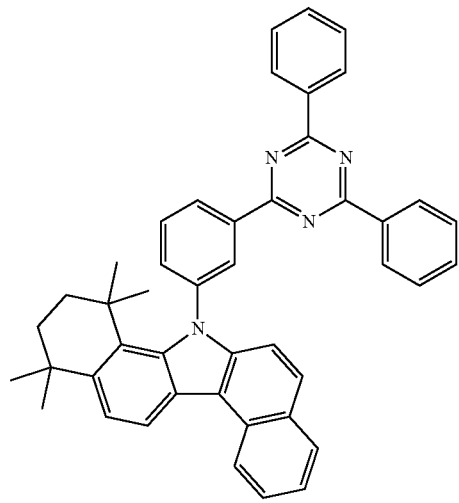
632
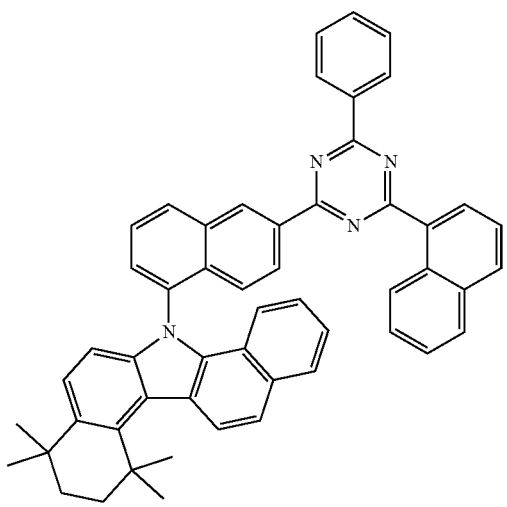
633
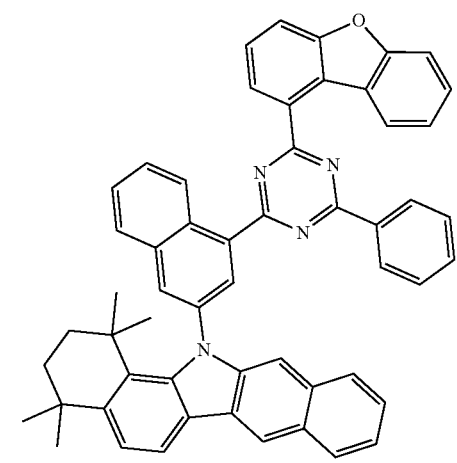
274
-continued
634
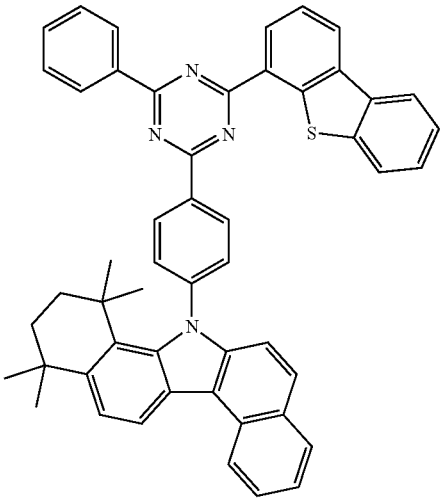
635
636
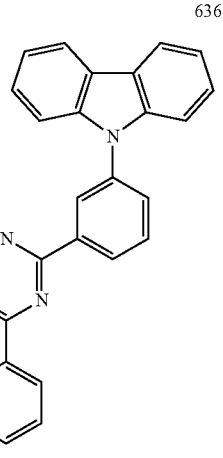

275
-continued
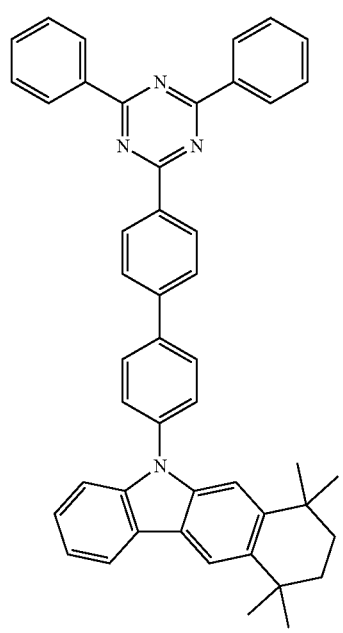
637
276
-continued
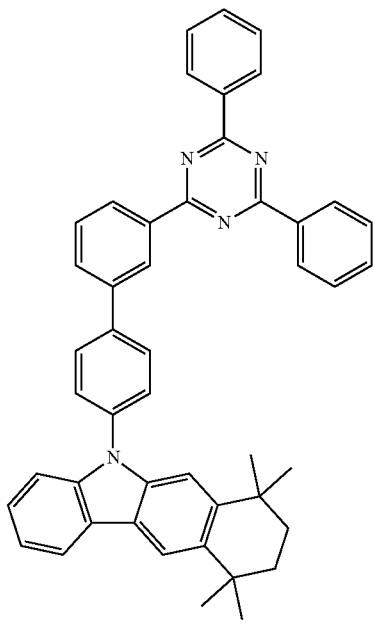
639
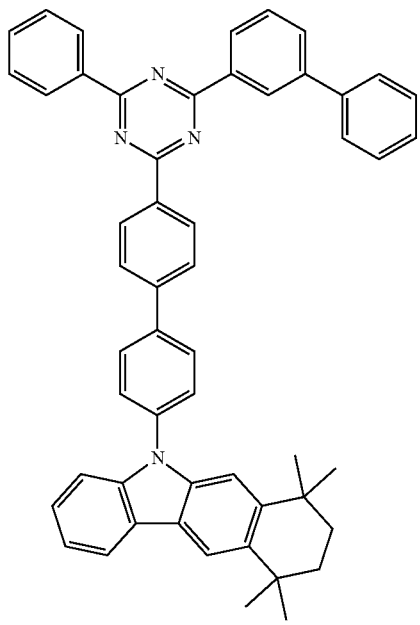
638
640

277
-continued
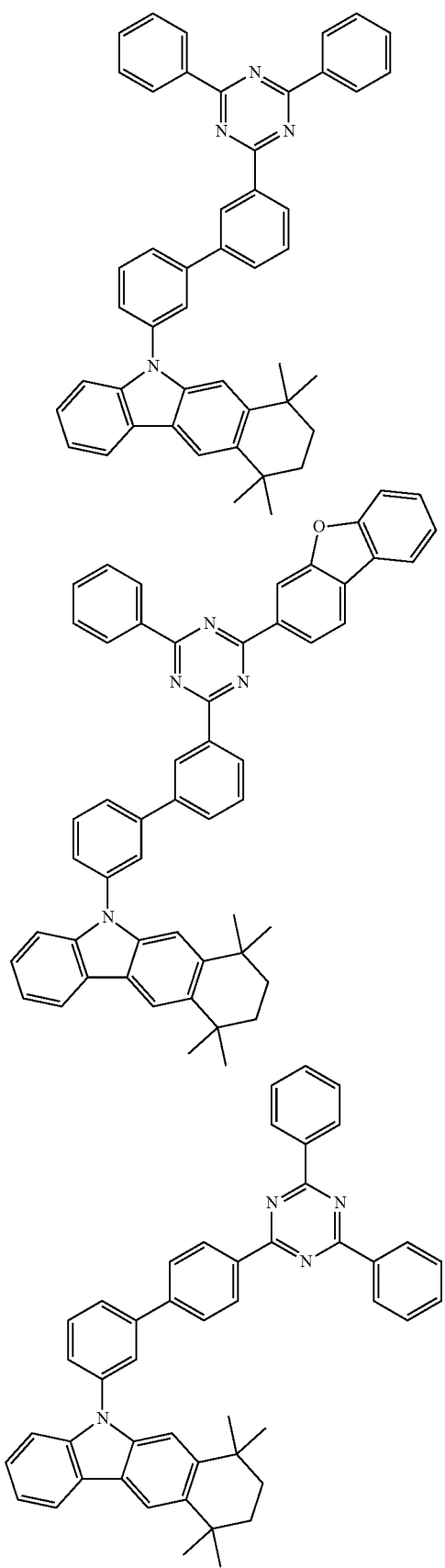
278
-continued
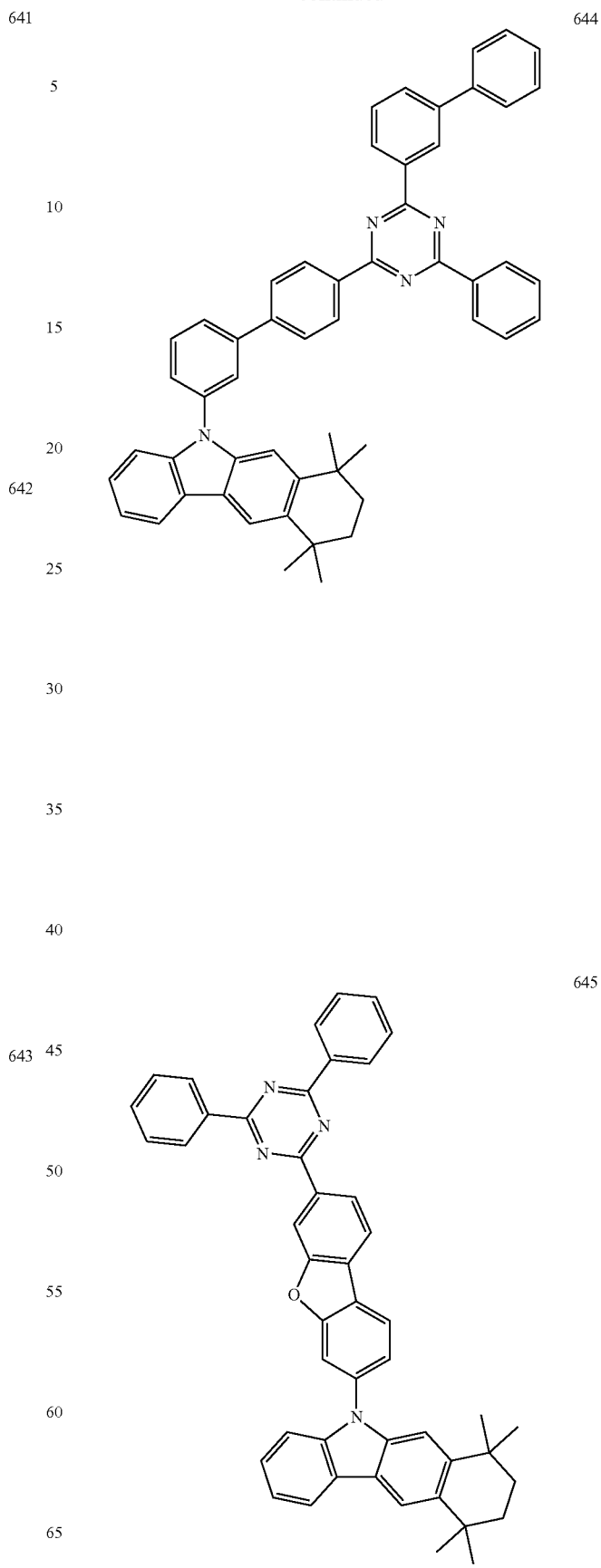

-continued
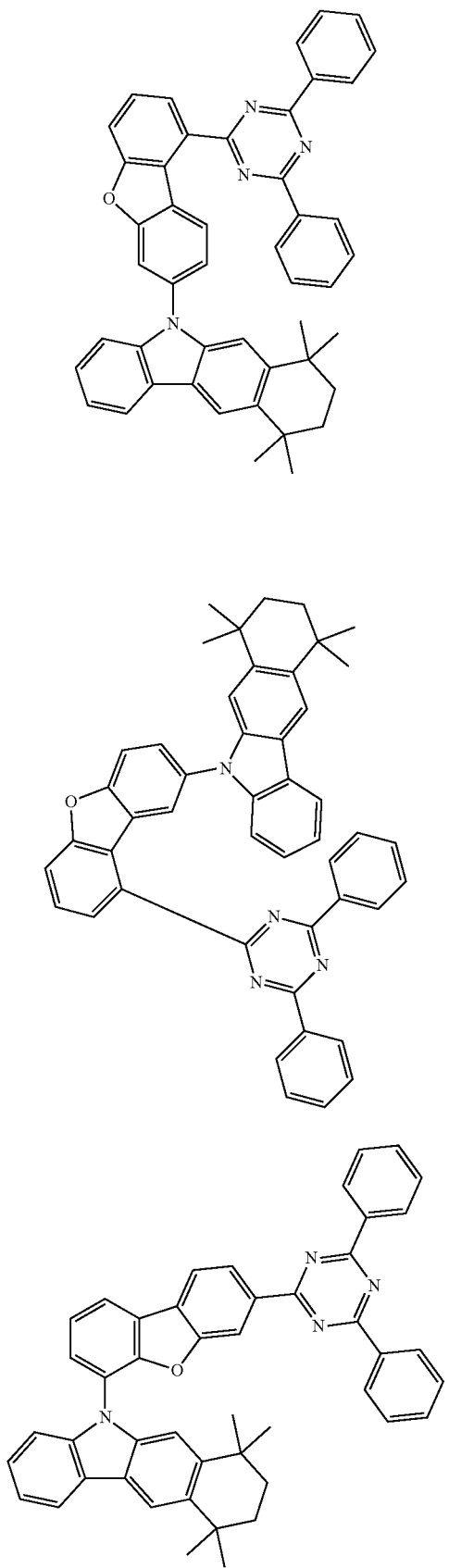
-continued
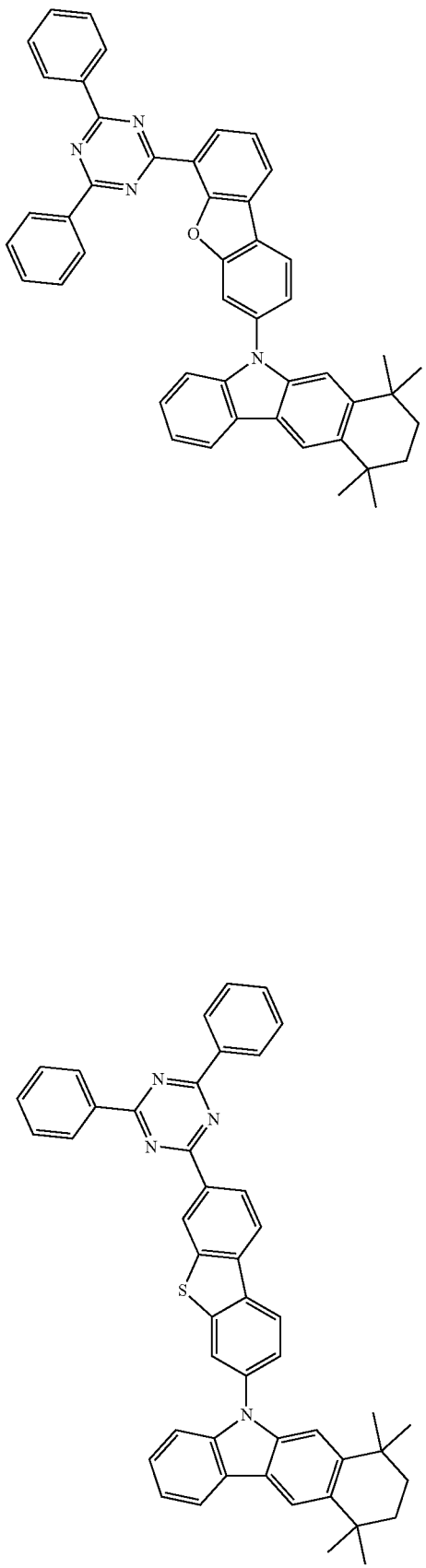

651 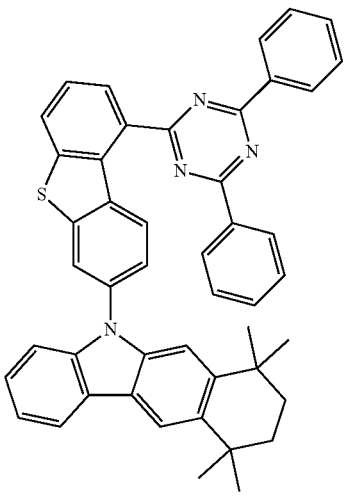

652 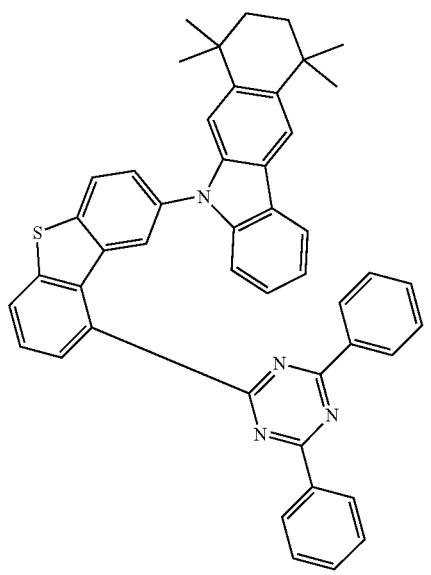

653 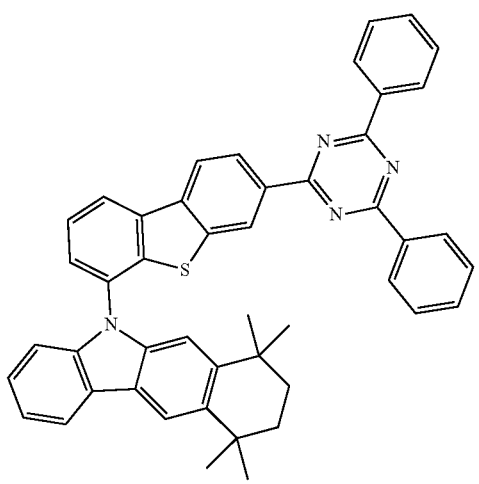

654

[Structure 654]

In a second aspect, the present disclosure provides an organic electroluminescent device, including an anode, a cathode, and a functional layer disposed between the anode and the cathode; where the functional layer includes the nitrogen-containing compound according to the first aspect of the present disclosure.

The nitrogen-containing compound provided in the present disclosure can be used for forming at least one organic film layer in the functional layer so as to improve the characteristics such as the luminous efficiency and service life of the organic electroluminescent device.

Optionally, the functional layer includes an organic luminescent layer including the nitrogen-containing compound. The organic luminescent layer may be composed of the nitrogen-containing compound provided by the present disclosure, and may also be composed of the nitrogen-containing compound provided by the present disclosure and other materials together.

Optionally, the functional layer further includes a hole transport layer, and the hole transport layer is located between the anode and the organic luminescent layer.

In one embodiment, the hole transport layer includes a first hole transport layer and a second hole transport layer, the first hole transport layer being closer to the anode relative to the second hole transport layer.

According to one specific embodiment, the organic electroluminescent device is shown in FIG. 1, and the organic electroluminescent device may include an anode 100, a hole injection layer 310, a first hole transport layer 321, a second hole transport layer (a hole auxiliary layer) 322, an organic luminescent layer 330, an electron transport layer 340, an electron injection layer 350, and a cathode 200 which are sequentially stacked.

Optionally, the anode 100 includes the following anode materials which are preferably materials having a large work function that facilitate hole injection into the functional layer. Specific examples of the anode materials include metals such as nickel, platinum, vanadium, chromium, copper, zinc, and gold, or their alloy; metal oxides such as zinc oxide, indium oxide, indium tin oxide (ITO) and indium zinc oxide (IZO); combined metals and oxides, such as ZnO:Al or SnO$_2$:Sb; or a conductive polymer such as poly(3-methylthiophene), poly[3,4-(ethylene-1,2-dioxy)thiophene] (PEDT), polypyrrole, and polyaniline, but are not limited to this. A transparent electrode containing indium tin oxide (ITO) as the anode is preferably included.

In the present disclosure, the hole transport layer may include one or more hole transport materials, and the hole transport layer materials may be selected from a carbazole polymer, carbazole connected triarylamine compounds or other types of compounds, and in particular may be selected from compounds shown below or any combination of them:

HT-1

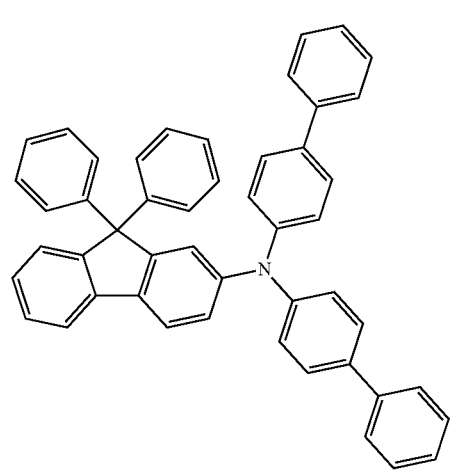

HT-2

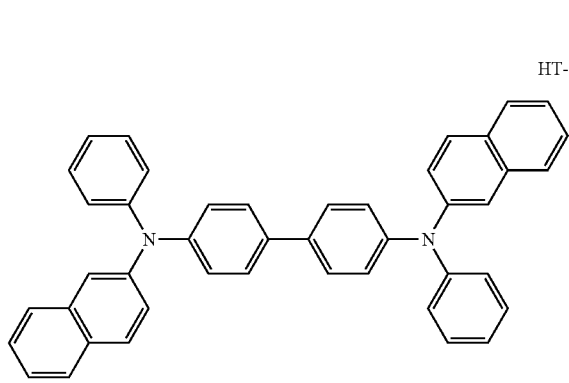

HT-3

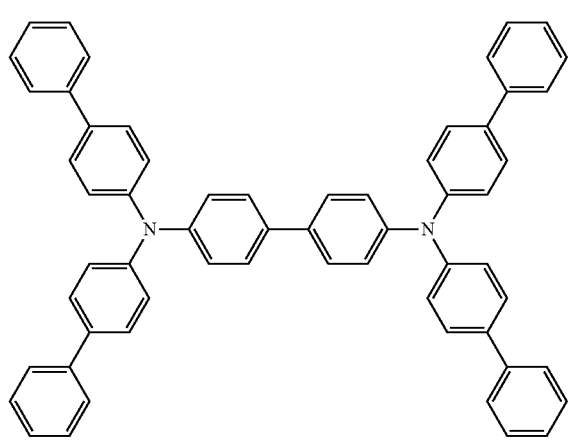

HT-4

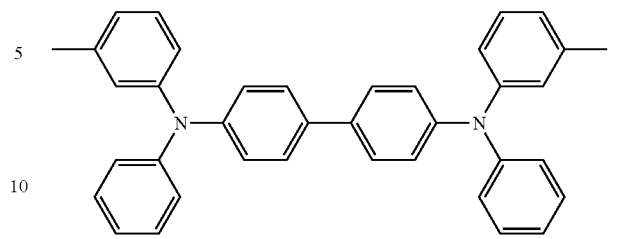

HT-5

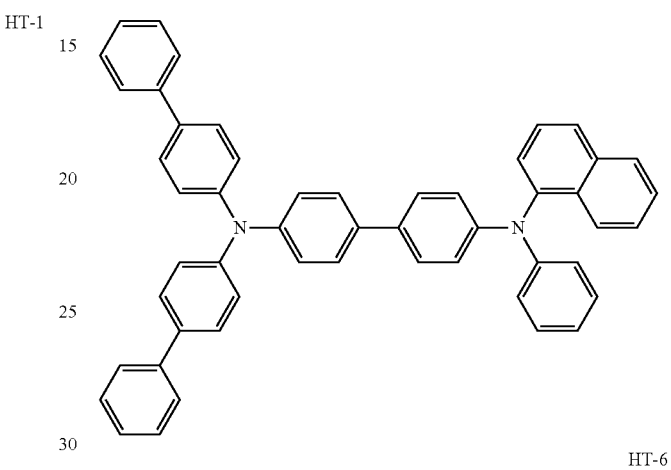

HT-6

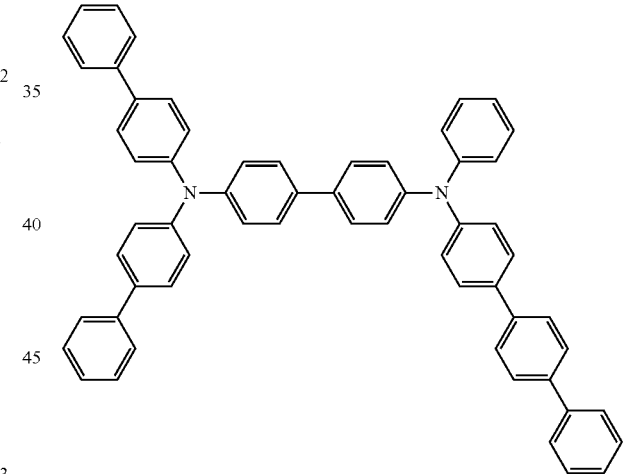

HT-7

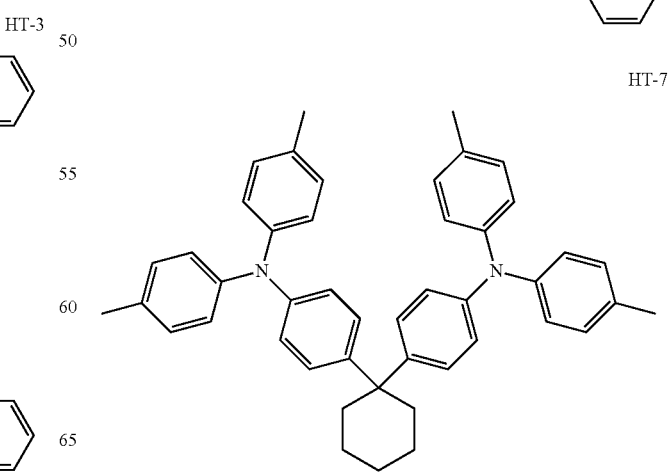

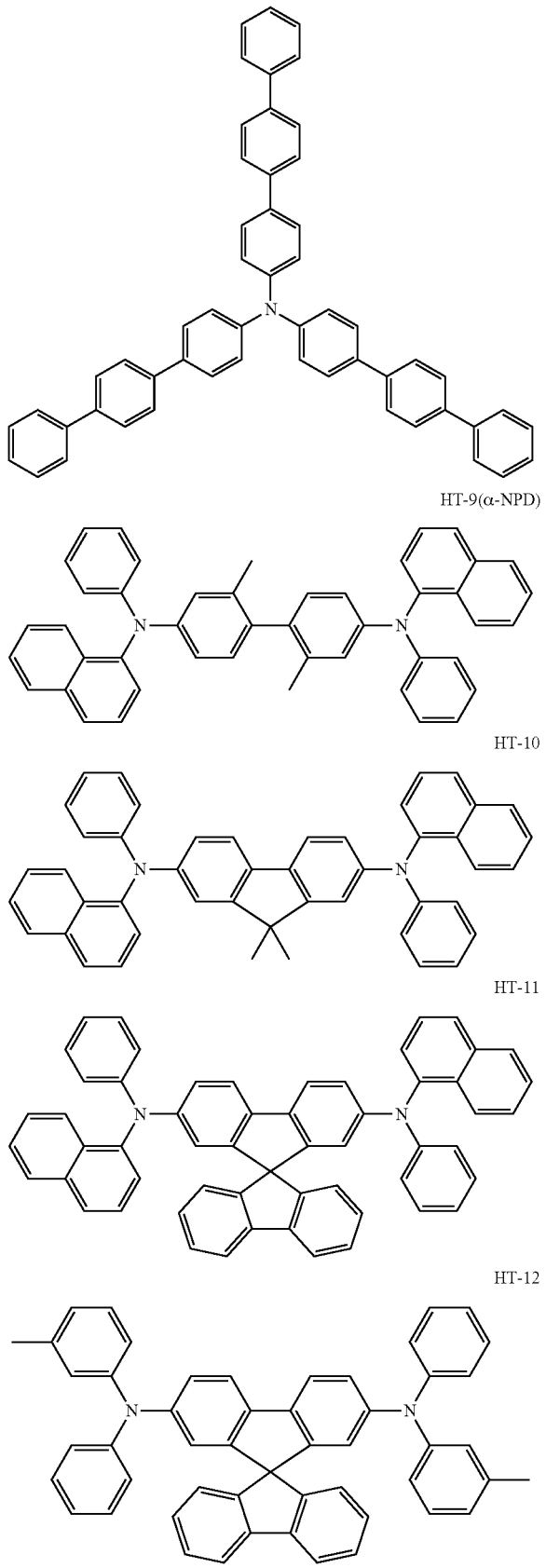

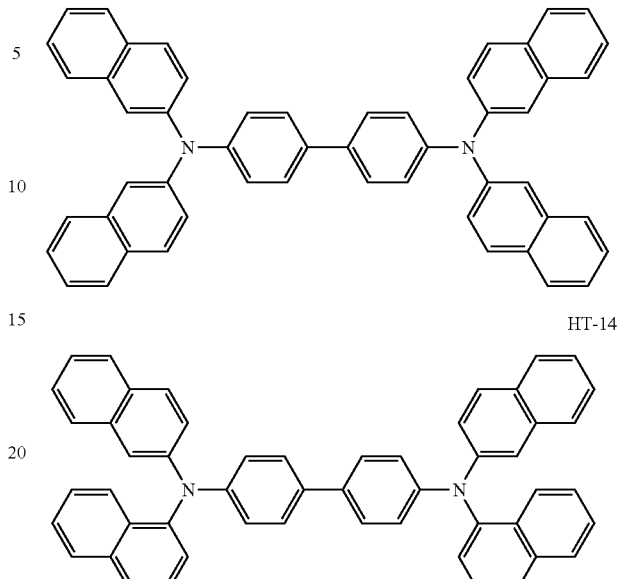

In one embodiment, the first hole transport layer 321 may consist of α-NPD.

In one embodiment of the present disclosure, the second hole transport layer 322 consists of HT-1.

Optionally, the hole injection layer 310 may be further disposed between the anode 100 and the first hole transport layer 321 to enhance the ability to inject holes to the first hole transport layer 321. The hole injection layer 310 can be made of a benzidine derivative, a starburst arylamine compound, a phthalocyanine derivative or other materials, which is not specially limited in the present disclosure. A material of the hole injection layer 310 may be selected from, for example, the following compounds or any combination of them;

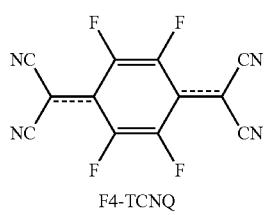

F4-TCNQ

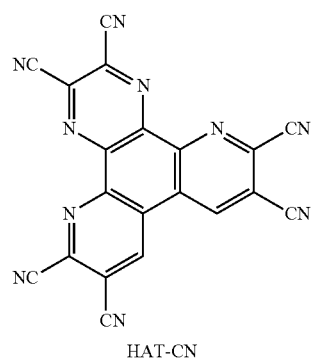

HAT-CN

287
-continued
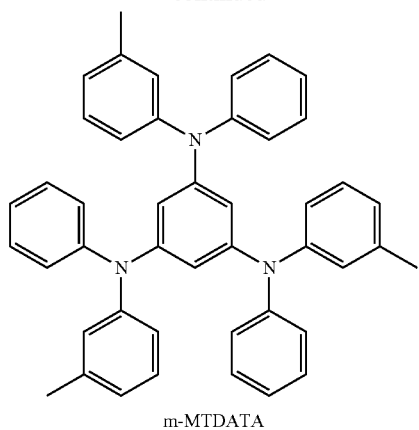
m-MTDATA
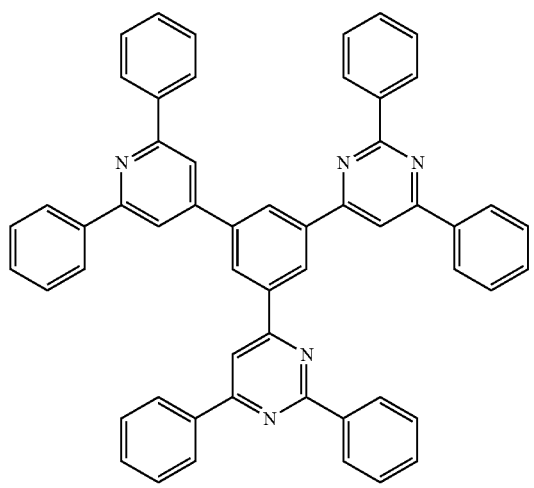
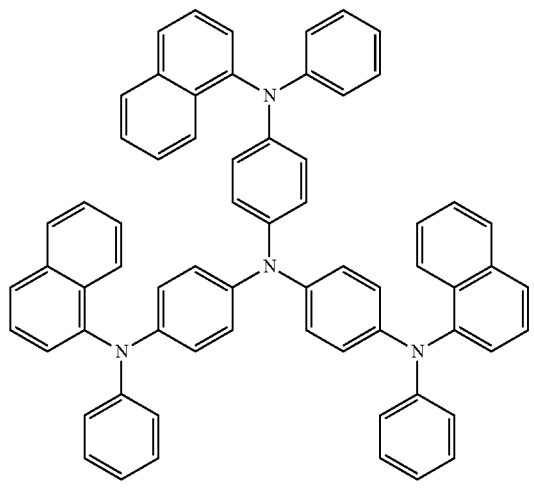
1T-NATA
288
-continued
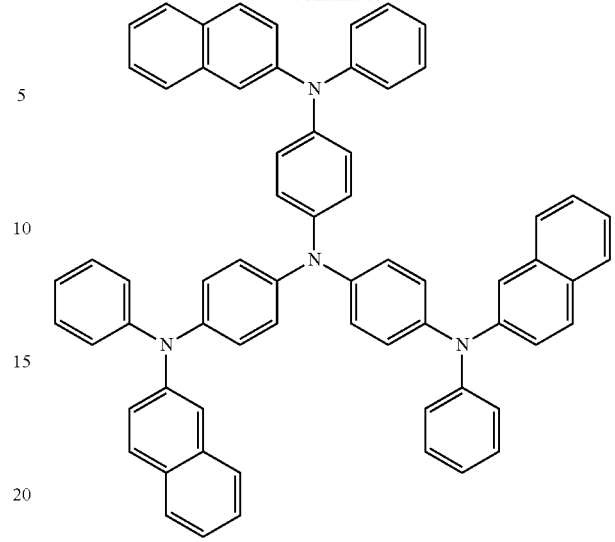
2T-NATA
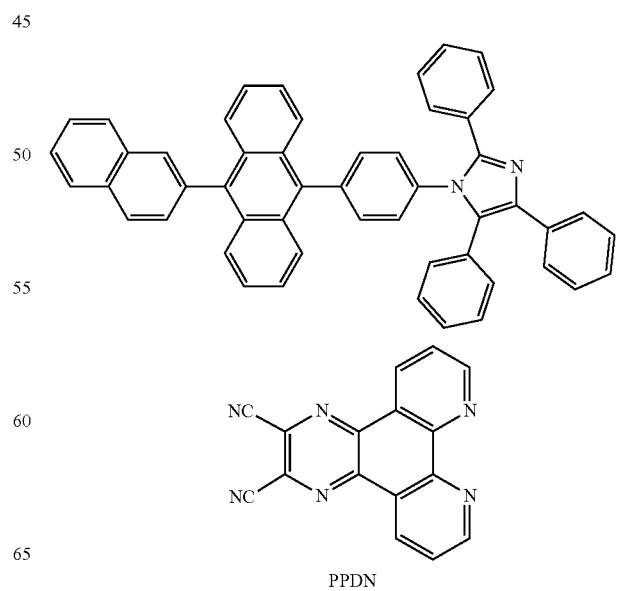
NATA
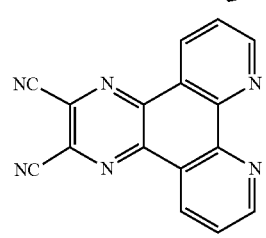
PPDN -continued

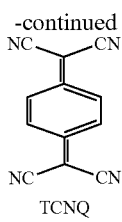
TCNQ

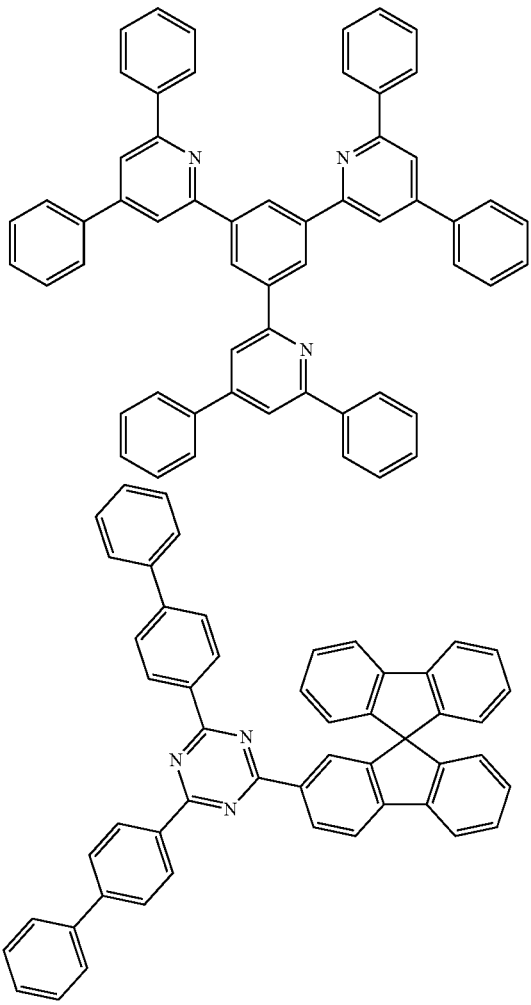

In one embodiment of the present disclosure, the hole injection layer 310 is composed of HAT-CN.

Optionally, the organic luminescent layer 330 may be composed of a single luminescent material, and may also include a host material and a dopant material. Optionally, the organic luminescent layer 330 is composed of the host material and the dopant material, holes injected into the organic luminescent layer 330 and electrons injected into the organic luminescent layer 330 can be recombined in the organic luminescent layer 330 to form excitons, the excitons transfer energy to the host material, the host material transfers energy to the dopant material, and then the dopant material can emit light.

The host material of the organic luminescent layer 330 may include a metal chelated compound, a distyryl derivative, an aromatic amine derivative, a dibenzofuran derivative, or other types of materials. Optionally, the host material includes the nitrogen-containing compound of the present disclosure.

The dopant material of the organic luminescent layer 330 may be a compound having a condensed aryl ring or its derivative, a compound having a heteroaryl ring or its derivative, an aromatic amine derivative, or other materials, which is not specially limited in the present disclosure. The dopant material is also referred to as a doping material or a dopant. The dopant material can be divided into fluorescent dopants and phosphorescent dopants according to luminescence types. For example, specific examples of the phosphorescent dopants include, but are not limited to,

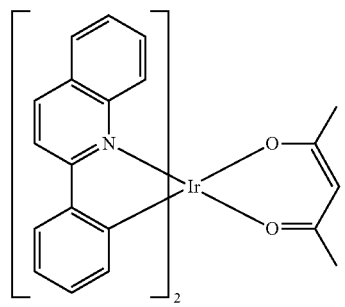

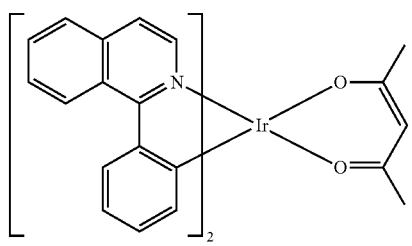

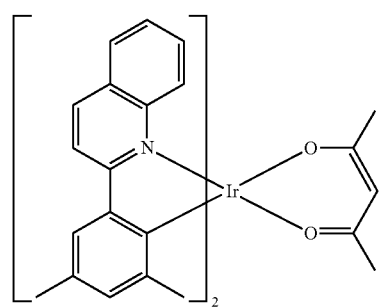

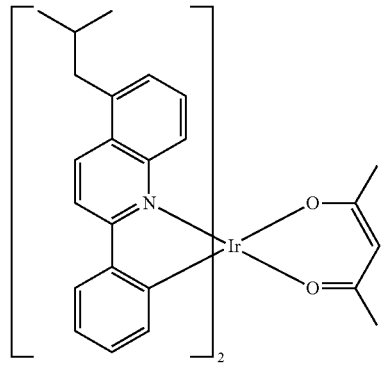

291
-continued
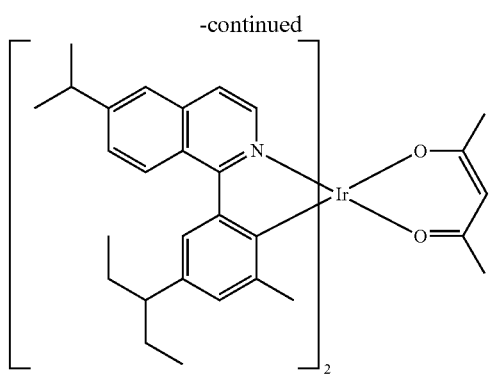
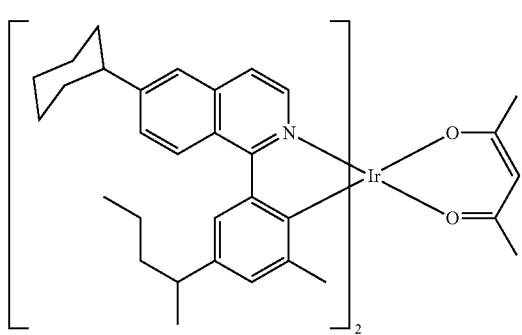
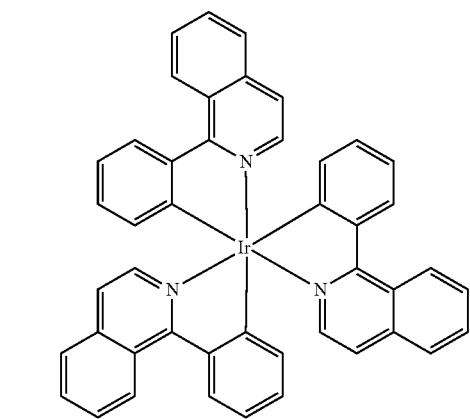
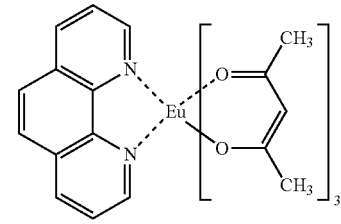
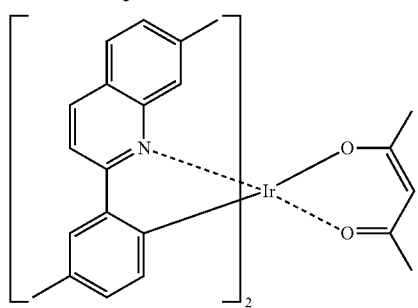
292
-continued
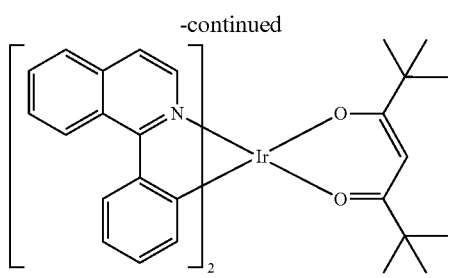
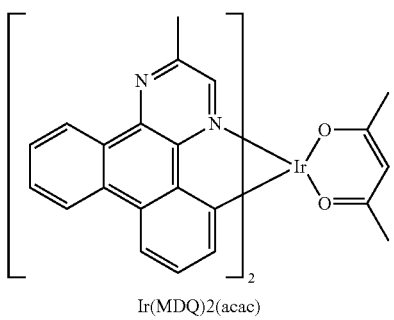
Ir(MDQ)2(acac)
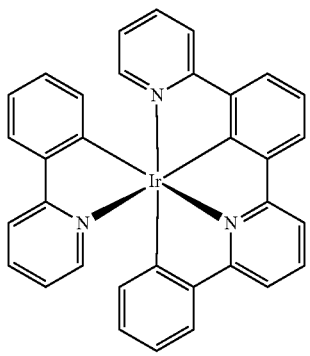
fac-Ir(ppy)₃
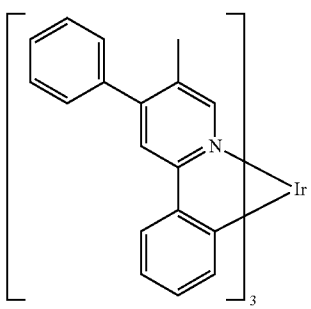
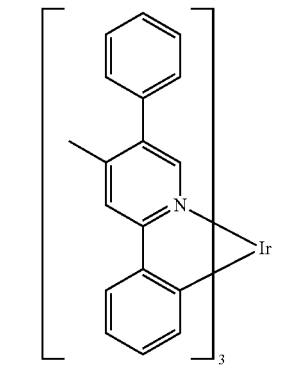

-continued

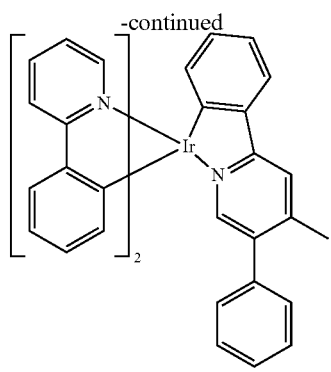

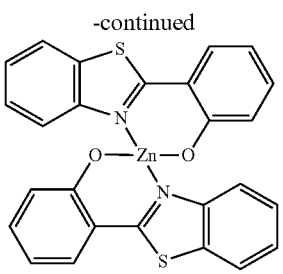

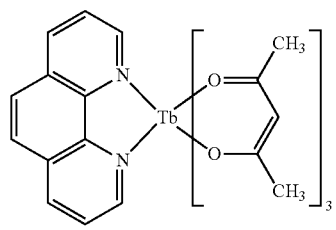

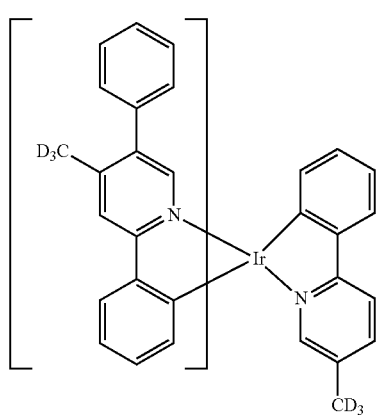

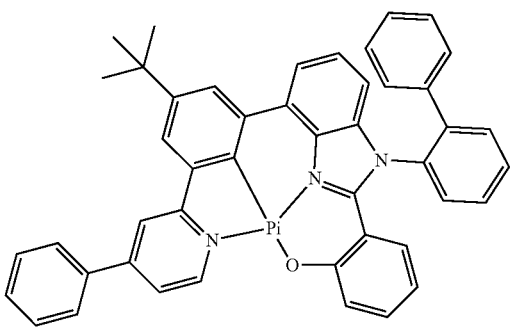

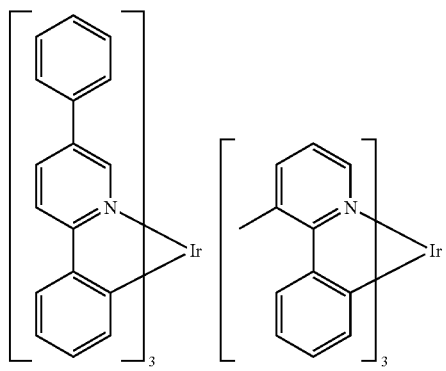

In one embodiment of the present disclosure, the organic electroluminescent device is a red organic electroluminescent device. In one more particular embodiment, the host material of the organic luminescent layer 330 includes the nitrogen-containing compound as provided in the first aspect of the present disclosure. The dopant material may be, for example, Ir(MDQ)$_2$(acac).

In one embodiment of the present disclosure, the organic electroluminescent device is a green organic electroluminescent device. In one more particular embodiment, the host material of the organic luminescent layer 330 includes the nitrogen-containing compound as provided in the first aspect of the present disclosure. The dopant material may be, for example, fac-Ir(ppy)$_3$.

The electron transport layer 340 may be of a single-layer structure or a multi-layer structure, and may include one or more electron transport materials, and the electron transport materials may be selected from, but are not limited to, ET-1, LiQ, a benzimidazole derivative, an oxadiazole derivative, a quinoxaline derivative, or other electron transport materials, which are not particularly limited in the present disclosure. A material of the electron transport layer 340 includes, but is not limited to, the following compounds:

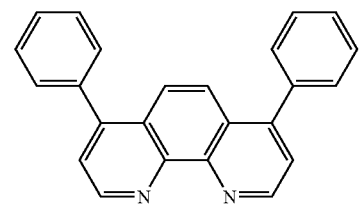
(ET-2)
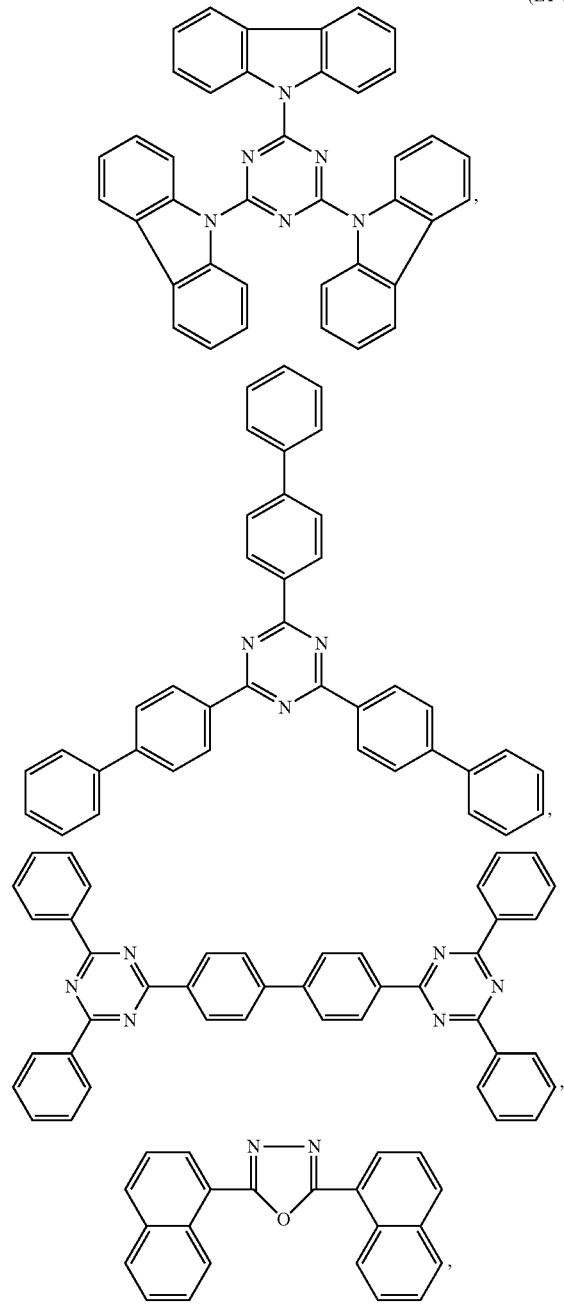
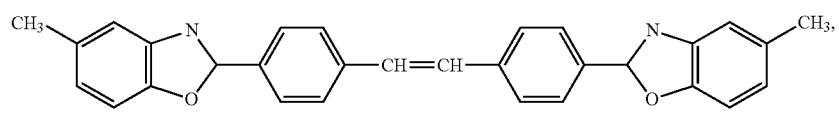

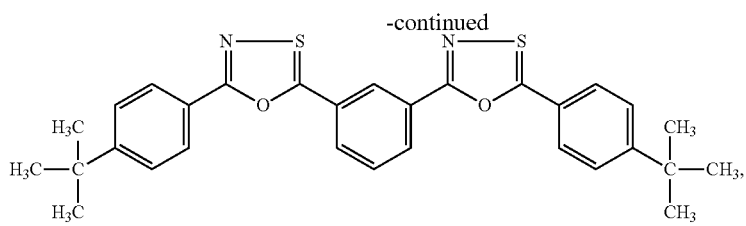

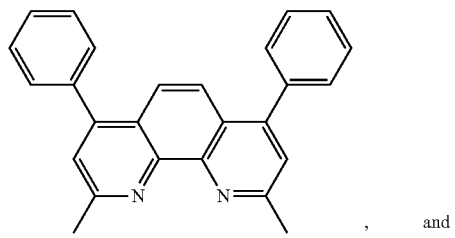, and (ET-1)

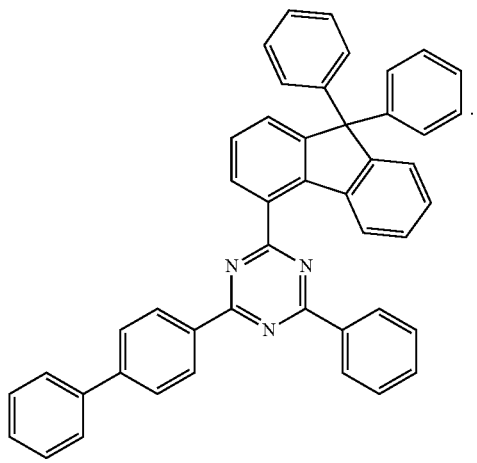

In one embodiment of the present disclosure, the electron transport layer 340 may consist of ET-1 and LiQ, or ET-2 and LiQ.

In the present disclosure, the cathode 200 may include a cathode material, which is a material with a small work function that facilitates electron injection into the functional layer. Specific examples of the cathode material include, but are not limited to, metals such as magnesium, calcium, sodium, potassium, titanium, indium, yttrium, lithium, gadolinium, aluminum, silver, tin, and lead, or their alloy; or a multilayer material such as LiF/Al, Liq/Al, LiO$_2$/Al, LiF/Ca, LiF/Al, and BaF$_2$/Ca. Optionally, a metal electrode including magnesium and silver as the cathode is included.

Optionally, the electron injection layer 350 may be further disposed between the cathode 200 and the electron transport layer 340 to enhance the ability to inject electrons into the electron transport layer 340. The electron injection layer 350 may include an inorganic material such as an alkali metal sulfide, an alkali metal halide, or may include a complex of an alkali metal and an organic substance. In one embodiment of the present disclosure, the electron injection layer 350 may include ytterbium (Yb).

According to a third aspect of the present disclosure, provided is an electronic apparatus, including the organic electroluminescent device according to the second aspect of the present disclosure.

Figure 2:
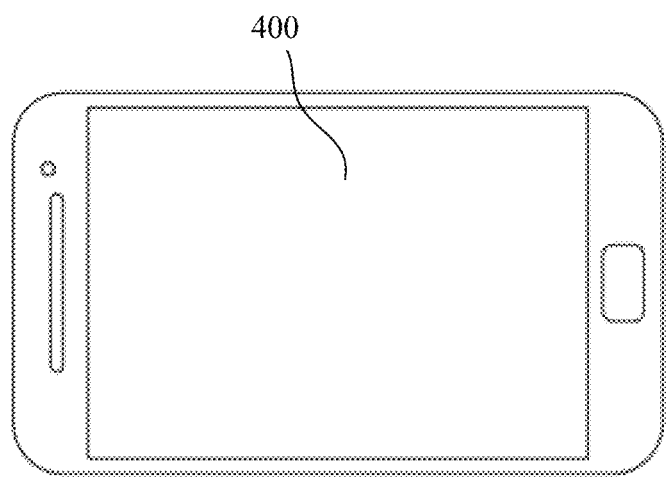
FIG. 2 is a structural schematic diagram of an electronic device according to an embodiment of the present disclosure.

According to one embodiment, as shown in FIG. 2, the electronic apparatus provided is an electronic device 400 including the organic electroluminescent device described above. The electronic apparatus 400 may be, for example, a display device, a lighting device, an optical communication device, or other type of electronic devices, and may include, for example, but is not limited to, a computer screen, a mobile phone screen, a television, electronic paper, an emergency lighting lamp, an optical module, and the like.

A synthesis method of the nitrogen-containing compound of the present disclosure is specifically illustrated below with reference to synthesis examples, but the present disclosure is not limited in any way accordingly.

SYNTHESIS EXAMPLES

Those skilled in the art will recognize that chemical reactions described in the present disclosure may be used to suitably prepare a number of organic compounds of the present disclosure, and that other methods for preparing the compounds of the present disclosure are deemed to be within the scope of the present disclosure. For example, the synthesis of those non-exemplified compounds according to the present disclosure can be successfully accomplished by those skilled in the art by modification methods such as appropriately protecting interfering groups, by utilizing other known reagents other than those described in the present disclosure, or by making some conventional modification of reaction conditions. Compounds of which synthesis methods were not mentioned in the present disclosure were all commercially available raw material products.

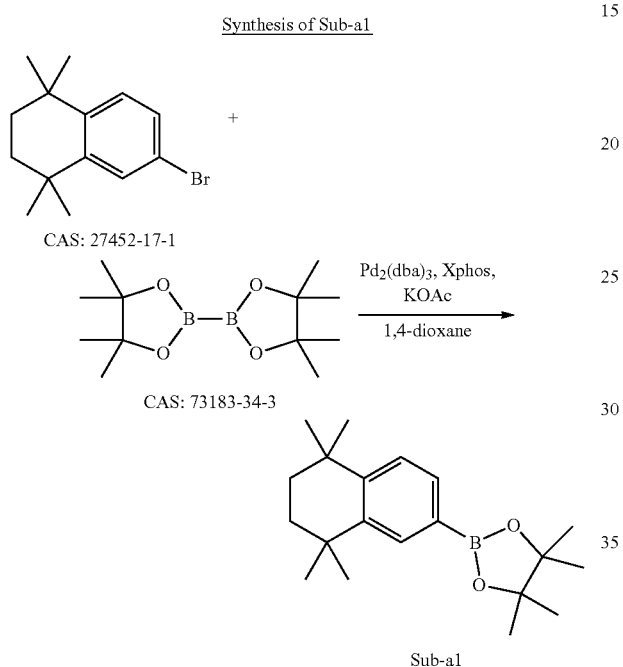

6-Bromo-1,1,4,4-tetramethyl-1,2,3,4-tetrahydronaphthalene (13.36 g, 50 mmol), bis(pinacolato)diboron (15.24 g, 60 mmol), potassium acetate (10.8 g, 110 mmol) and 1,4-dioxane (160 mL) were sequentially added to a 500 mL three-necked flask under a nitrogen atmosphere, and the mixture was stirred and heated, after the mixture was heated to 40° C., tris(dibenzylideneacetone)dipalladium (Pd$_2$(dba)$_3$, 0.46 g, 0.5 mmol) and 2-dicyclohexylphosphino-2',4',6'-triisopropylbiphenyl (Xphos, 0.48 g, 1 mmol) were added rapidly, heating was continued to be performed to reflux, and stirring was performed overnight. After the mixture was cooled to room temperature, 200 mL of water was added to the mixture, well stirring was performed for 30 min to precipitate a solid, suction filtration was performed in vacuum, and the obtained filter cake was washed with deionized water to be neutral, and was subjected to drip washing with 100 mL of absolute ethanol to obtain a gray solid; and a crude product was slurried once with n-heptane, dissolved with 200 mL of toluene and allowed to pass through a silica gel column to remove a catalyst, and an eluate was concentrated to obtain a white solid Sub-a1 (12.73 g, yield: 81%).

Referring to the synthesis of Sub-a1, Sub-a2 was synthesized by using a reactant A shown in Table 1 instead of 6-bromo-1,1,4,4-tetramethyl-1,2,3,4-tetrahydronaphthalene.

TABLE 1

Synthesis of Sub-a2

| Reactant A | Sub-a2 | Yield (%) |
|---|---|---|
| (structure shown)<br>CAS: 2595048-93-2 | Sub-a2 (structure shown) | 74 |

Raw materials Sub-a1 (17.28 g, 55 mmol), o-bromonitrobenzene (10.10 g, 50 mmol), tetrakis(triphenylphosphine)palladium (Pd(PPh$_3$)$_4$, 0.58 g, 0.5 mmol), anhydrous potassium carbonate (13.82 g, 100 mmol), toluene (180 mL), anhydrous ethanol (45 mL) and deionized water (45 mL) were added sequentially to a 500 mL three-necked flask under a nitrogen atmosphere, the mixture was stirred and heated to reflux, and a reaction was carried out for 16 h. After the reaction mixture was cooled to room temperature, the reaction solution was extracted with dichloromethane (100 mL×3), organic phases were mixed, dried over anhydrous magnesium sulfate, and filtered, and the obtained filtrate was concentrated in vacuum to remove a solvent to obtain a crude product. The crude product was purified by silica gel column chromatography with n-heptane as a mobile phase to obtain Sub-b1 (12.06 g, yield: 78%) as a white solid.

Referring to the synthesis of Sub-b1, Sub-b2 to Sub-b7 were synthesized by using a reactant B shown in Table 2 instead of Sub-a1 and a reactant C shown in Table 2 instead of o-bromonitrobenzene.

TABLE 2

Synthesis of Sub-b2 to Sub-b7

| Intermediate No. | Reactant B | Reactant C | Sub structure and No. | Yield (%) |
|---|---|---|---|---|
| Sub-b2 | Sub-a1 | CAS: 4185-55-1 | Sub-b2 | 76 |
| Sub-b3 | Sub-a1 | CAS: 67116-33-0 | Sub-b3 | 81 |
| Sub-b4 | Sub-a1 | CAS: 4185-62-0 | Sub-b4 | 74 |
| Sub-b5 | Sub-a1 | CAS: 17024-21-4 | Sub-b5 | 72 |
| Sub-b6 | Sub-a2 | CAS: 577-19-5 | Sub-b6 | 62 |

TABLE 2-continued

Synthesis of Sub-b2 to Sub-b7

| Intermediate No. | Reactant B | Reactant C | Sub structure and No. | Yield (%) |
|---|---|---|---|---|
| Sub-b7 | Sub-a2 | CAS: 4185-62-0 | Sub-b7 | 58 |

Synthesis of Sub-c1

Sub-b1 + (carbazole intermediate) →(PPh₃, o-DCB)→ Sub-c1 + Sub-c6

The Sub-b1 (15.47 g, 50 mmol), triphenylphosphine (32.78 g, 125 mmol) and o-dichlorobenzene (160 mL) were added to a 250 mL three-necked flask under a nitrogen atmosphere, the mixture was stirred and heated to reflux, and a reaction was carried out for 16 h. After the system was cooled to room temperature, the reaction solution was concentrated in vacuum to remove a solvent to obtain a crude product. The crude product was purified by silica gel column chromatography with n-heptane as a mobile phase to give Sub-c1 (4.44 g, yield: 32%) and Sub-c6 (6.24 g, yield: 45%) as white solids.

Referring to the synthesis of Sub-c1 and Sub-c6, Sub-c2 to Sub-c8 were synthesized by using a reactant Z shown in Table 3 instead of Sub-b1.

TABLE 3

Synthesis of Sub-c2 to Sub-c8

| Intermediate No. | Reactant Z | Sub structure and No. | Yield (%) |
|---|---|---|---|
| Sub-c2 | Sub-b2 | Sub-c2 | 63 |

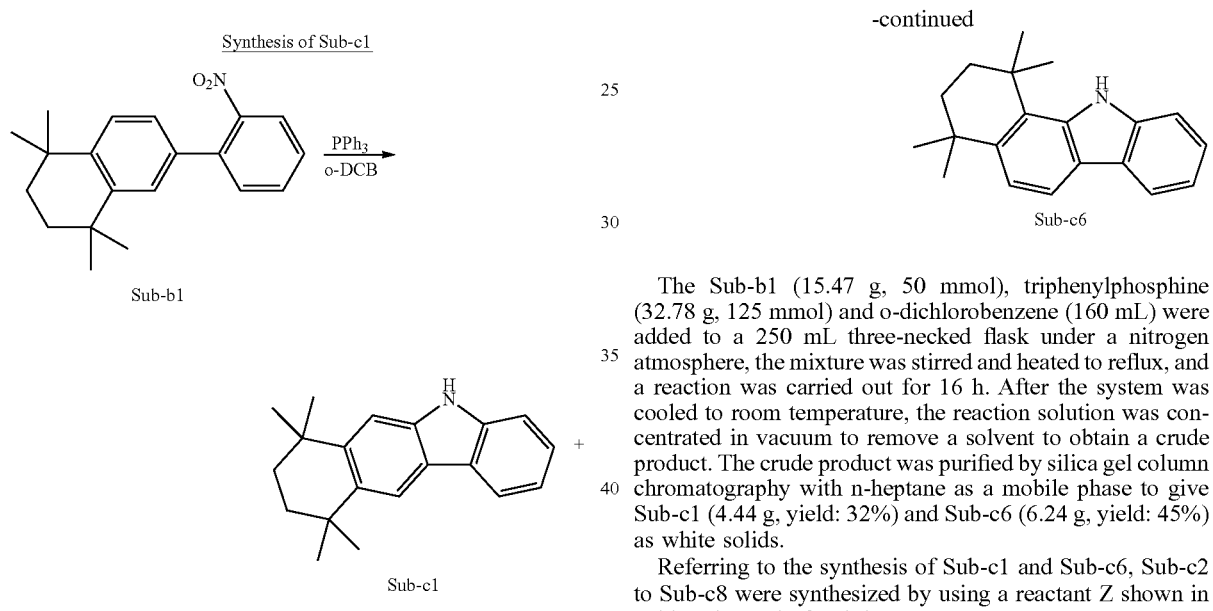

TABLE 3-continued

Synthesis of Sub-c2 to Sub-c8

| Intermediate No. | Reactant Z | Sub structure and No. | Yield (%) |
|---|---|---|---|
| Sub-c3 | Sub-b3 | Sub-c3 | 66 |
| Sub-c4 | Sub-b4 | Sub-c4 | 59 |
| Sub-c5 | Sub-b5 | Sub-c5 | 64 |
| Sub-c7 | Sub-b6 | Sub-c7 | 67 |
| Sub-c8 | Sub-b7 | Sub-c8 | 58 |

Synthesis of Sub-d1

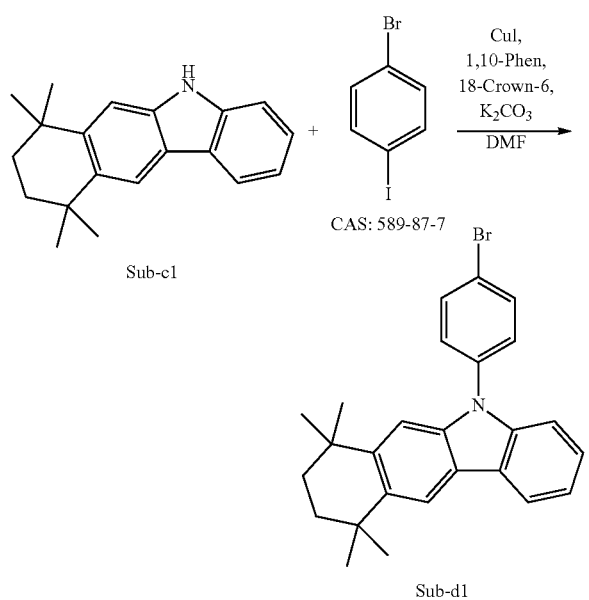

The Sub-c1 (13.87 g, 50 mmol), p-bromoiodobenzene (15.56 g, 55 mmol), cuprous iodide (1.90 g, 10 mmol), 1,10-phenanthroline (3.60, 20 mmol), 18-crown-6 ether (1.32 g, 5 mmol), anhydrous potassium carbonate (15.2 g, 110 mmol) and DMF (160 mL) were added to a 500 mL three-necked flask under a nitrogen atmosphere, the mixture was heated to reflux and stirred for 16 h. After the mixture was cooled to room temperature, the reaction mixture was extracted with dichloromethane (150 mL×3), and organic phases were mixed, dried over anhydrous magnesium sulfate, filtered, and concentrated in vacuum to remove a solvent to obtain a crude product. The crude product was purified by silica gel column chromatography using n-heptane as a mobile phase to obtain Sub-d1 (18.81 g, yield: 87%) as a white solid.

Referring to the synthesis of Sub-d1, Sub-d2 to Sub-d22 were synthesized by using a reactant D shown in Table 4 instead of Sub-c1 and a reactant E shown in Table 4 instead of p-bromoiodobenzene.

TABLE 4

Synthesis of Sub-d2 to Sub-d22

| Intermediate No. | Reactant D | Reactant E |
|---|---|---|
| Sub-d2 | Sub-c1 | CAS: 591-18-4 |
| Sub-d3 | Sub-c1 | CAS: 63279-58-3 |
| Sub-d4 | Sub-c1 | CAS: 389806-32-0 |

TABLE 4-continued
Synthesis of Sub-d2 to Sub-d22
Sub-d5
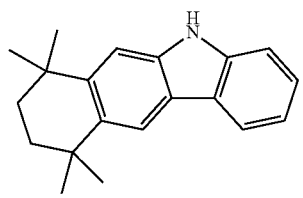 [SMILES: CC1(C)CCC(C)(C)c2cc3c(cc21)[nH]c1ccccc13]
Sub-c1
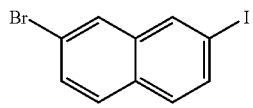
CAS: 1261807-30-0
Sub-d6
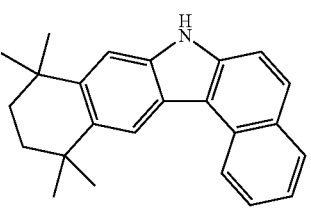 [SMILES: CC1(C)CCC(C)(C)c2cc3c(cc21)[nH]c1ccc2ccccc2c13]
Sub-c2
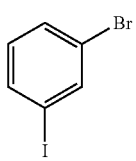
CAS: 591-18-4
Sub-d7
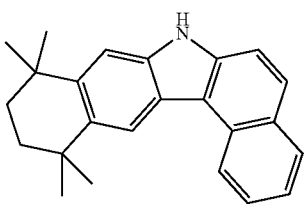 [SMILES: CC1(C)CCC(C)(C)c2cc3c(cc21)[nH]c1ccc2ccccc2c13]
Sub-c2
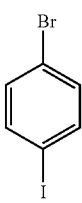
CAS: 589-87-7
Sub-d8
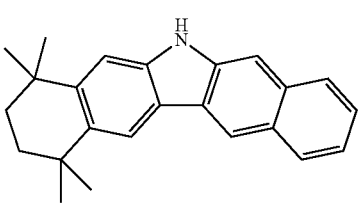 [SMILES: CC1(C)CCC(C)(C)c2cc3c(cc21)[nH]c1cc2ccccc2cc13]
Sub-c3
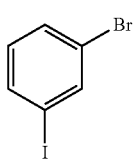
CAS: 591-18-4
Sub-d9
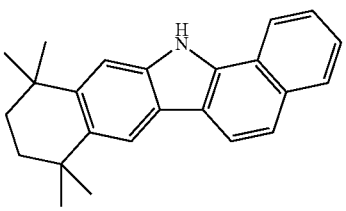 [SMILES: CC1(C)CCC(C)(C)c2cc3c(cc21)[nH]c1c2ccccc2ccc31]
Sub-c4
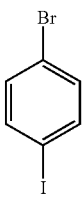
CAS: 589-87-7
Sub-d10
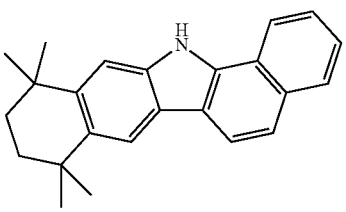 [SMILES: CC1(C)CCC(C)(C)c2cc3c(cc21)[nH]c1c2ccccc2ccc31]
Sub-c4
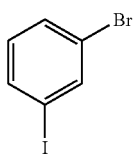
CAS: 591-18-4

TABLE 4-continued
Synthesis of Sub-d2 to Sub-d22
Sub-d11
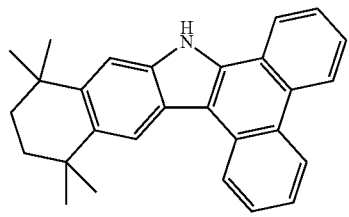 [SMILES: CC1(C)CCC(C)(C)c2cc3c(cc21)[nH]c1c2ccccc2c2ccccc2c31]
Sub-c5
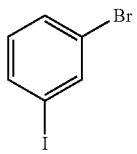
CAS: 591-18-4
Sub-d12
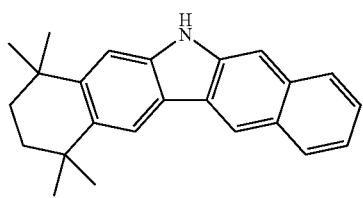 [SMILES: CC1(C)CCC(C)(C)c2cc3c(cc21)[nH]c1cc2ccccc2cc13]
Sub-c3
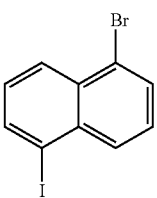 [SMILES: Brc1cccc2c(I)cccc12]
CAS: 77332-64-0
Sub-d13
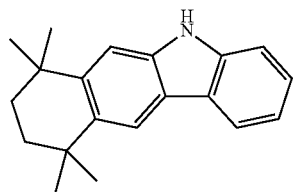 [SMILES: CC1(C)CCC(C)(C)c2cc3c(cc21)[nH]c1ccccc13]
Sub-c1
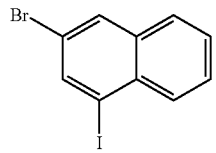
CAS: 1261843-11-1
Sub-d14
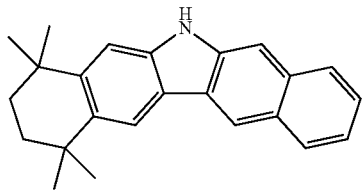 [SMILES: CC1(C)CCC(C)(C)c2cc3c(cc21)[nH]c1cc2ccccc2cc13]
Sub-c3
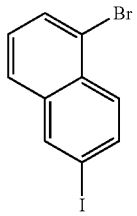 [SMILES: Brc1cccc2cc(I)ccc12]
CAS: 1261752-97-9
Sub-d15
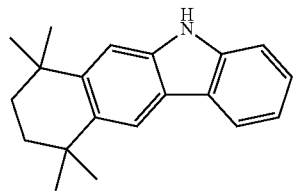 [SMILES: CC1(C)CCC(C)(C)c2cc3c(cc21)[nH]c1ccccc13]
Sub-c1
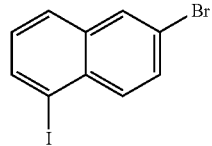 [SMILES: Brc1ccc2c(I)cccc2c1]
CAS: 1261510-93-3
Sub-d16
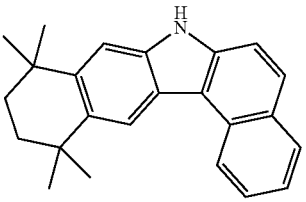 [SMILES: CC1(C)CCC(C)(C)c2cc3c(cc21)[nH]c1ccc2ccccc2c13]
Sub-c2
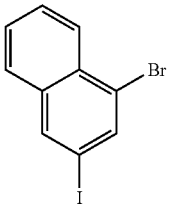 [SMILES: Brc1cc(I)cc2ccccc12]
CAS: 676267-02-0

TABLE 4-continued
Synthesis of Sub-d2 to Sub-d22
Sub-d17 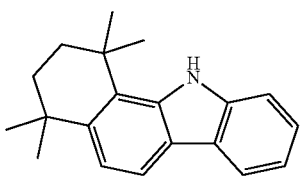 [SMILES: CC1(C)CCC(C)(C)c2c1ccc1c2[nH]c2ccccc21]
Sub-c6
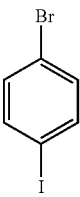
CAS: 589-87-7
Sub-d18 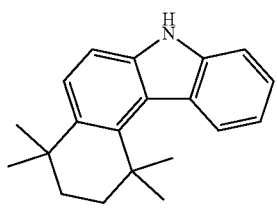 [SMILES: CC1(C)CCC(C)(C)c2c1ccc1[nH]c3ccccc3c21]
Sub-c7
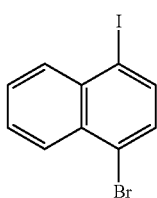 [SMILES: Brc1ccc(I)c2ccccc12]
CAS: 63279-58-3
Sub-d19 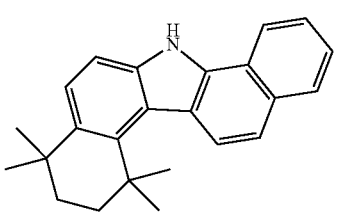 [SMILES: CC1(C)CCC(C)(C)c2c1ccc1[nH]c3c4ccccc4ccc3c21]
Sub-c8
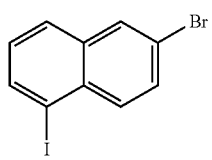 [SMILES: Brc1ccc2c(I)cccc2c1]
CAS: 1261510-93-3
Sub-d20 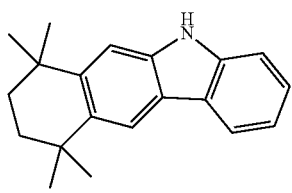 [SMILES: CC1(C)CCC(C)(C)c2cc3c(cc21)[nH]c1ccccc13]
Sub-c1
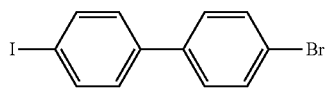 [SMILES: Brc1ccc(-c2ccc(I)cc2)cc1]
CAS: 105946-82-5
Sub-d21 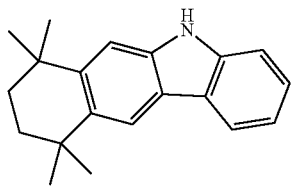 [SMILES: CC1(C)CCC(C)(C)c2cc3c(cc21)[nH]c1ccccc13]
Sub-c1
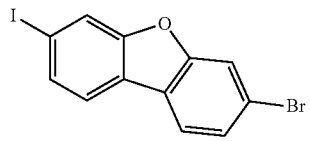 [SMILES: Brc1ccc2c(c1)oc1cc(I)ccc12]
CAS: 105946-82-5
Sub-d22 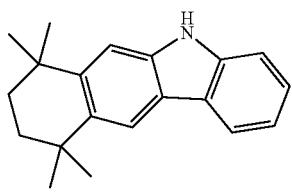 [SMILES: CC1(C)CCC(C)(C)c2cc3c(cc21)[nH]c1ccccc13]
Sub-c1
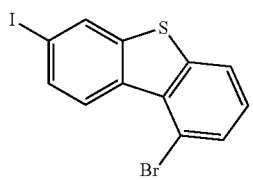 [SMILES: Brc1cccc2sc3cc(I)ccc3c12]
CAS: 105946-82-5

TABLE 4-continued

Synthesis of Sub-d2 to Sub-d22

| Intermediate No. | Sub and structure No. | Yield (%) |
|---|---|---|
| Sub-d2 | Sub-d2 | 85 |
| Sub-d3 | Sub-d3 | 67 |
| Sub-d4 | Sub-d4 | 75 |

TABLE 4-continued
Synthesis of Sub-d2 to Sub-d22
| Sub-d5 | 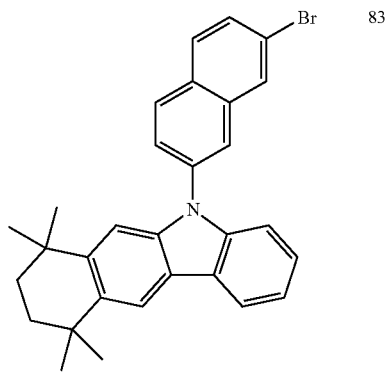 | 83 |
Sub-d5
| Sub-d6 | 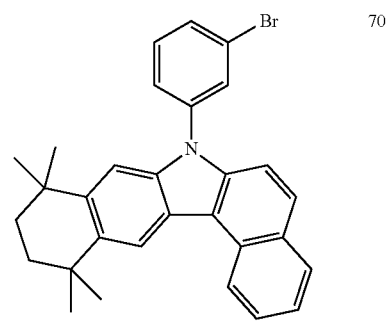 | 70 |
Sub-d6
| Sub-d7 | 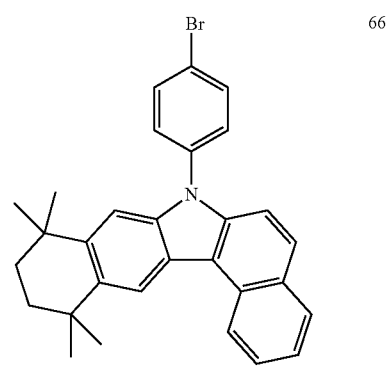 | 66 |
Sub-d7
| Sub-d8 | 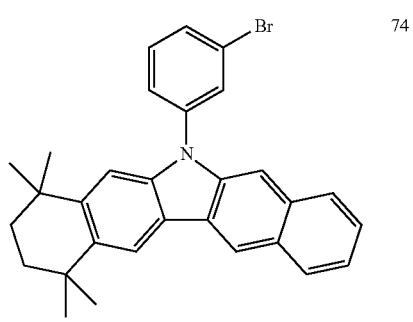 | 74 |
Sub-d8

TABLE 4-continued
Synthesis of Sub-d2 to Sub-d22
| Sub-d9 | 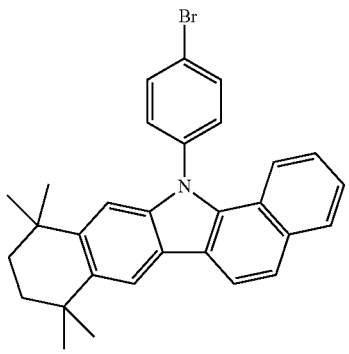 [SMILES: CC1(C)CCC(C)(C)c2cc3c(cc21)c1ccc2ccccc2c1n3-c1ccc(Br)cc1] | 76 |
Sub-d9
| Sub-d10 | 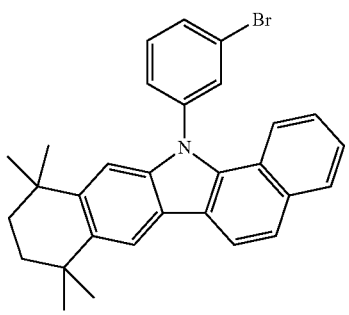 [SMILES: CC1(C)CCC(C)(C)c2cc3c(cc21)c1ccc2ccccc2c1n3-c1cccc(Br)c1] | 82 |
Sub-d10
| Sub-d11 | 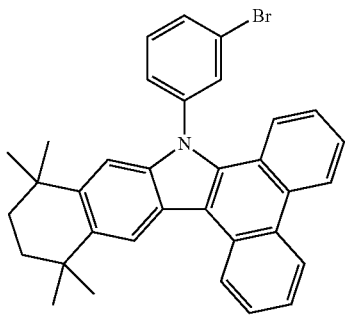 [SMILES: CC1(C)CCC(C)(C)c2cc3c(cc21)c1c2ccccc2c2ccccc2c1n3-c1cccc(Br)c1] | 69 |
Sub-d11
| Sub-d12 | 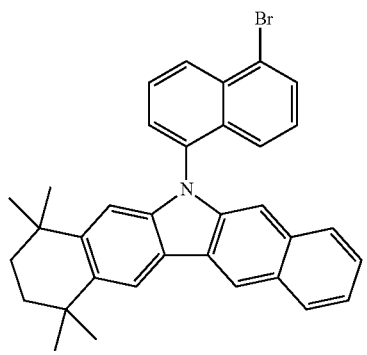 [SMILES: CC1(C)CCC(C)(C)c2cc3c(cc21)c1cc2ccccc2cc1n3-c1cccc2c(Br)cccc12] | 68 |
Sub-d12

TABLE 4-continued
Synthesis of Sub-d2 to Sub-d22
| Sub-d13 | 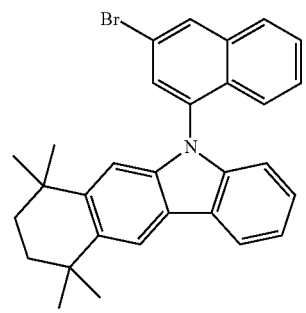 [SMILES: CC1(C)CCC(C)(C)c2cc3c(cc21)c1ccccc1n3-c1cc(Br)cc2ccccc12] | 66 |
| --- | --- | --- |
| Sub-d14 | 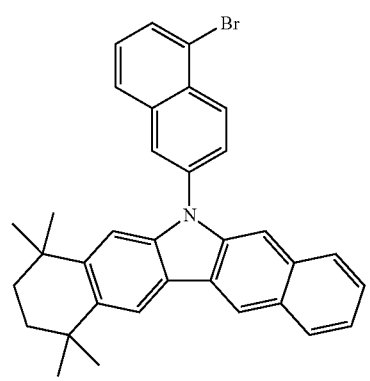 [SMILES: CC1(C)CCC(C)(C)c2cc3c(cc21)c1cc2ccccc2cc1n3-c1ccc2c(Br)cccc2c1] | 72 |
| Sub-d15 | 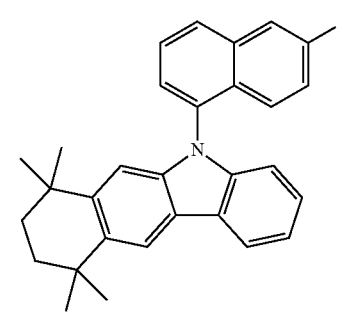 | 72 |
| Sub-d16 | 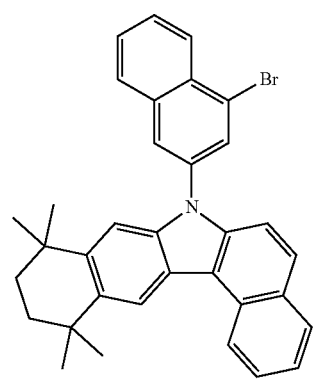 [SMILES: CC1(C)CCC(C)(C)c2cc3c(cc21)c1c2ccccc2ccc1n3-c1cc(Br)c2ccccc2c1] | 77 |

TABLE 4-continued
Synthesis of Sub-d2 to Sub-d22
| Sub-d17 | 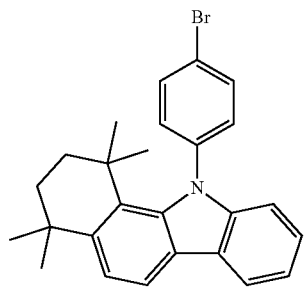 [SMILES: CC1(C)CCC(C)(C)c2c1ccc1c3ccccc3n(-c3ccc(Br)cc3)c21] | 82 |
| Sub-d18 | 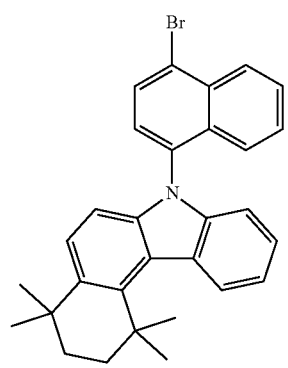 [SMILES: CC1(C)CCC(C)(C)c2c1ccc1c2c2ccccc2n1-c1ccc(Br)c2ccccc12] | 79 |
| Sub-d19 | 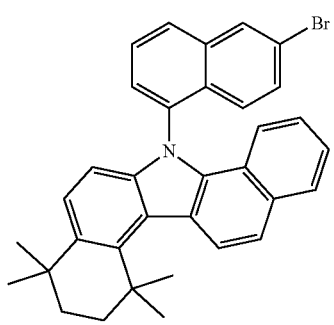 [SMILES: CC1(C)CCC(C)(C)c2c1ccc1c2c2ccc3ccccc3c2n1-c1cccc2cc(Br)ccc12] | 68 |
| Sub-d20 | 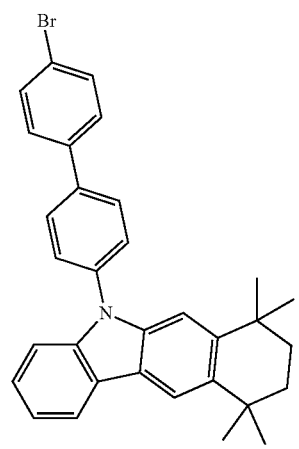 [SMILES: CC1(C)CCC(C)(C)c2cc3c(cc21)c1ccccc1n3-c1ccc(-c2ccc(Br)cc2)cc1] | 62 |

TABLE 4-continued

Synthesis of Sub-d2 to Sub-d22

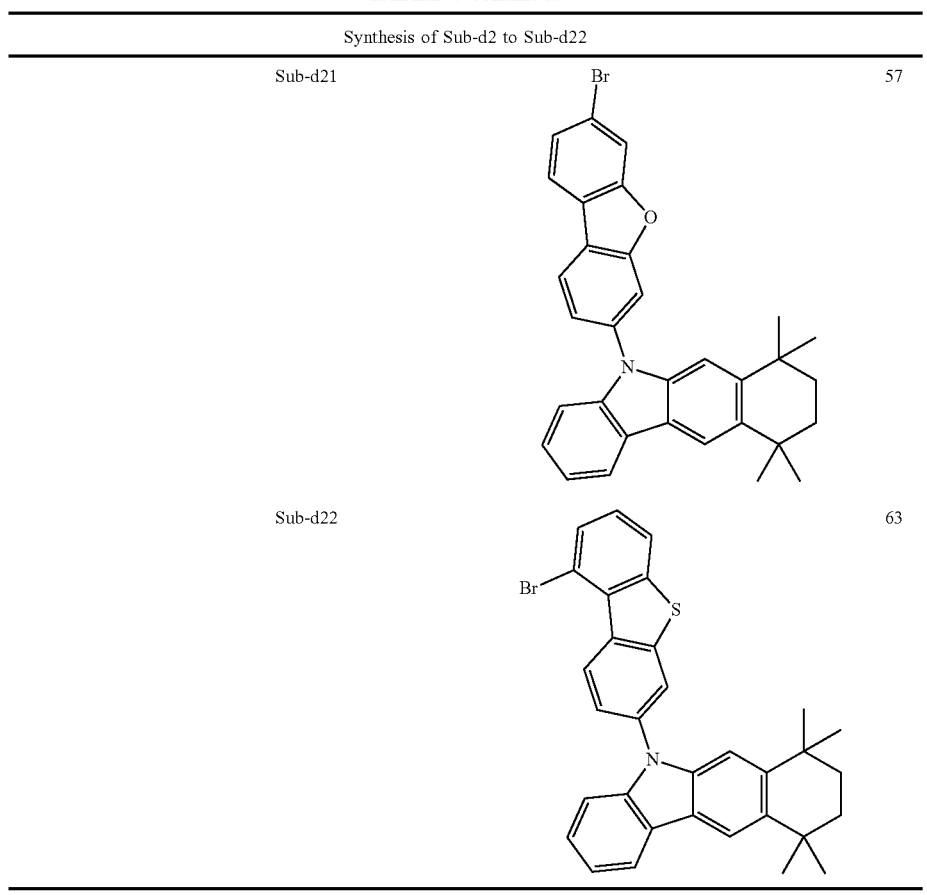

Synthesis of Sub-e1

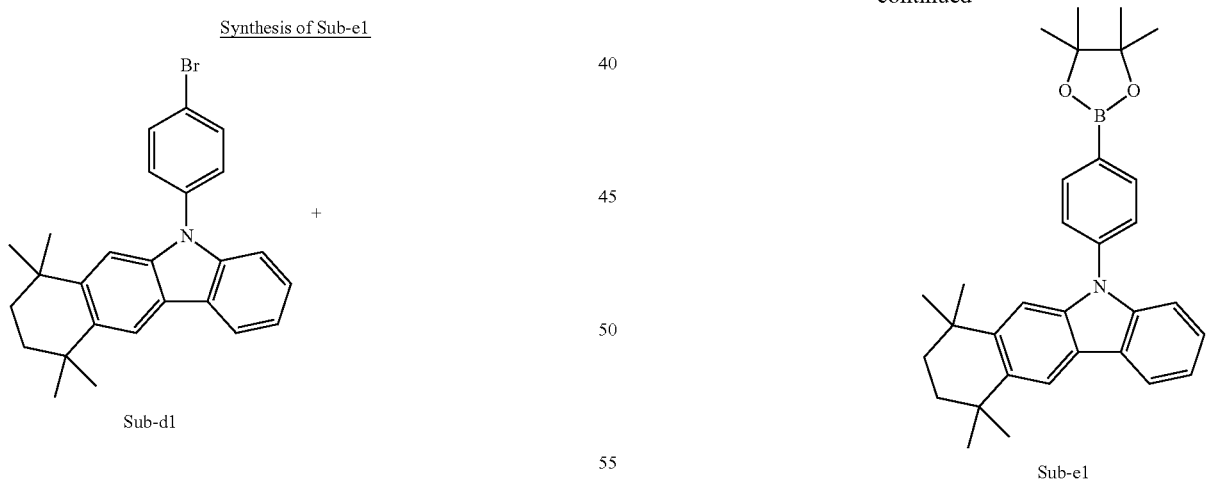

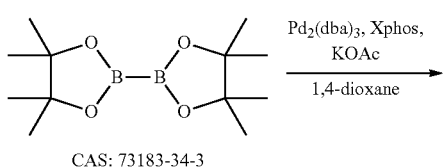

Sub-d1 (21.62 g, 50 mmol), bis(pinacolato)diboron (15.24 g, 60 mmol), potassium acetate (10.8 g, 110 mmol) and 1,4-dioxane (160 mL) were sequentially added to a 500 mL three-necked flask under a nitrogen atmosphere, stirring and heating were started, after the mixture was heated to 40° C., tris(dibenzylideneacetone)dipalladium (Pd$_2$(dba)$_3$, 0.46 g, 0.5 mmol) and 2-dicyclohexylphosphino-2',4',6'-triisopropylbiphenyl (Xphos, 0.48 g, 1 mmol) were added rapidly, heating was continued to be performed to reflux, and a reaction was carried out overnight under stirring. After the reaction solution was cooled to room temperature, 200 mL of water was added to the solution, well stirring was performed for 30 min, suction filtration was performed in vacuum, and the obtained filter cake was washed with deionized water to be neutral, and was subjected to drip washing with 100 mL of absolute ethanol to obtain a gray solid; and a crude product was slurried once with n-heptane, dissolved in 200 mL of toluene and purified by a flash silica gel column to remove a catalyst, and an eluate was concentrated to obtain a white solid Sub-e1 (17.26 g, yield: 72N).

Referring to the synthesis of Sub-e1, Sub-e2 to Sub-e22 were synthesized by using a reactant F shown in Table 5 instead of Sub-d1.

TABLE 5

Synthesis of Sub-e2 to Sub-e22

| Intermediate No. | Reactant F | Sub structure and No. | Yield (%) |
|---|---|---|---|
| Sub-e2 | 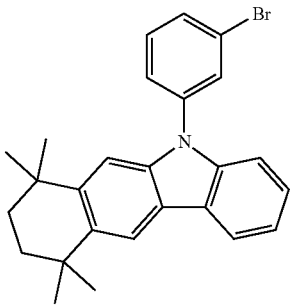 [SMILES: CC1(C)CCC(C)(C)c2cc3c(cc21)c1ccccc1n3-c1cccc(Br)c1] Sub-d2 | 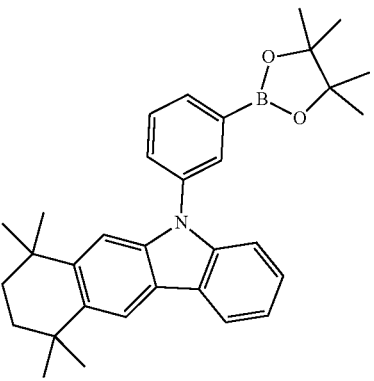 [SMILES: CC1(C)CCC(C)(C)c2cc3c(cc21)c1ccccc1n3-c1cccc(B2OC(C)(C)C(C)(C)O2)c1] Sub-e2 | 68 |
| Sub-e3 | 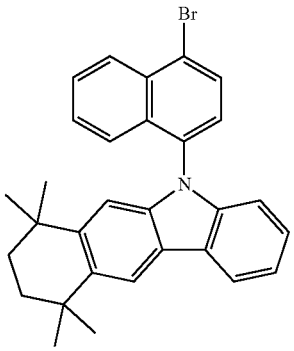 [SMILES: CC1(C)CCC(C)(C)c2cc3c(cc21)c1ccccc1n3-c1ccc(Br)c2ccccc12] Sub-d3 | 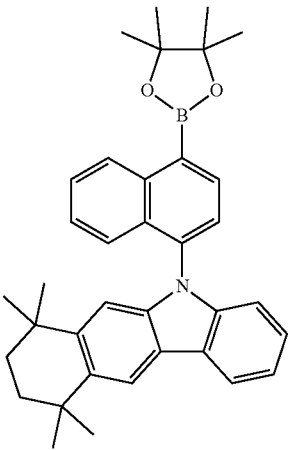 [SMILES: CC1(C)CCC(C)(C)c2cc3c(cc21)c1ccccc1n3-c1ccc(B2OC(C)(C)C(C)(C)O2)c2ccccc12] Sub-e3 | 68 |

TABLE 5-continued

Synthesis of Sub-e2 to Sub-e22

| Intermediate No. | Reactant F | Sub structure and No. | Yield (%) |
| --- | --- | --- | --- |
| Sub-e4 | Sub-d4 | Sub-e4 | 73 |
| Sub-e5 | Sub-d5 | Sub-e5 | 66 |
| Sub-e6 | Sub-d6 | Sub-e6 | 74 |

TABLE 5-continued

Synthesis of Sub-e2 to Sub-e22

| Intermediate No. | Reactant F | Sub structure and No. | Yield (%) |
|---|---|---|---|
| Sub-e7 | Sub-d7 | Sub-e7 | 67 |
| Sub-e8 | Sub-d8 | Sub-e8 | 75 |
| Sub-e9 | Sub-d9 | Sub-e9 | 72 |

333
334
TABLE 5-continued
Synthesis of Sub-e2 to Sub-e22
| Intermediate No. | Reactant F | Sub structure and No. | Yield (%) |
|---|---|---|---|
| Sub-e10 | 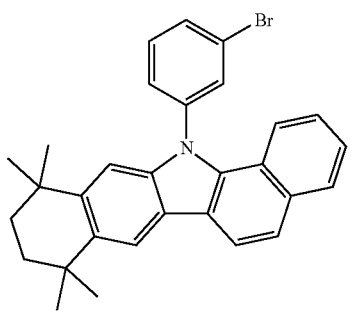 [SMILES: CC1(C)CCC(C)(C)c2cc3c(cc21)c1ccc2ccccc2c1n3-c1cccc(Br)c1]<br>Sub-d10 | 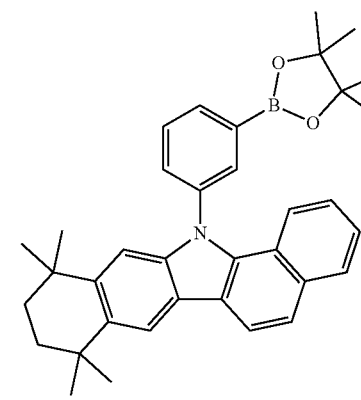<br>Sub-e10 | 74 |
| Sub-e11 | 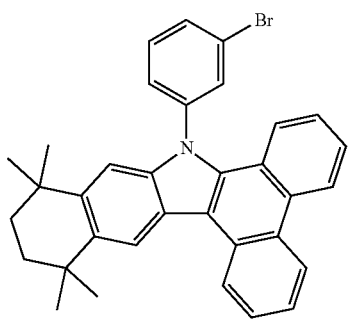 [SMILES: CC1(C)CCC(C)(C)c2cc3c(cc21)c1c2ccccc2c2ccccc2c1n3-c1cccc(Br)c1]<br>Sub-d11 | 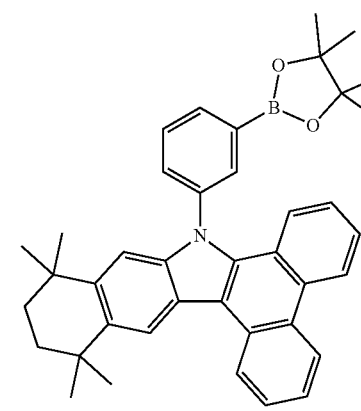<br>Sub-e11 | 72 |
| Sub-e12 | 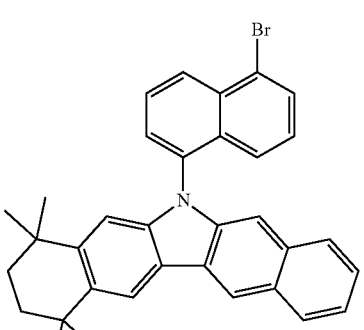<br>Sub-d12 | 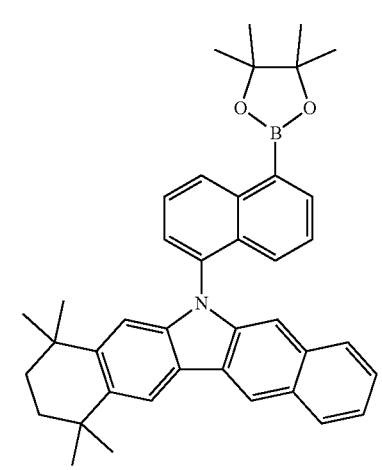 [SMILES: CC1(C)CCC(C)(C)c2cc3c(cc21)c1cc2ccccc2cc1n3-c1cccc2c(B3OC(C)(C)C(C)(C)O3)cccc12]<br>Sub-e12 | 70 |

TABLE 5-continued

Synthesis of Sub-e2 to Sub-e22

| Intermediate No. | Reactant F | Sub structure and No. | Yield (%) |
|---|---|---|---|
| Sub-e13 | Sub-d13 | Sub-e13 | 65 |
| Sub-e14 | Sub-d14 | Sub-e14 | 74 |
| Sub-e15 | Sub-d15 | Sub-e15 | 69 |

TABLE 5-continued

Synthesis of Sub-e2 to Sub-e22

| Intermediate No. | Reactant F | Sub structure and No. | Yield (%) |
|---|---|---|---|
| Sub-e16 | Sub-d16 | Sub-e16 | 69 |
| Sub-e17 | Sub-d17 | Sub-e17 | 76 |
| Sub-e18 | Sub-d18 | Sub-e18 | 74 |

TABLE 5-continued
Synthesis of Sub-e2 to Sub-e22
| Intermediate No. | Reactant F | Sub structure and No. | Yield (%) |
|---|---|---|---|
| Sub-e19 | 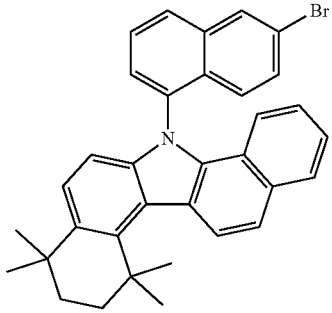 [SMILES: CC1(C)CCC(C)(C)c2c1ccc1c2c2ccc3ccccc3c2n1-c1cccc2cc(Br)ccc12] Sub-d19 | 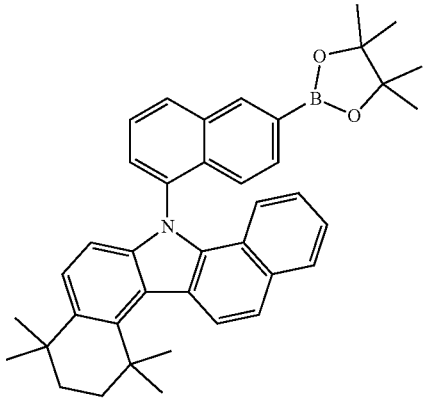 Sub-e19 | 71 |
| Sub-e20 | 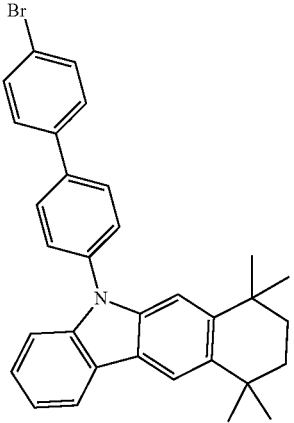 [SMILES: CC1(C)CCC(C)(C)c2cc3c(cc21)c1ccccc1n3-c1ccc(-c2ccc(Br)cc2)cc1] Sub-d20 | 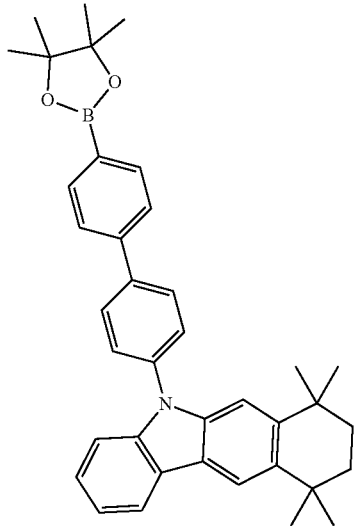 [SMILES: CC1(C)CCC(C)(C)c2cc3c(cc21)c1ccccc1n3-c1ccc(-c2ccc(B3OC(C)(C)C(C)(C)O3)cc2)cc1] | 70 |
| Sub-e21 | 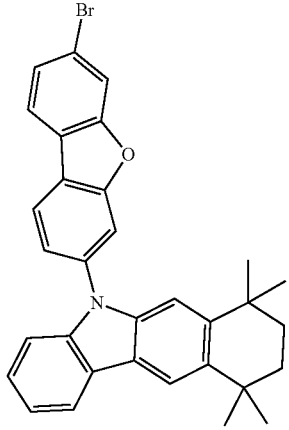 [SMILES: CC1(C)CCC(C)(C)c2cc3c(cc21)c1ccccc1n3-c1ccc2c(c1)oc1cc(Br)ccc12] Sub-d21 | 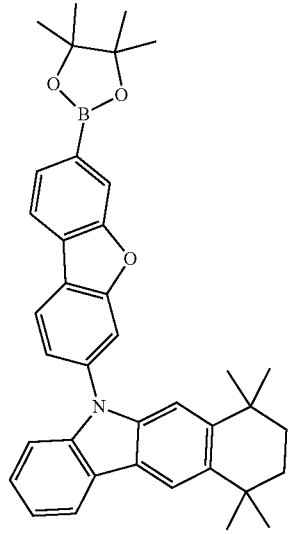 [SMILES: CC1(C)CCC(C)(C)c2cc3c(cc21)c1ccccc1n3-c1ccc2c(c1)oc1cc(B3OC(C)(C)C(C)(C)O3)ccc12] | 72 |

TABLE 5-continued

Synthesis of Sub-e2 to Sub-e22

| Intermediate No. | Reactant F | Sub structure and No. | Yield (%) |
|---|---|---|---|
| Sub-e22 | | | 76 |

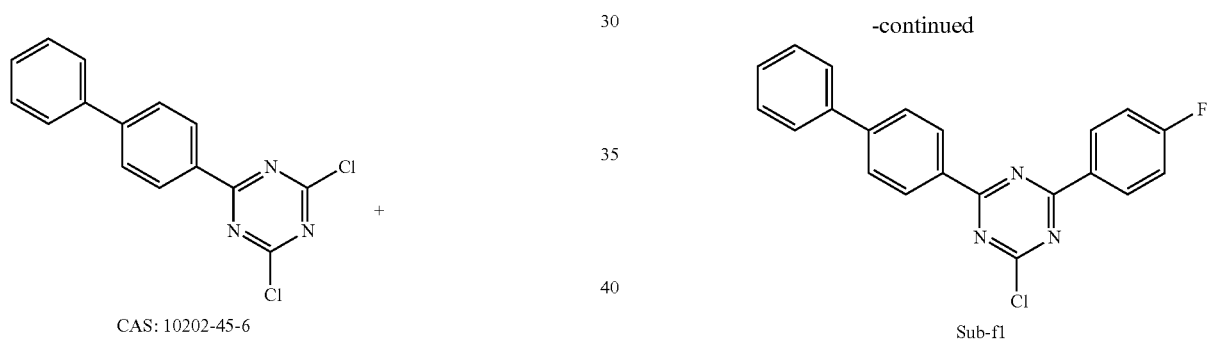

Sub-d22

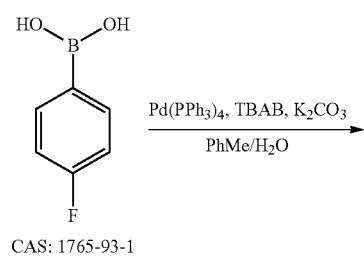

CAS: 10202-45-6

+

HO\B/OH on 4-fluorophenyl

CAS: 1765-93-1

Pd(PPh₃)₄, TBAB, K₂CO₃
―――――――――――→
PhMe/H₂O

-continued

Sub-f1

2-(4-Biphenyl)-4,6-dichloro-1,3,5-triazine (22.66 g, 75 mmol), 4-fluorobenzeneboronic acid (6.99 g, 50 mmol), tetrakis(triphenylphosphine)palladium (0.58 g, 0.5 mmol), tetrabutyl ammonium bromide (TBAB, 1.61 g, 5 mmol), anhydrous potassium carbonate (13.82 g, 100 mmol), toluene (220 mL), and deionized water (55 mL) were sequentially added to a 500 mL three-necked flask under a nitrogen atmosphere, the mixture was stirred and heated to 65° C. to 70° C. and stirred for 16 h. After the reaction solution was cooled to room temperature, the reaction solution was extracted with dichloromethane (100 mL×3), an organic phase was dried over anhydrous magnesium sulfate, filtered, and concentrated in vacuum to remove a solvent to obtain a crude product. The crude product was recrystallized with toluene to obtain a white solid Sub-f1 (11.03 g, yield: 61%).

Referring to the synthesis of Sub-f1, Sub-f2 to Sub-f35 were synthesized by using a reactant G shown in Table 6 instead of 2-(4-biphenyl)-4,6-dichloro-1,3,5-triazine and a reactant H shown in Table 6 instead of 4-fluorobenzeneboronic acid.

TABLE 6
Synthesis of Sub-f2 to Sub-f35
| Intermediate No. | Reactant G | Reactant H |
|---|---|---|
| Sub-f2 | 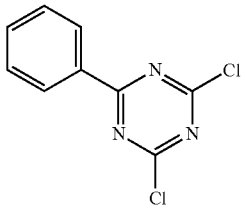 [SMILES: Clc1nc(Cl)nc(-c2ccccc2)n1]<br>CAS: 1700-02-3 | 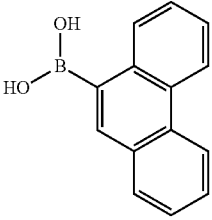 [SMILES: OB(O)c1cc2ccccc2c2ccccc12]<br>CAS: 68572-87-2 |
| Sub-f3 | 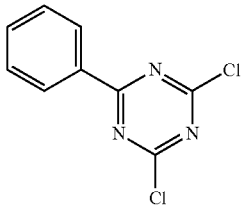 [SMILES: Clc1nc(Cl)nc(-c2ccccc2)n1]<br>CAS: 1700-02-3 | 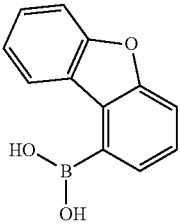<br>CAS: 162607-19-4 |
| Sub-f4 | 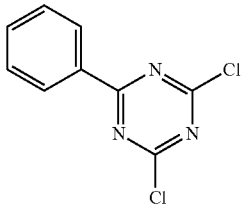 [SMILES: Clc1nc(Cl)nc(-c2ccccc2)n1]<br>CAS: 1700-02-3 | 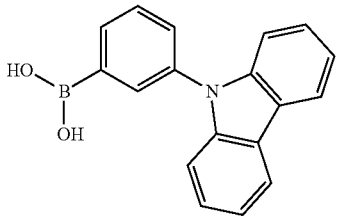 [SMILES: OB(O)c1cccc(-n2c3ccccc3c3ccccc32)c1]<br>CAS: 864377-33-3 |
| Sub-f5 | 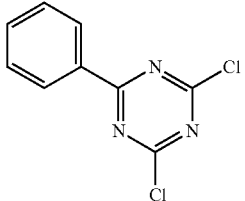 [SMILES: Clc1nc(Cl)nc(-c2ccccc2)n1]<br>CAS: 1700-02-3 | 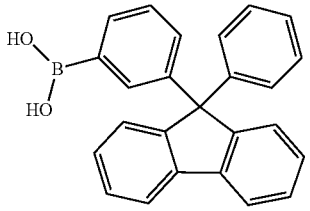 [SMILES: OB(O)c1cccc(C2(c3ccccc3)c3ccccc3-c3ccccc32)c1]<br>CAS: 1292285-28-9 |
| Sub-f6 | 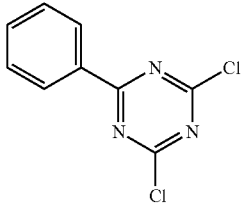 [SMILES: Clc1nc(Cl)nc(-c2ccccc2)n1]<br>CAS: 1700-02-3 | 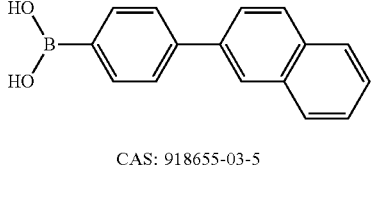<br>CAS: 918655-03-5 |

TABLE 6-continued
Synthesis of Sub-f2 to Sub-f35
Sub-f7 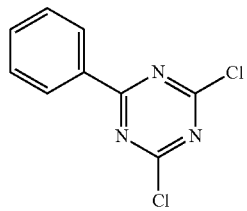 [SMILES: Clc1nc(Cl)nc(-c2ccccc2)n1]
CAS: 1700-02-3
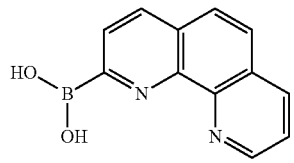 [SMILES: OB(O)c1ccc2ccc3cccnc3c2n1]
CAS: 1009112-34-8
Sub-f8 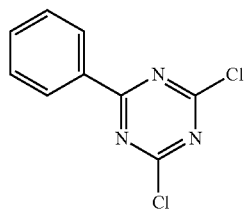 [SMILES: Clc1nc(Cl)nc(-c2ccccc2)n1]
CAS: 1700-02-3
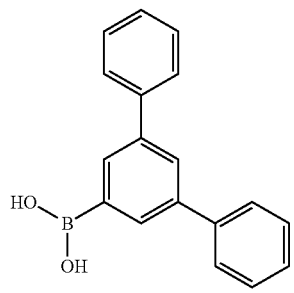 [SMILES: OB(O)c1cc(-c2ccccc2)cc(-c2ccccc2)c1]
CAS: 128388-54-5
Sub-f9 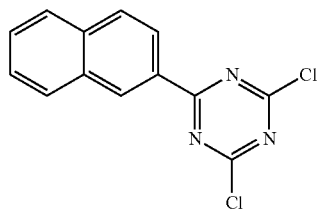 [SMILES: Clc1nc(Cl)nc(-c2ccc3ccccc3c2)n1]
CAS: 112719-97-8
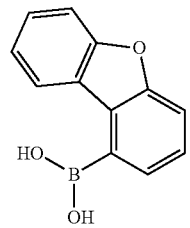 [SMILES: OB(O)c1cccc2oc3ccccc3c12]
CAS: 162607-19-4
Sub-f10 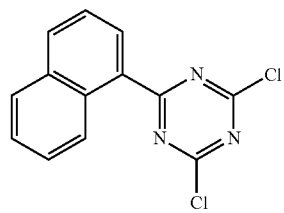 [SMILES: Clc1nc(Cl)nc(-c2cccc3ccccc23)n1]
CAS: 59336-36-6
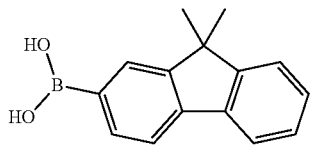
CAS: 333432-28-3
Sub-f11 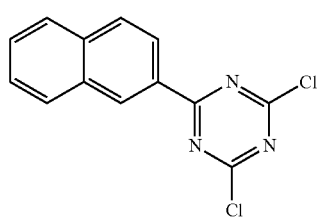 [SMILES: Clc1nc(Cl)nc(-c2ccc3ccccc3c2)n1]
CAS: 112719-97-8
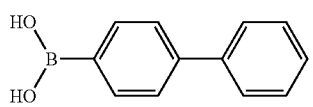
CAS: 5122-94-1

TABLE 6-continued
Synthesis of Sub-f2 to Sub-f35
Sub-f12
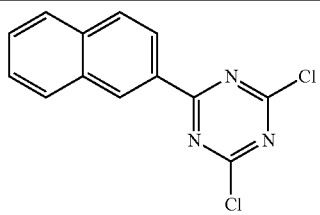
CAS: 112719-97-8
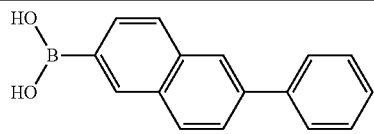
CAS: 876442-90-9
Sub-f13
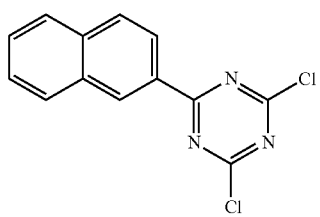 [SMILES: Clc1nc(Cl)nc(-c2ccc3ccccc3c2)n1]
CAS: 112719-97-8
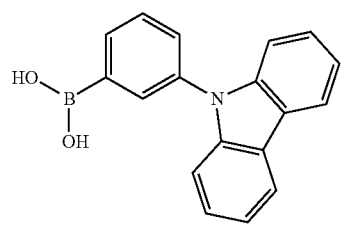 [SMILES: OB(O)c1cccc(-n2c3ccccc3c3ccccc32)c1]
CAS: 864377-33-3
Sub-f14
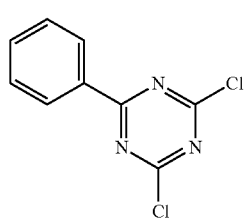 [SMILES: Clc1nc(Cl)nc(-c2ccccc2)n1]
CAS: 1700-02-3
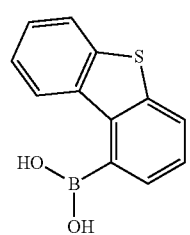
CAS: 1245943-60-5
Sub-f15
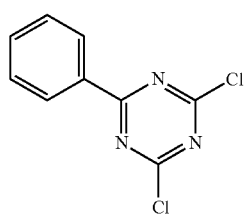 [SMILES: Clc1nc(Cl)nc(-c2ccccc2)n1]
CAS: 1700-02-3
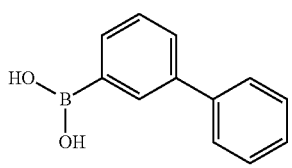 [SMILES: OB(O)c1cccc(-c2ccccc2)c1]
CAS: 5122-95-2
Sub-f16
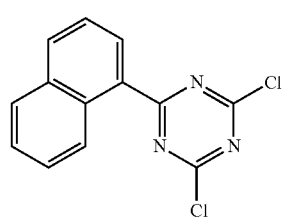 [SMILES: Clc1nc(Cl)nc(-c2cccc3ccccc23)n1]
CAS: 59336-36-6
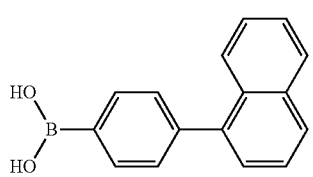 [SMILES: OB(O)c1ccc(-c2cccc3ccccc23)cc1]
CAS: 870774-25-7
Sub-f17
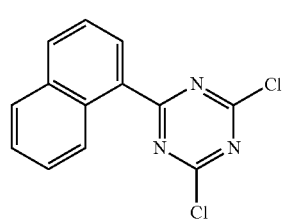 [SMILES: Clc1nc(Cl)nc(-c2cccc3ccccc23)n1]
CAS: 59336-36-6
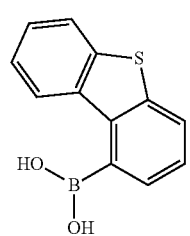
CAS: 1245943-60-5

TABLE 6-continued
Synthesis of Sub-f2 to Sub-f35
Sub-f18 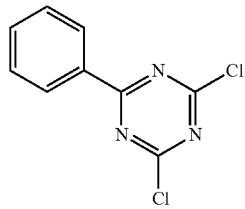 [SMILES: Clc1nc(Cl)nc(-c2ccccc2)n1]
CAS: 1700-02-3
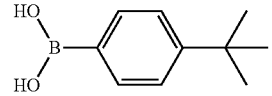
CAS: 123324-71-0
Sub-f19 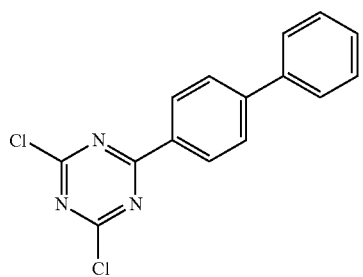 [SMILES: Clc1nc(Cl)nc(-c2ccc(-c3ccccc3)cc2)n1]
CAS: 10202-45-6
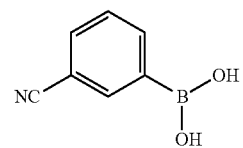 [SMILES: N#Cc1cccc(B(O)O)c1]
CAS: 150255-96-2
Sub-f20 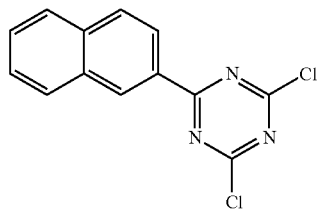 [SMILES: Clc1nc(Cl)nc(-c2ccc3ccccc3c2)n1]
CAS: 112719-97-8
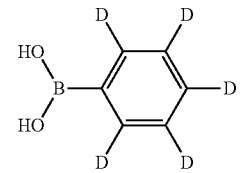
CAS: 215527-70-1
Sub-f21 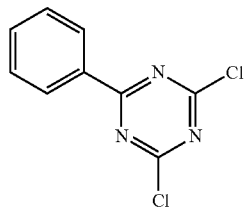 [SMILES: Clc1nc(Cl)nc(-c2ccccc2)n1]
CAS: 1700-02-3
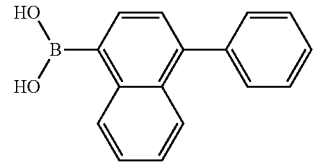 [SMILES: OB(O)c1ccc(-c2ccccc2)c2ccccc12]
CAS: 372521-91-0
Sub-f22 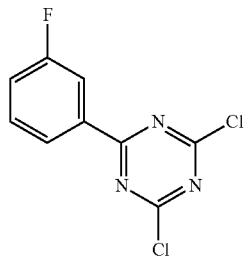 [SMILES: Fc1cccc(-c2nc(Cl)nc(Cl)n2)c1]
CAS: 102528-19-8
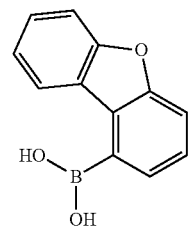
CAS: 162607-19-4

TABLE 6-continued
Synthesis of Sub-f2 to Sub-f35
Sub-f23 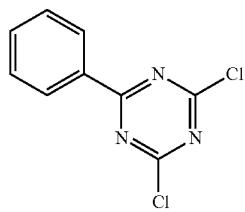 [SMILES: Clc1nc(Cl)nc(-c2ccccc2)n1]
CAS: 1700-02-3
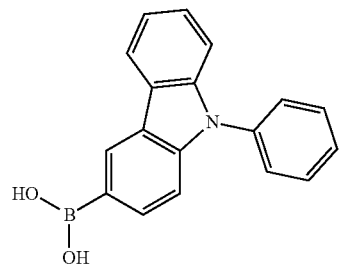 [SMILES: OB(O)c1ccc2c(c1)c1ccccc1n2-c1ccccc1]
CAS: 854952-58-2
Sub-f24 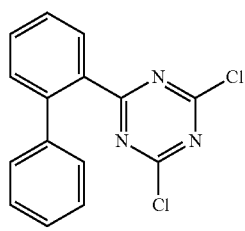 [SMILES: Clc1nc(Cl)nc(-c2ccccc2-c2ccccc2)n1]
CAS: 2134165-04-9
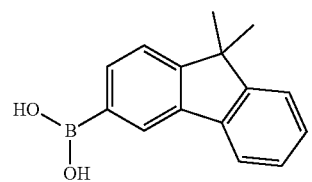 [SMILES: CC1(C)c2ccccc2-c2cc(B(O)O)ccc21]
CAS: 1251773-34-8
Sub-f25 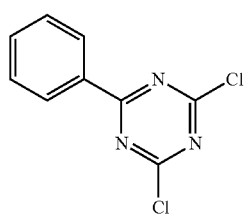 [SMILES: Clc1nc(Cl)nc(-c2ccccc2)n1]
CAS: 1700-02-3
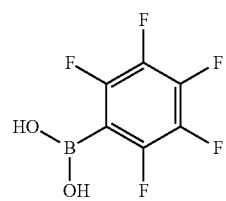 [SMILES: OB(O)c1c(F)c(F)c(F)c(F)c1F]
CAS: 1582-24-7
Sub-f26 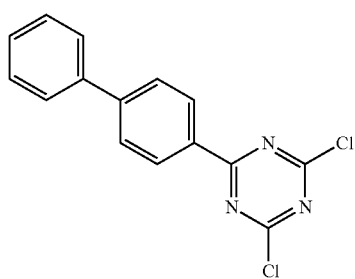 [SMILES: Clc1nc(Cl)nc(-c2ccc(-c3ccccc3)cc2)n1]
CAS: 10202-45-6
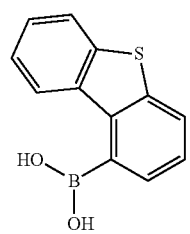
CAS: 1245943-60-5
Sub-f27
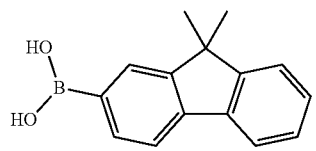
CAS: 333432-28-3

TABLE 6-continued
Synthesis of Sub-f2 to Sub-f35
Sub-f28 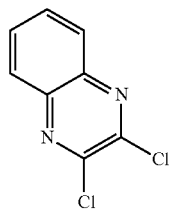 [SMILES: Clc1nc2ccccc2nc1Cl]
CAS: 2213-63-0
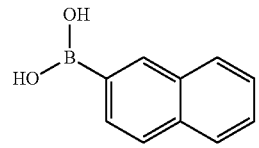 [SMILES: OB(O)c1ccc2ccccc2c1]
CAS: 32316-92-0
Sub-f29 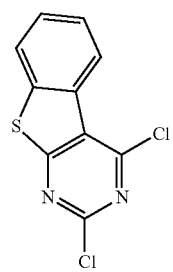 [SMILES: Clc1nc(Cl)c2c(n1)sc1ccccc12]
CAS: 76872-40-7
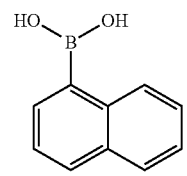 [SMILES: OB(O)c1cccc2ccccc12]
CAS: 13922-41-3
Sub-f30 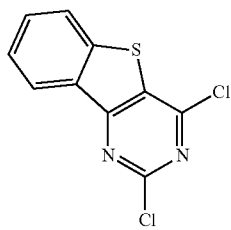
CAS: 160199-05-3
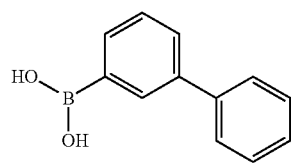 [SMILES: OB(O)c1cccc(-c2ccccc2)c1]
CAS: 5122-95-2
Sub-f31 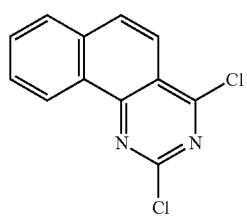 [SMILES: Clc1nc(Cl)c2ccc3ccccc3c2n1]
CAS: 1598130-46-1
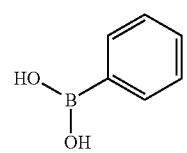
CAS: 98-80-6
Sub-f32 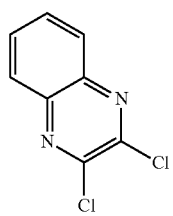 [SMILES: Clc1nc2ccccc2nc1Cl]
CAS: 2213-63-0
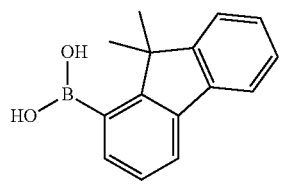 [SMILES: CC1(C)c2ccccc2-c2cccc(B(O)O)c21]
CAS: 1251825-71-4

TABLE 6-continued
Synthesis of Sub-f2 to Sub-f35
Sub-f33
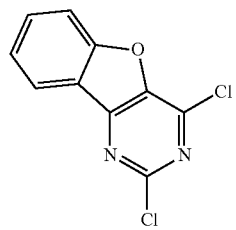
CAS: 160199-95-1
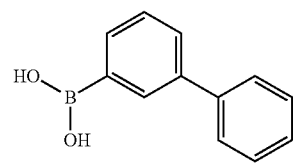 [SMILES: OB(O)c1cccc(-c2ccccc2)c1]
CAS: 5122-95-2
Sub-f34
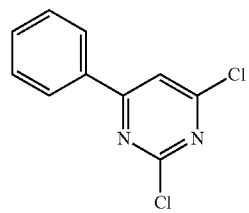 [SMILES: Clc1cc(-c2ccccc2)nc(Cl)n1]
CAS: 26032-72-4
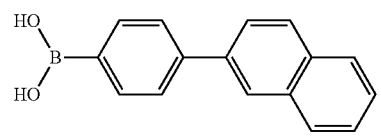 [SMILES: OB(O)c1ccc(-c2ccc3ccccc3c2)cc1]
CAS: 918655-03-5
Sub-f35
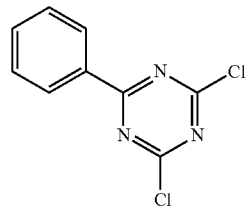 [SMILES: Clc1nc(Cl)nc(-c2ccccc2)n1]
CAS: 1700-02-3
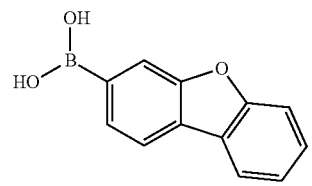 [SMILES: OB(O)c1ccc2c(c1)oc1ccccc12]
CAS: 395087-89-5
| | Sub structure and No. | Yield (%) |
|---|---|---|
| Sub-f2 | 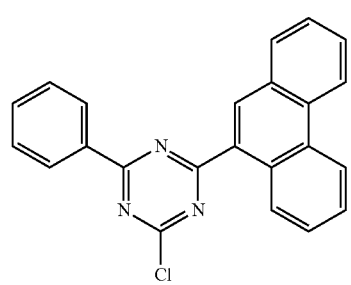 [SMILES: Clc1nc(-c2ccccc2)nc(-c2cc3ccccc3c3ccccc23)n1]<br>Sub-f2 | 63 |
| Sub-f3 | 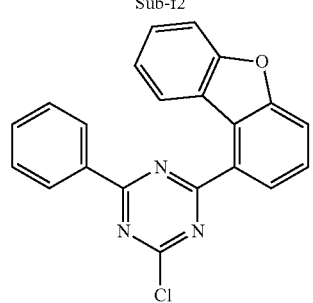<br>Sub-f3 | 55 |

TABLE 6-continued
Synthesis of Sub-f2 to Sub-f35
| Sub-f4 | 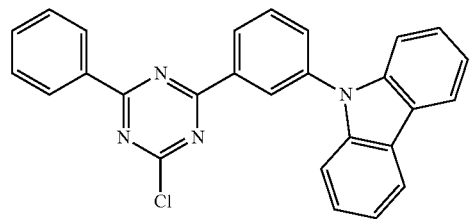 [SMILES: Clc1nc(-c2ccccc2)nc(-c2cccc(-n3c4ccccc4c4ccccc43)c2)n1] Sub-f4 | 61 |
| Sub-f5 | 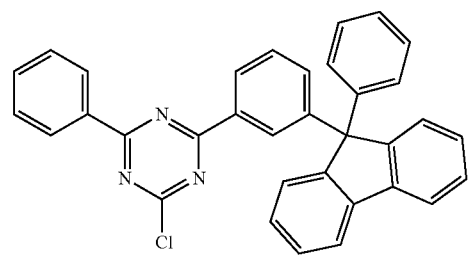 [SMILES: Clc1nc(-c2ccccc2)nc(-c2cccc(C3(c4ccccc4)c4ccccc4-c4ccccc43)c2)n1] Sub-f5 | 65 |
| Sub-f6 | 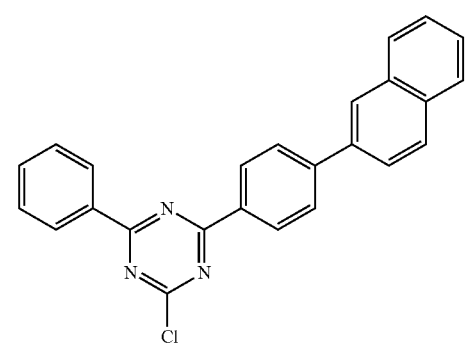 [SMILES: Clc1nc(-c2ccccc2)nc(-c2ccc(-c3ccc4ccccc4c3)cc2)n1] Sub-f6 | 60 |
| Sub-f7 | 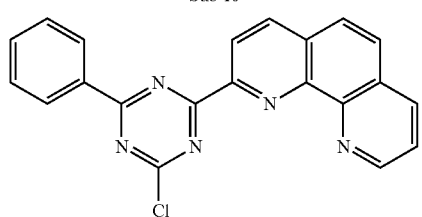 Sub-f7 | 61 |
| Sub-f8 | 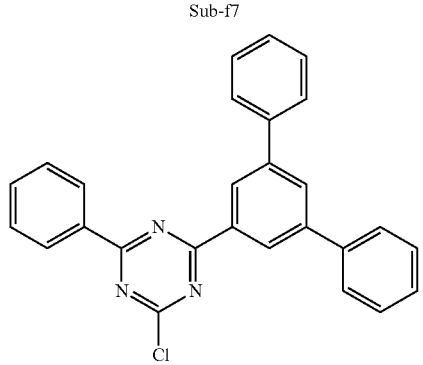 Sub-f8 | 55 |

TABLE 6-continued
Synthesis of Sub-f2 to Sub-f35
| Sub-f9 | 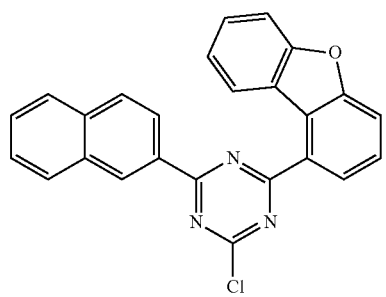 [SMILES: Clc1nc(-c2ccc3ccccc3c2)nc(-c2cccc3oc4ccccc4c23)n1] Sub-f9 | 57 |
| Sub-f10 | 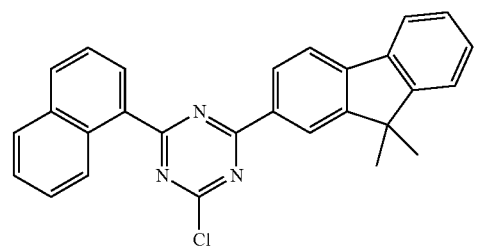 [SMILES: CC1(C)c2ccccc2-c2ccc(-c3nc(Cl)nc(-c4cccc5ccccc45)n3)cc21] Sub-f10 | 55 |
| Sub-f11 | 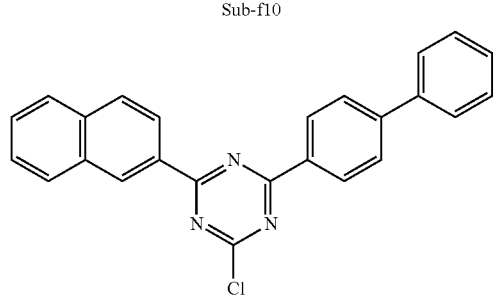 Sub-f11 | 61 |
| Sub-f12 | 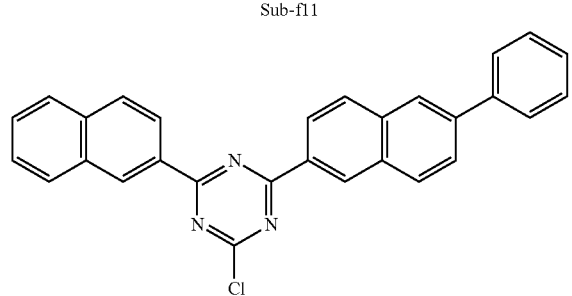 Sub-f12 | 56 |
| Sub-f13 | 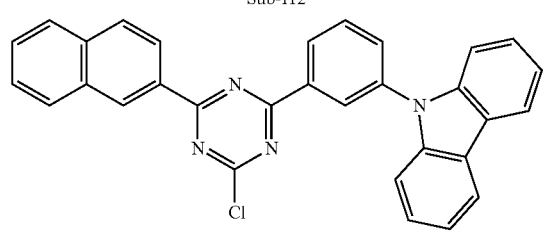 Sub-f13 | 61 |

TABLE 6-continued
Synthesis of Sub-f2 to Sub-f35
| Sub-f14 | 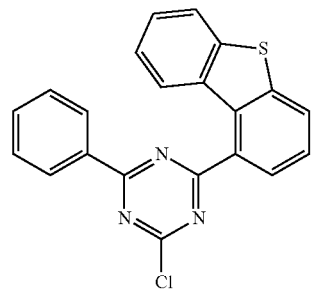 [SMILES: Clc1nc(-c2ccccc2)nc(-c2cccc3sc4ccccc4c23)n1] Sub-f14 | 57 |
| Sub-f15 | 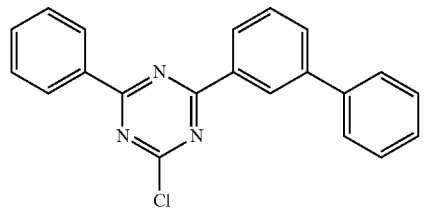 [SMILES: Clc1nc(-c2ccccc2)nc(-c2cccc(-c3ccccc3)c2)n1] Sub-f15 | 63 |
| Sub-f16 | 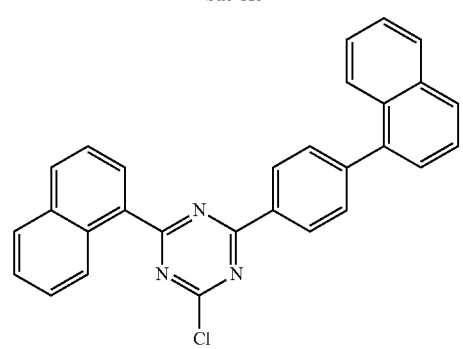 Sub-f16 | 58 |
| Sub-f17 | 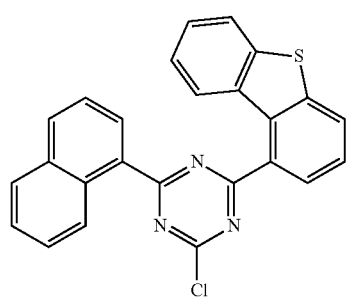 [SMILES: Clc1nc(-c2cccc3ccccc23)nc(-c2cccc3sc4ccccc4c23)n1] Sub-f17 | 64 |
| Sub-f18 | 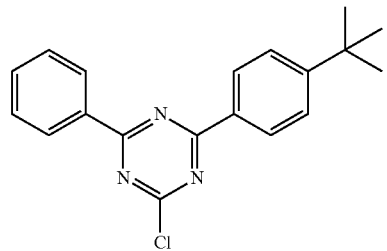 [SMILES: CC(C)(C)c1ccc(-c2nc(Cl)nc(-c3ccccc3)n2)cc1] Sub-f18 | 64 |

TABLE 6-continued
Synthesis of Sub-f2 to Sub-f35
| Sub-f19 | 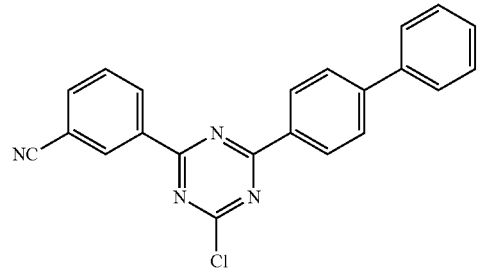 [SMILES: N#Cc1cccc(-c2nc(Cl)nc(-c3ccc(-c4ccccc4)cc3)n2)c1] Sub-f19 | 61 |
| Sub-f20 | 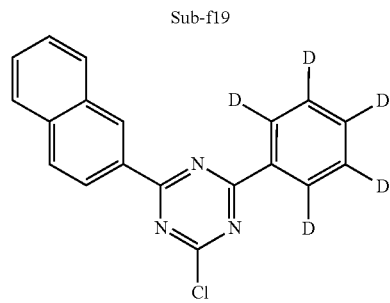 Sub-f20 | 58 |
| Sub-f21 | 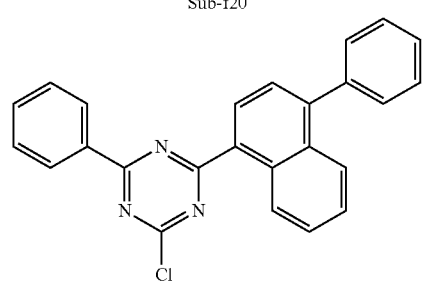 Sub-f21 | 56 |
| Sub-f22 | 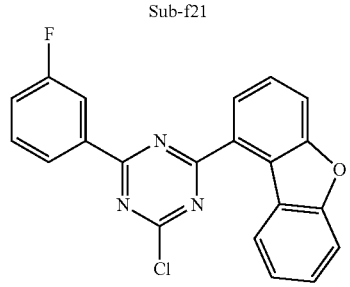 Sub-f22 | 57 |
| Sub-f23 | 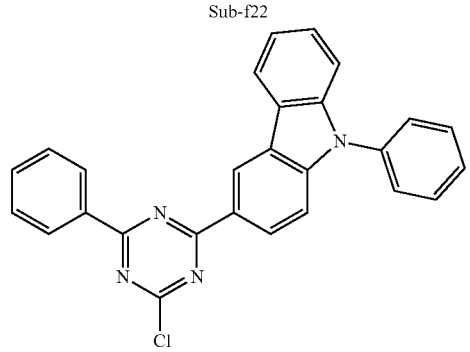 Sub-f23 | 64 |

TABLE 6-continued
Synthesis of Sub-f2 to Sub-f35
| Sub-f24 | 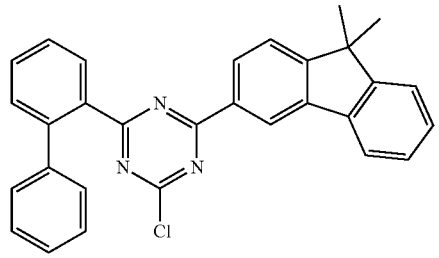 [SMILES: CC1(C)c2ccccc2-c2cc(-c3nc(Cl)nc(-c4ccccc4-c4ccccc4)n3)ccc21] | 60 |
| --- | --- | --- |
| | Sub-f24 | |
| Sub-f25 | 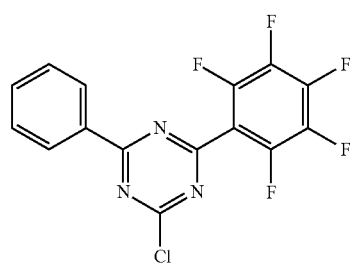 [SMILES: Fc1c(F)c(F)c(-c2nc(Cl)nc(-c3ccccc3)n2)c(F)c1F] | 63 |
| | Sub-f25 | |
| Sub-f26 | 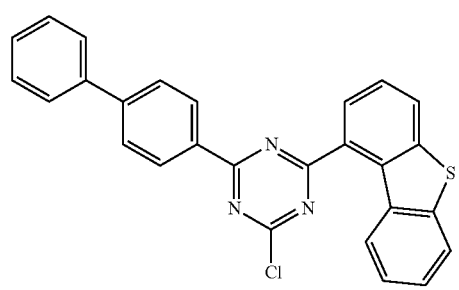 [SMILES: Clc1nc(-c2ccc(-c3ccccc3)cc2)nc(-c2cccc3sc4ccccc4c23)n1] | 64 |
| | Sub-f26 | |
| Sub-f27 | 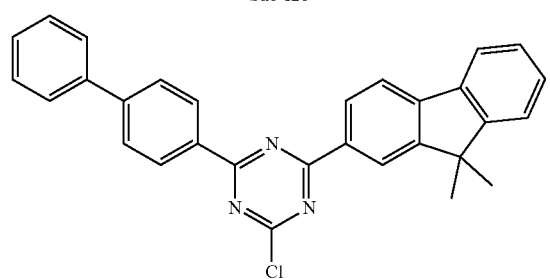 | 62 |
| | Sub-f27 | |
| Sub-f28 | 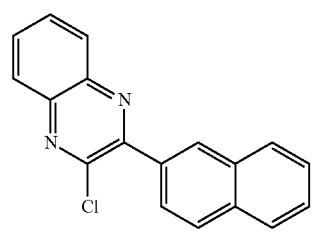 [SMILES: Clc1nc2ccccc2nc1-c1ccc2ccccc2c1] | 61 |
| | Sub-f28 | |

TABLE 6-continued

Synthesis of Sub-f2 to Sub-f35

| | | |
|---|---|---|
| Sub-f29 | Sub-f29 | 55 |
| Sub-f30 | Sub-f30 | 65 |
| Sub-f31 | Sub-f31 | 65 |
| Sub-f32 | Sub-f32 | 60 |
| Sub-f33 | Sub-f33 | 58 |
| Sub-f34 | Sub-f34 | 64 |

TABLE 6-continued

Synthesis of Sub-f2 to Sub-f35

Sub-f35

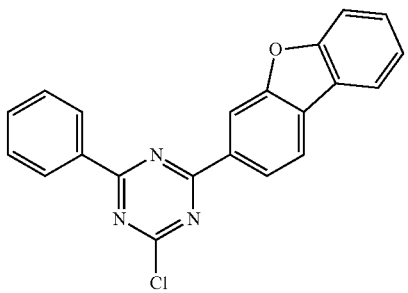 [SMILES: Clc1nc(-c2ccccc2)nc(-c2ccc3c(c2)oc2ccccc23)n1]

Sub-f35

Synthesis of a compound 3

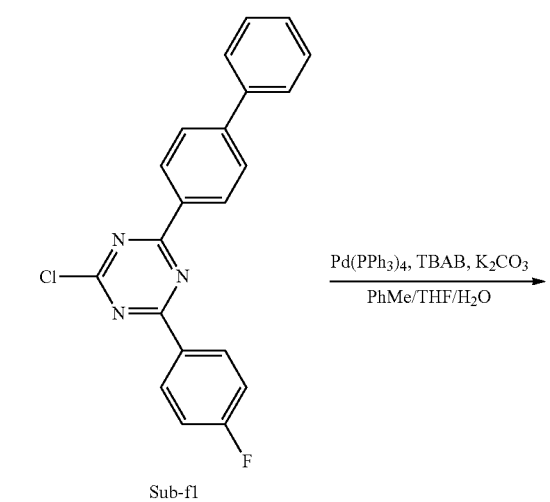

Sub-d1

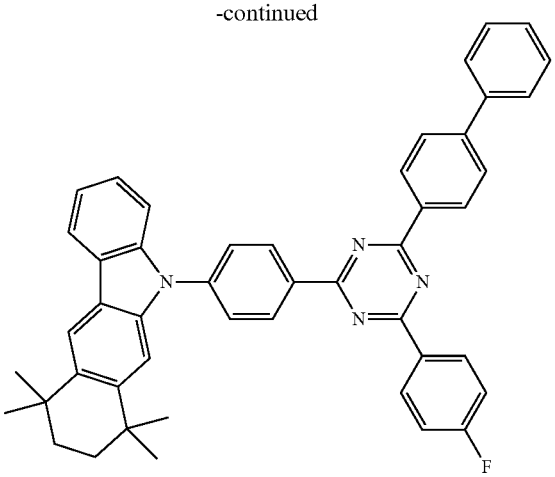

3

Sub-d1 (10.54 g, 22 mmol), Sub-f1 (7.24 g, 20 mmol), tetrakis(triphenylphosphine)palladium (0.23 g, 0.2 mmol), tetrabutyl ammonium bromide (0.64 g, 5 mmol), anhydrous potassium carbonate (5.53 g, 40 mmol), toluene (100 mL), tetrahydrofuran (25 mL), and deionized water (25 mL) were added sequentially to a 250 mL three-necked flask under a nitrogen atmosphere. The reaction mixture was heated to reflux and stirred for 16 h. After the mixture was cooled to room temperature, the reaction solution was extracted with dichloromethane (100 mL×3), an organic phase was dried over anhydrous magnesium sulfate, filtered and distilled in vacuum to remove a solvent to obtain a crude product. The crude product was recrystallized with toluene to obtain the compound 3 (11.81 g, yield: 87%) as a white solid. Mass spectrum: m/z=679.3 [M+H]$^+$ Referring to the synthesis of the compound 3, the following compounds of the present disclosure were synthesized by using a reactant J shown in Table 7 instead of Sub-d1 and a reactant K shown in Table 7 instead of Sub-f1:

TABLE 7

Synthesis of compounds

| Compound | Reactant J | Reactant K |
|---|---|---|
| 8 | Sub-e1 | Sub-f2 |
| 21 | Sub-e1 | Sub-f3 |

TABLE 7-continued
Synthesis of compounds
| 28 | 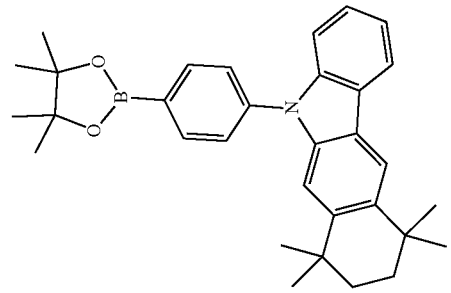 Sub-e1 | 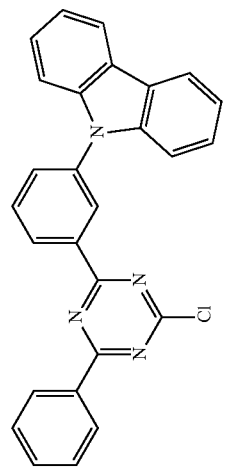 Sub-f4 |
| --- | --- | --- |
| 35 | 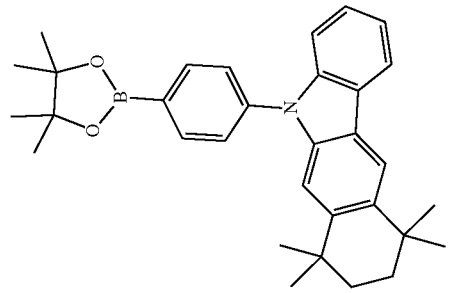 Sub-e1 | 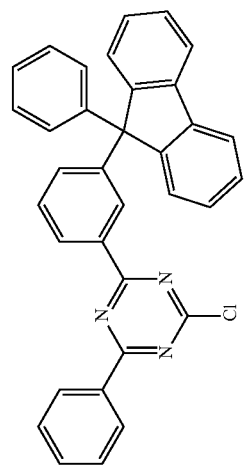 Sub-f5 |

TABLE 7-continued
Synthesis of compounds
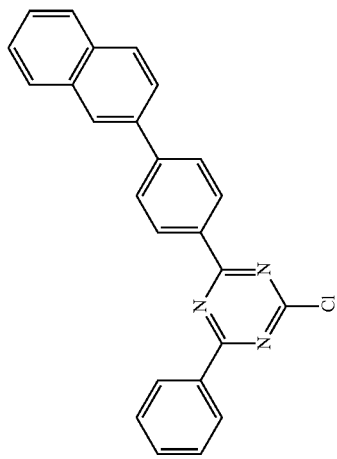
Sub-e2
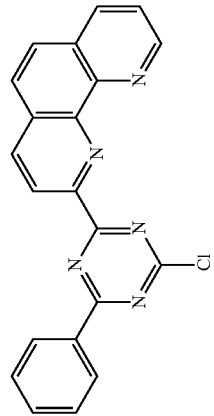
Sub-f6
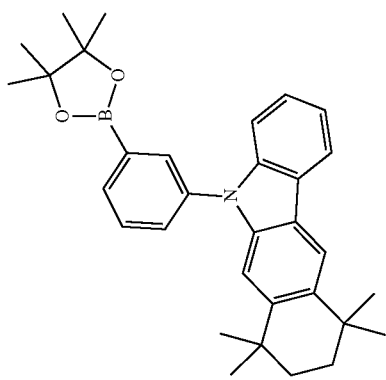
Sub-e2
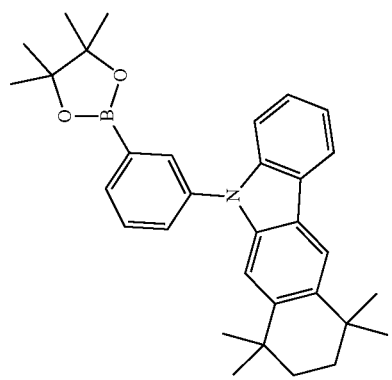
Sub-f7

TABLE 7-continued
Synthesis of compounds
| 67 | 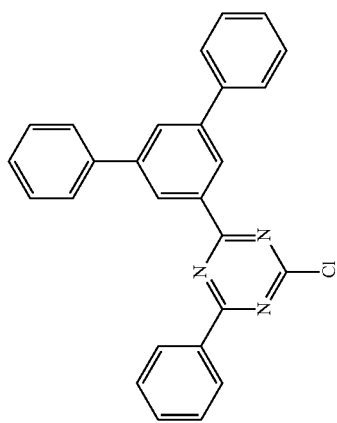 Sub-e2 | 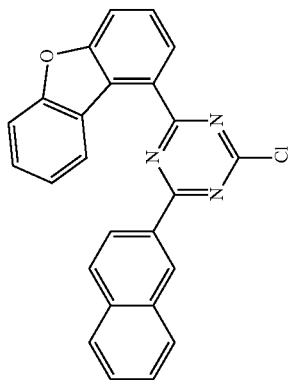 Sub-e1 |
| 85 | 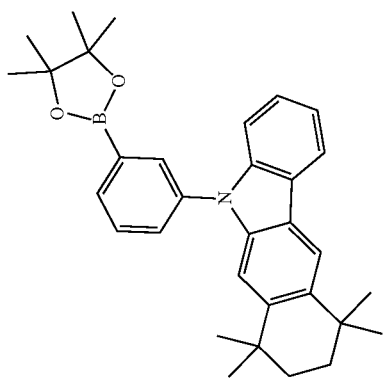 Sub-f8 | 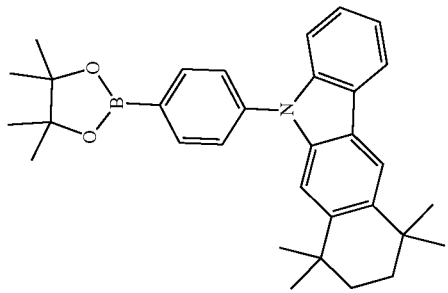 Sub-f9 |

TABLE 7-continued
Synthesis of compounds
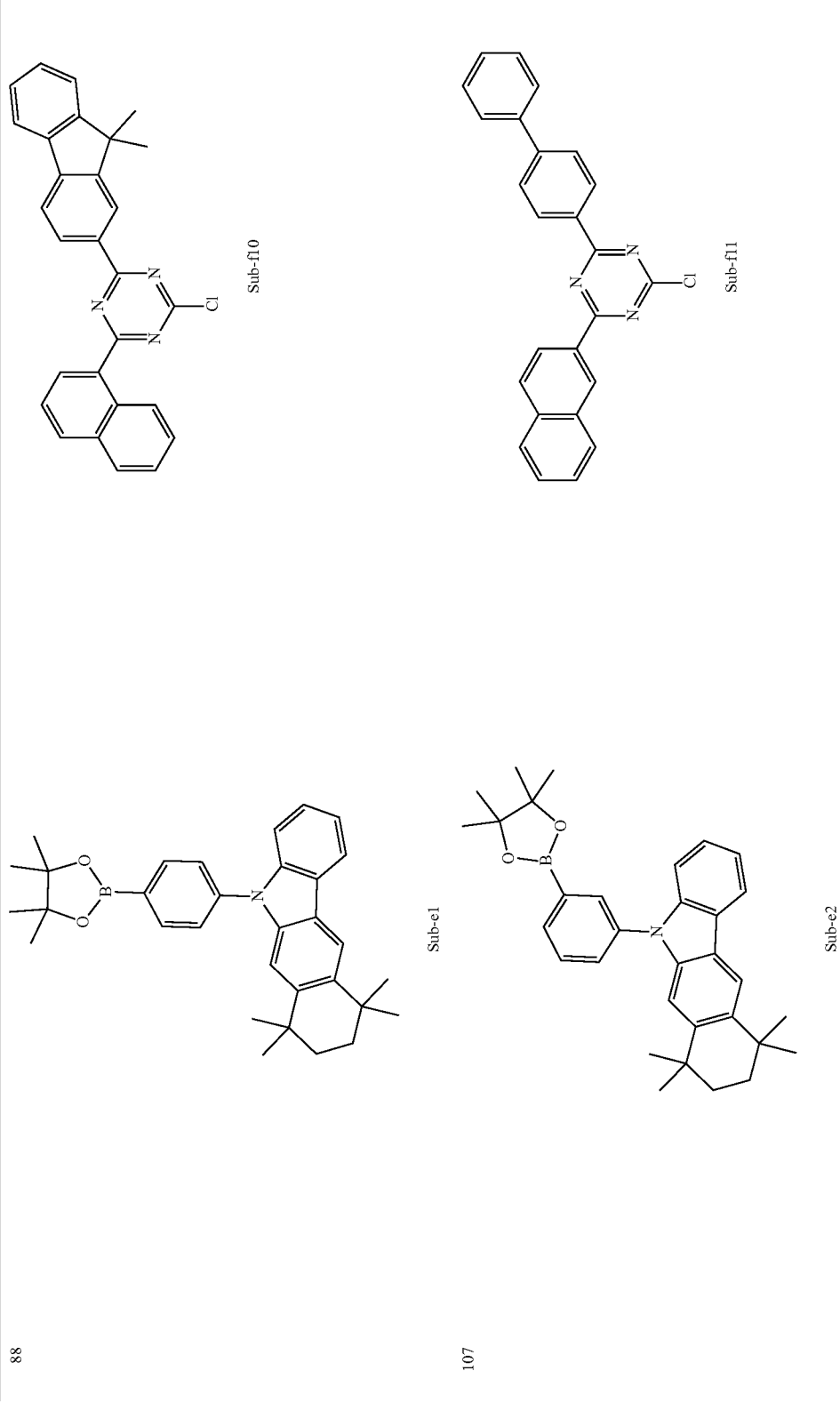

TABLE 7-continued
Synthesis of compounds
| 119 | 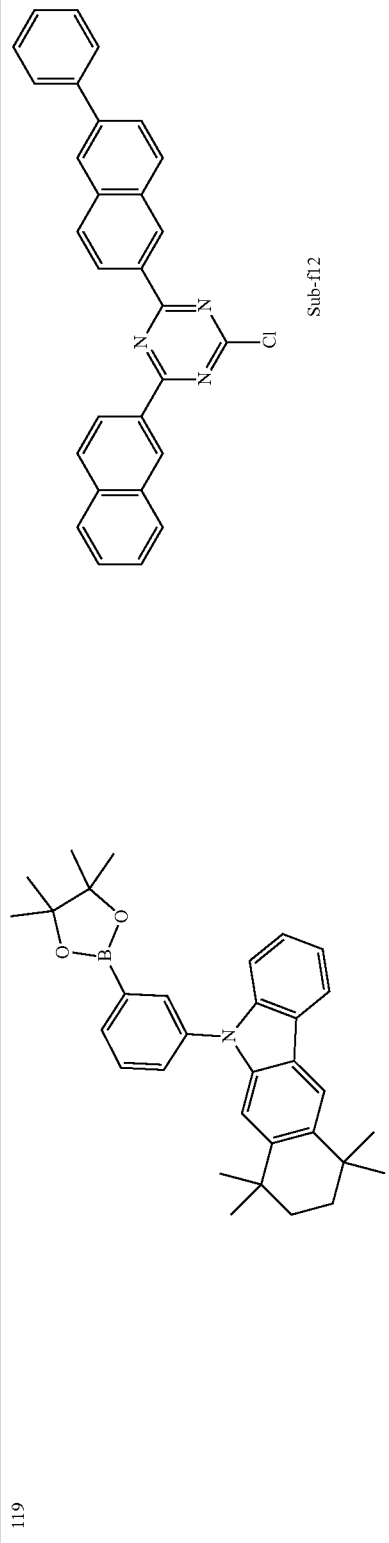 Sub-e2 | 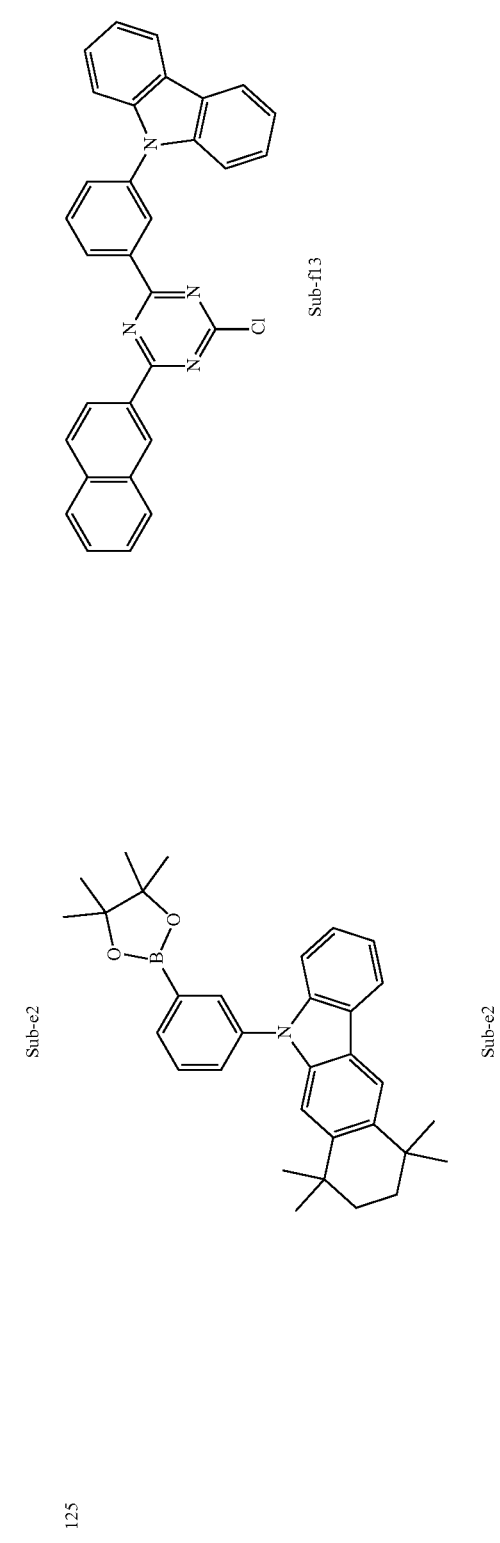 Sub-f12 |
| --- | --- | --- |
| 125 | Sub-e2 | Sub-f13 |

TABLE 7-continued
Synthesis of compounds
| 143 | 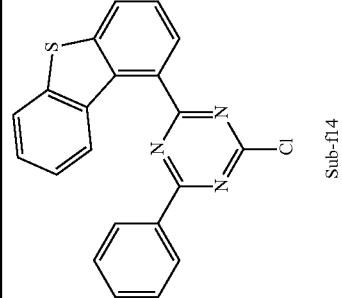 Sub-e3 | 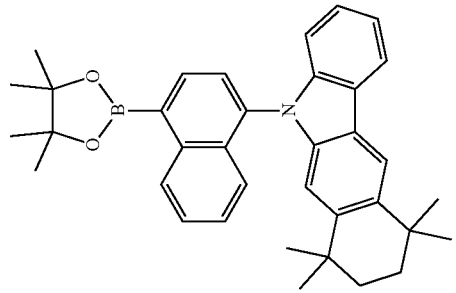 Sub-f14 |
| --- | --- | --- |
| 192 | 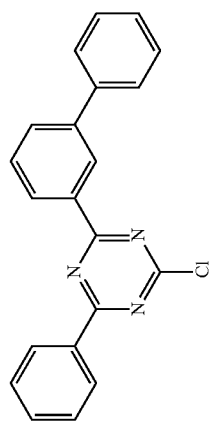 Sub-e4 | 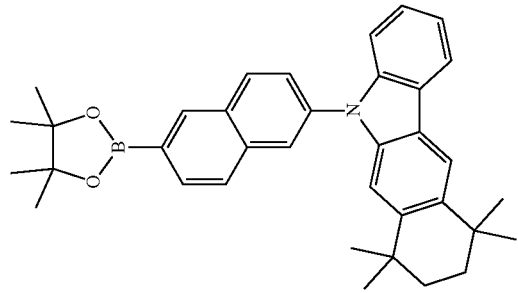 Sub-f15 |

TABLE 7-continued
Synthesis of compounds
| 224 | 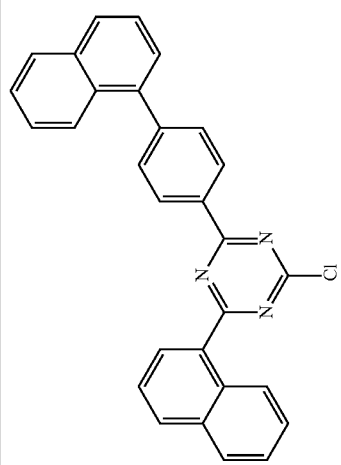 Sub-f16 | 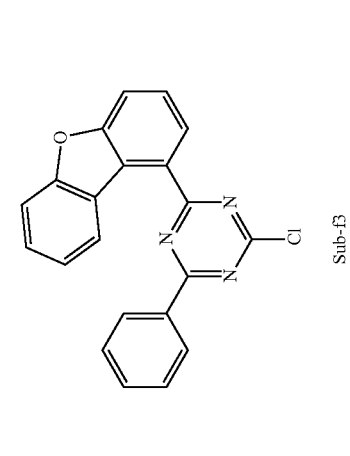 Sub-f3 |
| 241 | 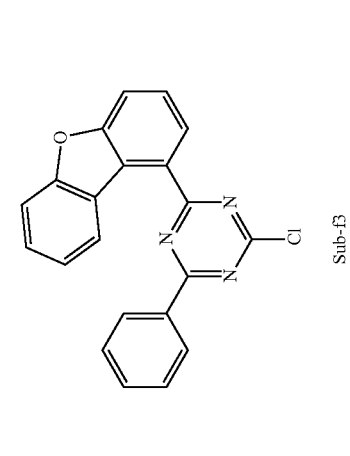 Sub-e4 | Sub-e5 |

TABLE 7-continued
Synthesis of compounds
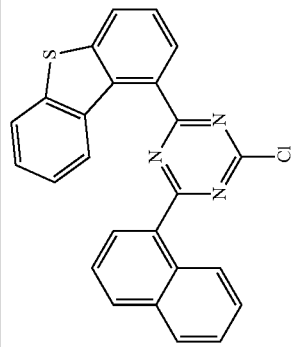
Sub-f17
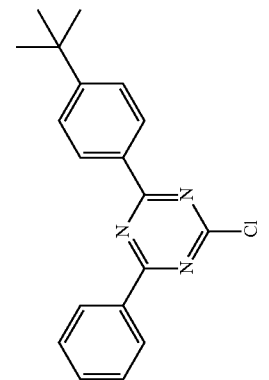
Sub-f18
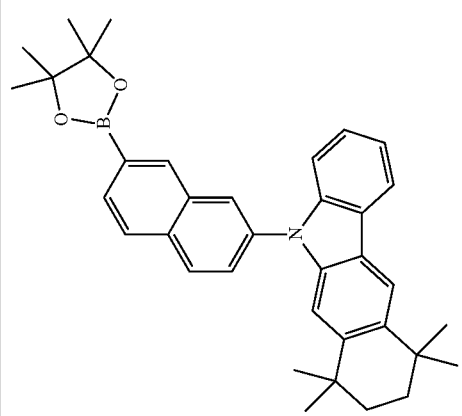
Sub-e5
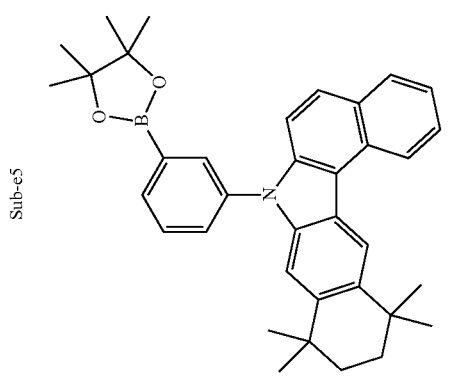
Sub-e6

TABLE 7-continued
Synthesis of compounds
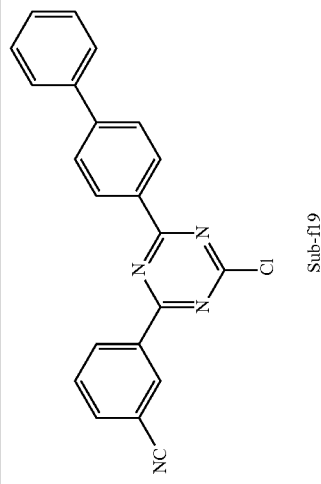
Sub-f19
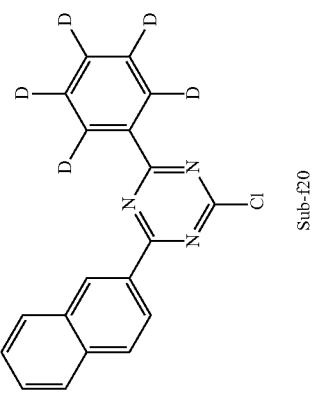
Sub-f20
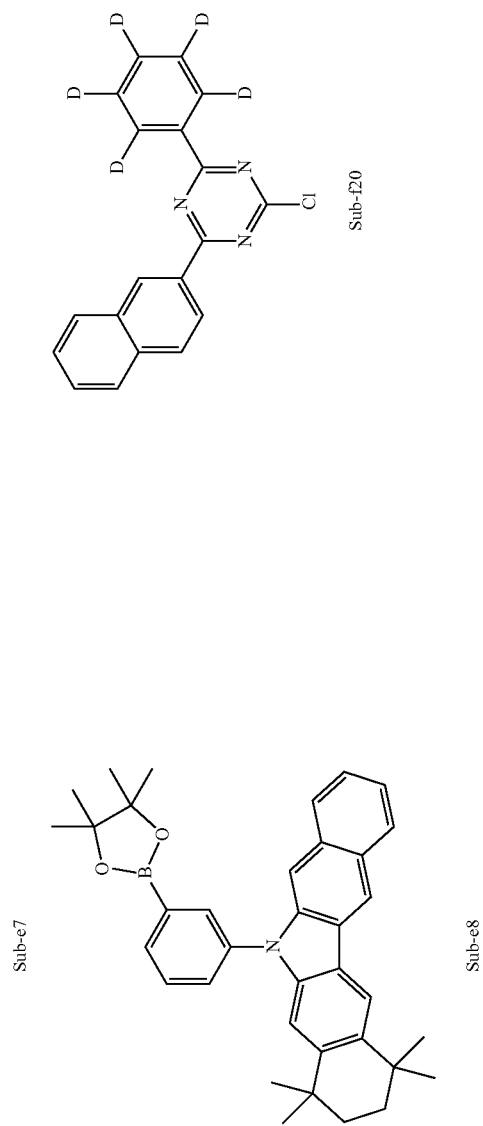
Sub-e7
Sub-e8
285
319

TABLE 7-continued
Synthesis of compounds
| 331 | 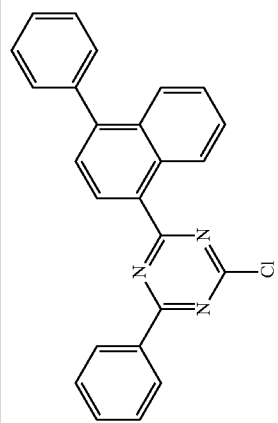 Sub-f21 | 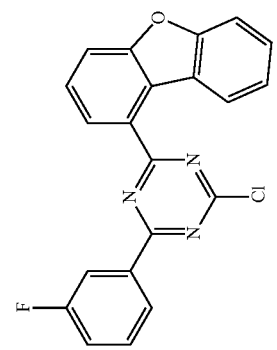 Sub-f22 |
| 359 | 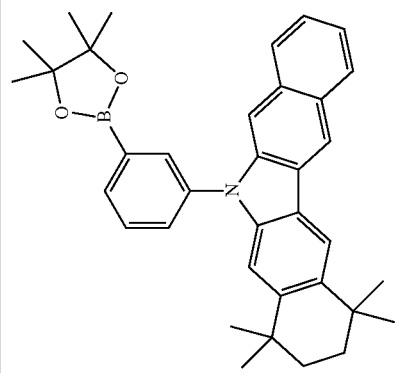 Sub-e8 | 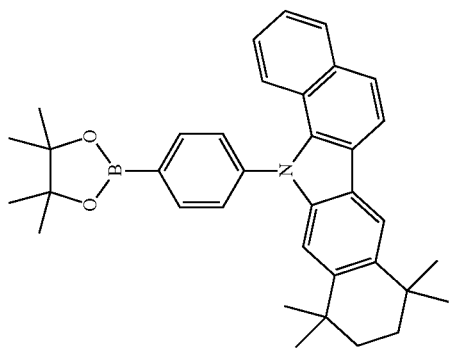 Sub-e9 |

TABLE 7-continued
Synthesis of compounds
| 372 | 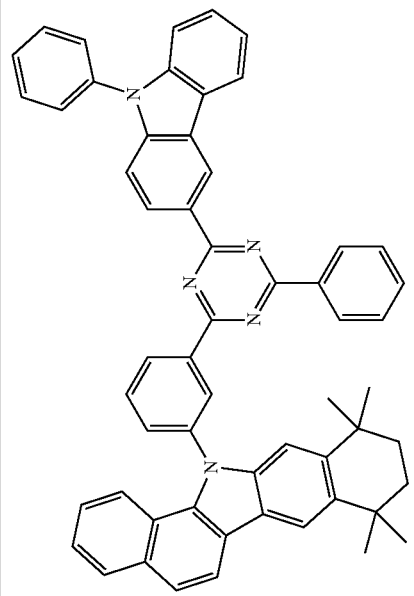 Sub-f22 | 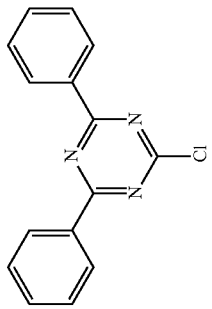 CAS: 3842-55-5 |
| --- | --- | --- |
| 386 | 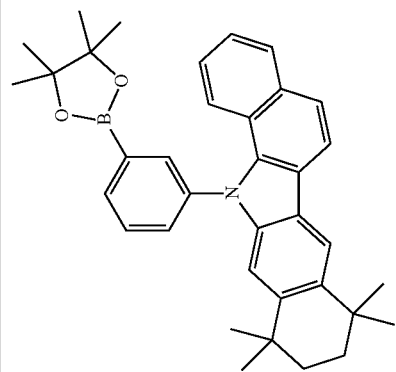 Sub-e10 | 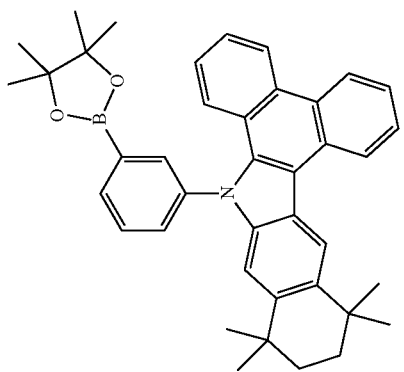 Sub-e11 |

TABLE 7-continued
Synthesis of compounds
| | |
|---|---|
| 408 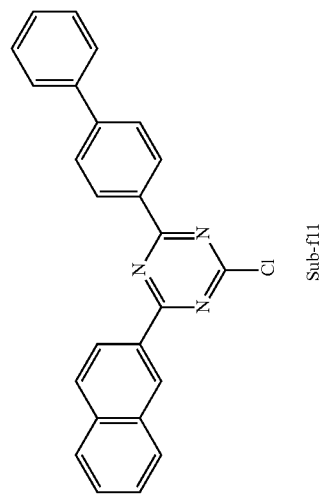 Sub-e6 | 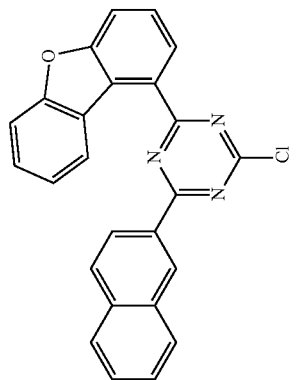 Sub-f11 |
| 413 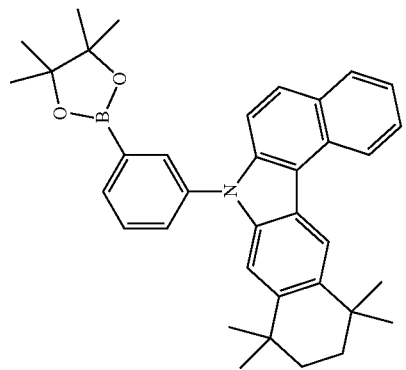 Sub-e9 | 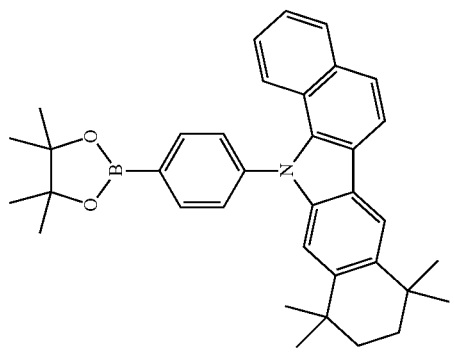 Sub-f9 |

TABLE 7-continued
Synthesis of compounds
| 442 | 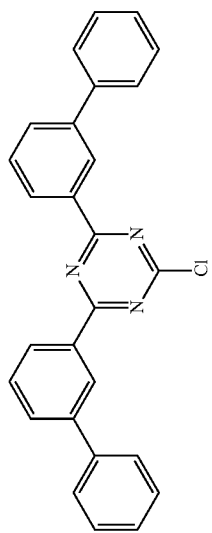 Sub-e8 | 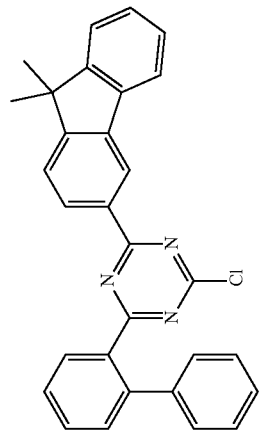 CAS: 1205748-61-3 |
| --- | --- | --- |
| 452 | 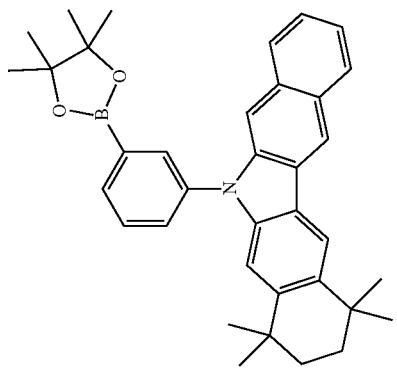 Sub-e8 | 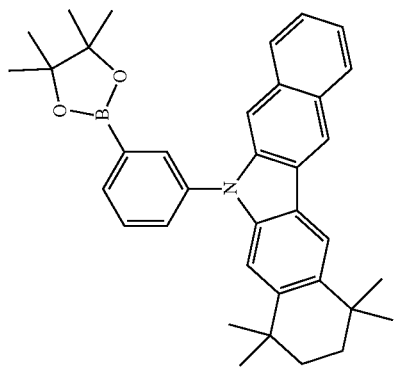 Sub-f24 |

TABLE 7-continued
Synthesis of compounds
| 487 | 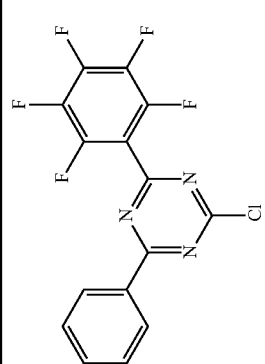 Sub-e12 | 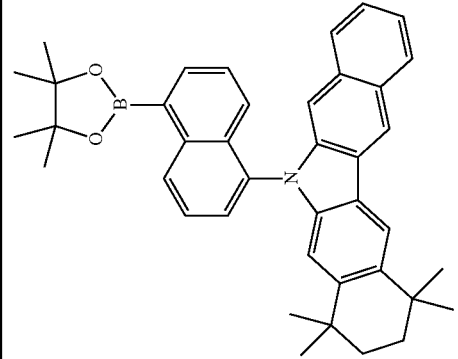 Sub-f25 |
| --- | --- | --- |
| 496 | 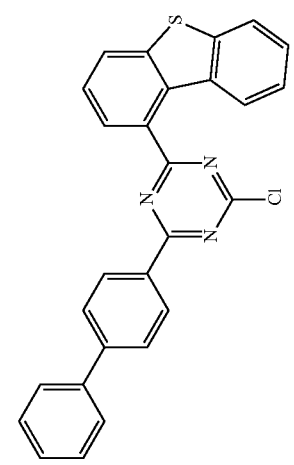 Sub-e13 | 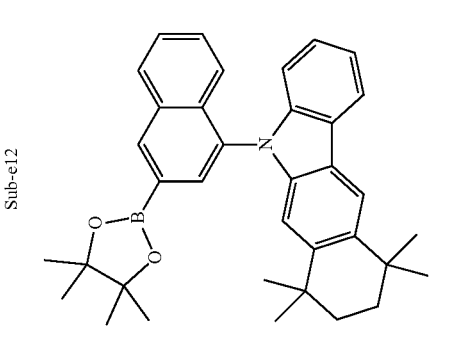 Sub-f26 |

TABLE 7-continued
Synthesis of compounds
| 512 | 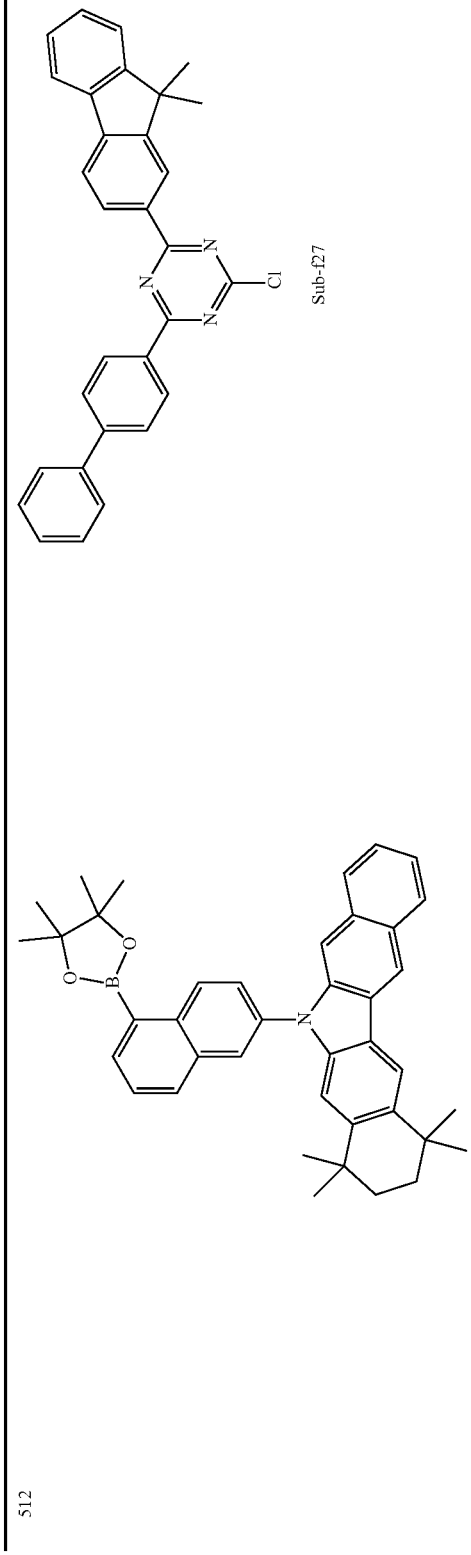 Sub-e14 | 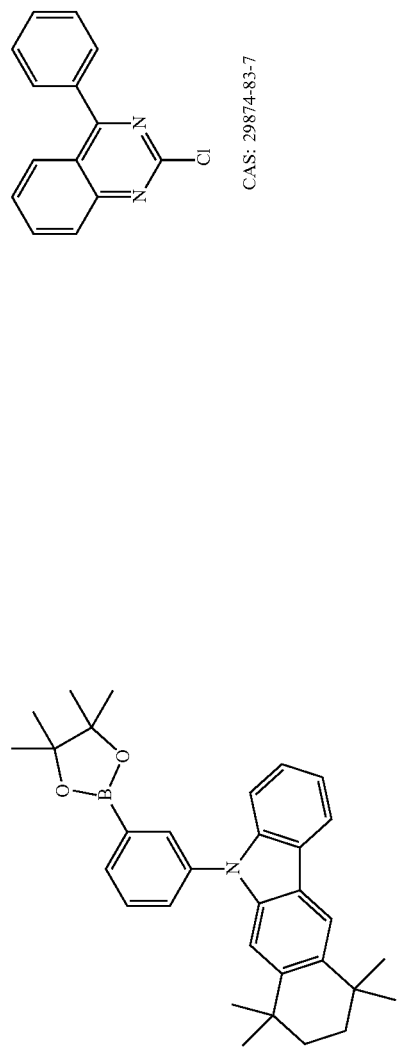 Sub-f27 |
| 517 | Sub-e2 | CAS: 2974-83-7 |

TABLE 7-continued
Synthesis of compounds
| 518 | 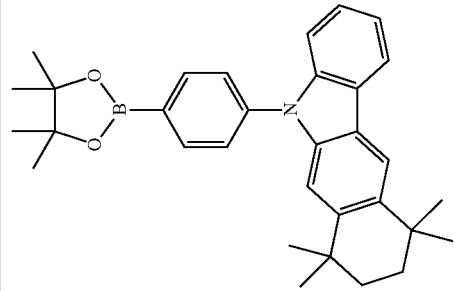 Sub-e1 | 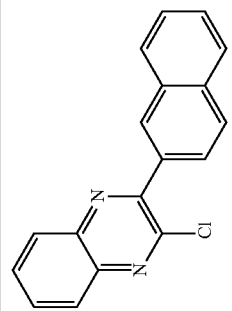 Sub-f28 |
| --- | --- | --- |
| 529 | 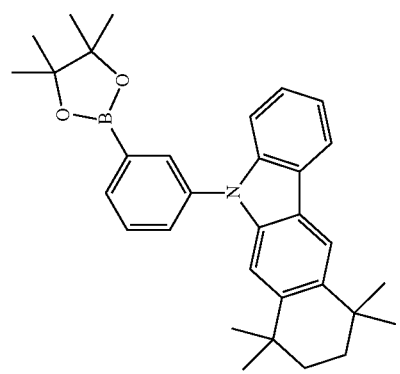 Sub-e2 | 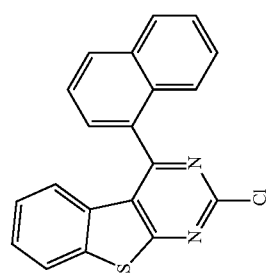 Sub-f29 |

TABLE 7-continued
Synthesis of compounds
| 530 | 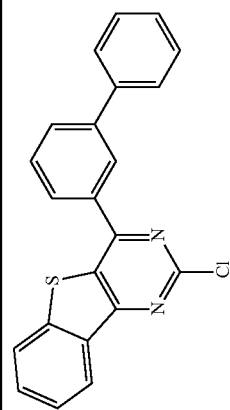 Sub-e1 | 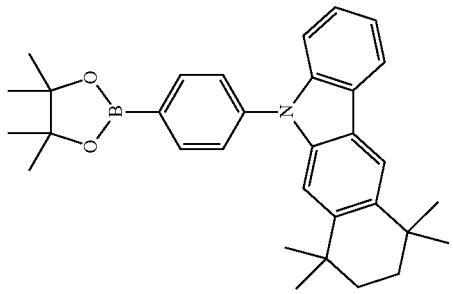 Sub-f30 |
| 539 | 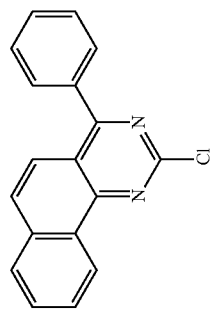 Sub-e1 | 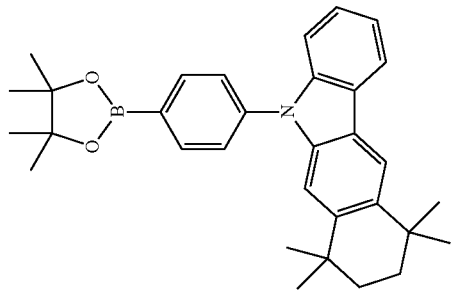 Sub-f31 |

TABLE 7-continued
Synthesis of compounds
| 555 | 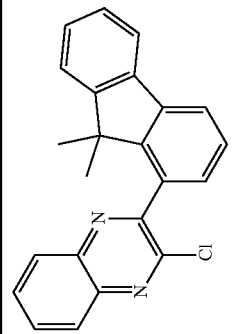 Sub-f32 | 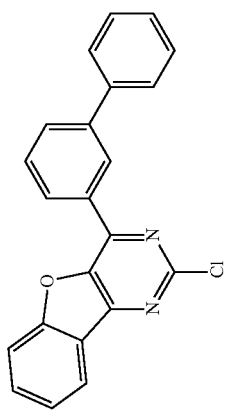 Sub-f33 |
|---|---|---|
| 567 | 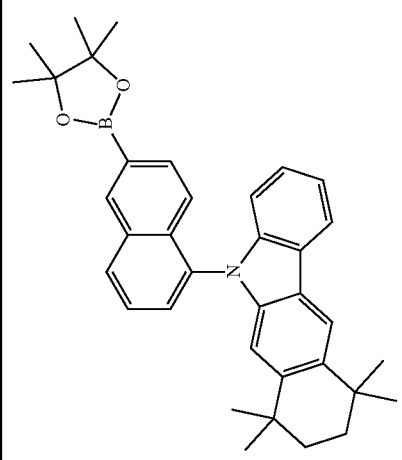 Sub-e15 | 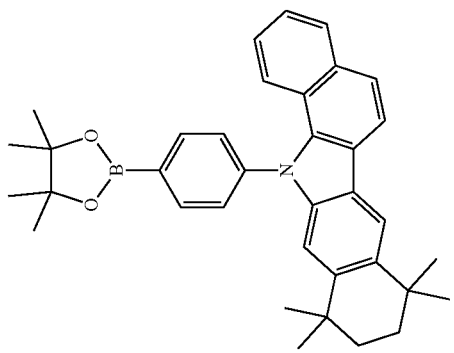 Sub-e9 |

TABLE 7-continued
Synthesis of compounds
| 571 | 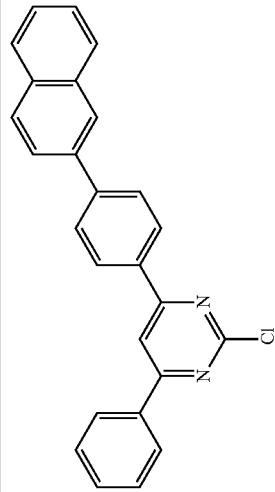 Sub-e9 | 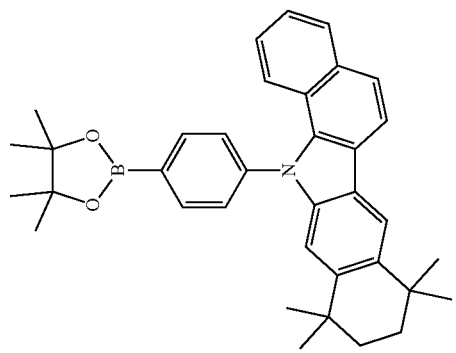 Sub-f34 |
| --- | --- | --- |
| 588 | 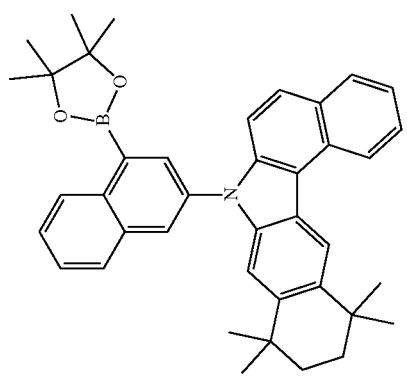 Sub-e16 | 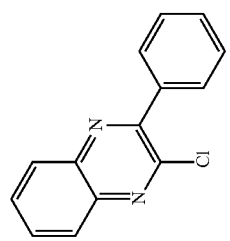 CAS: 7065-92-1 |

TABLE 7-continued
Synthesis of compounds
| | | |
|---|---|---|
| 589 | 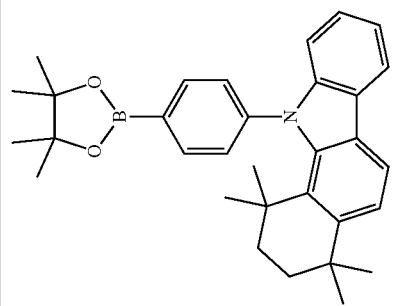 Sub-e17 | 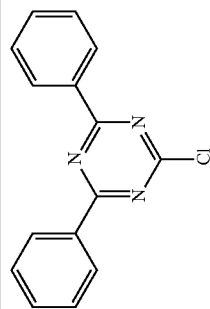 CAS: 3842-55-5 |
| 602 | 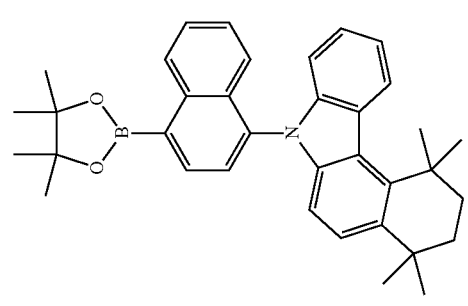 Sub-e18 | 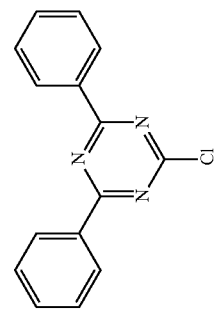 CAS: 3842-55-5 |

TABLE 7-continued
Synthesis of compounds
| | |
|---|---|
| 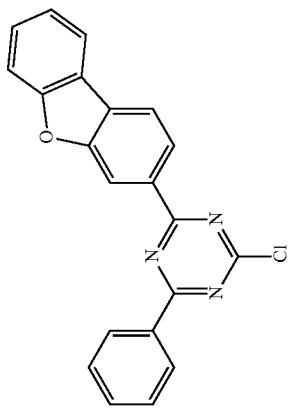 Sub-f35 | 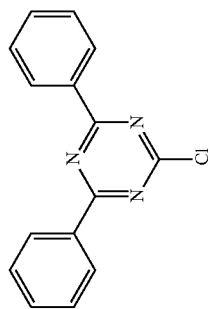 CAS: 3842-55-5 |
| 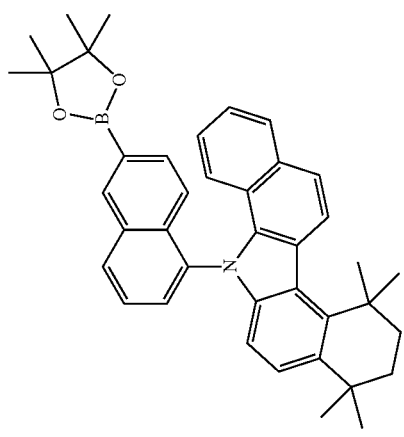 Sub-e19 | 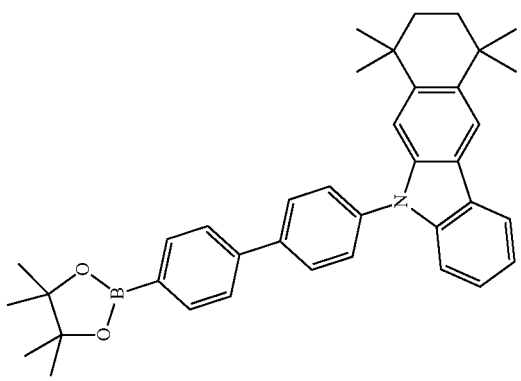 Sub-e20 |
| 620 | 637 |

TABLE 7-continued
Synthesis of compounds
| 645 | 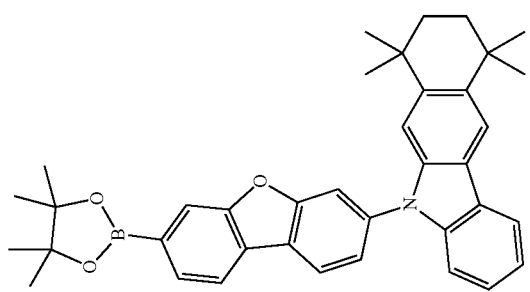 Sub-e21 | 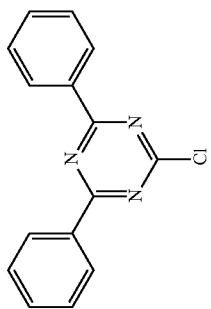 CAS: 3842-55-5 |
| --- | --- | --- |
| 651 | 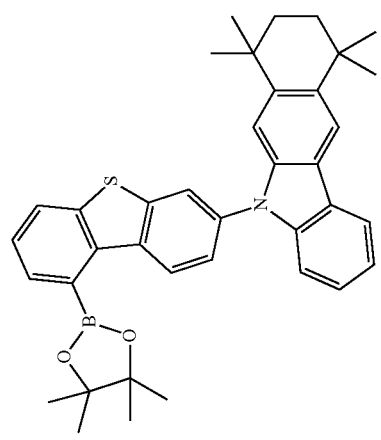 Sub-e22 | 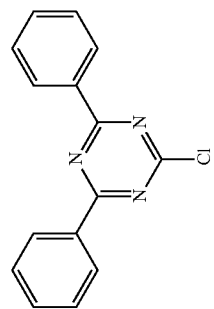 CAS: 3842-55-5 |

TABLE 7-continued
Synthesis of compounds
| Compound | Compound structure and No. | m/z [M + H]+ | Yield (%) |
|---|---|---|---|
| 8 | 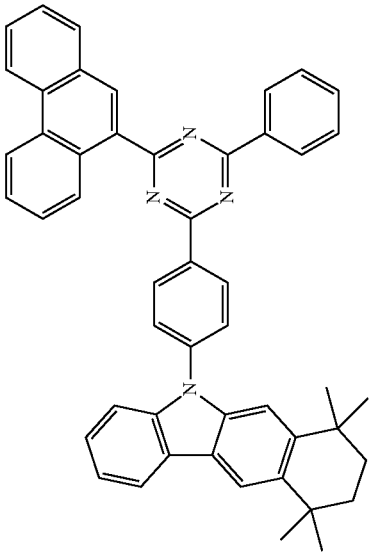 8 | 685.3 | 79 |
| 21 | 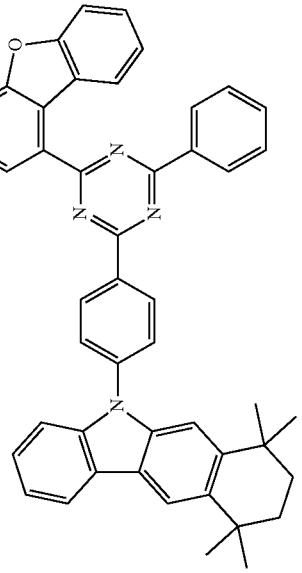 21 | 675.3 | 75 |

TABLE 7-continued
Synthesis of compounds
| 28 | 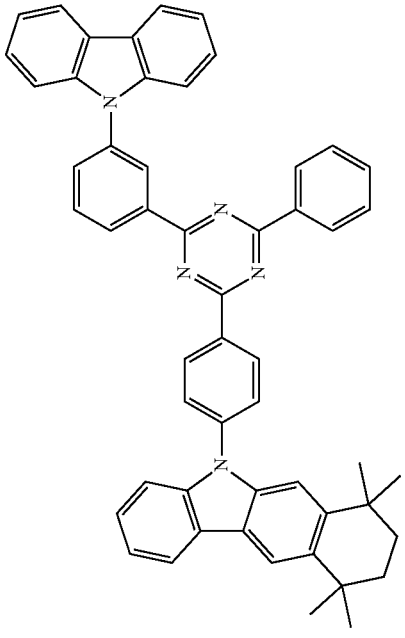 | 750.4 | 80 |
| 35 | 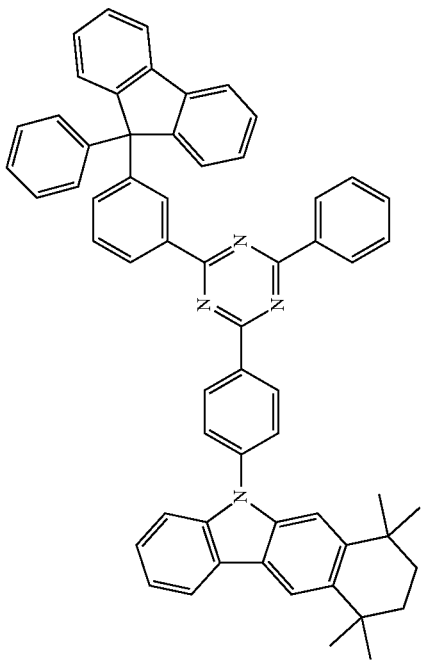 | 825.4 | 81 |

TABLE 7-continued
Synthesis of compounds
| | | |
|---|---|---|
| 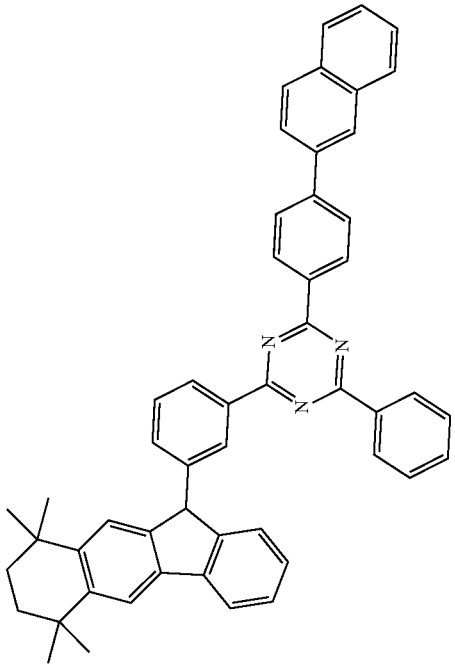 | 711.3 | 85 |
| 55 | | |
| 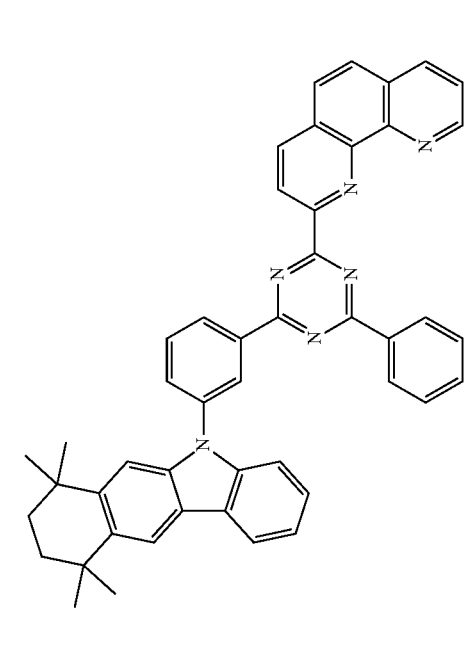 | 687.3 | 79 |
| 60 | | 60 |

TABLE 7-continued

Synthesis of compounds

| | | |
|---|---|---|
| 67 | [Structure] | 737.4 83 67 |
| 85 | [Structure] | 725.3 78 85 |

TABLE 7-continued
Synthesis of compounds
| | | |
|---|---|---|
| 88 | 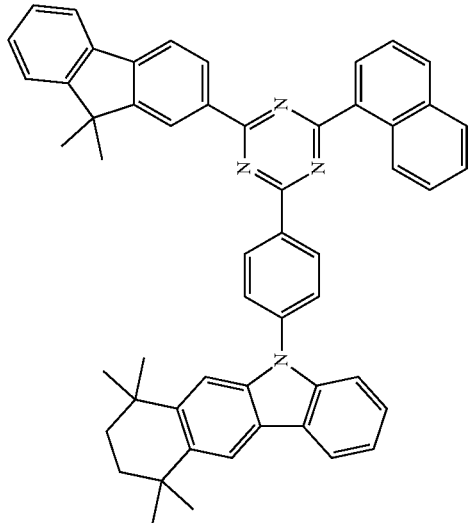 751.4 | 70 |
| 107 | 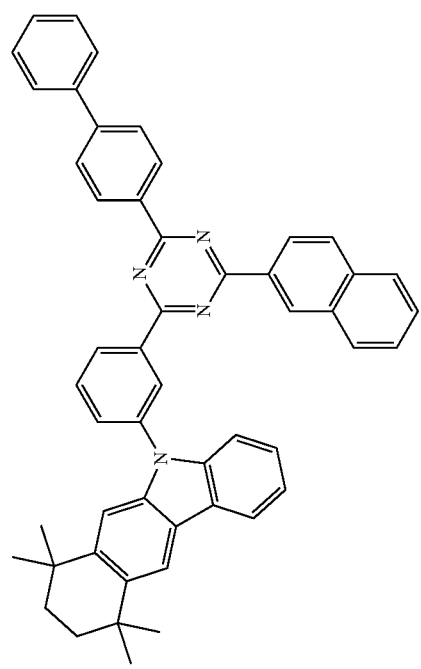 711.3 | 75 |

TABLE 7-continued

Synthesis of compounds

| 119 | | 761.4 | 83 |
| 125 | | 800.4 | 85 |

TABLE 7-continued

Synthesis of compounds

| | | | |
|---|---|---|---|
| 143 | (structure) | 741.3 | 78 |
| 192 | (structure) | 711.3 | 83 |

TABLE 7-continued
Synthesis of compounds
| 224 | 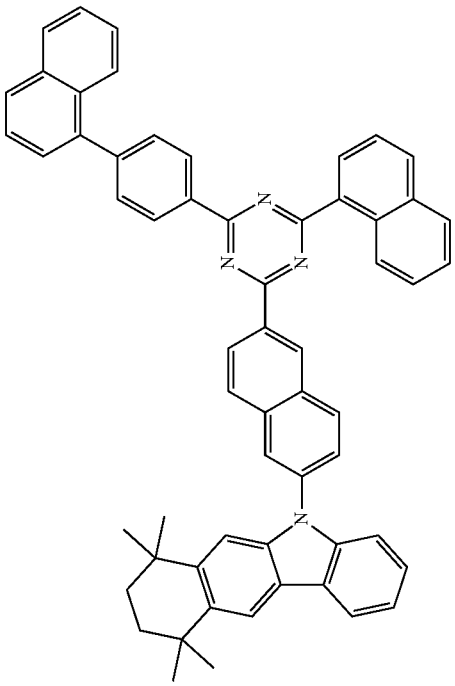 | 811.4 | 70 |
| 241 | 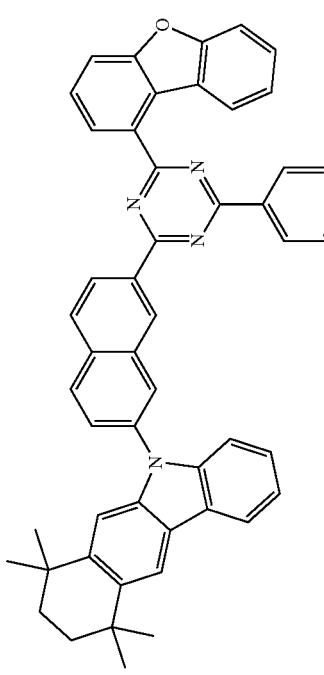 | 725.3 | 84 |

TABLE 7-continued
Synthesis of compounds
| 266 | 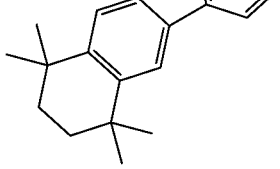 | 791.3 | 87 |
| 282 | 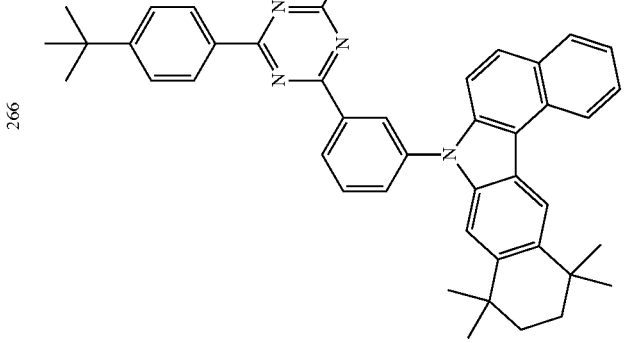 | 691.4 | 72 |

TABLE 7-continued
Synthesis of compounds
| 285 | 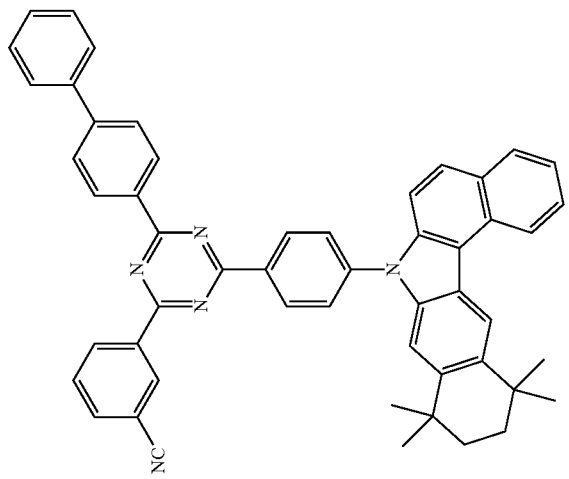 | 736.4 | 73 |

TABLE 7-continued
Synthesis of compounds
| 319 | 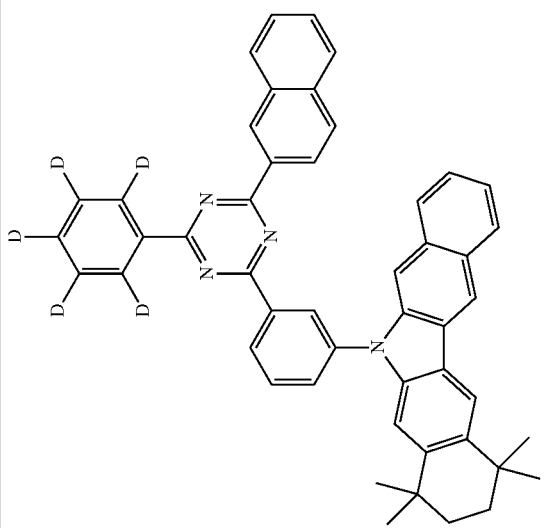 319 | 690.4 | 79 |

TABLE 7-continued
Synthesis of compounds
| | | |
|---|---|---|
| 331 | 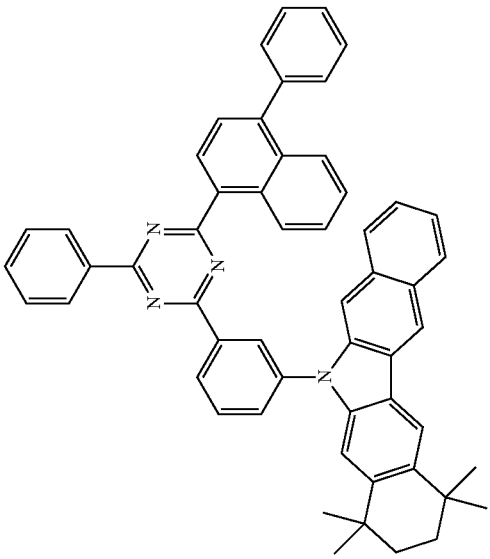 | 761.4 | 76 |
331

TABLE 7-continued
Synthesis of compounds
| | | |
|---|---|---|
| 359 | 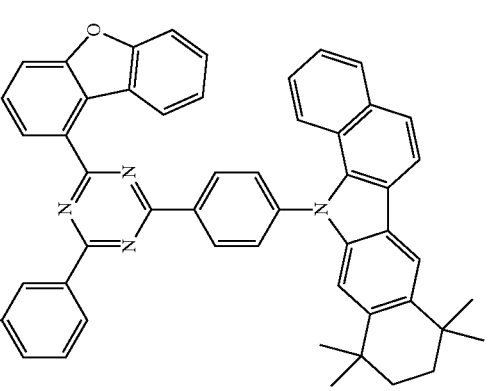 | 743.3 76 |
| 372 | 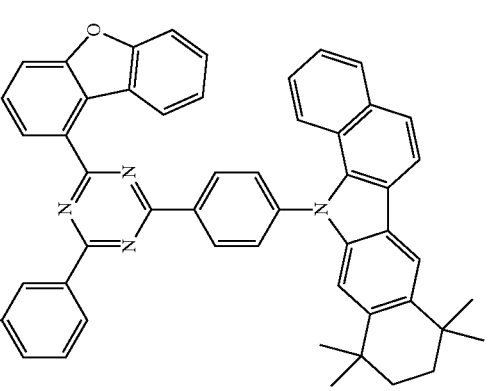 | 800.4 78 |

TABLE 7-continued
Synthesis of compounds
| | | |
|---|---|---|
| 386 | 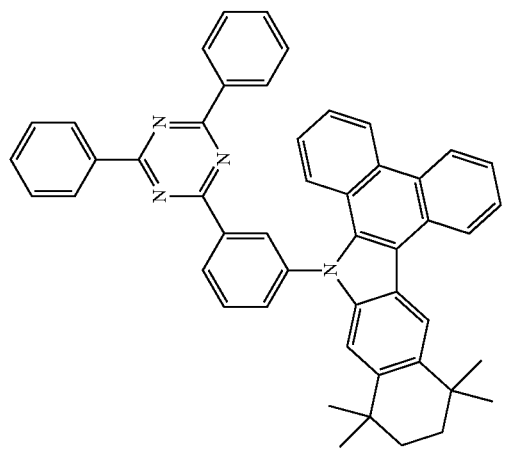 | 685.3 74 |
386

TABLE 7-continued
Synthesis of compounds
| 408 | 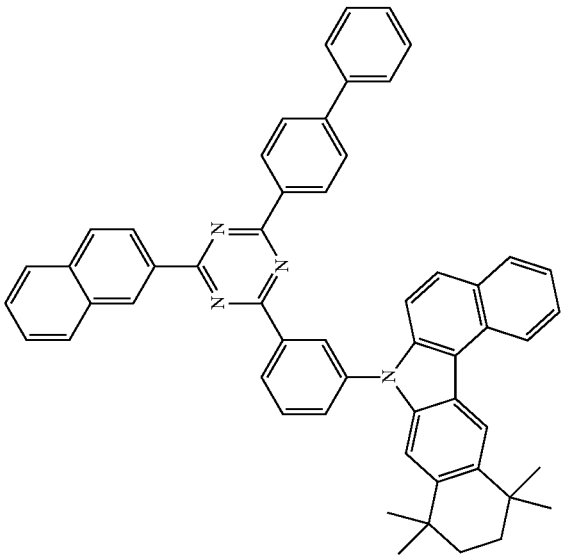 408 | 761.4 | 76 |

TABLE 7-continued

Synthesis of compounds

| 413 | | 775.4 | 74 |

TABLE 7-continued
Synthesis of compounds
| 442 | 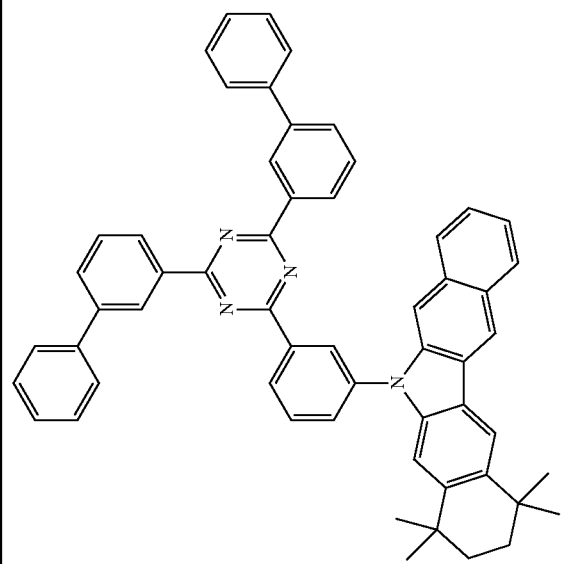 | 787.4 | 82 |

| Synthesis of compounds | | |
|---|---|---|
| 452 | 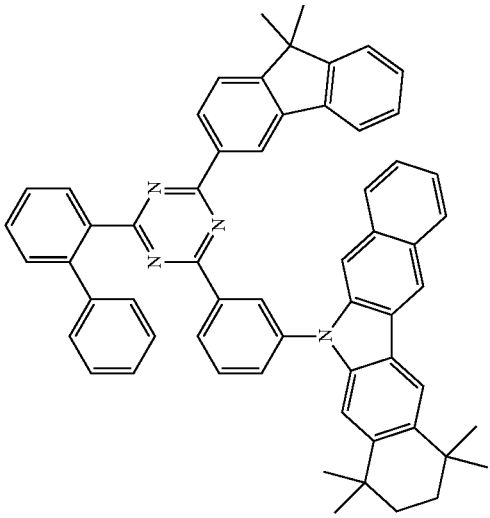 452 | 827.4 | 87 |

TABLE 7-continued
Synthesis of compounds
| 487 | 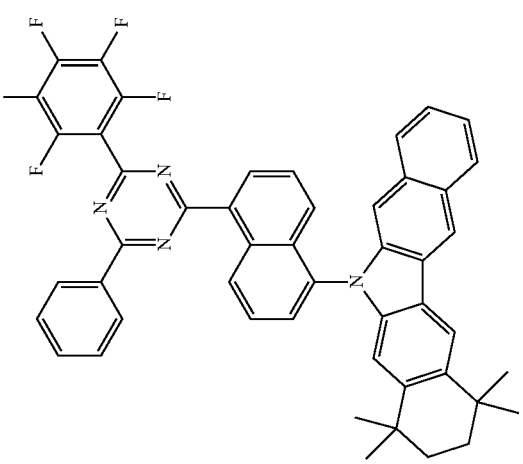 | 775.3 | 84 |
487

TABLE 7-continued
Synthesis of compounds
| | | |
|---|---|---|
| 496 | 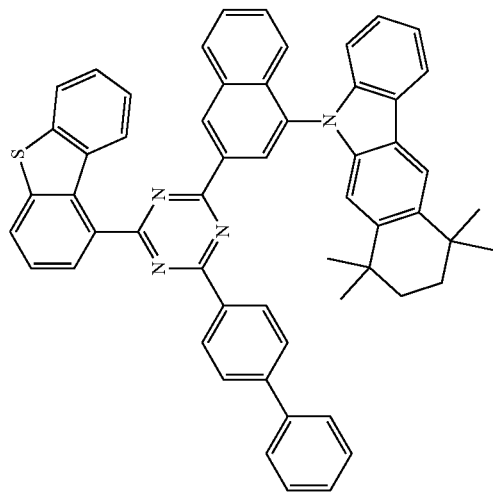<br>496 | 817.3 | 71 |

TABLE 7-continued
Synthesis of compounds
| | | |
|---|---|---|
| 512 | 877.4 | 74 |
| 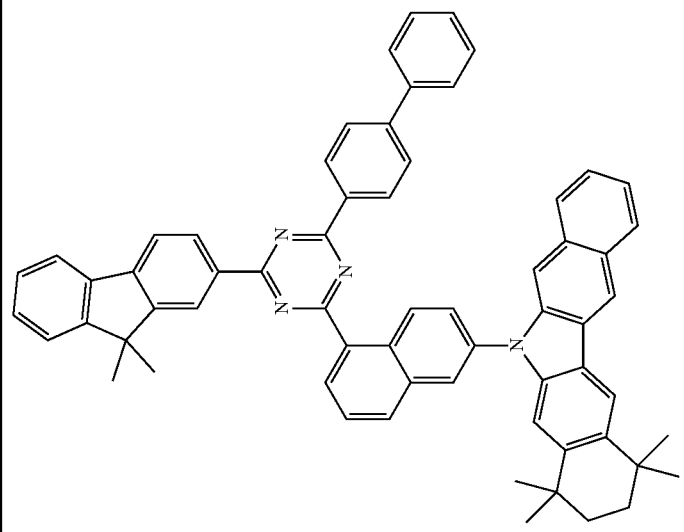 | | 512 |

TABLE 7-continued
Synthesis of compounds
| | | | |
|---|---|---|---|
| 517 | 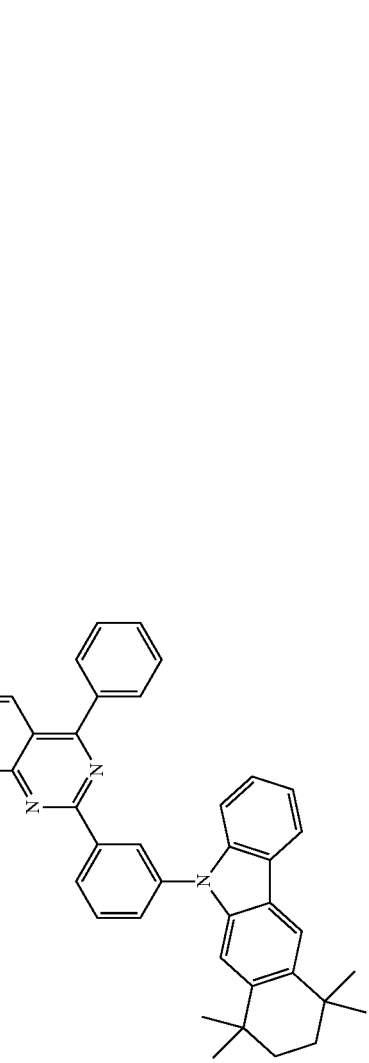 | 558.3 | 82 |
| 518 | 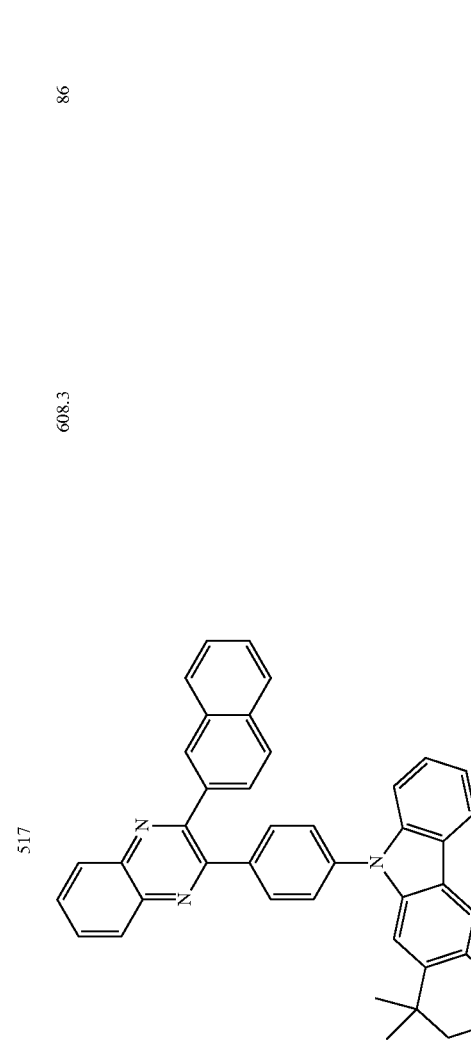 | 608.3 | 86 |

TABLE 7-continued
Synthesis of compounds
| | | |
|---|---|---|
| 529 | 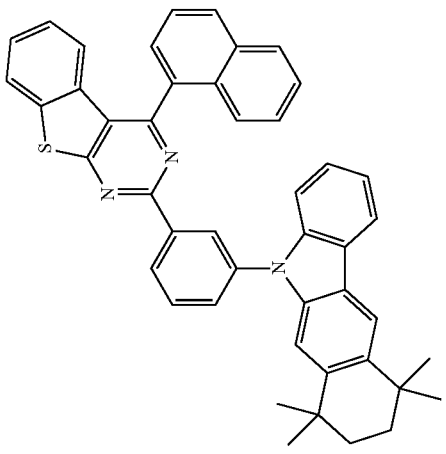 | 664.3 | 83 |
| 530 | 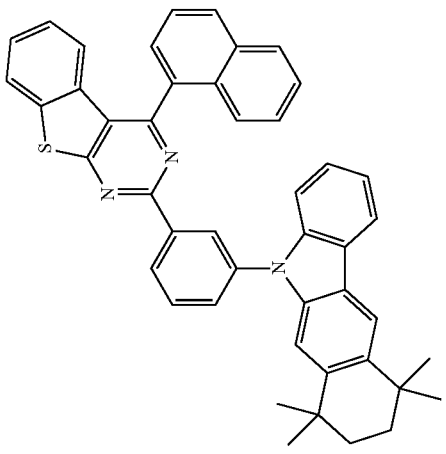 | 690.3 | 83 |

TABLE 7-continued
Synthesis of compounds
| | | |
|---|---|---|
| 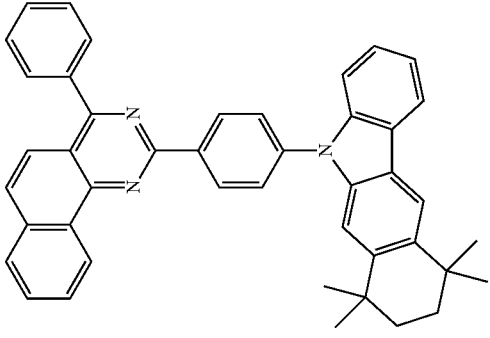 | 539 | 608.3 | 76 |
| 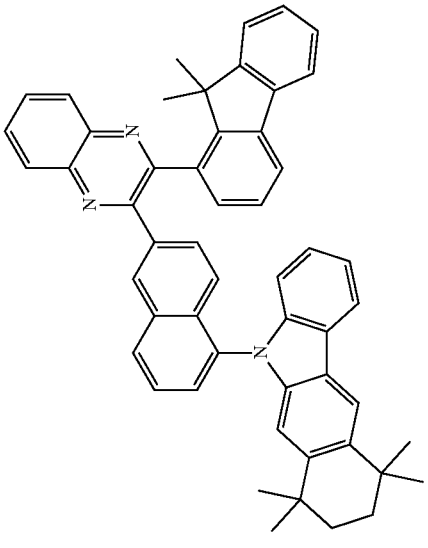 | 555 | 724.4 | 73 |

TABLE 7-continued
Synthesis of compounds
| 567 | 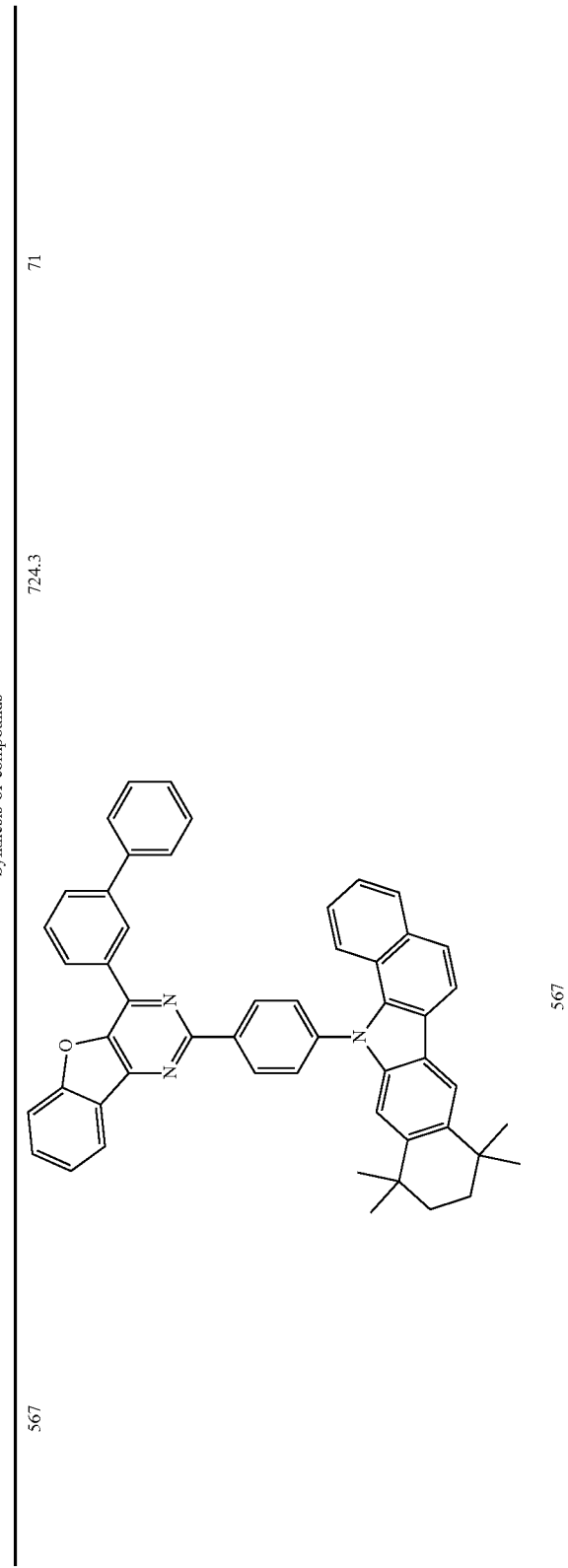 | 724.3 | 71 |
567

TABLE 7-continued
Synthesis of compounds
| | | |
|---|---|---|
| 571 | 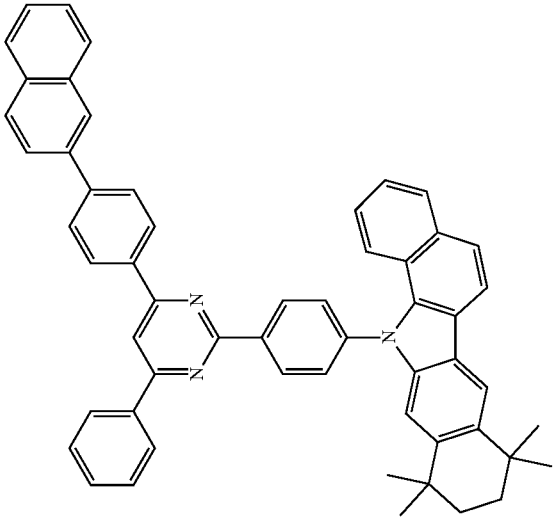 | 760.4 78 |
| 588 | 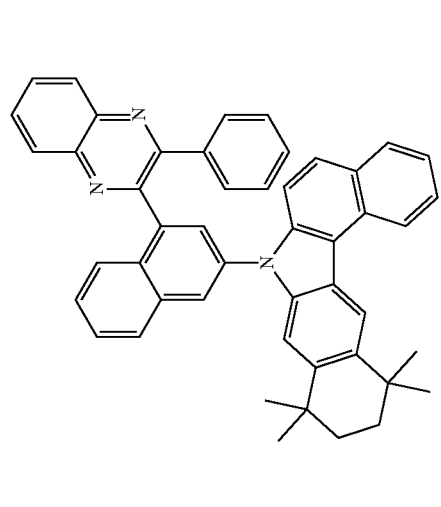 | 658.3 68 |

TABLE 7-continued
Synthesis of compounds
| | | |
|---|---|---|
| 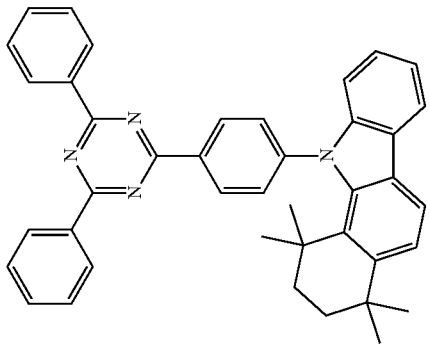 589 | 585.3 | 79 |
| 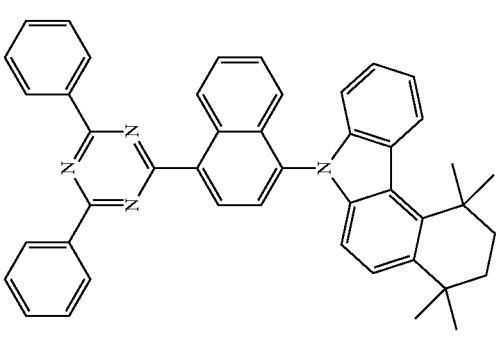 602 | 635.3 | 75 |

TABLE 7-continued
Synthesis of compounds
| | | | |
|---|---|---|---|
| 620 | 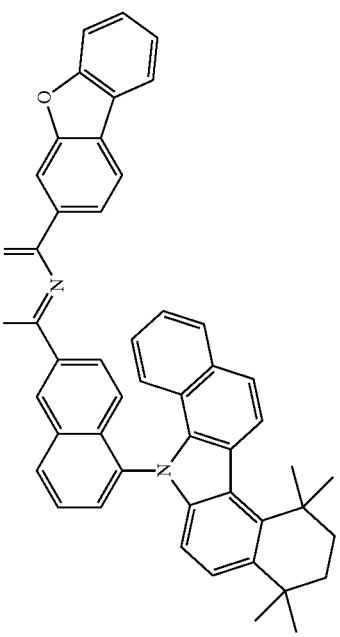 | 775.4 | 72 |
620

TABLE 7-continued
Synthesis of compounds
| 637 | 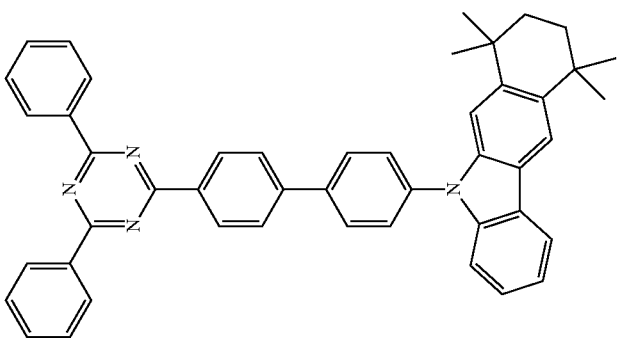 | 661.3 | 68 |
637

TABLE 7-continued
Synthesis of compounds
| | | | |
|---|---|---|---|
| 645 | 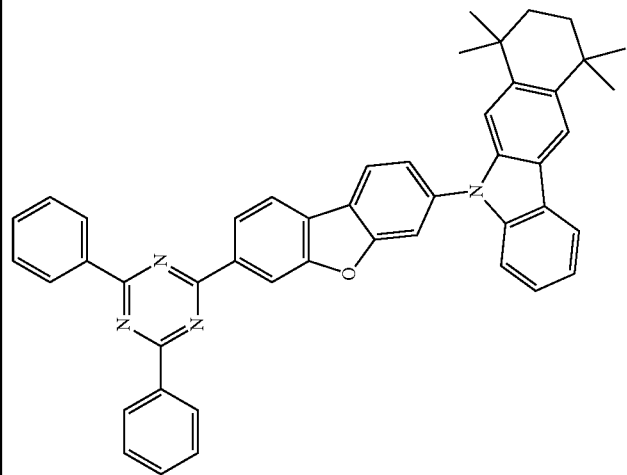 | 675.3 | 65 |
| | 645 | | |

TABLE 7-continued
Synthesis of compounds
| | | |
|---|---|---|
| 651 | 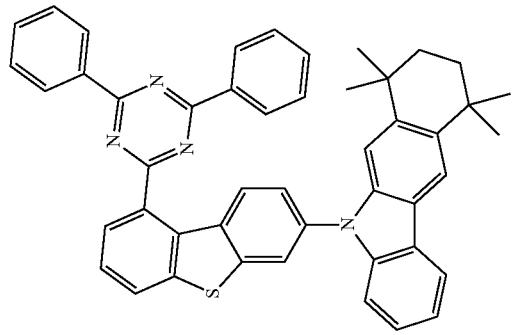 | 651 |
| | 691.3 | |
| | 63 | |

NMR for a compound 85: $^1$H-NMR (400 MHz, CD$_2$Cl$_2$) δ ppm: 8.84 (s, 1H), 8.56-8.46 (m, 3H), 8.35 (d, 1H), 8.26 (d, 1H), 8.16-8.06 (m, 2H), 8.03-7.96 (m, 2H), 7.83-7.76 (m, 3H), 7.74-7.59 (m, 5H), 7.56-7.45 (m, 3H), 7.38-7.32 (m, 2H), 7.26 (t, 1H), 1.74 (s, 4H), 1.34 (d, 12H).

NMR for a compound 408: $^1$H-NMR (400 MHz, CD$_2$Cl$_2$) δ ppm: 8.81 (s, 1H), 8.56-8.49 (m, 2H), 8.42 (d, 1H), 8.27 (d, 1H), 8.19 (d, 2H), 8.13 (d, 1H), 8.01, (d, 1H), 8.03-7.93 (m, 3H), 7.89-7.72 (m, 6H), 7.67-7.59 (m, 2H), 7.55-7.45 (m, 5H), 7.44-7.36 (m, 3H), 1.77 (s, 4H), 1.39 (d, 12H).

Organic Electroluminescent Device Manufacture and Evaluation:

Example 1: Manufacture of Red Organic Electroluminescent Device

An anode was pretreated by the following process: surface treatment was performed with UV ozone and O$_2$:N$_2$ plasma on an ITO/Ag/ITO substrate with a thicknesses of 100 Å, 1000 Å, and 100 Å in sequence to increase the work function of the anode, and the surface of the ITO/Ag/ITO substrate was cleaned with an organic solvent to remove impurities and oil on the surface of the substrate.

HAT-CN was evaporated on the experimental substrate (the anode) in vacuum to form a hole injection layer (HIL) having a thickness of 100 Å, and then α-NPD was vacuum evaporated on the hole injection layer to form a first hole transport layer having a thickness of 1080 Å.

A compound HT-1 was vacuum evaporated on the first hole transport layer to form a second hole transport layer having a thickness of 890 Å.

Next, RH-P, a compound 8 and Ir(MDQ)$_2$(acac) were co-evaporated on the second hole transport layer at an evaporation rate ratio of 49%:49%:2% to form a red electroluminescent layer (EML) having a thickness of 400 Å.

A compound ET-1 and LiQ were mixed in a weight ratio of 1:1 and evaporated on the electroluminescent layer to form an electron transport layer (ETL) having a thickness of 350 Å, Yb was evaporated on the electron transport layer to form an electron injection layer (EIL) having a thickness of 10 Å, and then magnesium (Mg) and silver (Ag) were mixed in an evaporation rate of 1:9 and vacuum evaporated on the electron injection layer to form a cathode having a thickness of 130 Å.

In addition, CP-1 was evaporated on the above cathode in vacuum to form an organic capping layer having a thickness of 800 Å, thus completing the manufacture of a red organic electroluminescent device.

Examples 2 to 38

An organic electroluminescent device was manufactured by the same method as that in Example 1 except that compounds in Table 8 below (collectively referred to as "compounds X") were used instead of the compound 8 in Example 1 when the electroluminescent layer was manufactured.

Comparative Examples 1 to 3

An organic electroluminescent device was manufactured by the same method as that in Example 1 except that a compound A, a compound B, and a compound C were respectively used instead of the compound 8 in Example 1 when the electroluminescent layer was manufactured.

In the examples and Comparative examples, the structures of main compounds employed are as follows:

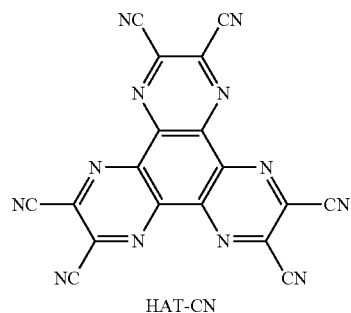

HAT-CN

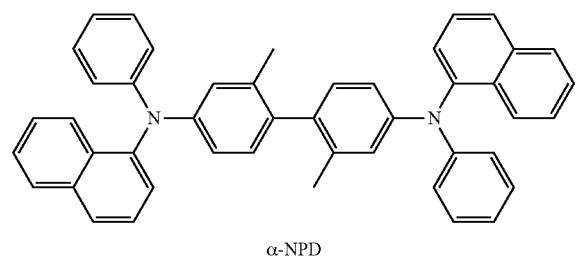

α-NPD

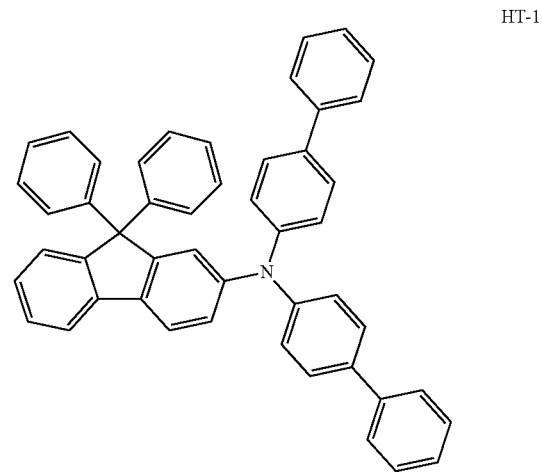

HT-1

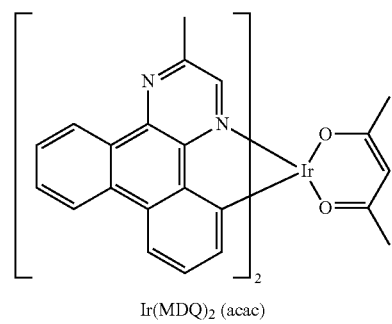

Ir(MDQ)$_2$ (acac)

-continued
ET-1
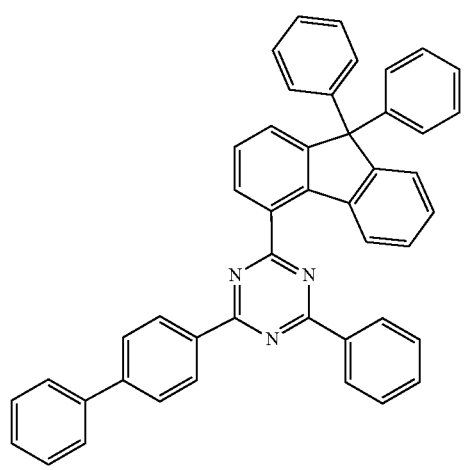
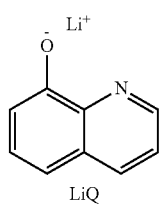
LiQ
CP-1
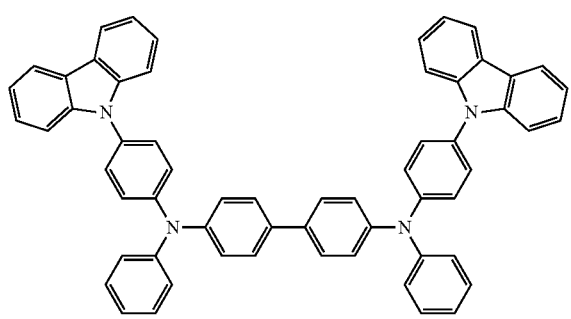
RH-P
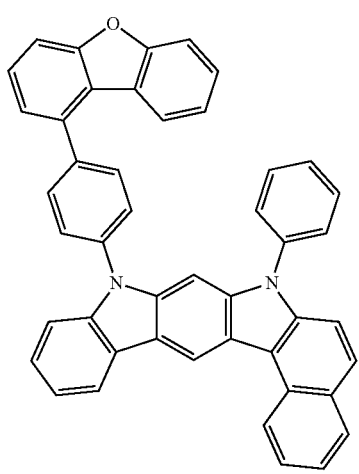
-continued
Compound A
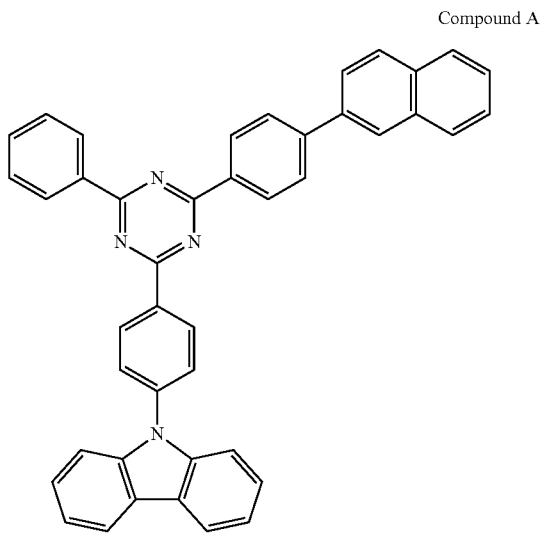
Compound B
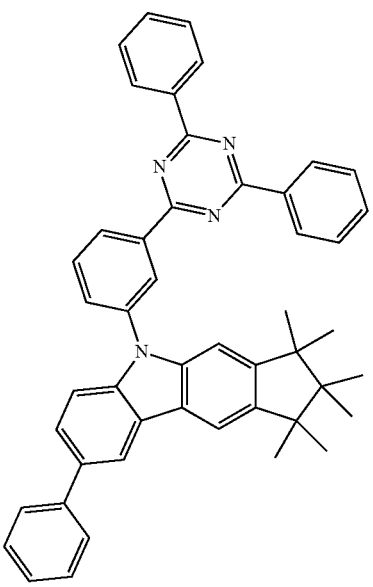
Compound C
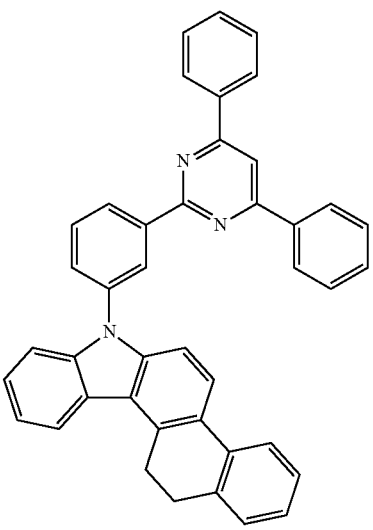

The red organic electroluminescent devices manufactured in Examples 1 to 38 and Comparative examples 1 to 3 were subjected to performance tests, and specifically, the current-voltage-brightness (IVL) performance of the devices was tested under the condition of 10 mA/cm², and the T95 device service life was tested under the condition of 20 mA/cm², and the test results are shown in Table 8.

TABLE 8

| Example No. | Electroluminescent layer RH-P:compound X:Ir(MDQ)$_2$(acac) | Operating voltage Volt (V) | Current efficiency Cd/A | CIEx | CIEy | T95 (h) @ 20 mA/cm² |
|---|---|---|---|---|---|---|
| Example 1 | Compound 8 | 3.61 | 63.1 | 0.680 | 0.320 | 505 |
| Example 2 | Compound 55 | 3.51 | 64.8 | 0.680 | 0.320 | 520 |
| Example 3 | Compound 60 | 3.60 | 64.1 | 0.680 | 0.320 | 506 |
| Example 4 | Compound 85 | 3.61 | 62.1 | 0.680 | 0.320 | 503 |
| Example 5 | Compound 88 | 3.64 | 62.9 | 0.680 | 0.320 | 508 |
| Example 6 | Compound 107 | 3.60 | 64.0 | 0.680 | 0.320 | 512 |
| Example 7 | Compound 119 | 3.62 | 62.9 | 0.680 | 0.320 | 498 |
| Example 8 | Compound 125 | 3.64 | 63.7 | 0.680 | 0.320 | 494 |
| Example 9 | Compound 143 | 3.59 | 63.1 | 0.680 | 0.320 | 515 |
| Example 10 | Compound 192 | 3.59 | 64.4 | 0.680 | 0.320 | 502 |
| Example 11 | Compound 224 | 3.59 | 63.8 | 0.680 | 0.320 | 499 |
| Example 12 | Compound 241 | 3.62 | 63.0 | 0.680 | 0.320 | 516 |
| Example 13 | Compound 266 | 3.60 | 63.7 | 0.680 | 0.320 | 496 |
| Example 14 | Compound 282 | 3.60 | 62.8 | 0.680 | 0.320 | 564 |
| Example 15 | Compound 285 | 3.61 | 62.5 | 0.680 | 0.320 | 572 |
| Example 16 | Compound 319 | 3.58 | 62.7 | 0.680 | 0.320 | 576 |
| Example 17 | Compound 331 | 3.63 | 64.8 | 0.680 | 0.320 | 574 |
| Example 18 | Compound 359 | 3.58 | 65.0 | 0.680 | 0.320 | 573 |
| Example 19 | Compound 372 | 3.60 | 63.2 | 0.680 | 0.320 | 562 |
| Example 20 | Compound 386 | 3.60 | 64.2 | 0.680 | 0.320 | 573 |
| Example 21 | Compound 408 | 3.64 | 63.4 | 0.680 | 0.320 | 560 |
| Example 22 | Compound 413 | 3.62 | 62.9 | 0.680 | 0.320 | 566 |
| Example 23 | Compound 442 | 3.64 | 63.5 | 0.680 | 0.320 | 565 |
| Example 24 | Compound 452 | 3.60 | 63.7 | 0.680 | 0.320 | 567 |
| Example 25 | Compound 487 | 3.64 | 63.4 | 0.680 | 0.320 | 569 |
| Example 26 | Compound 496 | 3.59 | 63.5 | 0.680 | 0.320 | 570 |
| Example 27 | Compound 512 | 3.63 | 63.8 | 0.680 | 0.320 | 561 |
| Example 28 | Compound 517 | 3.64 | 56.0 | 0.680 | 0.320 | 513 |
| Example 29 | Compound 518 | 3.62 | 56.3 | 0.680 | 0.320 | 512 |
| Example 30 | Compound 529 | 3.64 | 56.3 | 0.680 | 0.320 | 519 |
| Example 31 | Compound 530 | 3.64 | 56.2 | 0.680 | 0.320 | 517 |
| Example 32 | Compound 539 | 3.59 | 55.7 | 0.680 | 0.320 | 521 |
| Example 33 | Compound 555 | 3.64 | 55.8 | 0.680 | 0.320 | 522 |
| Example 34 | Compound 567 | 3.59 | 55.7 | 0.680 | 0.320 | 572 |
| Example 35 | Compound 571 | 3.64 | 56.7 | 0.680 | 0.320 | 562 |
| Example 36 | Compound 588 | 3.62 | 56.4 | 0.680 | 0.320 | 571 |
| Example 37 | Compound 602 | 3.57 | 56.4 | 0.680 | 0.320 | 514 |
| Example 38 | Compound 620 | 3.54 | 55.9 | 0.680 | 0.320 | 570 |
| Comparative example 1 | Compound A | 3.68 | 46.6 | 0.680 | 0.320 | 344 |
| Comparative example 2 | Compound B | 3.67 | 45.1 | 0.680 | 0.320 | 425 |
| Comparative example 3 | Compound C | 3.65 | 47.3 | 0.680 | 0.320 | 336 |

It can be seen from Table 8 that the compound of the present disclosure is used as a red host material of an organic electroluminescent device, and the luminous efficiency of the device is improved by at least 17.7% and the T95 service life is improved by at least 16.2% when the compound of the present disclosure is used as the red host material compared with Comparative examples 1 to 3.

Example 39: Green Organic Electroluminescent Device

An anode was pretreated by the following process: surface treatment was performed with UV ozone and O$_2$:N$_2$ plasma on an ITO/Ag/ITO substrate with thicknesses of 100 Å, 1000 Å, and 100 Å in sequence to increase the work function of the anode, and the surface of the ITO substrate was cleaned with an organic solvent to remove impurities and oil on the surface of the ITO substrate.

HAT-CN was evaporated on the experimental substrate (the anode) in vacuum to form a hole injection layer (TIL) having a thickness of 100 Å, and then α-NPD was evaporated on the hole injection layer in vacuum to form a first hole transport layer having a thickness of 1080 Å.

A compound HT-1 was evaporated on the first hole transport layer in vacuum to form a second hole transport layer having a thickness of 350 Å.

A compound 3, GH-P and fac-Ir(ppy)$_3$ were co-evaporated on the second hole transport layer at an evaporation rate ratio of 45%:45%:10% to form an organic electroluminescent layer (a green luminescent layer) having a thickness of 350 Å.

A compound ET-2 and LiQ were mixed in a weight ratio of 1:1 and evaporated on the electroluminescent layer to form an electron transport layer (ETL) having a thickness of 350 Å, Yb was evaporated on the electron transport layer to form an electron injection layer (EIL) having a thickness of 10 Å, and then magnesium (Mg) and silver (Ag) were mixed at an evaporation rate of 1:9 and evaporated on the electron injection layer in vacuum to form a cathode having a thickness of 130 Å.

In addition, CP-1 was evaporated on the above cathode in vacuum to form an organic capping layer having a thickness of 800 Å, thus completing the manufacture of the green organic electroluminescent device.

Examples 40 to 47

An organic electroluminescent device was manufactured by the same method as that in Example 39 except that compounds in Table 9 below (collectively referred to as "compounds Y") were used instead of the compound 3 in Example 39 when the electroluminescent layer was manufactured.

Comparative Examples 4 to 5

An organic electroluminescent device was manufactured by the same method as that in Example 39 except that a compound D and a compound E were respectively used instead of the compound 3 in Example 39 when the electroluminescent layer was manufactured.

In Examples 40 to 47 and Comparative examples 4 to 5, the structures of main compounds employed are as follows:

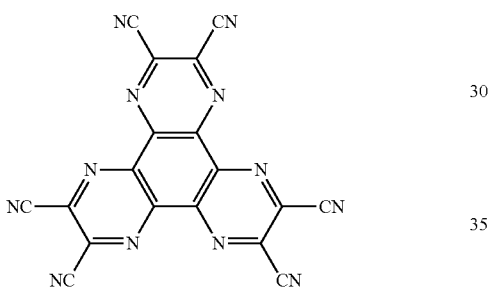

HAT-CN

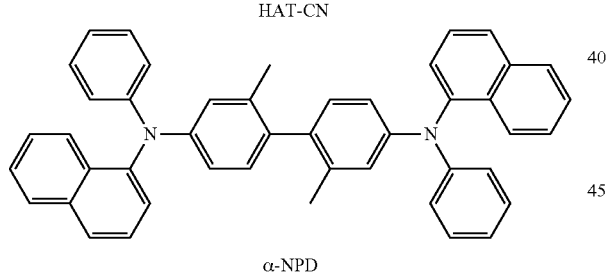

α-NPD

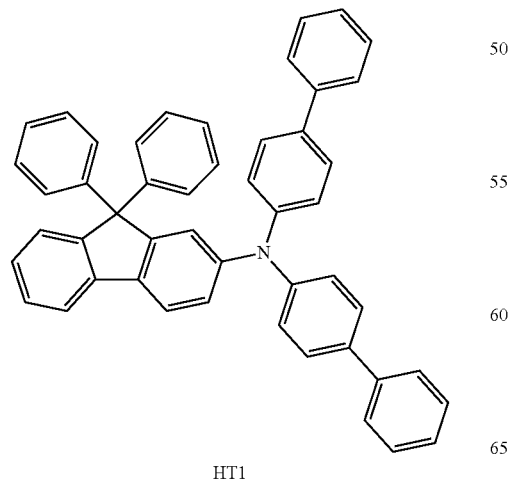

HT1

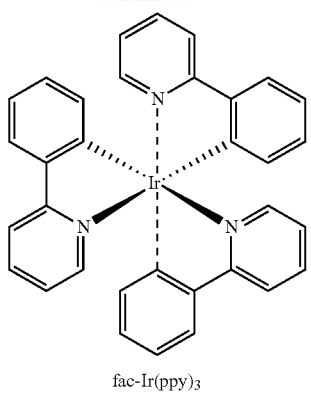

fac-Ir(ppy)₃

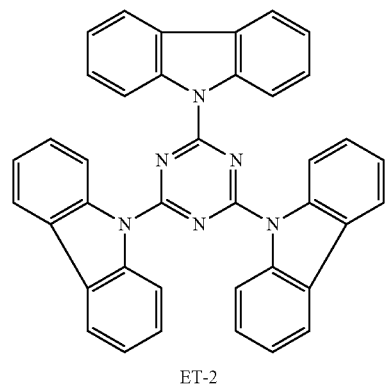

ET-2

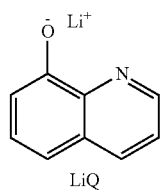

LiQ

CP-1

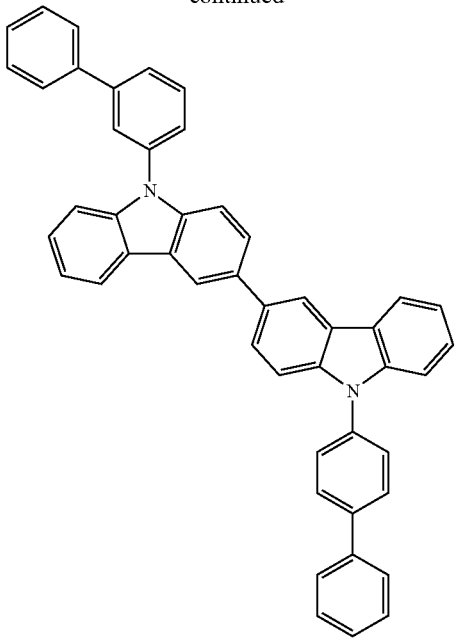

GH-P

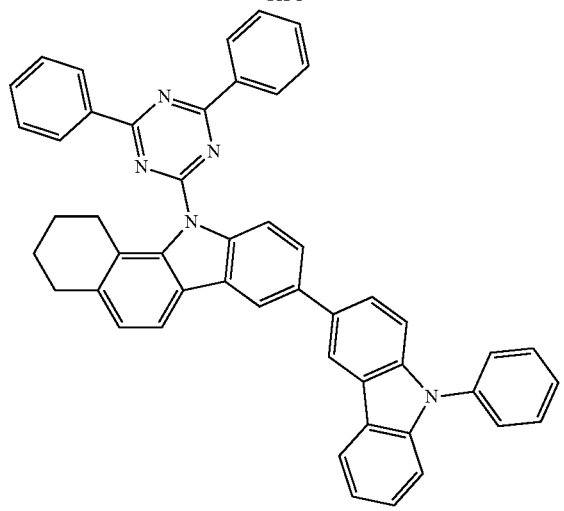

Compound D

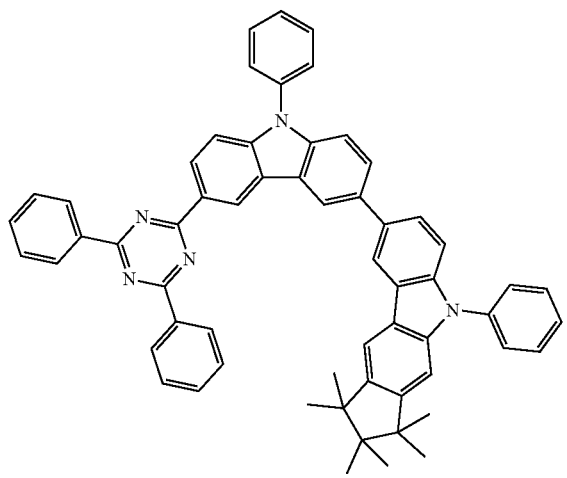

Compound E

The green organic electroluminescent devices manufactured in Examples 39 to 47 and Comparative examples 4 to 5 were subjected to performance tests, and specifically, the current-voltage-brightness (IVL) performance of the devices was tested under the condition of 10 mA/cm$^2$, and the T95 device service life was tested under the condition of 20 mA/cm$^2$, and the test results are shown in Table 9.

Table 9

| Example No. | Electroluminescent layer GH-P:compound Y:fac-Ir(ppy)$_3$ | Operating voltage Volt (V) | Current efficiency Cd/A | CIEx | CIEy | T95 (h) @ 20 mA/cm$^2$ |
|---|---|---|---|---|---|---|
| Example 39 | Compound 3 | 4.22 | 102.2 | 0.220 | 0.730 | 390 |
| Example 40 | Compound 21 | 4.28 | 106.9 | 0.220 | 0.730 | 375 |
| Example 41 | Compound 28 | 4.23 | 106.9 | 0.220 | 0.730 | 377 |
| Example 42 | Compound 35 | 4.23 | 104.6 | 0.220 | 0.730 | 391 |
| Example 43 | Compound 67 | 4.30 | 105.7 | 0.220 | 0.730 | 389 |
| Example 44 | Compound 589 | 4.27 | 103.6 | 0.220 | 0.730 | 385 |
| Example 45 | Compound 637 | 4.26 | 104.2 | 0.680 | 0.320 | 379 |
| Example 46 | Compound 645 | 4.28 | 106.4 | 0.680 | 0.320 | 382 |
| Example 47 | Compound 651 | 4.30 | 105.8 | 0.680 | 0.320 | 386 |
| Comparative example 4 | Compound D | 4.28 | 88.0 | 0.220 | 0.730 | 270 |
| Comparative example 5 | Compound E | 4.26 | 76.8 | 0.220 | 0.730 | 327 |

Referring to Table 9 above, it can be seen that when the compound of the present disclosure is used as a green host material in an organic electroluminescent device, the luminous efficiency of the device is improved by at least 15.9% and the T95 service life is improved by at least 14.7%.

According to the test results of the above device examples, as a host material of a electroluminescent layer of an OLED device, the compound of the present disclosure can significantly improve the luminous efficiency and service life of the device. The reason is that a structure of the compound of the present disclosure includes tetramethylcyclohexanocarbazole and nitrogen-containing heteroarylene, where the nitrogen-containing heteroarylene is connected to a nitrogen atom of a carbazolyl through an aromatic group, and this special connection mode enables a target molecule to make full use of a larger conjugation plane of a carbazolyl molecule, improving the charge mobility of the target molecule. At the same time, the structure of the tetramethylcyclohexane group may further enhance the charge transport ability of the carbazolyl through a hyperconjugation effect. In addition, four methyl on cyclohexane are located outside the conjugation plane of the carbazolyl in steric configuration, forming a certain steric hindrance, and intermolecular stacking of the target molecule is finely regulated, so that the target molecule may form a better amorphous thin film. Thus, when the compound of the present disclosure is used as a host material, the carrier balance in a luminescent layer can be improved, a carrier recombination region can be broadened, the exciton generation and utilization efficiency can be increased, and the luminous efficiency of the device can be improved; and at the same time, the compound of the present disclosure can form a better amorphous film when used as the host material, improving the service life of the device.

It will be understood by those of ordinary skill in the art that the above embodiments are specific examples for implementing the present disclosure, and that various changes may be made in form and detail in actual application without departing from the scope of the present disclosure.

The invention claimed is:

1. A nitrogen-containing compound, having a structure represented by formula 1:

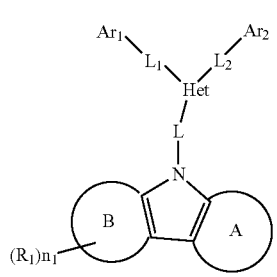

Formula 1 wherein ring A has a structure shown in formula A-1 or a structure shown in formula A-2:

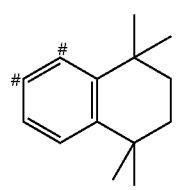

A-1

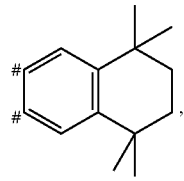

A-2 and a # position represents a site that is fused with a # position of

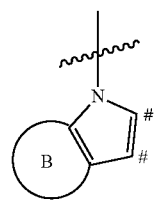

in the formula 1;

ring B is selected from the following structures:

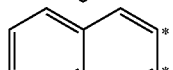

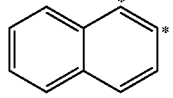

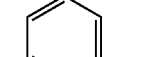

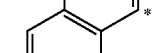

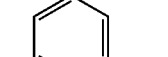

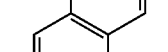

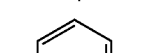

491

-continued

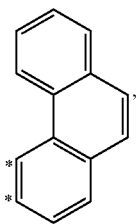

a * position represents a site that is fused with a * position of

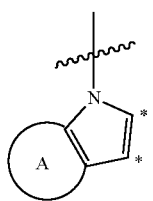

in the formula 1;

Het is selected from the following groups:

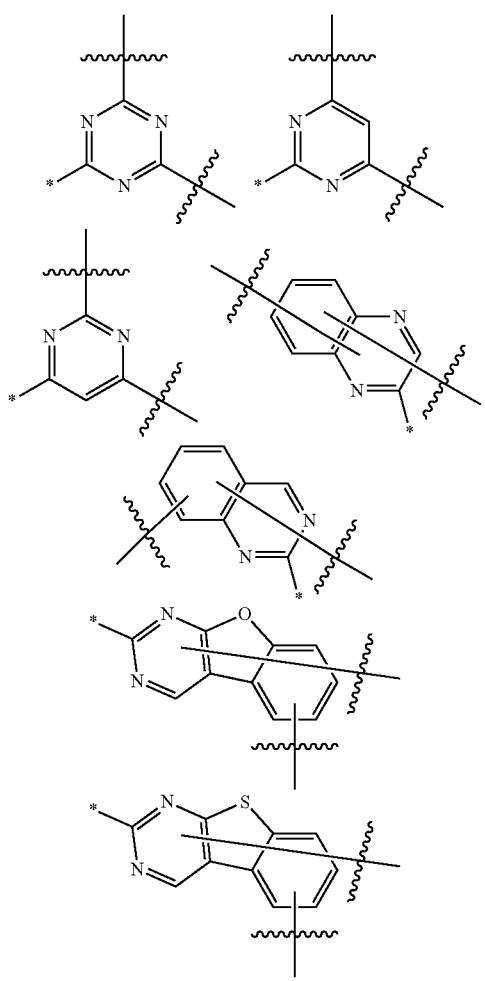

492

-continued

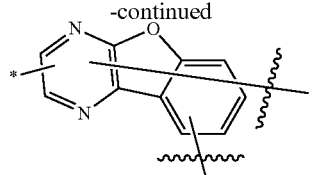

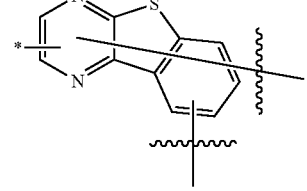

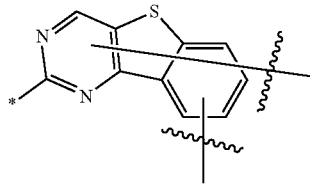

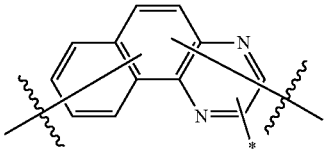

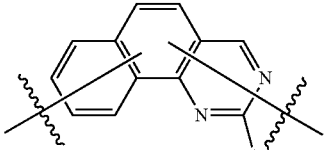

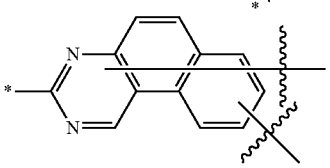

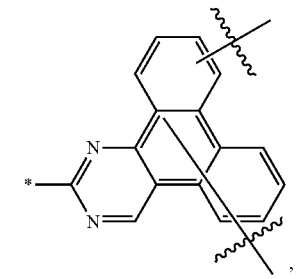

wherein ———* denotes a bond connected to L, and the remaining two connecting bonds -ξ- are respectively connected to $L_1$ and $L_2$;

each $R_1$ is independently selected from deuterium, fluorine, cyano, methyl, ethyl, isopropyl, tert-butyl or phenyl;

$n_1$ is selected from 0, 1, 2, 3, 4, 5 or 6;

L is selected from substituted or unsubstituted phenylene, substituted or unsubstituted naphthylene, substituted or unsubstituted biphenylene, substituted or unsubstituted dibenzothienylene, substituted or unsubstituted dibenzofurylene, or substituted or unsubstituted fluorenylene;

L₁ and L₂ are each independently selected from a single bond, substituted or unsubstituted phenylene, substituted or unsubstituted naphthylene, substituted or unsubstituted biphenylene, substituted or unsubstituted dibenzothienylene, substituted or unsubstituted dibenzofurylene, substituted or unsubstituted carbazolylene, or substituted or unsubstituted fluorenylene;

substituents in L₁, L₂ and L are the same or different, and are each independently selected from deuterium, fluorine, cyano, methyl, ethyl, isopropyl, tert-butyl, trifluoromethyl, trideuteromethyl, trimethylsilyl or phenyl;

Ar₁ is selected from a substituted or unsubstituted group W, and Ar₂ is selected from hydrogen, or a substituted or unsubstituted group W; wherein the unsubstituted group W is selected from the group consisting of:

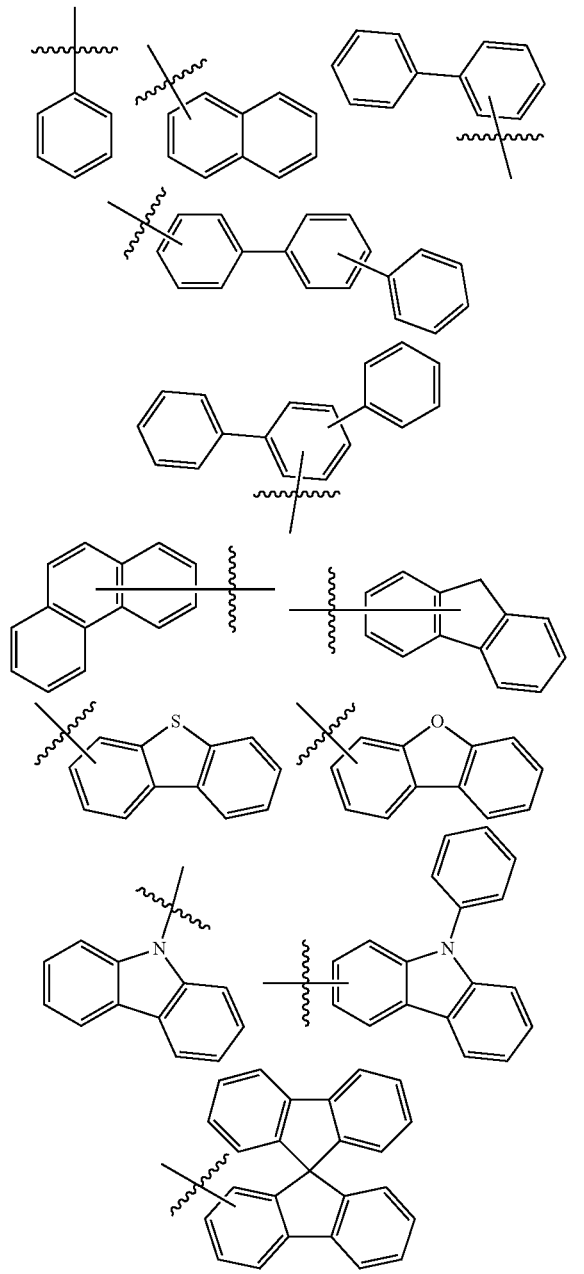

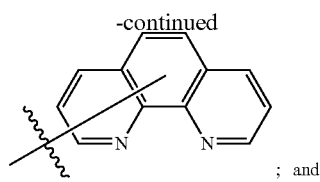

; and the substituted group W has one or two or more substituents each independently selected from deuterium, fluorine, cyano, trideuteromethyl, trimethylsilyl, methyl, ethyl, isopropyl, tert-butyl, phenyl, naphthyl, dibenzofuranyl, dibenzothienyl or carbazolyl, and when the number of the substituents on the group W is greater than 1, the substituents are the same or different.

2. The nitrogen-containing compound according to claim 1, wherein

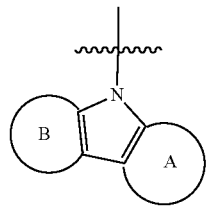

in the formula 1 is selected from the following structures:

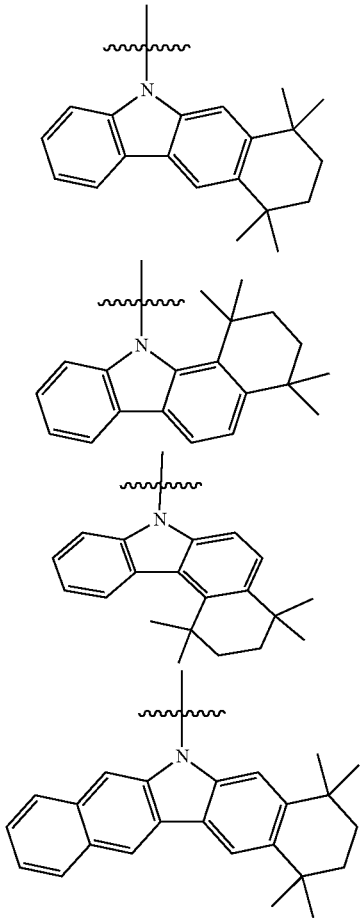

-continued
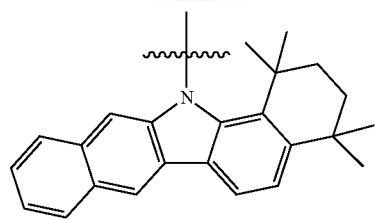
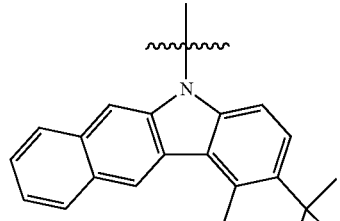
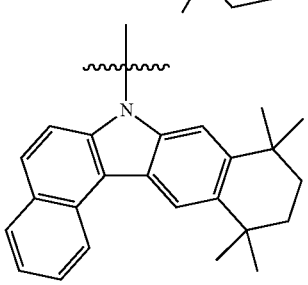
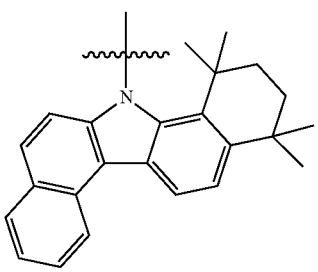
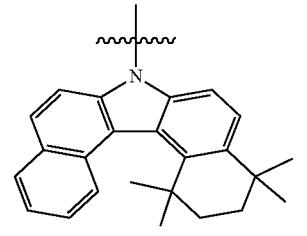
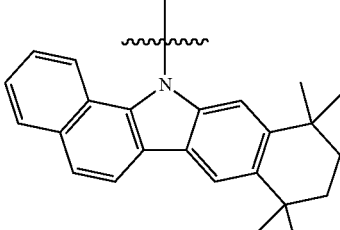
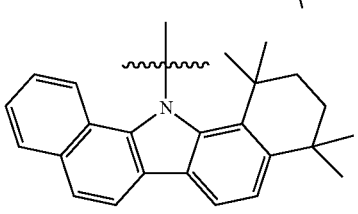
-continued
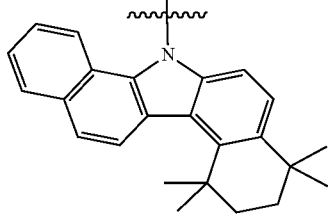
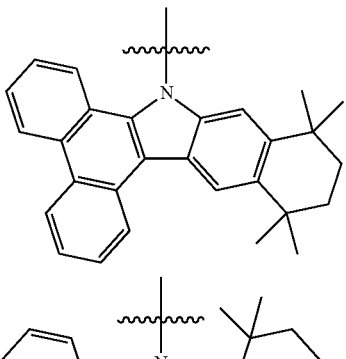
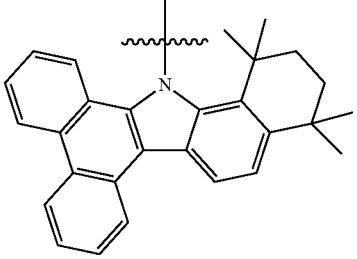
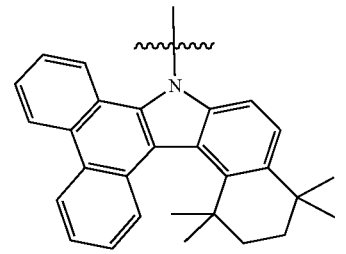
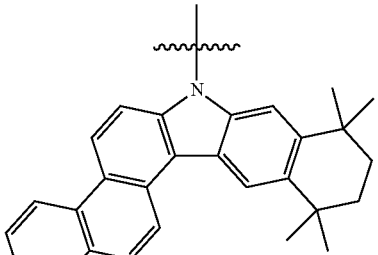
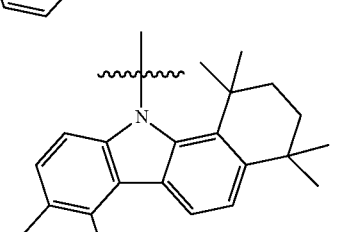

497
-continued
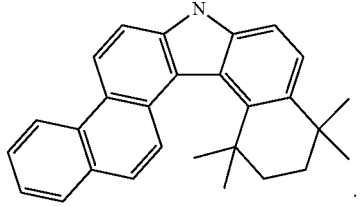
498
-continued
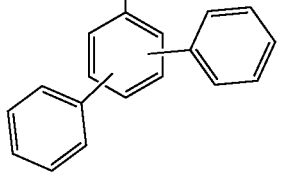
3. The nitrogen-containing compound according to claim 1, wherein Ar₁ is selected from the group consisting of the following groups, and Ar₂ is selected from hydrogen or the group consisting of the following groups:
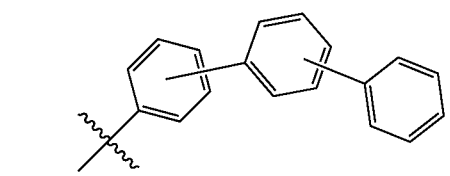
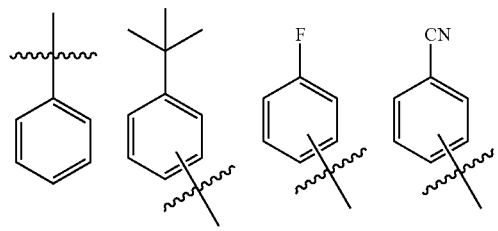
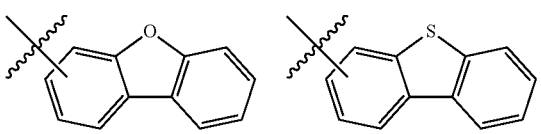
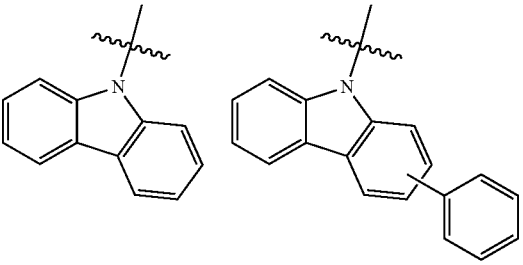
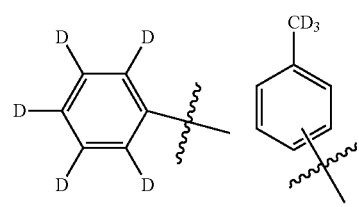
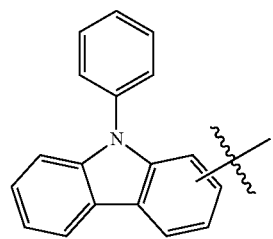
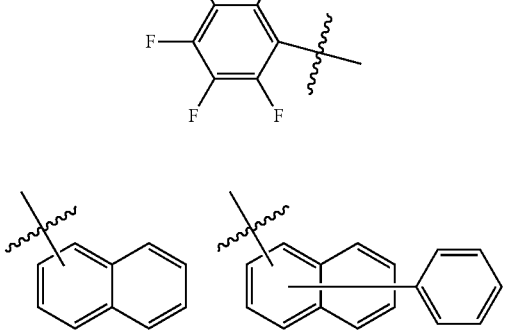
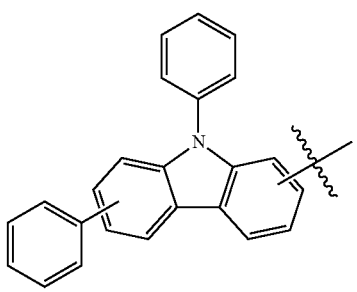
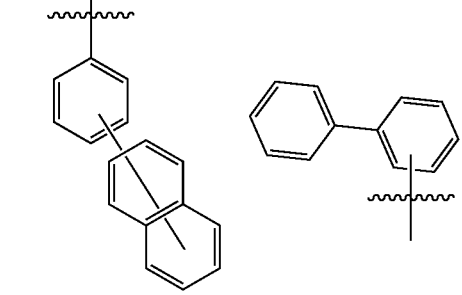

499
-continued
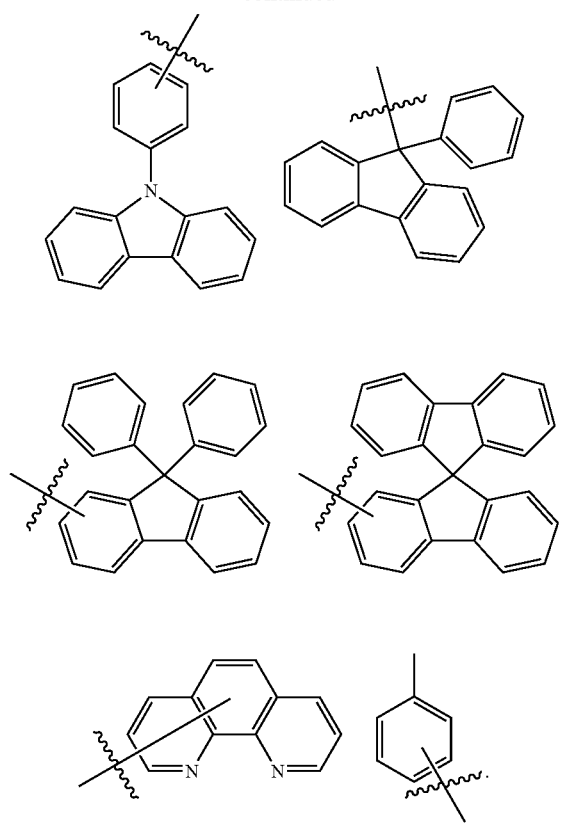
4. The nitrogen-containing compound according to claim 1, wherein Het is selected from the group consisting of the following nitrogen-containing heteroarylene:
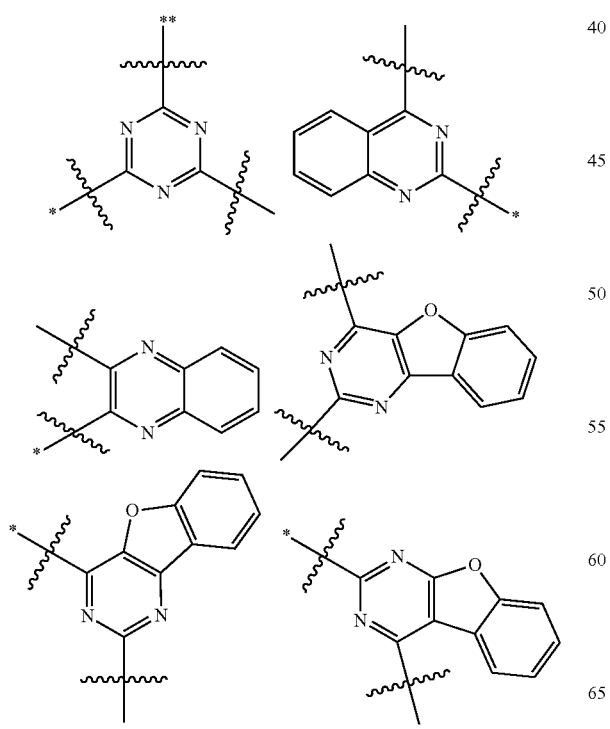
500
-continued
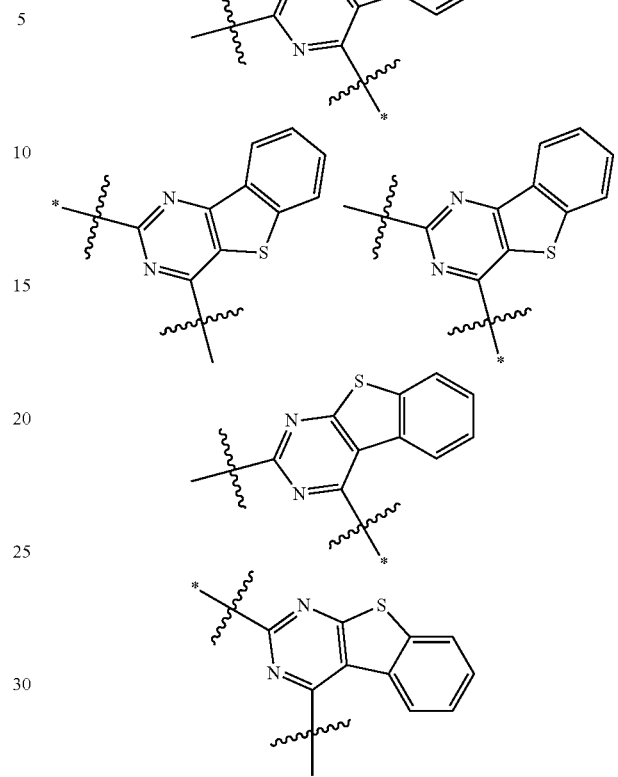
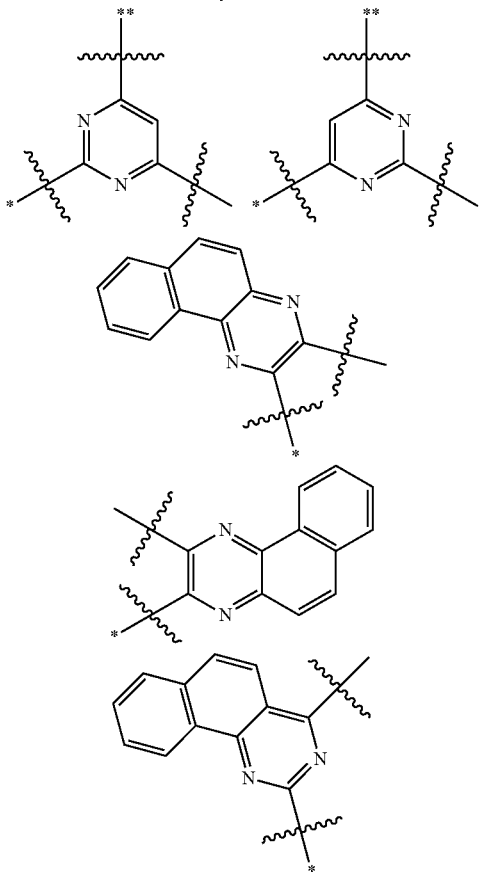

501

-continued

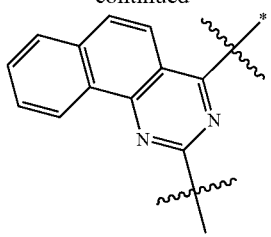

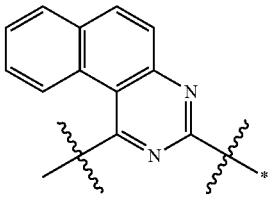

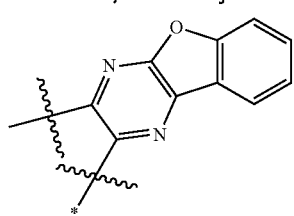

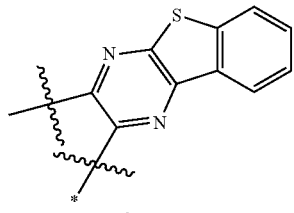

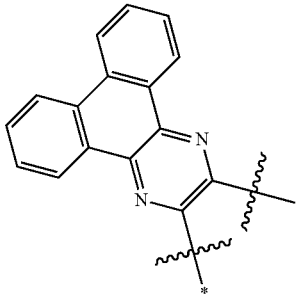

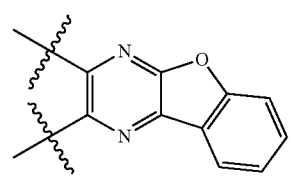

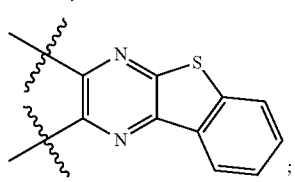

wherein *-§- denotes a position where Het is connected to L, -§- denotes a position where Het is connected to L₁, *-§- denotes a position that is connected to L₂, and where *-§- is absent in the formula means that L₂ is a single bond and Ar₂ is hydrogen in

502

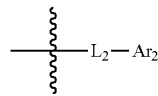

connected at this position.

5. The nitrogen-containing compound according to claim 1, wherein

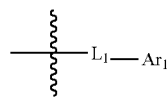

is selected from the group consisting of the following groups, and

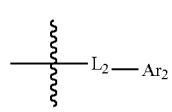

is selected from hydrogen or the group consisting of the following groups:

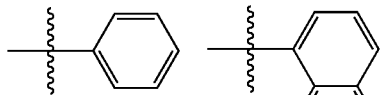

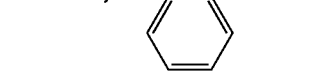

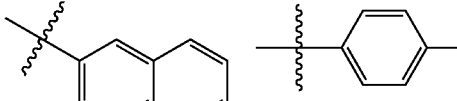

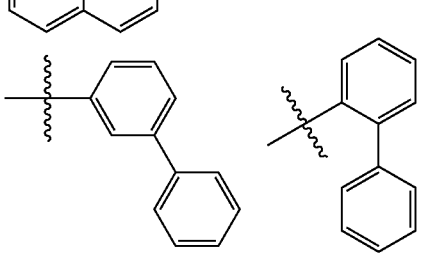

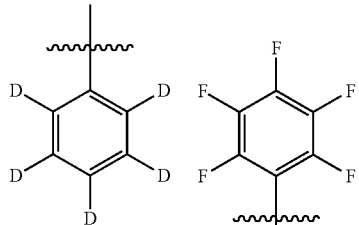

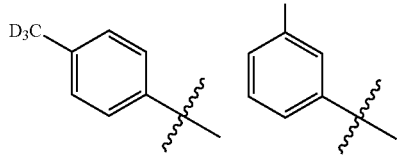

503
-continued
504
-continued
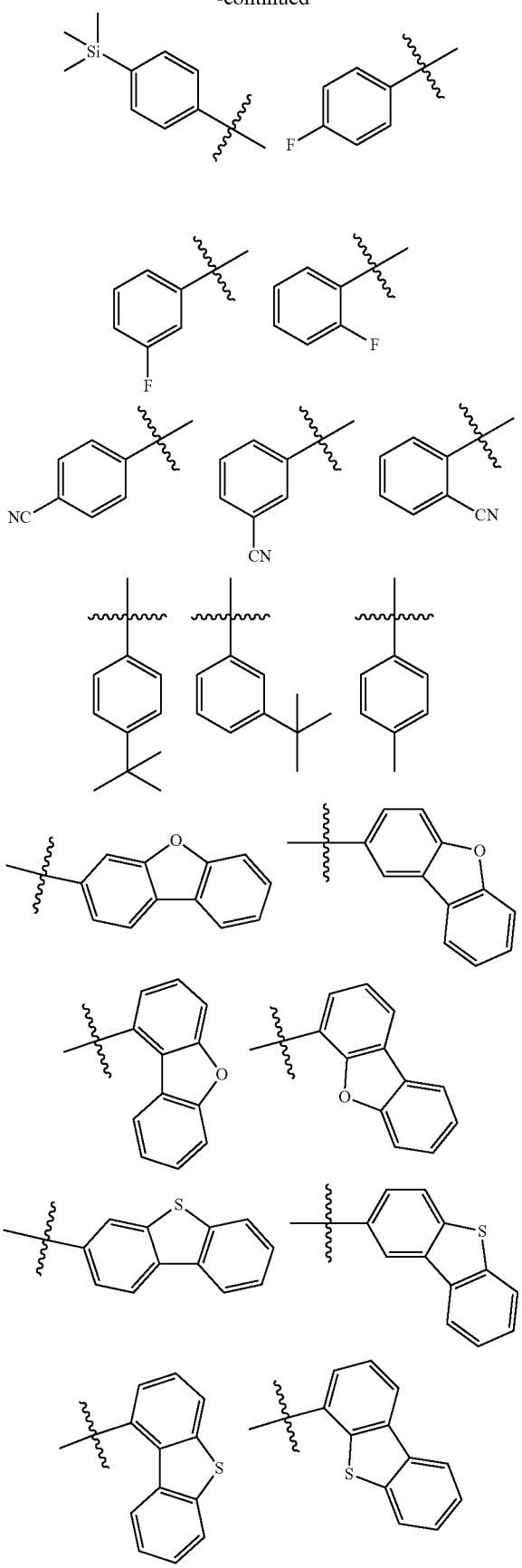
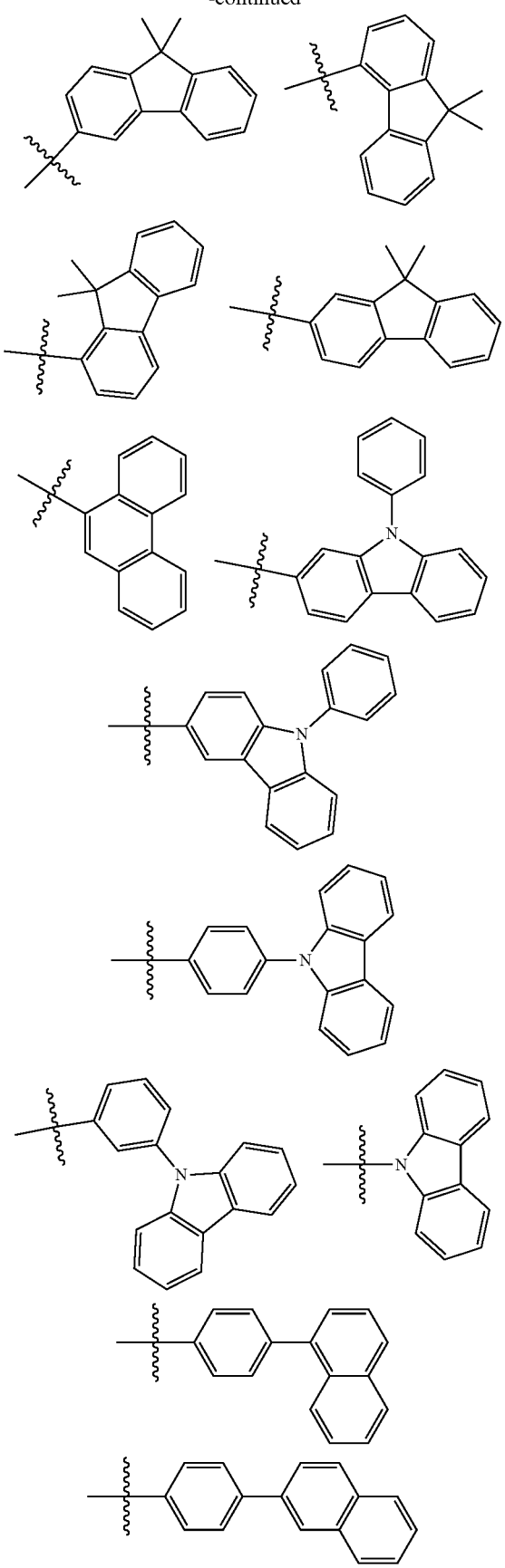

505
-continued
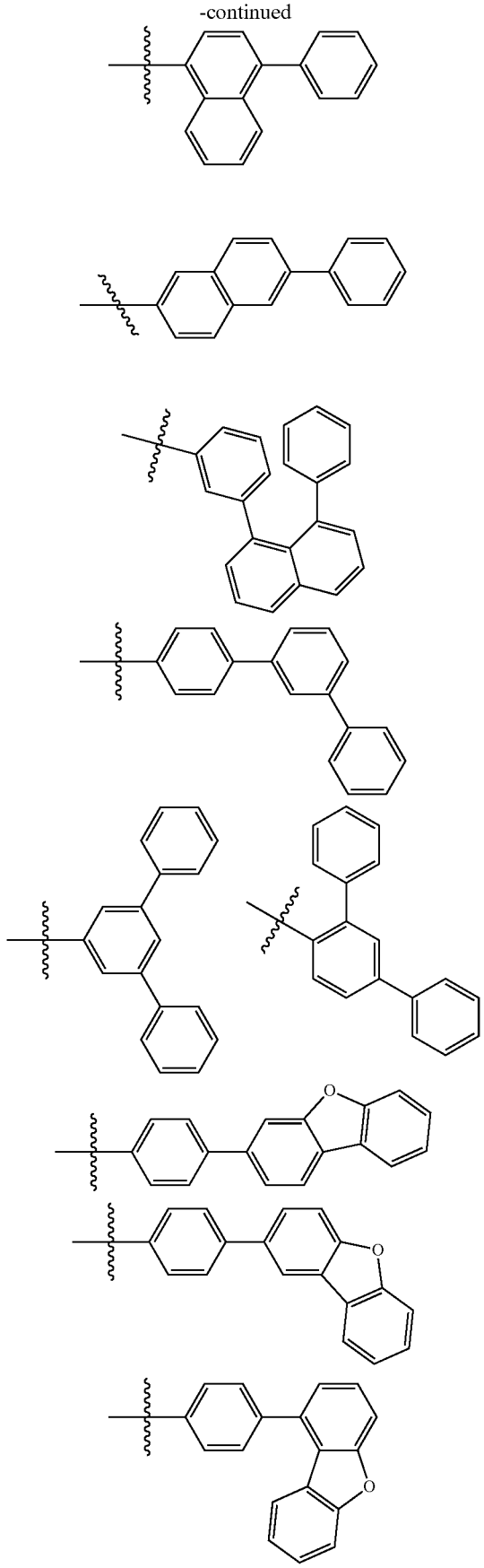
506
-continued
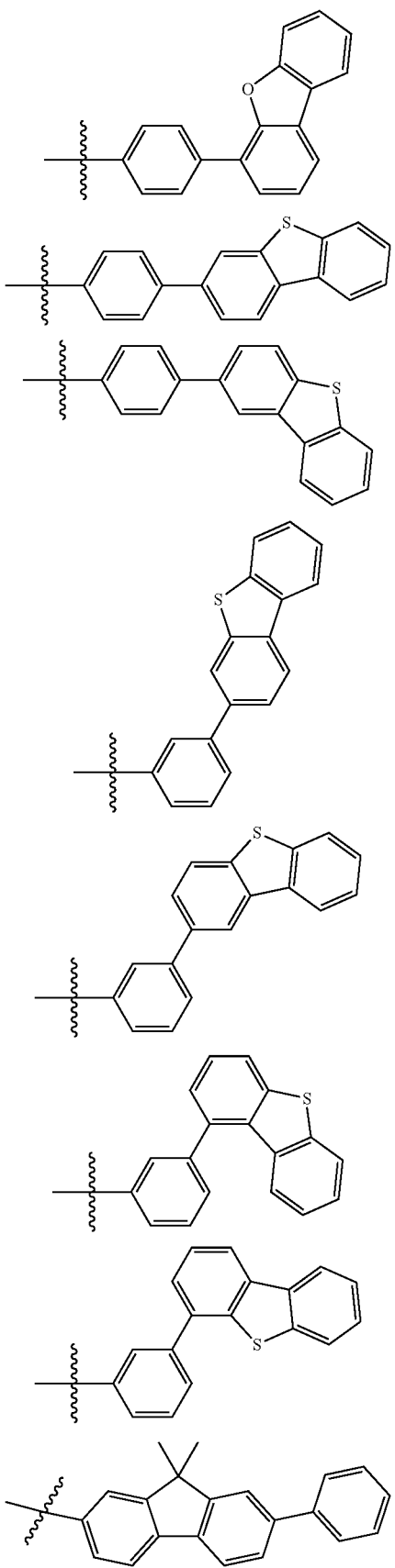

507
-continued
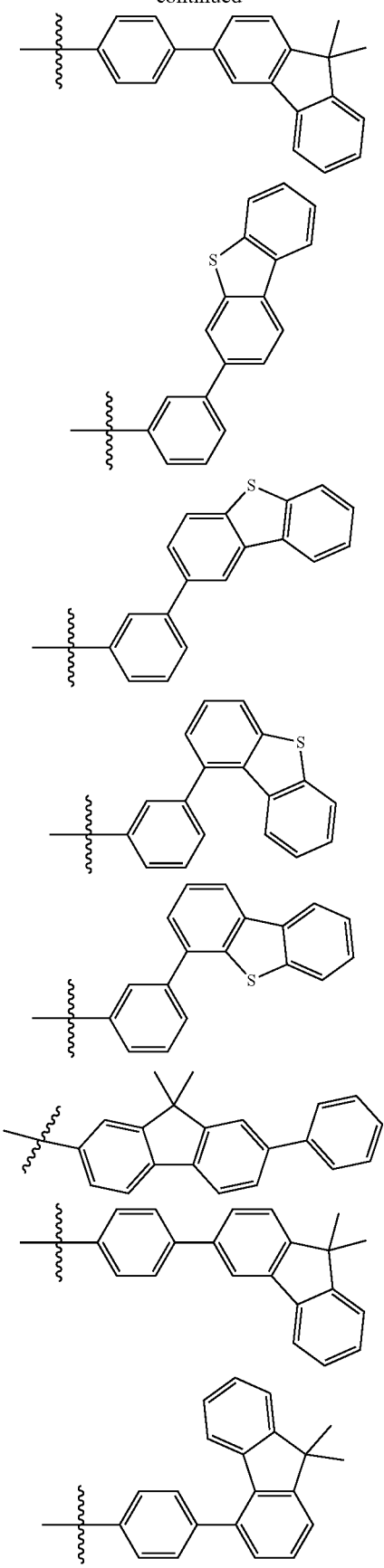
508
-continued
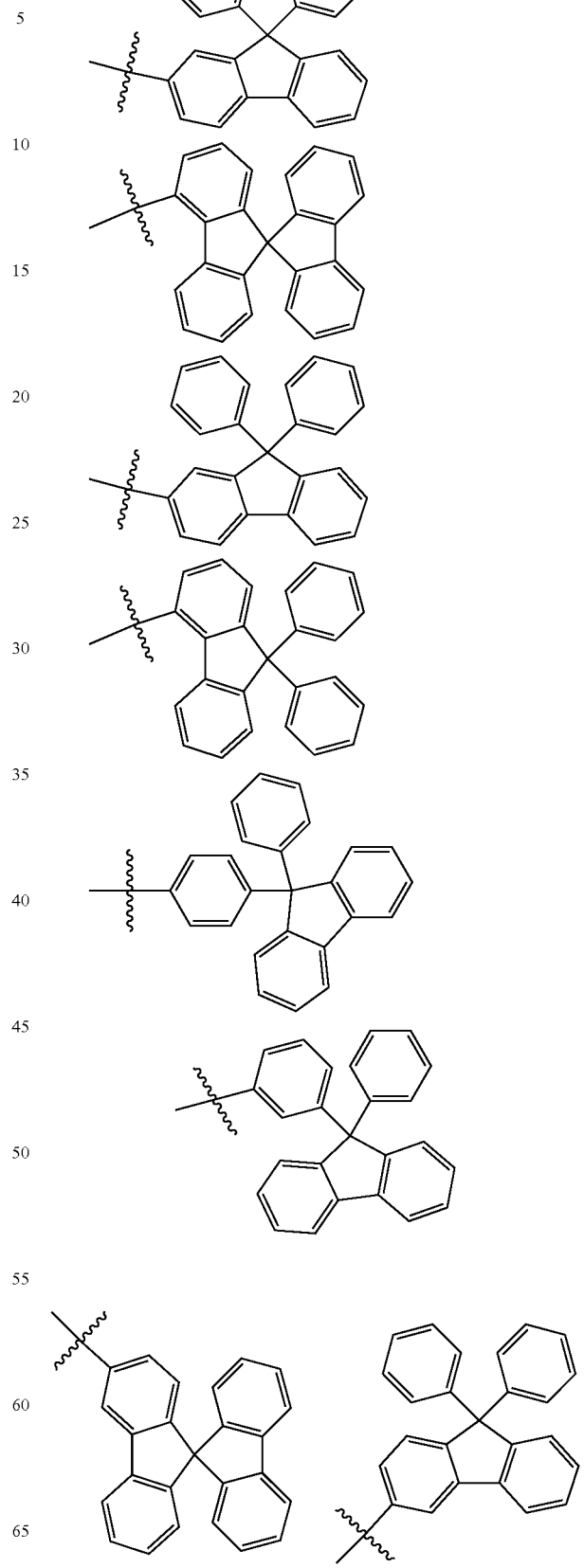

509
-continued
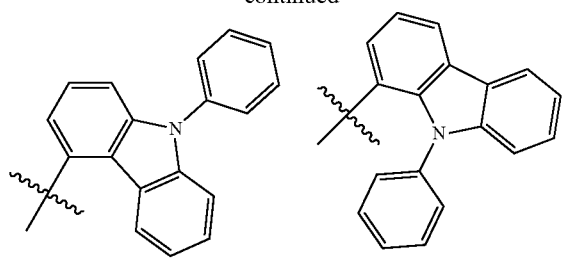
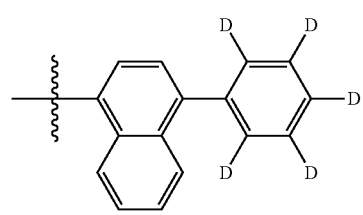
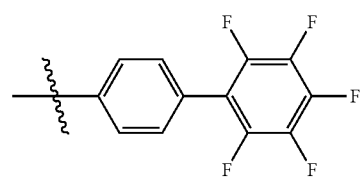
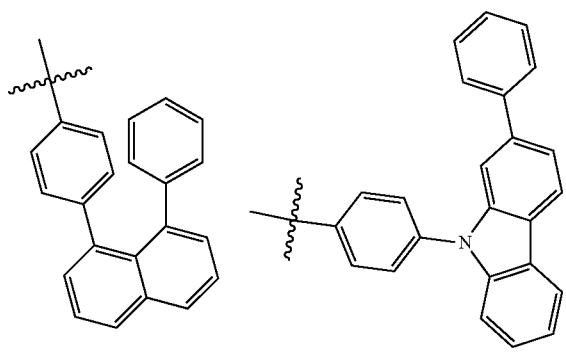
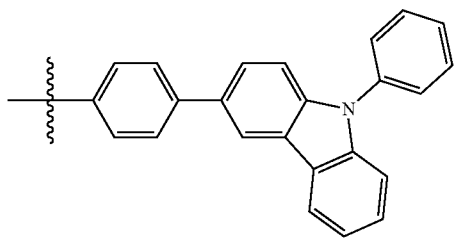
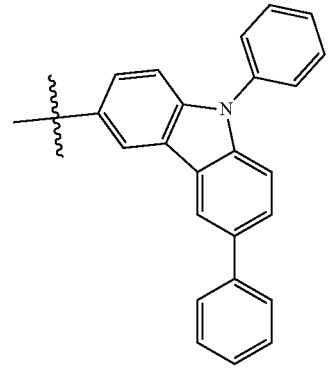
510
-continued
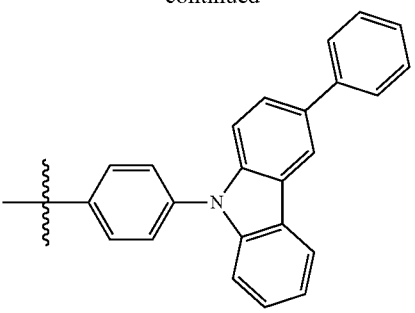
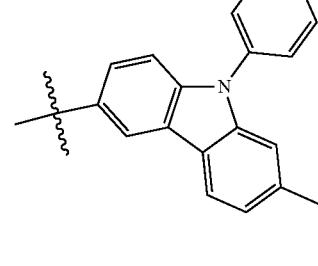
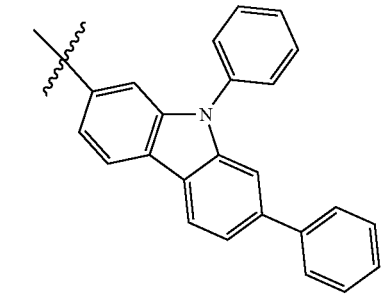
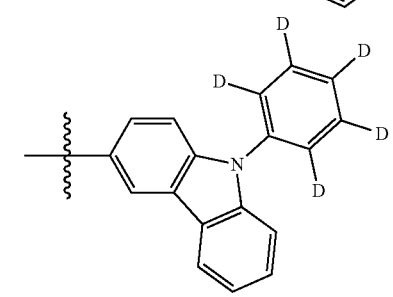
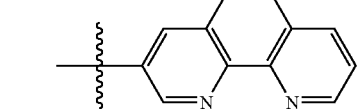
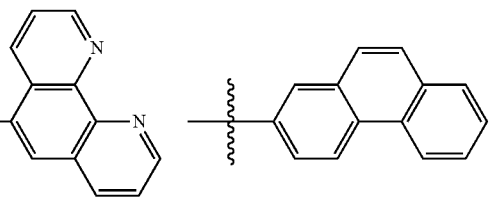
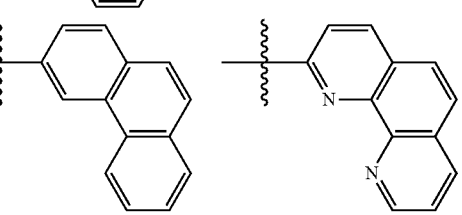

511
-continued
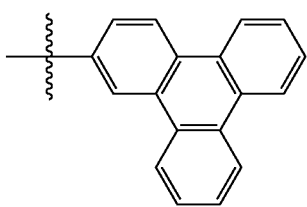
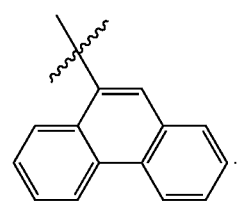
512
-continued
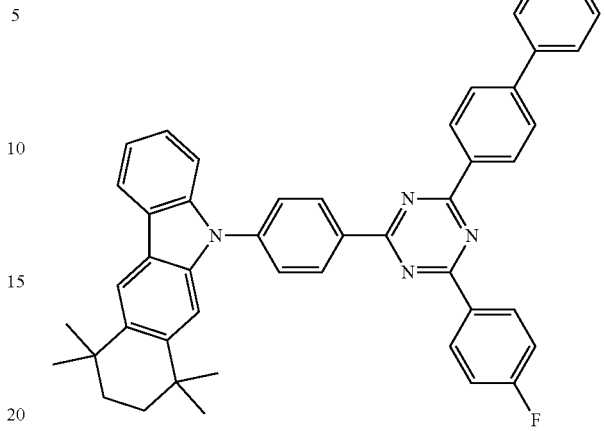
3
6. The nitrogen-containing compound according to claim 1, wherein the nitrogen-containing compound is selected from the group consisting of the following compounds:
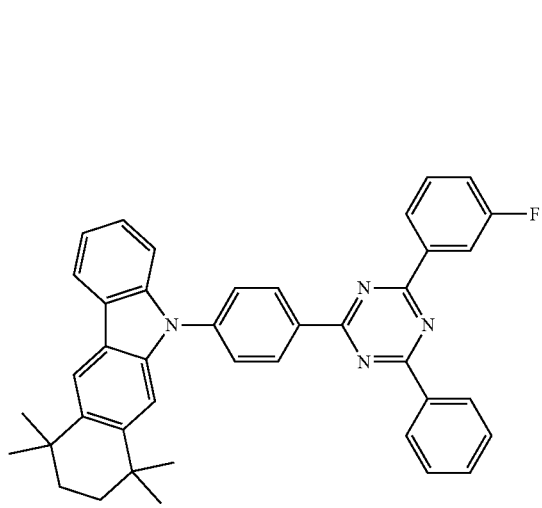
1
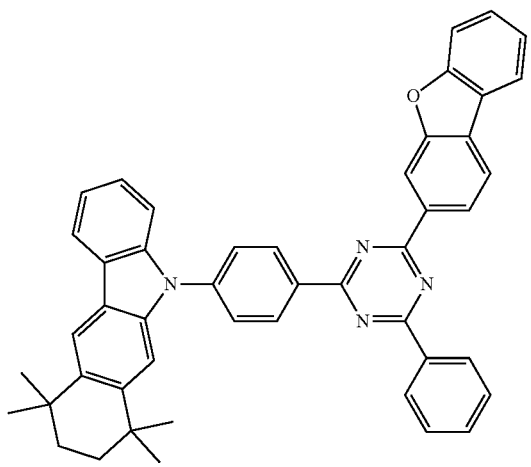
4
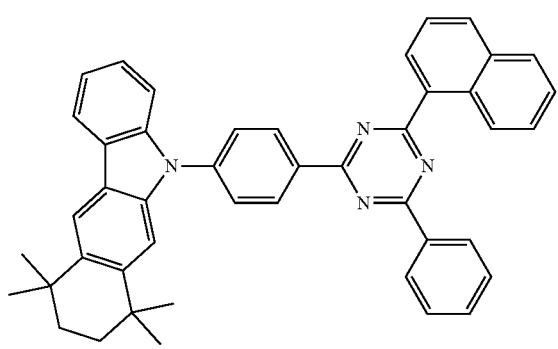
2
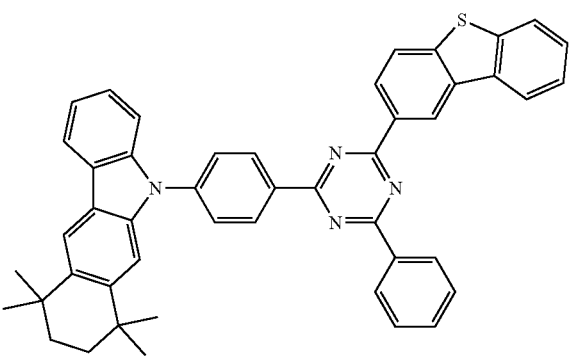
5

513
-continued
514
-continued
6
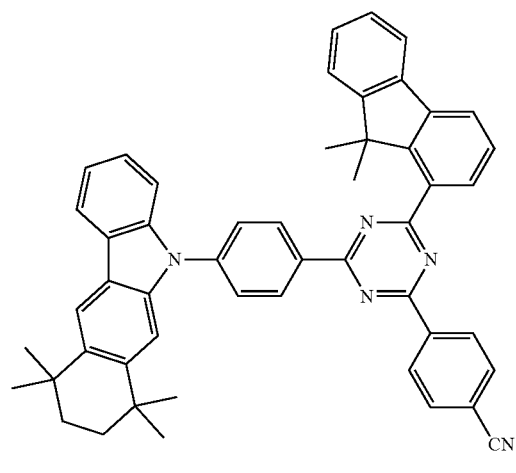
5
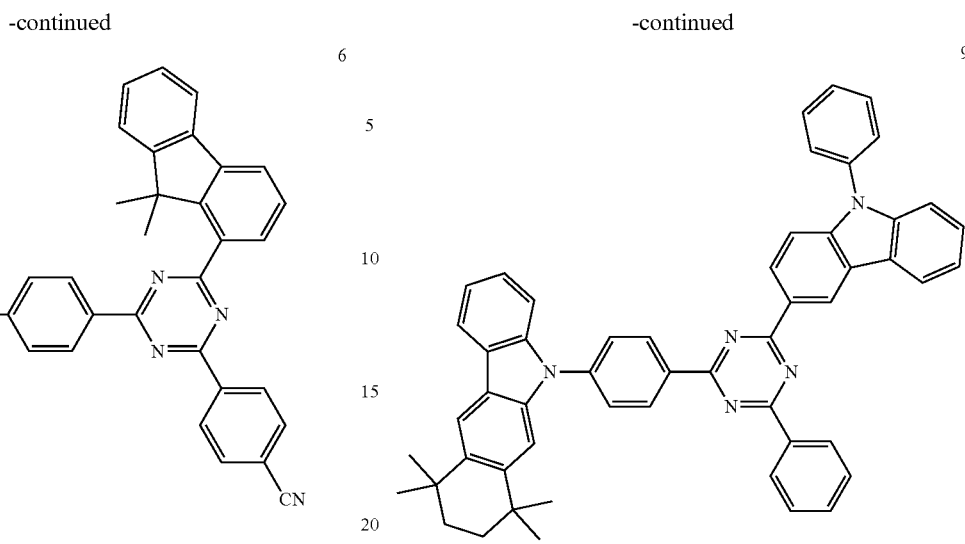
9
7
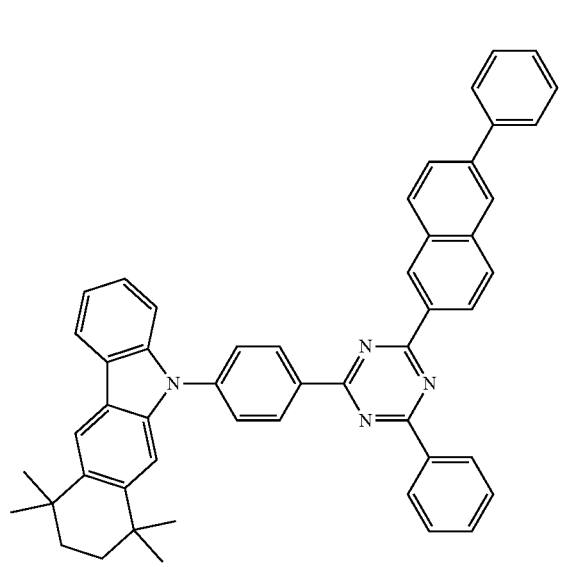
10
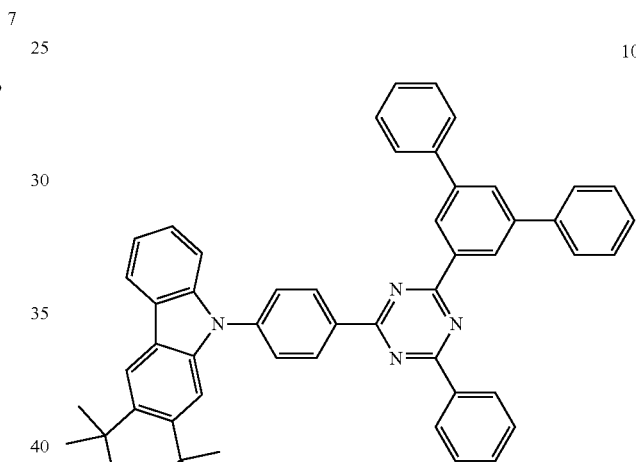
8
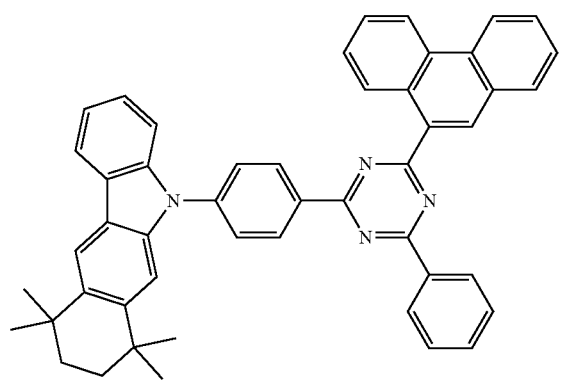 [SMILES: CC1(C)CCC(C)(C)c2cc3c(cc21)c1ccccc1n3-c1ccc(-c2nc(-c3ccccc3)nc(-c3cc4ccccc4c4ccccc34)n2)cc1]
11
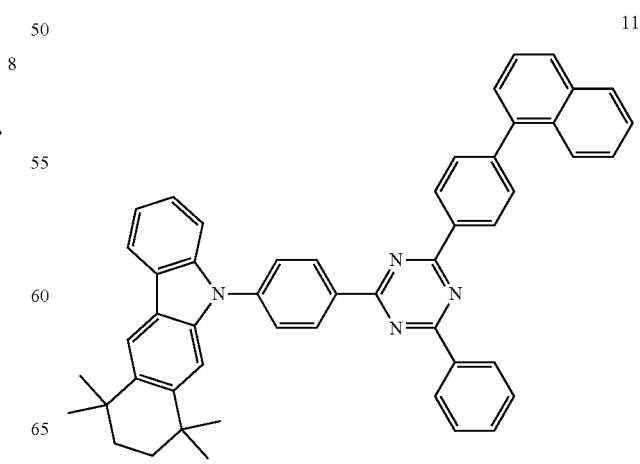

515
-continued
12
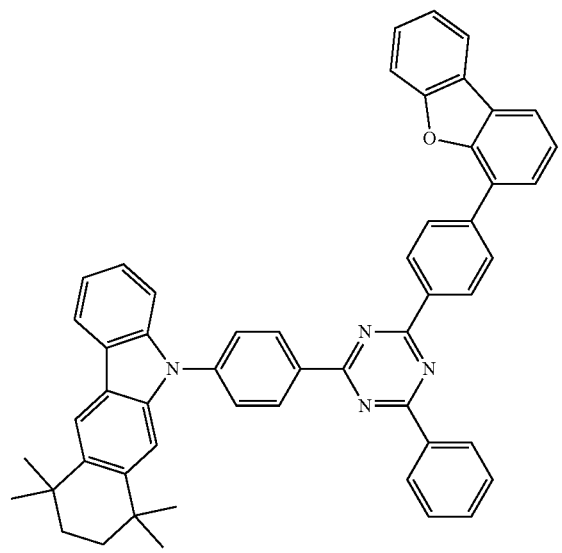
13
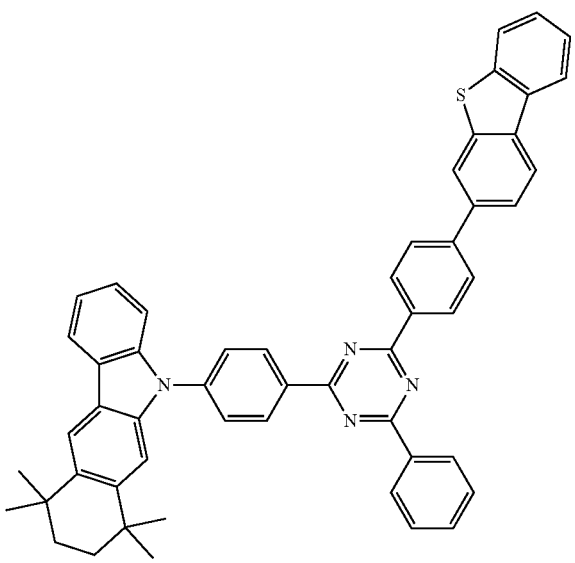
516
-continued
14
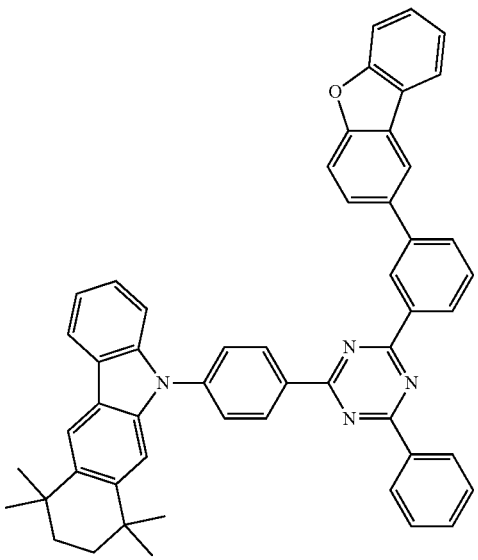
15
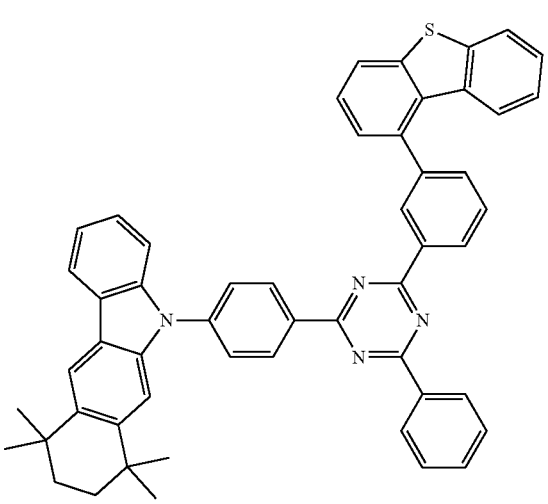
19
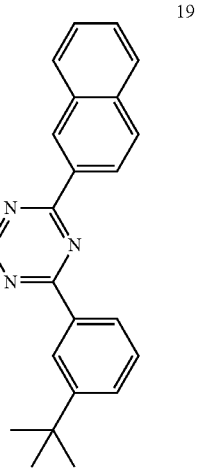

517
-continued
20
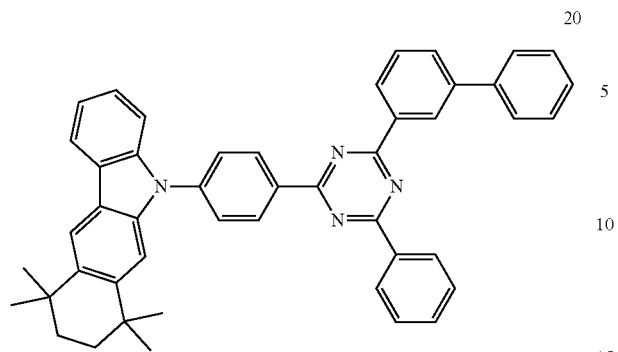
21
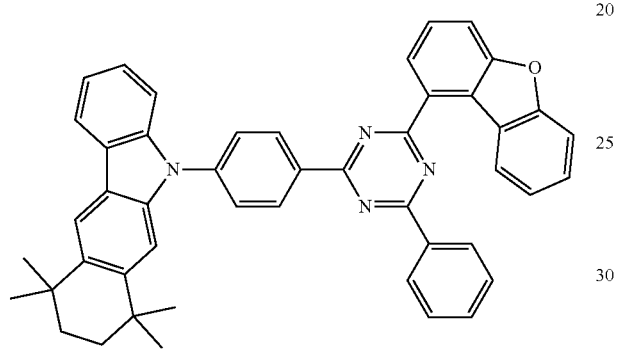
22
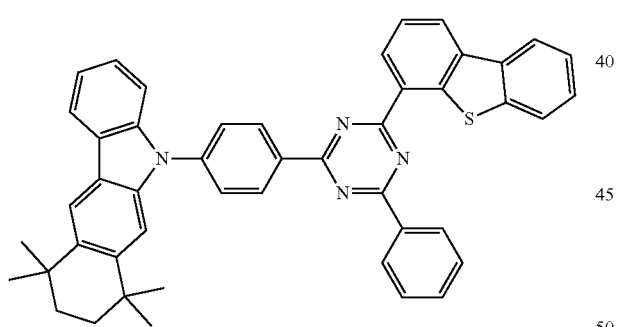
23
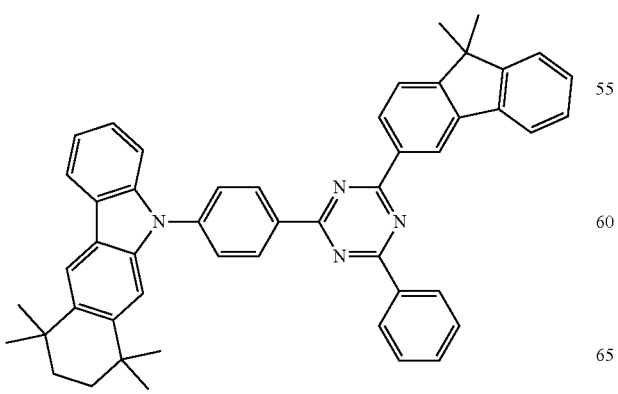
518
-continued
24
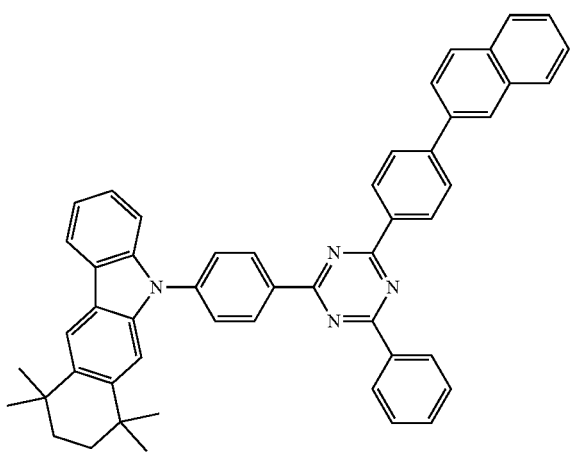
25
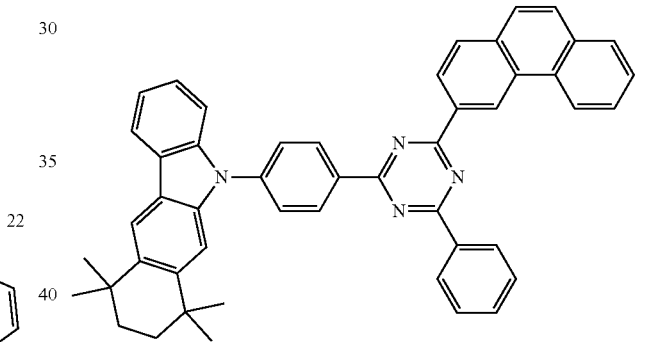
26
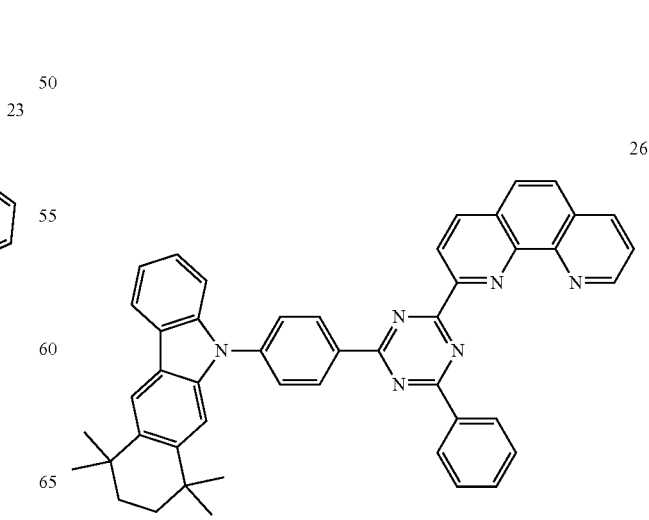

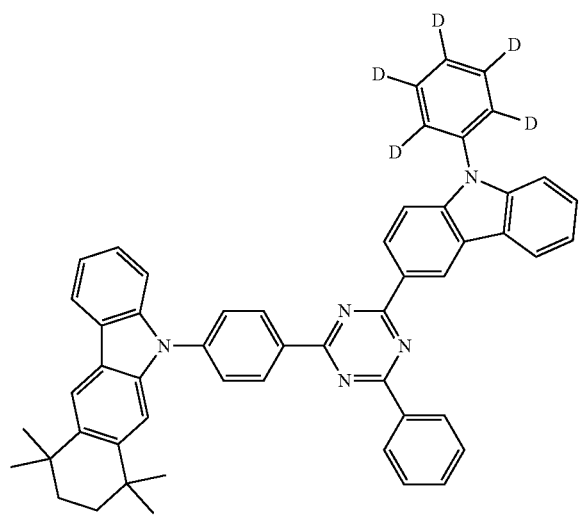
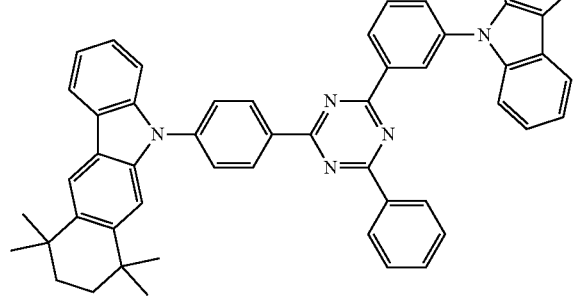
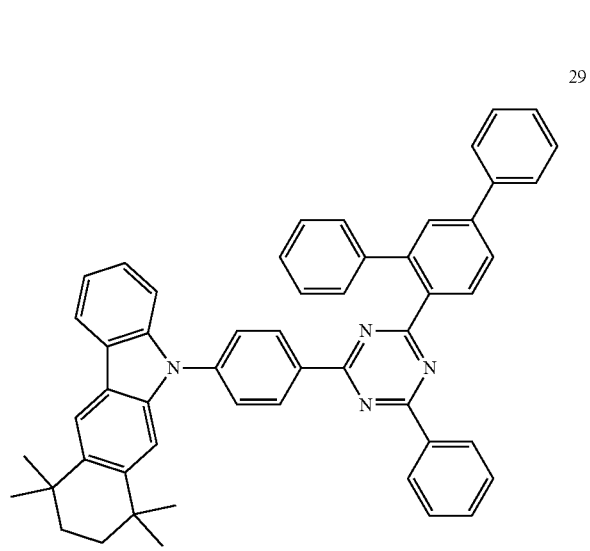
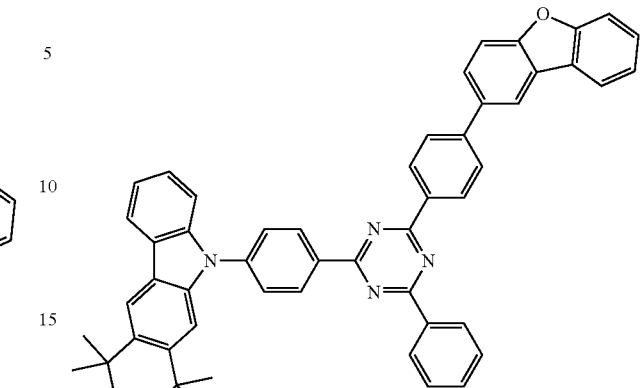
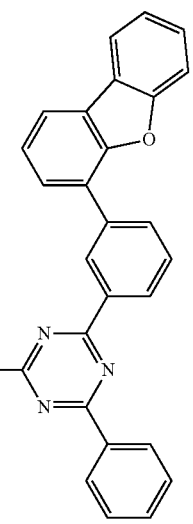

33
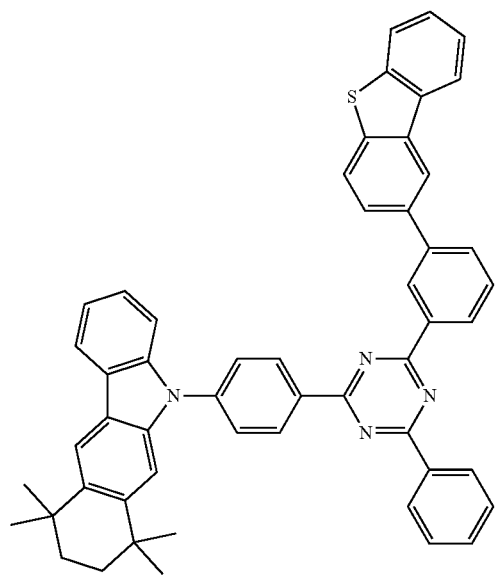
38
41
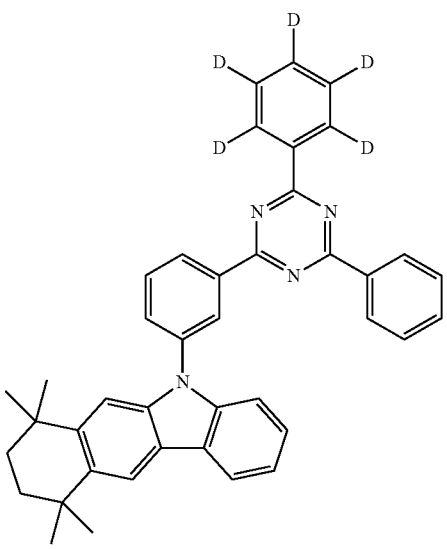
42
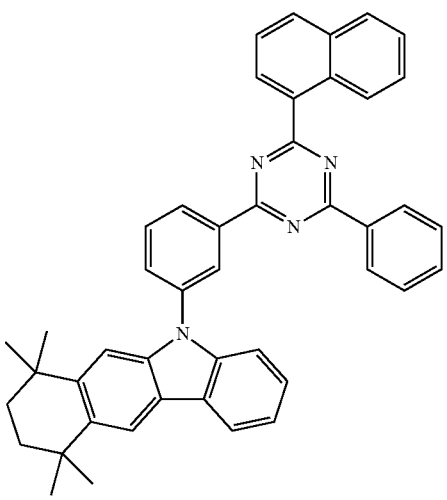
43
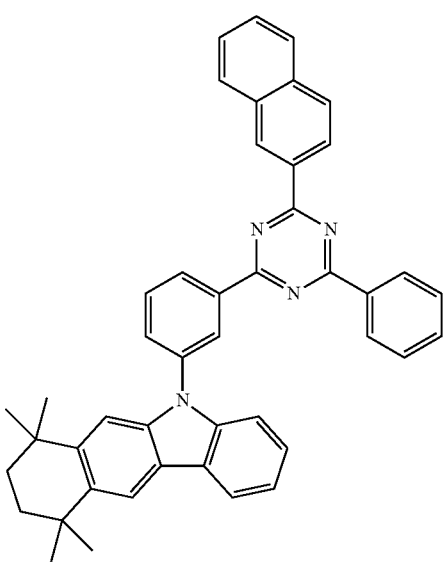

-continued
44
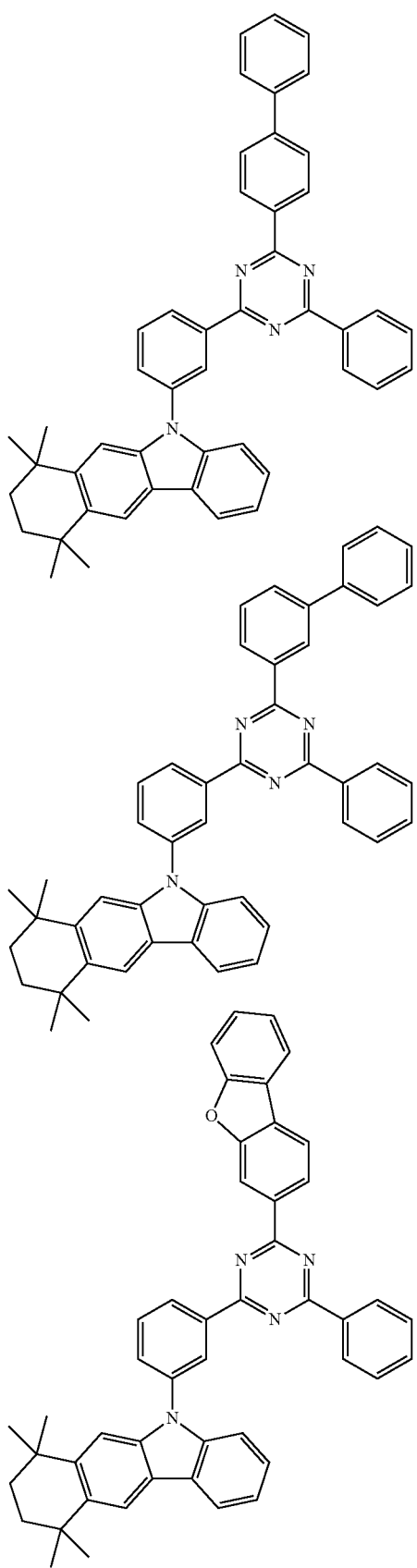
45
46
-continued
47
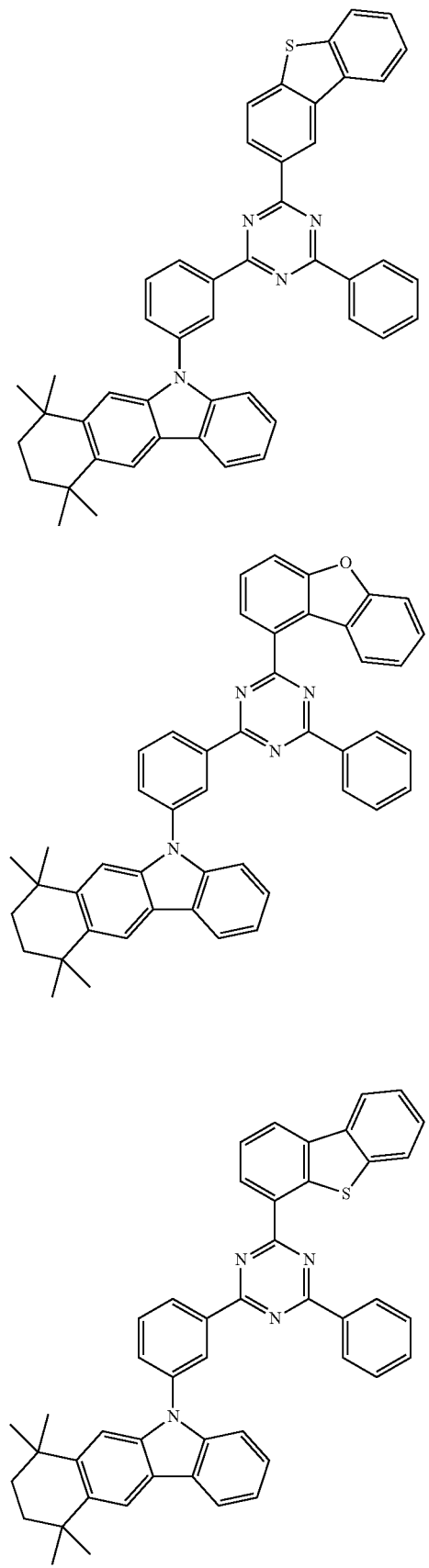
48
49

525
-continued
526
-continued
50
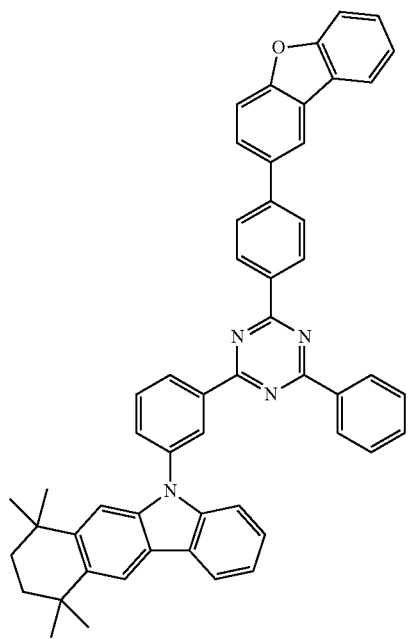
52
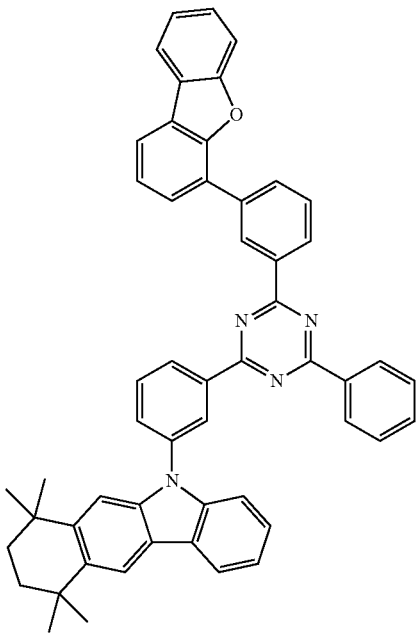
51
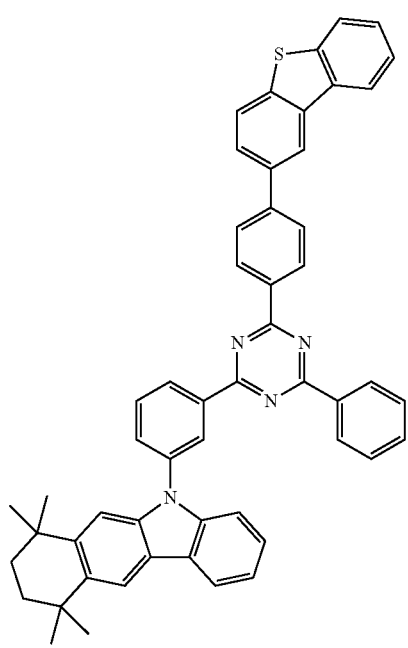
53
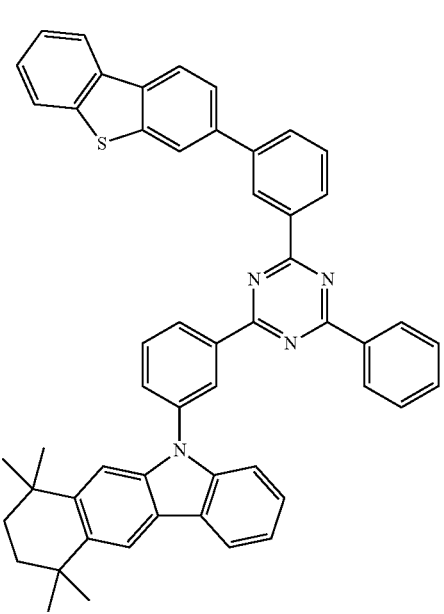

527
-continued
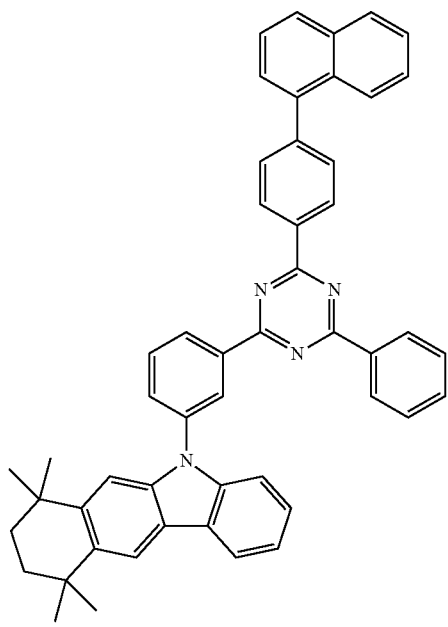
528
-continued
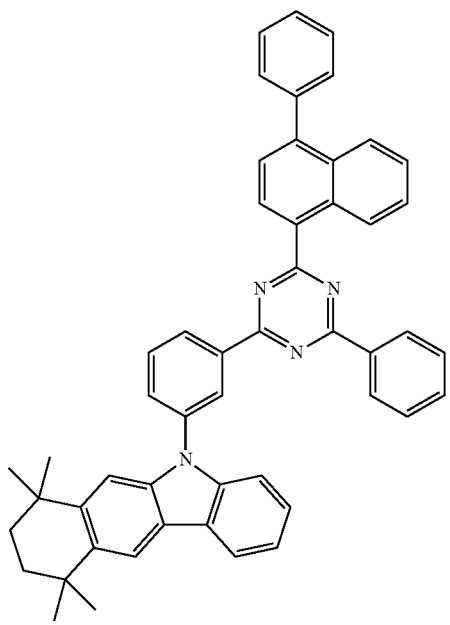
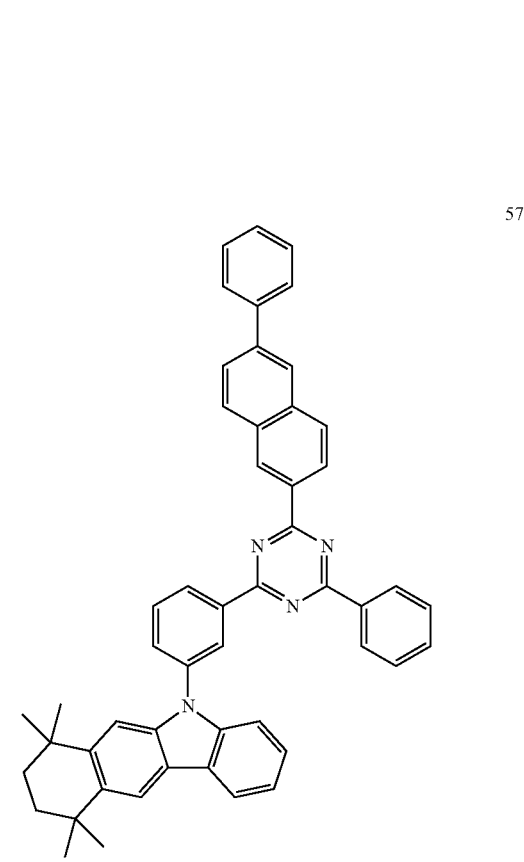

529
-continued
58
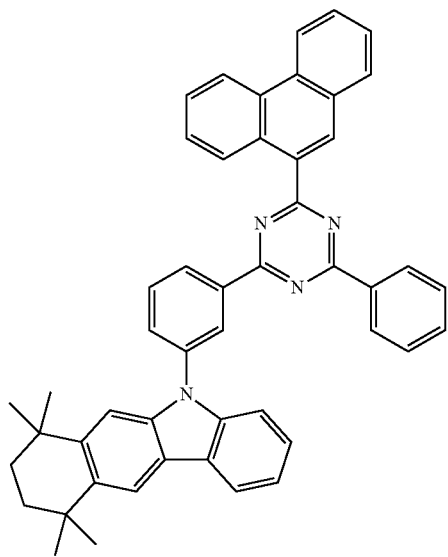
59
61
-continued
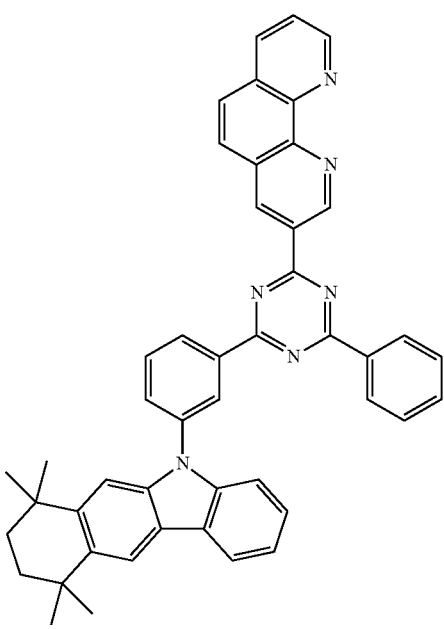
62
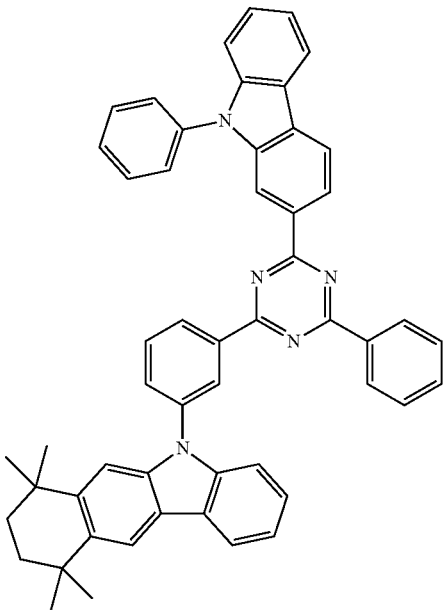
60

531
-continued
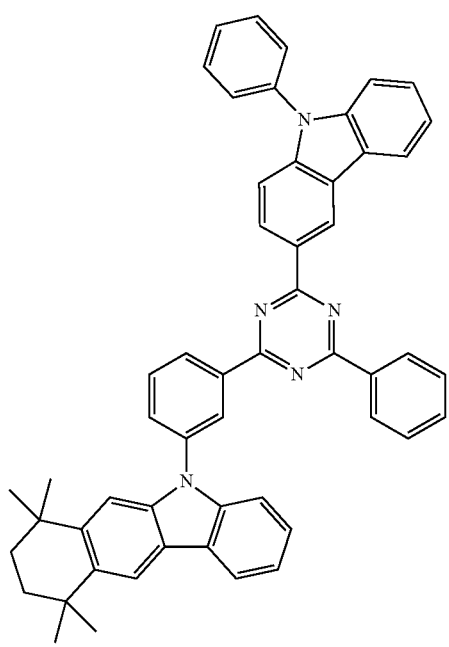
63
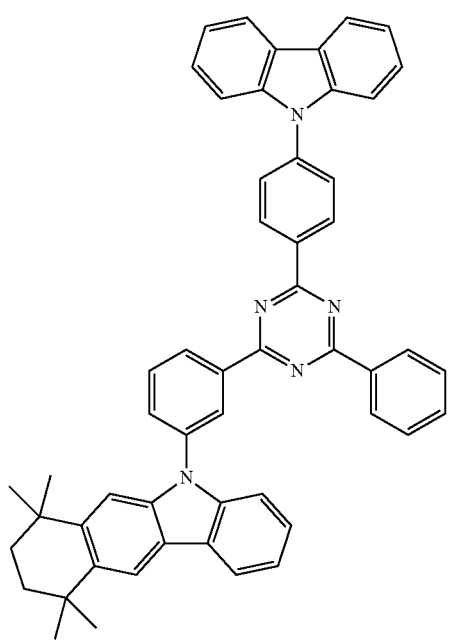
64
532
-continued
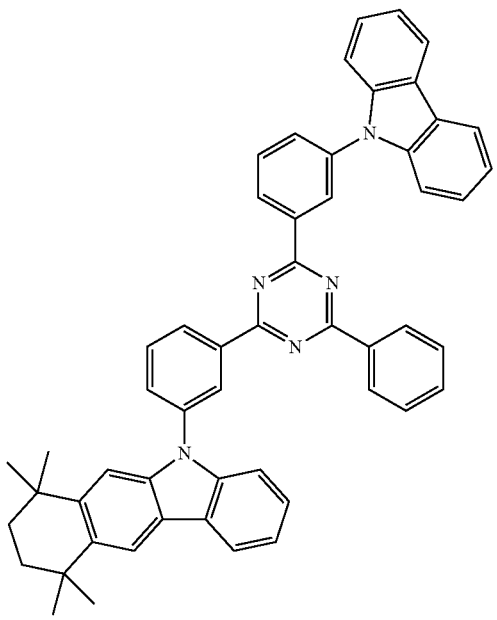
65
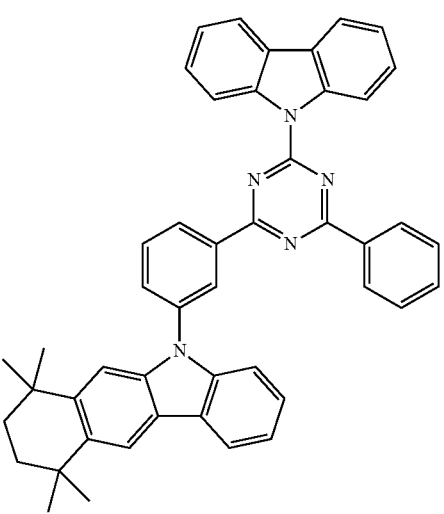
66

533
-continued
534
-continued
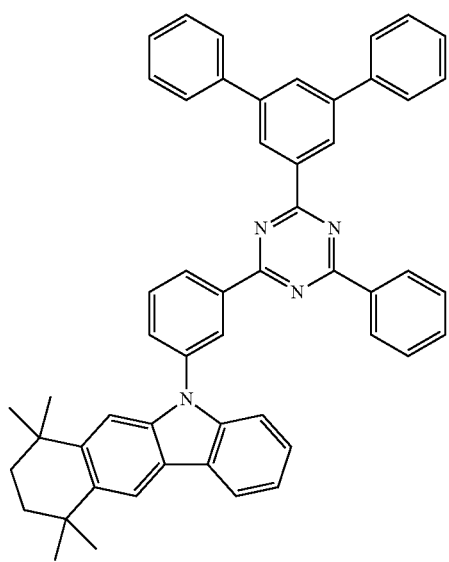
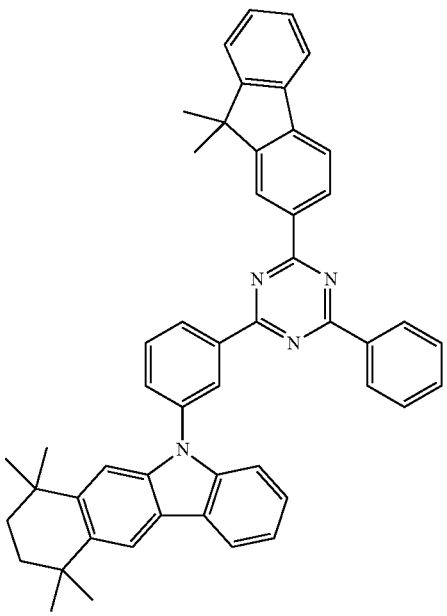

73
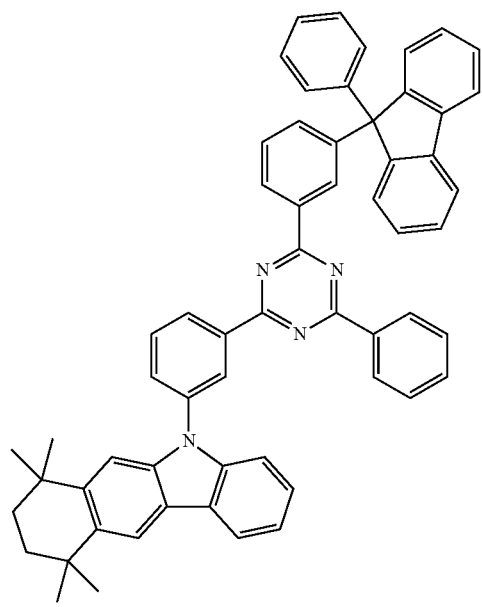
77
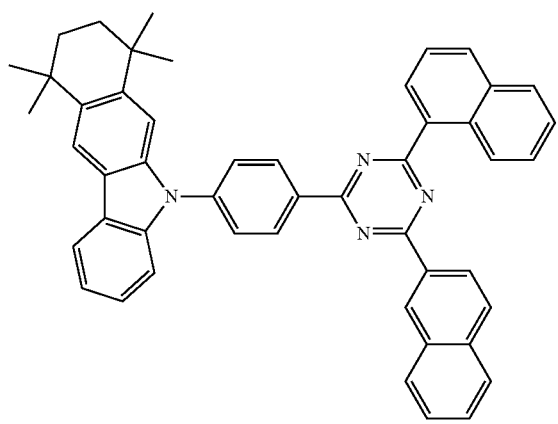
78
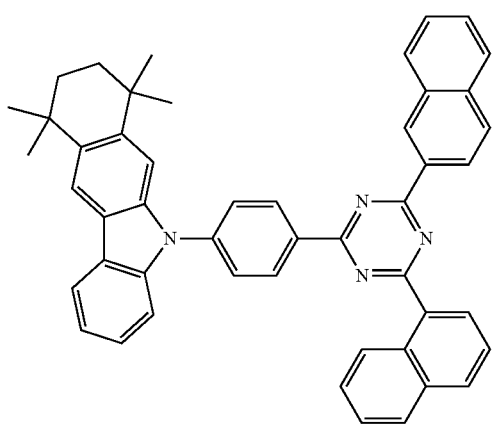
79
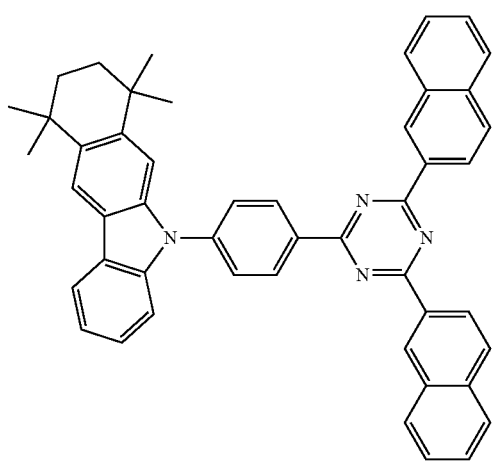
80
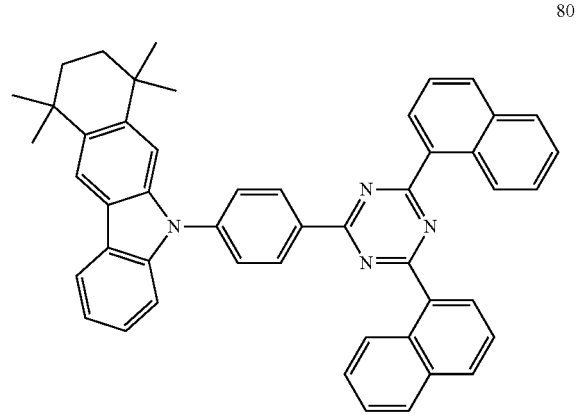
81
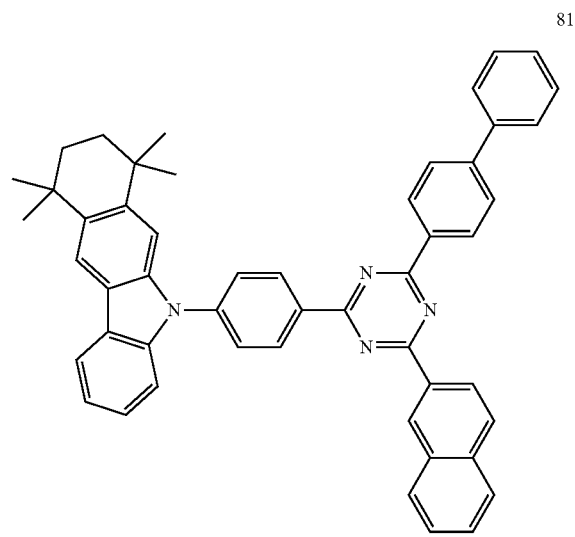

537 538
-continued -continued
82
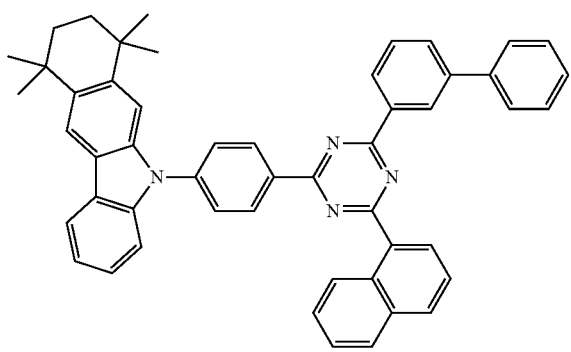
85
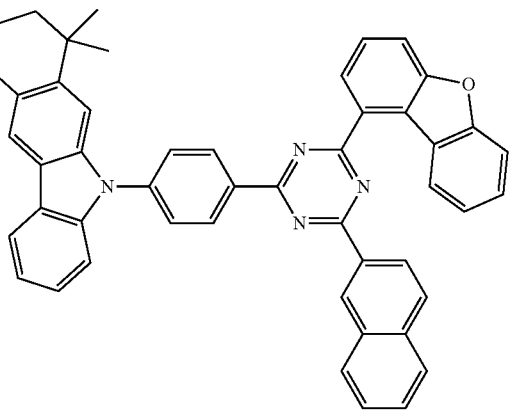
83
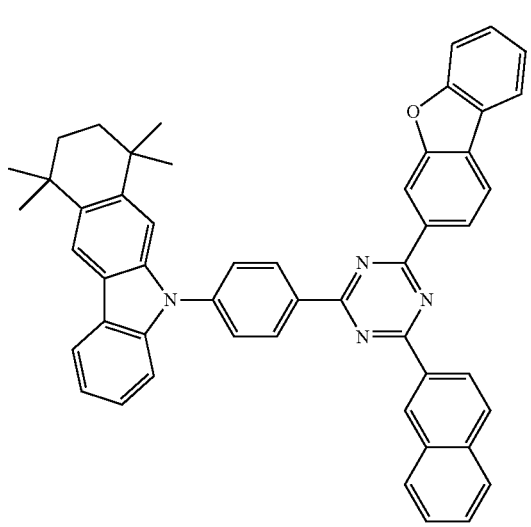
86
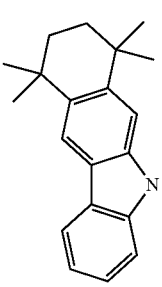
84
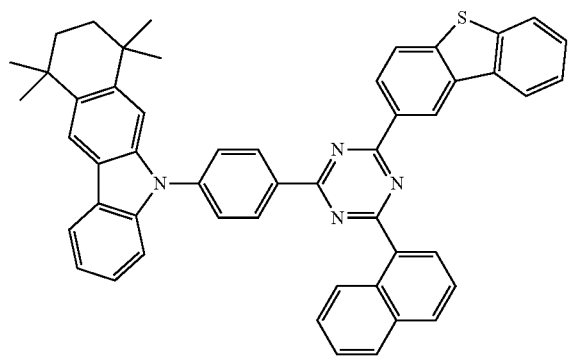
87
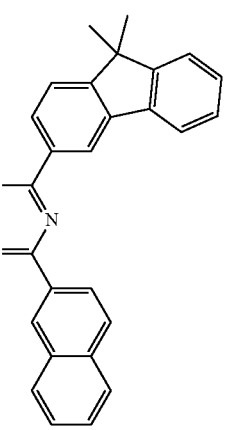

539
-continued
540
-continued
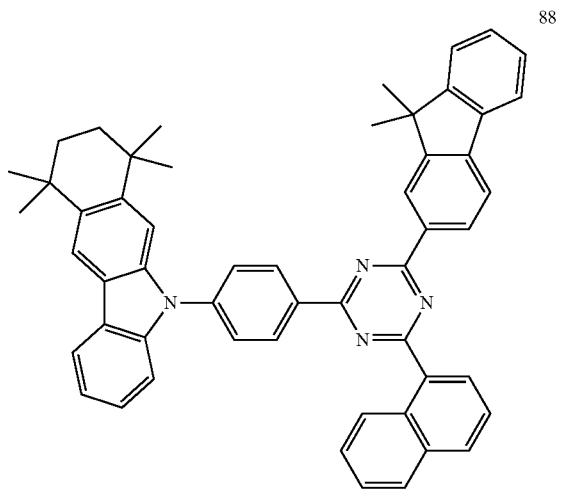
88
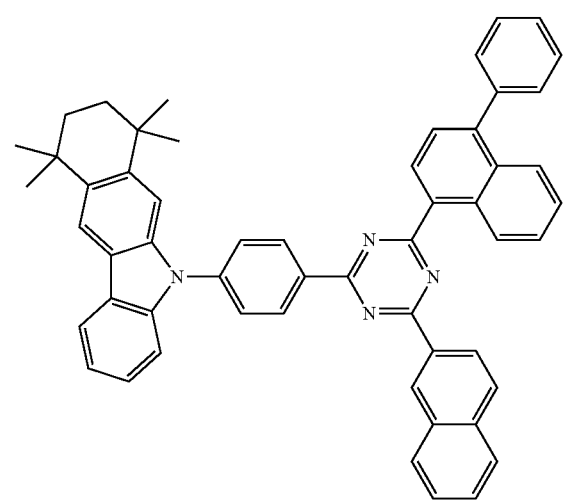
91
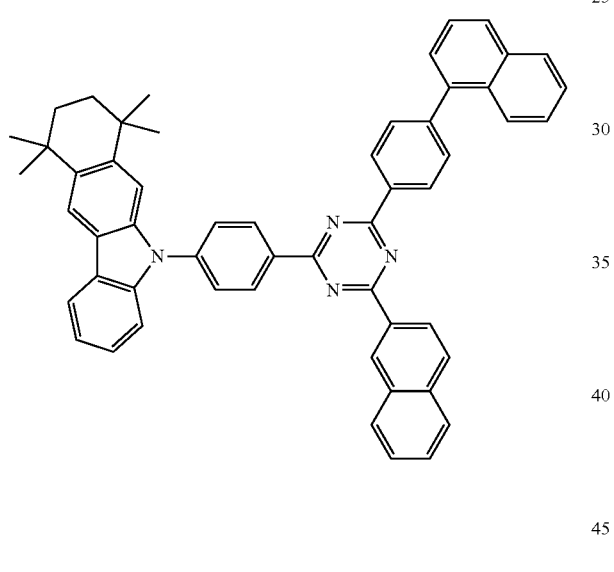
89
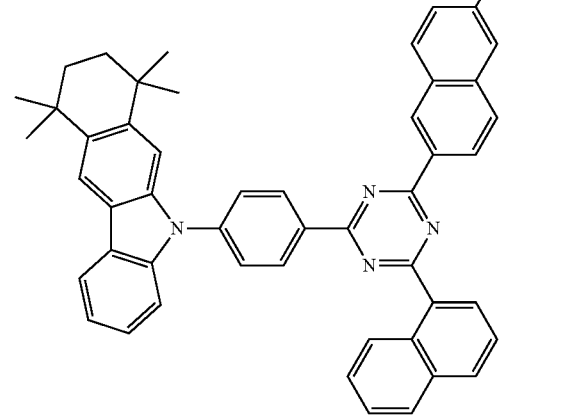
92
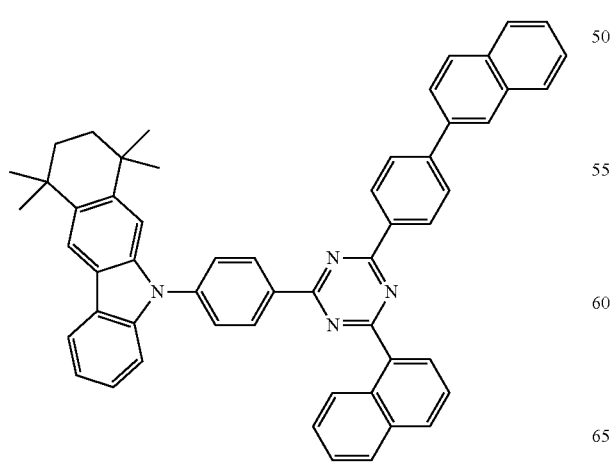
90
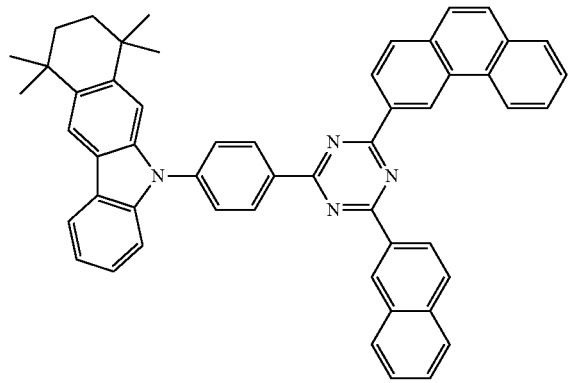
93

541
-continued
94
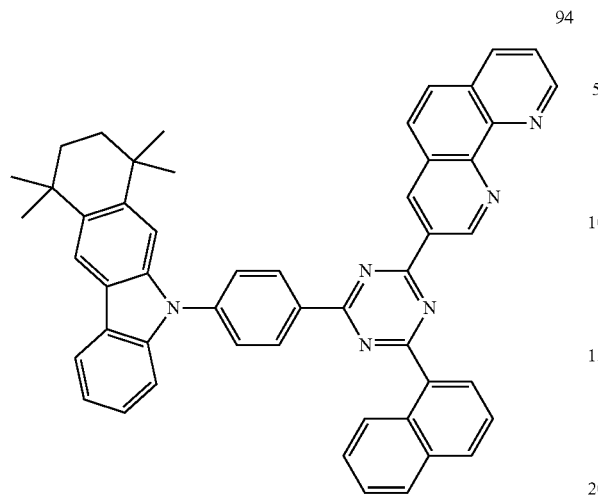
95
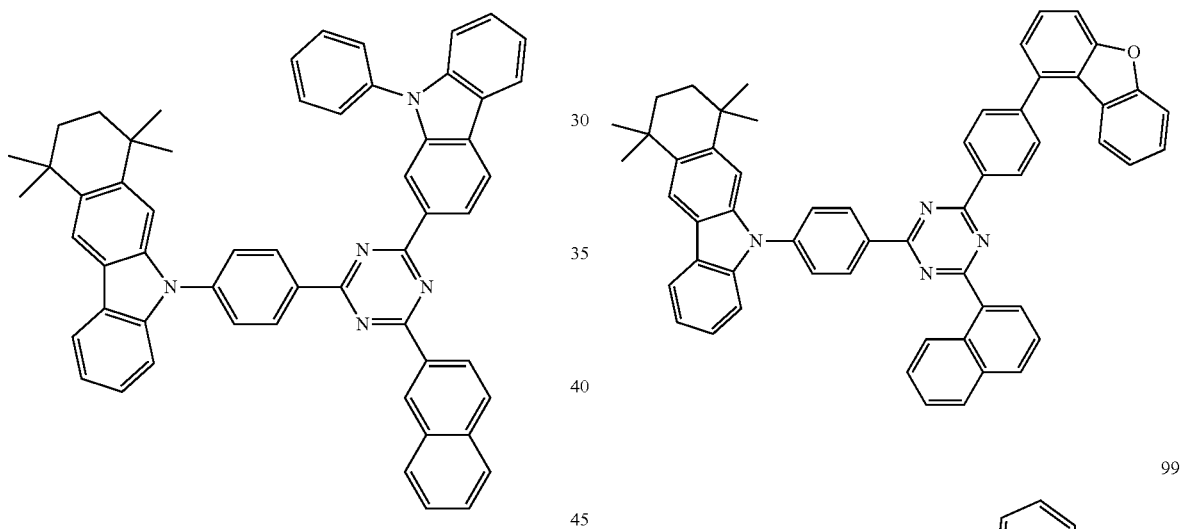
96
542
-continued
97
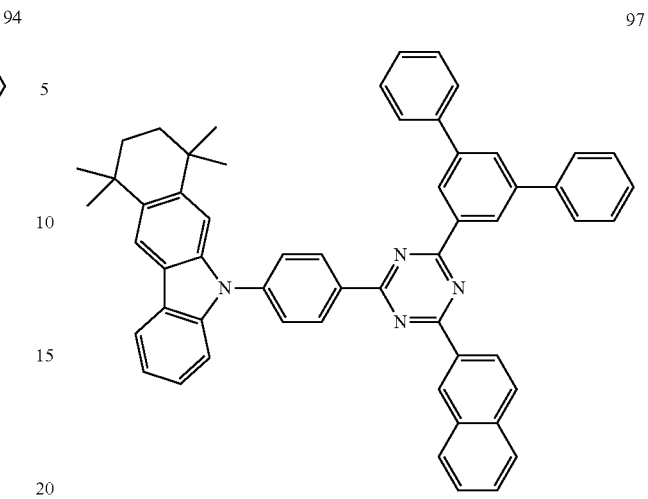
98
99
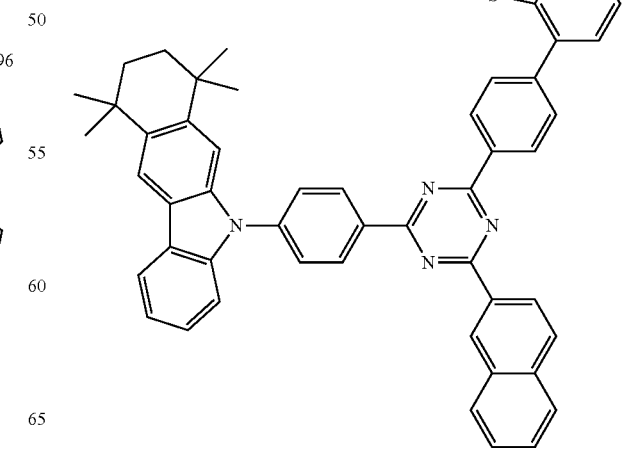

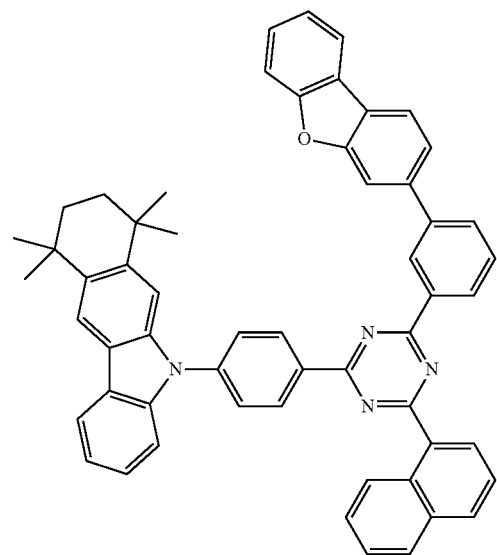
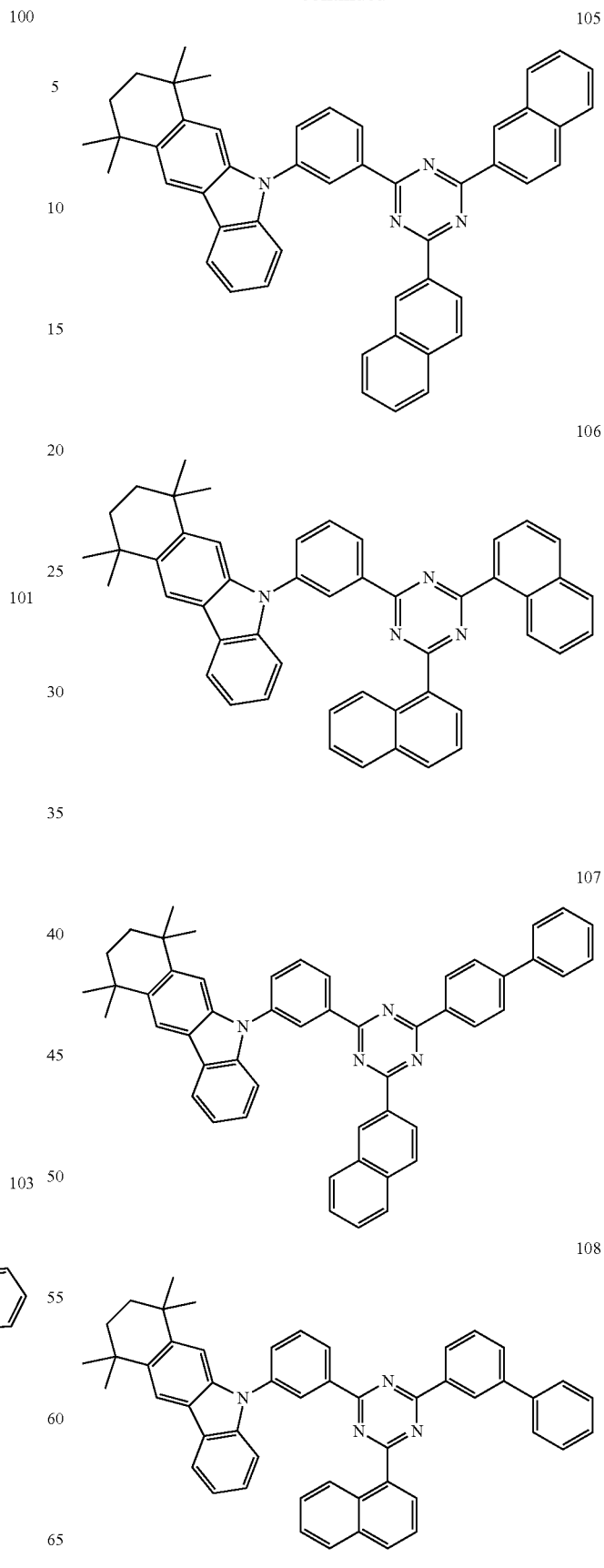

109
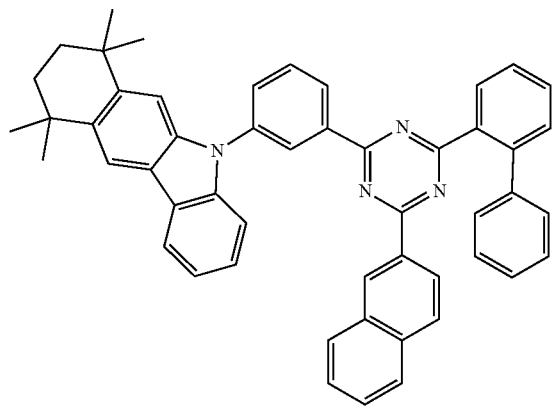
110
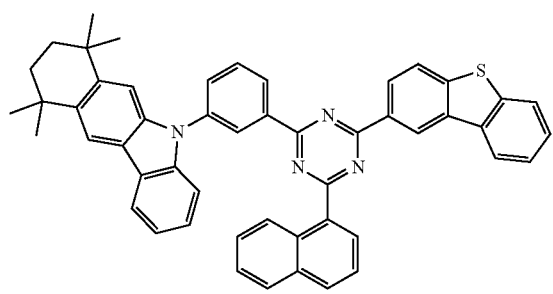
111
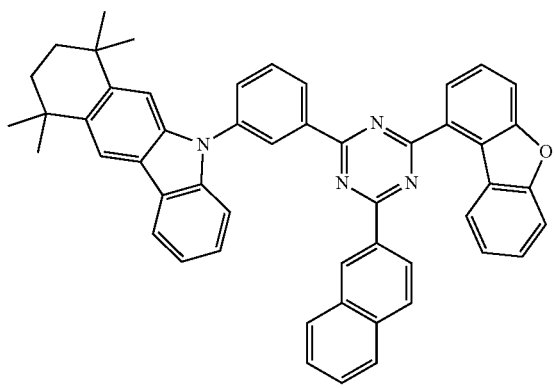
112
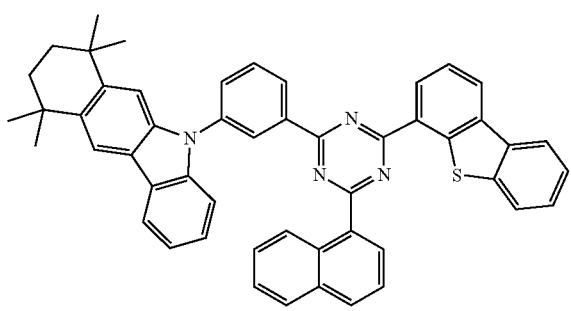

-continued
113
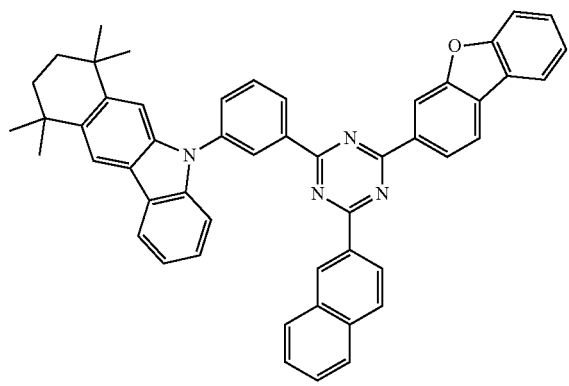
114
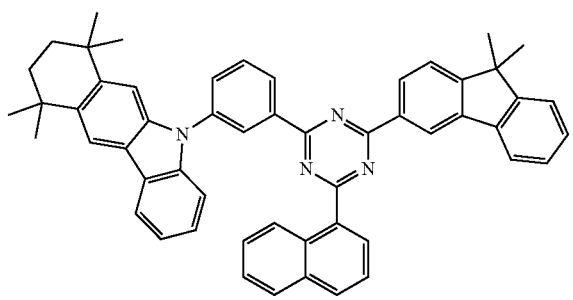
115
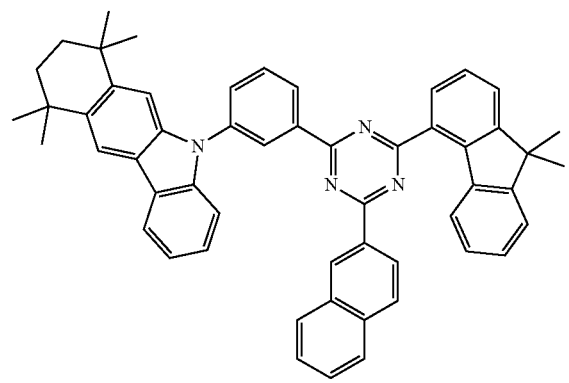
116
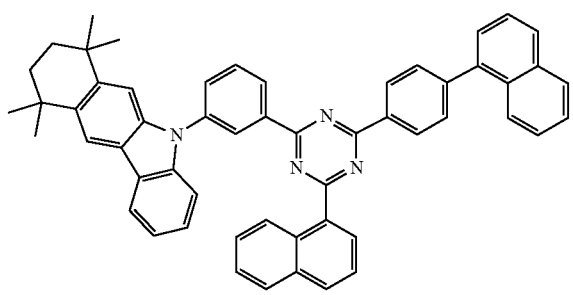

117
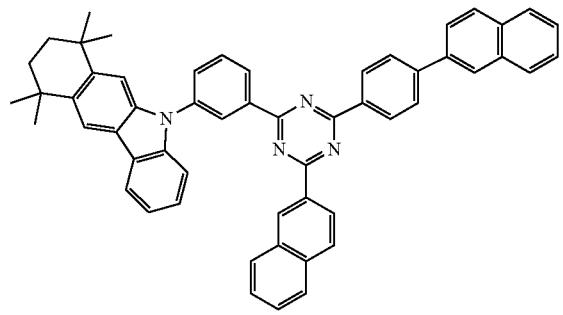
118
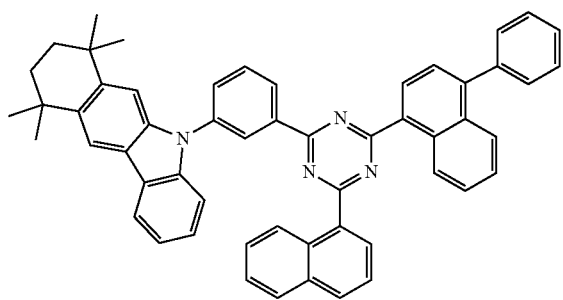
119
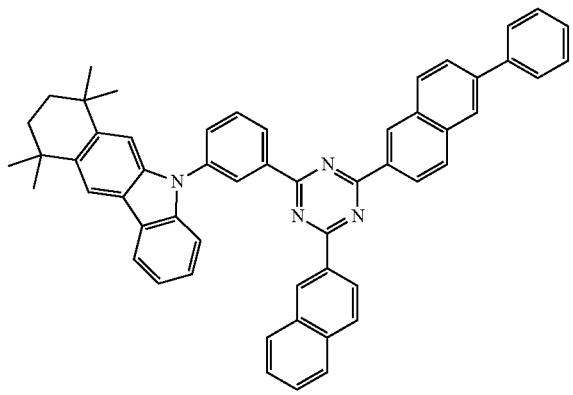
120
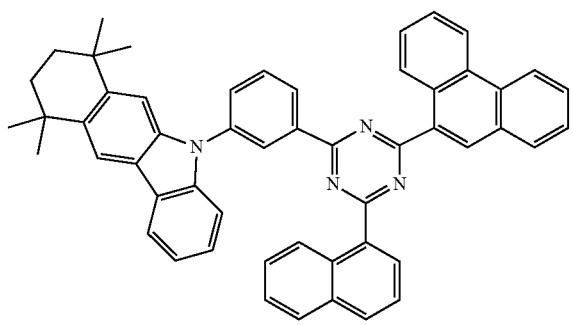

121
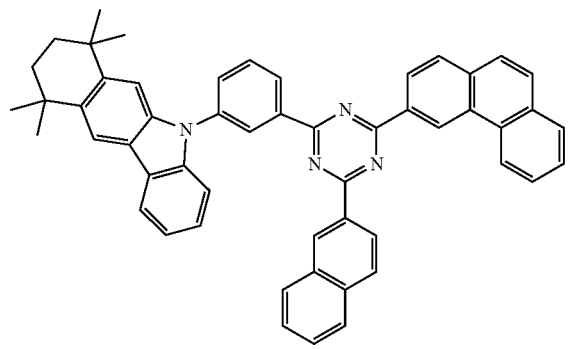
122
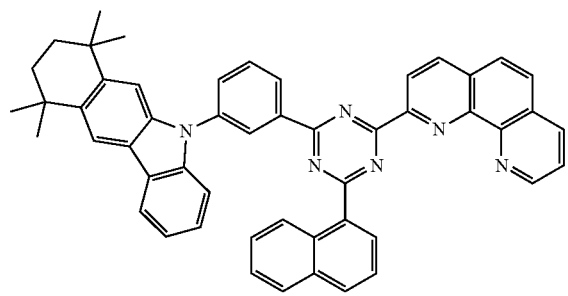
123
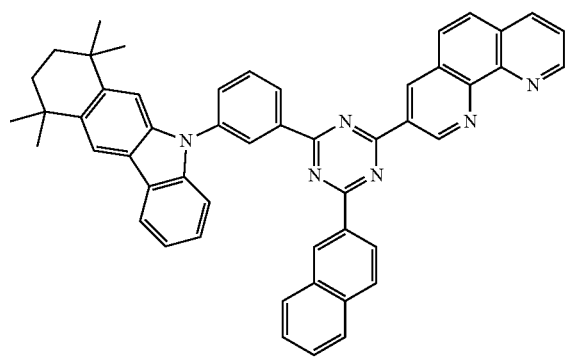
124
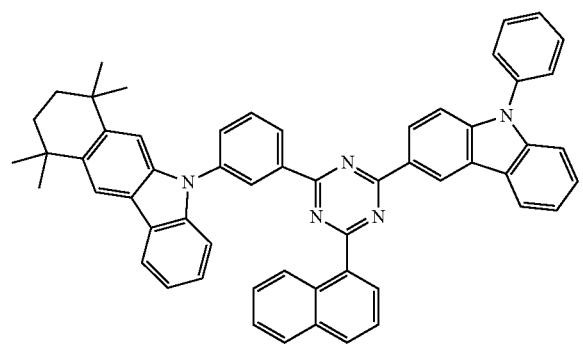

125
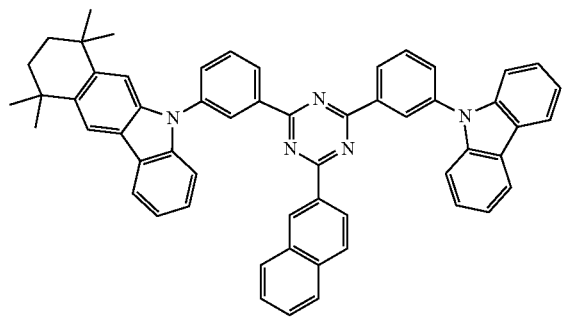
126
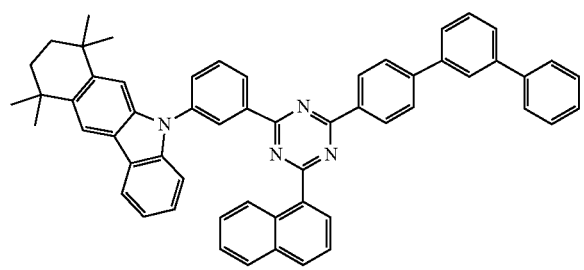
127
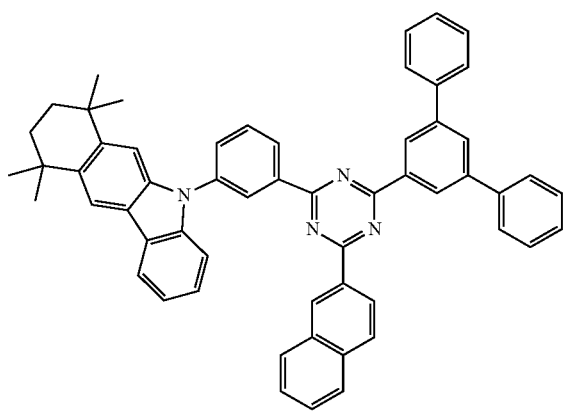
128
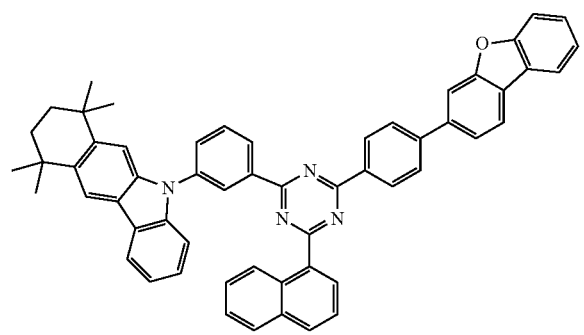

129
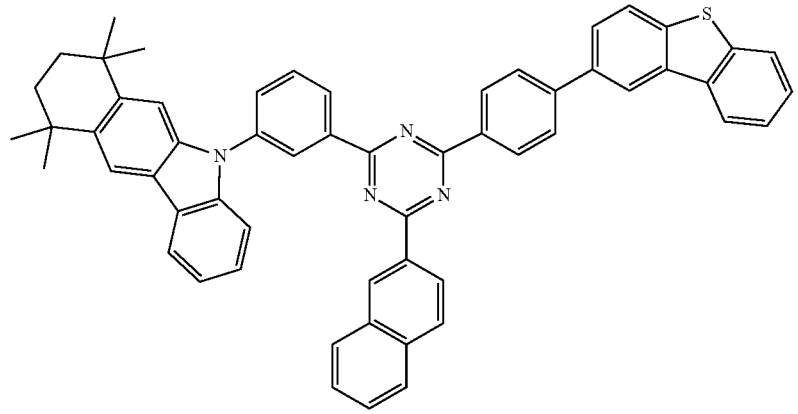
130
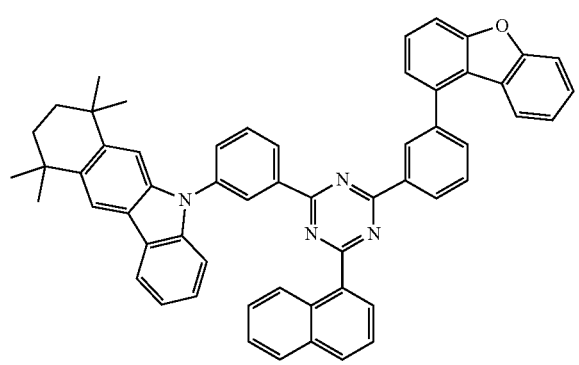
131
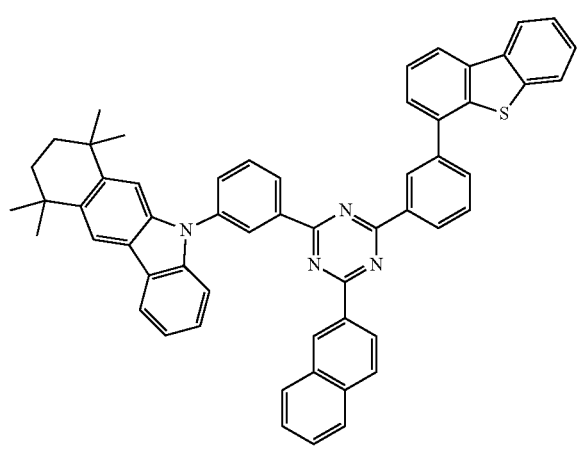
133
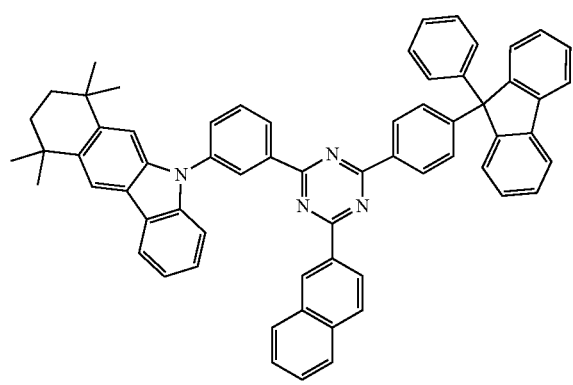
135
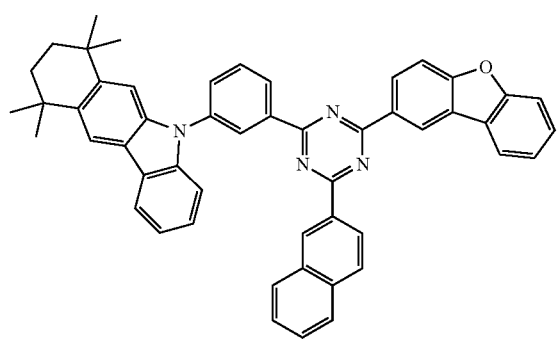
136
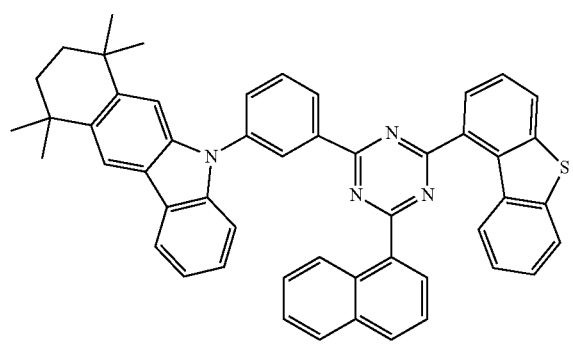
137
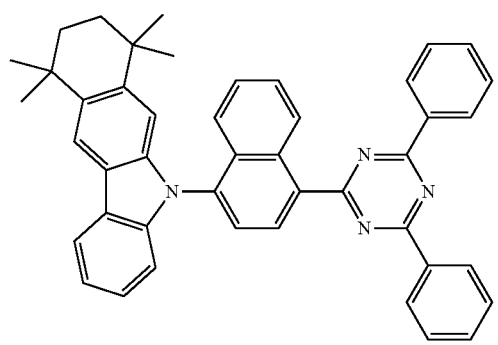

-continued
138
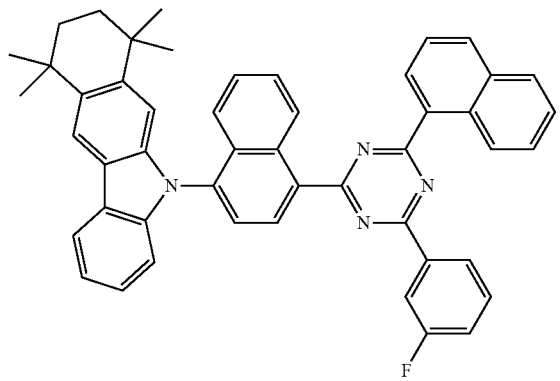
139
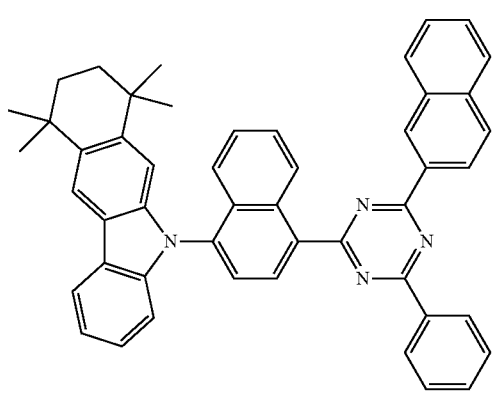
140
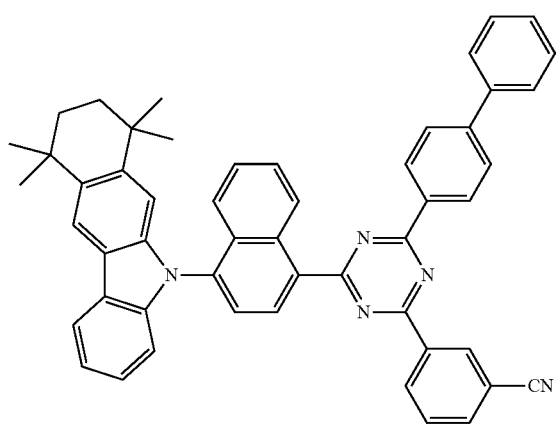
141
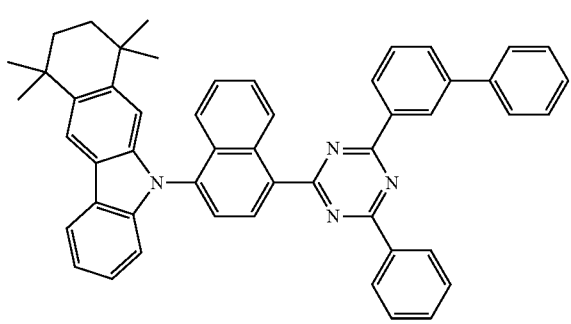
-continued
142
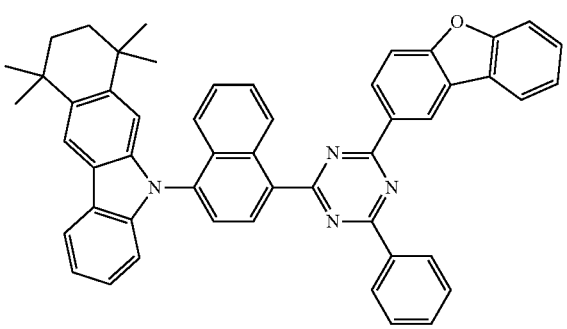

559
-continued
143
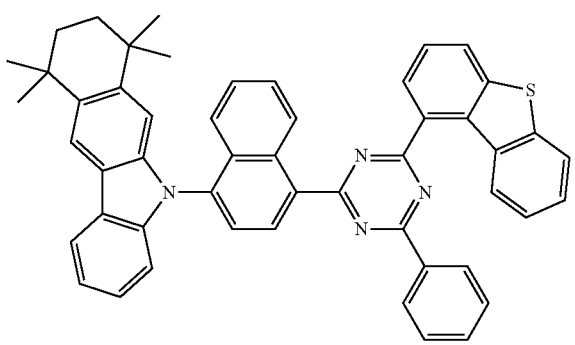 [SMILES: CC1(C)CCC(C)(C)c2cc3c(cc21)c1ccccc1n3-c1ccc(-c2nc(-c3ccccc3)nc(-c3cccc4sc5ccccc5c34)n2)c2ccccc12]
144
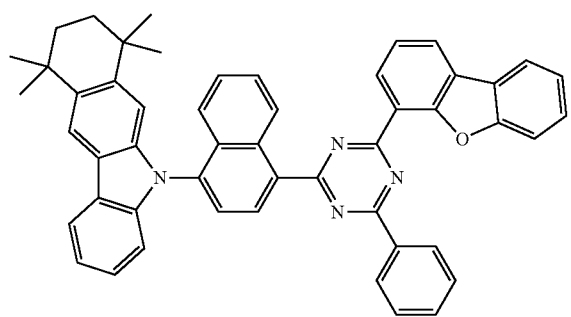
145
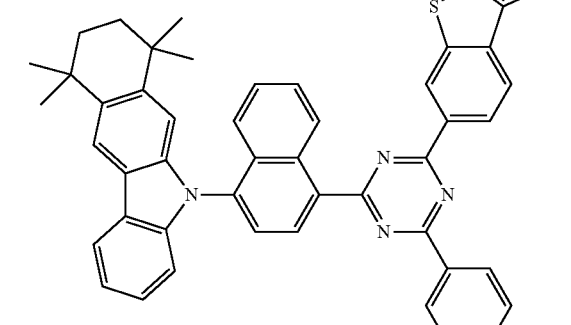
146
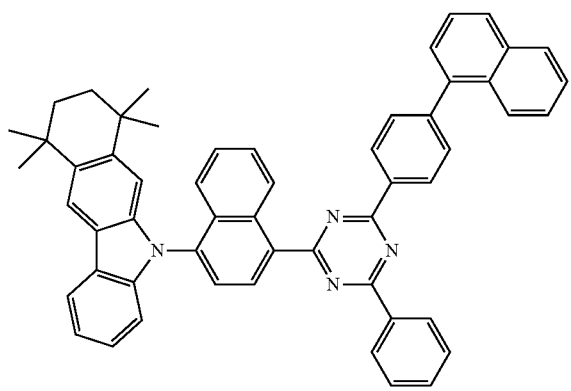
560
-continued
147
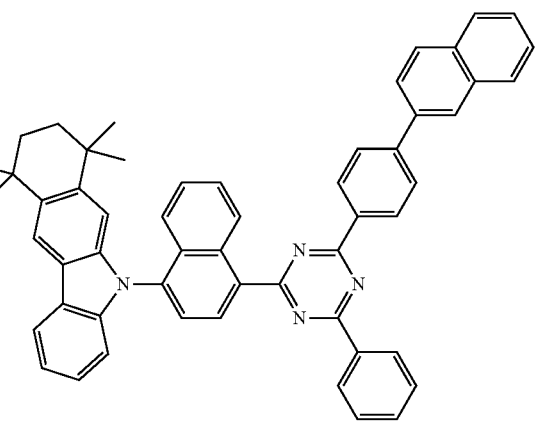
148
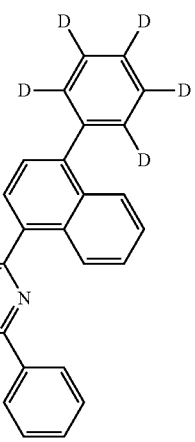
149
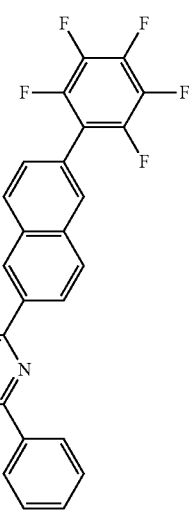

561
-continued
150
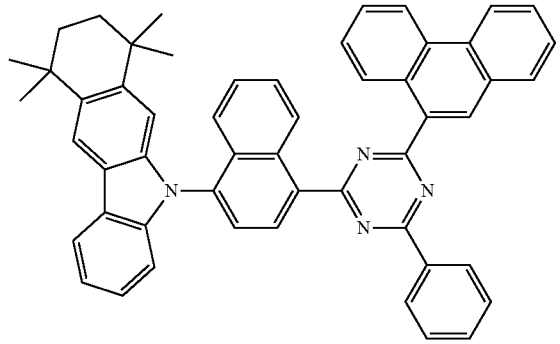
151
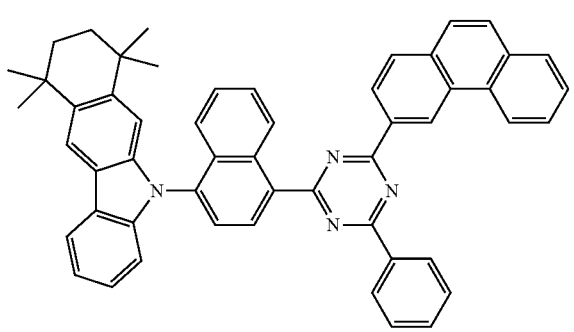
152
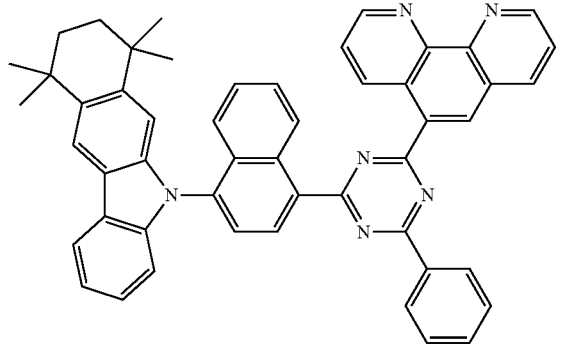
153
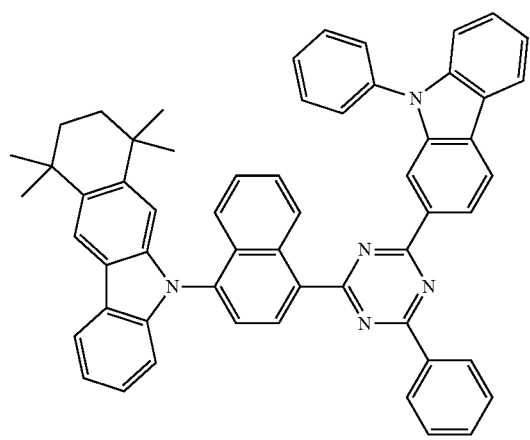
562
-continued
154
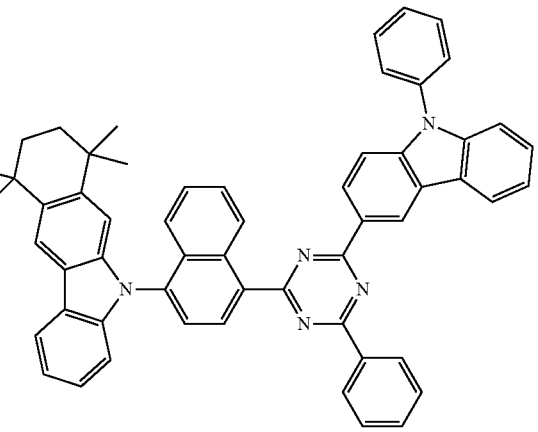
155
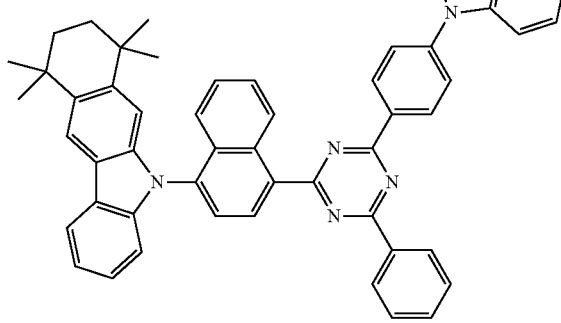
156
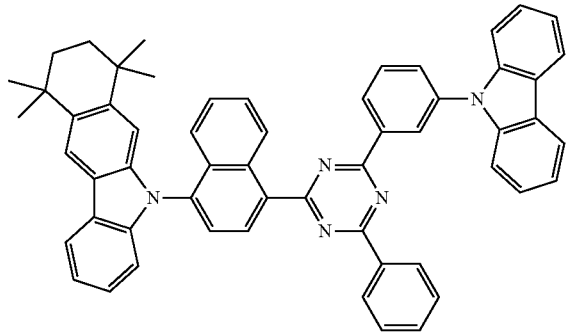

157
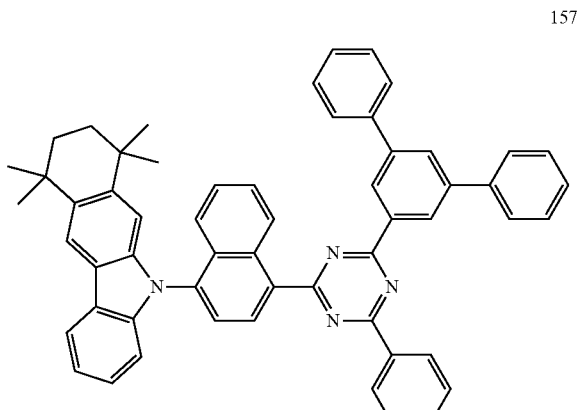
158
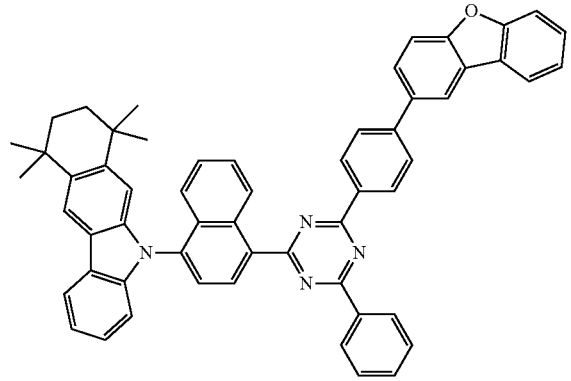
159
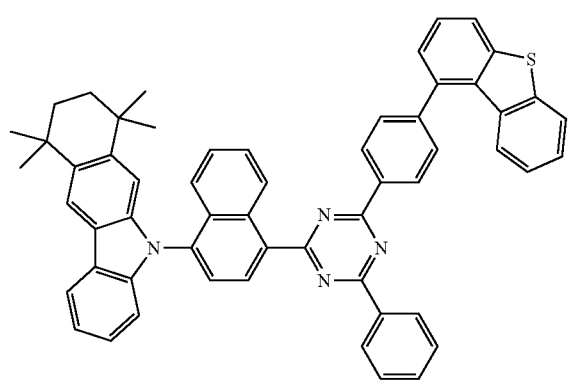
160
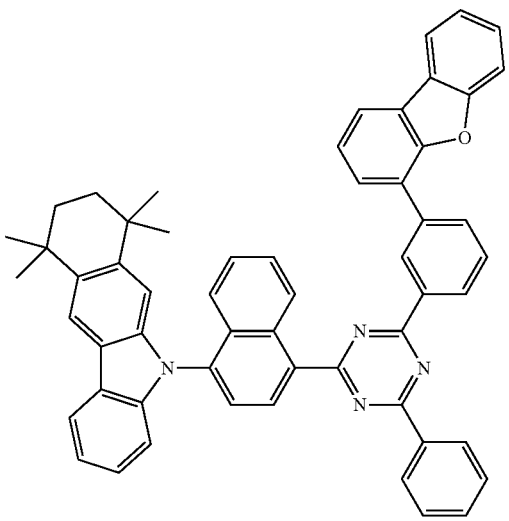
161
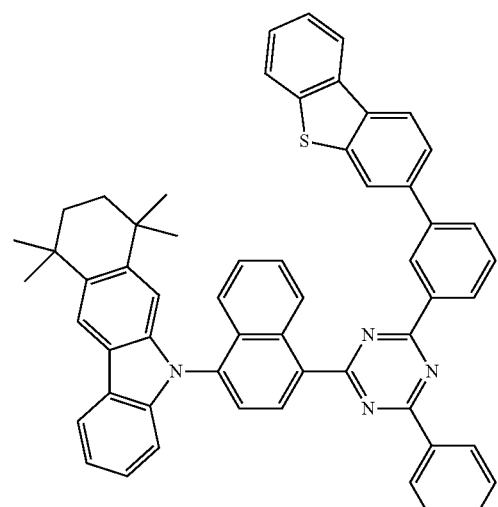
163
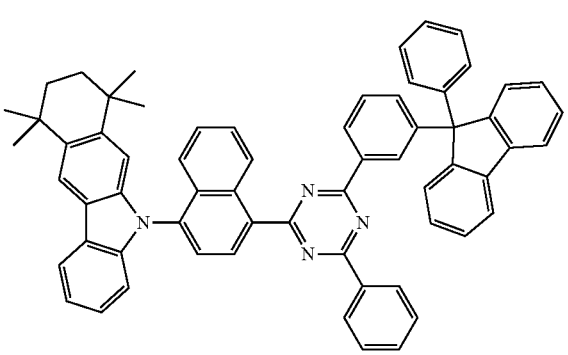

165
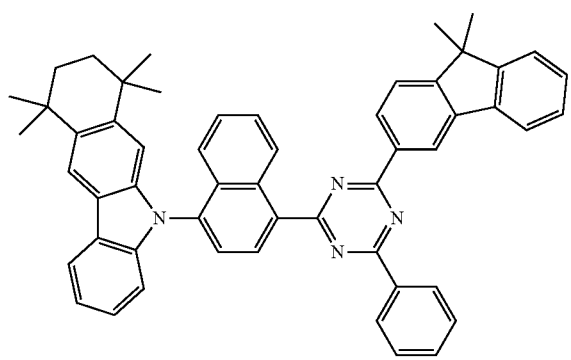
166
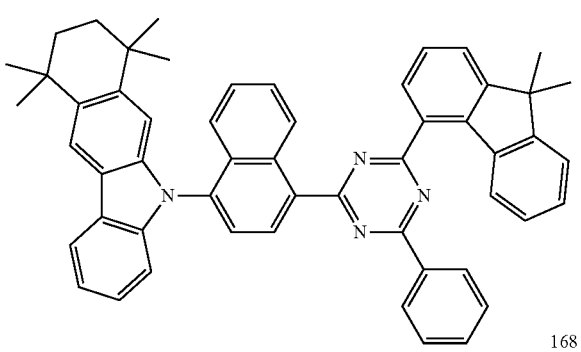
168
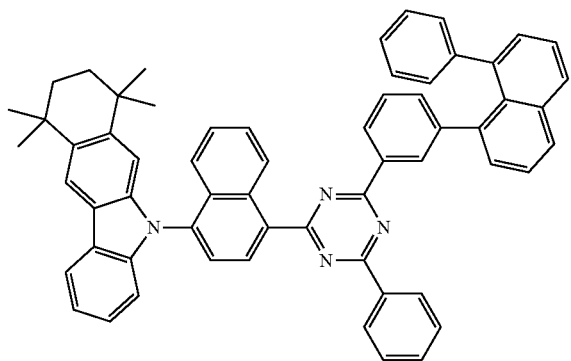
169
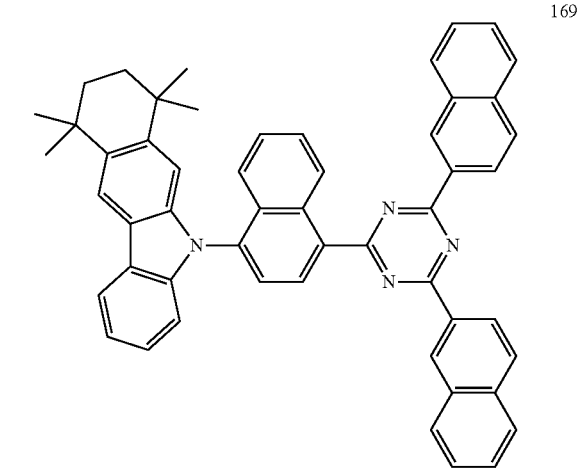
170
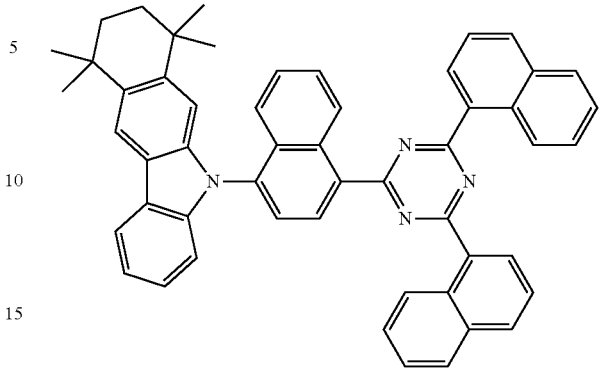
171
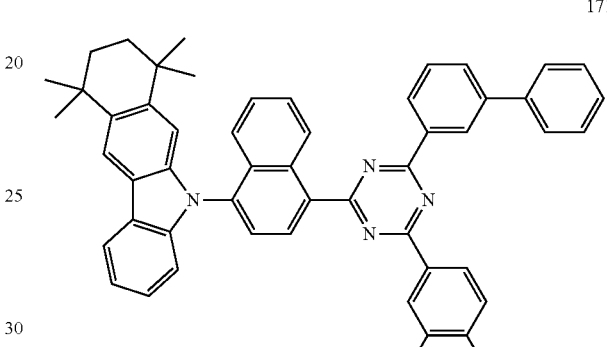
172
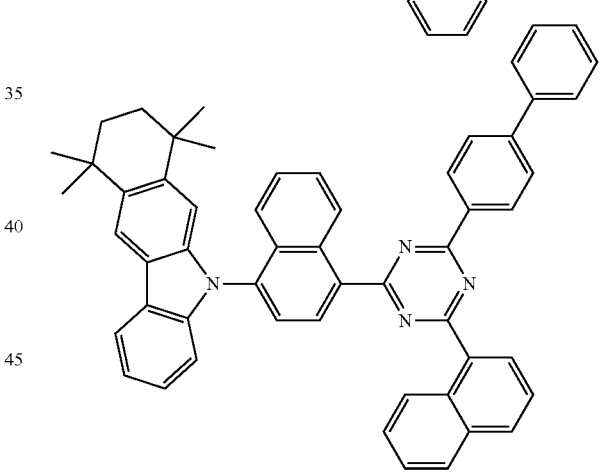
173
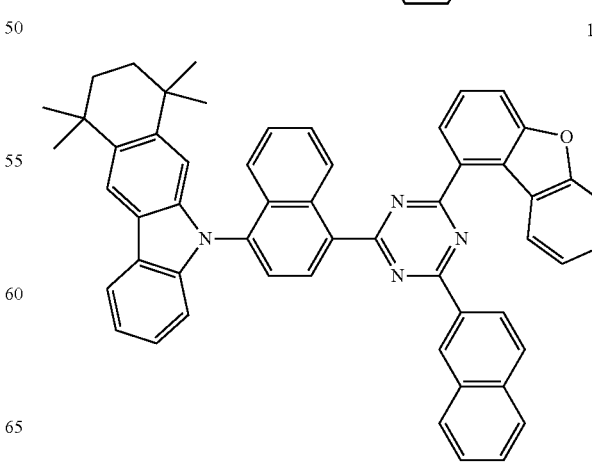

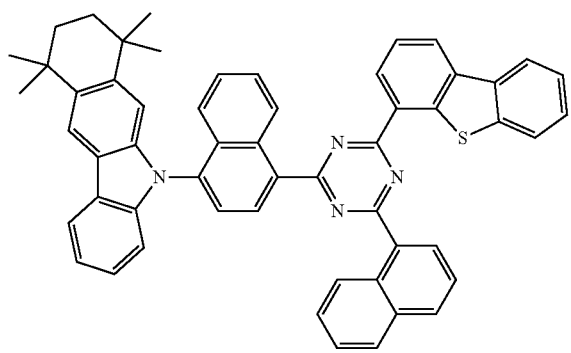
174
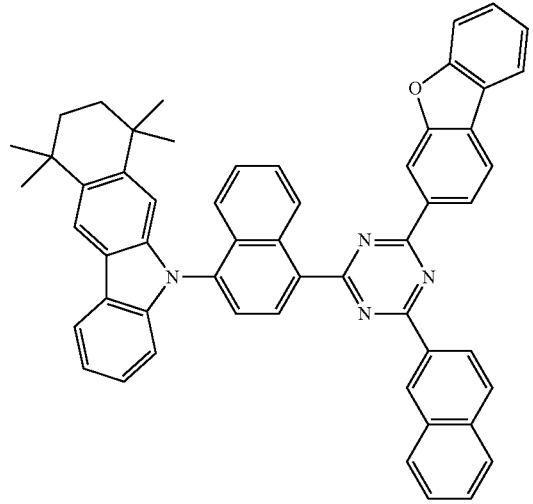
175
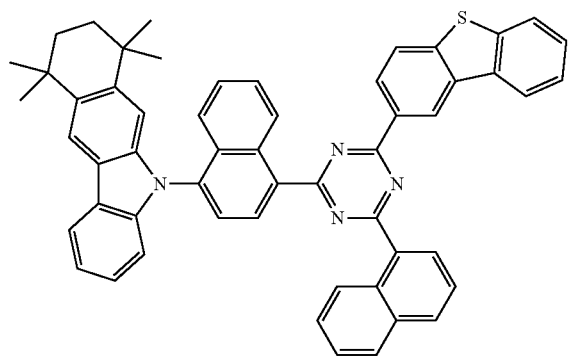
176
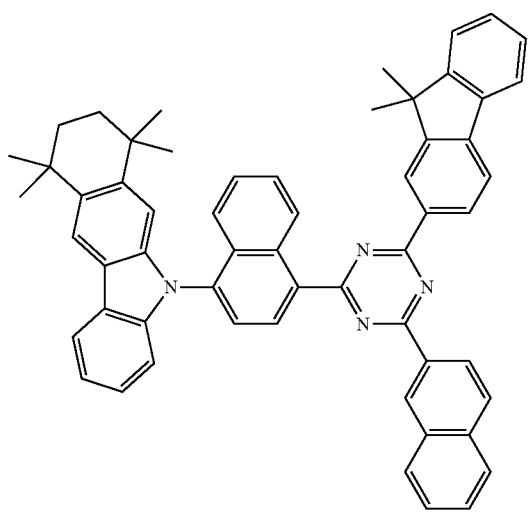
177
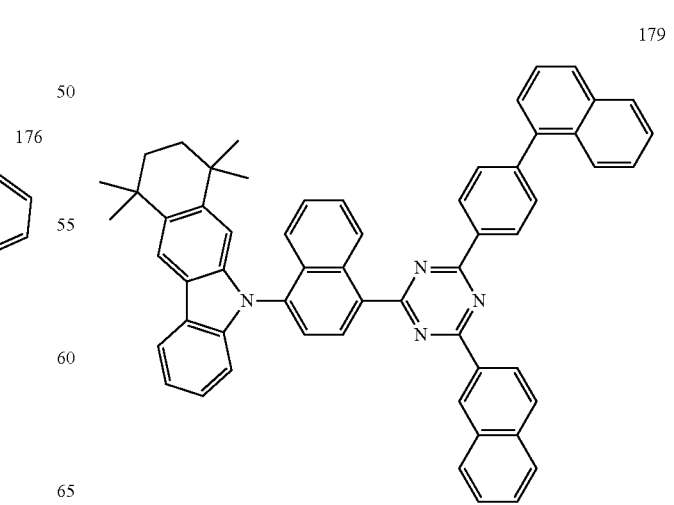
178
179

569
-continued
180
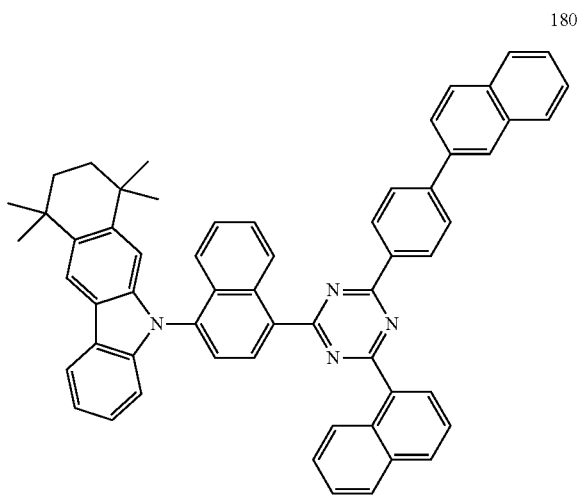
181
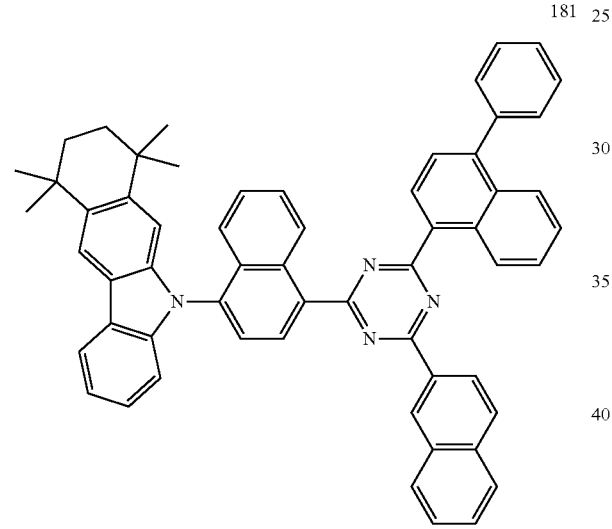
182
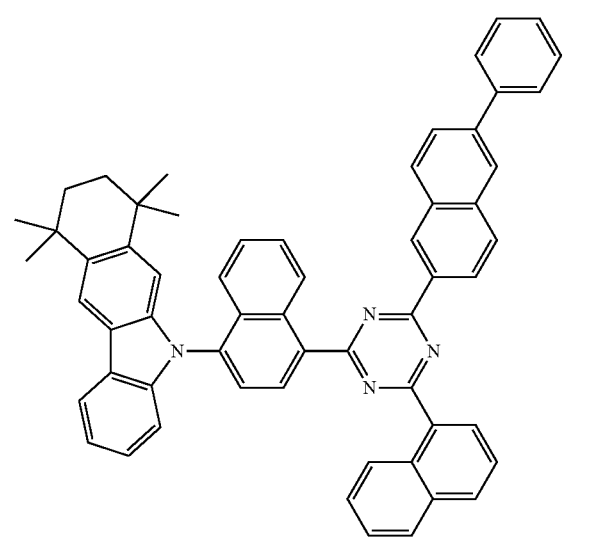
570
-continued
183
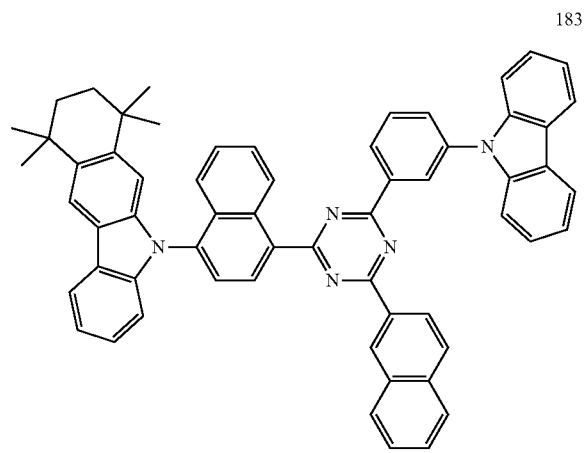
184
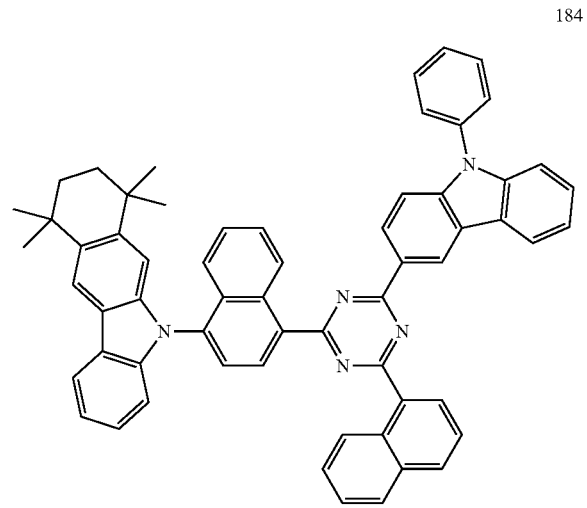
185
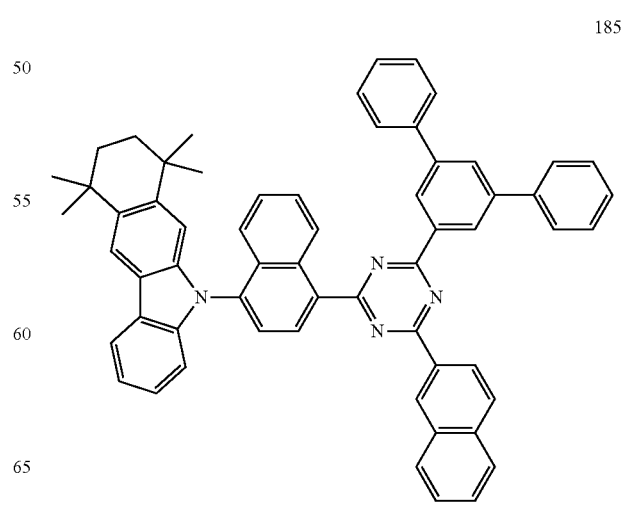

186
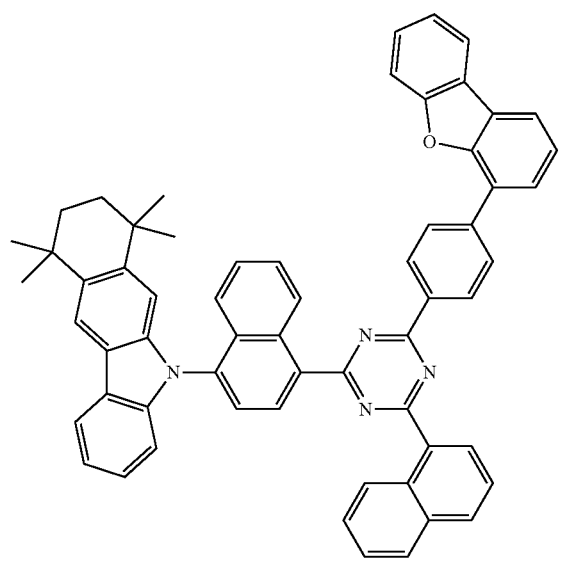
187
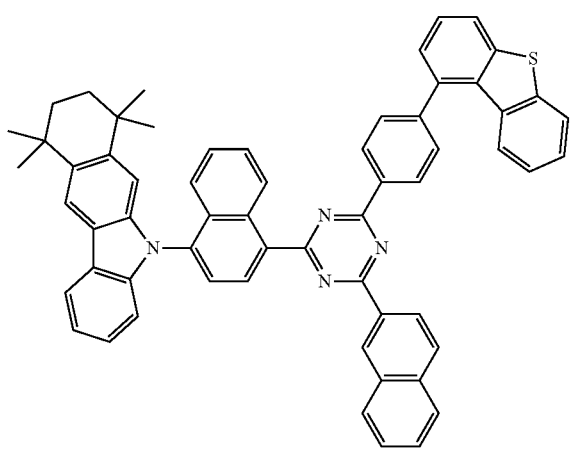
188
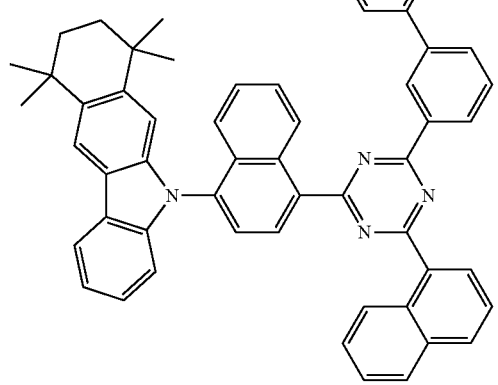
190
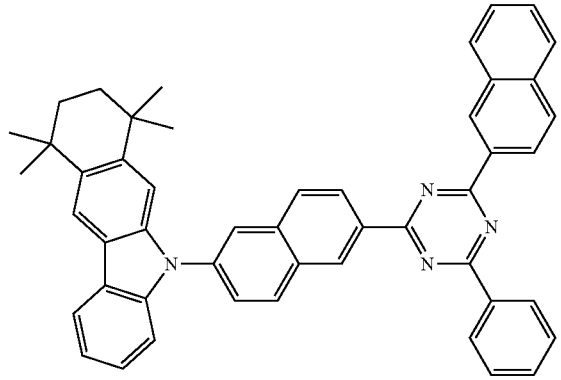
191
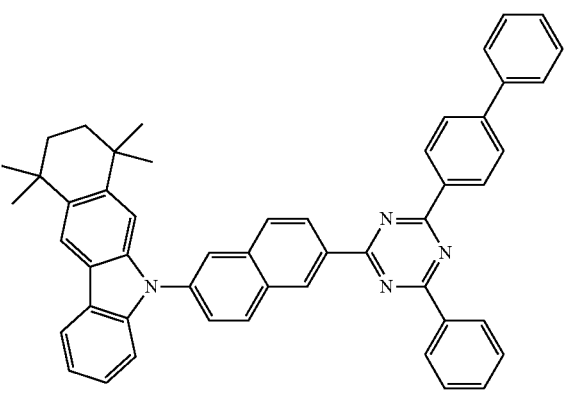
192
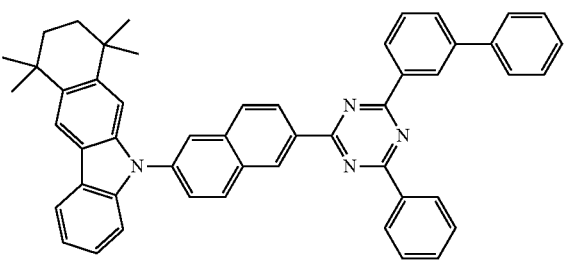 [SMILES: CC1(C)CCC(C)(C)c2cc3c(cc21)c1ccccc1n3-c1ccc2cc(-c3nc(-c4ccccc4)nc(-c4cccc(-c5ccccc5)c4)n3)ccc2c1]
193
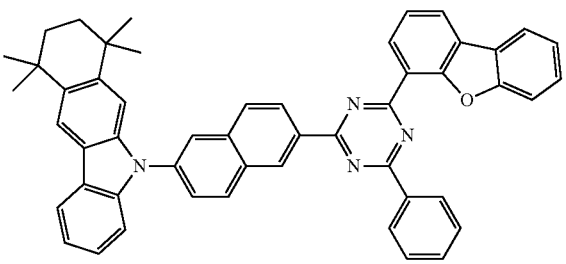

194 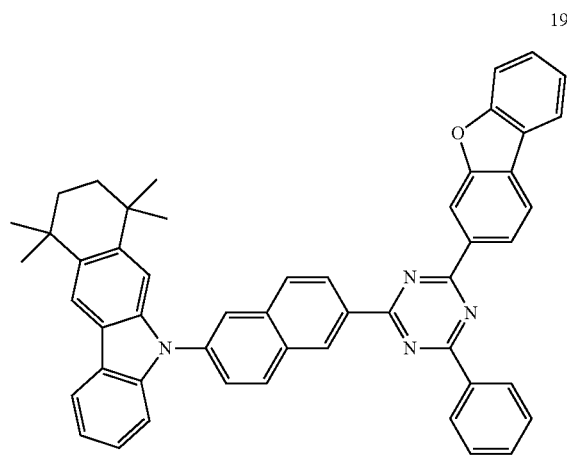
195 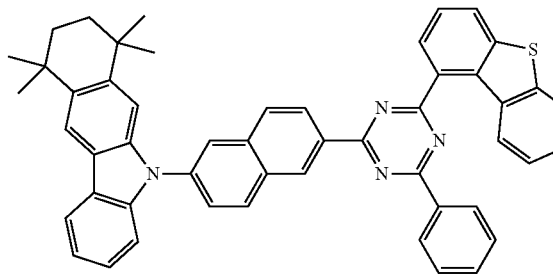
196 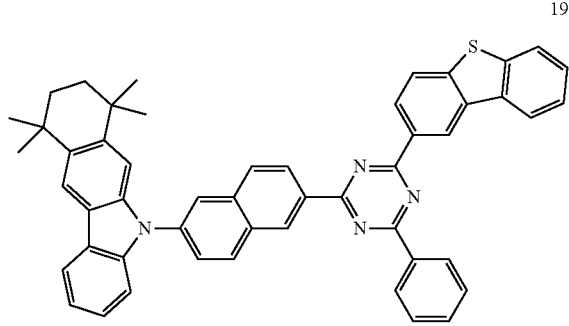
197 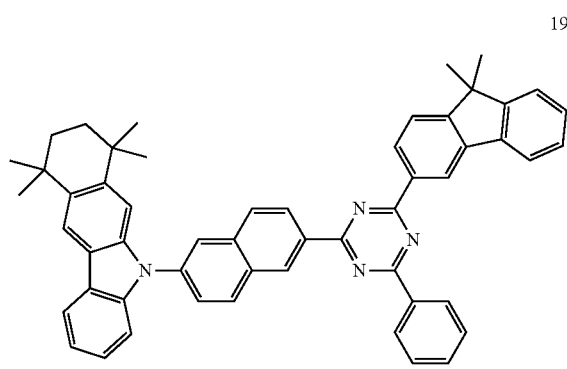
198 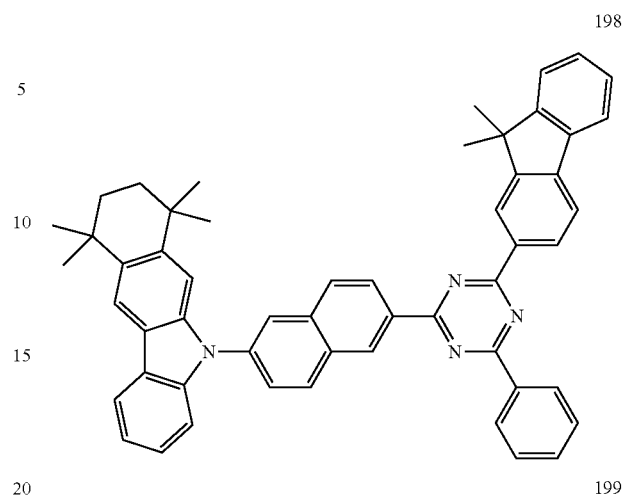
199 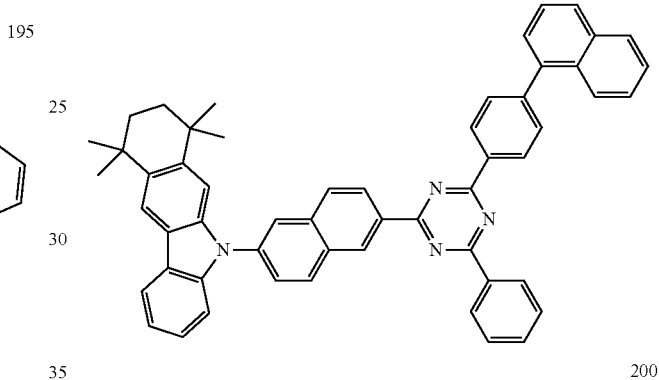
200 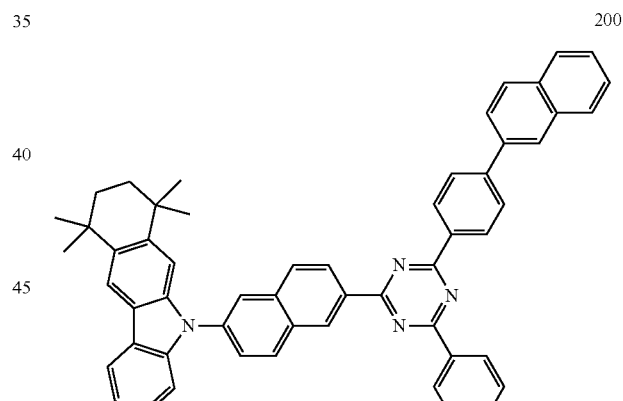
201 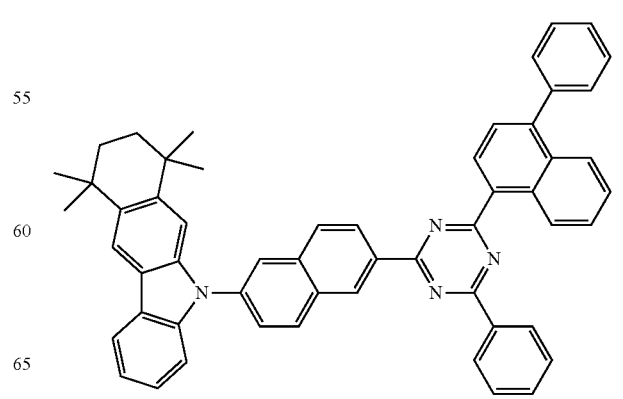

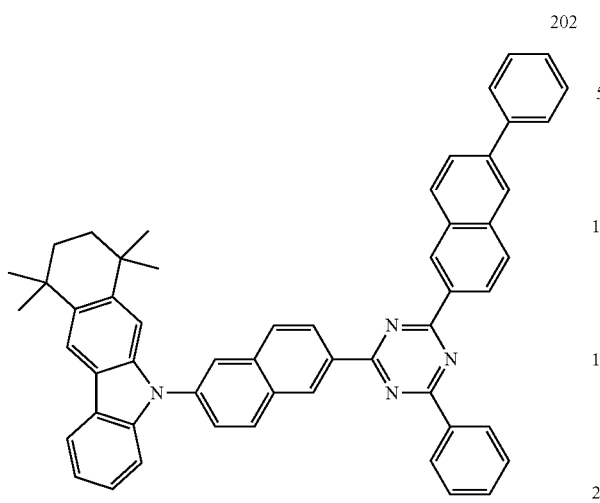
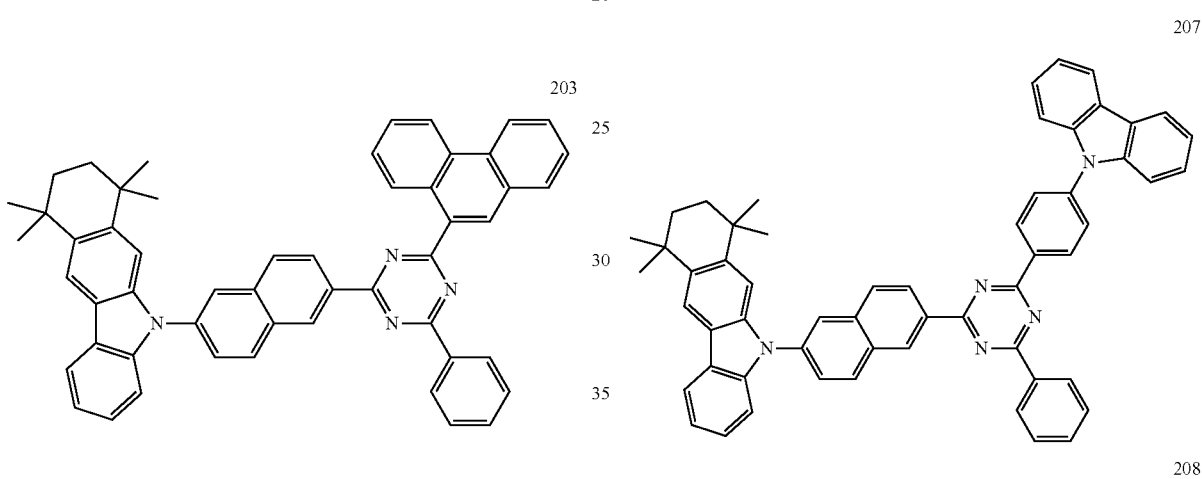
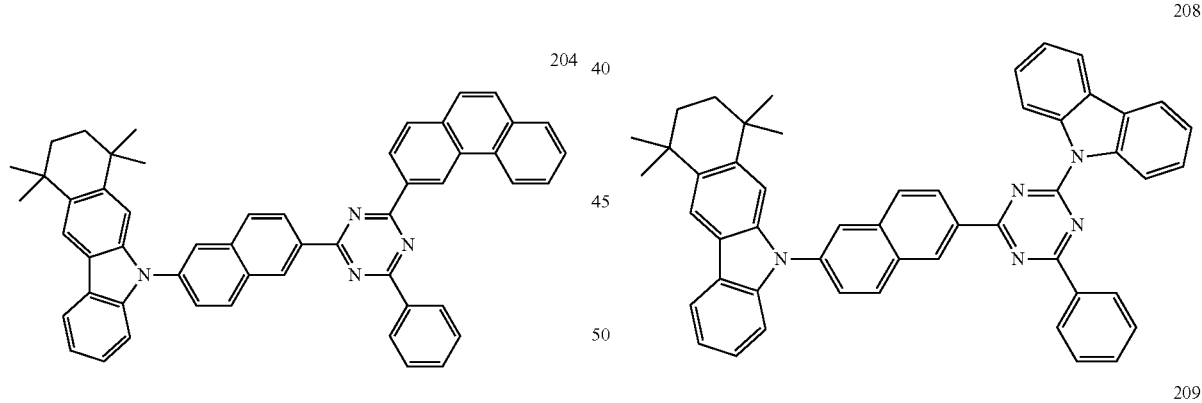
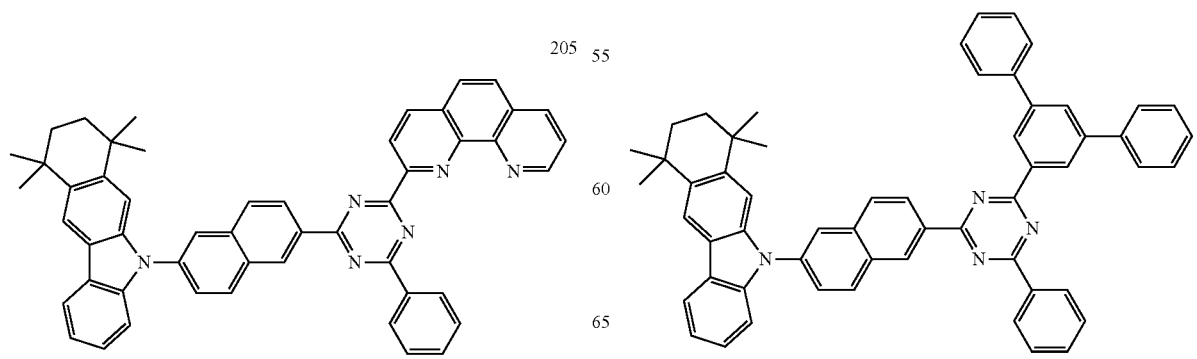

577
-continued
578
-continued
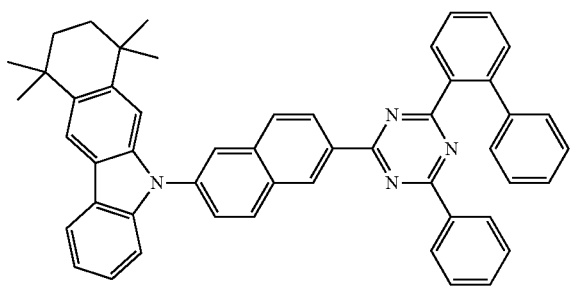
210
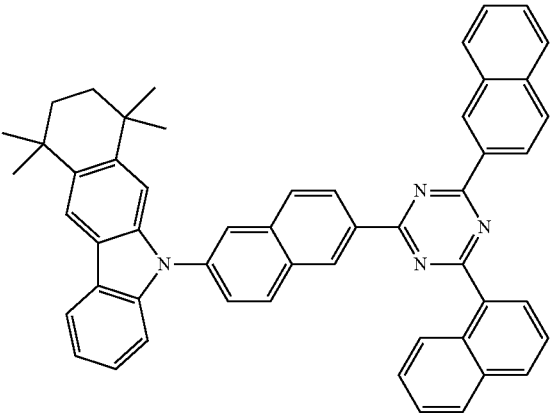
214
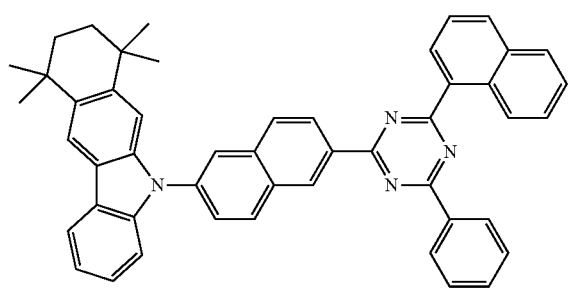
211
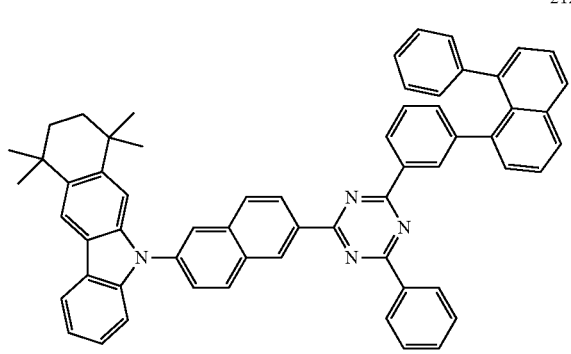
212
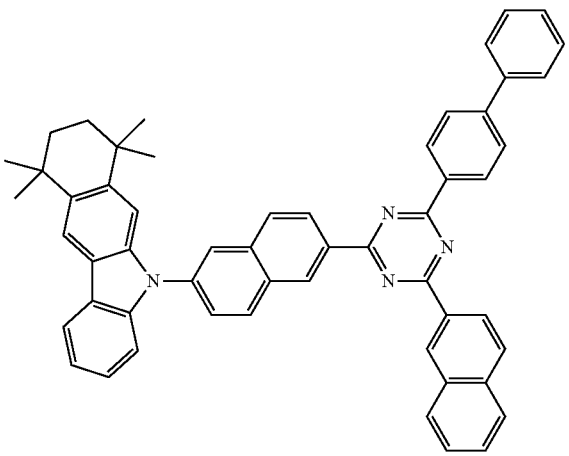
215
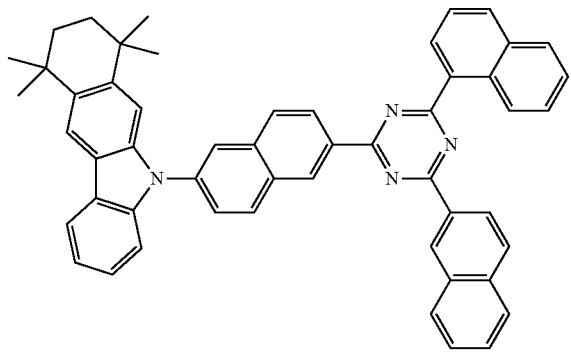
213
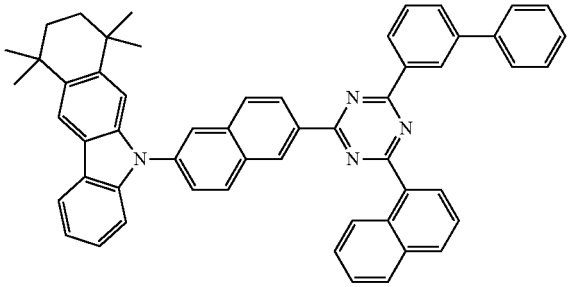
216

217
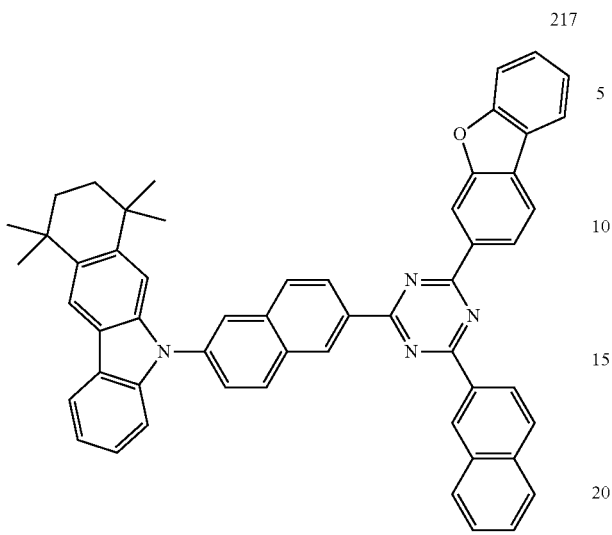
221
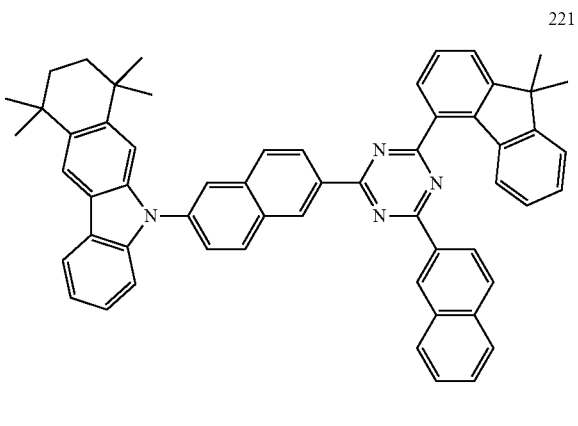
218
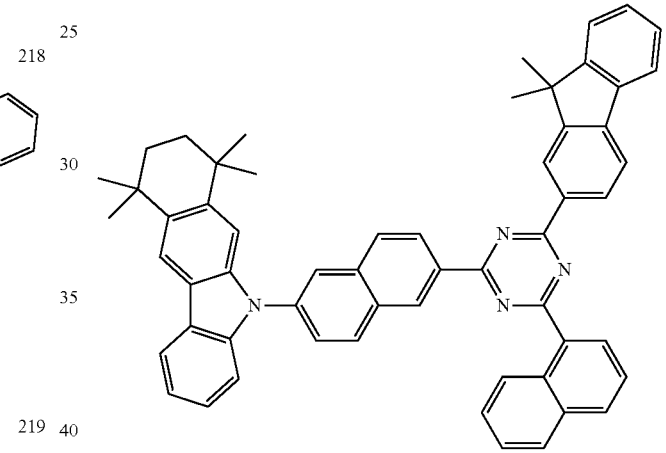
222
219
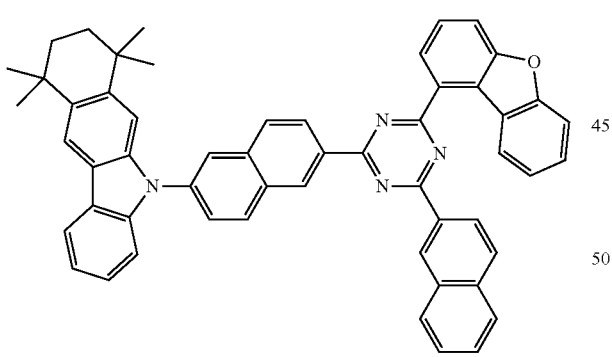
223
220
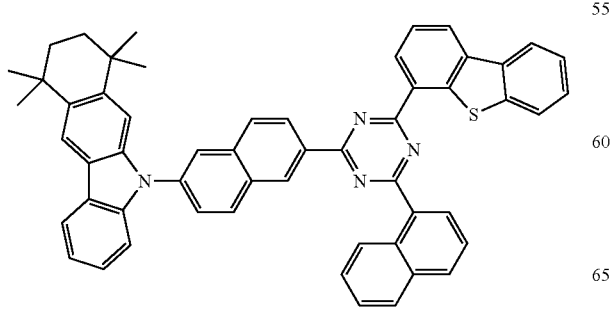
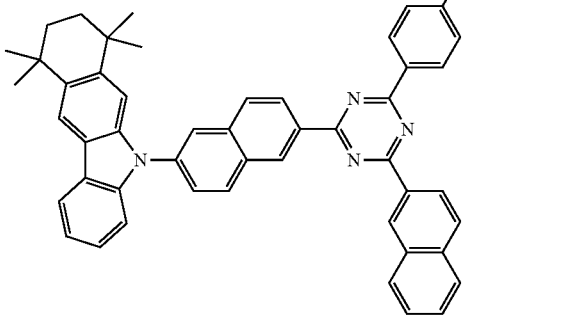

224
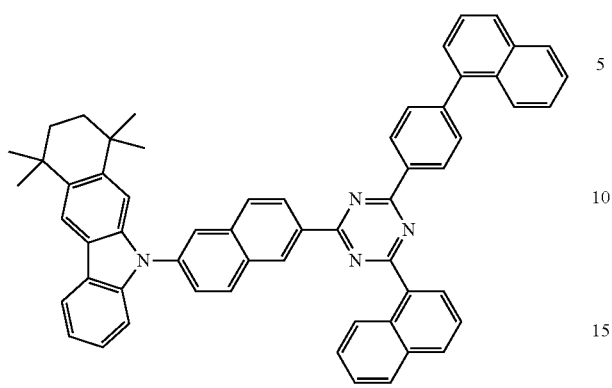
225
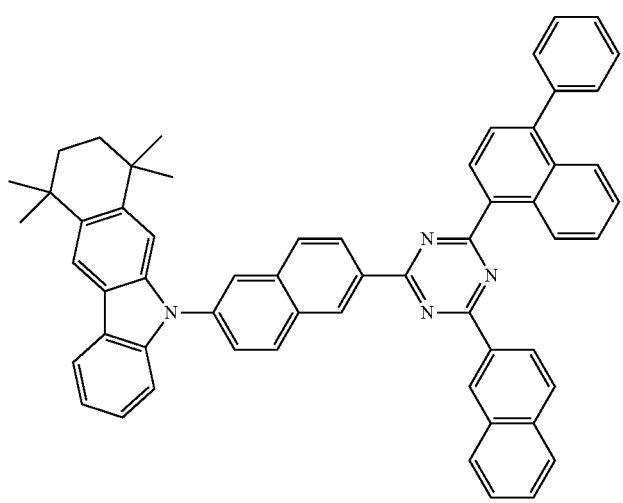
226
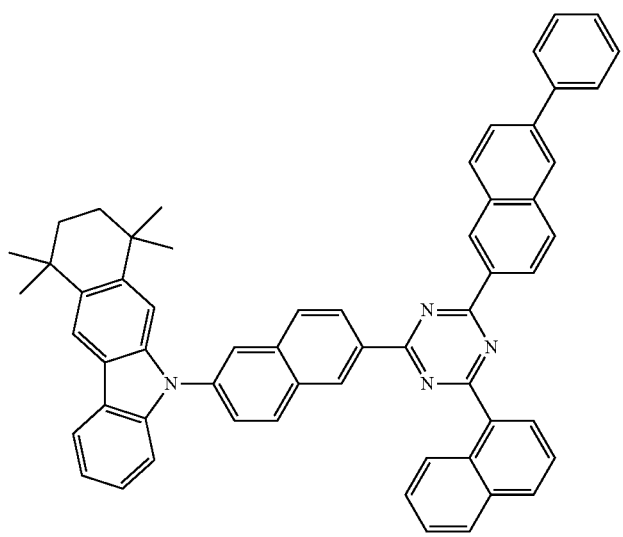

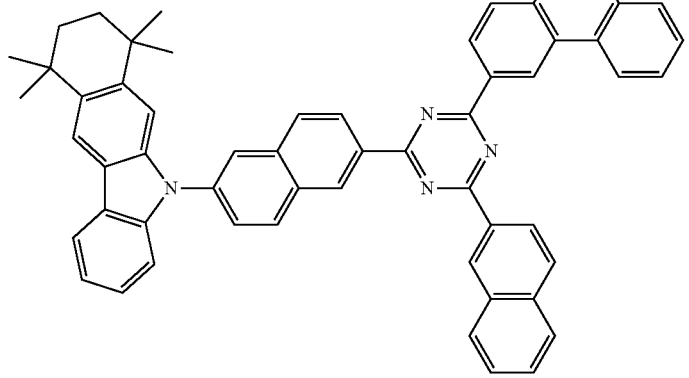
227
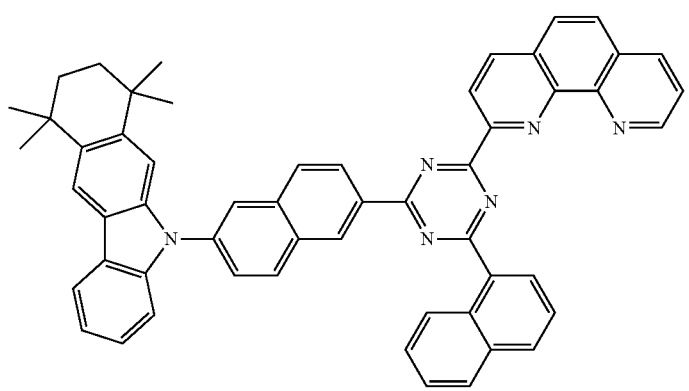
228
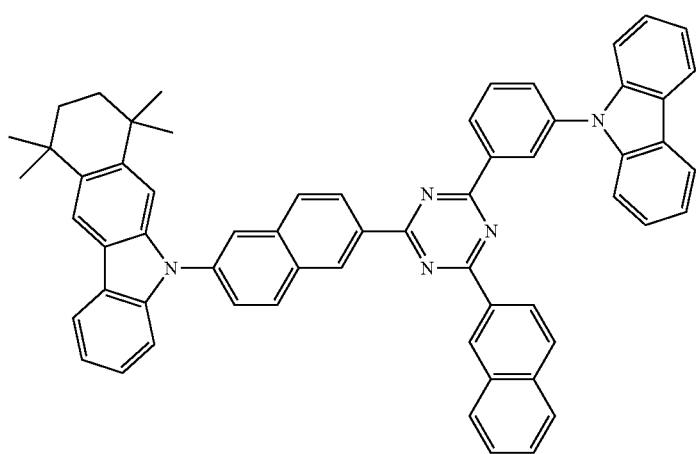
229

-continued
230
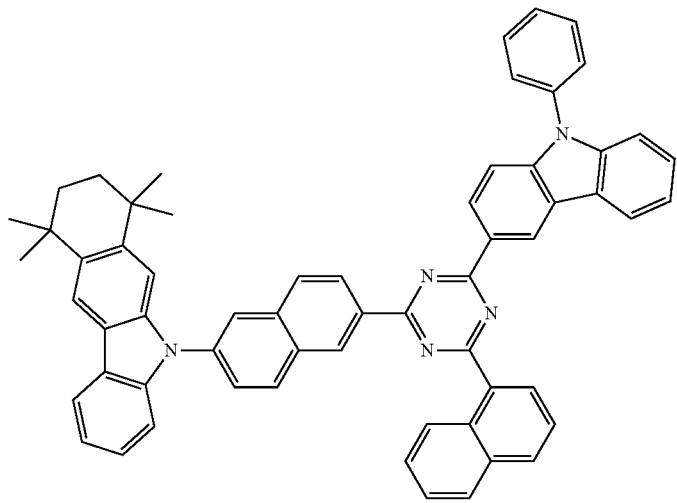
231
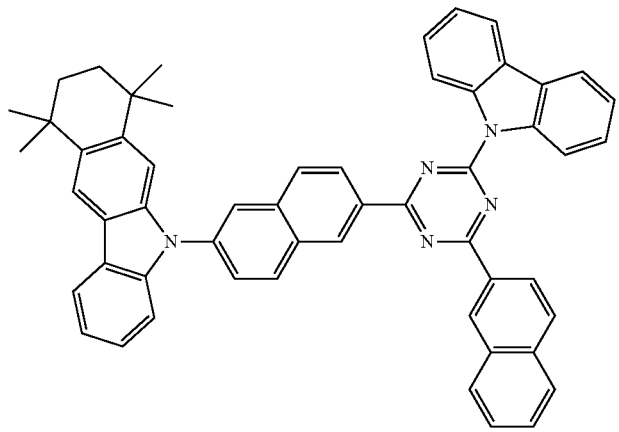
232
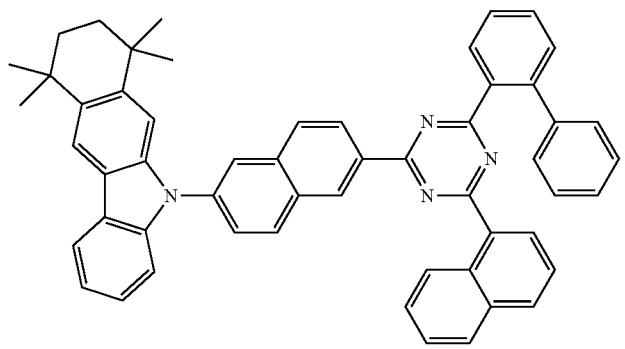
233
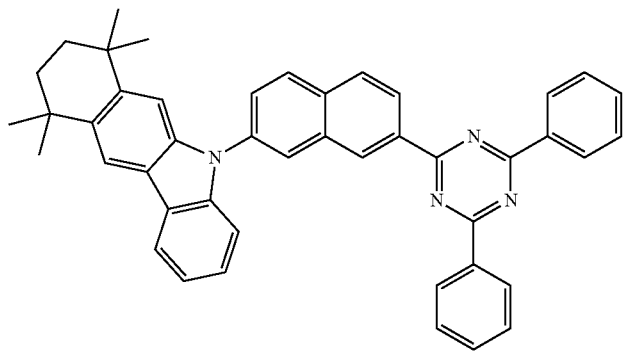

234
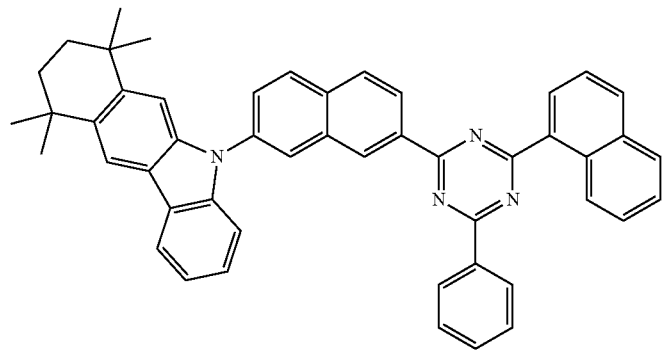
235
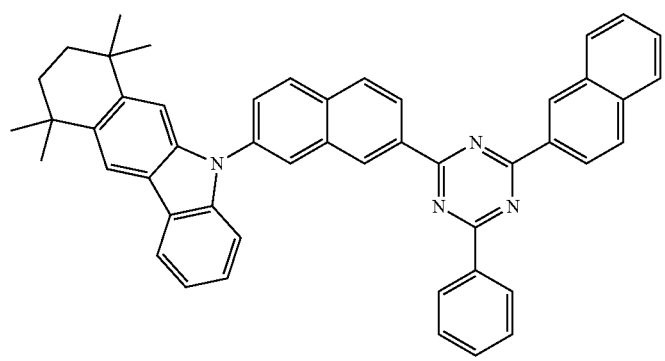
236
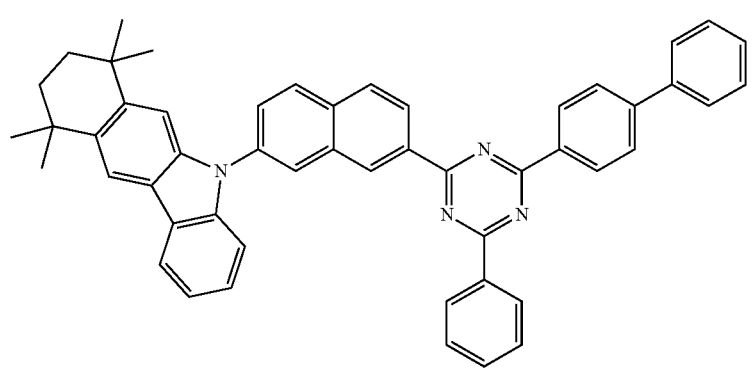
237
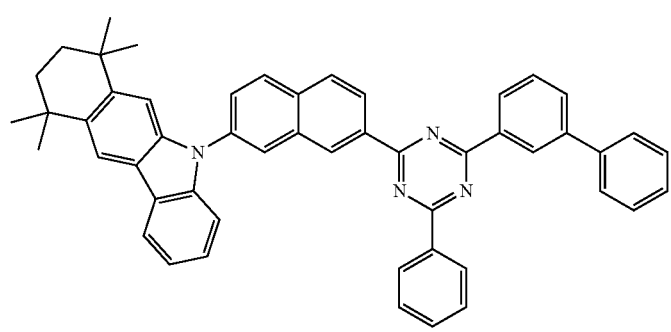

-continued
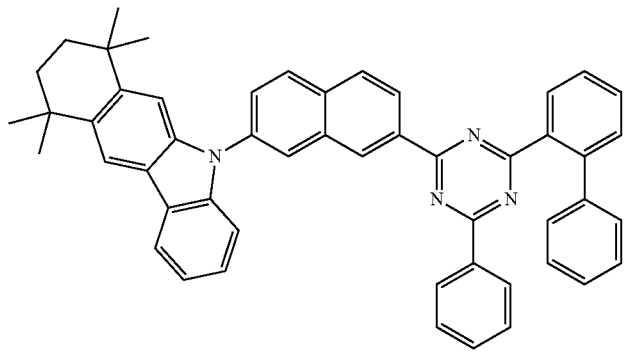
238
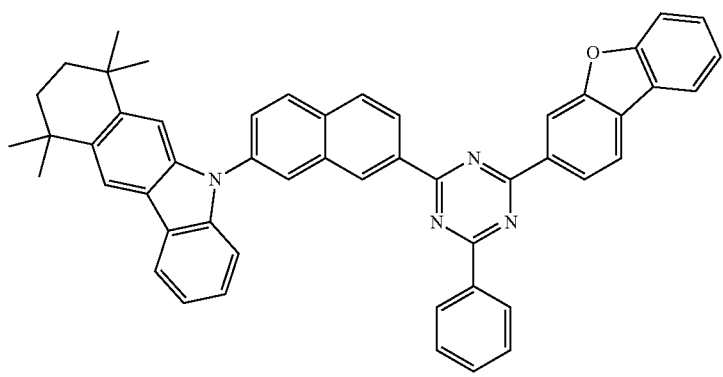
239
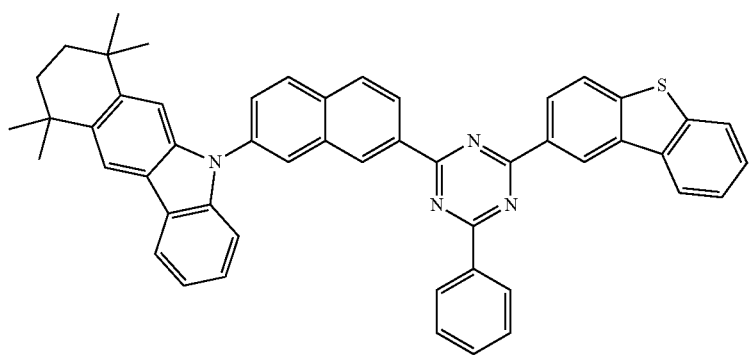
240
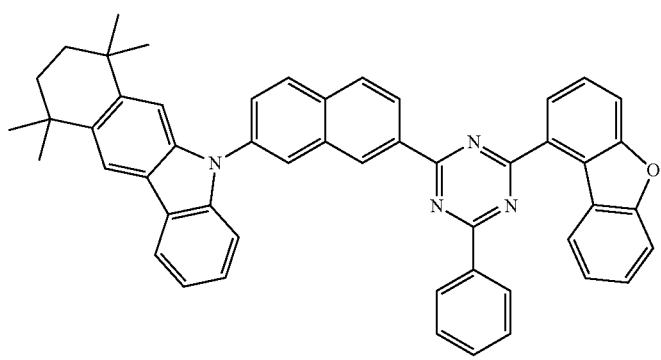 [SMILES: CC1(C)CCC(C)(C)c2cc3c(cc21)c1ccccc1n3-c1ccc2ccc(-c3nc(-c4ccccc4)nc(-c4cccc5oc6ccccc6c45)n3)cc2c1]
241

242
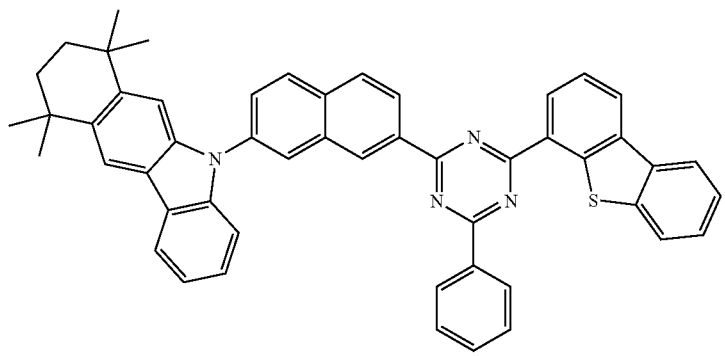
243
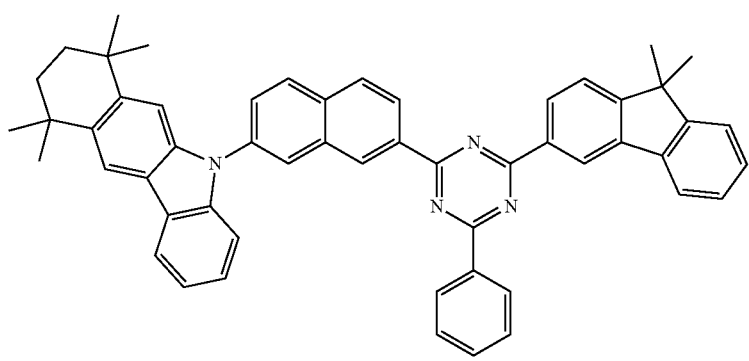
244
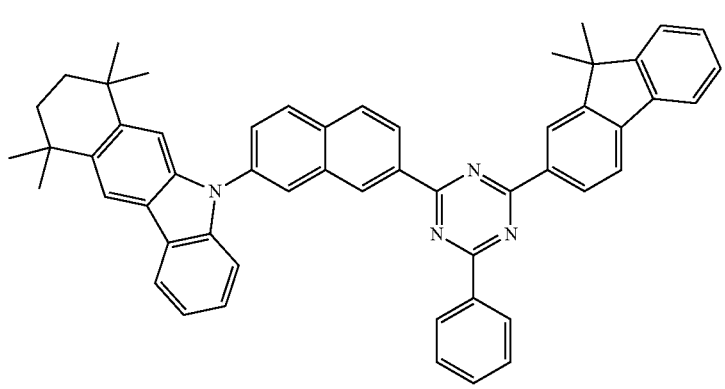
245
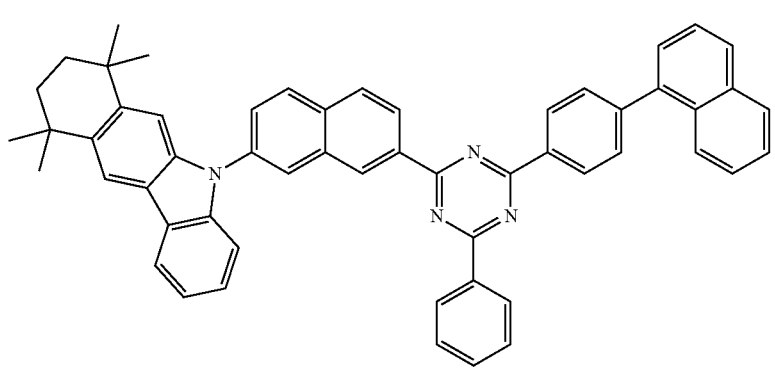

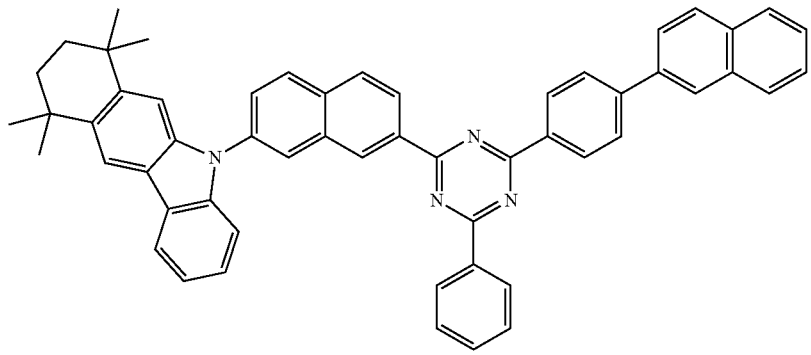
246
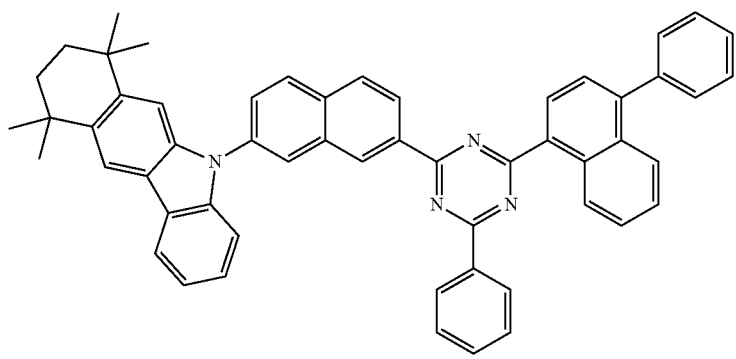
247
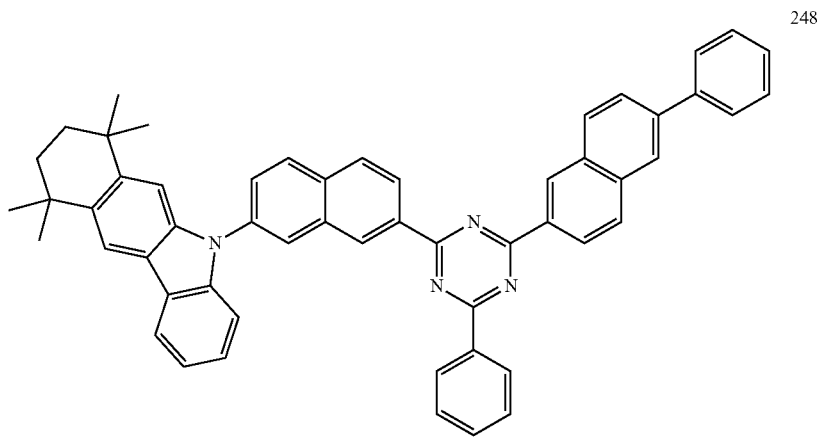
248
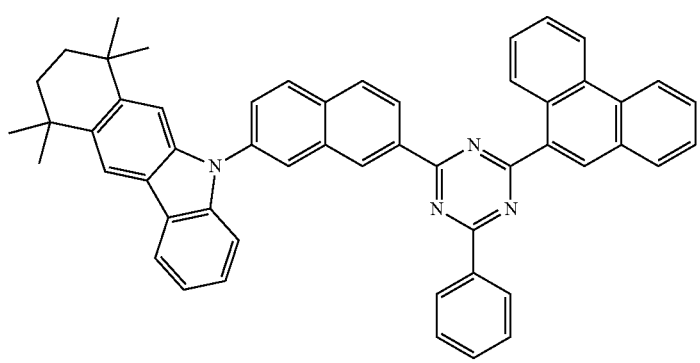
249

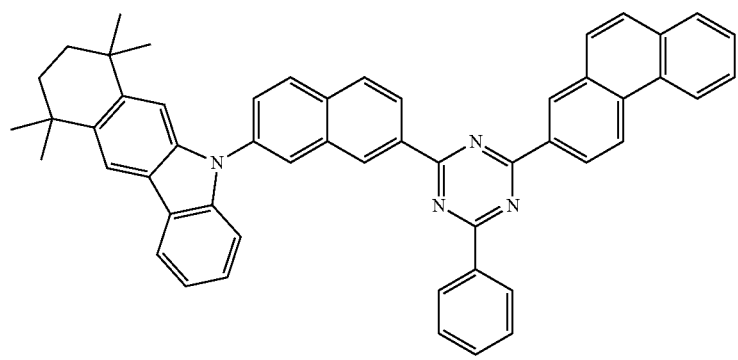
250
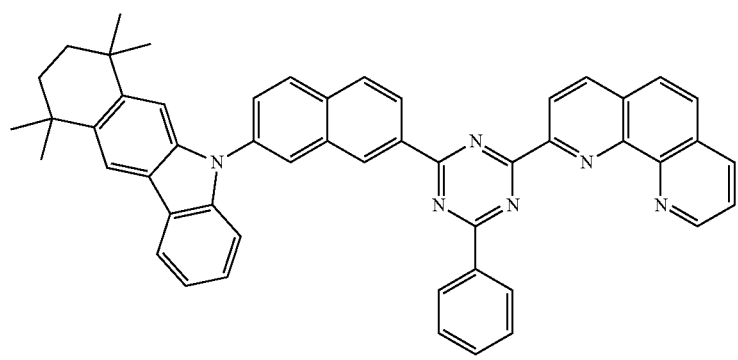
251
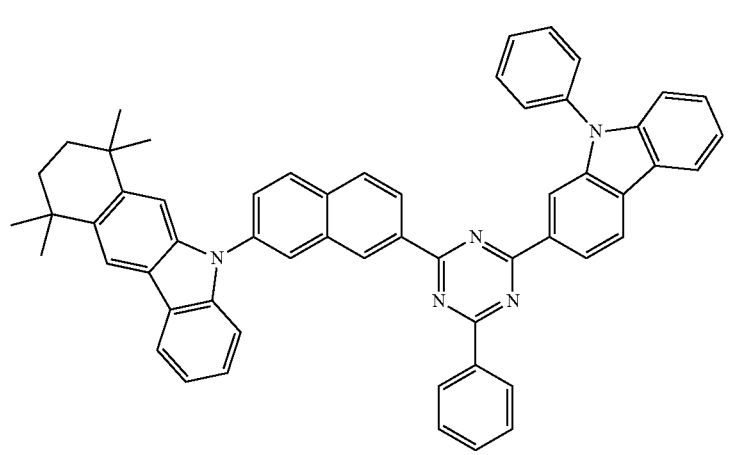
252
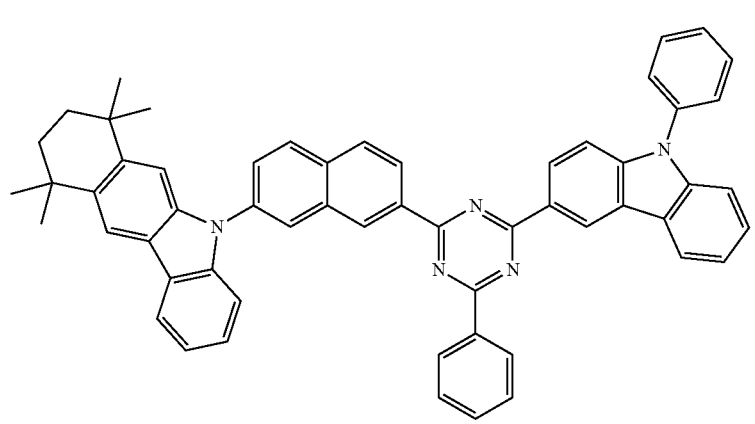
253

254
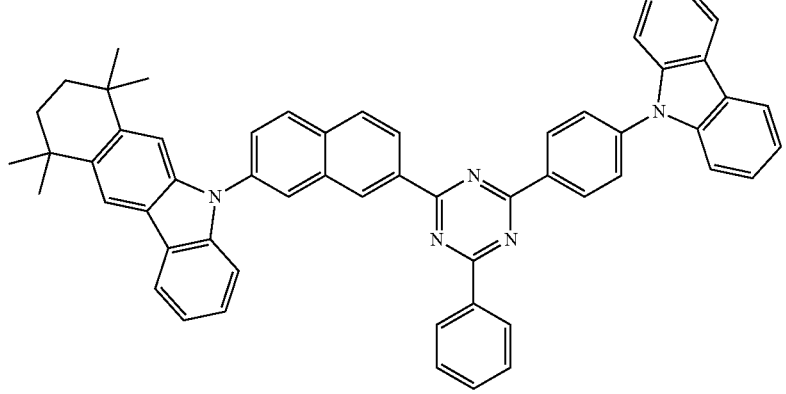
255
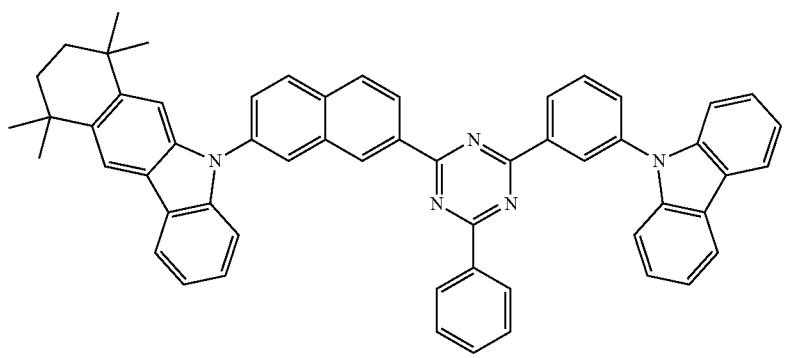
256
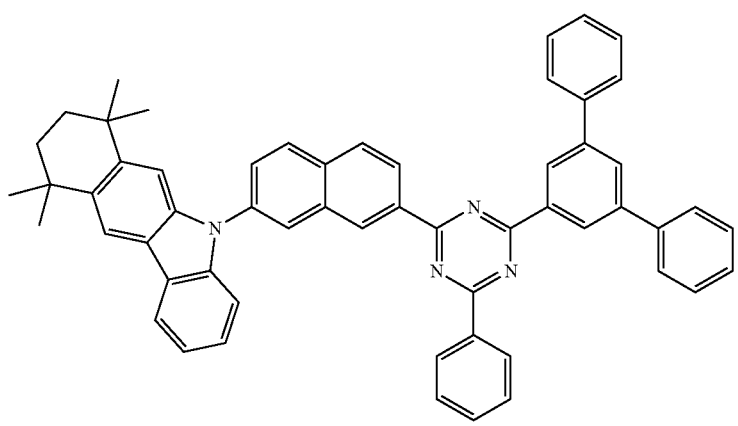
257
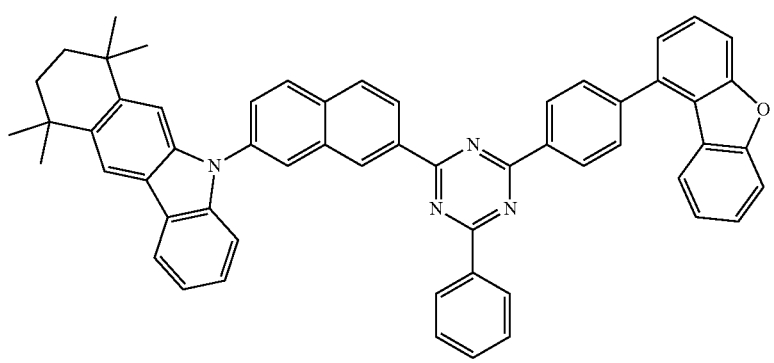

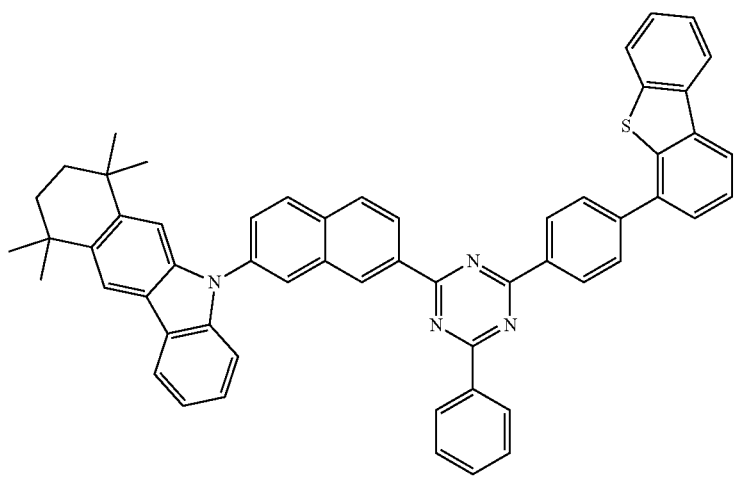
258
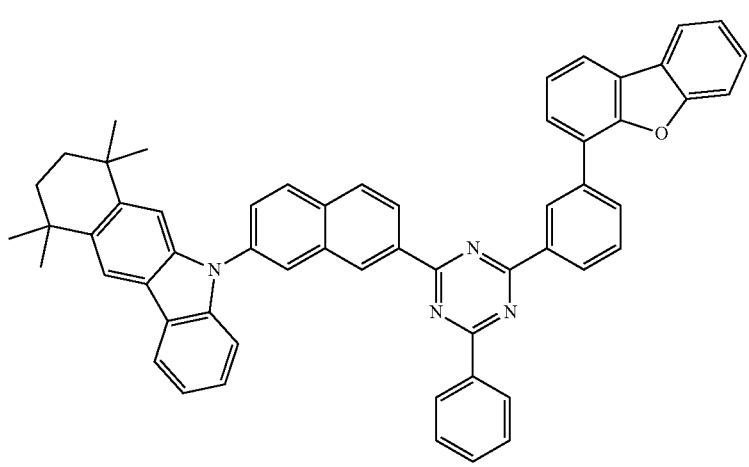
259
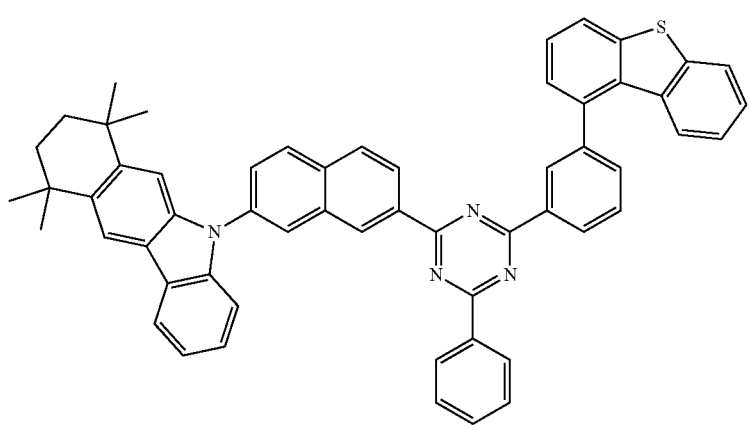
260

261
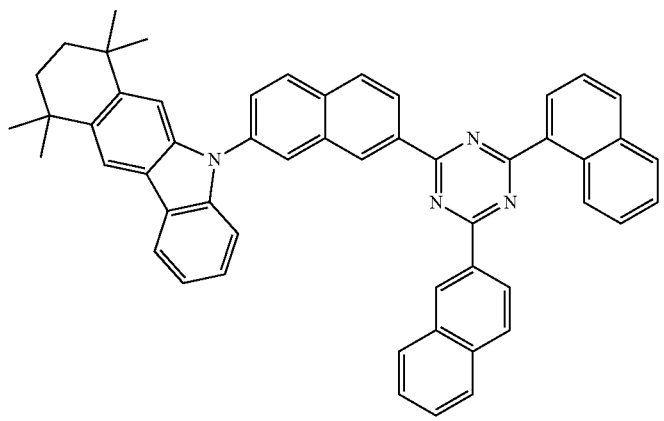
262
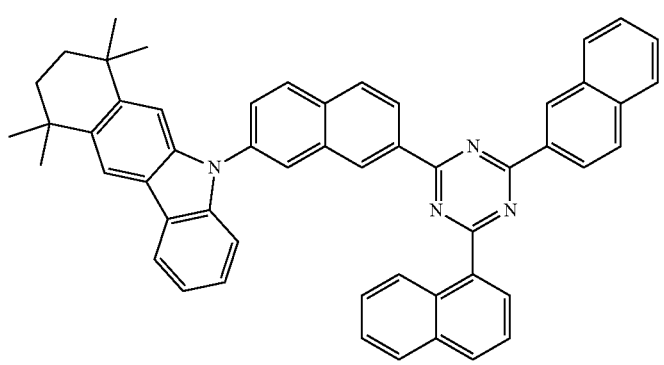
263
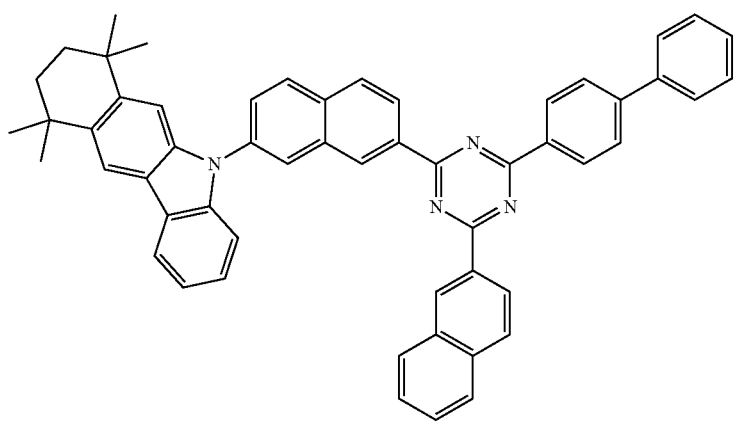
264
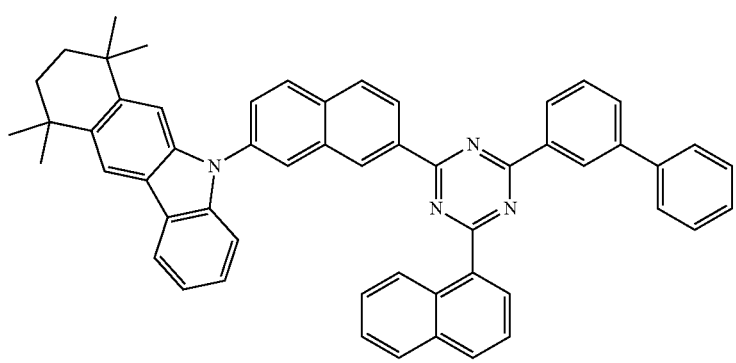

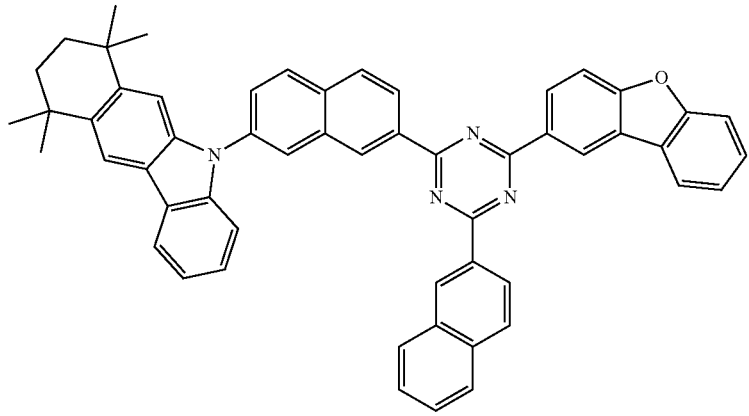
265
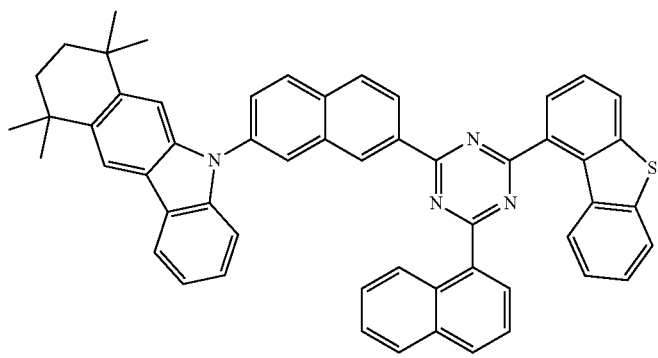 [SMILES: CC1(C)CCC(C)(C)c2cc3c(cc21)c1ccccc1n3-c1ccc2ccc(-c3nc(-c4cccc5ccccc45)nc(-c4cccc5sc6ccccc6c45)n3)cc2c1]
266
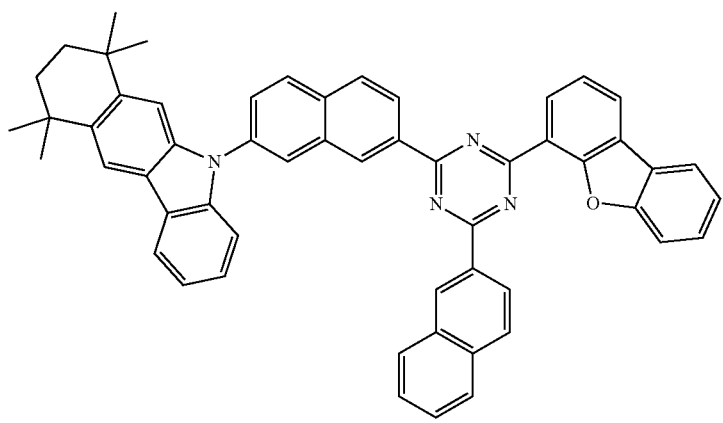
267
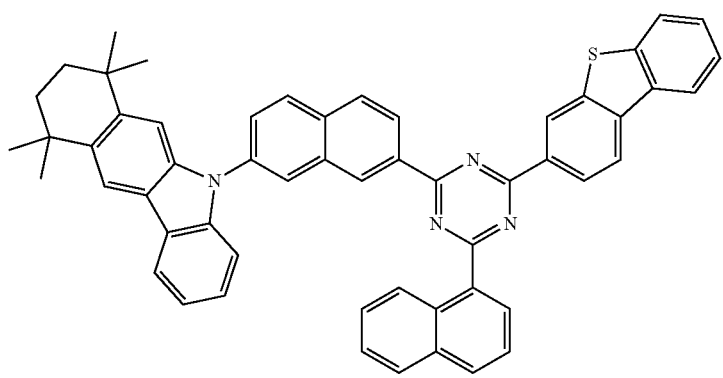
268

269
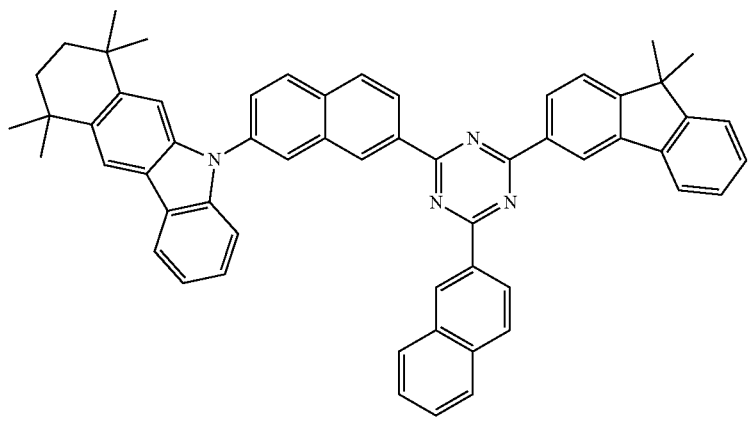
270
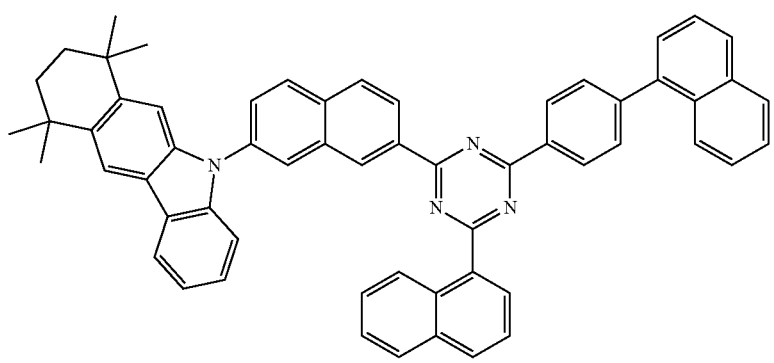
271
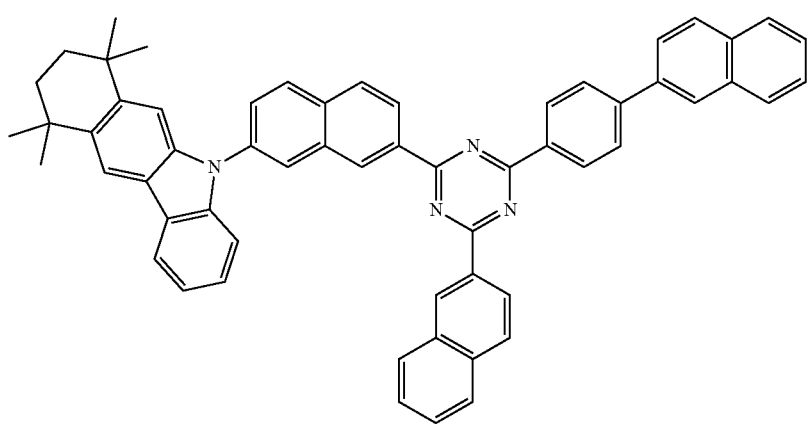
272
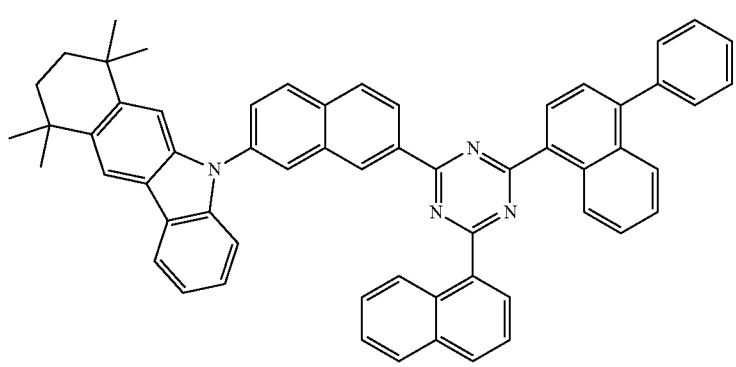

273
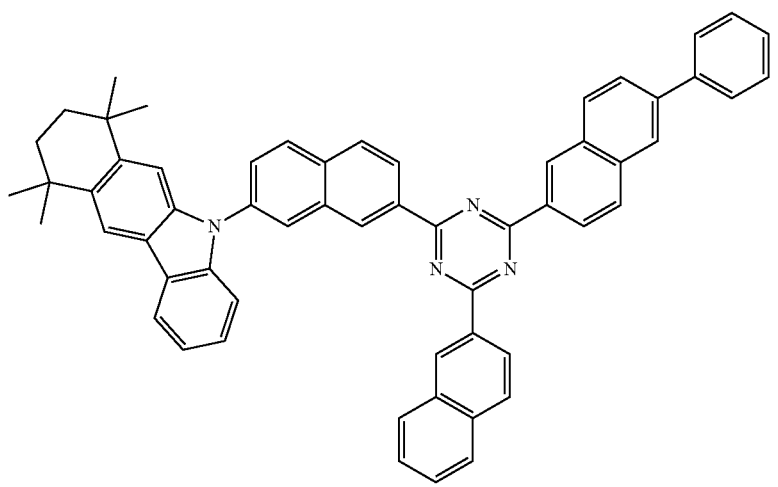
274
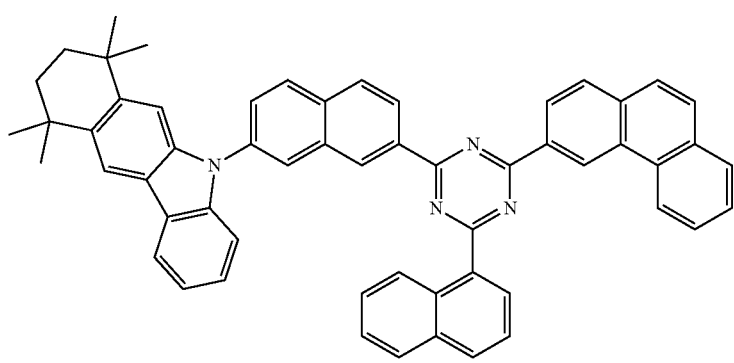
275
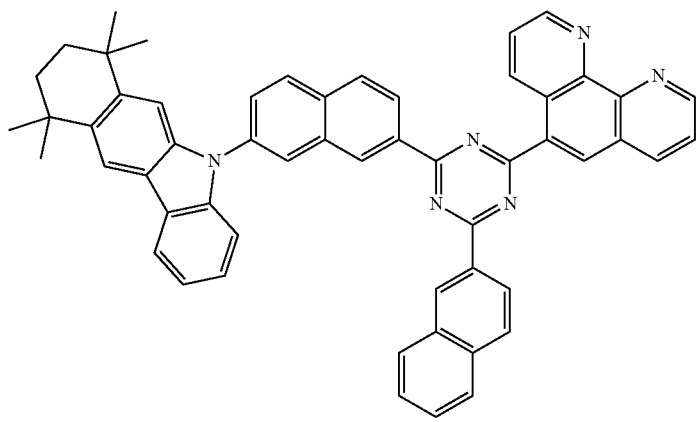
276
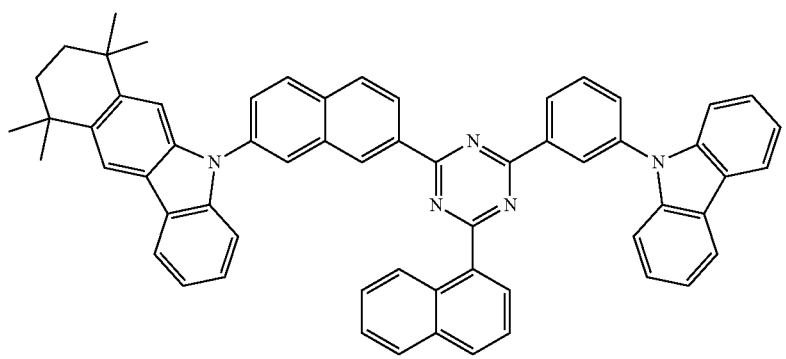

277
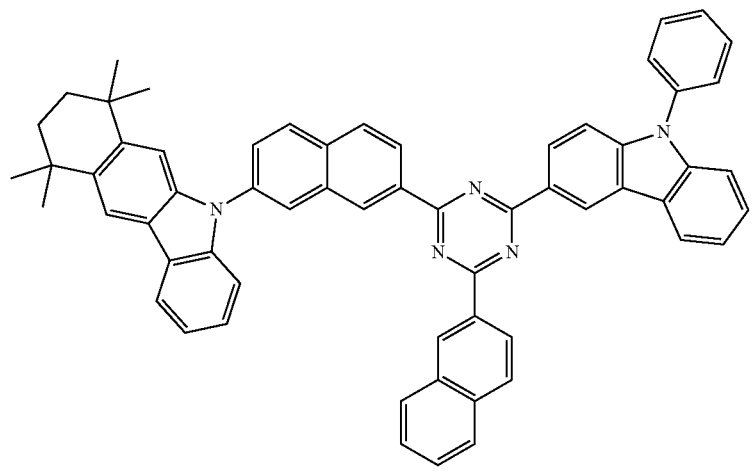
278
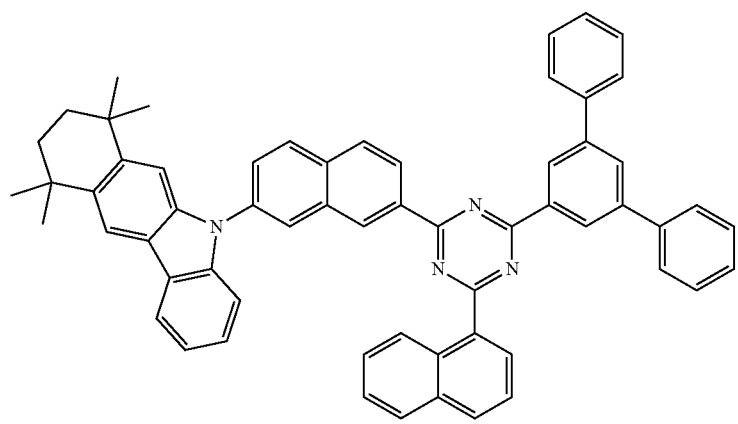
279
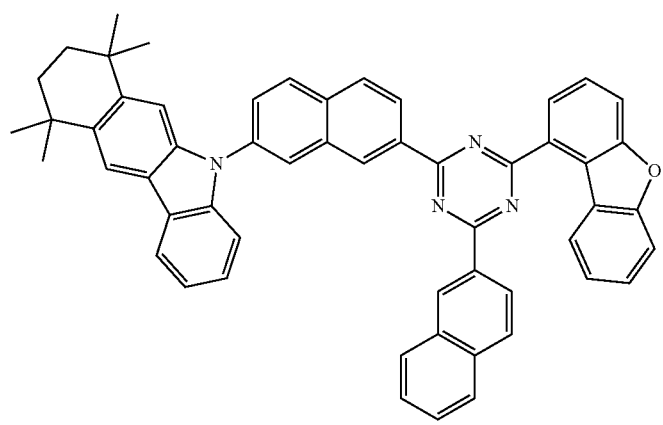
280
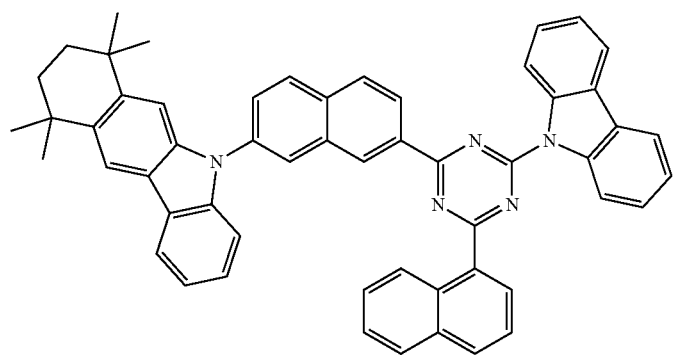

-continued
281
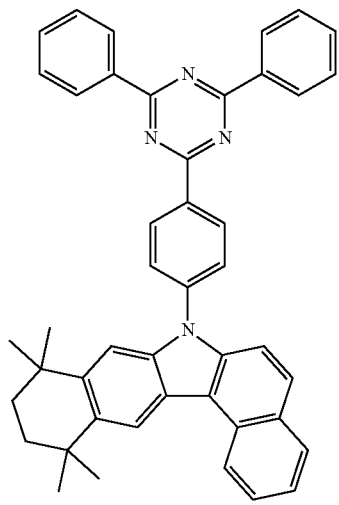
282
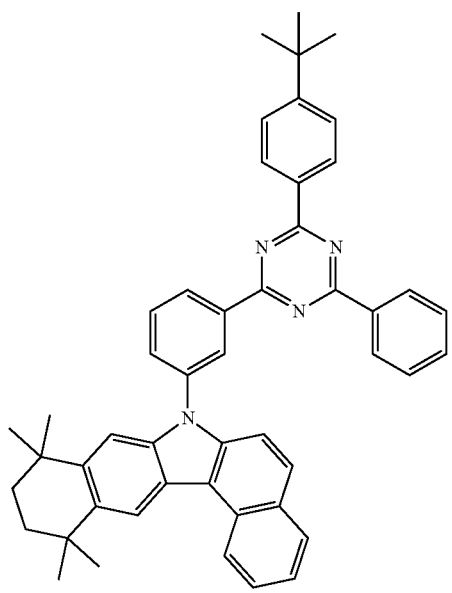 [SMILES: CC(C)(C)c1ccc(-c2nc(-c3ccccc3)nc(-c3cccc(-n4c5cc6c(cc5c5c7ccccc7ccc54)C(C)(C)CCC6(C)C)c3)n2)cc1]
283
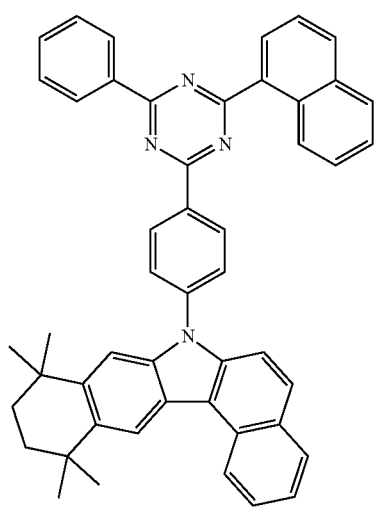

284
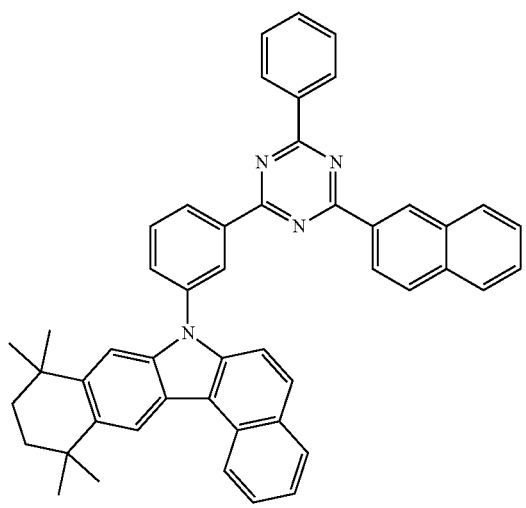
285
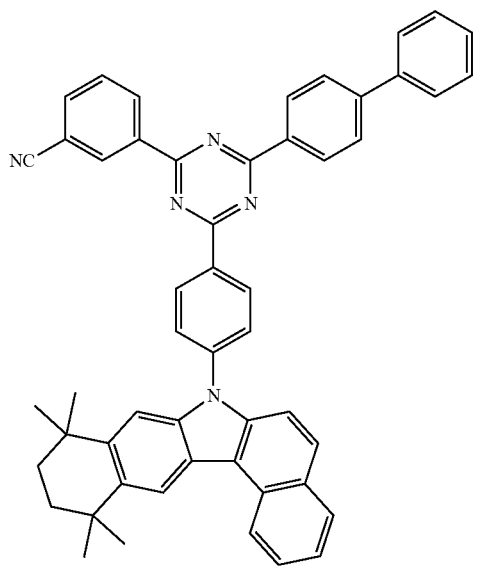 [SMILES: CC1(C)CCC(C)(C)c2cc3c(cc21)c1c2ccccc2ccc1n3-c1ccc(-c2nc(-c3ccc(-c4ccccc4)cc3)nc(-c3cccc(C#N)c3)n2)cc1]
286
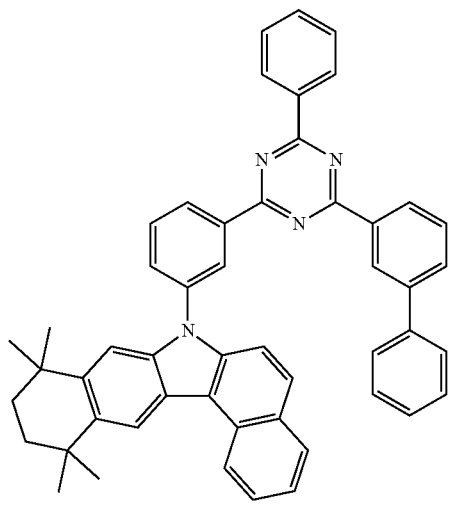

615
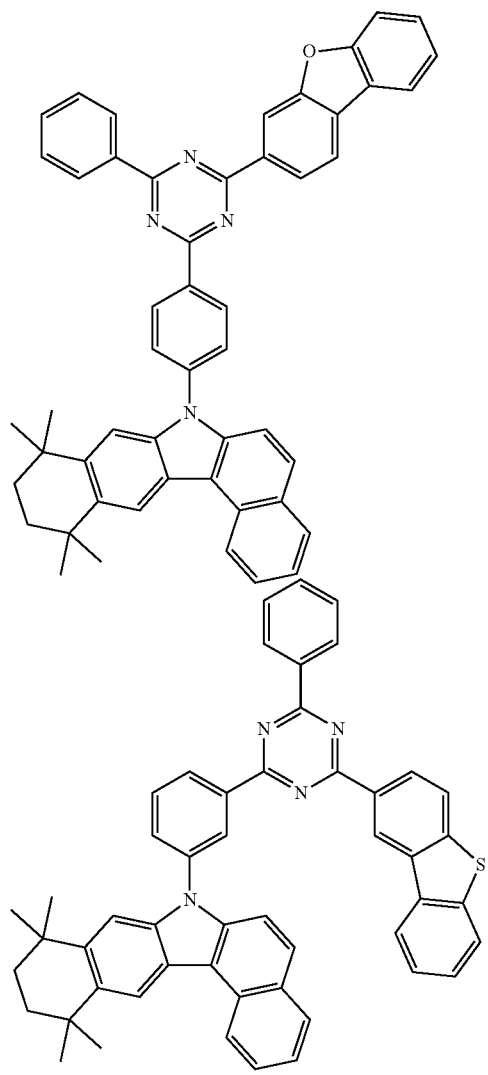
-continued
287
288
616
289
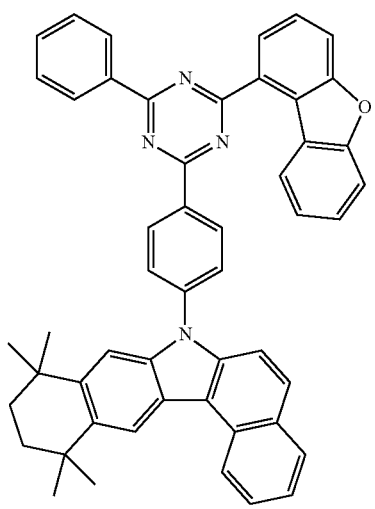
-continued
290
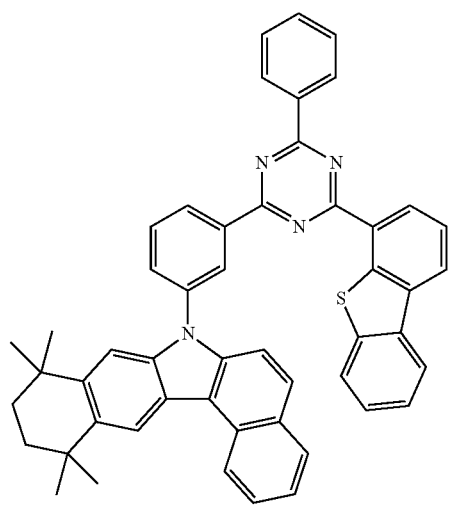

291
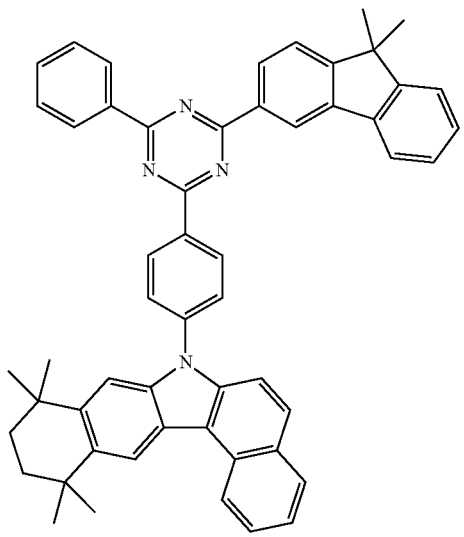
292
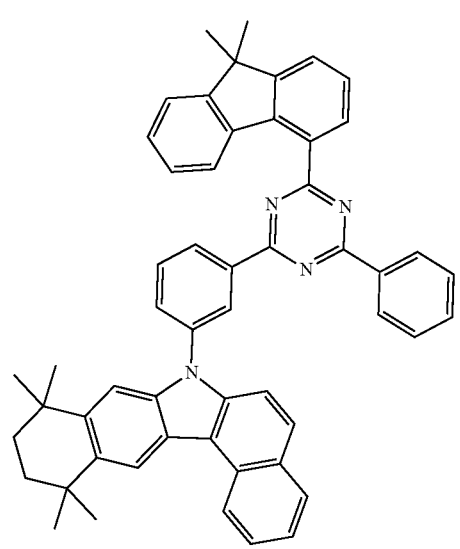
293
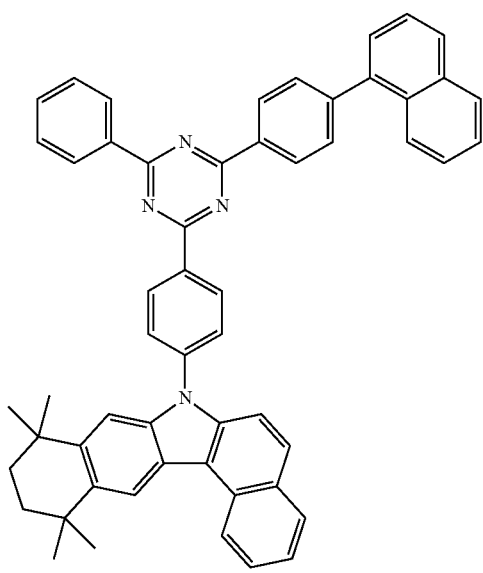
294
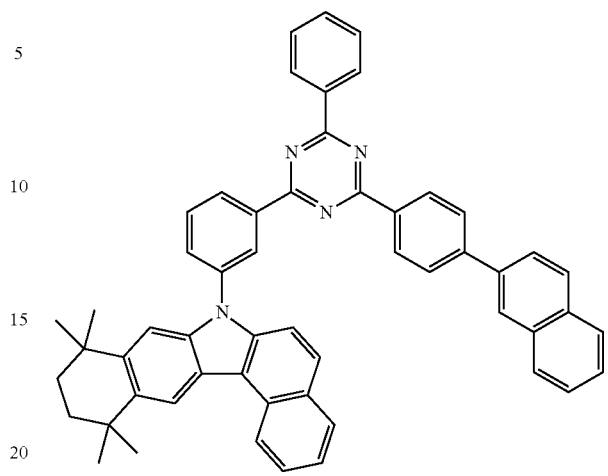
295
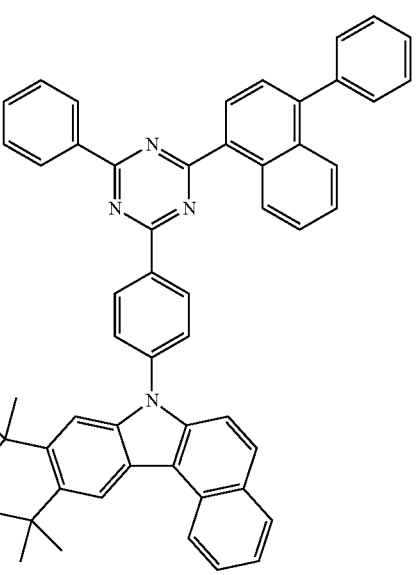
296
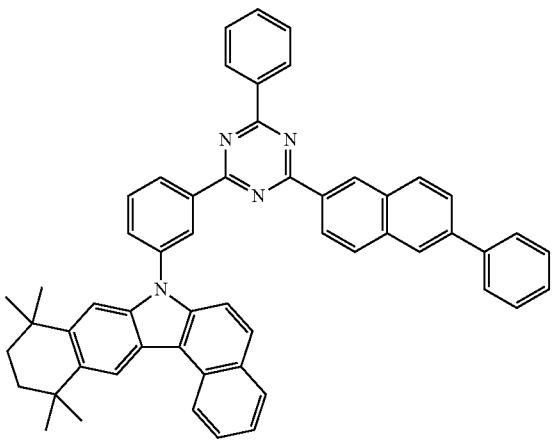

619
-continued
297
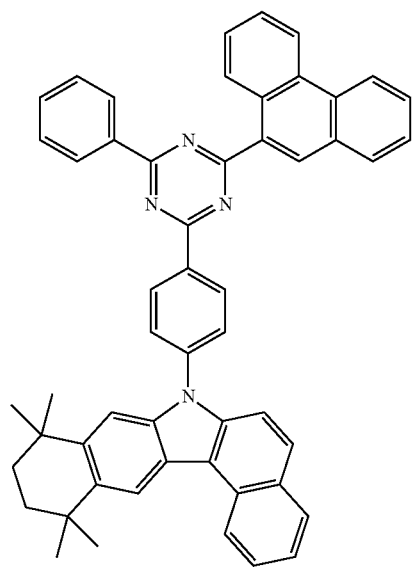
298
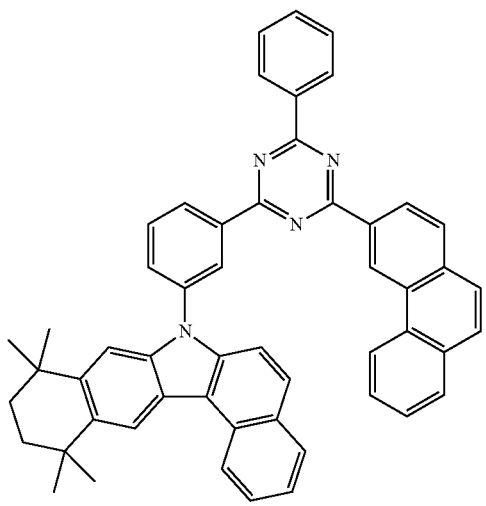
299
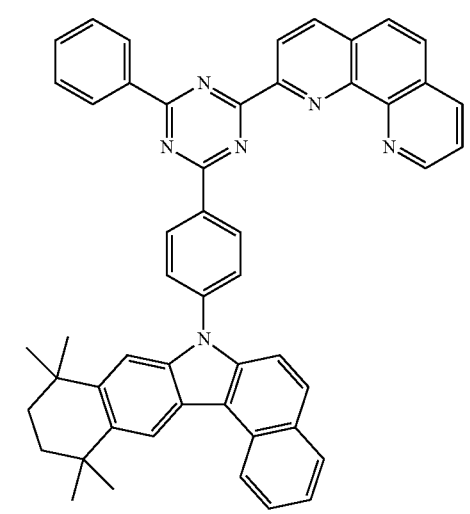
620
-continued
300
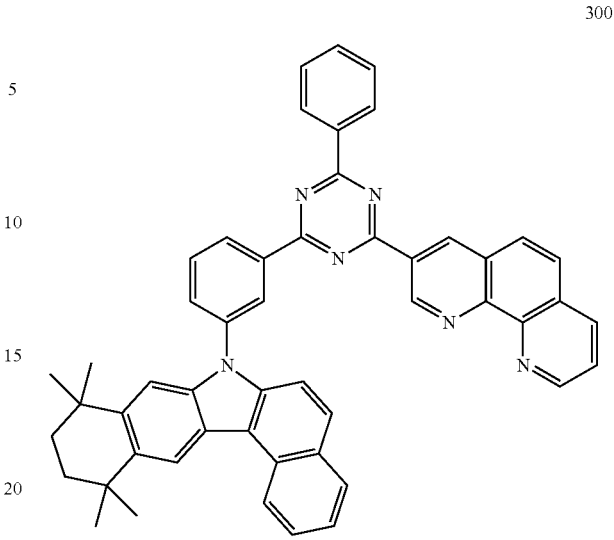
301
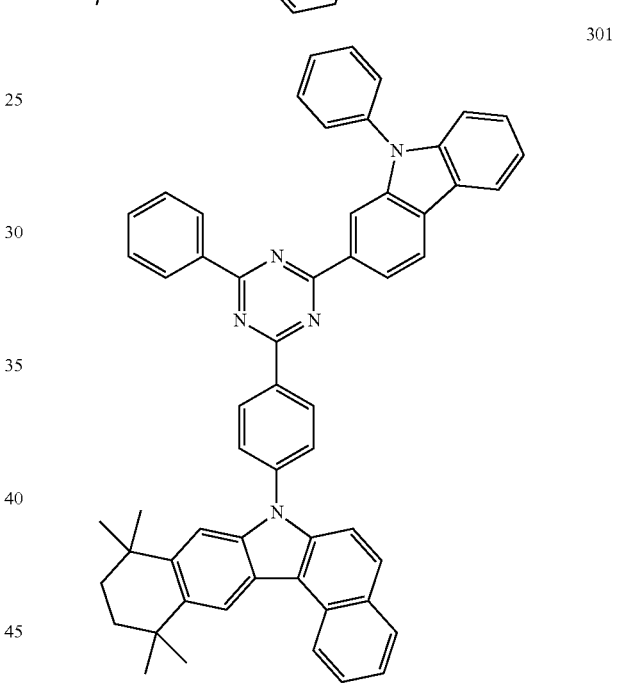
302
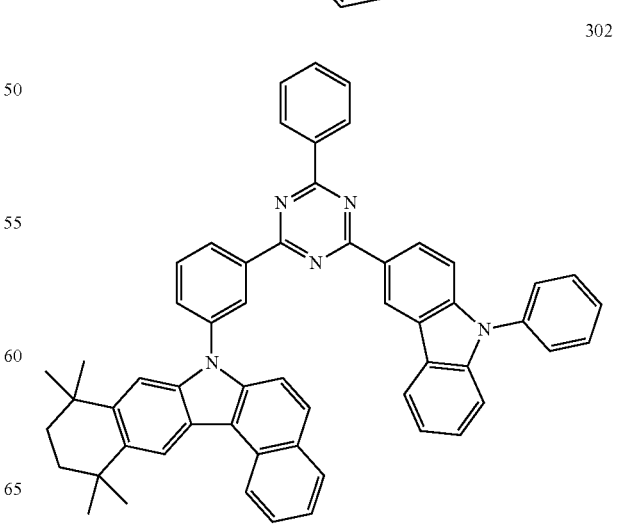

621
-continued
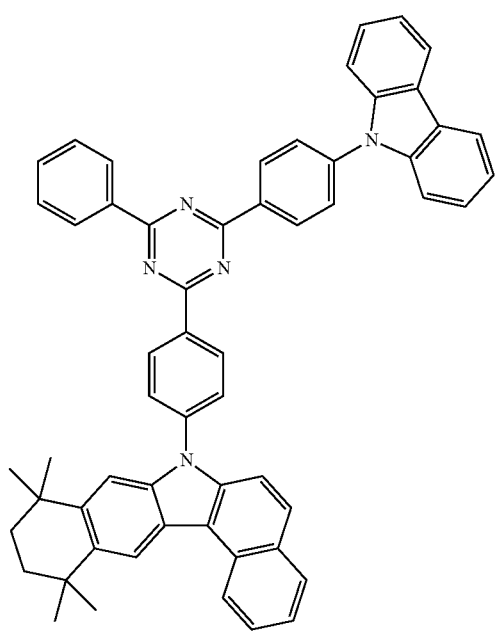
303
622
-continued
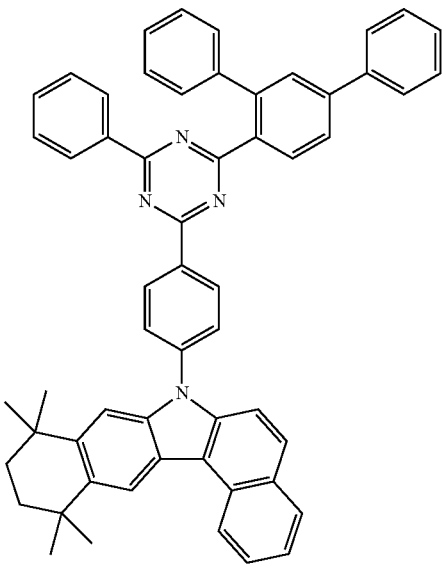
305
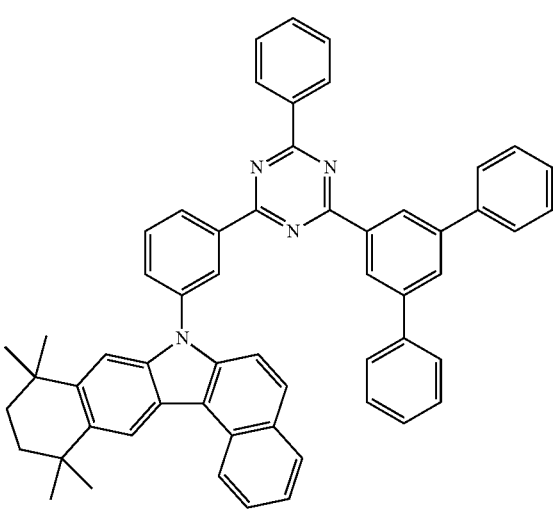
306
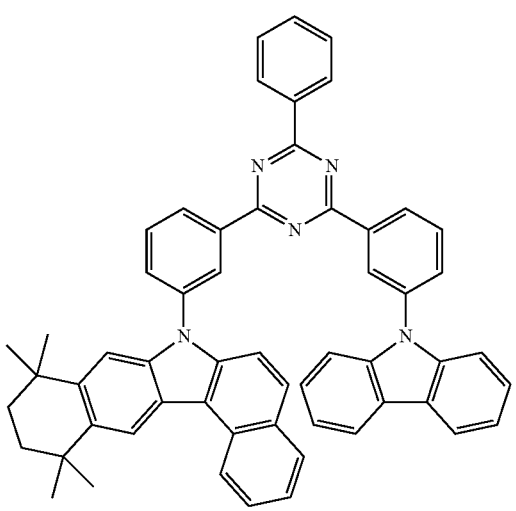
304
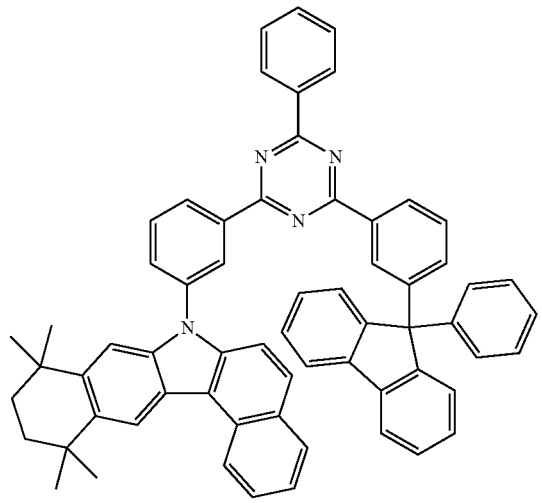
308

310
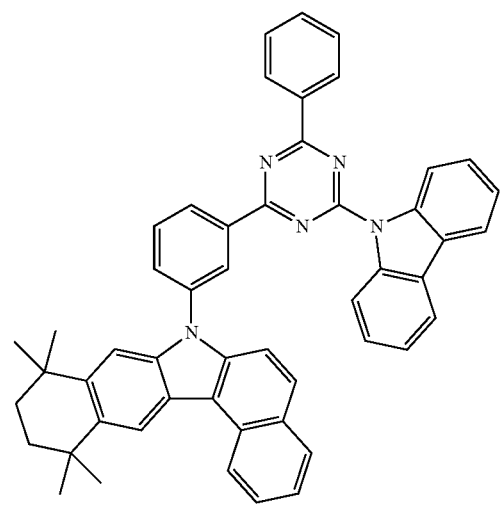
313
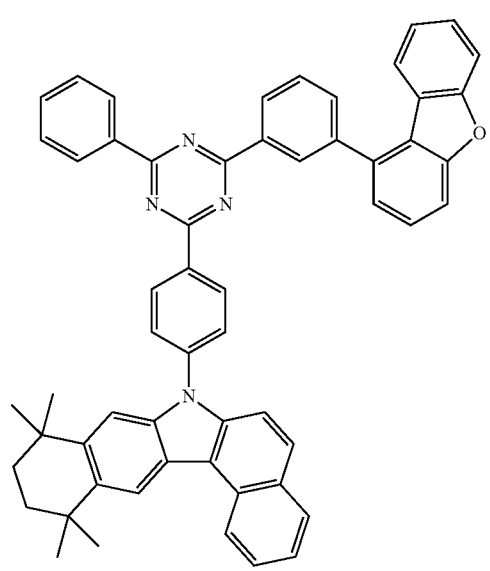
314
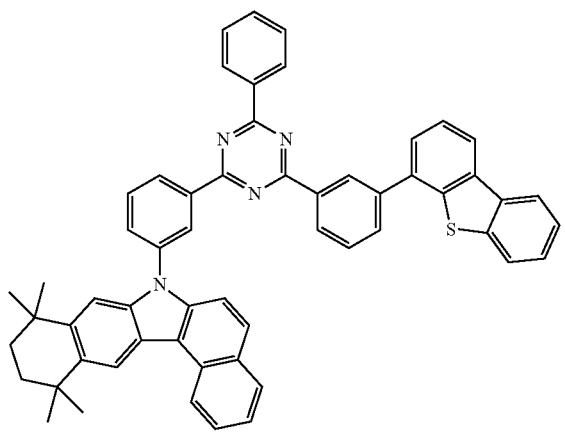
315
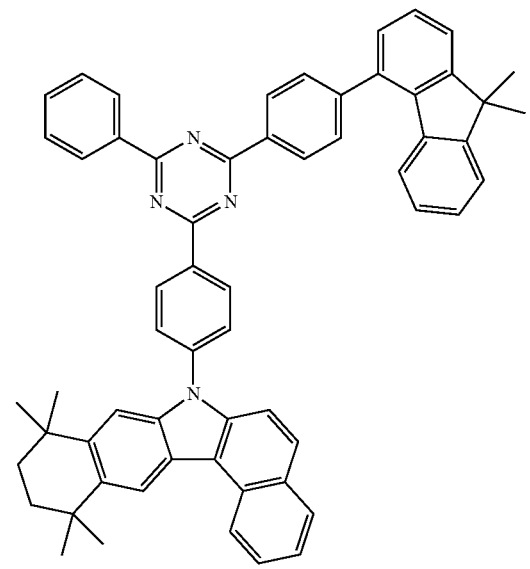
317
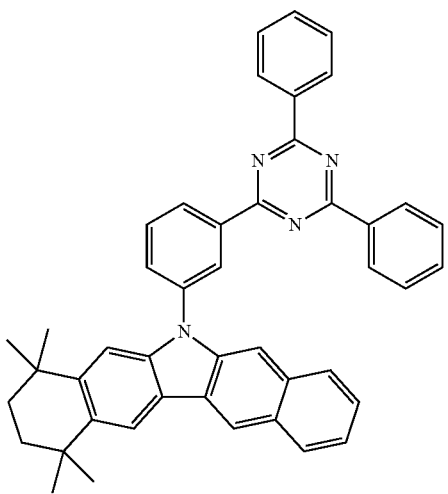
318
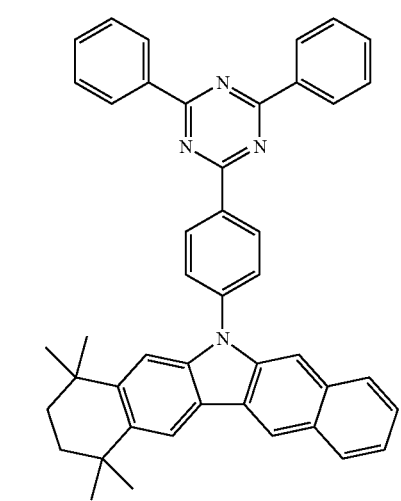

319
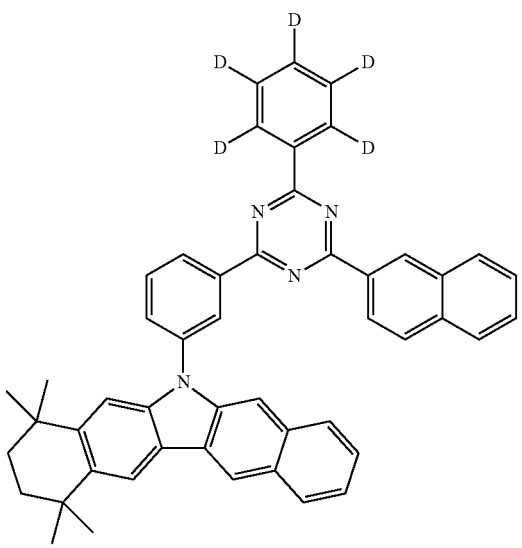 [SMILES: [2H]c1c([2H])c([2H])c(-c2nc(-c3cccc(-n4c5cc6c(cc5c5cc7ccccc7cc54)C(C)(C)CCC6(C)C)c3)nc(-c3ccc4ccccc4c3)n2)c([2H])c1[2H]]
320
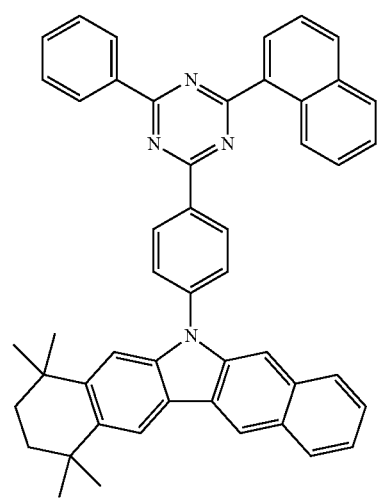
322
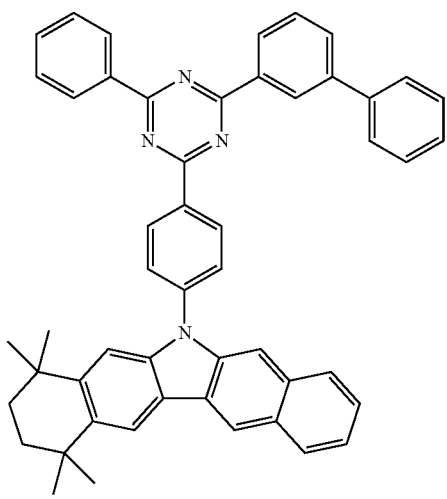
323
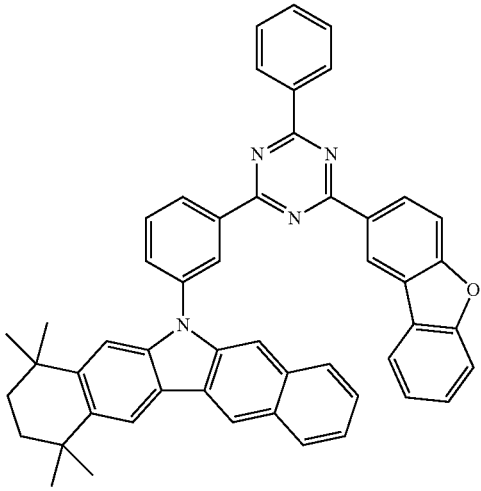
324
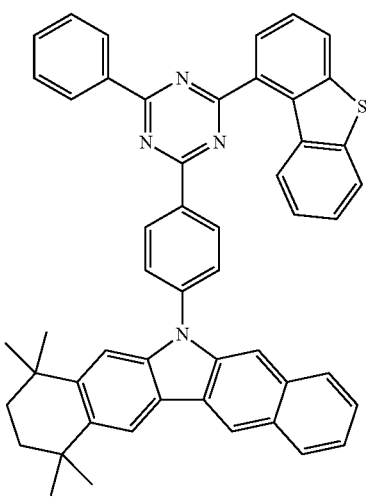
325
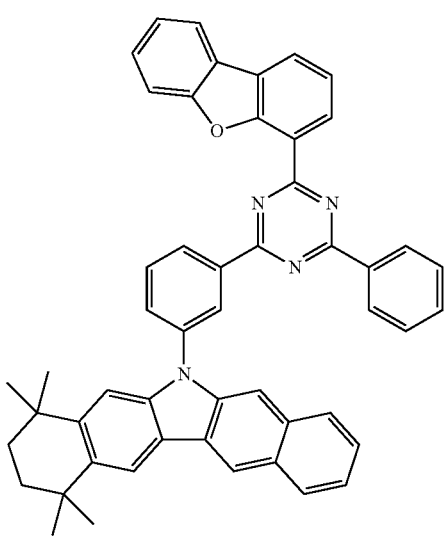

-continued
326
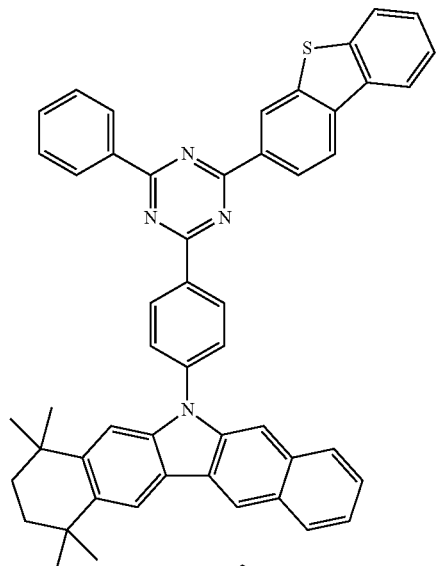
327
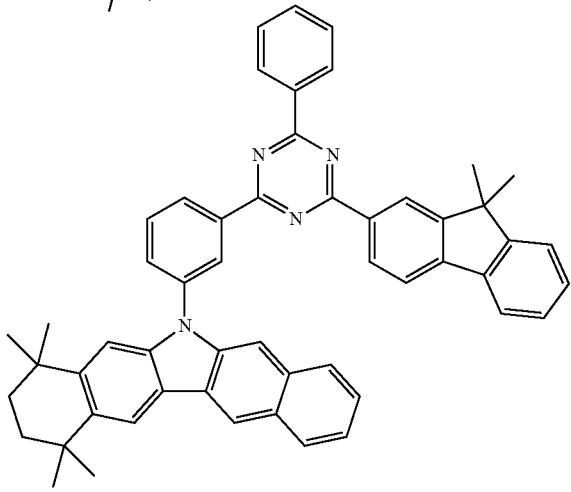
328
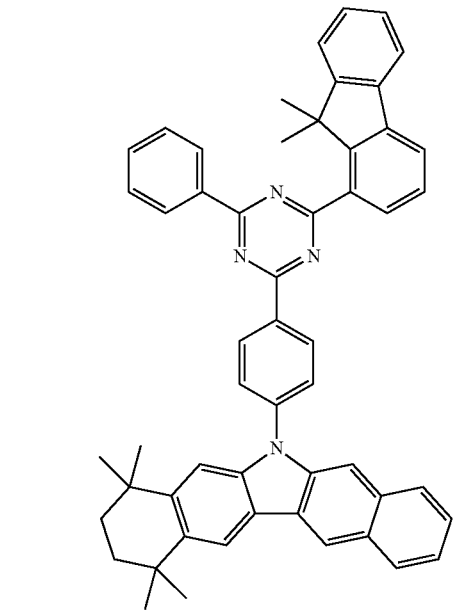
-continued
329
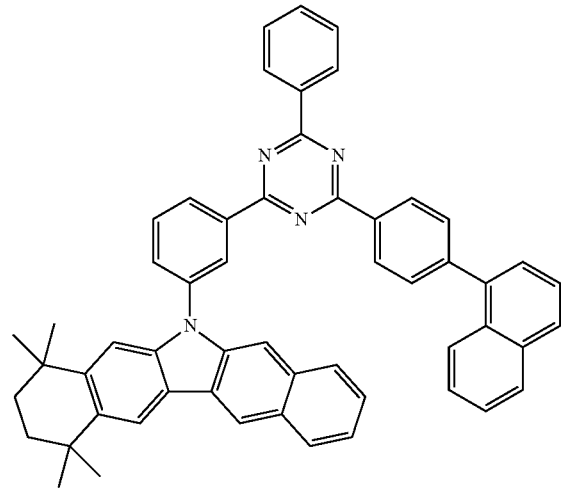
330
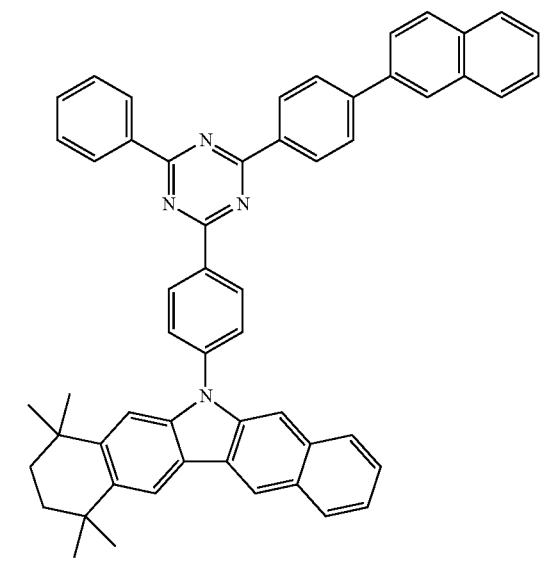
331
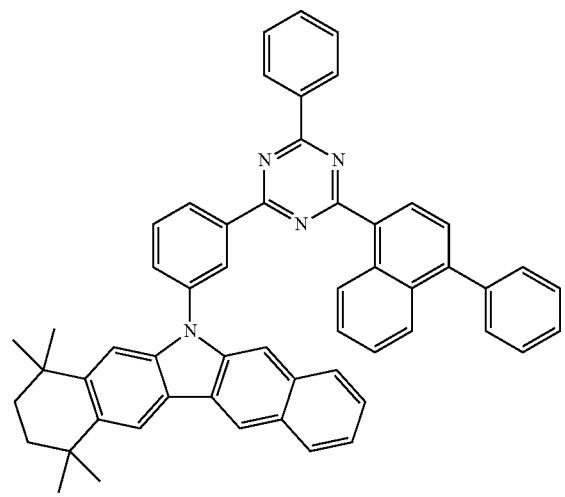 [SMILES: CC1(C)CCC(C)(C)c2cc3c(cc21)c1cc2ccccc2cc1n3-c1cccc(-c2nc(-c3ccccc3)nc(-c3ccc(-c4ccccc4)c4ccccc34)n2)c1]

629
-continued
332
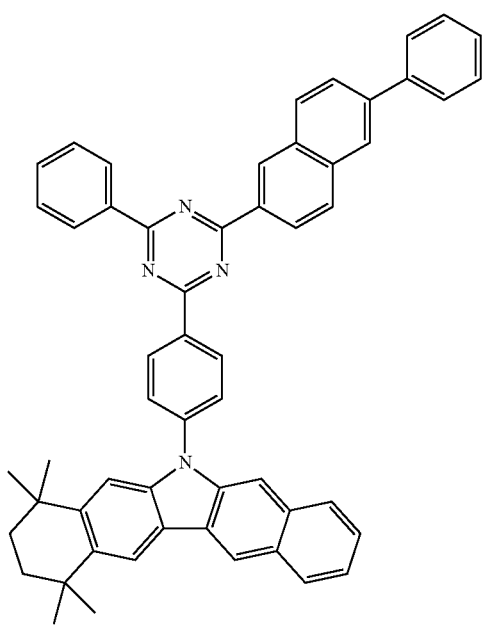
333
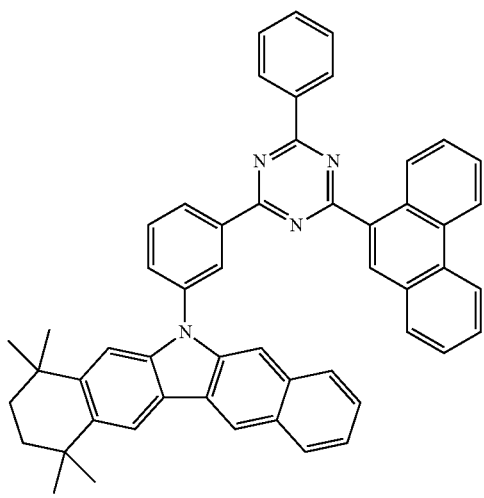
334
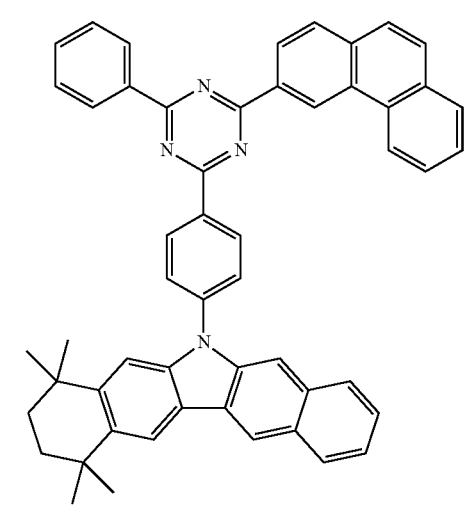
630
-continued
335
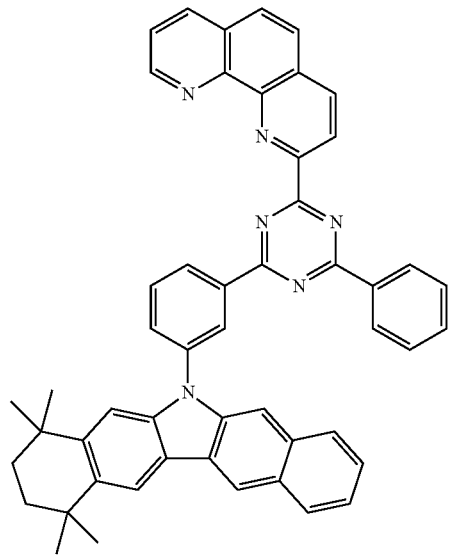
336
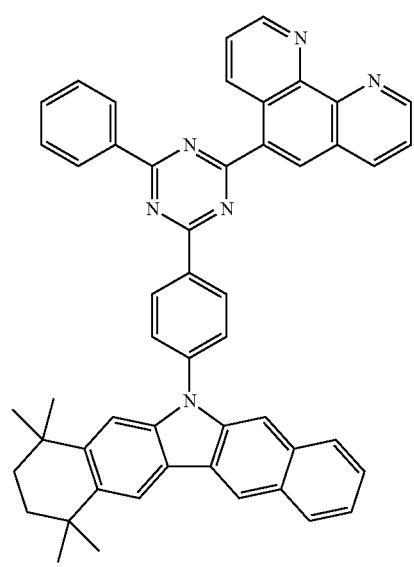
337
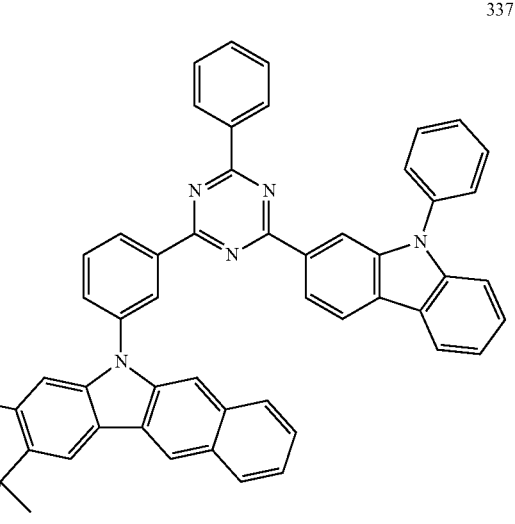

338
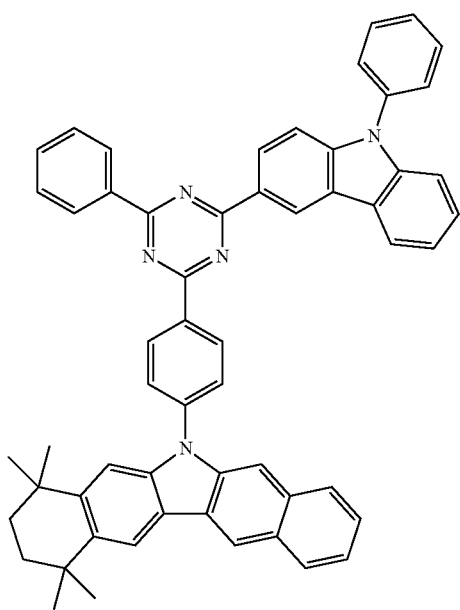
340
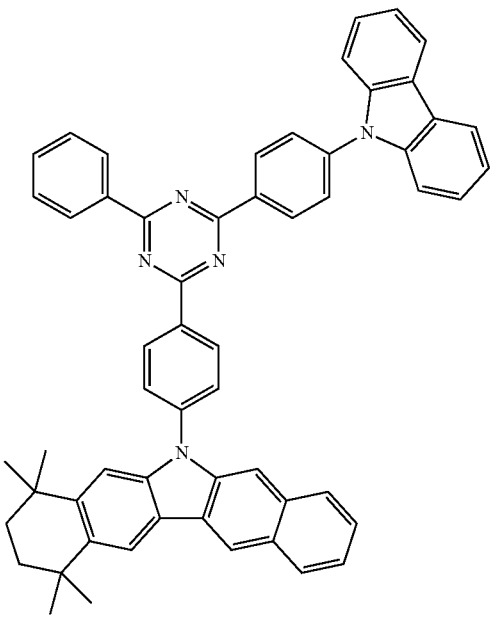
339
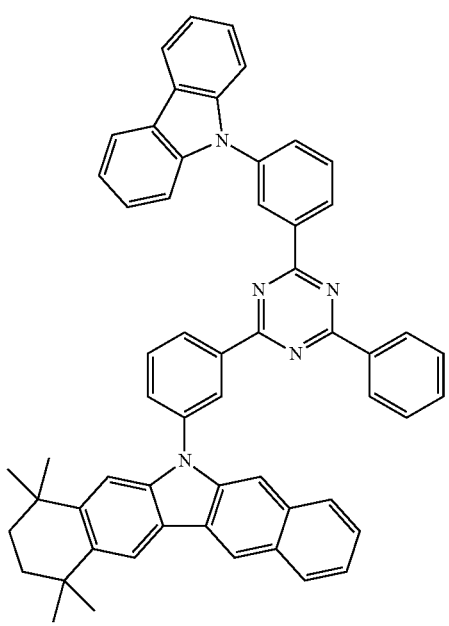
341
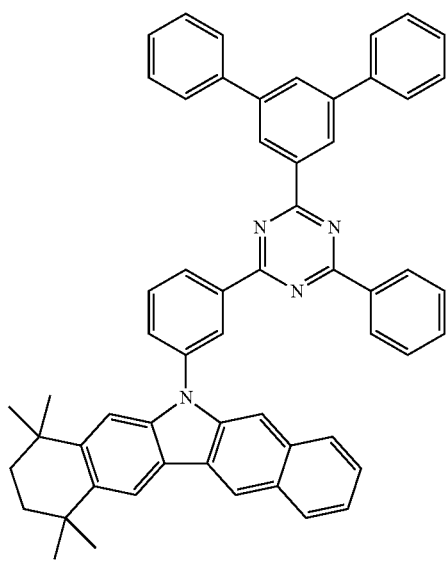

-continued
342
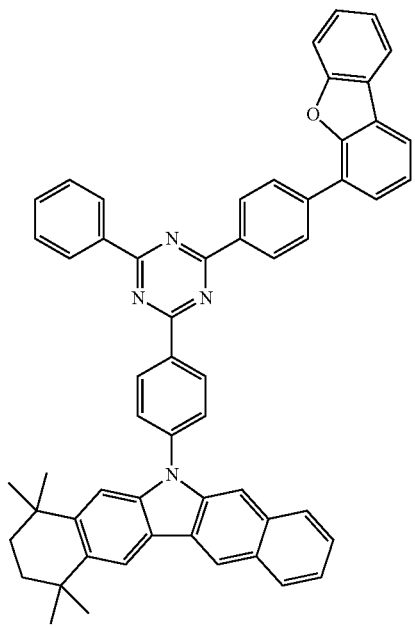
343
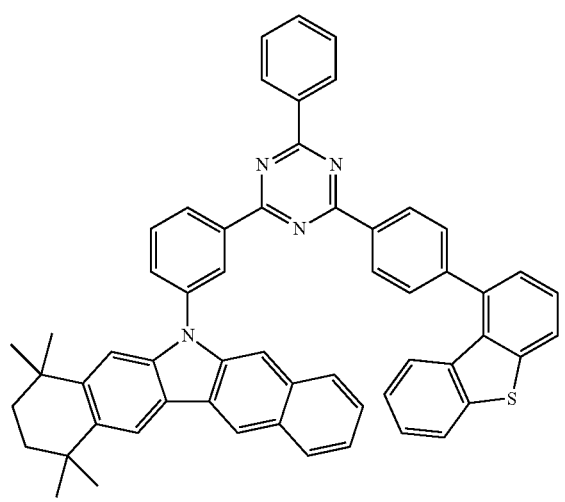
344
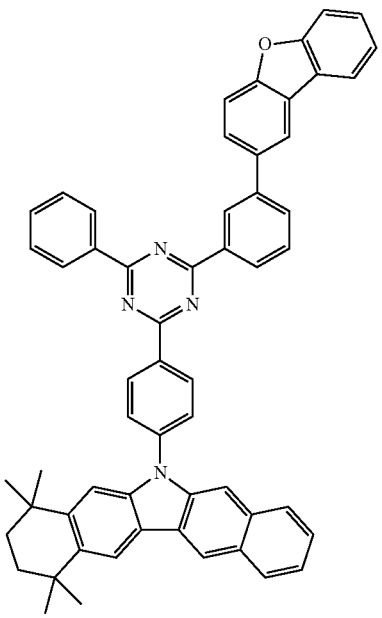
345
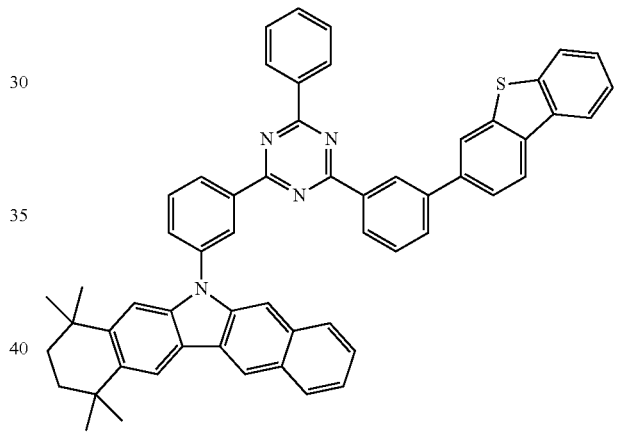
347
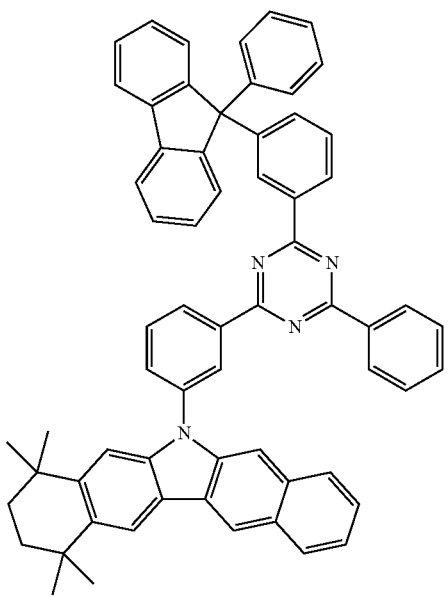

349
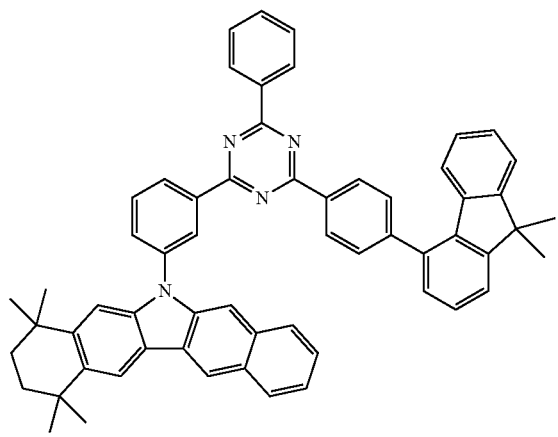
353
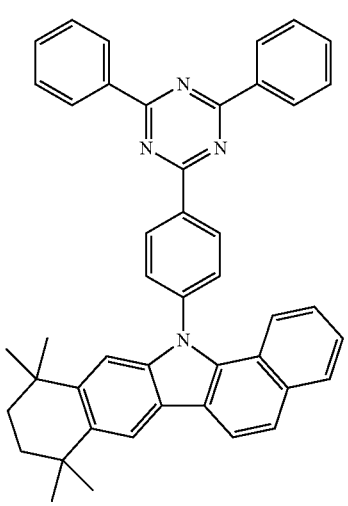
354
355
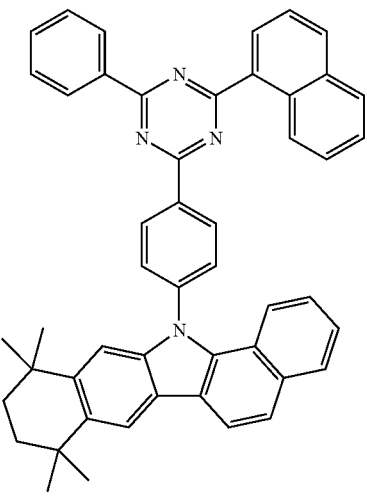
356
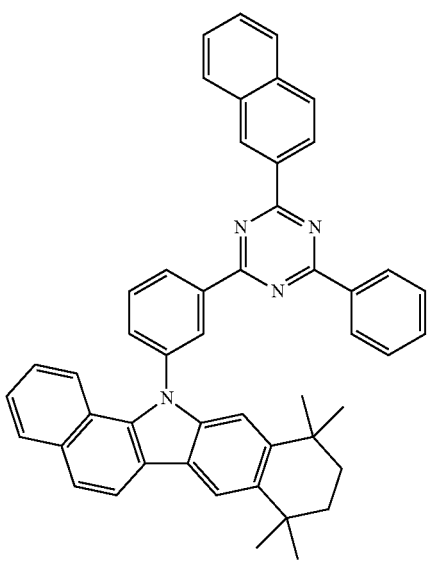
357
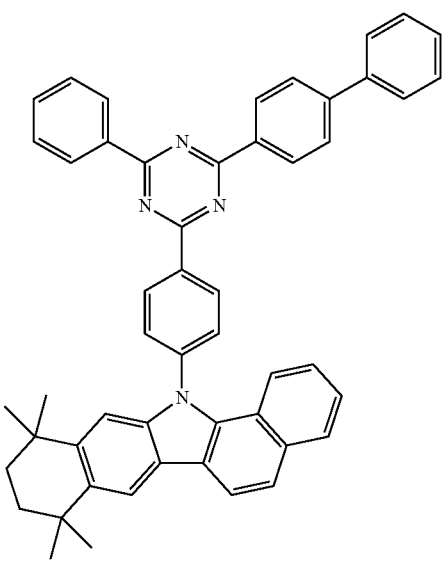

-continued
358
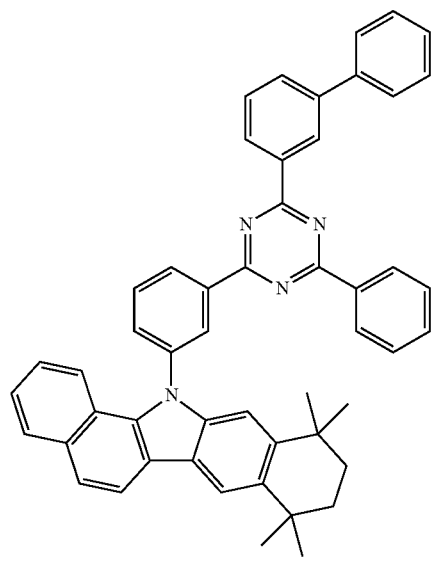
359
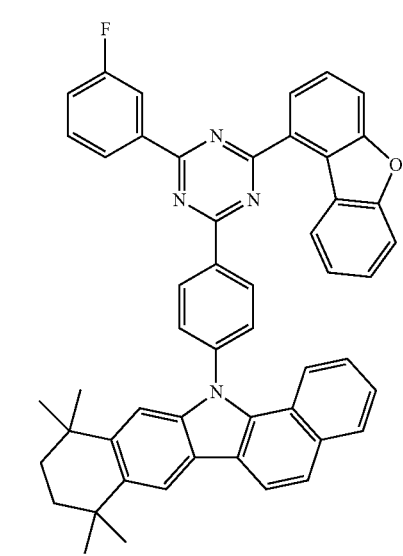 [SMILES: CC1(C)CCC(C)(C)c2cc3c(cc21)c1ccc2ccccc2c1n3-c1ccc(-c2nc(-c3cccc(F)c3)nc(-c3cccc4oc5ccccc5c34)n2)cc1]
360
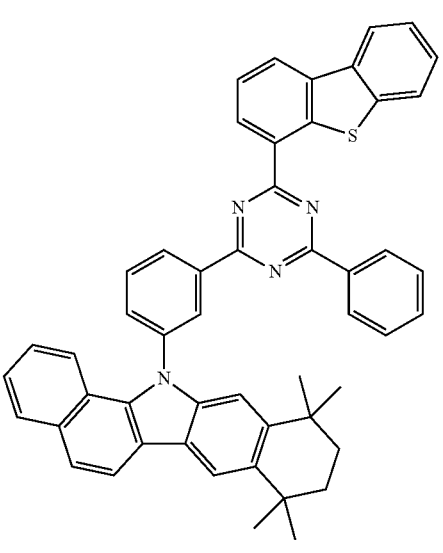
-continued
361
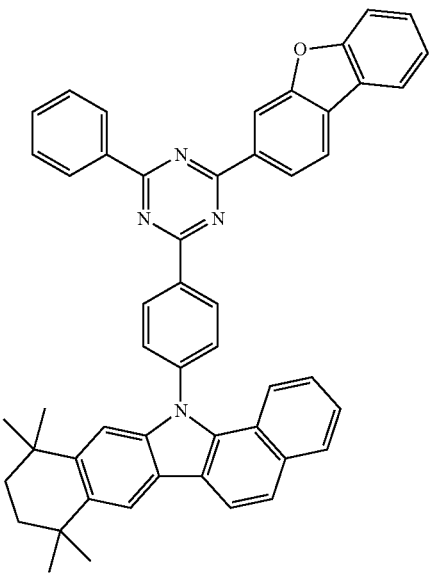
362
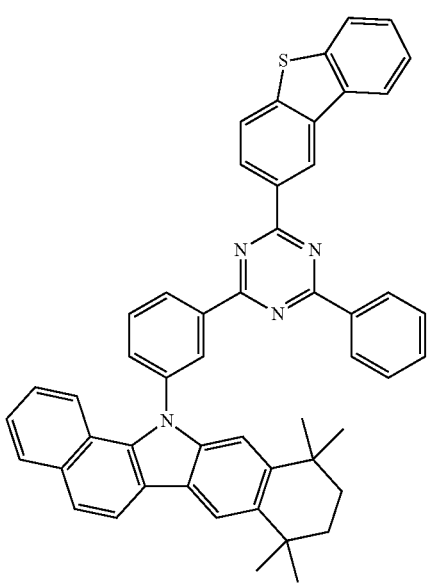
363
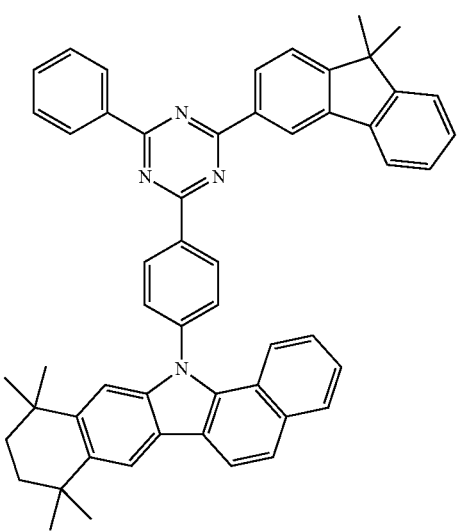

639
-continued
364
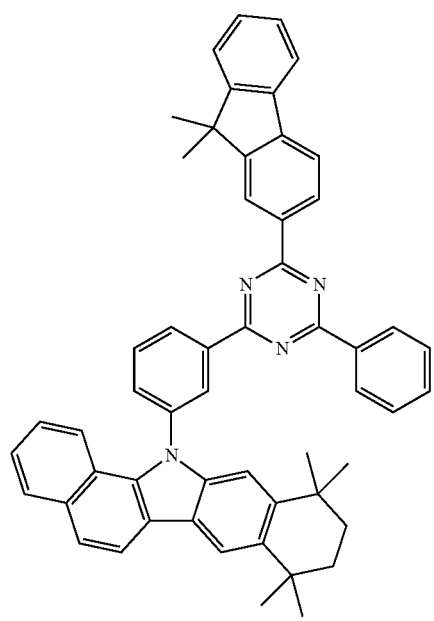
365
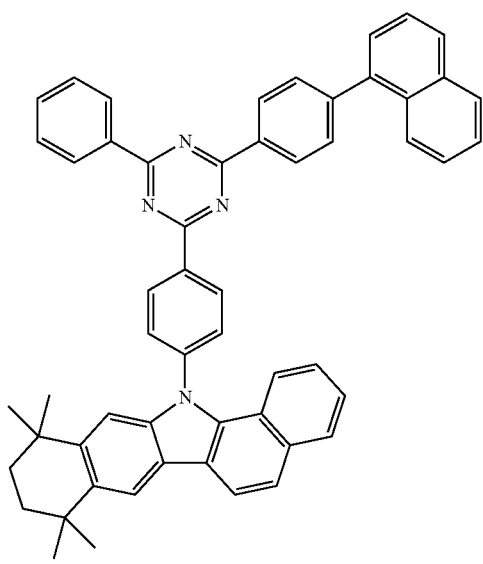
640
-continued
366
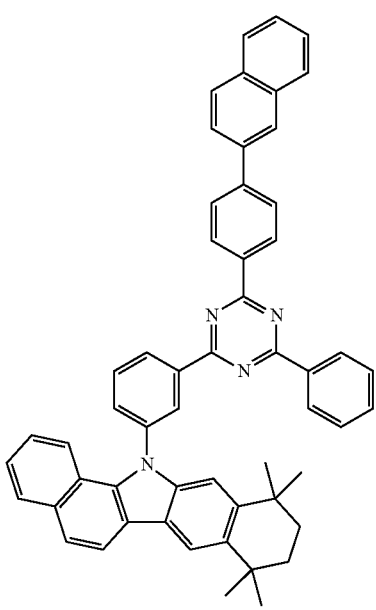
367
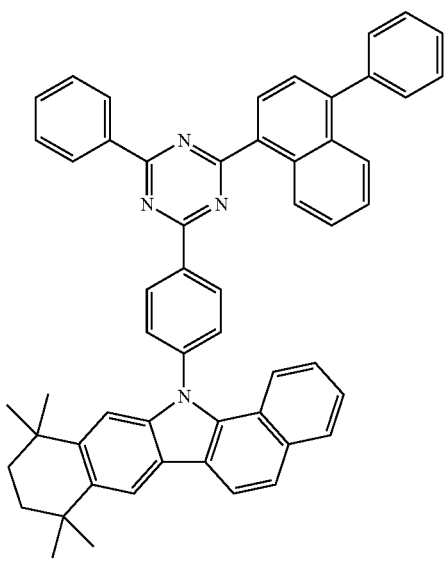

641
-continued
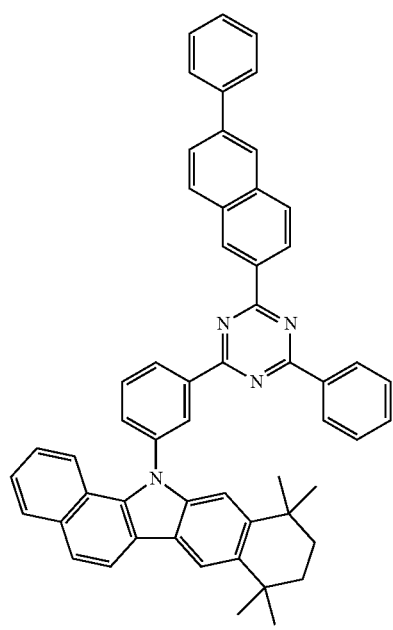
368
642
-continued
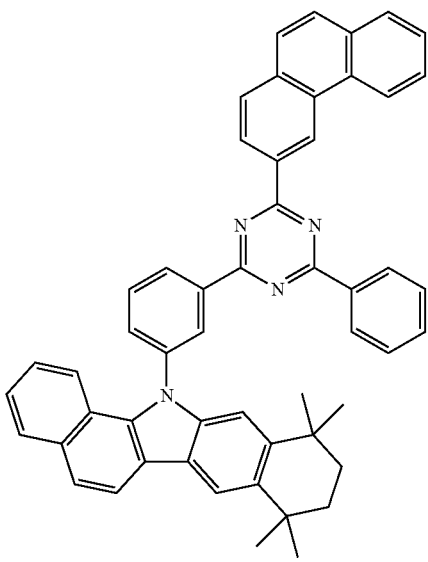
370
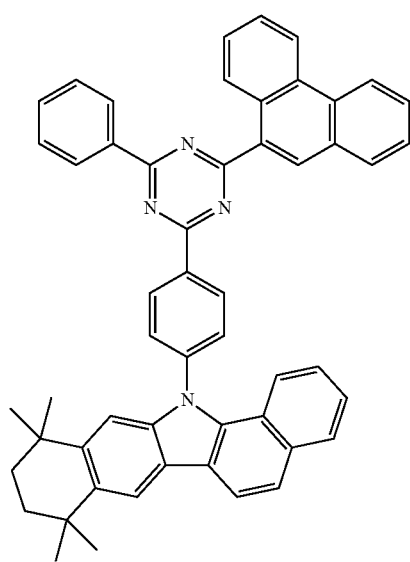
369
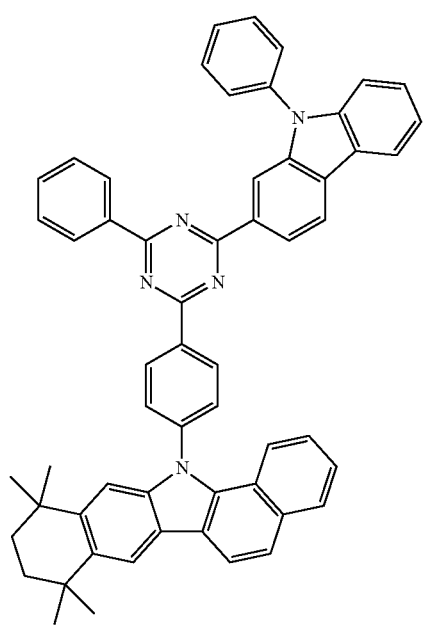
371

372
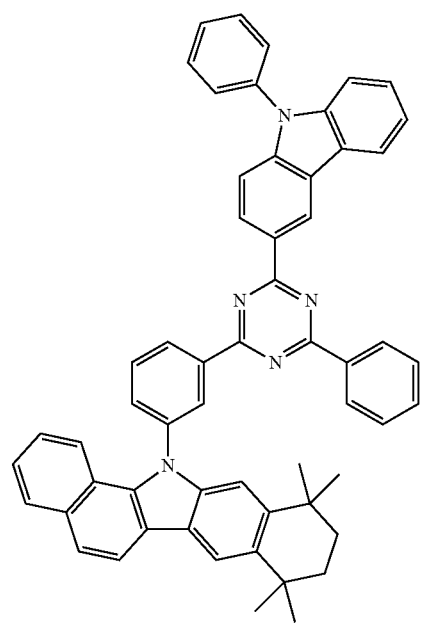
374
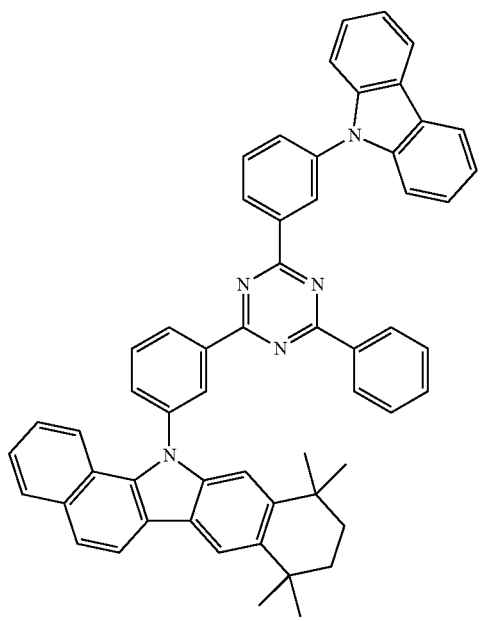
373
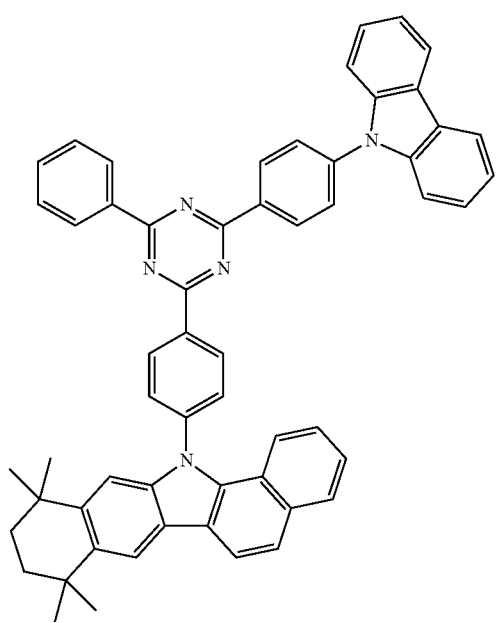
375
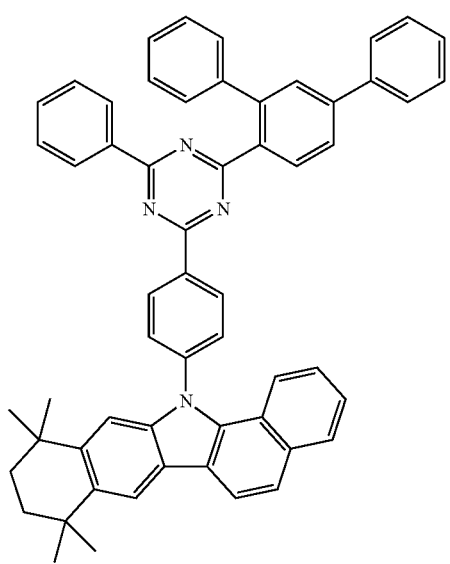

645
-continued
376
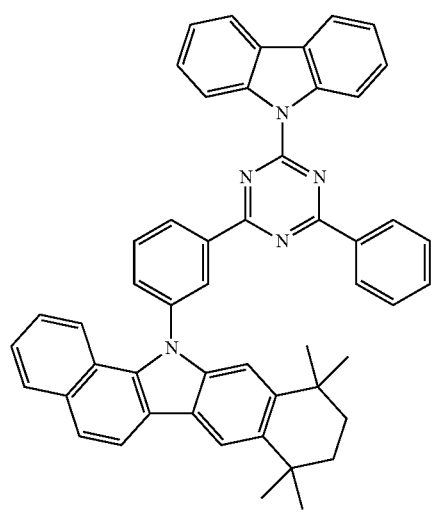
377
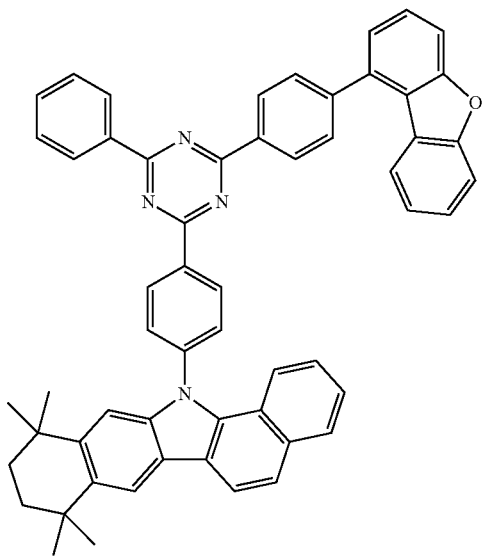
646
-continued
378
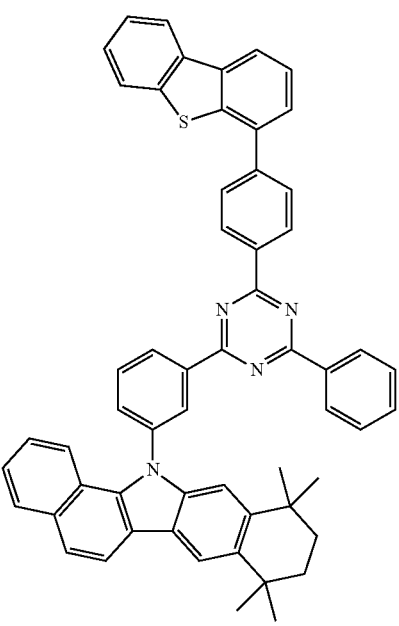
379
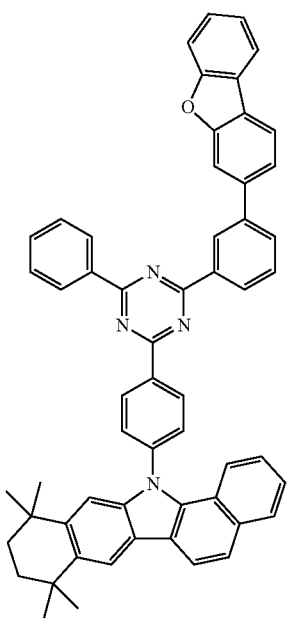

380
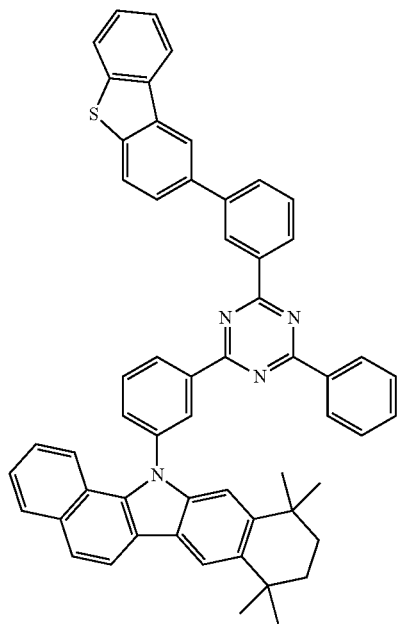
384
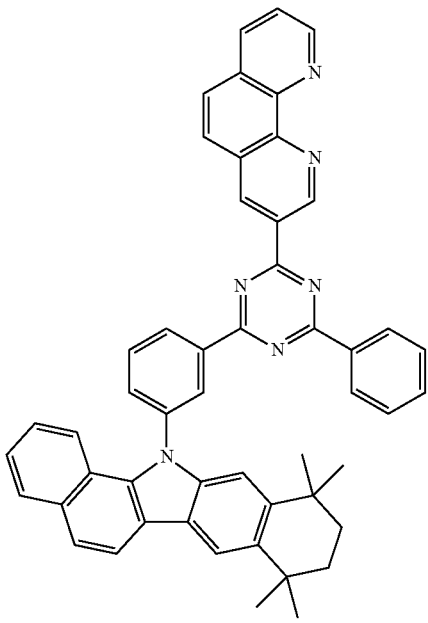
382
385

-continued
386
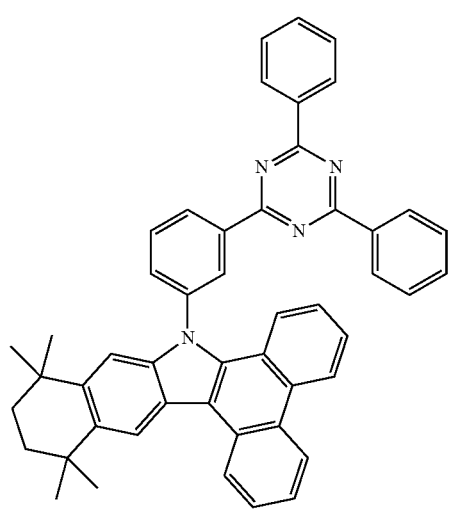 [SMILES: CC1(C)CCC(C)(C)c2cc3c(cc21)c1c2ccccc2c2ccccc2c1n3-c1cccc(-c2nc(-c3ccccc3)nc(-c3ccccc3)n2)c1]
387
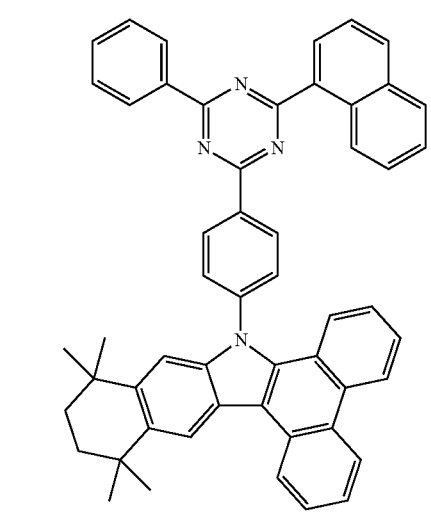
388
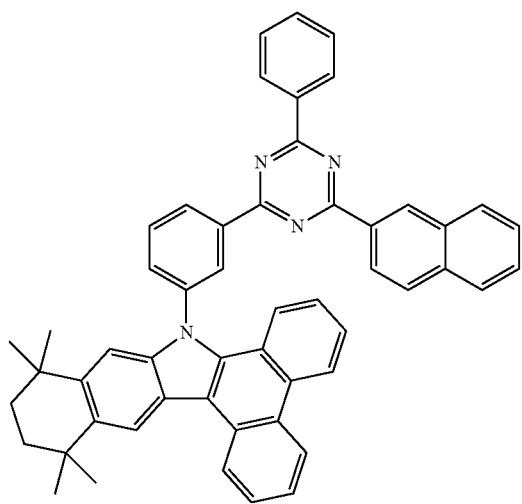
-continued
389
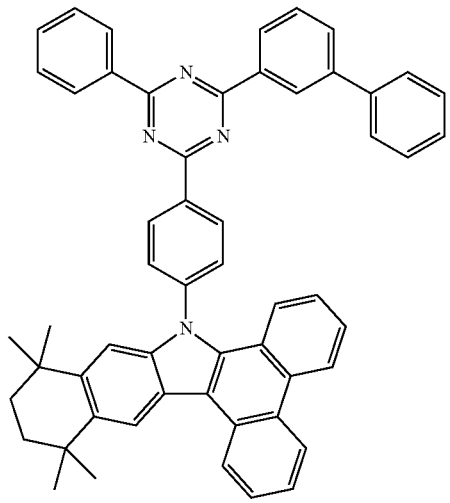
390
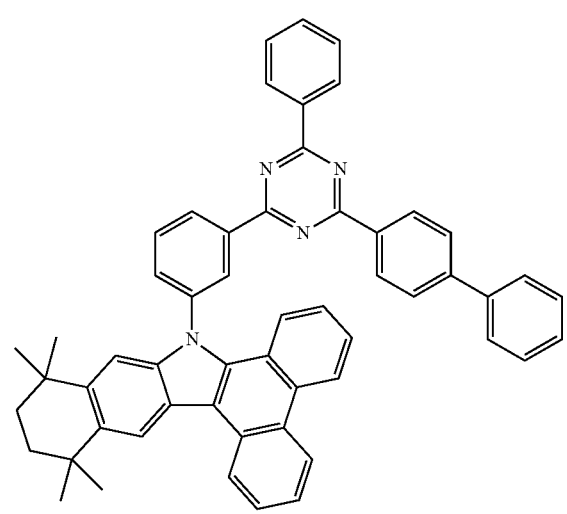
391
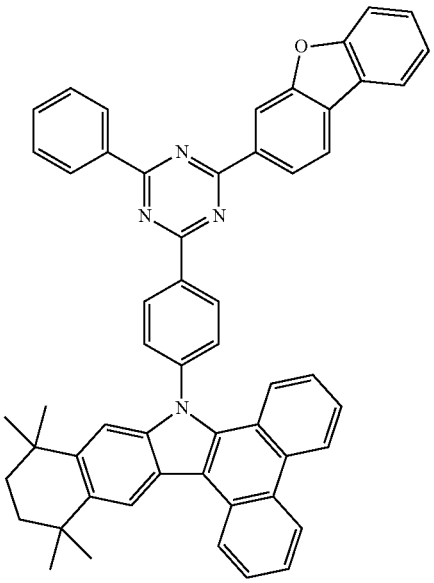

651
-continued
392
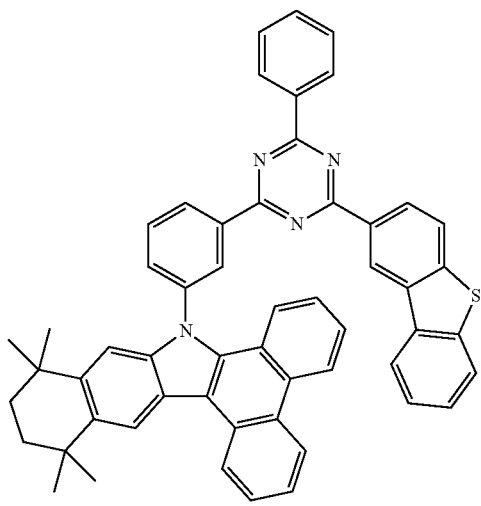
393
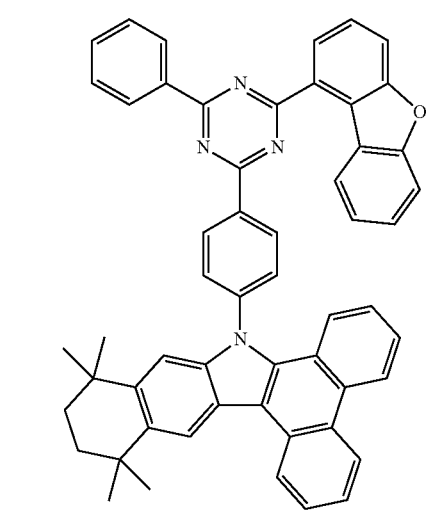
394
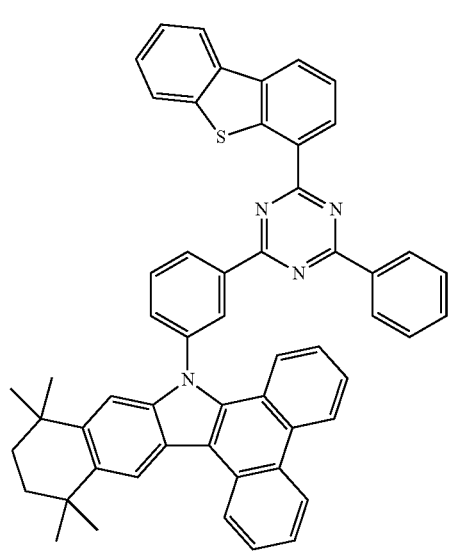
652
-continued
395
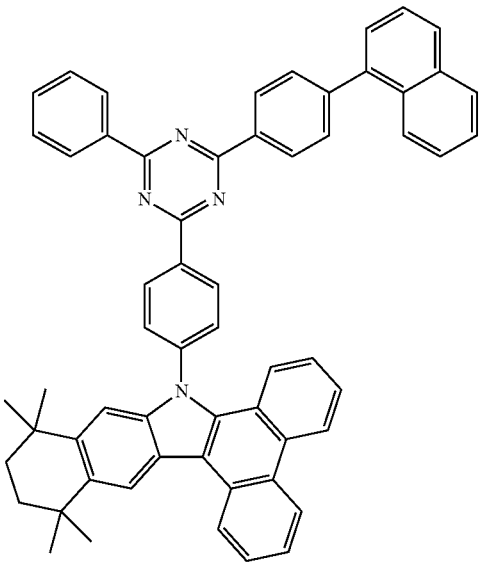
396
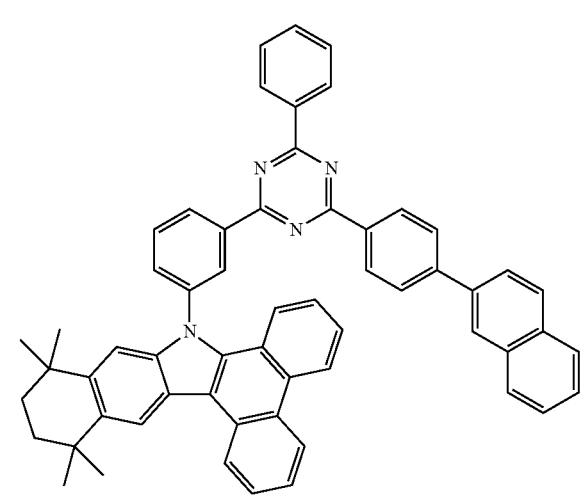
397
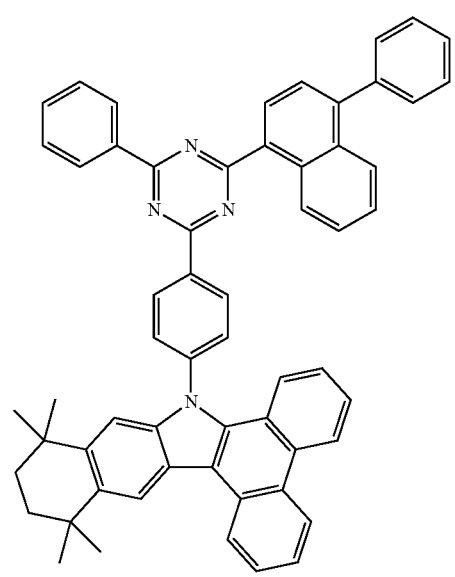

653
-continued
398
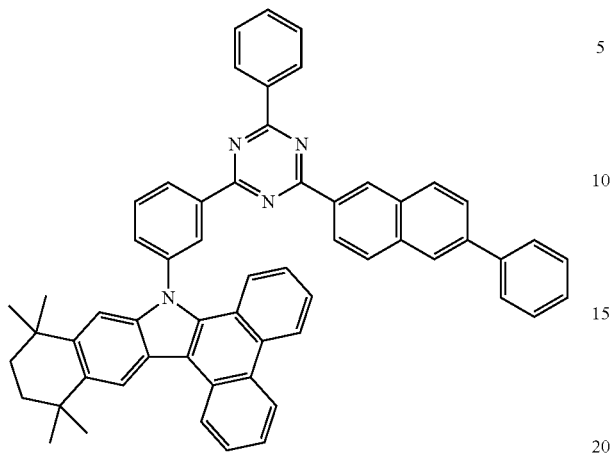
654
-continued
400
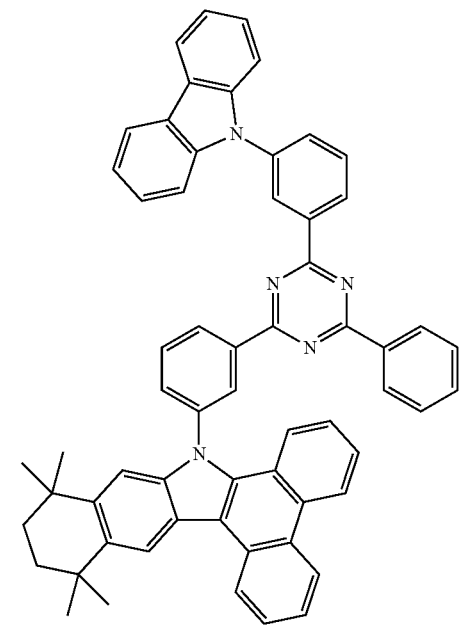
399
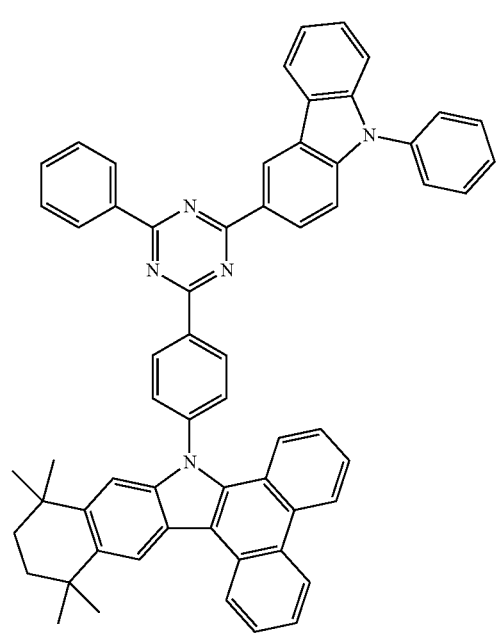
401
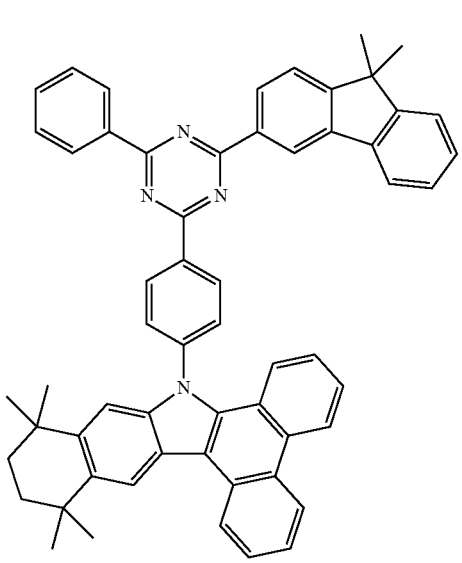

-continued
402
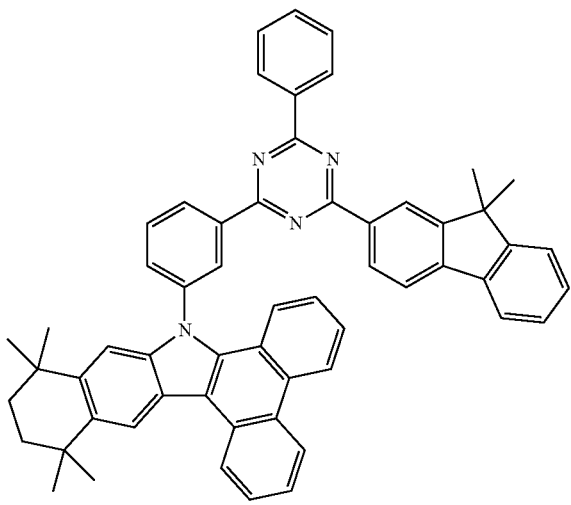
403
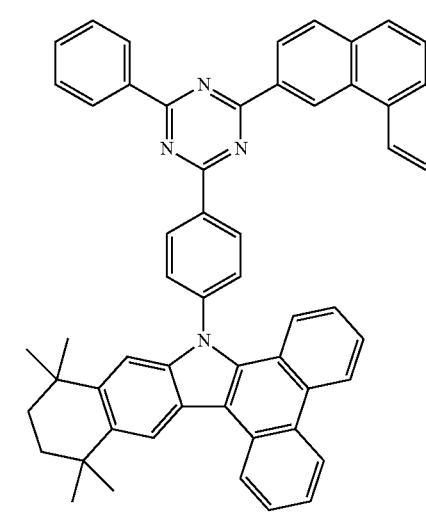
404
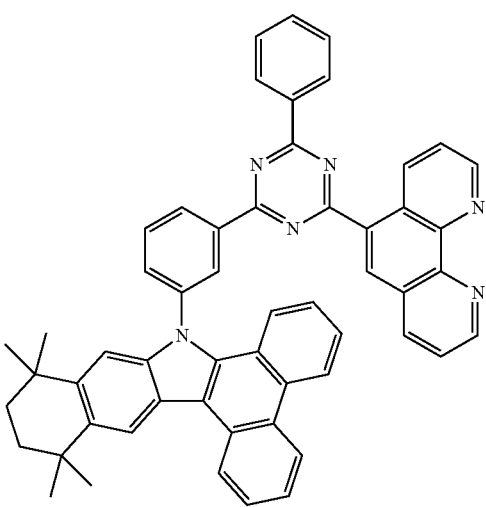
-continued
405
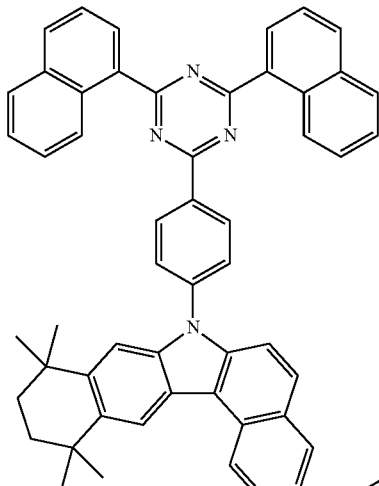
406
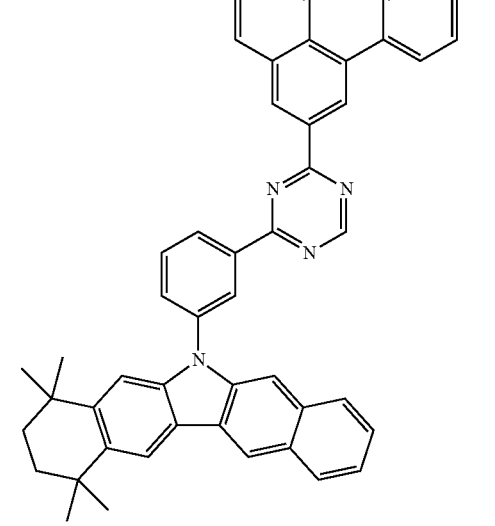
407
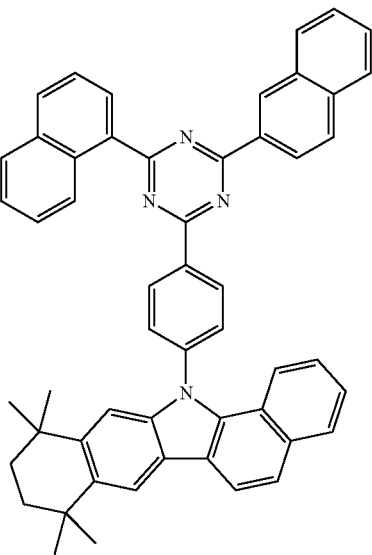

408
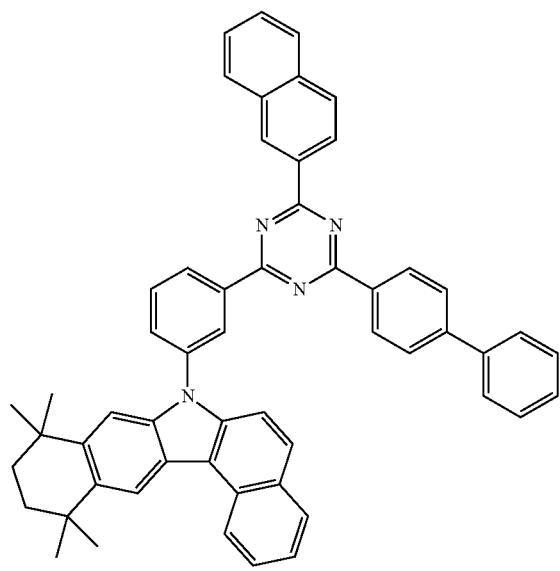 [SMILES: CC1(C)CCC(C)(C)c2cc3c(cc21)c1c2ccccc2ccc1n3-c1cccc(-c2nc(-c3ccc(-c4ccccc4)cc3)nc(-c3ccc4ccccc4c3)n2)c1]
409
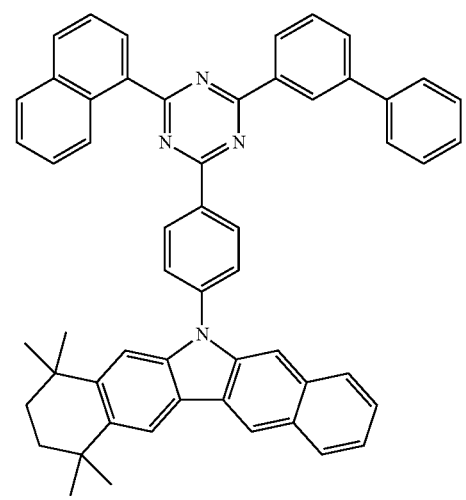
410
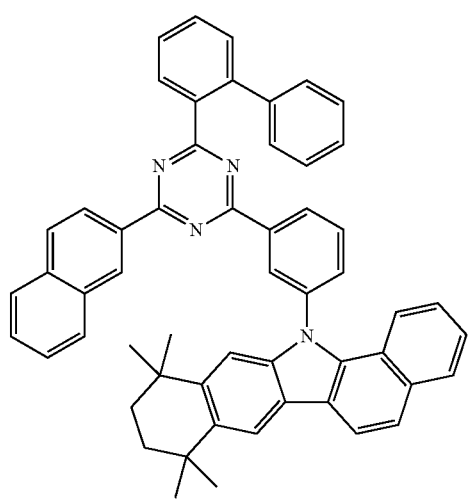
411
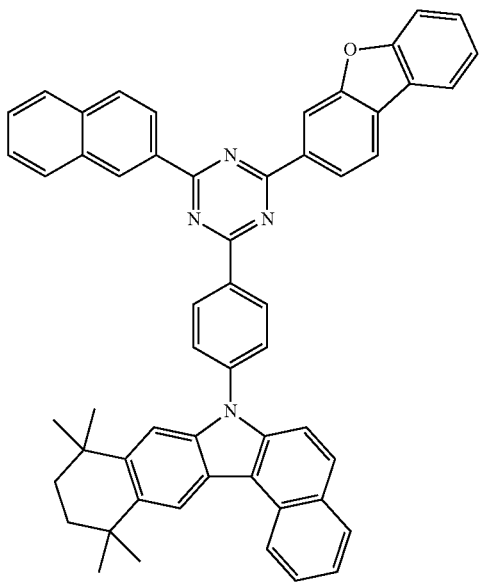
412
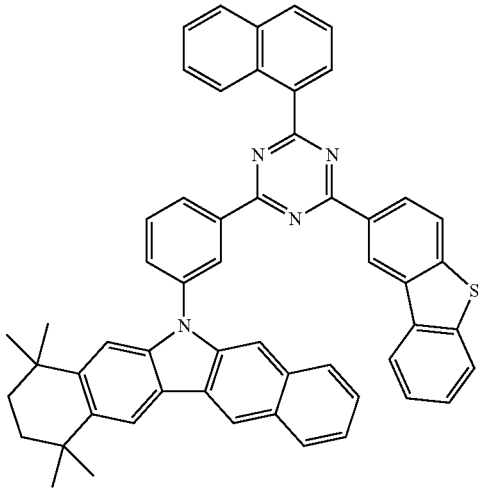
413
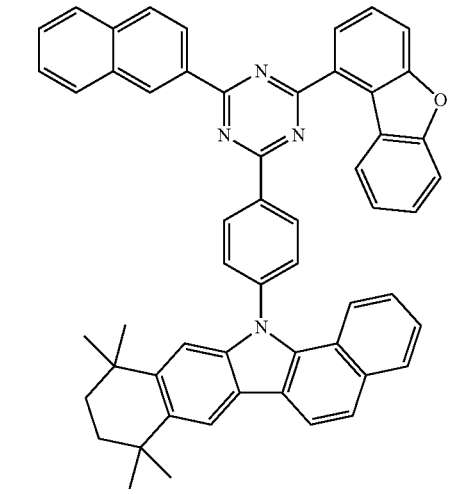 [SMILES: CC1(C)CCC(C)(C)c2cc3c(cc21)c1ccc2ccccc2c1n3-c1ccc(-c2nc(-c3ccc4ccccc4c3)nc(-c3cccc4oc5ccccc5c34)n2)cc1]

414
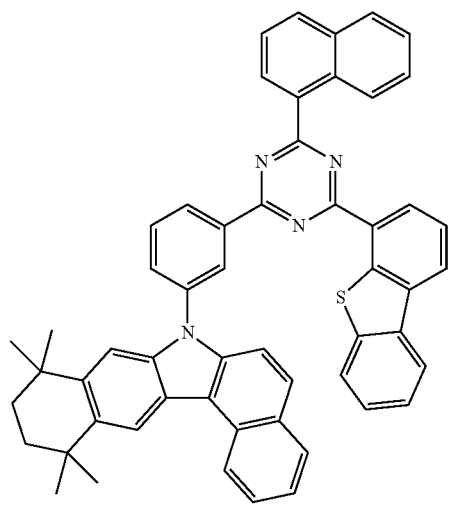
415
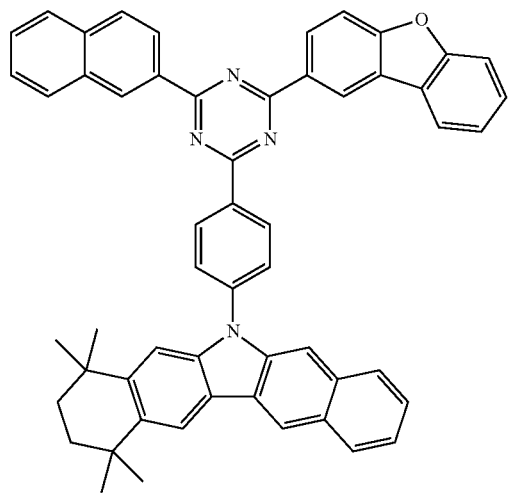
416
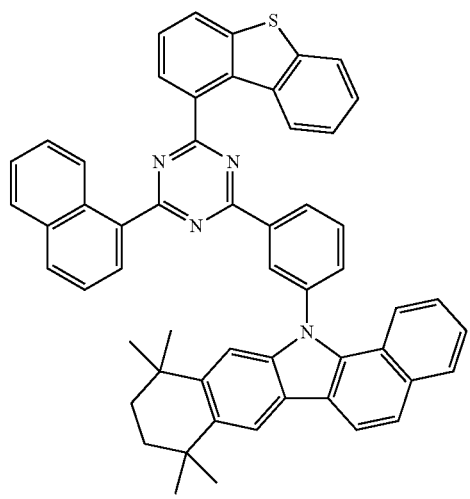
417
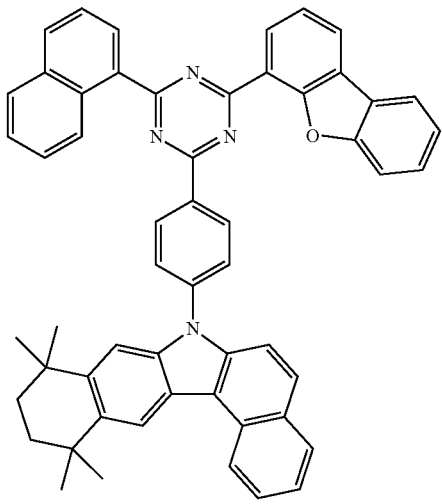
418
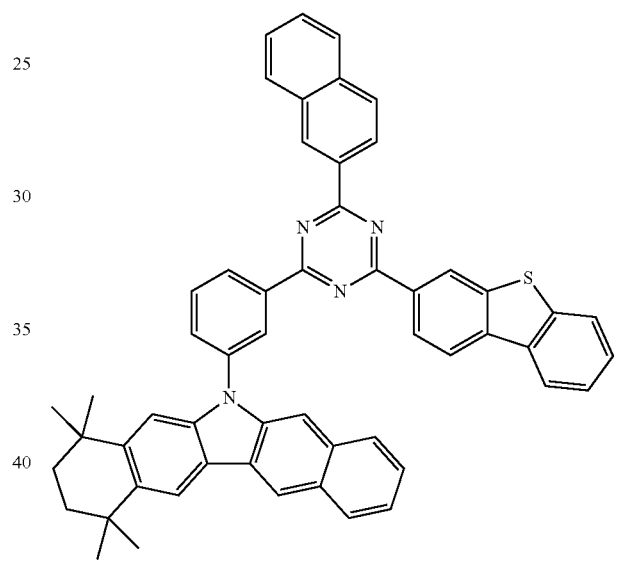
419
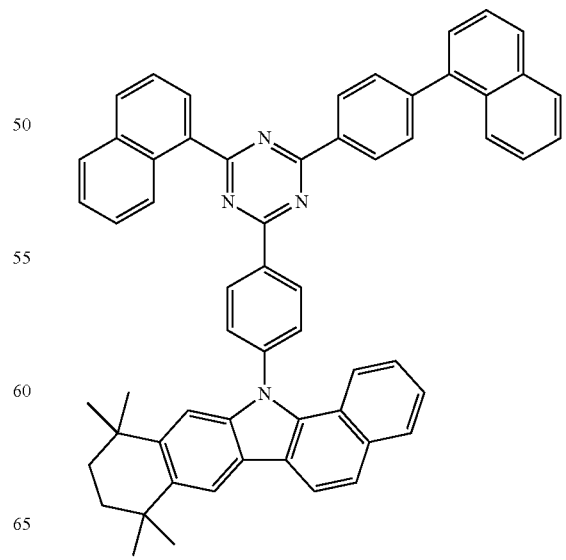

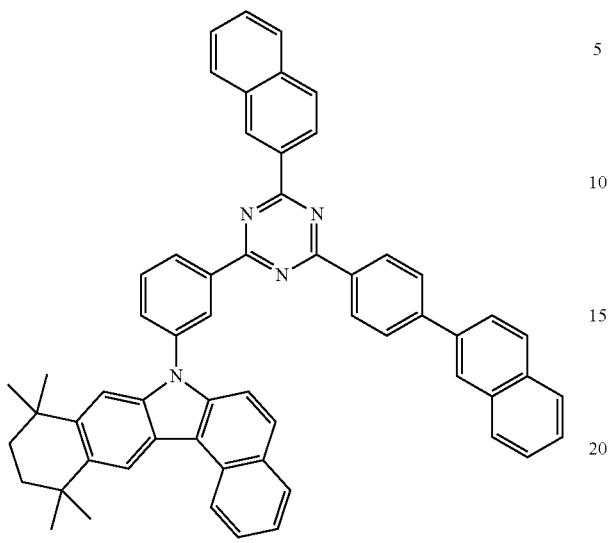
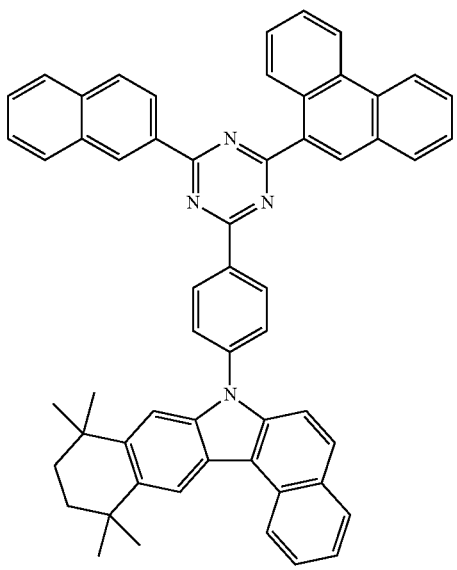
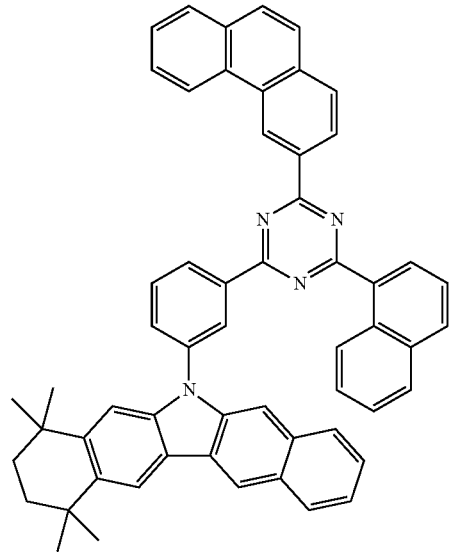
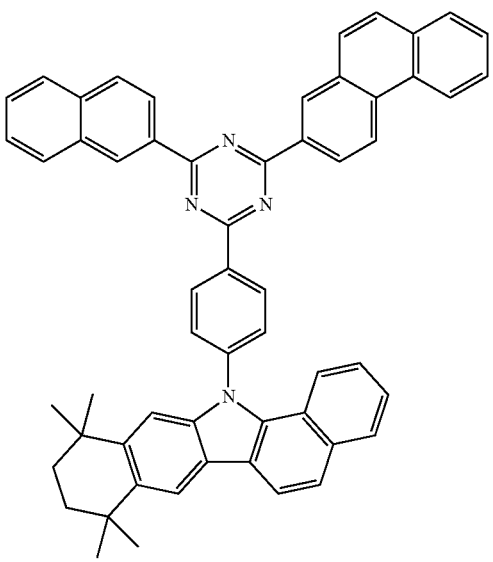

663
-continued
426
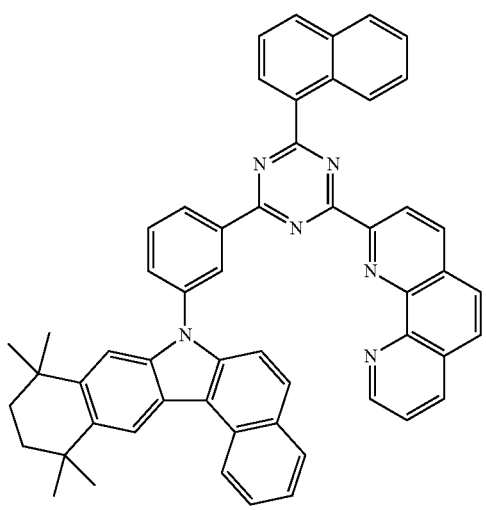
427
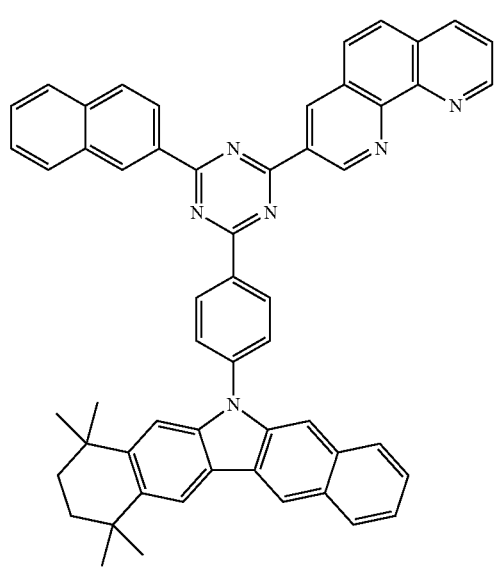
428
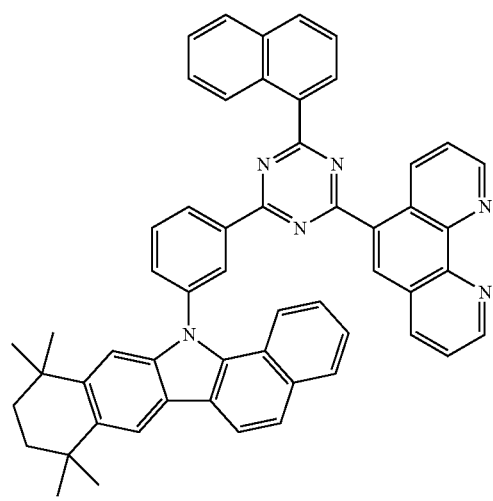
664
-continued
429
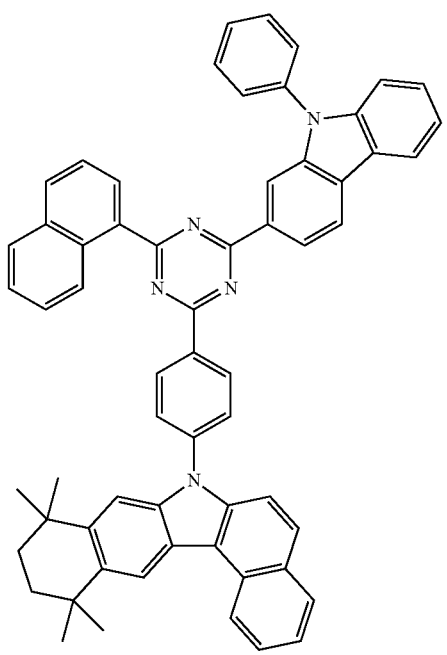
430
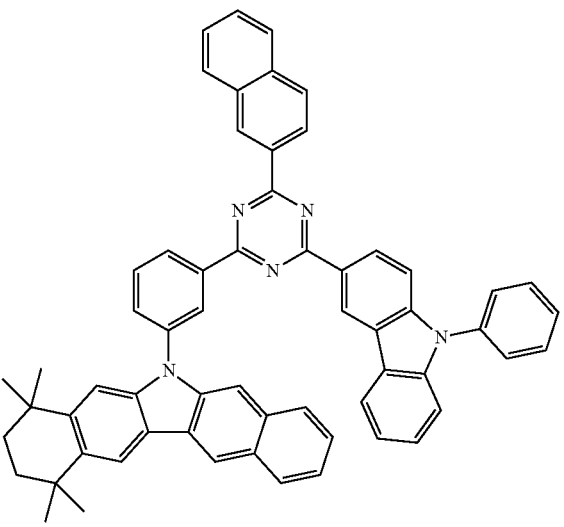

665
-continued
431
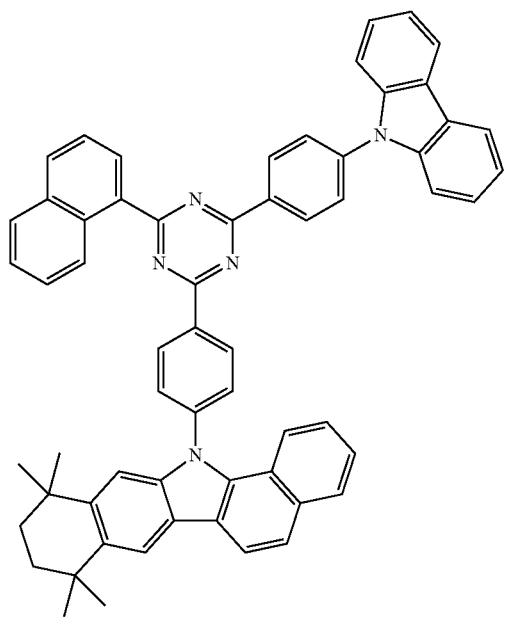
432
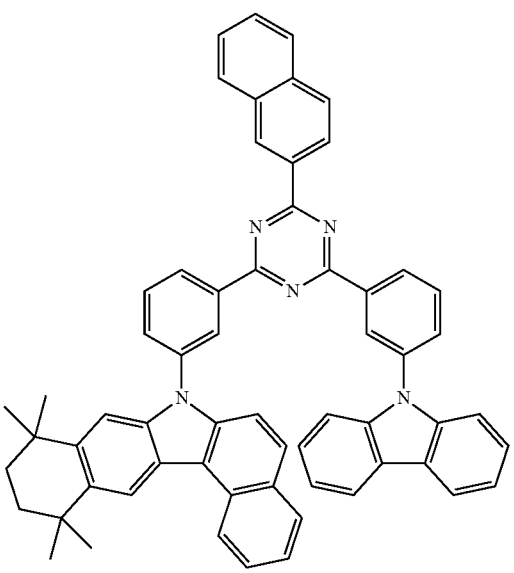
666
433
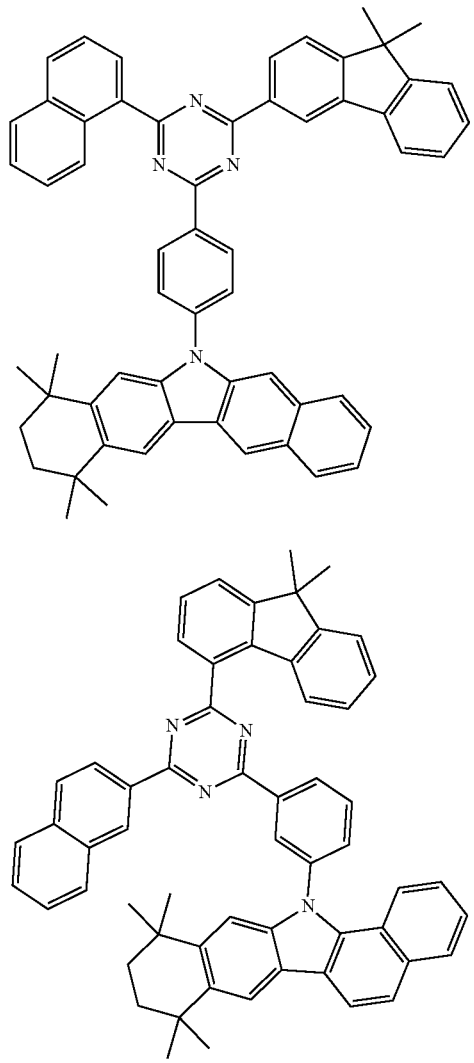
434
435
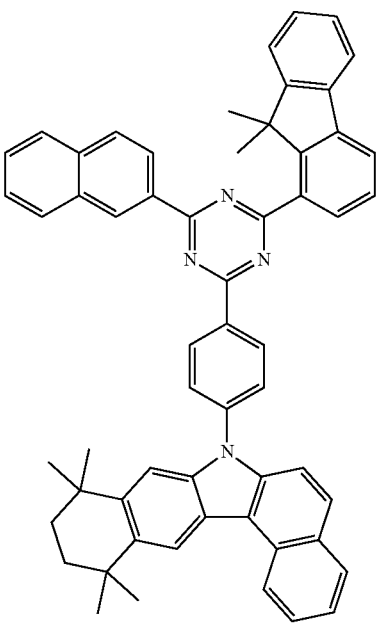

436
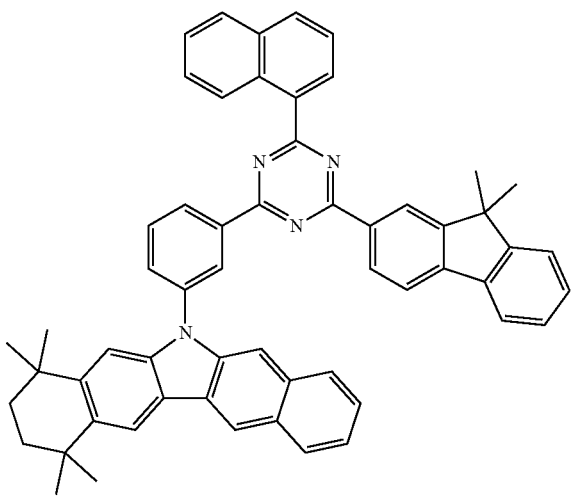
437
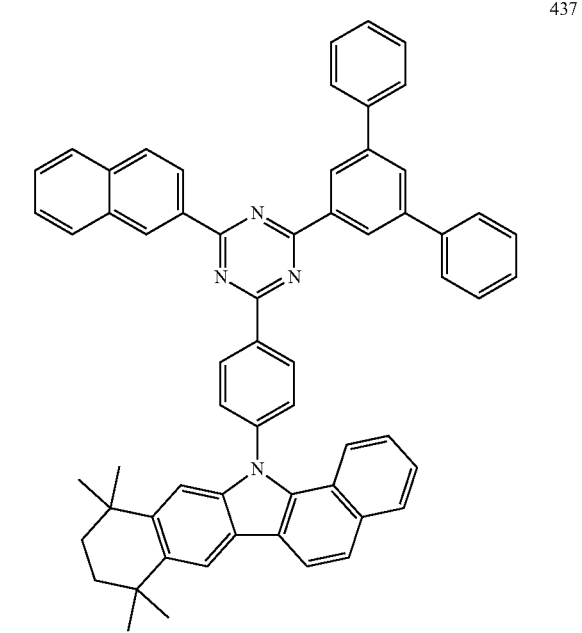
438
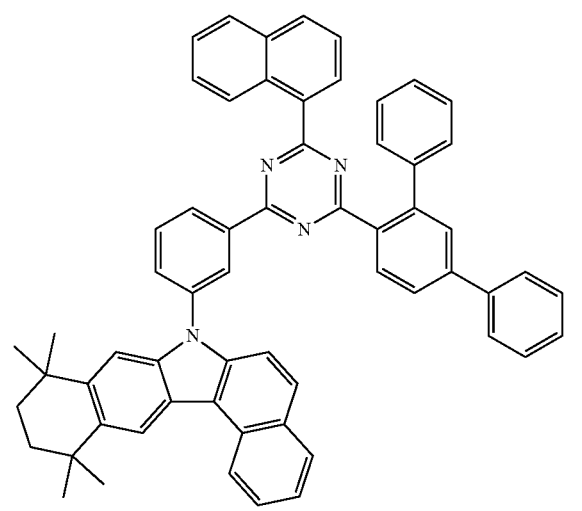
439
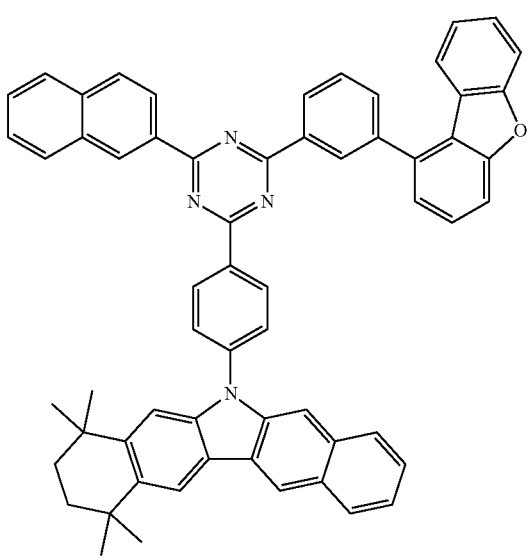
440
441
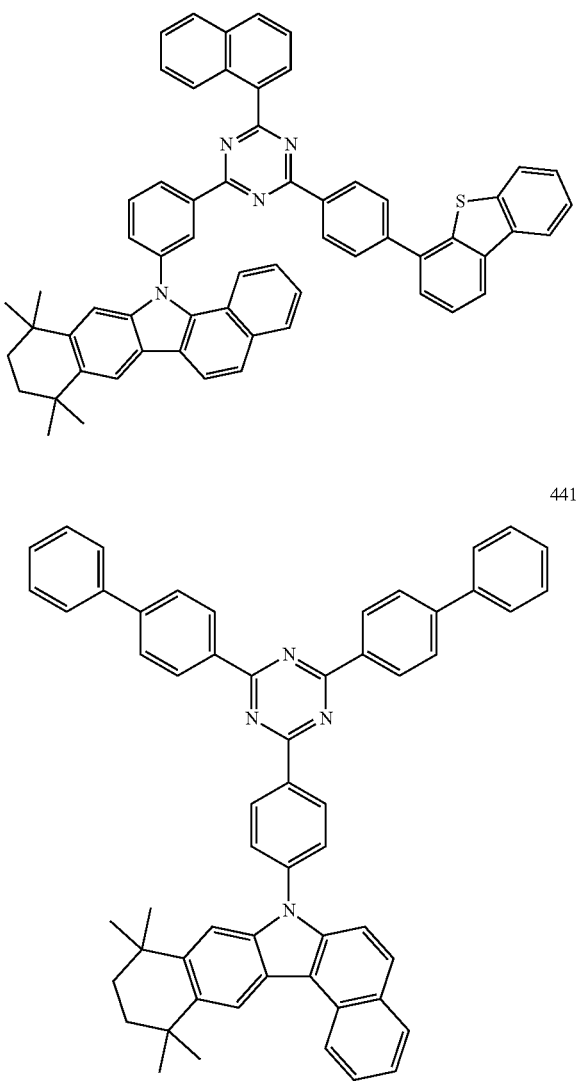

669
-continued
442
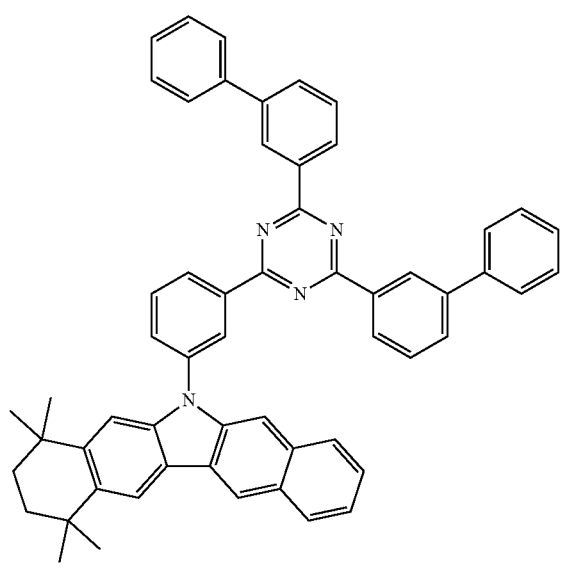 [SMILES: CC1(C)CCC(C)(C)c2cc3c(cc21)c1cc2ccccc2cc1n3-c1cccc(-c2nc(-c3cccc(-c4ccccc4)c3)nc(-c3cccc(-c4ccccc4)c3)n2)c1]
443
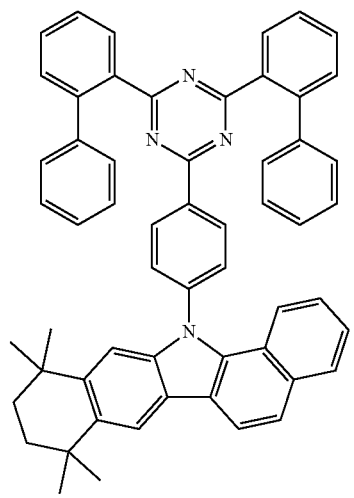
444
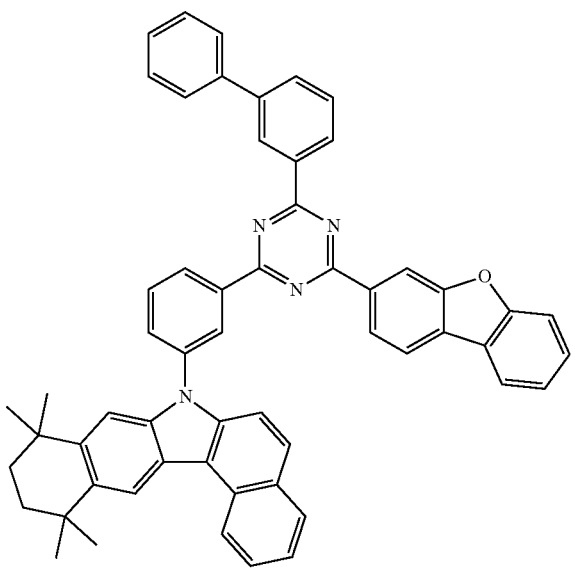
670
-continued
445
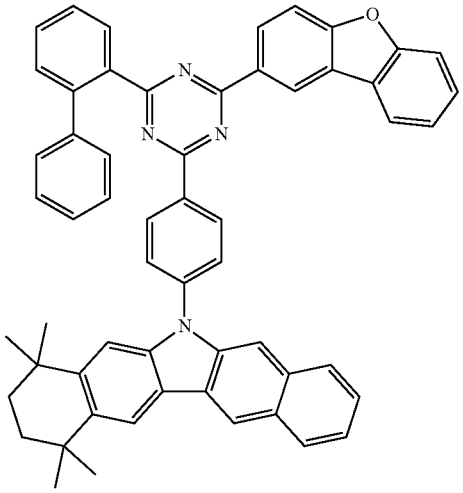
446
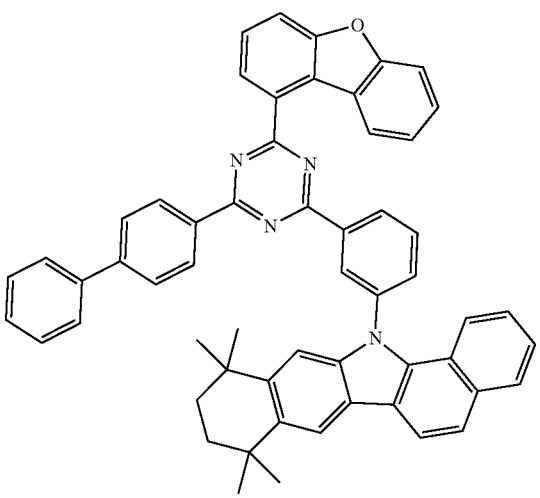
447
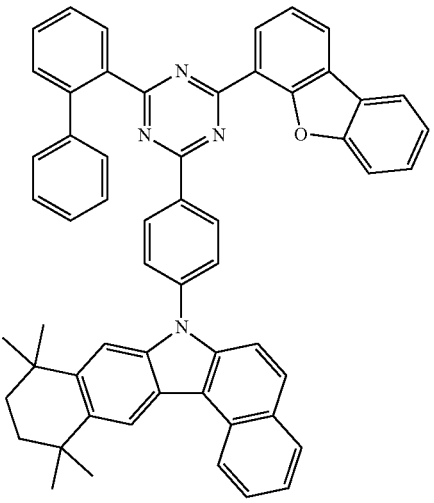

-continued
448
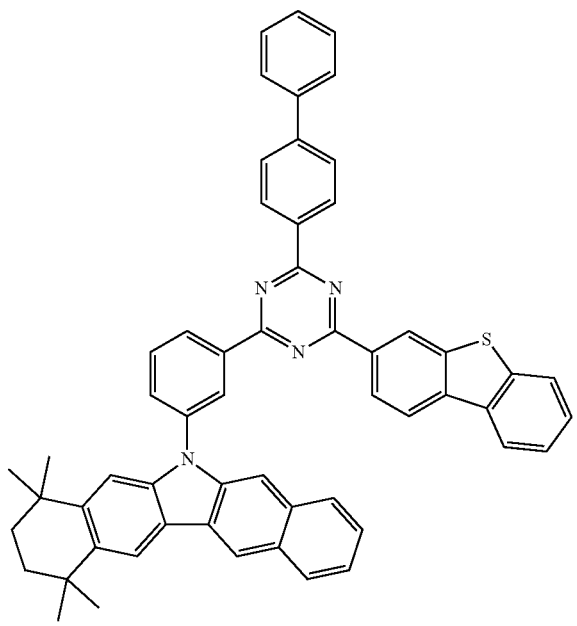
449
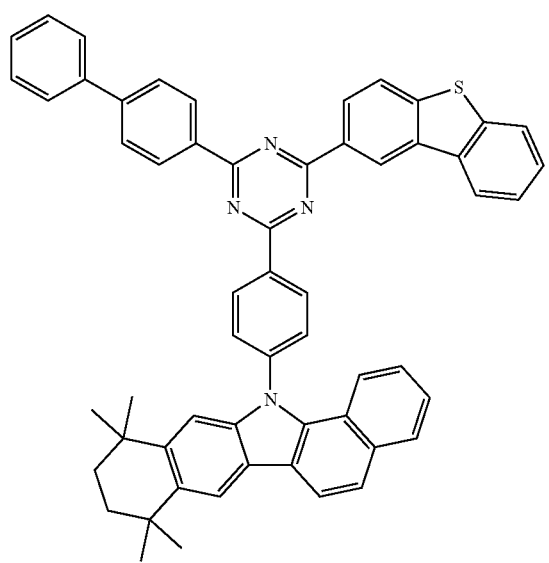
-continued
450
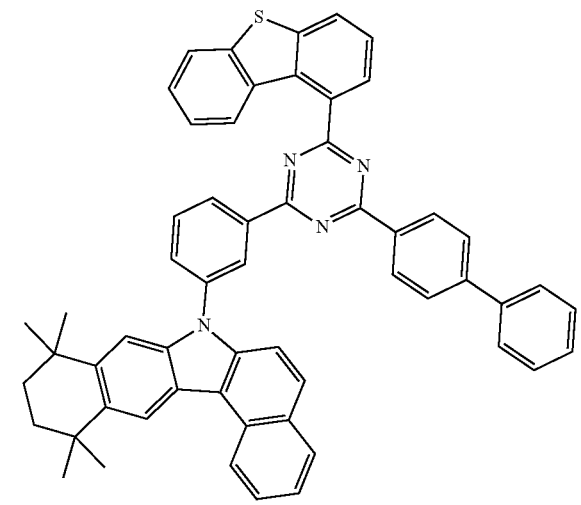
451
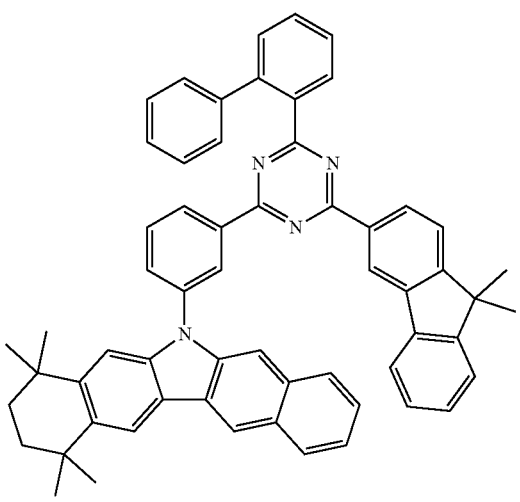
452

673
-continued
453
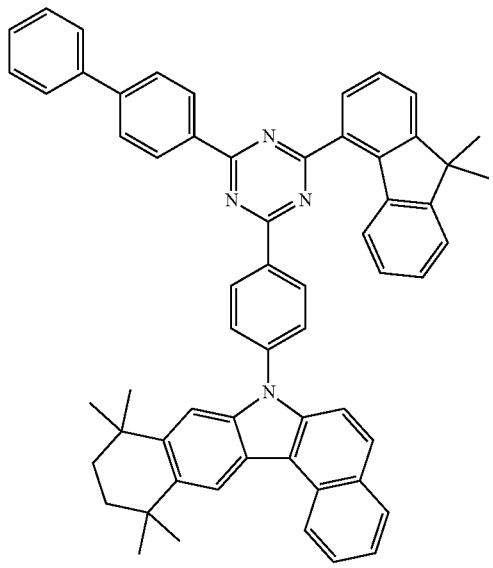
454
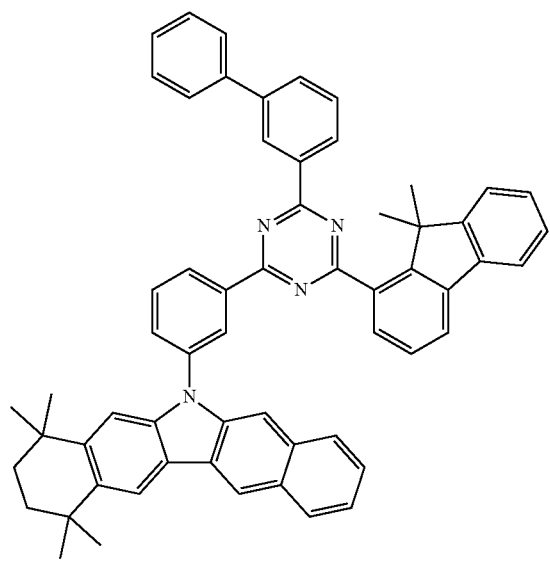
674
-continued
455
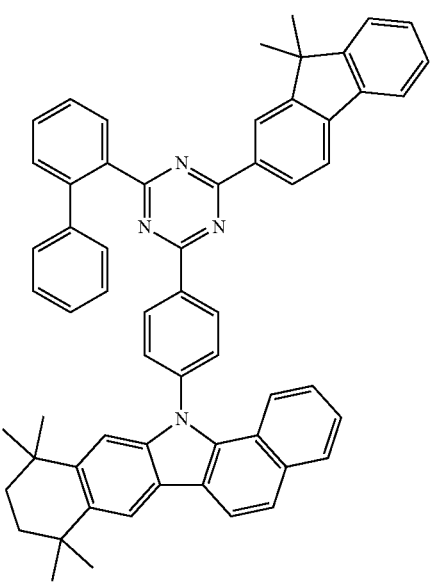
456
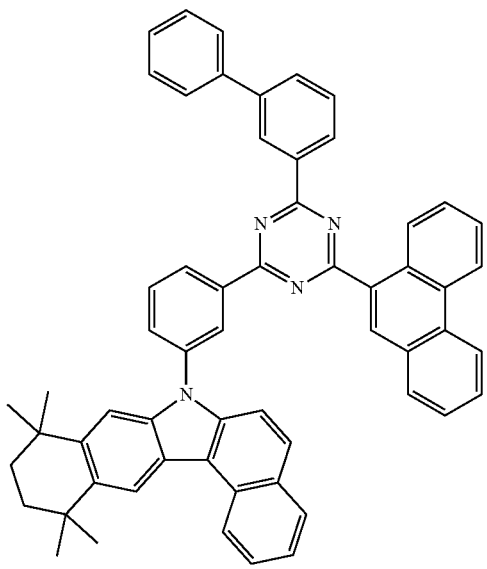
457
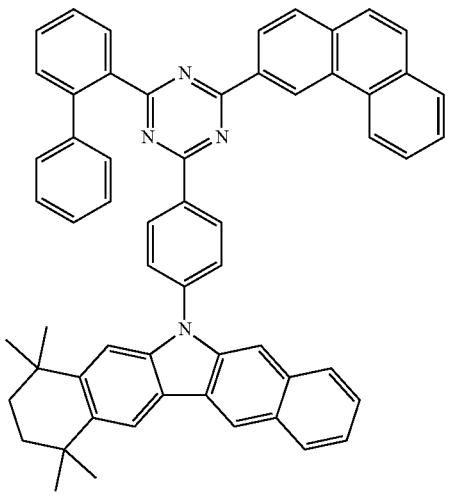

458
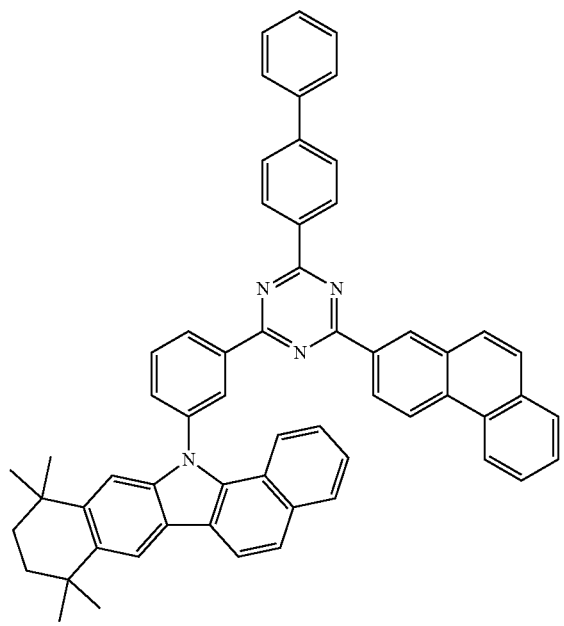
460
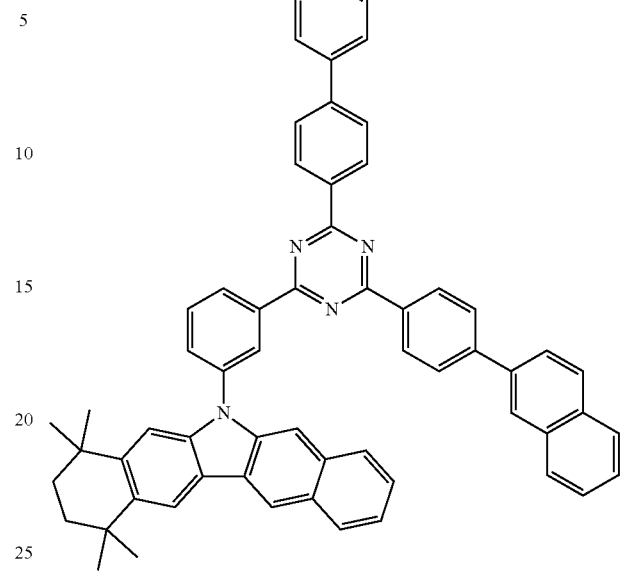
459
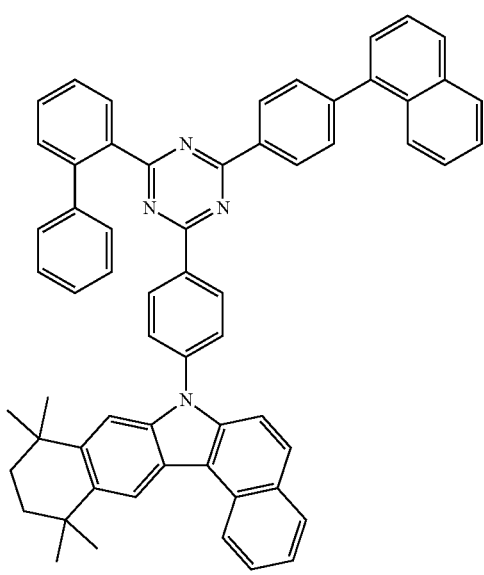
461
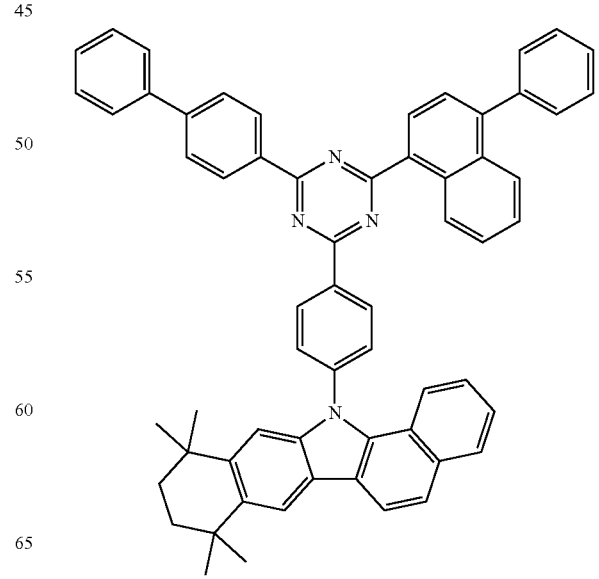

462
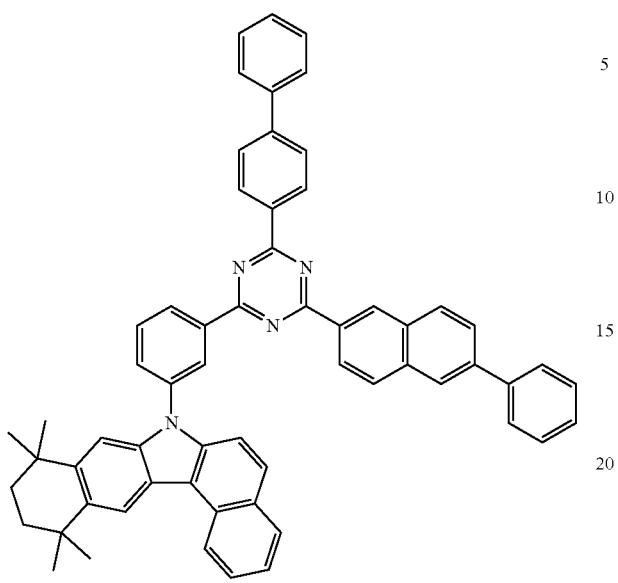
463
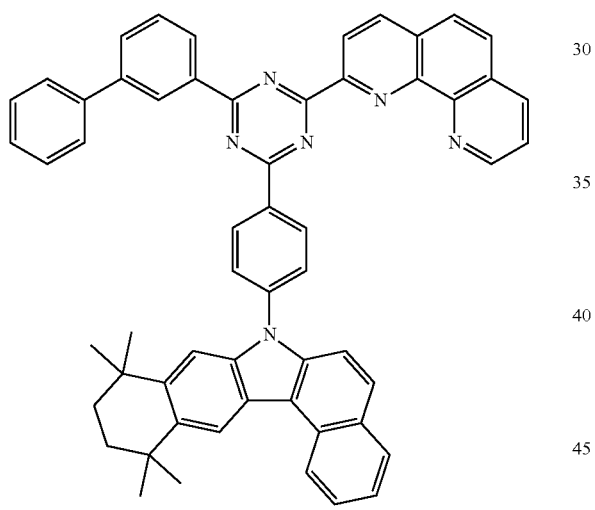
464
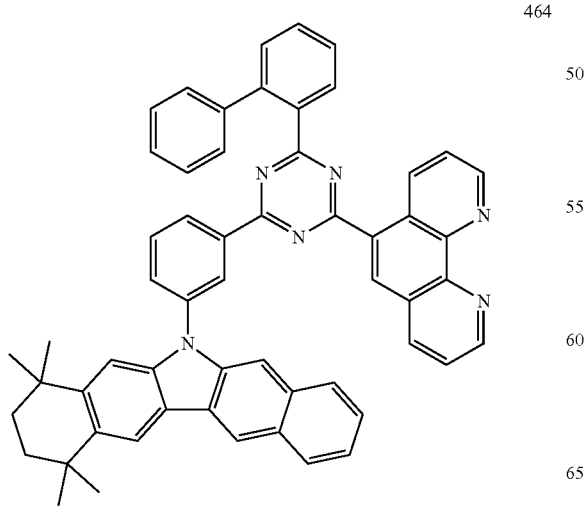
465
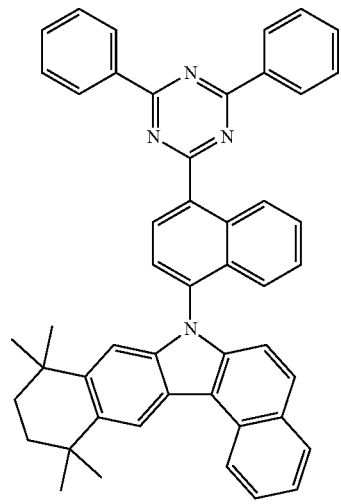
466
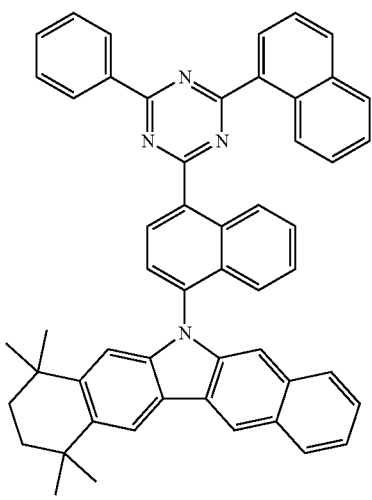
467
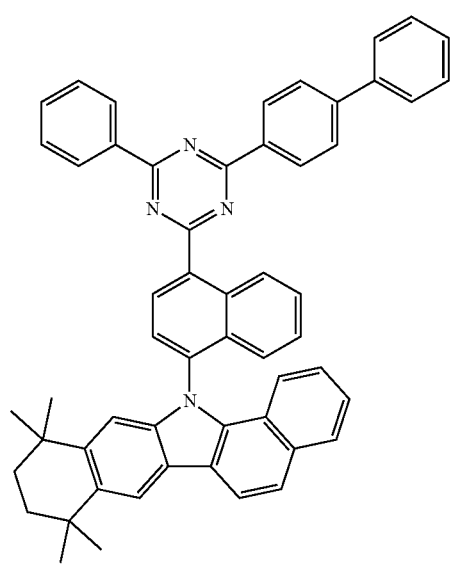

679
-continued
468
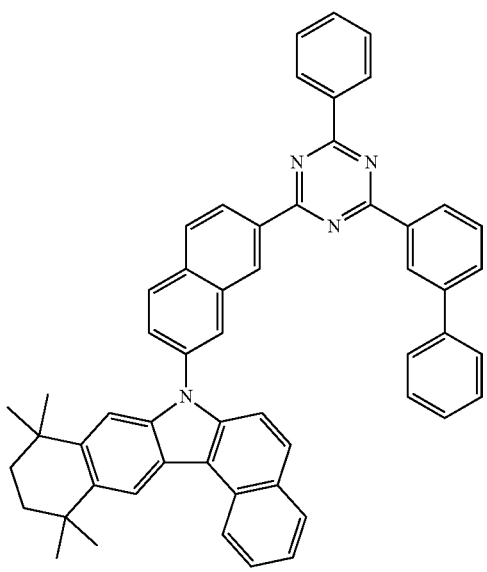
680
-continued
470
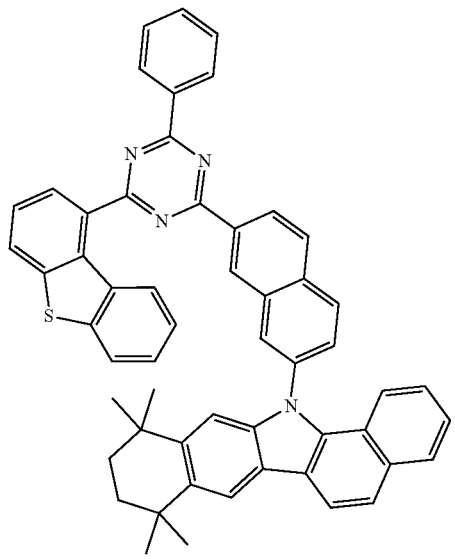
469
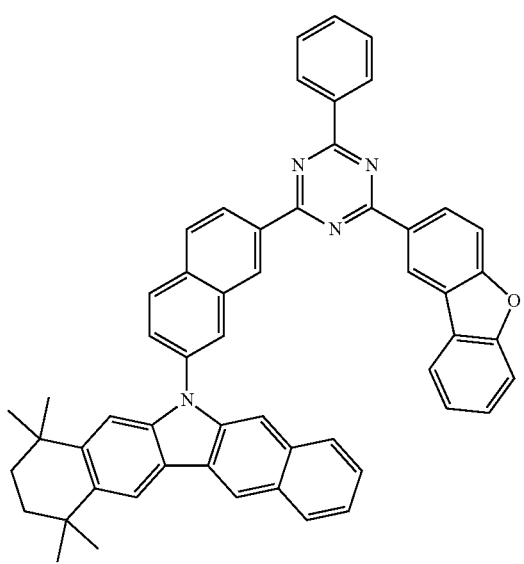
471
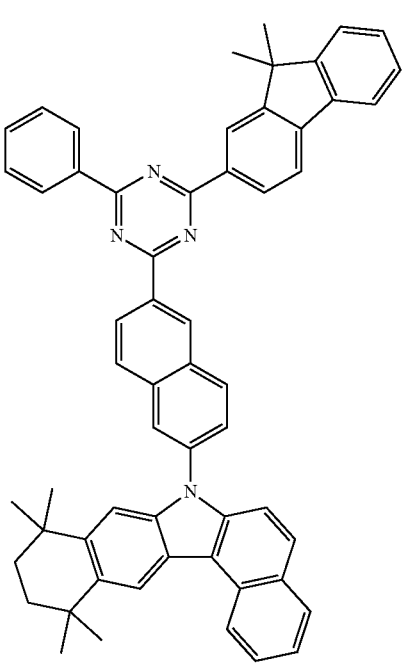

681
-continued
682
-continued
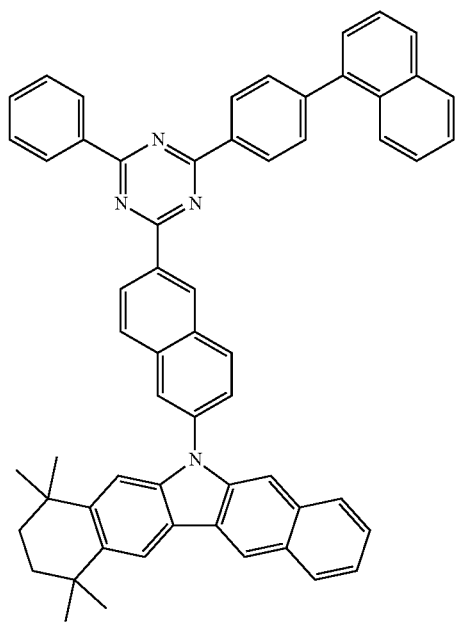
472
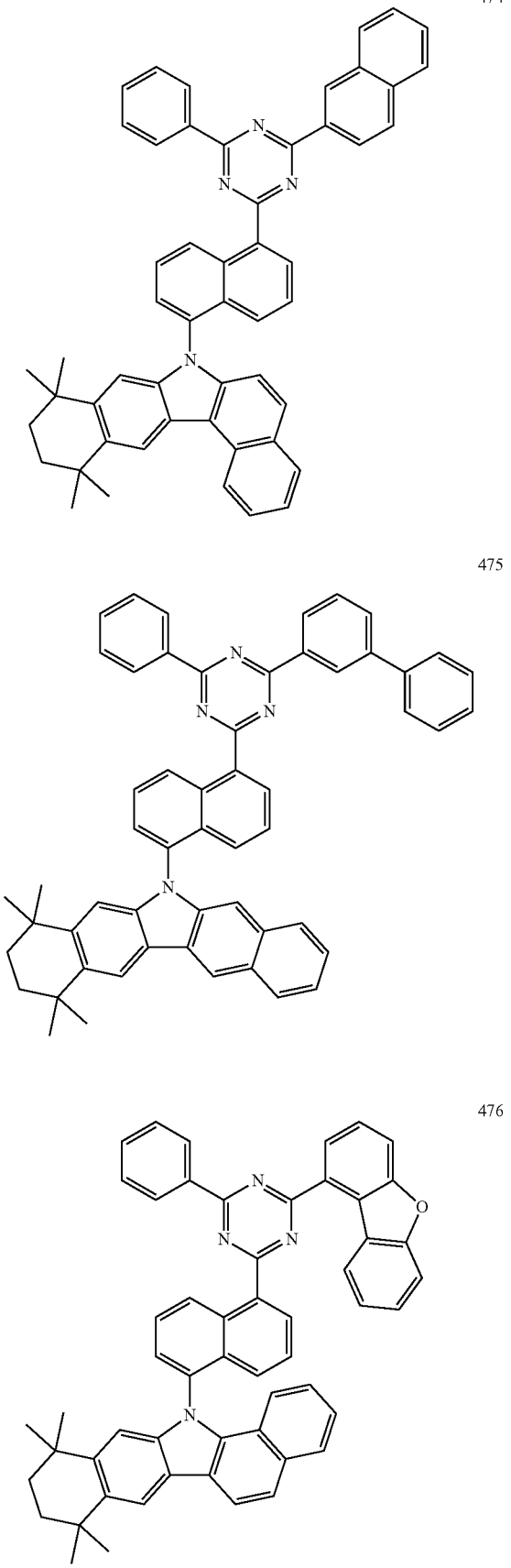

477
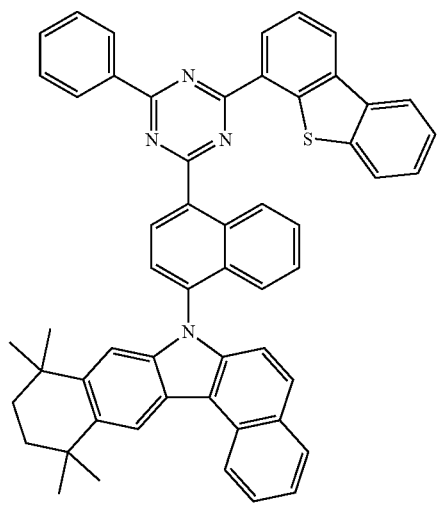
478
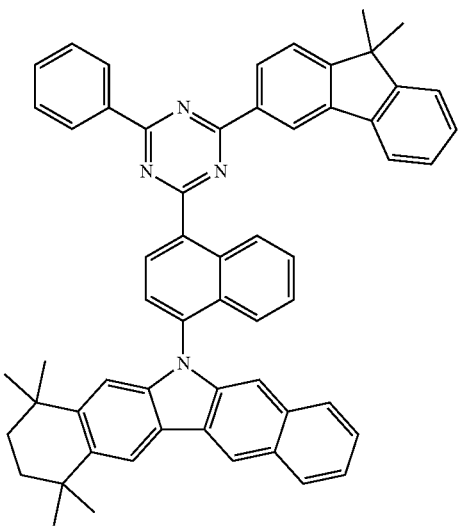
479
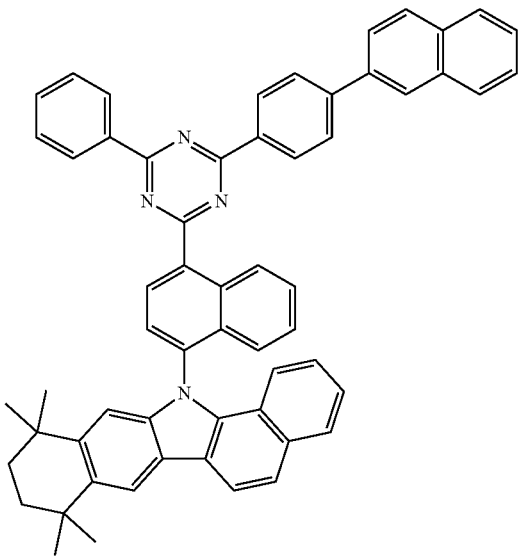
480
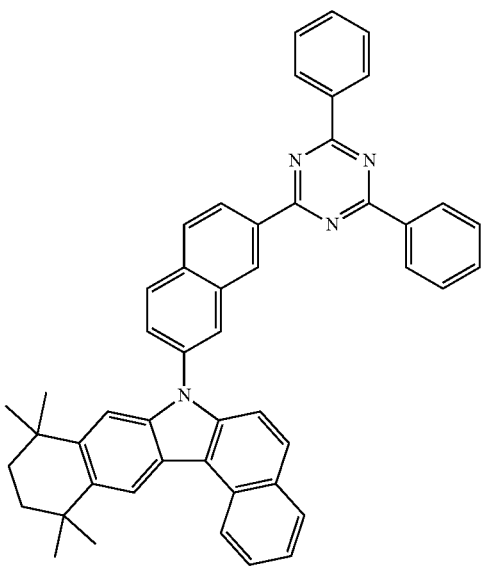
481
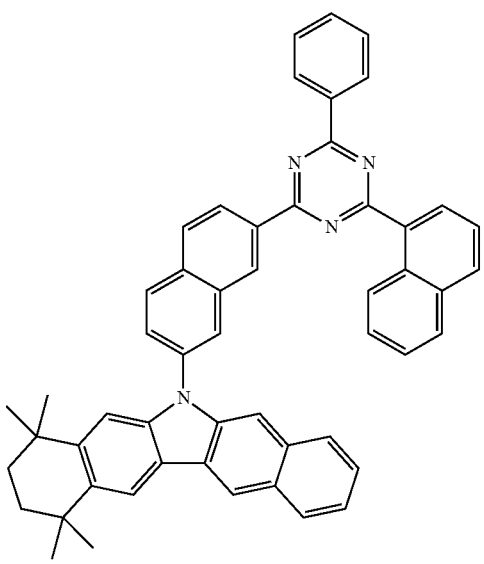

482
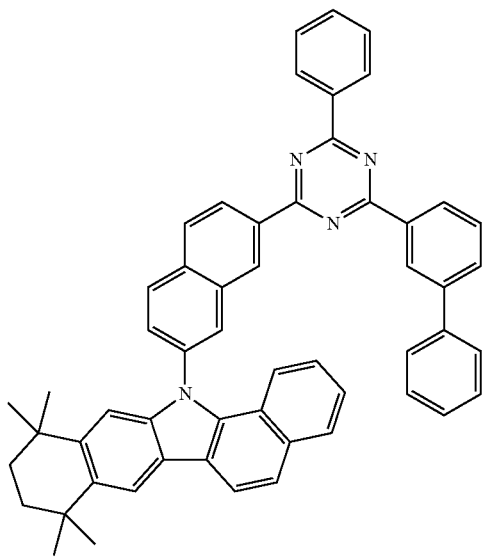
483
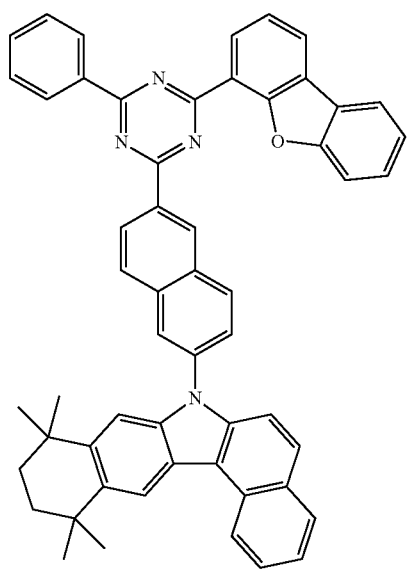
484
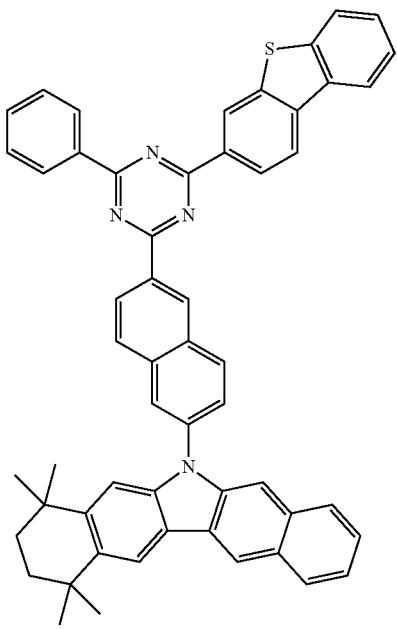
485
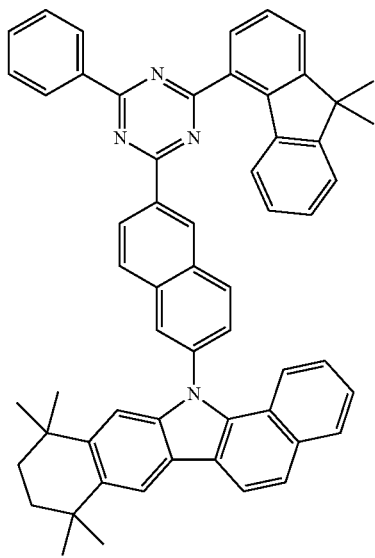

687
-continued
486
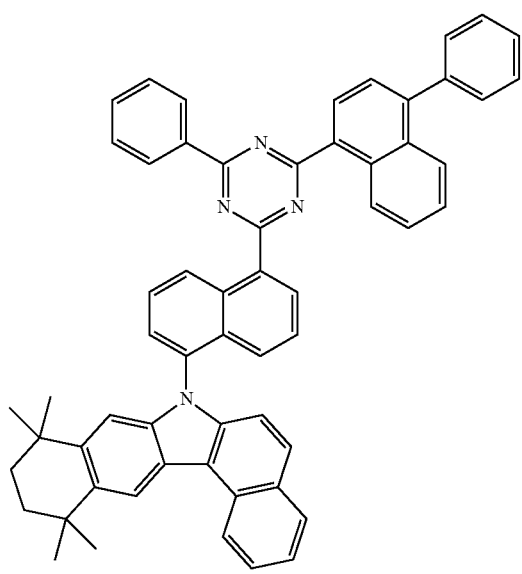
487
488
-continued
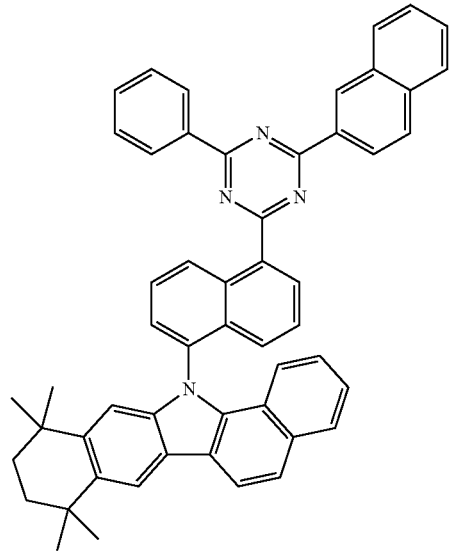
489
490
688

689
-continued
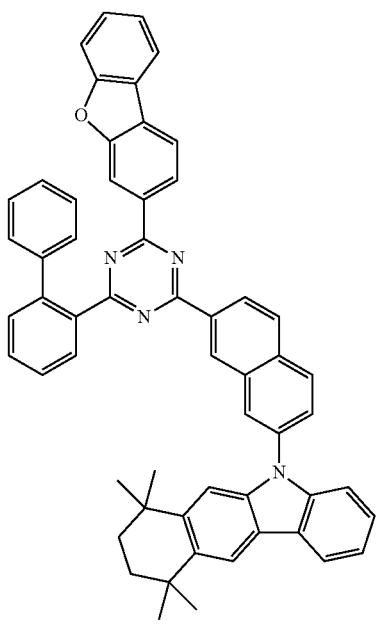
491
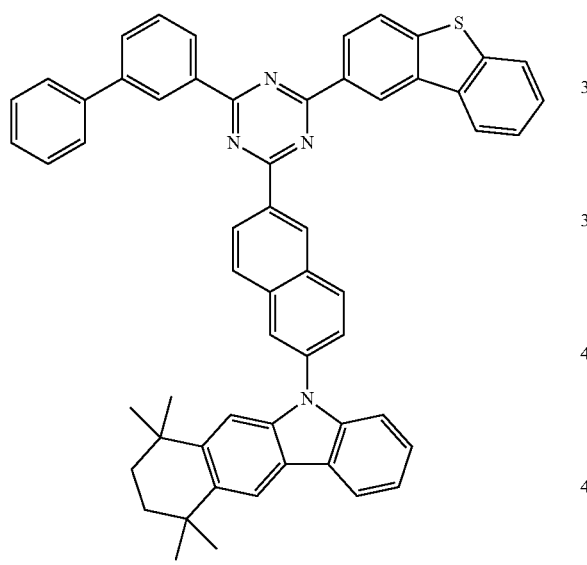
492
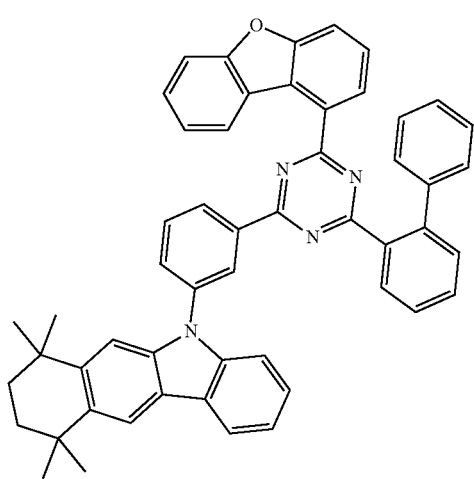
493
690
-continued
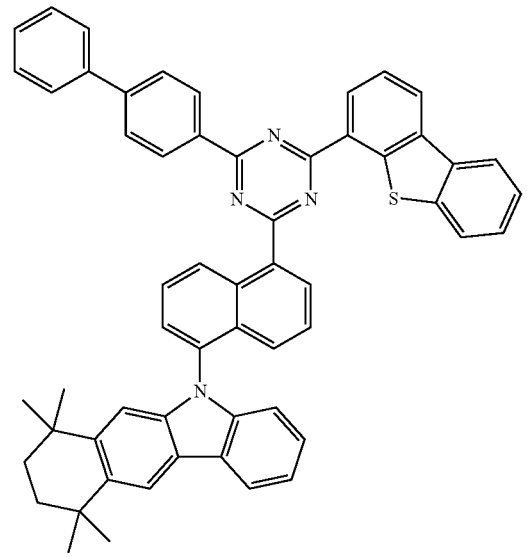
494
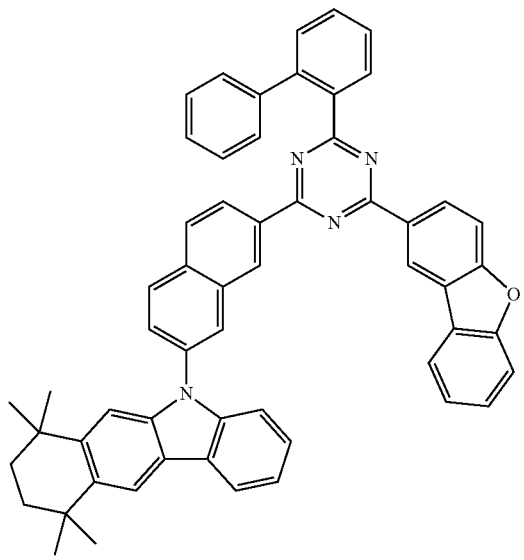
495
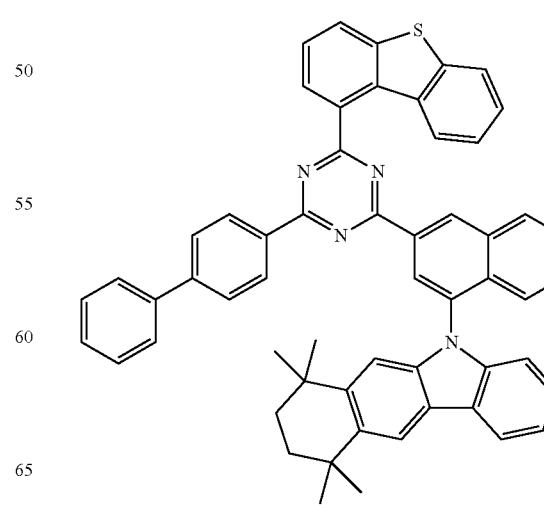
496

691
-continued
497
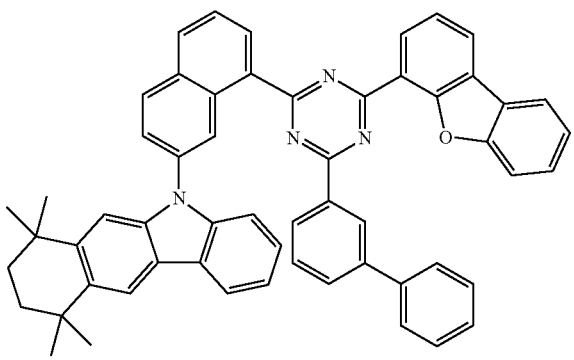
498
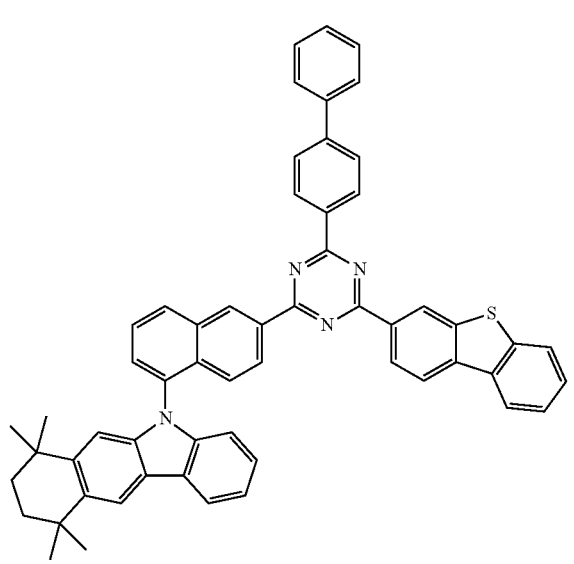
499
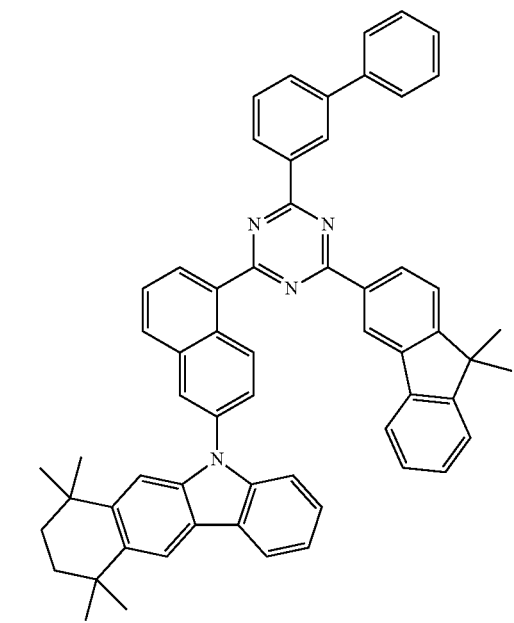
692
-continued
500
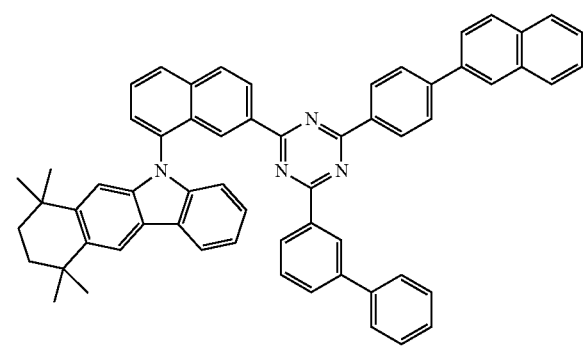
501
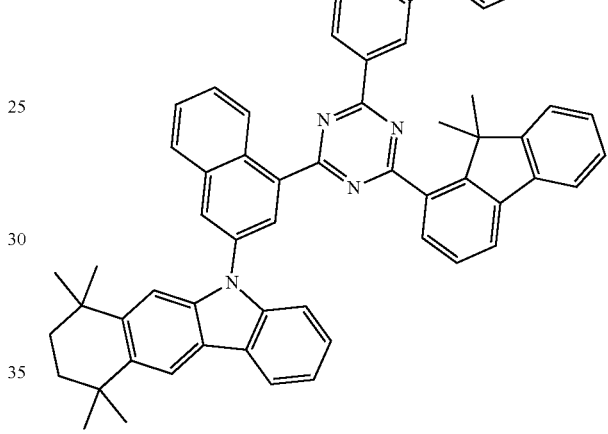
502
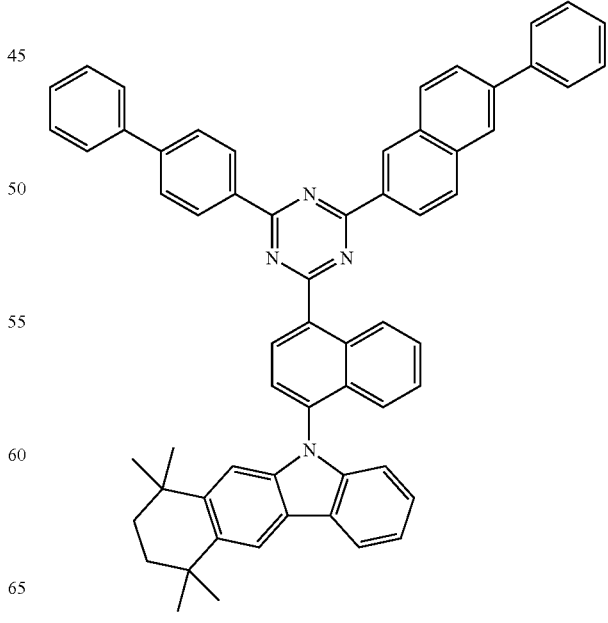

503
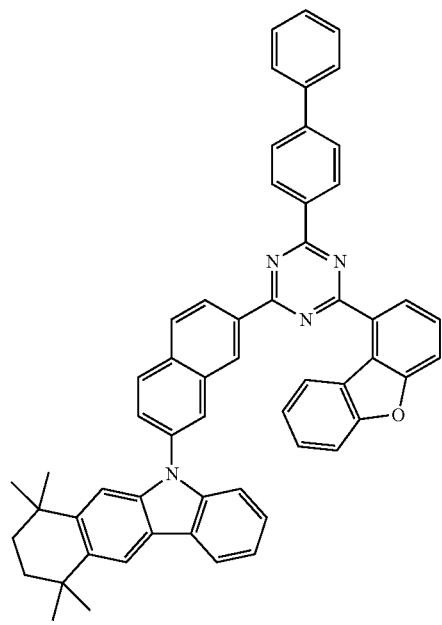
504
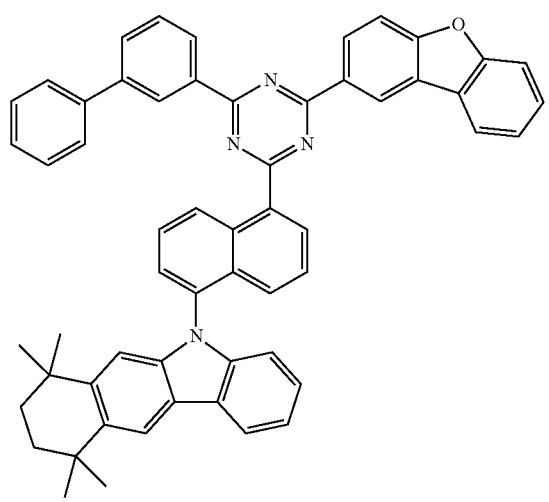
505 506 507
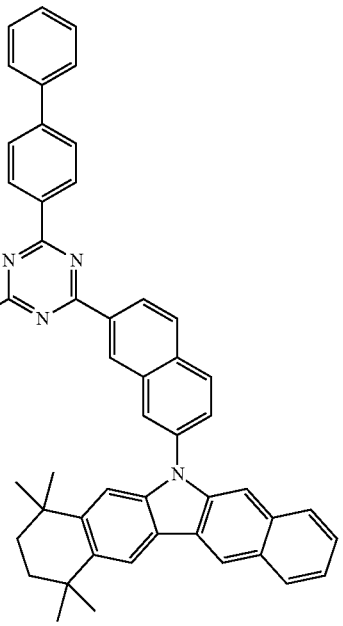
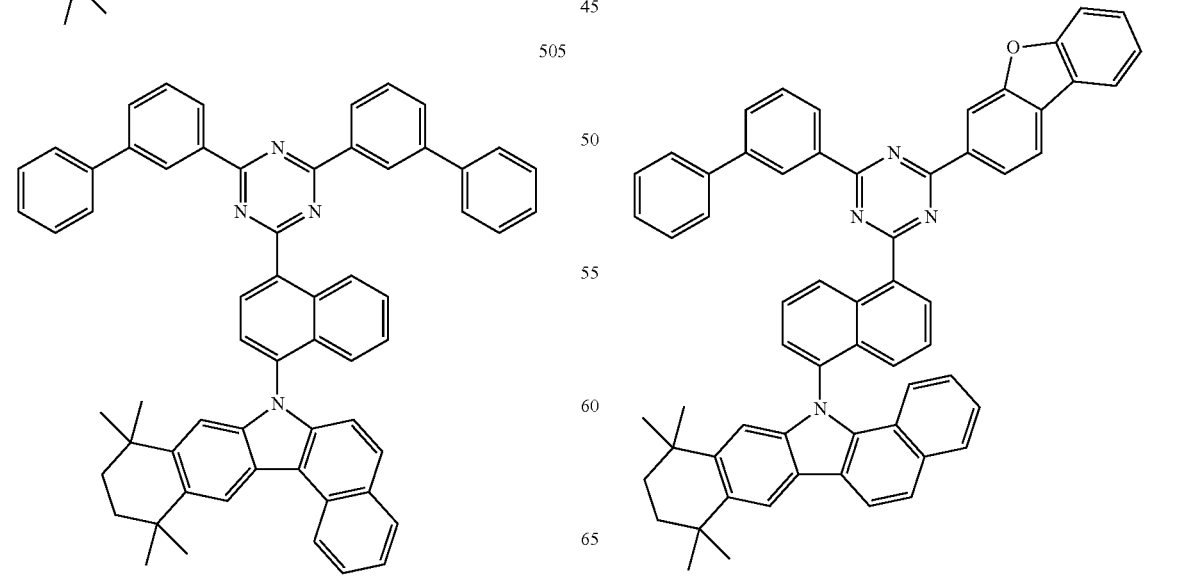

695
-continued
508
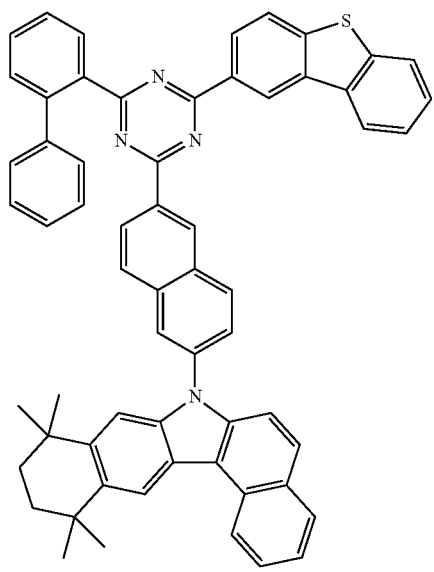
509
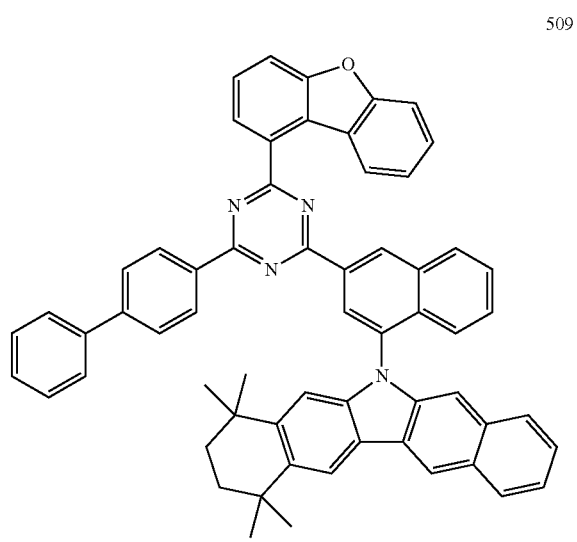
510
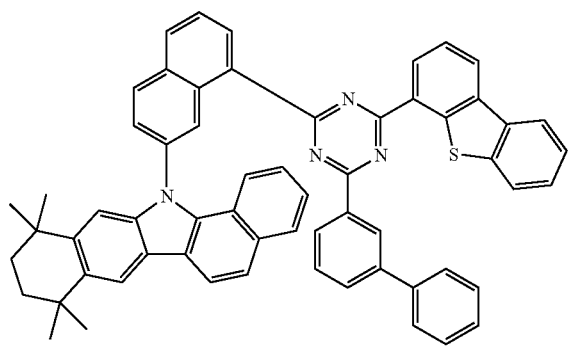
696
-continued
511
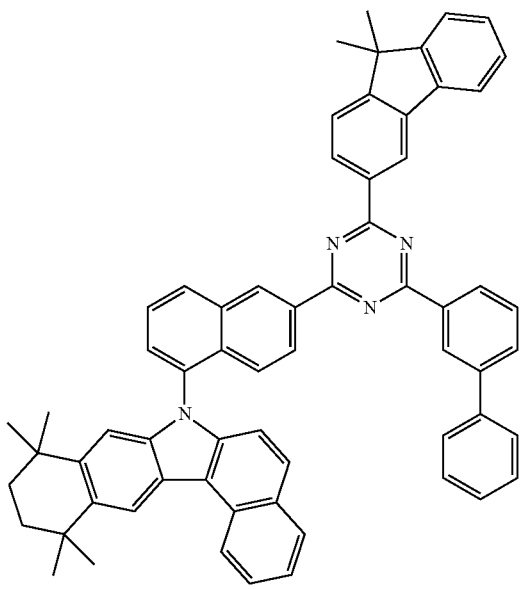
512
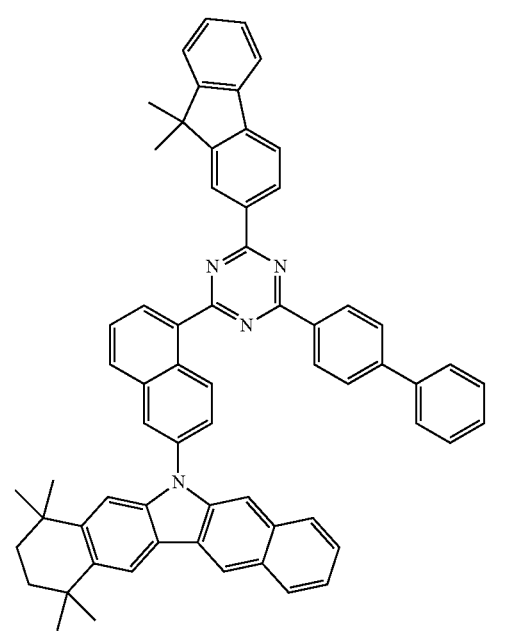 [SMILES: CC1(C)CCC(C)(C)c2cc3c(cc21)c1cc2ccccc2cc1n3-c1ccc2c(-c3nc(-c4ccc(-c5ccccc5)cc4)nc(-c4ccc5c(c4)C(C)(C)c4ccccc4-5)n3)cccc2c1]

513
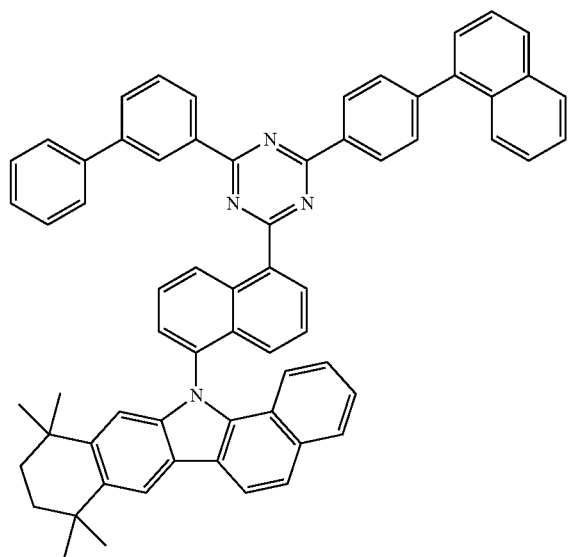
514
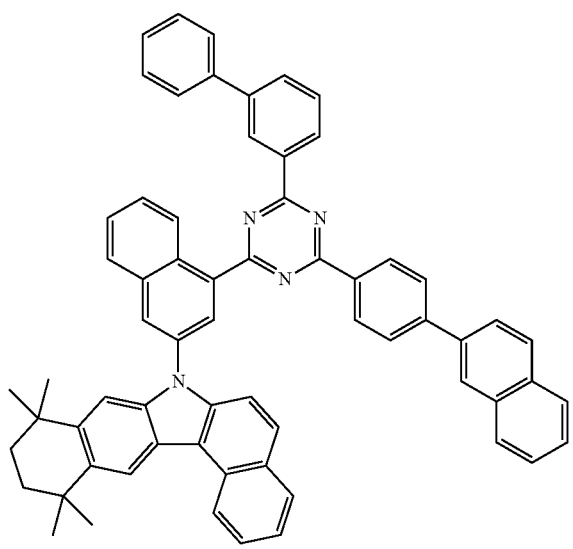
515
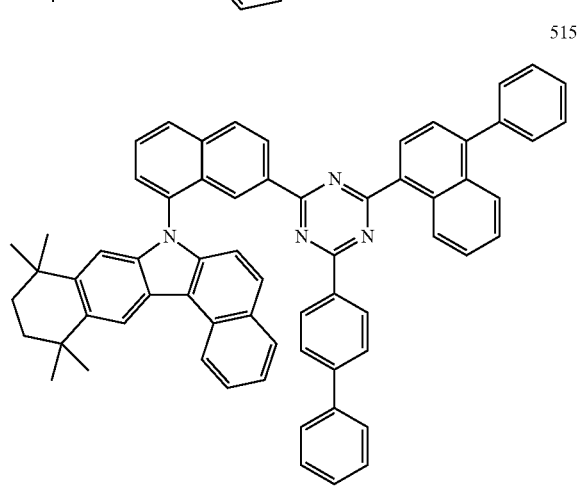
516
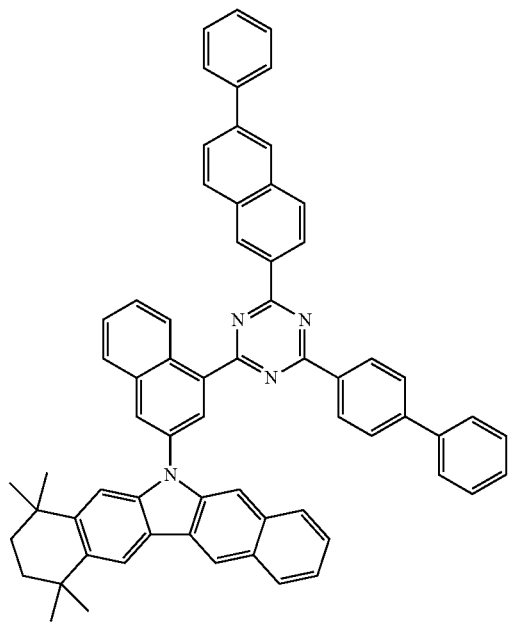
517
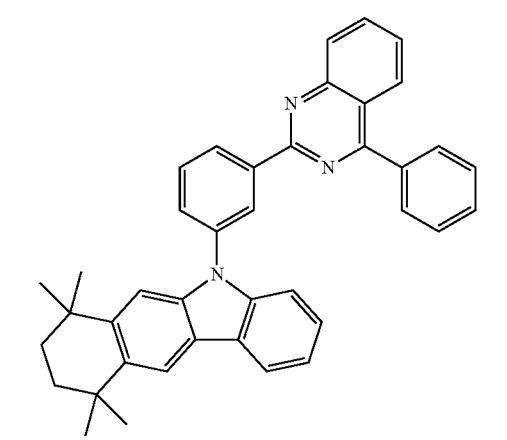 [SMILES: CC1(C)CCC(C)(C)c2cc3c(cc21)c1ccccc1n3-c1cccc(-c2nc(-c3ccccc3)c3ccccc3n2)c1]
518
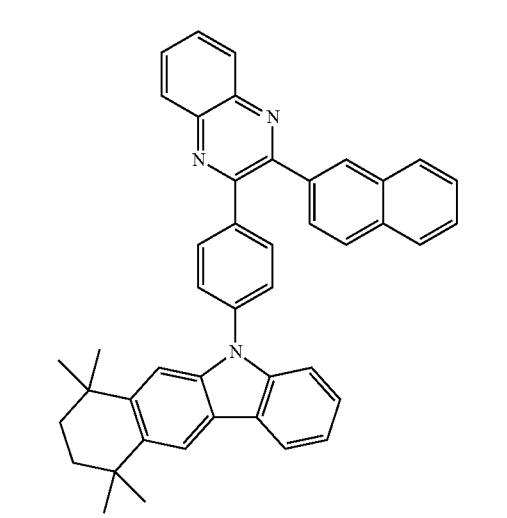 [SMILES: CC1(C)CCC(C)(C)c2cc3c(cc21)c1ccccc1n3-c1ccc(-c2nc3ccccc3nc2-c2ccc3ccccc3c2)cc1]

-continued
519
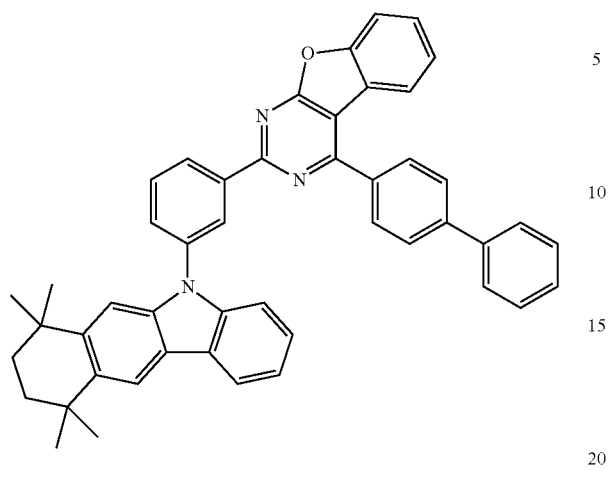
520
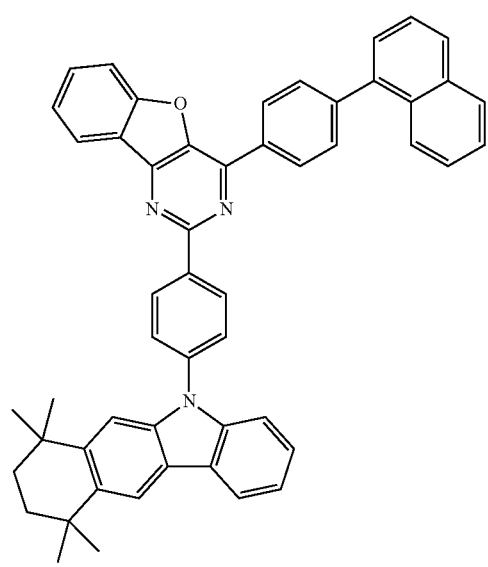
521
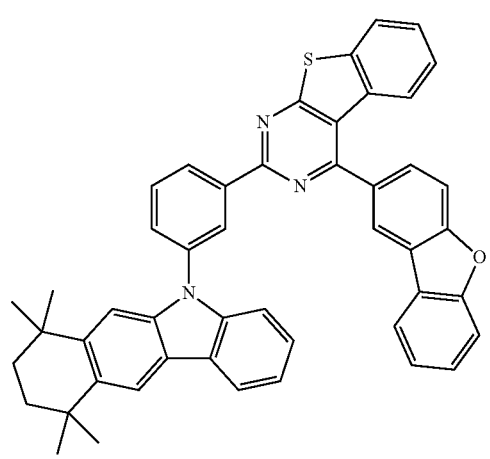
-continued
522
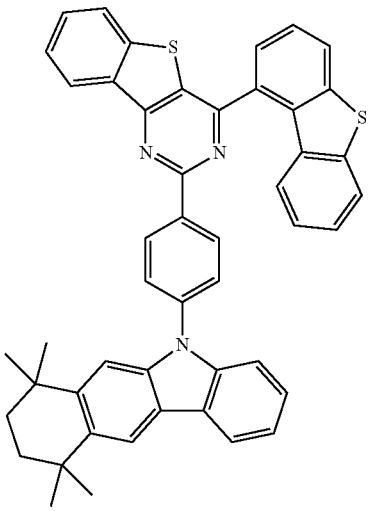
523
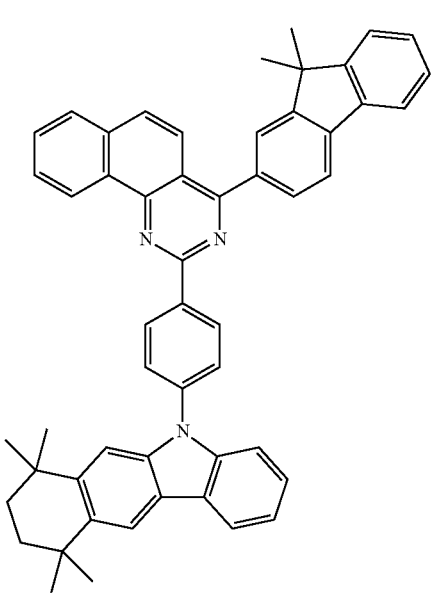
524
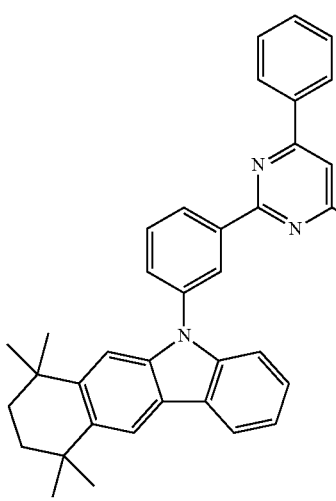

-continued
525
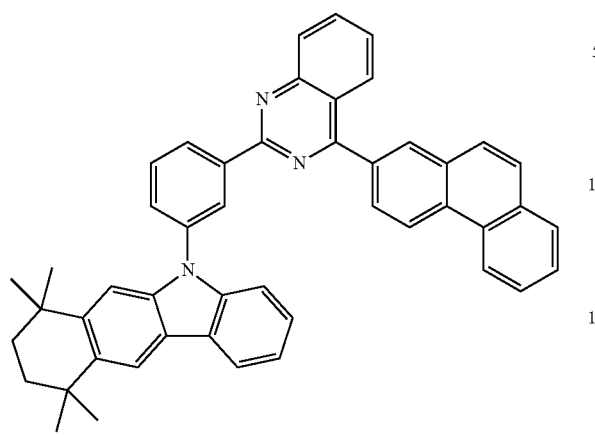
526
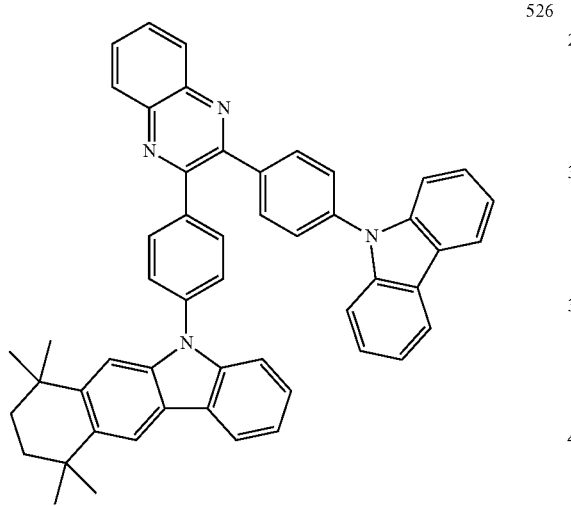
527
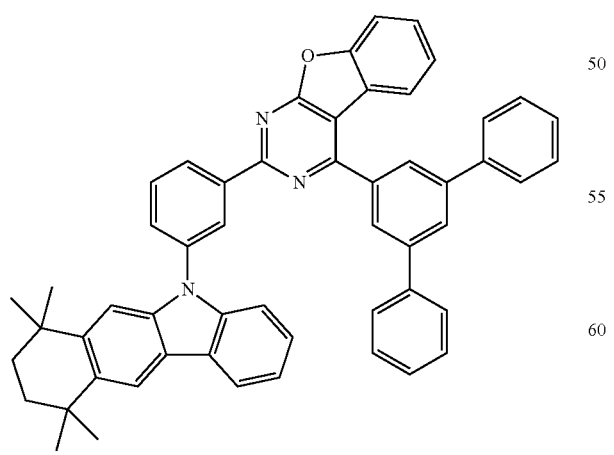
-continued
528
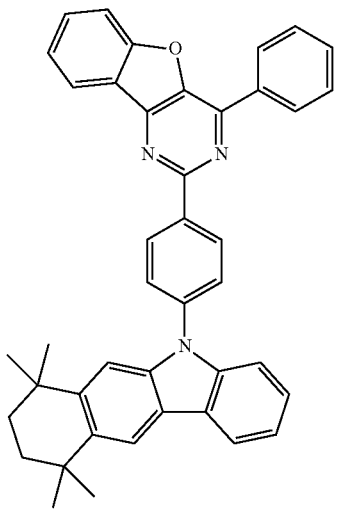
529
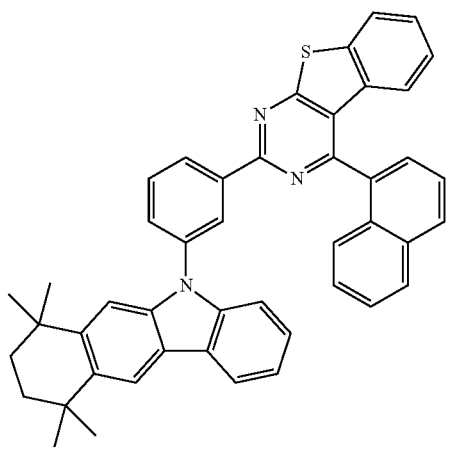 [SMILES: CC1(C)CCC(C)(C)c2cc3c(cc21)c1ccccc1n3-c1cccc(-c2nc(-c3cccc4ccccc34)c3c(n2)sc2ccccc23)c1]
530
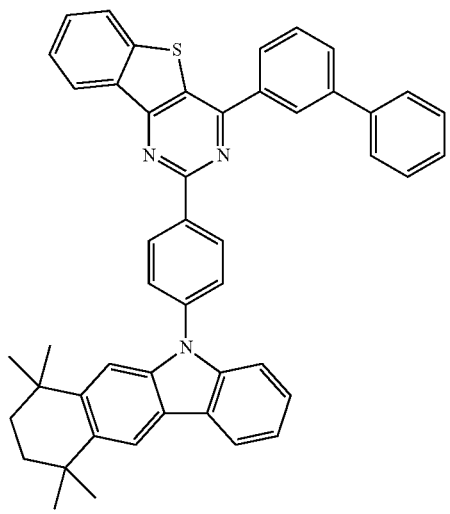 [SMILES: CC1(C)CCC(C)(C)c2cc3c(cc21)c1ccccc1n3-c1ccc(-c2nc(-c3cccc(-c4ccccc4)c3)c3sc4ccccc4c3n2)cc1]

703
-continued
531
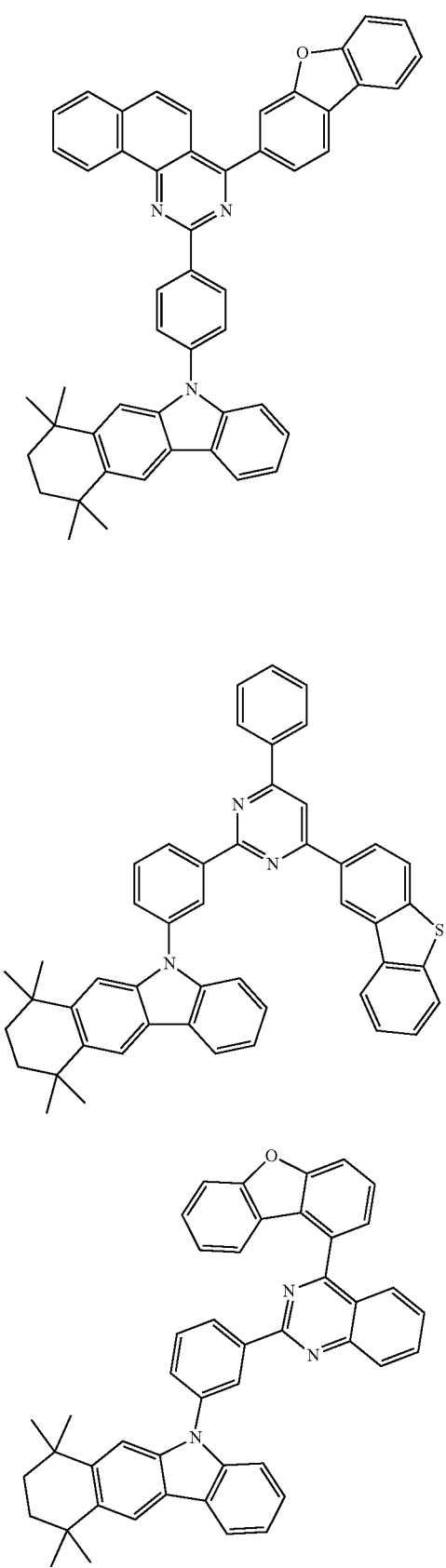
532
533
704
-continued
534
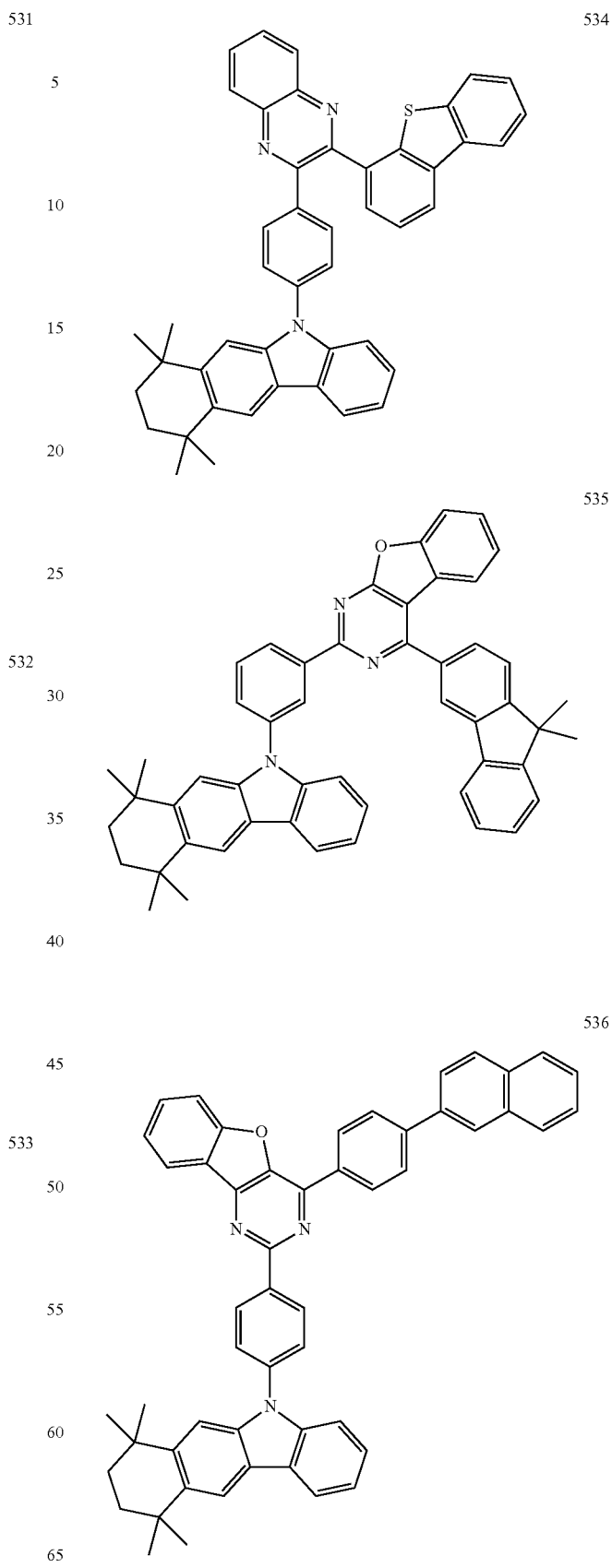
535
536

-continued
537
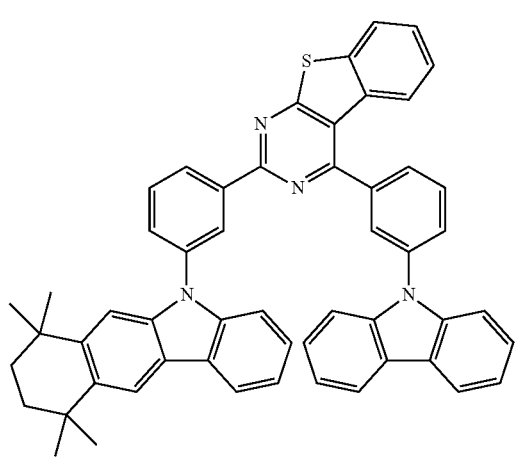
538
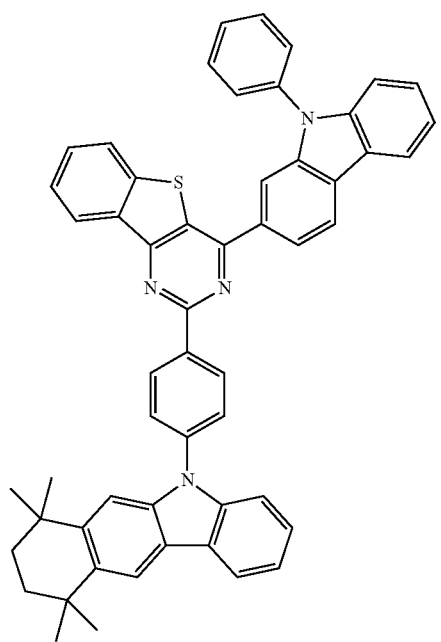
539
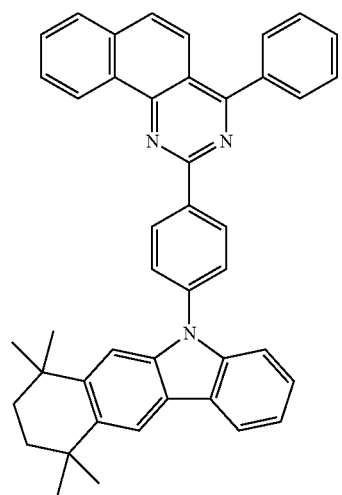 [SMILES: CC1(C)CCC(C)(C)c2cc3c(cc21)c1ccccc1n3-c1ccc(-c2nc(-c3ccccc3)c3ccc4ccccc4c3n2)cc1]
540
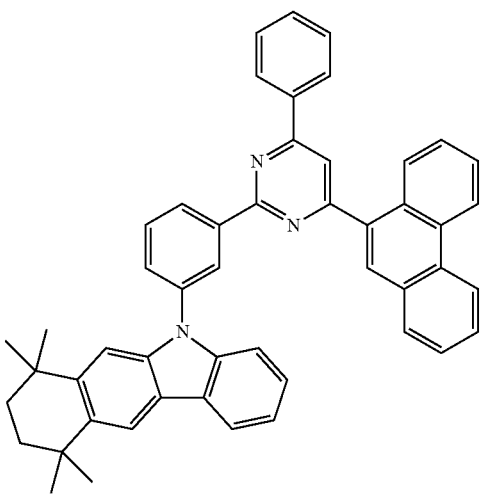
541
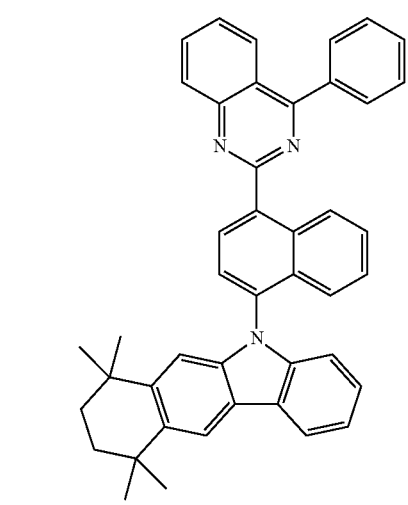
542
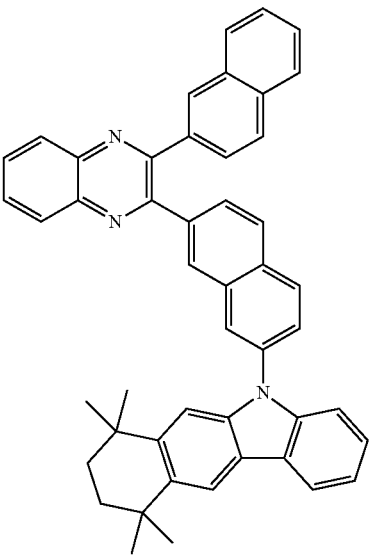

707
-continued
543
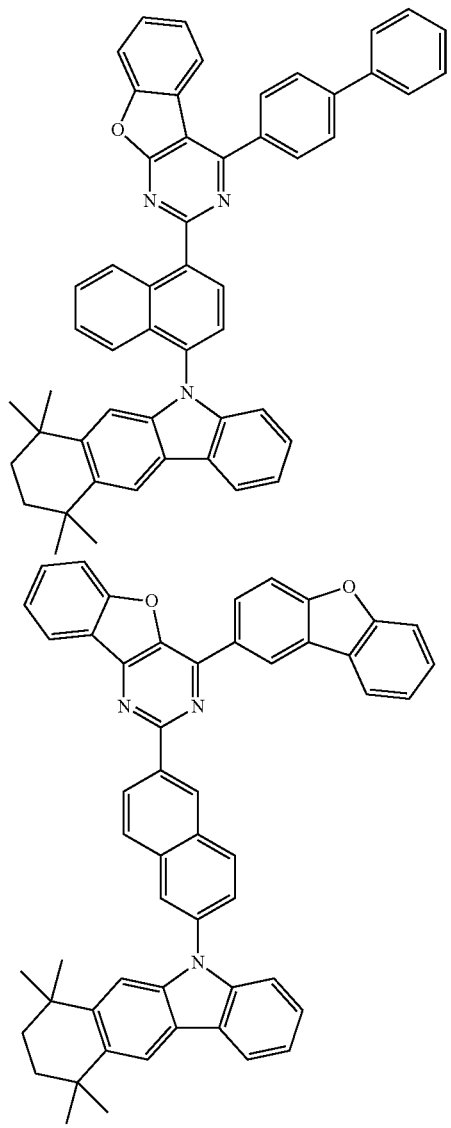
544
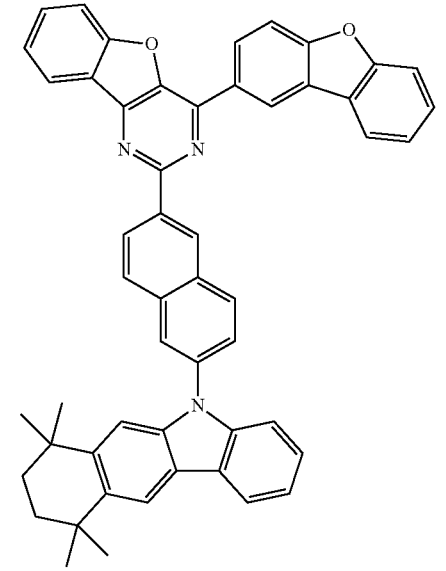
545
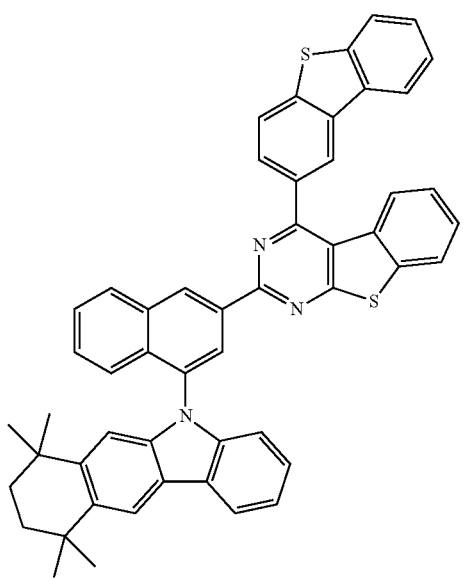
708
-continued
546
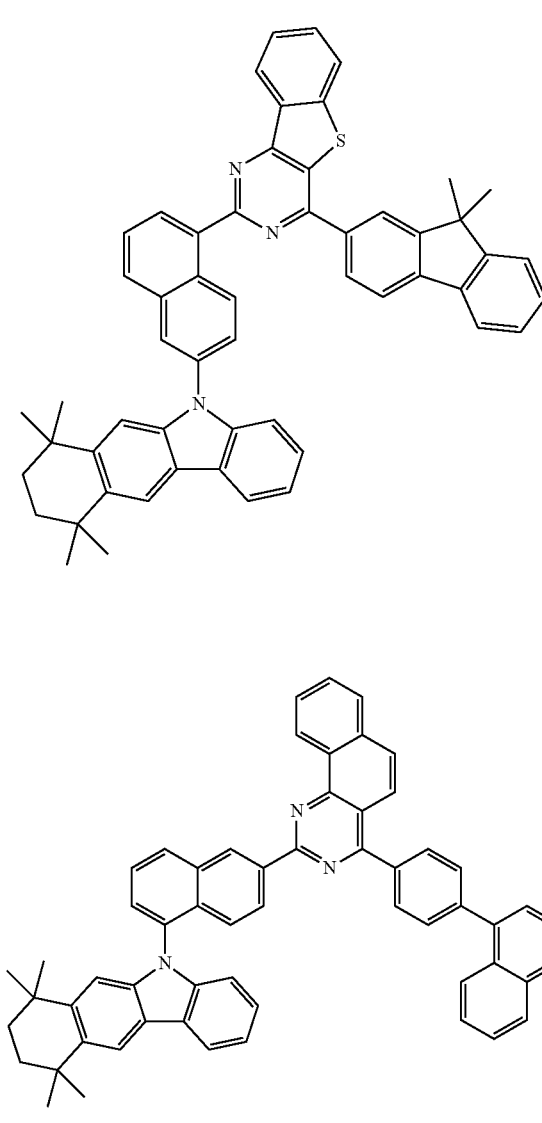
547
548

709
-continued
549
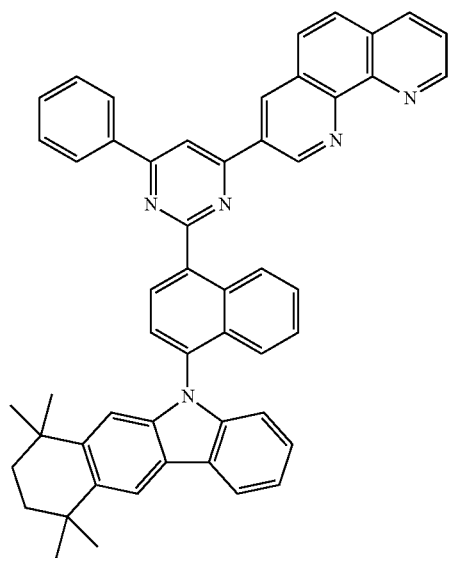
550
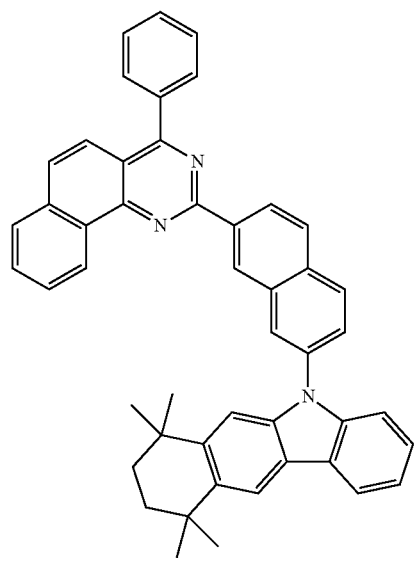
551
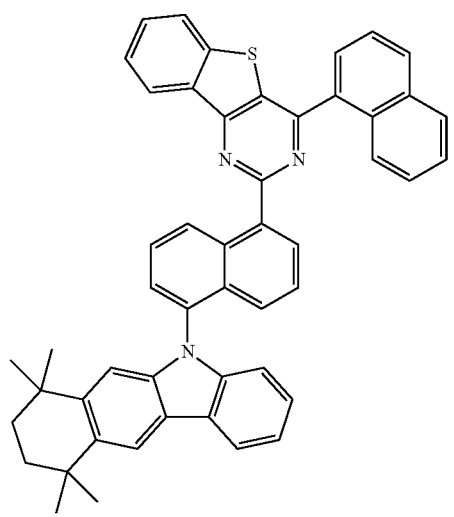
710
-continued
552
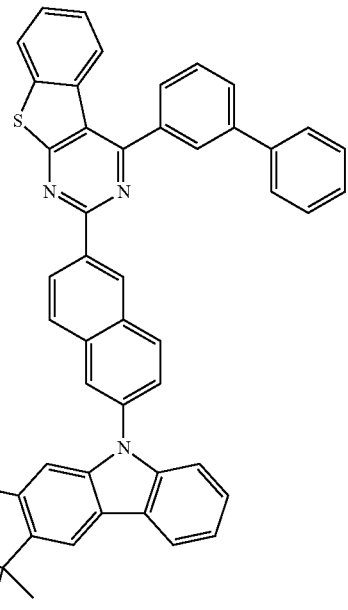
553
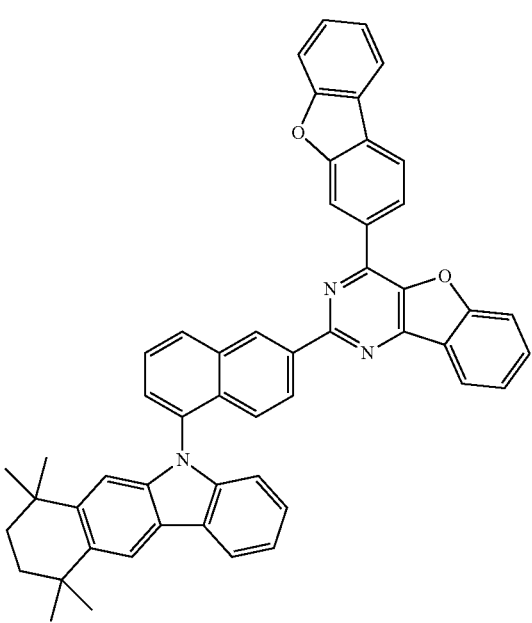

711
-continued
554
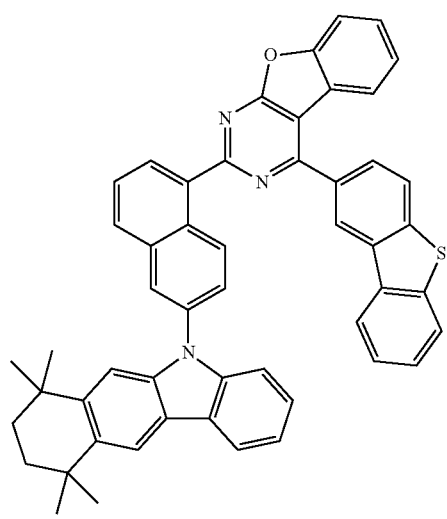
555
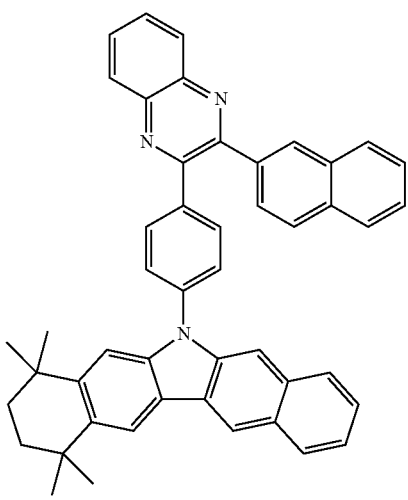
556
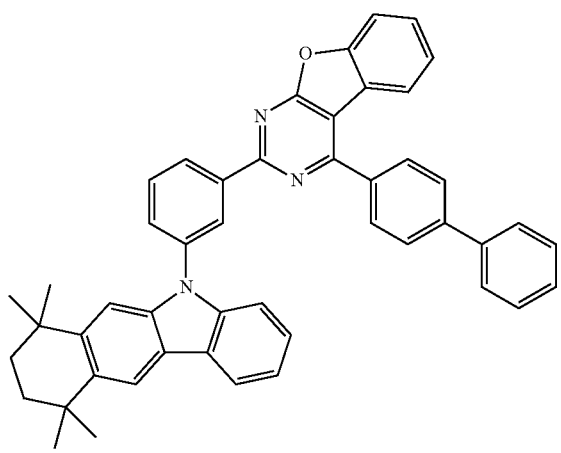
712
-continued
557
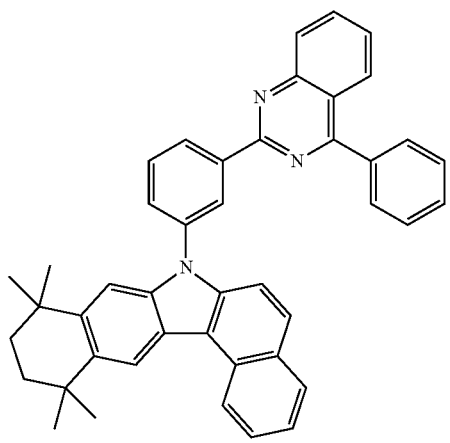
558
559

713
-continued
560
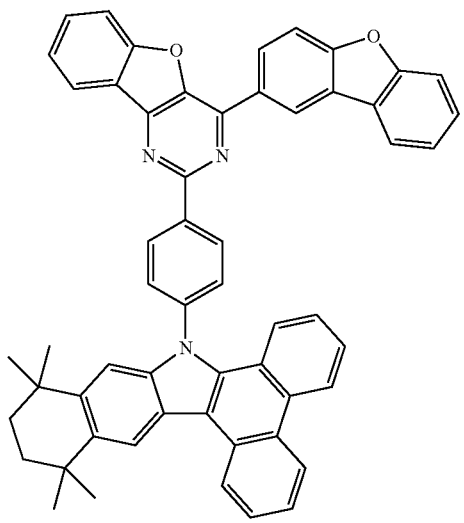
561
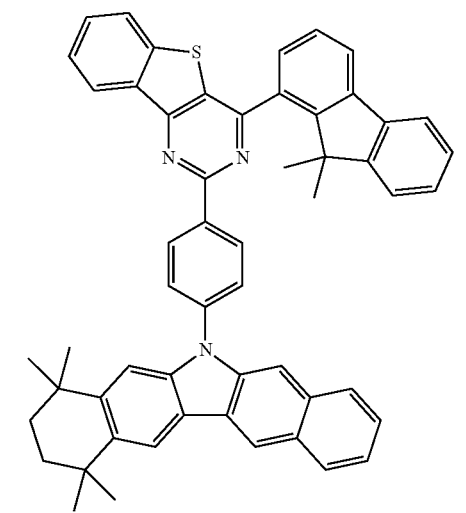
562
714
-continued
563
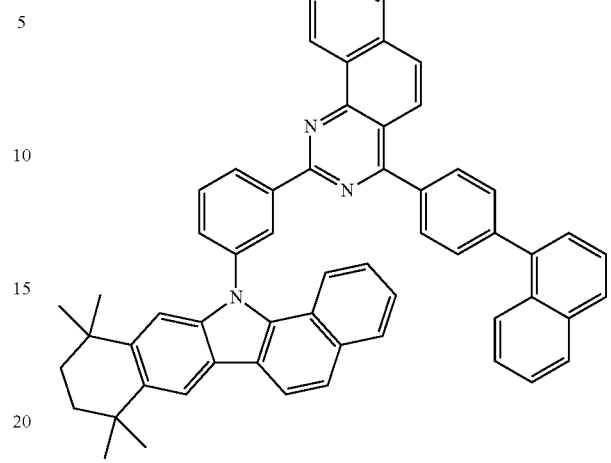
564
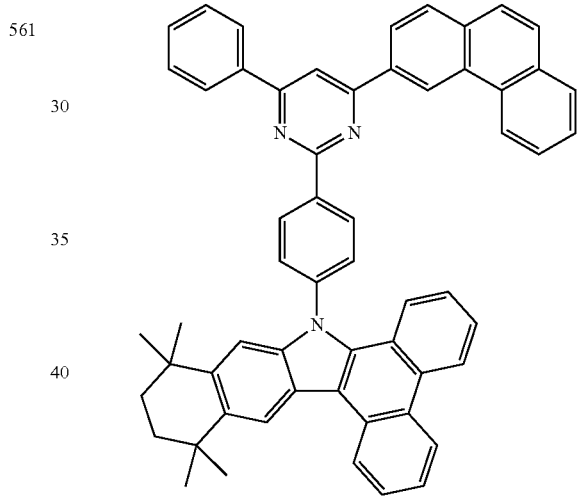
565
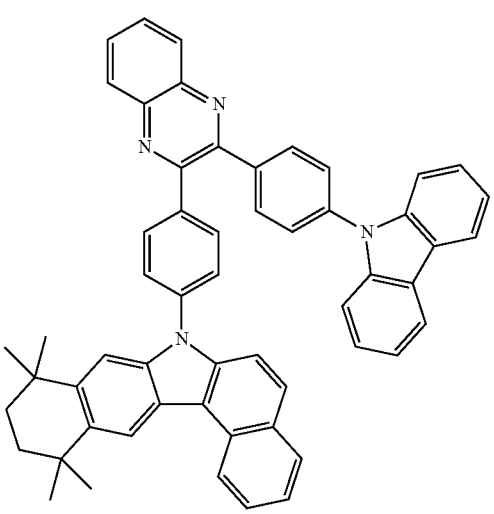

566
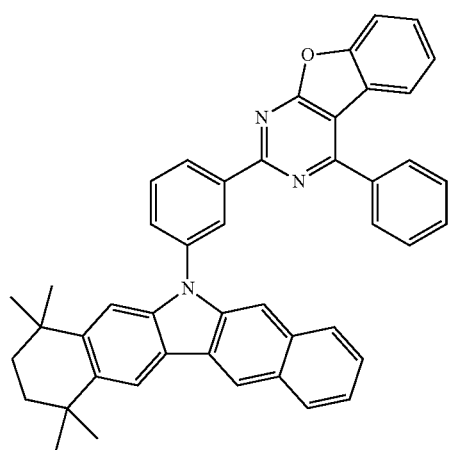
567
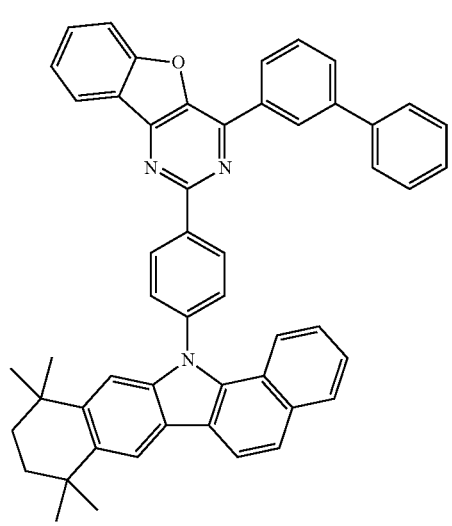 [SMILES: CC1(C)CCC(C)(C)c2cc3c(cc21)c1ccc2ccccc2c1n3-c1ccc(-c2nc(-c3cccc(-c4ccccc4)c3)c3oc4ccccc4c3n2)cc1]
568
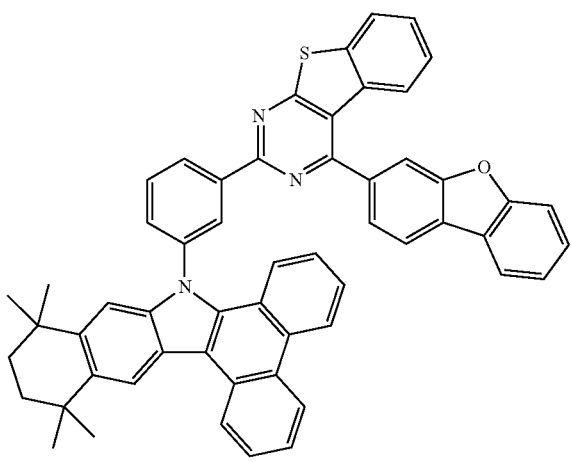
569
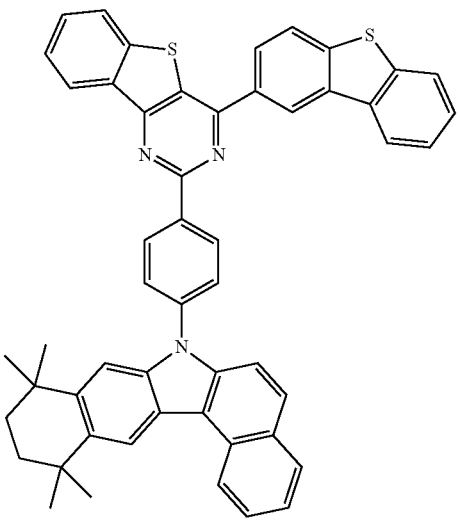
570
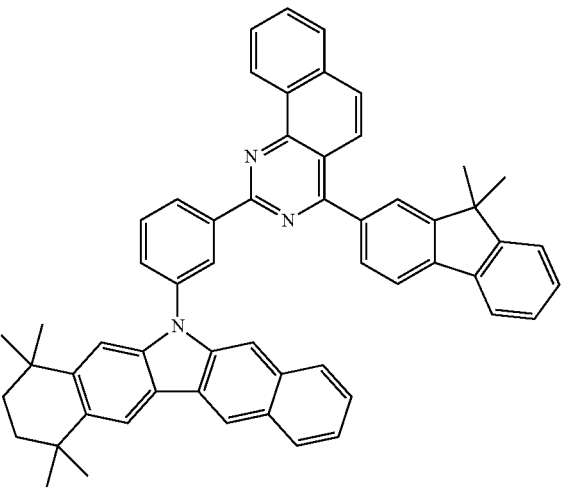
571
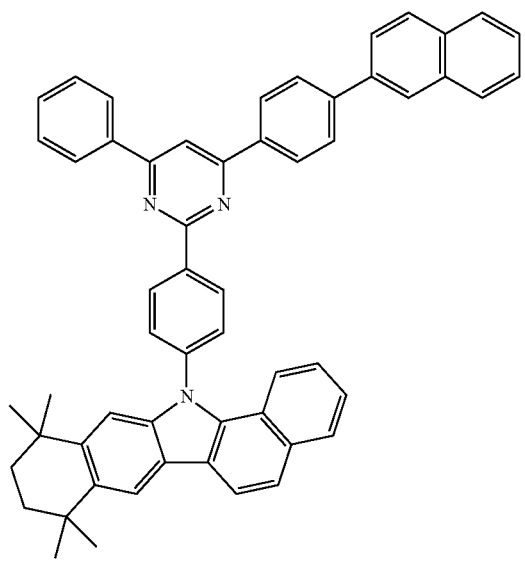 [SMILES: CC1(C)CCC(C)(C)c2cc3c(cc21)c1ccc2ccccc2c1n3-c1ccc(-c2nc(-c3ccccc3)cc(-c3ccc(-c4ccc5ccccc5c4)cc3)n2)cc1]

717
-continued
572
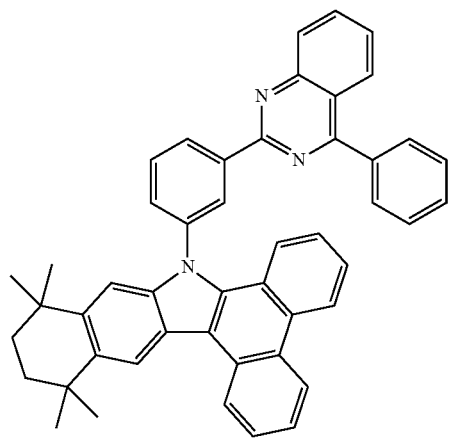
573
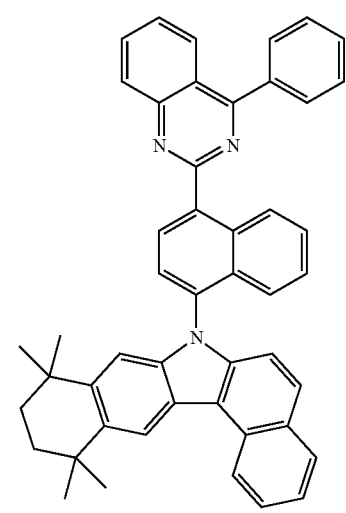
574
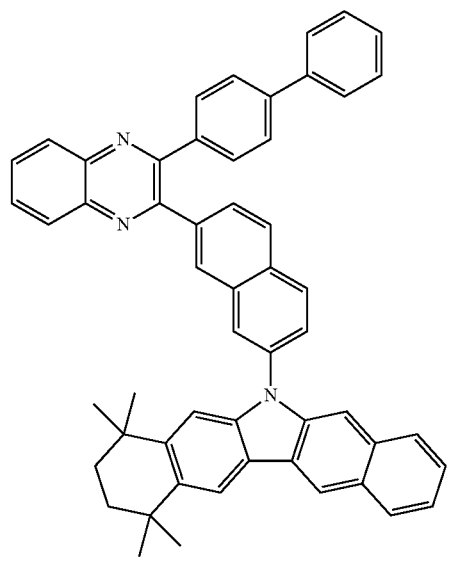
718
-continued
575
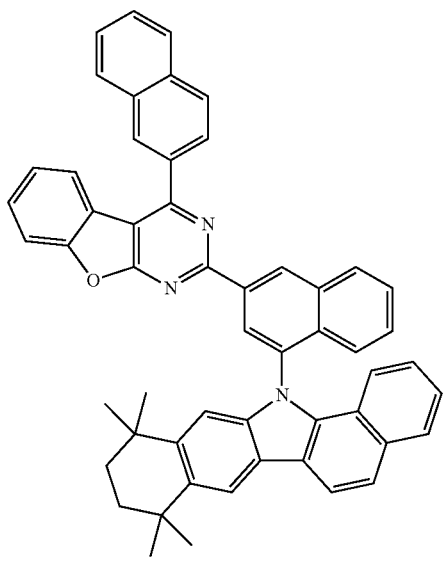
576
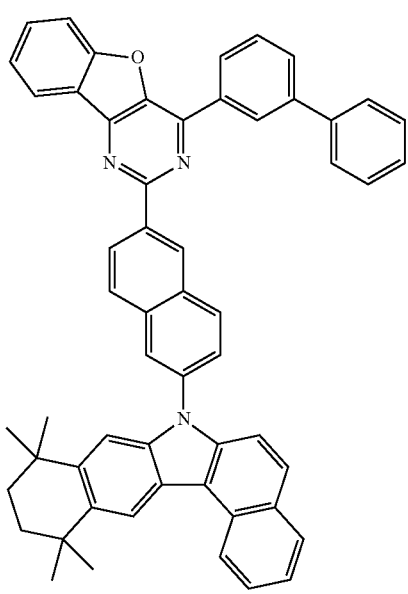

719
-continued
577
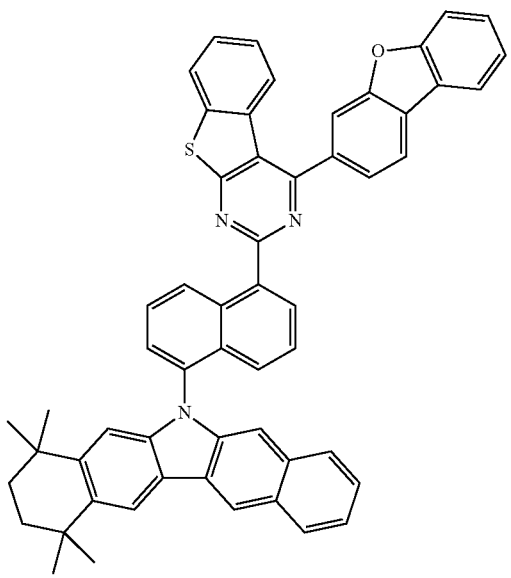
578
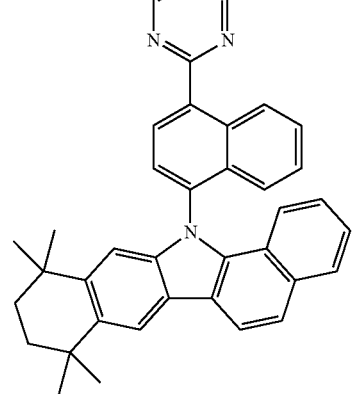
720
-continued
579
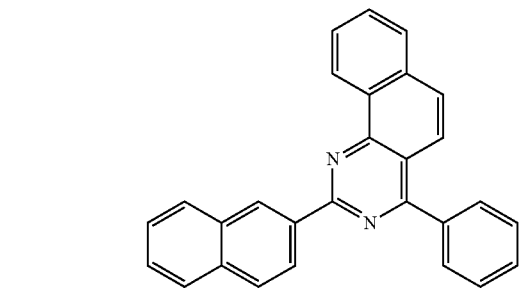
580
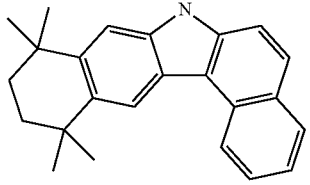
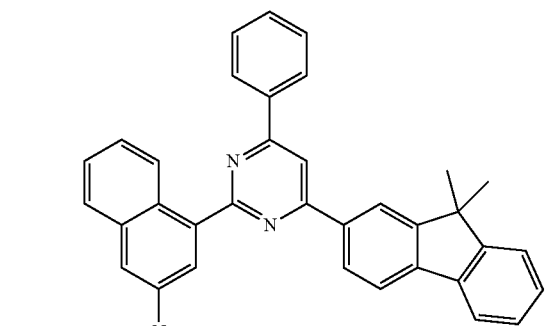
581
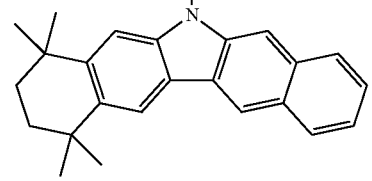
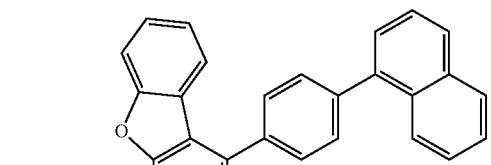

582
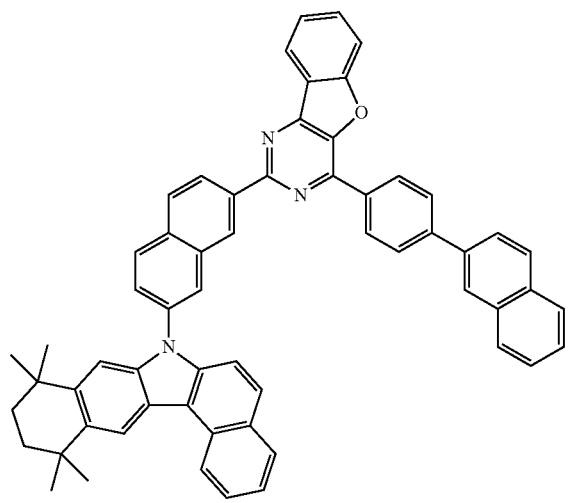
583
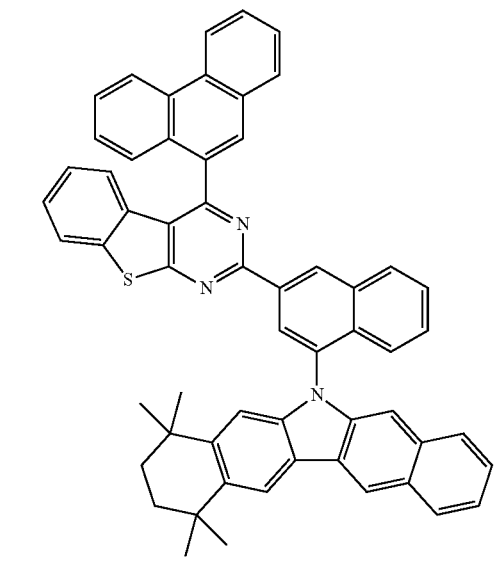
584
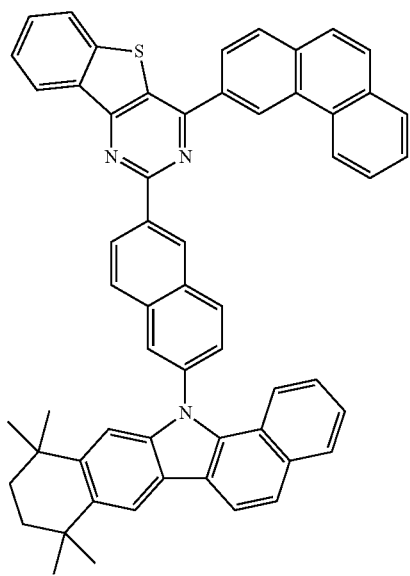
585
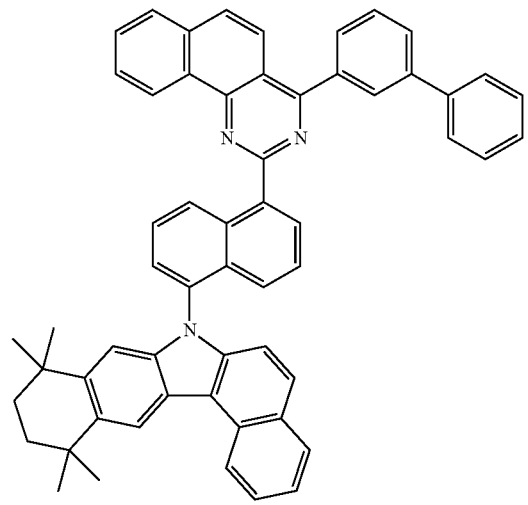
586
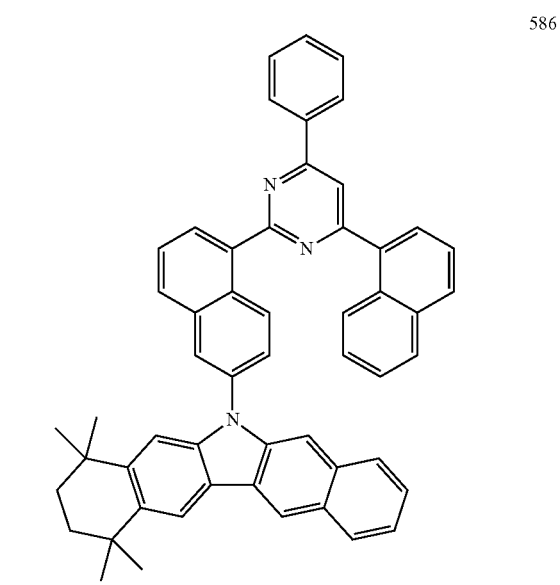
587
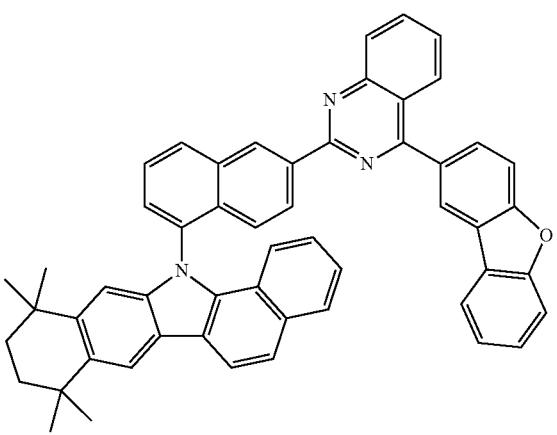

723
-continued
588
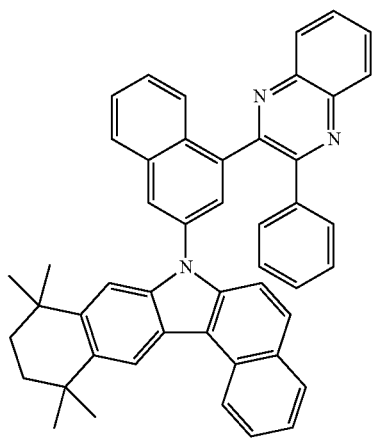 [SMILES: CC1(C)CCC(C)(C)c2cc3c(cc21)c1c2ccccc2ccc1n3-c1cc(-c2nc3ccccc3nc2-c2ccccc2)c2ccccc2c1]
589
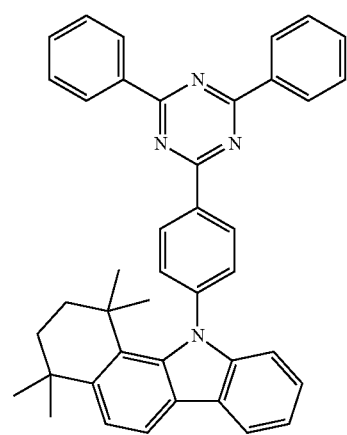 [SMILES: CC1(C)CCC(C)(C)c2c1ccc1c3ccccc3n(-c3ccc(-c4nc(-c5ccccc5)nc(-c5ccccc5)n4)cc3)c21]
590
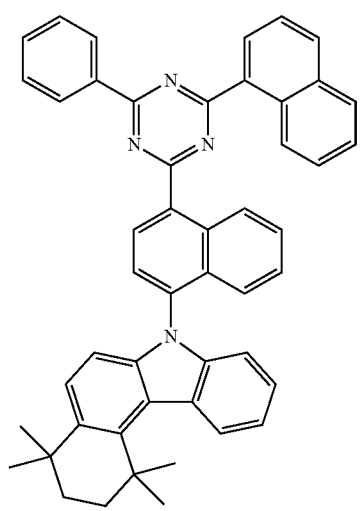
724
-continued
591
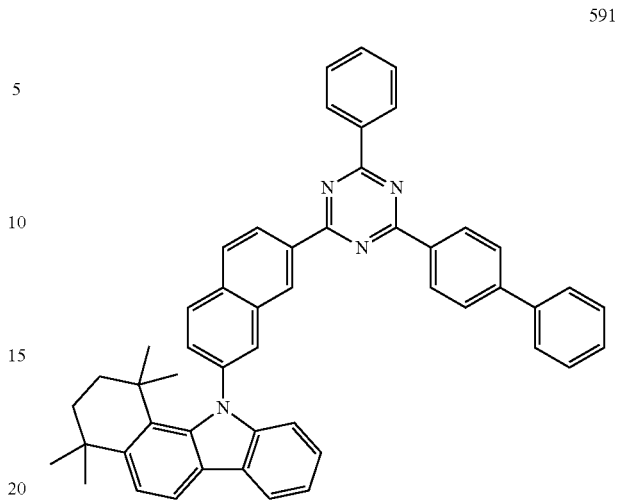
592
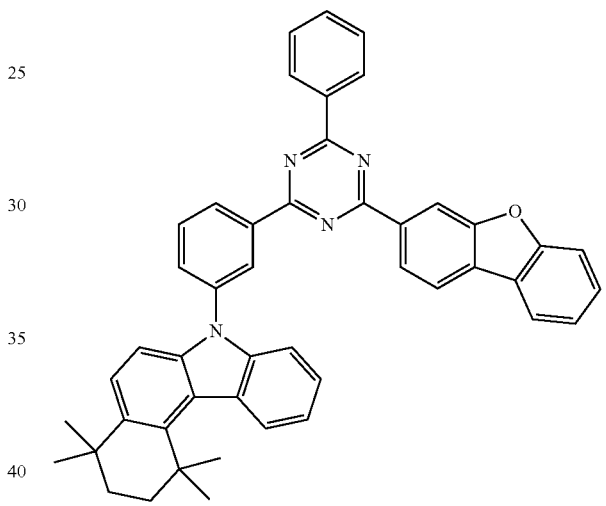
593
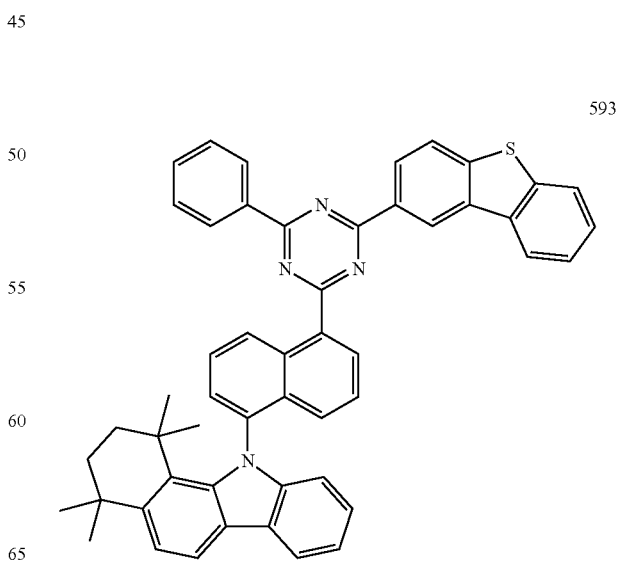

725
-continued
594
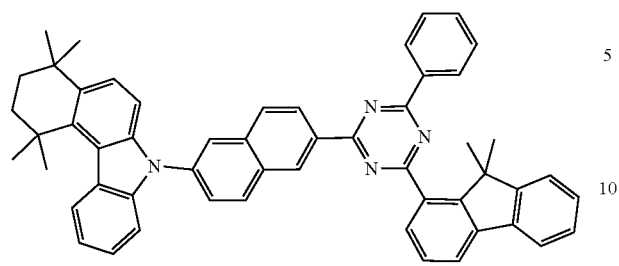
595
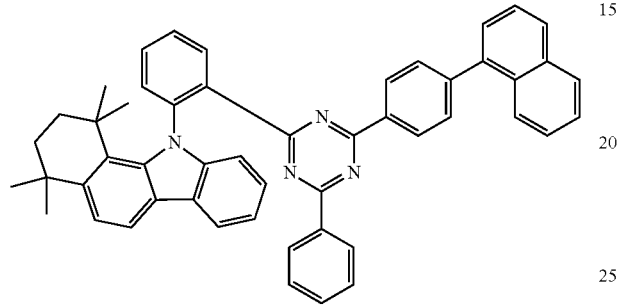
596
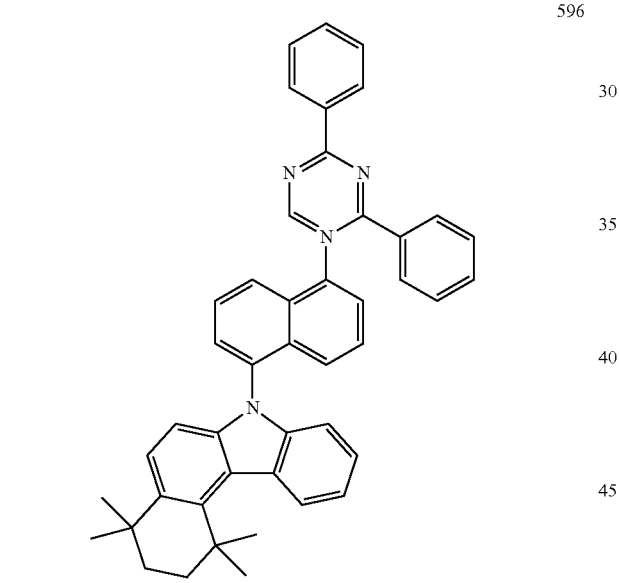
597
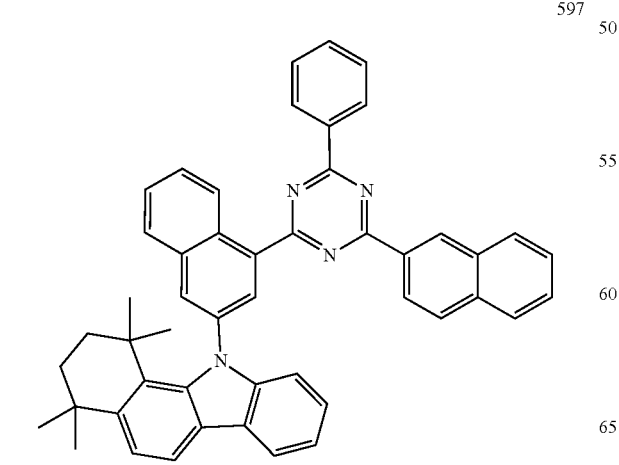
726
-continued
598
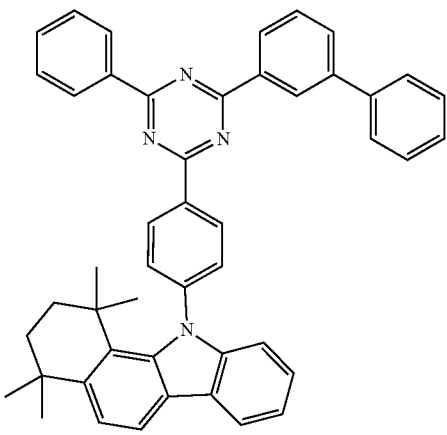
599
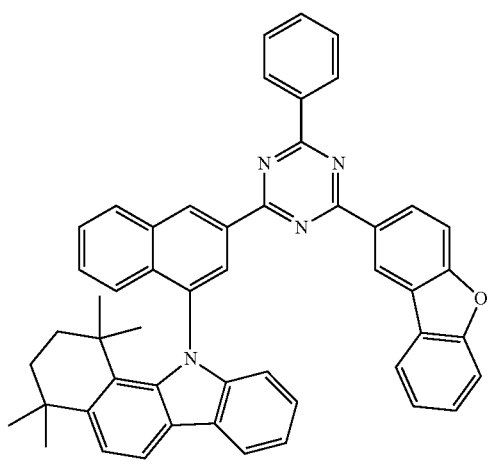
600
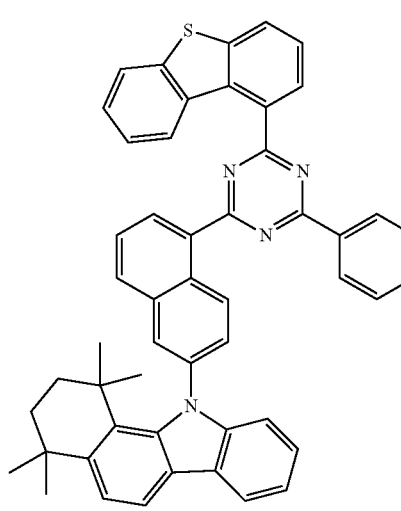

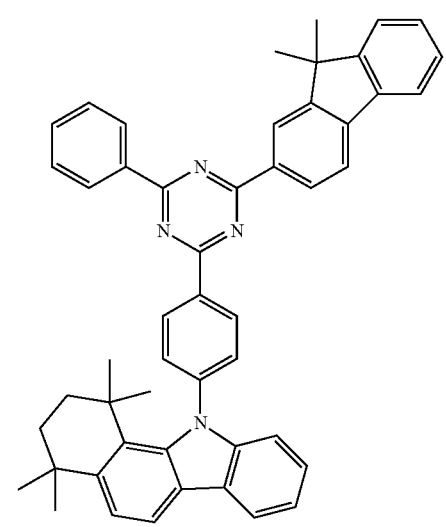
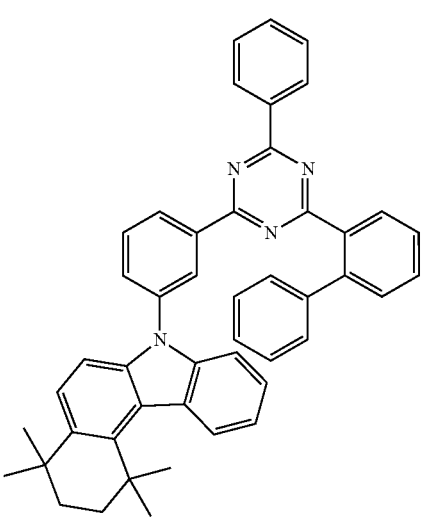
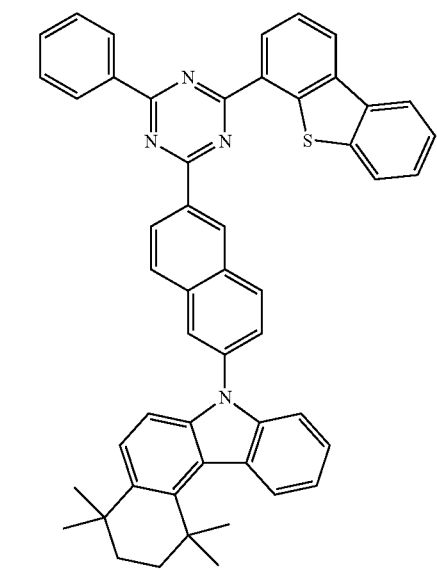

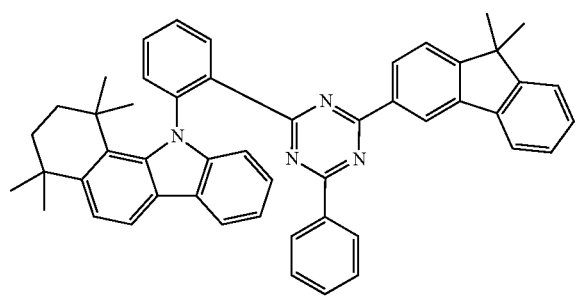
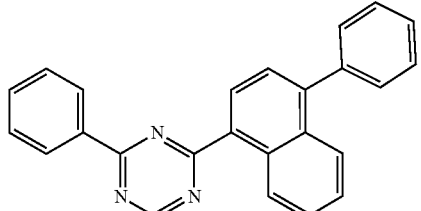
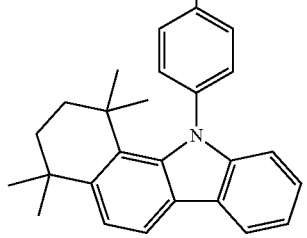
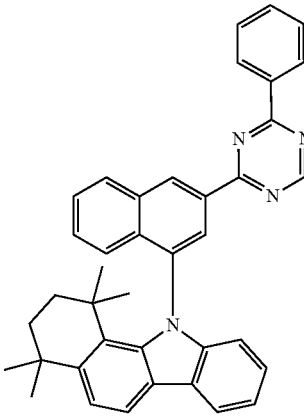
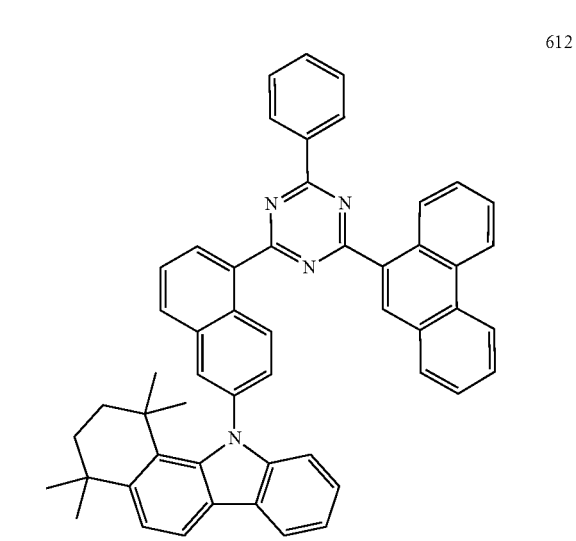

731
-continued
613
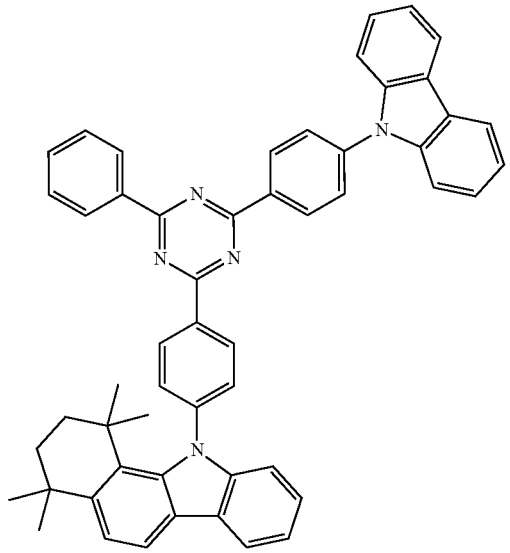
614
615
732
-continued
616
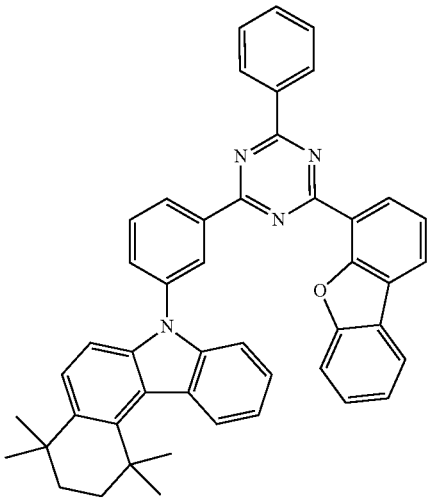
617
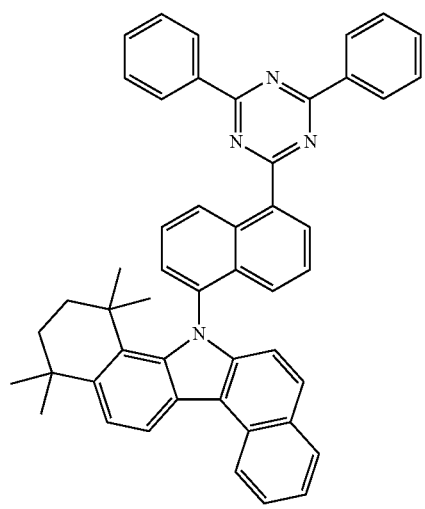
618
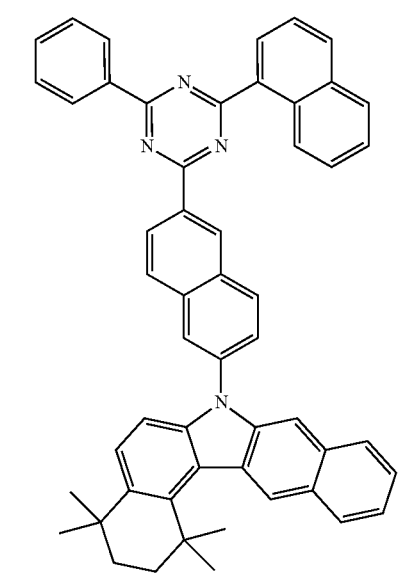

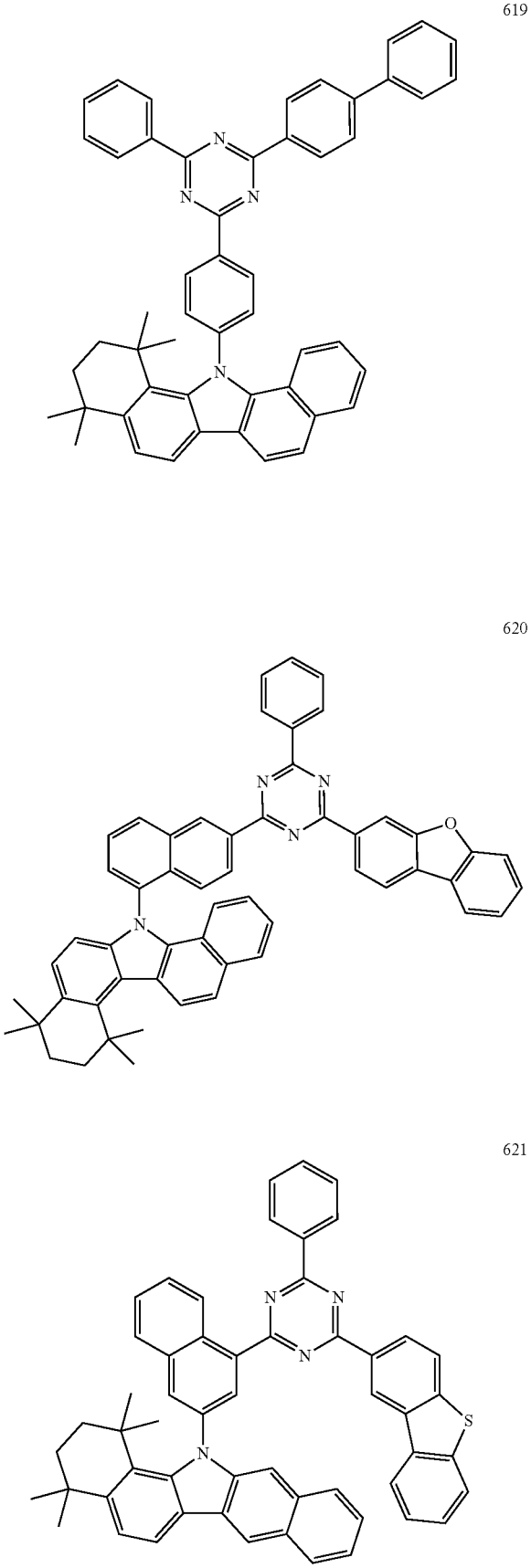
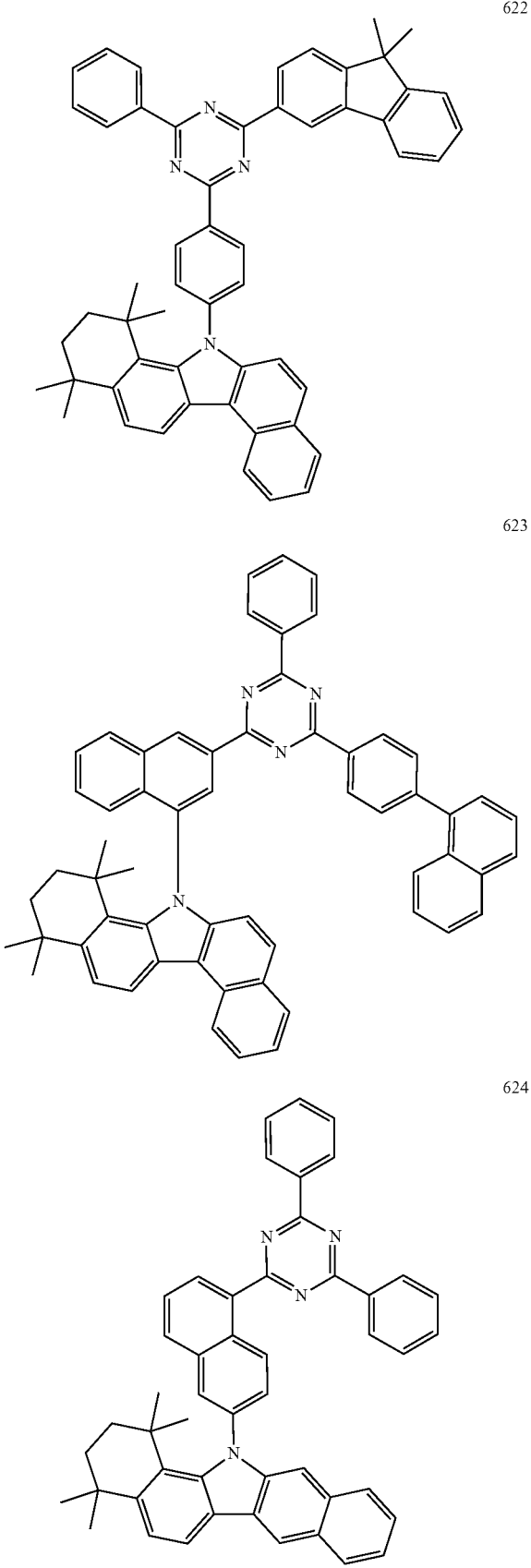

735
-continued
736
-continued
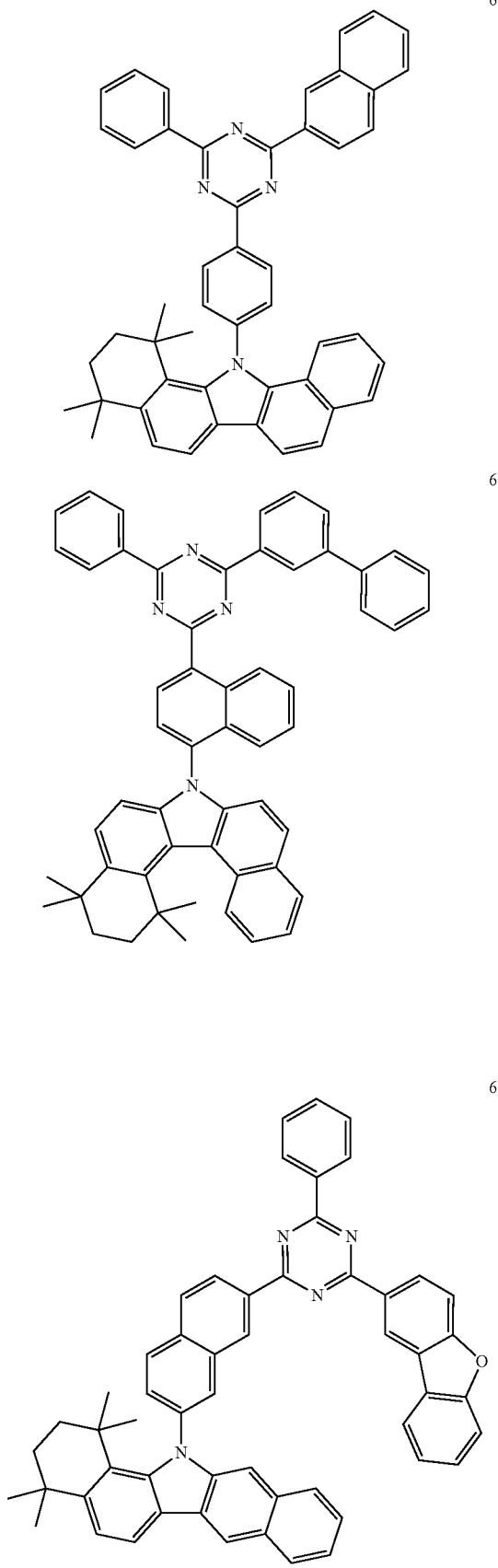
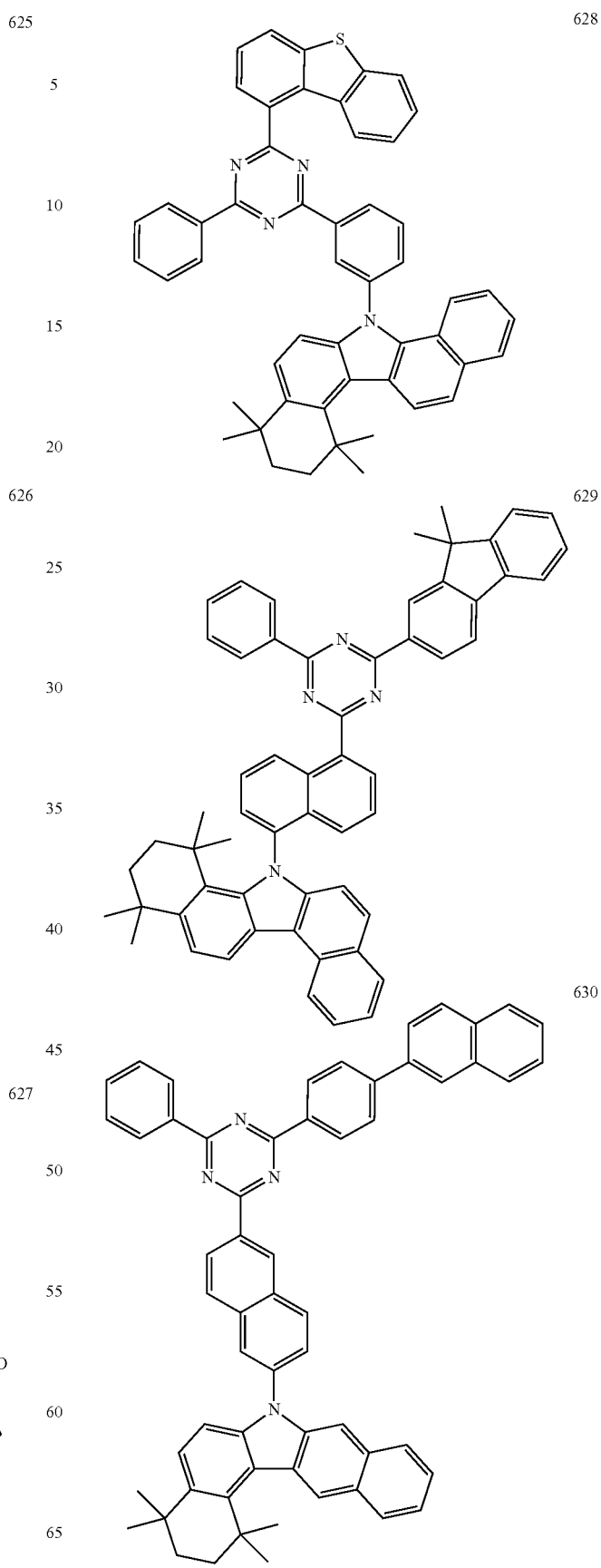

-continued
631
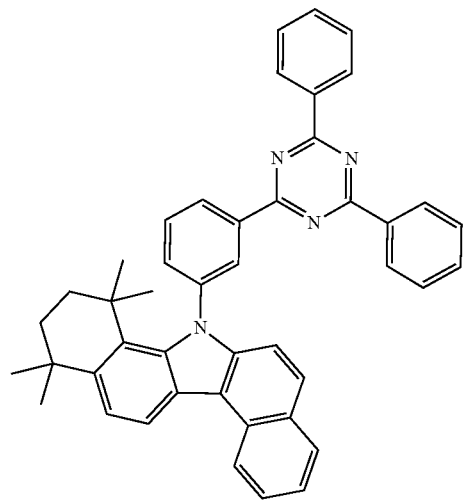
632
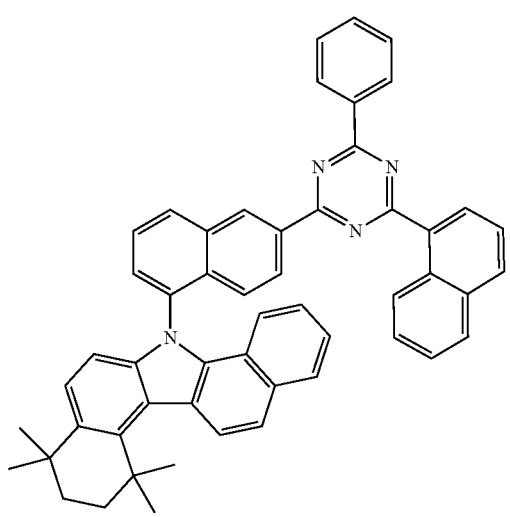
633
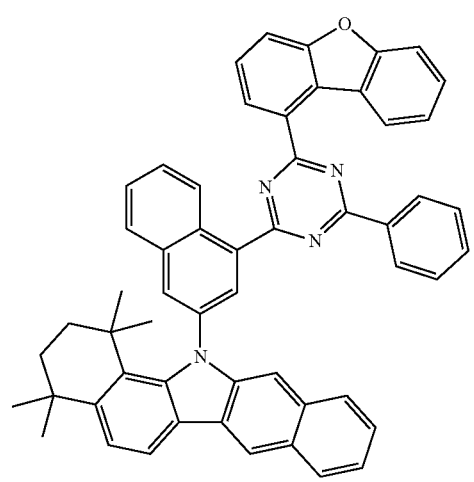
-continued
634
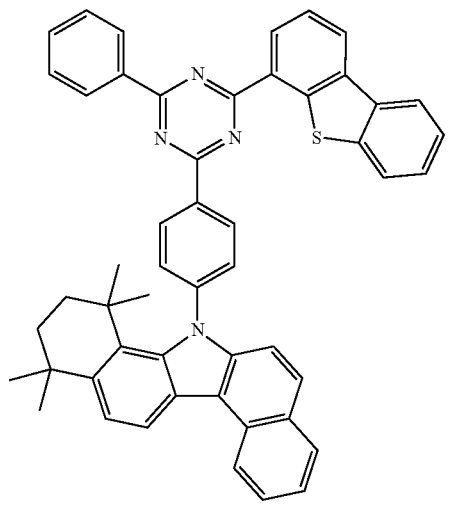
635
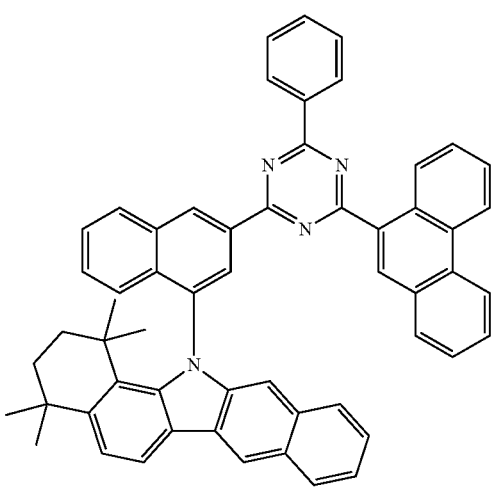
636
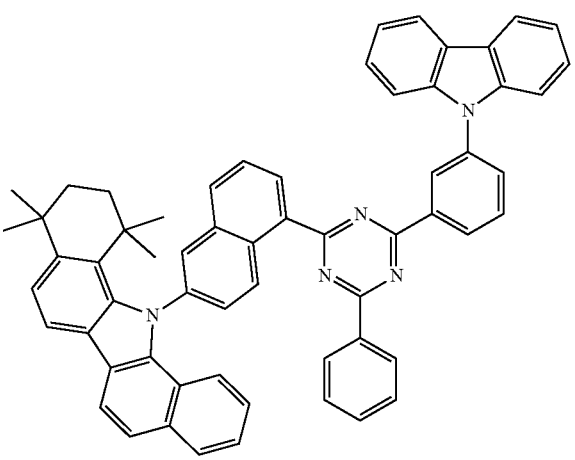

739
-continued
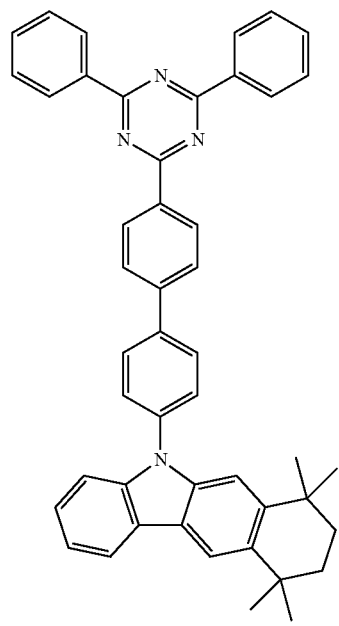 [SMILES: CC1(C)CCC(C)(C)c2cc3c(cc21)c1ccccc1n3-c1ccc(-c2ccc(-c3nc(-c4ccccc4)nc(-c4ccccc4)n3)cc2)cc1]
740
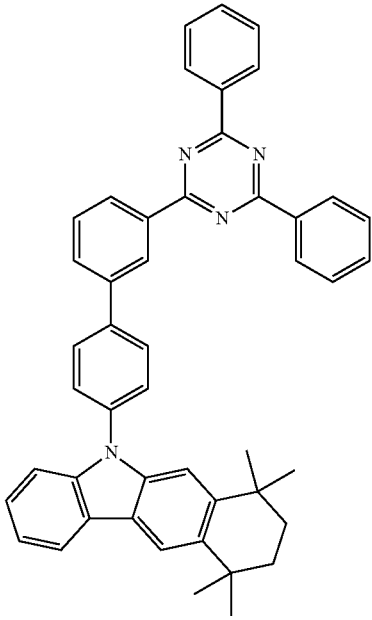
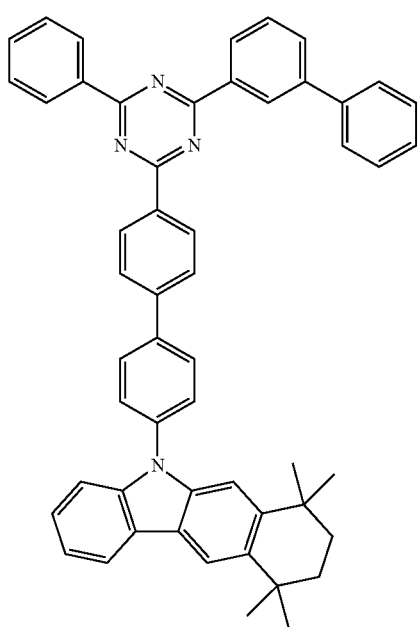
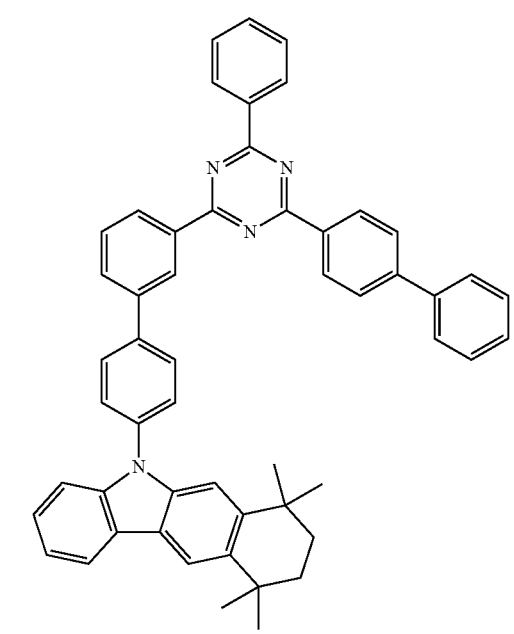

741
-continued
341
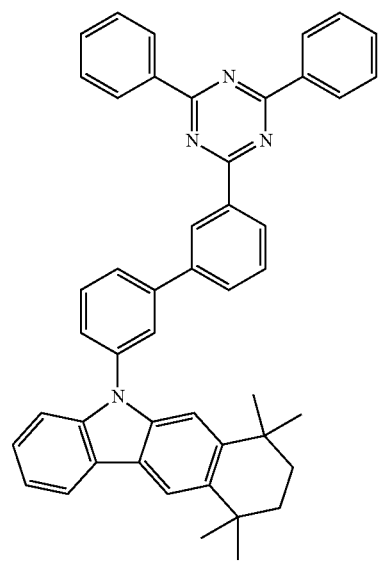
742
-continued
643
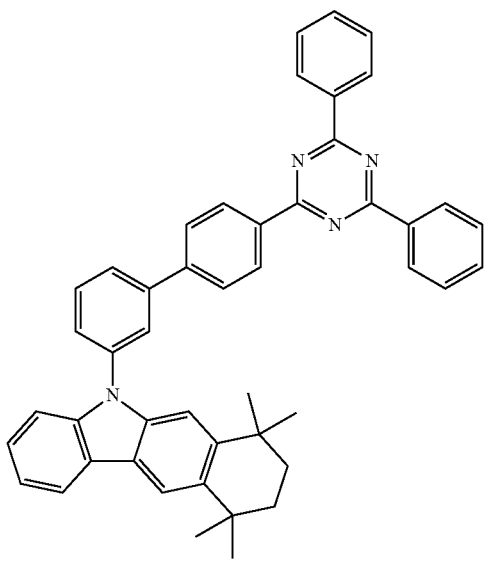
642
644
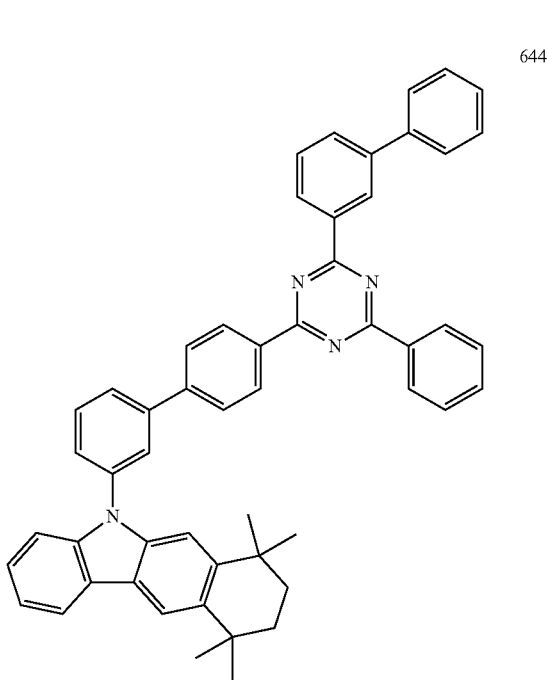

743
-continued
645
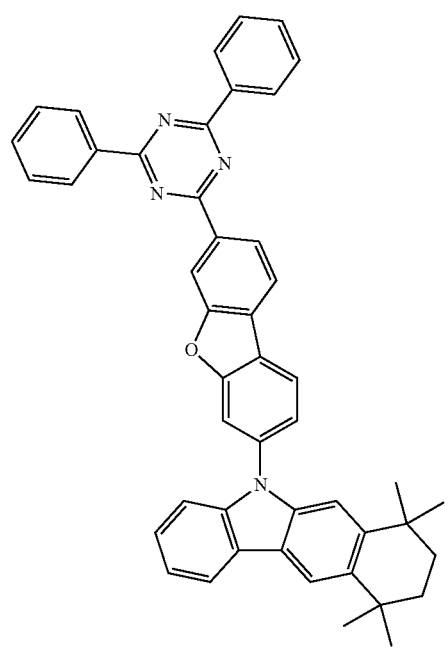
646
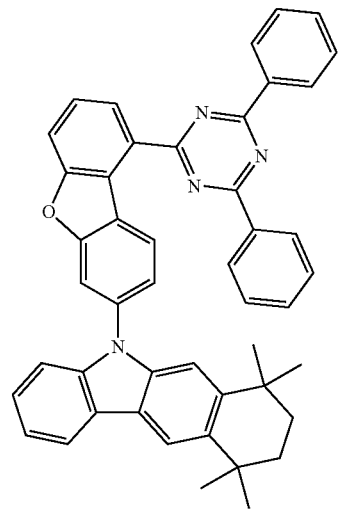
744
-continued
647
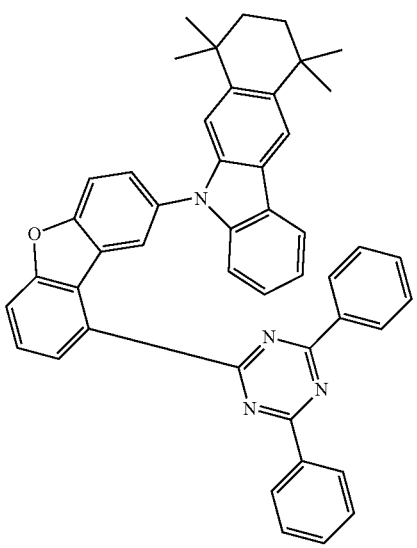
648
649

745
-continued
650
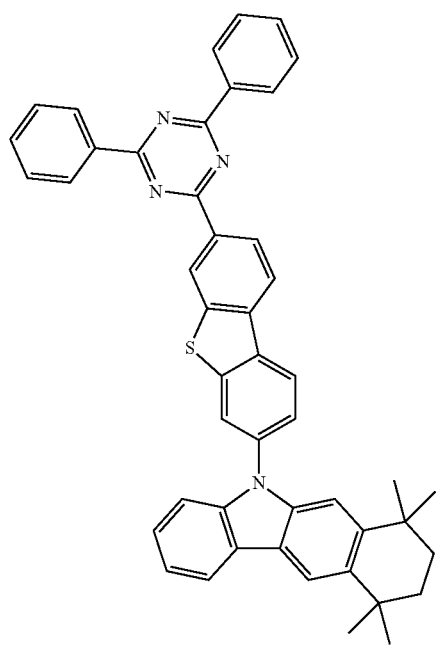
651
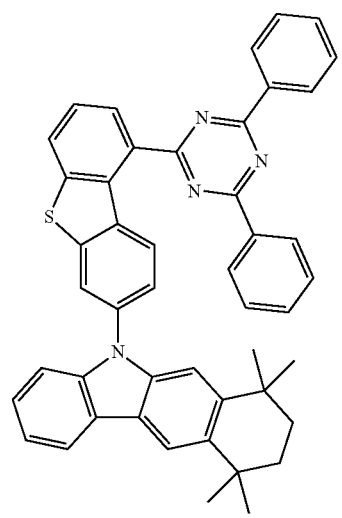 [SMILES: CC1(C)CCC(C)(C)c2cc3c(cc21)c1ccccc1n3-c1ccc2c(c1)sc1cccc(-c3nc(-c4ccccc4)nc(-c4ccccc4)n3)c12]
746
-continued
652
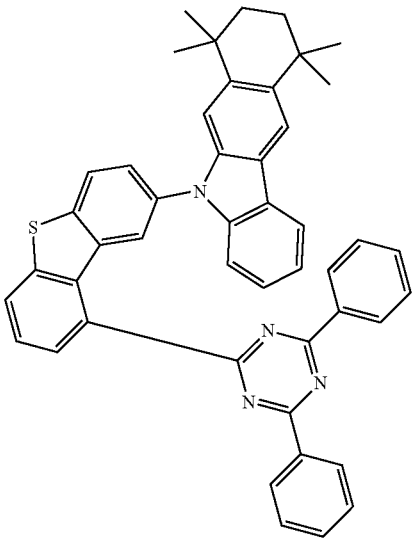
653
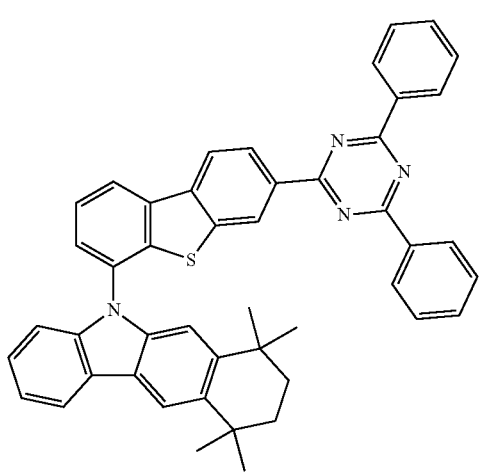
654
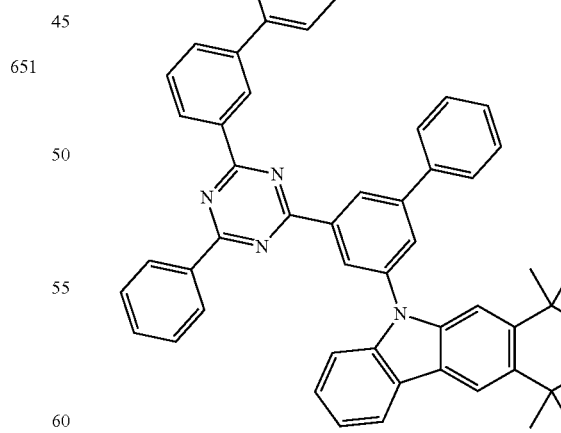
7. An organic electroluminescent device, comprising an anode and a cathode which are oppositely arranged, and a functional layer disposed between the anode and the cathode; wherein the functional layer comprises the nitrogen-containing compound according to claim 1.

8. An electronic apparatus, comprising the organic electroluminescent device according to claim 7.

9. The organic electroluminescent device according to claim 7, wherein the functional layer comprises an organic luminescent layer comprising the nitrogen-containing compound.

* * * * *

UNITED STATES PATENT AND TRADEMARK OFFICE
CERTIFICATE OF CORRECTION

PATENT NO. : 12,084,432 B2
APPLICATION NO. : 18/288600
DATED : September 10, 2024
INVENTOR(S) : Xianbin Xu et al.

Page 1 of 7

It is certified that error appears in the above-identified patent and that said Letters Patent is hereby corrected as shown below:

In the Specification

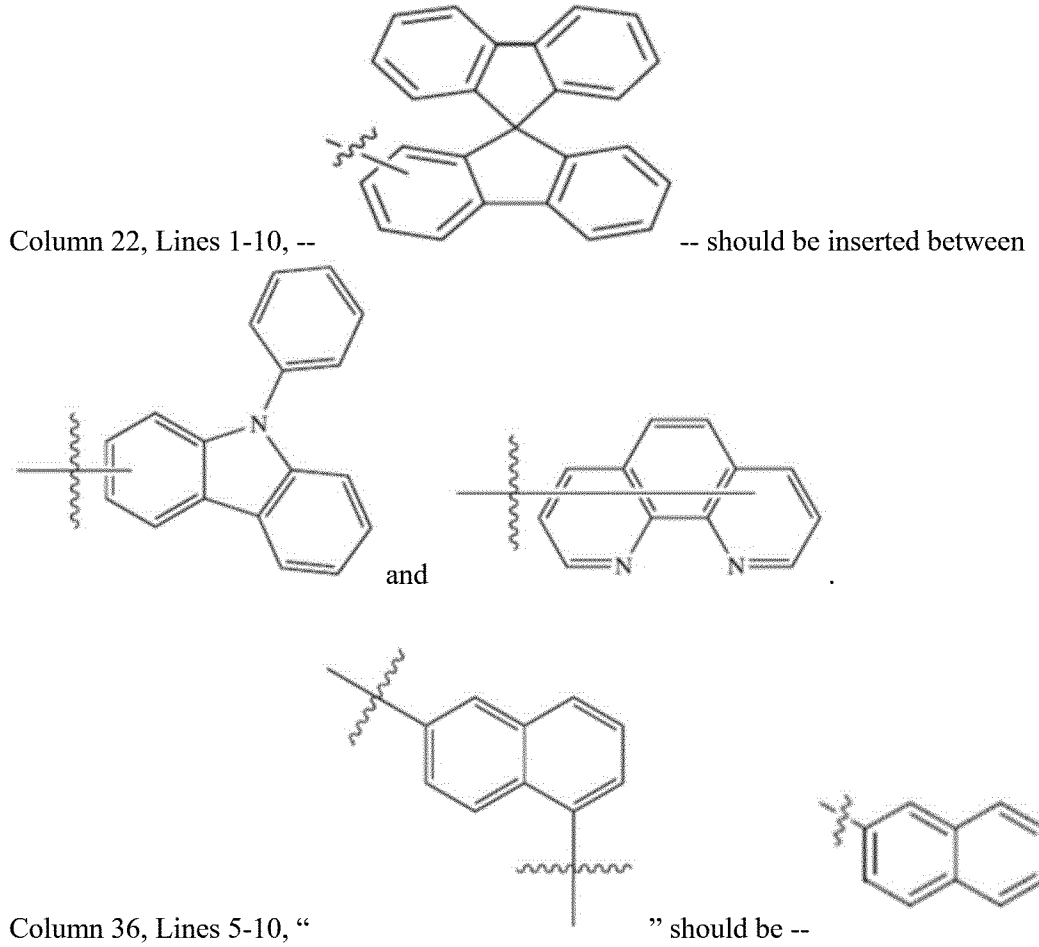

Column 22, Lines 1-10, --            -- should be inserted between            and            .

Column 36, Lines 5-10, "            " should be --            --.

Signed and Sealed this
Twenty-fifth Day of February, 2025

Coke Morgan Stewart
*Acting Director of the United States Patent and Trademark Office*

CERTIFICATE OF CORRECTION (continued)　　　　　　　　　　　　　　　　　　　　Page 2 of 7
U.S. Pat. No. 12,084,432 B2

Column 37, Line 50-55, " 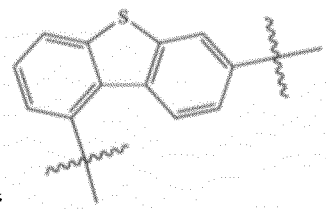 " should be

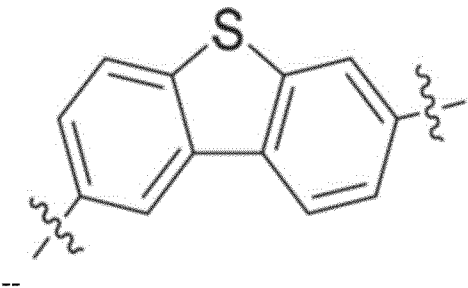

--　　　　　　　　　　--.

Column 227, Lines 25-50, " 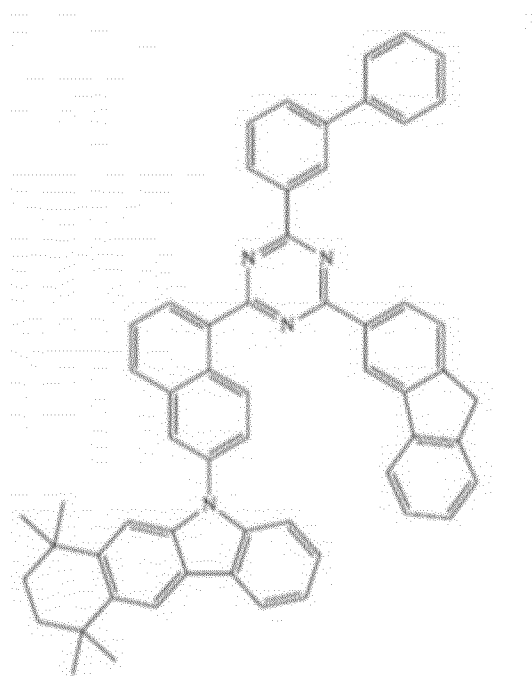 " should be

CERTIFICATE OF CORRECTION (continued)
U.S. Pat. No. 12,084,432 B2

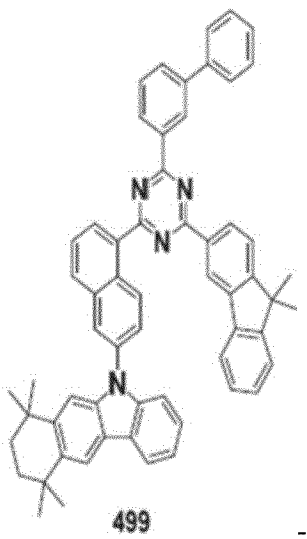

-- 499 --.

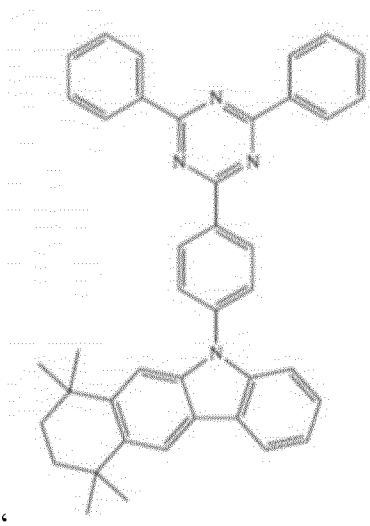

Column 259, Lines 25-40, "    " should be

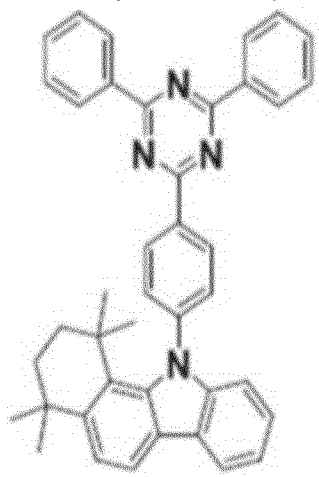

-- 589 --.

Column 293, Line 35-50, " 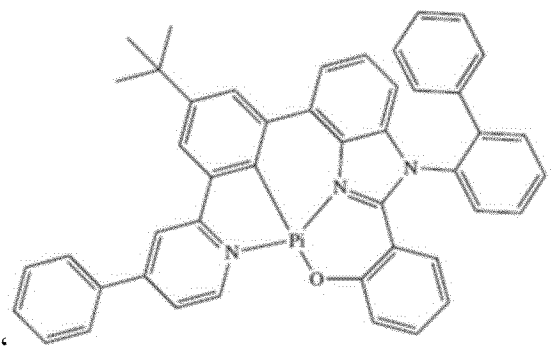 " should be
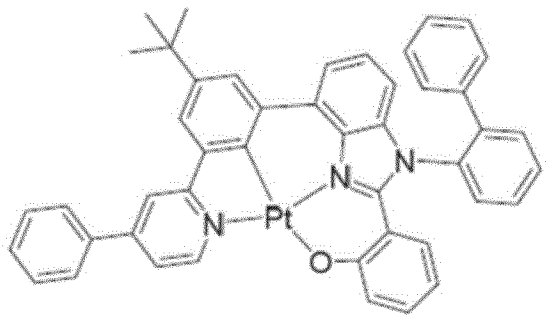
--                                          --.
Column 294, Line 30-40, " 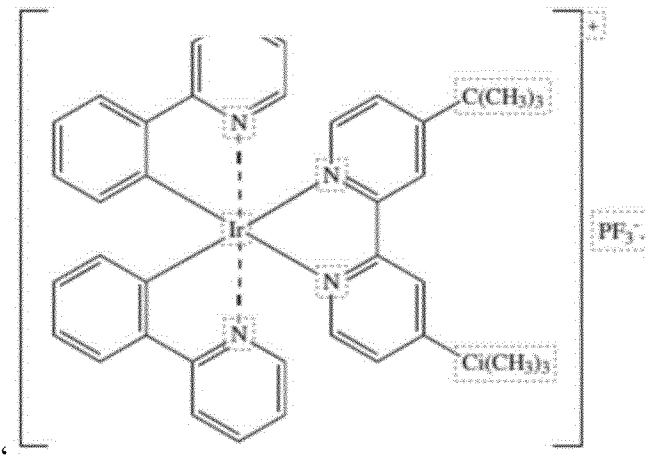 " should be
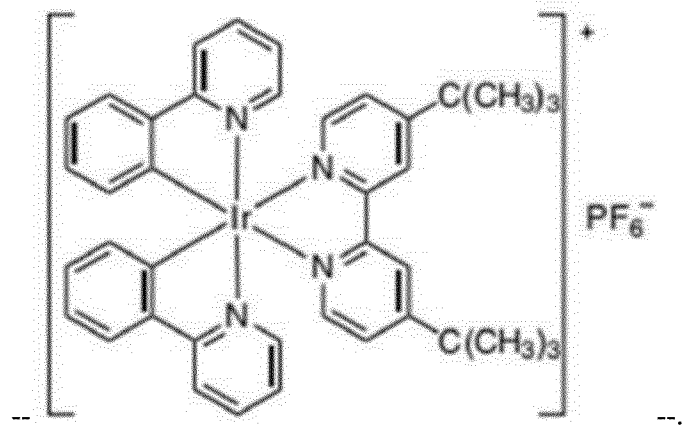
--                                          --.

CERTIFICATE OF CORRECTION (continued)
U.S. Pat. No. 12,084,432 B2

Column 393, Table 7, " 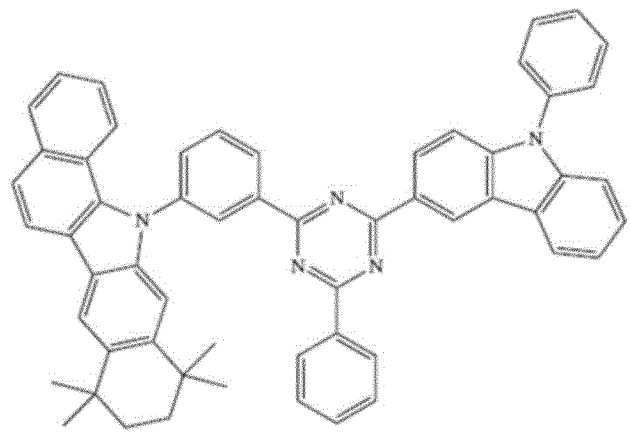 " should be

-- 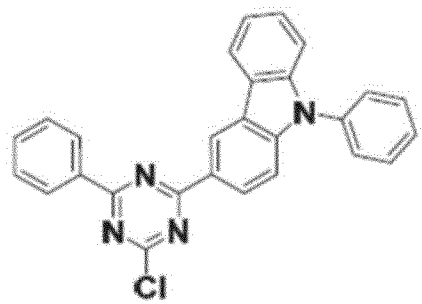 --.

Column 421, Table 7, " 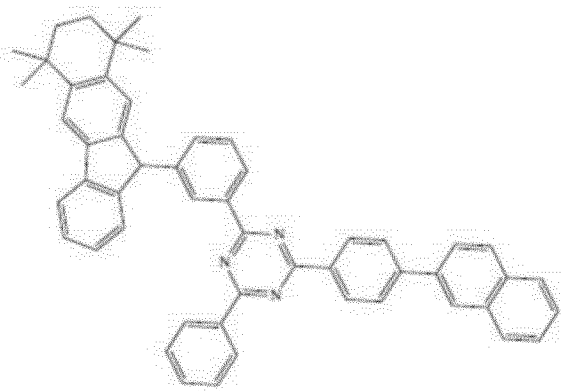 " should be

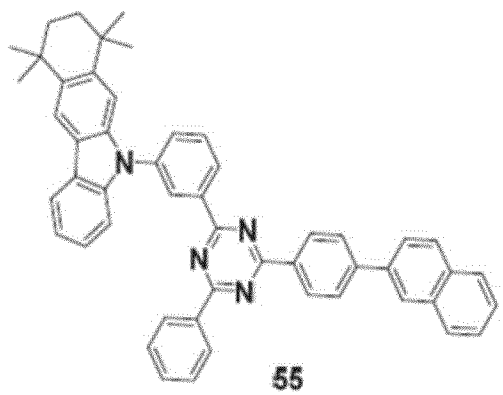
--                     55                    --.
Column 432, Table 7, the number of the compound should be -- 241 -- instead of "24".
In the Claims
Claim 1 at Column 492, Lines 10-15, -- 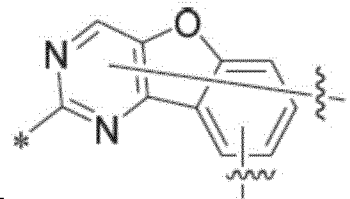 -- should be inserted between
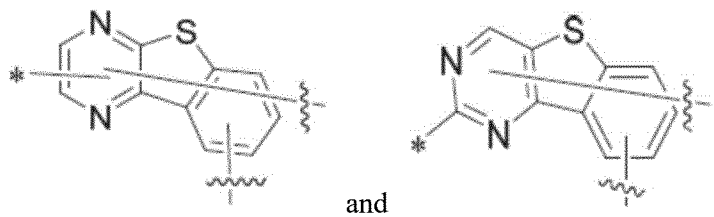
and                    .
Claim 4 at Column 501, Lines 35-45, " 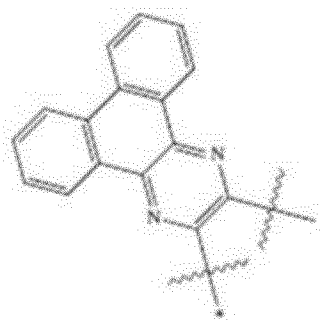 " should be deleted.
Claim 5 at Column 509, Lines 25-30, " 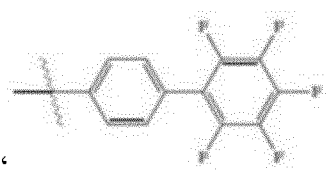 " should be

CERTIFICATE OF CORRECTION (continued)
U.S. Pat. No. 12,084,432 B2

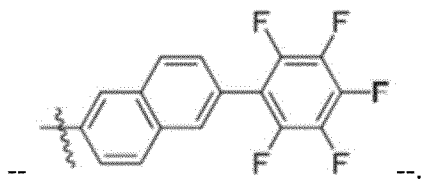
--.

Claim 6 at Column 712, Lines 50-65, " 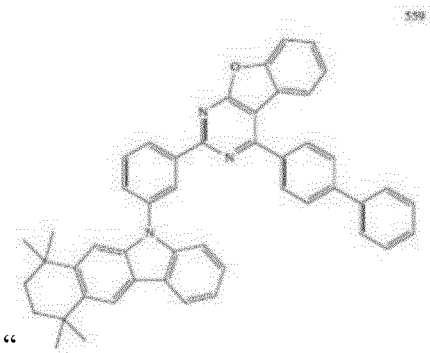 " should be

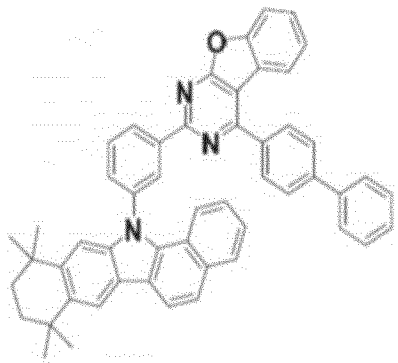
--.

Claim 6 at Column 740, Line 40, the number of the compound should be -- 640 -- instead of "340".

Claim 6 at Column 741, Line 1, the number of the compound should be -- 641 -- instead of "341".